(12) United States Patent
Shiraishi et al.

(10) Patent No.: US 7,262,185 B2
(45) Date of Patent: Aug. 28, 2007

(54) BENZAZEPINE DERIVATIVE, PROCESS FOR PRODUCING THE SAME, AND USE

(75) Inventors: Mitsuru Shiraishi, Amagasaki (JP); Masanori Baba, Kagoshima (JP); Masaki Seto, Tsukuba (JP); Yoshio Aramaki, Osaka (JP); Naoyuki Kanzaki, Osaka (JP); Naoki Miyamoto, Tsukuba (JP); Yuji Iizawa, Osaka (JP)

(73) Assignee: Takeda Chemical Industries Ltd., Osaka (JP)

( * ) Notice: Subject to any disclaimer, the term of this patent is extended or adjusted under 35 U.S.C. 154(b) by 205 days.

(21) Appl. No.: 10/486,002

(22) PCT Filed: Aug. 7, 2002

(86) PCT No.: PCT/JP02/08045

§ 371 (c)(1),
(2), (4) Date: Feb. 5, 2004

(87) PCT Pub. No.: WO03/014110

PCT Pub. Date: Feb. 20, 2003

(65) Prior Publication Data

US 2004/0235822 A1 Nov. 25, 2004

(30) Foreign Application Priority Data

Aug. 8, 2001 (JP) .............................. 2001-240718

(51) Int. Cl.
*A61P 43/00* (2006.01)
*A61K 31/55* (2006.01)
*A61K 31/18* (2006.01)
*C07D 401/12* (2006.01)
*C07D 417/12* (2006.01)

(52) U.S. Cl. .................. 514/213.01; 540/593
(58) Field of Classification Search .......... 514/213.01; 540/593
See application file for complete search history.

(56) References Cited

U.S. PATENT DOCUMENTS

| 6,096,780 A | 8/2000 | Shiraishi et al. ............. 514/431 |
| 6,166,006 A * | 12/2000 | Shiraishi et al. ......... 514/213.01 |
| 6,172,061 B1 * | 1/2001 | Nishimura et al. ....... 514/231.5 |
| 6,235,771 B1 | 5/2001 | Shiraishi et al. ............. 514/431 |
| 6,413,947 B1 | 7/2002 | Shiraishi et al. ............. 514/110 |
| 6,936,602 B1 * | 8/2005 | Shiraishi et al. ......... 514/213.01 |

FOREIGN PATENT DOCUMENTS

| WO | WO99/32100 | 7/1999 |
| WO | WO99/32468 | 7/1999 |
| WO | WO 00/37455 | 6/2000 |
| WO | WO 00/76993 | 12/2000 |

OTHER PUBLICATIONS

Horuk, Chemokine Receptors, Cytokine and Growth Factor Reviews, vol. 12, No. 4, pp. 313-335, Dec. 2001.*
M. Shiraishi, et al., "Discovery of Novel, Potent, and Selective Small-Molecule CCR5 Antagonists as Anti-HIV-1 Agents: Synthesis and Biological Evaluation of Anilide Derivatives with a Quaternary Ammonium Moiety", J. Med. Chem., (2000), pp. 2049-2063, vol. 43.
M. Baba, et al., "A Small-Molecule, Nonpeptide CCR5 Antagonist with Highly Potent and Selective Anti-HIV-1 Activity", Proc. Natl. Acad. Sci USA, (1999), pp. 5698-5703, vol. 96.

* cited by examiner

*Primary Examiner*—Brenda Coleman
(74) *Attorney, Agent, or Firm*—Edwards Angell Palmer & Dodge LLP; David G. Conlin; Dwight D. Kim

(57) ABSTRACT

The present invention provides a novel benzazepine derivative represented by formula:

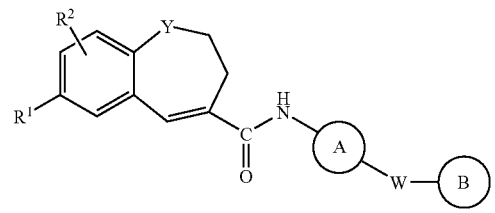

wherein, $R^1$ is a 5- or 6-membered aromatic ring, $R^2$ is lower alkyl group, etc., Y is an optionally substituted imino group, ring A and ring B are independently an optionally substituted aromatic ring, W is formula $—W^1—X^2—W^2—$ ($W^1$ and $W^2$ are independently $S(O)_{m1}$ (m1 is 0, 1, or 2), etc., and $X^2$ is an optionally substituted alkylene group etc.), a preparation method and use thereof.

17 Claims, 1 Drawing Sheet

BENZAZEPINE DERIVATIVE, PROCESS FOR PRODUCING THE SAME, AND USE

This application is the National Phase filing of International Patent Application No. PCT/JP02/08045, filed 07 Aug. 2002.

TECHNICAL FIELD

The present invention relates to a novel benzazepine derivative, a process for producing the same and use thereof.

BACKGROUND ART

In recent years, HIV (human immunodeficiency virus) protease inhibitors have been developed for the treatment of AIDS (acquired immunodeficiency syndrome), and by combining with conventional two HIV reverse transcriptase inhibitors, the treatment of AIDS have made a remarkable progress. However, these drugs are not sufficient for the eradication of AIDS, and development of new anti-AIDS drugs having different action mechanism have been desired.

As a receptor from which HIV invades target cell, CD4 has been so far known, and CCR5 as a second receptor of macrophage-tropic HIV and 7-transmembrane G protein-coupled chemokine receptor called CXCR4 as a second receptor of T cell-tropic HIV, have recently been found. These chemokine receptors are thought to play an essential role in the infection and transmission of HIV. In fact, it has been reported that humans who are resistant to HIV infection in spite of repeated exposures retains a homo deletion mutation of the CCR5 gene. Therefore, a CCR5 antagonist is expected to be a new anti-HIV drug. However, to date, there has not been a report of a CCR5 antagonist developed as a therapeutic agent against AIDS. Further, JP-A 2001-058992 and JP-A 2001-026586 disclose that a compound having CCR5 antagonism is useful as an agent for preventing or treating AIDS, but the compound has a different structure from that of compound of the present invention.

DISCLOSURE OF INVENTION

In order to investigate anti-AIDS drug based on CCR5 antagonism, it is necessary to clone the CCR5 gene from a human tissue derived cDNA library, to ligate said gene into an expression vector for animal cells, to introduce said gene into animal cells and to obtain cell strains expressing CCR5. In addition, using this transformant, it is necessary to screen a compound which strongly inhibits binding of CC chemokine RANTES, a natural ligand, to CCR5. However, there have been few reports on low-molecular weight compounds having the antagonism which are suitable for oral administration. The present invention is to provide a novel anilide derivative having CCR5 antagonism, which is useful for the treatment or prevention of infectious diseases of HIV, in particular, AIDS and is also suitable for oral administration, and a process for production and use thereof.

SUMMARY OF THE INVENTION

The present inventors have conducted extensive studies on compounds having CCR5 antagonism and as a result, found that a benzazepine derivative represented by the following formula (I) or a salt thereof [hereinafter, referred to as Compound (I) in some cases] possesses CC chemokine receptor (CCR) antagonism, in particular, potent CCR5 antagonism and a clinically desirable pharmaceutical effect such as remarkable inhibition of infection of human peripheral mononuclear cells, etc. with HIV and also that Compound (I) has superior absorbability when orally administered. Based on these findings, the present invention has been accomplished.

That is, the present invention provides:

(1) A compound represented by the formula (I):

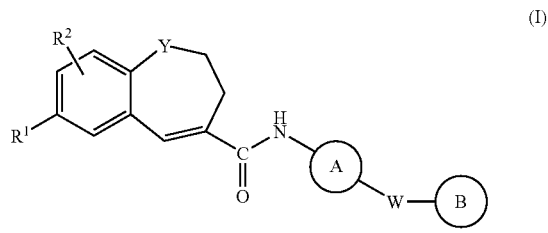

wherein, $R^1$ is a 5- or 6-membered aromatic ring which has a substituent represented by formula $R—Z^1—X^1—Z^2—$ (wherein, R is a hydrogen atom or an optionally substituted hydrocarbon group, $X^1$ is an optionally substituted alkylene chain, $Z^1$ and $Z^2$ are independently a heteroatom) and may have a further substituent, the group represented by R may bind to said 5- or 6-membered aromatic ring to form a ring, $R^2$ is a hydrogen atom, an optionally substituted lower alkyl group, an optionally substituted lower alkoxy group or a halogen atom, Y is an optionally substituted imino group, ring A and ring B are independently an optionally substituted aromatic ring, and W is a group represented by formula $—W^1—X^2—W^2—$ (wherein, $W^1$ and $W^2$ are independently O, $S(O)_{m1}$ (m1 is 0, 1 or 2), an optionally substituted imino group or a bond, and $X^2$ is an optionally substituted alkylene group, an optionally substituted alkenylene group or a bond)] or a salt thereof.

(2) A prodrug of the compound according to the above-mentioned (1);

(3) The compound according to the above-mentioned (1), wherein the 5- or 6-membered aromatic ring of $R^1$ is benzene;

(4). The compound according to the above-mentioned (1), wherein R is an optionally halogenated lower alkyl group;

(5) The compound according to the above-mentioned (1), wherein $X^1$ is $—(CH_2)_n—$ (wherein n is an integer of 1 to 4);

(6) The compound according to the above-mentioned (1), wherein $Z^1$ is —O—;

(7) The compound according to the above-mentioned (1), wherein $Z^2$ is —O—;

(8) The compound according to the above-mentioned (1), wherein Y is $—N(R^{5'})—$ (wherein $R^{5'}$ is a hydrogen atom, an optionally substituted hydrocarbon group, an optionally substituted 5- or 6-membered aromatic heterocyclic group or an optionally substituted acyl group);

(9) The compound according to the above-mentioned (8), wherein $R^{5'}$ is an optionally substituted $C_{1-4}$ alkyl, an optionally substituted benzyl or an optionally substituted 5- or 6-membered aromatic heterocyclic group;

(10) The compound according to the above-mentioned (1), wherein ring A is an optionally substituted benzene ring, an optionally substituted pyridine ring, an optionally substituted pyridazine ring or an optionally substituted benzimidazole ring;

(11) The compound according to the above-mentioned (1), wherein ring B is an imidazole ring substituted by an optionally substituted lower alkyl group, or a triazole ring substituted by an optionally substituted lower alkyl group;

(12) The compound according to the above-mentioned (1), wherein one of $W^1$ and $W^2$ is O, $S(O)_{m1}$ (wherein m1 is 0, 1 or 2) or —N($R^3$)— (wherein $R^3$ is a hydrogen atom or an optionally substituted lower alkyl group) and the other is a bond and $X^2$ is —$(CH_2)_p$— (wherein p is an integer of 1 to 3), or W is —CH(OH)—;

(13) The compound according to the above-mentioned (1), wherein ring A is a benzene ring, ring B is an optionally substituted imidazole ring or an optionally substituted triazole ring, one of $W^1$ and $W^2$ is $S(O)_{m1}$ (wherein m1 is 0, 1 or 2) and the other is a bond, and $X^2$ is —$(CH_2)_p$— (wherein p is an integer of 1 to 3), or W is —CH(OH)—;

(14) The compound according to the above-mentioned (1), wherein;

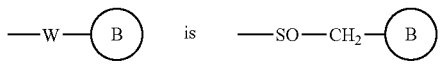

(15) The compound according to the above-mentioned (14), wherein the steric configuration of SO is (S) configuration;

(16) The compound according to the above-mentioned (1), wherein the compound is (−)-7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide, (−)-7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide, (−)-7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide, (−)-1-isobutyl-7-[4-(2-propoxyethoxy)phenyl]-N-[4-[([[1-propylimidazol-5-yl]methyl]sulfinyl]phenyl]-2,3-dihydro-1-benzazepine-4-carboxamide, (+)-7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide, or a salt thereof;

(17) A process for producing a compound represented by the formula:

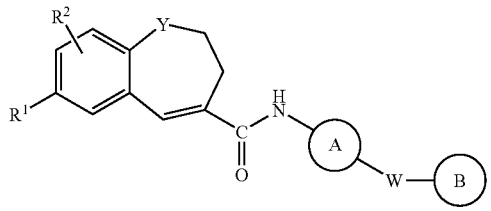

wherein, each symbol has the same meaning as defined in (1) or a salt thereof, which comprises subjecting to a condensation reaction of a compound represented by the formula:

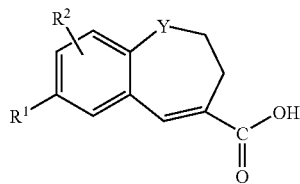

wherein, each symbol has the same meaning as defined in (1), a salt or a reactive derivative thereof, with a compound represented by the formula:

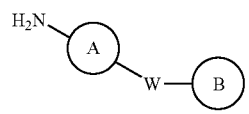

wherein, each symbol has the same meaning as defined in (1), or a salt thereof;

(18) A pharmaceutical composition comprising the compound according to the above-mentioned (1) or a prodrug thereof;

(19) The composition according to the above-mentioned (18), which is a CC chemokine receptor antagonist;

(20) The composition according to the above-mentioned (18), which is a CCR5 antagonist and/or CCR2 antagonist;

(21) The composition according to the above-mentioned (18), which is a preventive or therapeutic agent for HIV infection, chronic rheumatoid arthritis, autoimmune diseases, allergic diseases, ischemic brain cell disorders, myocardial infarction, nephritis, nephropathy or arteriosclerosis;

(22) The composition according to the above-mentioned (18), which is a blood for blood transfusion or a blood product;

(23) The composition according to the above-mentioned (18), which is an agent for the prevention or treatment of graft versus host disease and/or rejection in the transplant of organ or bone marrow.

BRIEF DESCRIPTION OF THE DRAWINGS

Figure 1:
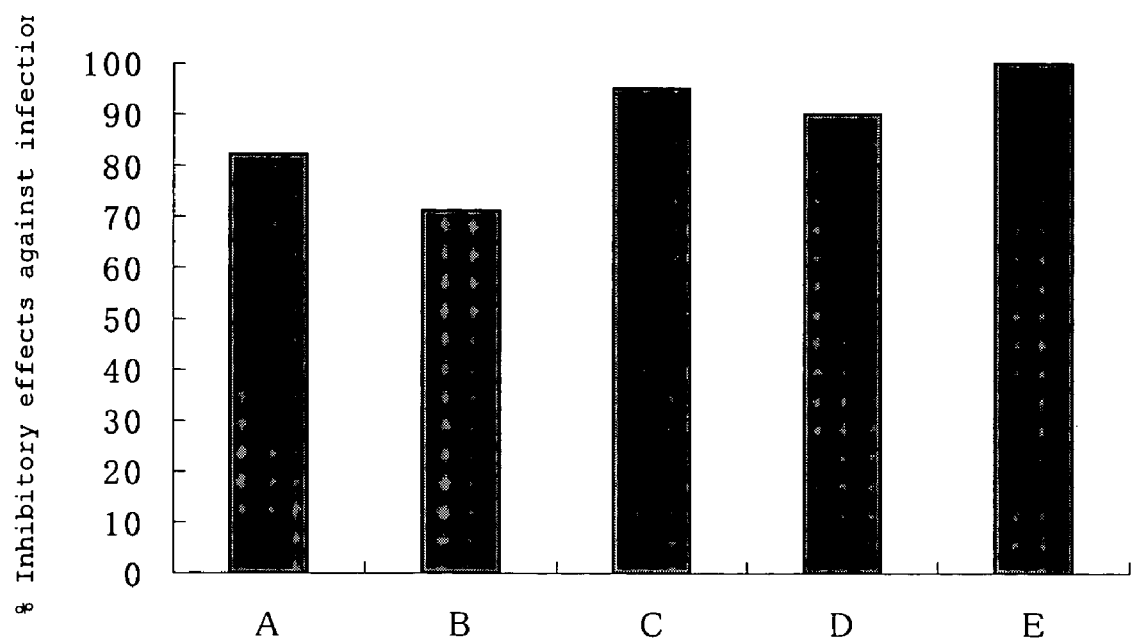
FIG. 1 is a graph showing the inhibitory effects against HIV infection of the compound according to the present invention.

In the formula (I) above, examples of the "5- or 6-membered aromatic ring" in the "5- or 6-membered aromatic ring, which has a substituent represented by the formula R—$Z^1$—$X^1$—$Z^2$— (wherein, R is a hydrogen atom or an optionally substituted hydrocarbon, $X^1$ is an optionally substituted alkylene chain, and $Z^1$ and $Z^2$ are independently a heteroatom) and may have a further substituent", represented by $R^1$ include a 6-membered aromatic hydrocarbon such as benzene, etc., and a 5- or 6-membered aromatic heterocyclic ring containing 1 to 4 hetero-atoms consisting of 1 or 2 kinds of hetero-atoms selected from nitrogen atom, sulfur atom and oxygen atom such as furan, thiophene, pyrrole, imidazole, pyrazole, thiazole, oxazole, isothiazole, isoxazole, tetrazole, pyridine, pyrazine, pyrimidine, pyridazine, triazole, etc., and among others, benzene, furan, thiophene, pyridine, etc., are preferable, and benzene, furan or thiophene is more preferable, and in particular, benzene is preferable.

Examples of the "hydrocarbon group" of the "optionally substituted hydrocarbon group" represented by R include (1) alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and more preferably, lower ($C_{1-4}$)alkyl, etc.);

(2) cycloalkyl (e.g., $C_{3-7}$cycloalkyl, etc. such as cyclopropyl, cyclobutyl, cyclopentyl, cyclohexyl, cycloheptyl, etc.);

(3) alkenyl (e.g., $C_{2-10}$alkenyl, such as allyl, crotyl, 2-pentenyl, 3-hexenyl, etc., preferably lower ($C_{2-6}$)alkenyl, etc.);

(4) cycloalkenyl (e.g., $C_{3-7}$cycloalkenyl, etc. such as 2-cyclopentenyl, 2-cyclohexenyl, 2-cyclopentenylmethyl, 2-cyclohexenylmethyl, etc.);

(5) alkynyl (e.g., $C_{2-10}$alkynyl such as ethynyl, 1-propynyl, 2-propynyl, 1-butynyl, 2-pentynyl, 3-hexynyl, etc., preferably lower ($C_{2-6}$)alkynyl, etc.);

(6) aralkyl (e.g., phenyl-$C_{1-4}$alkyl (e.g., benzyl, phenethyl, etc.) and the like);

(7) aryl (e.g., phenyl, naphthyl, etc.); and (8) cycloalkyl-alkyl (e.g., $C_{3-7}$cycloalkyl-$C_{1-4}$alkyl, etc. such as cyclopropylmethyl, cyclobutylmethyl, cyclopentylmethyl, cyclohexylmethyl, cycloheptylmethyl, etc.). Examples of the substituent that the above-mentioned (1) alkyl, (2) cycloalkyl, (3) alkenyl, (4) cycloalkenyl, (5) alkynyl, (6) aralkyl, (7) aryl and (8) cycloalkyl-alkyl may have include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.), etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), $C_{1-4}$alkylenedioxy (e.g., —O—$CH_2$—O—, —O—$CH_2$—$CH_2$—O—, etc.), an optionally substituted sulfonamide (for example, a group formed by bonding an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.), etc.) to —$SO_2$—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), an optionally substituted heterocyclic group, etc. The number of the substituents is preferably 1 to 3.

As used herein, examples of the "heterocyclic group" in the "optionally substituted heterocyclic group" as a substituent for the "optionally substituted hydrocarbon group" represented by R include a group formed by eliminating one hydrogen atom from aromatic or non-aromatic heterocyclic ring, etc. Examples of the aromatic heterocyclic ring include 5- or 6-membered aromatic heterocyclic rings containing 1 to 4 hetero-atoms consisting of 1 or 2 kinds of hetero-atoms selected from nitrogen atom, sulfur atom and oxygen atom such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc. Examples of the non-aromatic heterocyclic ring include 5- or 6-membered non-aromatic heterocyclic rings containing 1 to 4 hetero-atoms consisting of 1 or 2 kinds of hetero-atoms selected from nitrogen atom, sulfur atom and oxygen atom such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc. and non-aromatic heterocyclic ring wherein part or whole bond(s) of the above mentioned aromatic heterocyclic ring is (are) a saturated bond (preferably, aromatic heterocyclic ring such as pyrazole, thiazole, oxazole, tetrazole, etc.) and the like.

The "heterocyclic group" in the "optionally substituted heterocyclic group" as a substituent of the "optionally substituted hydrocarbon group" represented by R may have 1 to 3 substituents at any substitutable position. Examples of such substituent include halogen (e.g., fluorine, chlorine, bromine, iodine, etc.), nitro, cyano, hydroxy, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.), etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), $C_{1-4}$alkylenedioxy (e.g., —O—$CH_2$—O—, —O—$CH_2$—$CH_2$—O—, etc.), an optionally substituted sulfonamide (for example, a group formed by bonding an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.), etc.) to —$SO_2$—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), etc. (preferably, $C_{1-4}$alkyl, etc.).

In addition, when the group represented by the formula R—$Z^1$—$X^1$—$Z^2$— (wherein, each symbol has the same meaning as defined in the above) is a mono-valent group (which does not bind to the 5- or 6-membered aromatic ring to form a ring), as the group R, an optionally substituted alkyl group is preferable, an optionally halogenated lower alkyl group is more preferable, and in particular, an optionally halogenated $C_{1-4}$ alkyl group is preferable.

Examples of the "optionally substituted alkylene chain" represented by $X^1$ include an optionally substituted, straight or branched $C_{1-6}$alkylene, etc. The number of carbon atoms for the straight chain moiety of the alkylene chain is preferably 1 to 4, and inter alia, $X^1$ is preferably an optionally substituted straight $C_{1-4}$alkylene (preferably ethylene or propylene).

The substituent that the "alkylene chain" in the "optionally substituted alkylene chain" represented by $X^1$ may have, is any one which may bind to a divalent chain constituting a straight chain moiety, and includes, for example, lower $C_{1-6}$alkyl (e.g., methyl, ethyl, propyl, isopropyl, butyl, isobutyl, sec-butyl, tert-butyl, pentyl, isopentyl, neopentyl, hexyl, etc.), lower ($C_{3-7}$)cycloalkyl (e.g., cyclopropyl, cyclobutyl, cyclopentyl, cyclohexyl, cycloheptyl, etc.), formyl, lower ($C_{2-7}$)alkanoyl (e.g., acetyl, propionyl, butyryl, etc.), an optionally esterified phosphono group, an optionally esterified carboxyl group, hydroxy group, oxo group, etc., and preferably, lower $C_{1-6}$alkyl (preferably, $C_{1-3}$alkyl), hydroxy group, oxo group, etc.

Examples of the optionally esterified phosphono group include a group represented by $P(O)(OR^{7a})(OR^{8a})$ [wherein, $R^{7a}$ and $R^{8a}$ are each hydrogen, $C_{1-6}$ alkyl group or $C_{3-7}$cycloalkyl group, and $R^{7a}$ and $R^{8a}$ may bind together to form a 5- to 7-membered ring].

In the above formula, examples of $C_{1-6}$alkyl group represented by $R^{7a}$ and $R^{8a}$ include methyl, ethyl, propyl, isopropyl, butyl, isobutyl, sec-butyl, tert-butyl, pentyl, isopentyl, neopentyl, hexyl, etc., and examples of $C_{3-7}$cycloalkyl include cyclopropyl, cyclobutyl, cyclopentyl, cyclohexyl, cycloheptyl, etc., and preferably, straight lower $C_{1-6}$alkyl, more preferably lower $C_{1-3}$alkyl. $R^{7a}$ and $R^{8a}$ may be the same or different, and preferably the same. In addition, when $R^{7a}$ and $R^{8a}$ bind each other to form a 5- to 7-membered ring, $R^{7a}$ and $R^{8a}$ bind each other to form straight $C_{2-4}$alkylene side chain represented by —$(CH_2)_2$—, —$(CH_2)_3$—, and —$(CH_2)_4$—. The side chain may have a substituent, and examples of such substituents include hydroxy group, halogen, etc.

Examples of the ester of optionally esterified carboxyl group include a group wherein a carboxyl group binds to $C_{1-6}$alkyl group or $C_{3-7}$cycloalkyl group, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.

As $X^1$, an optionally substituted $C_{1-4}$alkylene is preferable, and among them, $C_{1-4}$alkylene optionally substituted with $C_{1-3}$alkyl, hydroxy group or oxo, is preferable, and in particular, a group represented by the formula: —$(CH_2)_n$— (n is an integer of 1 to 4) is preferable.

Examples of the heteroatom represented by $Z^1$ and $Z^2$ include —O—, —$S(O)_{m2}$— (m2 is an integer of 0 to 2), —$N(R^4)$— ($R^4$ is a hydrogen atom or an optionally substituted lower alkyl group), etc., and $Z^1$ is preferably —O— or —$S(O)_{m2}$- ($m_2$ is an integer of 0 to 2) and more preferably, —O—. In addition, $Z^2$ is preferably —O— or —$N(R^4)$— ($R^4$ is a hydrogen atom or an optionally substituted lower alkyl group) and more preferably —O—.

Examples of the optionally substituted lower alkyl group represented by $R^4$ include the same groups as those for the "optionally substituted lower alkyl group" exemplified with respect to the "optionally substituted hydrocarbon group" represented by R.

As the "substituent" that the "5- or 6-membered ring" of the "5- or 6-membered aromatic ring which has a substituent represented by the formula: $R-Z^1-X^1Z^2$—(wherein, each symbol has the same meaning as defined in the above) and may have a further substituent" represented by $R^1$ may have in addition to the group represented by the formula: $R-Z^1-X^1-Z^2$—, for example, halogen atom, nitro, cyano, an optionally substituted alkyl, an optionally substituted cycloalkyl, an optionally substituted hydroxy group, an optionally substituted thiol group (the sulfur atom may be oxidized, or may form an optionally substituted sulfinyl group or an optionally substituted sulfonyl group), an optionally substituted amino group, an optionally substituted acyl group, an optionally esterified or amidated carboxyl group, an optionally substituted aromatic group, etc. may be used.

Examples of the halogen as the substituent for $R^1$ include fluorine, chlorine, bromine, iodine, etc., and in particular, fluorine and chlorine are preferable.

Examples of the alkyl in the optionally substituted alkyl as the substituent for $R^1$ include straight or branched alkyl having a carbon number of 1 to 10, for example $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl. Examples of the substituent in the optionally substituted alkyl include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.)), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of the substituents is preferably 1 to 3.

Examples of the cycloalkyl in the optionally substituted cycloalkyl as the substituent for $R^1$ include $C_{3-7}$cycloalkyl such as cyclopropyl, cyclobutyl, cyclopentyl, cyclohexyl, cycloheptyl, etc. Examples of the substituent in the optionally substituted cycloalkyl include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of the substituents is preferably 1 to 3.

Examples of the substituent in the optionally substituted hydroxy group as the substituent for $R^1$ include:

(1) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.

(2) an optionally substituted cycloalkyl which may have a heteroatom (e.g., $C_{3-7}$cycloalkyl such as cyclopropyl, cyclobutyl, cyclopentyl, cyclohexyl, cycloheptyl, etc.; saturated 5- or 6-membered heterocyclic group containing 1 to 2 heteroatoms such as tetrahydrofuranyl, tetrahydrothienyl, pyrrolidinyl, pyrazolidinyl, piperidyl, piperazinyl, morpholinyl, thiomorpholinyl, tetrahydropyranyl, tetrahydrothiopyranyl, etc. (preferably tetrahydropyranyl, etc.); etc.);

(3) an optionally substituted alkenyl (e.g., $C_{2-10}$alkenyl such as allyl, crotyl, 2-pentenyl, 3-hexenyl, etc., preferably lower ($C_{2-6}$) alkenyl, etc.);

(4) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.);

(5) an optionally substituted aralkyl (e.g., phenyl-$C_{1-4}$ alkyl (e.g., benzyl, phenethyl, etc.) and the like.);

(6) formyl or an optionally substituted acyl (e.g., $C_{2-4}$alkanoyl (e.g., acetyl, propionyl, butyryl, isobutyryl, etc.), $C_{1-4}$alkylsulfonyl (e.g., methanesulfonyl, ethanesulfonyl, etc.) and the like.); and (7) an optionally substituted aryl (e.g., phenyl, naphthyl, etc.) and the like.

Examples of the substituent that the above mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl, and (7) optionally substituted aryl may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.), etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-6}$alkoxy (e.g., methoxy, ethoxy, propoxy, butoxy, trifluoromethoxy, trifluoroethoxy, etc.; preferably an optionally halogenated $C_{1-4}$alkoxy), formyl, $C_{2-4}$alkanoyl (e.g., acetyl, propionyl, etc.), $C_{1-4}$alkylsulfonyl (e.g., methanesulfonyl, ethanesulfonyl, etc.), an optionally substituted 5- or 6-membered aromatic heterocyclic ring [for example, 5- or 6-membered aromatic heterocyclic ring containing 1 to 4 hetero-atoms consisting of 1 or 2 kinds of hetero-atoms selected from nitrogen atom, sulfur atom and oxygen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; examples of the substituent that heterocyclic ring may have include halogen (e.g., fluorine, chlorine, bromine, iodine, etc.), nitro, cyano, hydroxy group, thiol group, amino group, carboxyl group, an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like, and the number of the substituents is preferably 1 to 3.]. The number of substituents is preferably 1 to 3.

Examples of the substituents in the optionally substituted thiol group as the substituent for $R^1$ include those similar to the above-exemplified "substituent in the optionally substituted hydroxy group as the substituent for $R^1$", and among them, (1) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(2) an optionally substituted cycloalkyl (e.g., $C_{3-7}$cycloalkyl such as cyclopropyl, cyclobutyl, cyclopentyl, cyclohexyl, cycloheptyl, etc.);

(3) an optionally substituted aralkyl (e.g., phenyl-$C_{1-4}$alkyl (e.g., benzyl, phenethyl, etc.) and the like.); and (4) an optionally substituted aryl (e.g., phenyl, naphthyl, etc.) and the like are preferable.

Examples of the substituents that the above-mentioned (1) optionally substituted alkyl, (2) optionally substituted cycloalkyl, (3) optionally substituted aralkyl, and (4) optionally substituted aryl may have include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the substituents in the optionally substituted amino group as the substituent of $R^1$ include the amino group that may have 1 to 2 substituents similar to the above-mentioned "substituent in the optionally substituted hydroxy group as the substituent of $R^1$" etc., and among them, (1) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(2) an optionally substituted cycloalkyl (e.g., $C_{3-7}$cycloalkyl, etc. such as cyclopropyl, cyclobutyl, cyclopentyl, cyclohexyl, cycloheptyl, etc.);

(3) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(4) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.);

(5) formyl or an optionally substituted acyl (e.g., $C_{2-4}$alkanoyl (e.g., acetyl, propionyl, butyryl, isobutyryl, etc.), $C_{1-4}$alkylsulfonyl (e.g., methanesulfonyl, ethanesulfonyl, etc.) and the like.); and (6) an optionally substituted aryl (e.g., phenyl, naphthyl, etc.) and the like are preferable.

Examples of the substituents that the above mentioned (1) optionally substituted alkyl, (2) optionally substituted cycloalkyl, (3) optionally substituted alkenyl, (4) optionally substituted cycloalkenyl, (5) optionally substituted acyl, and (6) optionally substituted aryl may have include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

In addition, the optionally substituted amino group as the substituent of $R^1$ may form a cyclic amino group (e.g., 5- or 6-membered cyclic amino such as tetrahydropyrrole, piperazine, piperidine, morpholine, thiomorpholine, pyrrole, imidazole, etc.) by binding the substituents of an amino group to each other. The cyclic amino group may have a substituent, and examples of such substituents include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the optionally substituted acyl group as a substituent of $R^1$ include a group formed by binding:

(1) hydrogen;

(2) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(3) an optionally substituted cycloalkyl (e.g., $C_{3-7}$cycloalkyl such as cyclopropyl, cyclobutyl, cyclopentyl, cyclohexyl, cycloheptyl, etc.);

(4) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(5) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.);

(6) an optionally substituted 5- or 6-membered monocyclic aromatic group (e.g., phenyl, 5- or 6-membered aromatic heterocyclic group (e.g., 5- or 6-membered aromatic heterocyclic group containing 1 to 4 hetero-atoms consisting of 1 or 2 kinds of hetero-atoms selected from nitrogen atom, sulfur atom and oxygen atom, such as furyl, thienyl, pyrrolyl, imidazolyl, pyrazolyl, thiazolyl, oxazolyl, isothiazolyl, isoxazolyl, tetrazolyl, pyridyl, pyrazinyl, pyrimidinyl, pyridazinyl, triazolyl, etc.; preferably pyridyl, thienyl, etc.); and (7) an optionally substituted 5- or 6-membered monocyclic non-aromatic heterocyclic group (e.g., a group formed by eliminating a hydrogen atom from 5- or 6-membered monocyclic non-aromatic heterocyclic ring containing 1 to 4 hetero-atoms consisting of 1 or 2 kinds of hetero-atoms selected from nitrogen atom, sulfur atom and oxygen atom, such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; preferably, dioxolanyl, etc.), etc., to a carbonyl group or a sulfonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl, etc.), etc. Examples of the substituents that the above-mentioned (2) optionally substituted alkyl, (3) optionally substituted cycloalkyl, (4) optionally substituted alkenyl, (5) optionally substituted cycloalkenyl, (6) optionally substituted 5- or 6-membered monocyclic aromatic group and (7) optionally substituted 5- or 6-membered monocyclic non-aromatic heterocyclic group may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), $C_{1-4}$alkylenedioxy (e.g., —O—$CH_2$—O—, —O—$CH_2$—$CH_2$—O—, etc.), an optionally substituted sulfonamide [for example, a group formed by bonding an optionally substituted amino group (e.g., amino, mono$C_{1-4}$alkylamino, di$C_{1-4}$alkylamino, 5- or 6-membered cyclic amino (e.g., tetrahydropyrrole, piperazine, piperidine, morpholine, thiomorpholine, pyrrole, imidazole, etc.), etc.) to —$SO_2$—, etc.], formyl, $C_{2-4}$alkanoyl (e.g., acetyl, propionyl, etc.), $C_{1-4}$alkylsulfonyl (e.g., methanesulfonyl, ethanesulfonyl, etc.), etc. The number of substituents is preferably 1 to 3.

Examples of the optionally esterified carboxyl group as the substituent of $R^1$ include a group formed by binding:

(1) hydrogen;

(2) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(3) an optionally substituted cycloalkyl (e.g., $C_{3-7}$cycloalkyl such as cyclopropyl, cyclobutyl, cyclopentyl, cyclohexyl, cycloheptyl, etc.);

(4) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(5) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.); and (6) an optionally substituted aryl (e.g., phenyl, naphthyl, etc.) and the like, to a carbonyloxy group, preferably carboxyl, lower ($C_{1-6}$) alkoxycarbonyl, aryloxycarbonyl (e.g., methoxycarbonyl, ethoxycarbonyl, propoxycarbonyl, phenoxycarbonyl, naphthoxycarbonyl, etc.), etc. Examples of the substituents that the above-mentioned (2) optionally substituted alkyl, (3) optionally substituted cycloalkyl, (4) optionally substituted alkenyl, (5) optionally substituted cycloalkenyl, and (6) optionally substituted aryl may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of the substituents is preferably 1 to 3.

In addition, examples of the optionally amidated carboxyl group as a substituent of $R^1$ include a group formed by binding "an optionally substituted amino group" to a carbonyl group, similar to the above mentioned "optionally substituted amino group as the substituent for $R^1$", preferably carbamoyl, mono$C_{1-6}$alkylcarbamoyl, di$C_{1-6}$alkylcarbamoyl, etc.

Examples of the aromatic groups in the optionally substituted aromatic group as a substituent of $R^1$ include 5- or 6-membered homocyclic or heterocyclic aromatic group such as phenyl, pyridyl, furyl, thienyl, pyrrolyl, imidazolyl, pyrazolyl, thiazolyl, oxazolyl, isothiazolyl, isoxazolyl, tetrazolyl, pyrazinyl, pyrimidinyl, pyridazinyl, triazolyl, oxadiazolyl, thiadiazolyl, etc. and condensed heterocyclic aromatic group such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc. Examples of the substituents for these aromatic groups include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$ alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

The same or different 1 to 4 (preferably 1 or 2) of these substituents for $R^1$ may substitute at any possible position on the ring.

In addition, when the group represented by R binds to the 5- or 6-membered aromatic ring to form a ring, the group represented by the formula R—$Z^1$—$X^1$—$Z^2$— (wherein, each symbol has the same meaning as defined in the above; R is preferably hydrogen) forms a divalent group such as lower ($C_{1-6}$) alkylenedioxy (e.g., —O—$CH_2$—O—, —O—$CH_2$—$CH_2$—O—, —O—$CH_2$—$CH_2$—$CH_2$—O—, etc.), oxy lower ($C_{1-6}$)alkyleneamino (e.g., —O—$CH_2$—NH—, —O—$CH_2$—$CH_2$—NH—, etc.), oxy lower ($C_{1-6}$) alkylenethio (e.g., —O—$CH_2$—S—, —O—$CH_2$—$CH_2$—S—, etc.), lower ($C_{1-6}$)alkylenediamino (e.g., —NH—$CH_2$—NH—, —NH—$CH_2$—$CH_2$—NH—, etc.), thia lower ($C_{1-6}$)alkyleneamino (e.g., —S—$CH_2$—NH—, —S—$CH_2$—$CH_2$—NH—, etc.), etc.

As the "substituent" that "5- or 6-membered ring" of the "5- or 6-membered aromatic ring which has a substituent represented by the formula R—$Z^1$—$X^1$—$Z^2$— (wherein, each symbol has the same meaning as defined in the above) and may have a further substituent" represented by $R^1$ may have in addition to the group represented by the formula R—$Z^1$—$X^1$—$Z^2$—, in particular, an optionally halogenated or lower ($C_{1-4}$)alkoxylated lower ($C_{1-4}$) alkyl (e.g., methyl, ethyl, t-butyl, trifluoromethyl, methoxymethyl, ethoxymethyl, propoxymethyl, butoxymethyl, methoxyethyl, ethoxyethyl, propoxyethyl, butoxyethyl, etc.), an optionally halogenated or lower ($C_{1-4}$)alkoxylated lower ($C_{1-4}$)alkoxy (e.g., methoxy, ethoxy, propoxy, butoxy, t-butoxy, trifluoromethoxy, methoxymethoxy, ethoxymethoxy, propoxymethoxy, butoxymethoxy, methoxyethoxy, ethoxyethoxy, propoxyethoxy, butoxyethoxy, methoxypropoxy, ethoxypropoxy, propoxypropoxy, butoxypropoxy, etc.), halogen (e.g., fluorine, chlorine, etc.), nitro, cyano, an amino optionally substituted with 1 to 2 lower ($C_{1-4}$)alkyls, formyl or lower ($C_{2-4}$)alkanoyl (e.g., amino, methylamino, dimethylamino, formylamino, acetylamino, etc.), 5- or 6-membered cyclic amino (e.g., 1-pyrrolidinyl, 1-piperadinyl, 1-piperidinyl, 4-morpholino, 4-thiomorpholino, 1-imidazolyl, 4-tetrahydropyranyl, etc.) and the like are exemplified.

In addition, when $R^1$ is benzene, the substitution position of the group represented by the formula: R—$Z^1$—$X^1$—$Z^2$— is preferably at the para position and the substitution position of the "substituent" which the "5- or 6-membered aromatic ring" may have in addition to the group represented by the formula: R—$Z^1$—$X^1$—$Z^2$—, is preferably at the meta position.

In the above formula, examples of the "optionally substituted imino group" represented by Y include a divalent group represented by the formula —N($R^5$)— [wherein, $R^5$ is a hydrogen atom or a substituent], etc.

$R^5$ is, preferably, a hydrogen atom, an optionally substituted hydrocarbon group, an optionally substituted heterocyclic group, an optionally substituted hydroxy group, an optionally substituted thiol group (the sulfur atom may be optionally oxidized, or may form an optionally substituted sulfinyl group or an optionally substituted sulfonyl group), an optionally substituted amino group, an optionally esterified or amidated carboxyl group, an optionally substituted acyl group, etc., and more preferably a hydrogen atom, an optionally substituted hydrocarbon group, an optionally substituted 5- or 6-membered aromatic heterocyclic group, an optionally substituted acyl group, etc.

As a preferred form of $R^5$, a hydrogen atom, an optionally substituted hydrocarbon group, an optionally substituted 5- or 6-membered aromatic heterocyclic group, an optionally substituted acyl group, etc. are exemplified, and $C_{1-4}$alkyl, $C_{1-4}$alkylsulfonyl, formyl, $C_{2-5}$alkanoyl, etc. are more preferred, $C_{1-4}$alkyl, formyl, $C_{2-5}$alkanoyl, etc. are further more preferred, and, in particular, propyl, cyclopropylmethyl or isobutyl is preferred. Other preferred examples of $R^5$ include a group represented by the formula: —$(CH_2)_k$—$R^6$ [wherein, k is 0 or 1, $R^6$ is an optionally substituted 5- or 6-membered monocyclic aromatic group (e.g., the same groups as those of the "(6) optionally substituted 5- or 6-membered monocyclic aromatic group" exemplified with respect to the optionally substituted acyl group as the substituent for $R^1$, etc.; preferably phenyl, pyrazolyl, thiazolyl, oxazolyl and tetrazolyl, each of which may be substituted with a halogen, an optionally halogenated $C_{1-4}$alkyl or an optionally halogenated $C_{1-4}$alkoxy, etc.)], etc.

In addition, specific examples of the "optionally substituted hydrocarbon group" as $R^5$ include those similar to the "optionally substituted hydrocarbon group" as R, and specific examples of the "optionally substituted heterocyclic group" as $R^5$ include those similar to the "optionally substituted heterocyclic group" as the substituent for the "optionally substituted hydrocarbon group" represented by R, and specific examples of the "optionally substituted hydroxy group", "optionally substituted thiol group", "optionally substituted amino group", "optionally esterified or amidated carboxyl group" and "optionally substituted acyl group" as $R^5$, include those similar to the "optionally substituted hydroxy group", "optionally substituted thiol group", "optionally substituted amino group", "optionally esterified or amidated carboxyl group" and "optionally substituted acyl group" as the substituent for $R^1$.

In the above formula (I), examples of the lower alkyl group of the "optionally substituted lower alkyl group" represented by $R^2$ include $C_{1-6}$alkyl such as methyl, ethyl, propyl, isopropyl, butyl, isobutyl, sec-butyl, tert-butyl, pentyl, isopentyl, neopentyl, hexyl, etc.

In the above formula (I), examples of the lower alkoxy group of the "optionally substituted lower alkoxy group" represented by $R^2$ include $C_{1-6}$alkoxy such as methoxy, ethoxy, propoxy, butoxy, etc.

Examples of the substituents that the "optionally substituted lower alkyl group" and "optionally substituted lower alkoxy group" may have, include halogen (e.g., fluorine, chlorine, bromine, iodine), hydroxy group, amino, mono (lower alkyl)amino, di(lower alkyl)amino, lower alkanoyl, etc.

Examples of the lower alkyl in the mono(lower alkyl)amino and di(lower alkyl)amino include those similar to the lower alkyl group of the "optionally substituted lower alkyl group" represented by the above $R^2$.

Examples of the lower alkanoyl include $C_{2-6}$alkanoyl such as acetyl, propionyl, butyryl, isobutyryl, etc.

In the above formula (I), examples of the "halogen atom" represented by $R^2$ include fluorine, chlorine, bromine, iodine, etc.

As $R^2$, among them, an optionally substituted lower $C_{1-6}$alkyl group and a halogen atom are preferred, and in particular, an optionally substituted methyl group and a halogen atom are preferred.

In the above formula (I), examples of the "aromatic ring" of "optionally further substituted aromatic ring" represented by ring A and ring B include 6-membered aromatic hydrocarbon such as benzene, etc., 5- or 6-membered aromatic heterocyclic ring containing 1 to 4 hetero-atoms consisting of 1 or 2 kinds of hetero-atoms selected from nitrogen atom, sulfur atom and oxygen atom such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc., or condensed aromatic heterocycle such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc. As ring A, among these, benzene, furan, thiophene, pyridine, pyridazine, benzimidazole, etc. are preferred, and benzene, pyridine, pyridazine, benzimidazole, etc., are more preferred, and in particular, benzene is preferred. As ring B, a nitrogen-containing aromatic heterocyclic ring such as imidazole, triazole, tetrazole, pyridine, imidazopyridine, etc. are preferred, and imidazole, triazole, pyridine, imidazopyridine, etc. are more preferred, and in particular, imidazole and triazole are preferred.

Examples of the "substituent" that the "aromatic ring" of the "optionally further substituted aromatic ring" represented by ring A and ring B may have, include halogen atom, nitro, cyano, an optionally substituted alkyl, an optionally substituted cycloalkyl, an optionally substituted hydroxy group, an optionally substituted thiol group (the sulfur atom may be oxidized, and may form an optionally substituted sulfinyl group or an optionally substituted sulfonyl group), an optionally substituted amino group, an optionally substituted acyl group, an optionally esterified carboxyl group, an optionally substituted aromatic group, etc.

Examples of the halogen as the substituent include fluorine, chlorine, bromine, iodine, etc., and preferably, fluorine and chlorine.

Examples of the alkyl in the optionally substituted alkyl as the "substituent" of ring A and ring B include straight or branched alkyl having 1 to 10 carbons, for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$)alkyl. Examples of the substituents in the optionally substituted alkyl include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as pyrrolidine, piperazine, piperidine, morpholine, thiomorpholine, pyrrole, imidazole, etc., etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the cycloalkyl in the optionally substituted cycloalkyl as the substituent of ring A and ring B include. $C_{3-7}$cycloalkyl such as cyclopropyl, cyclobutyl, cyclopentyl, cyclohexyl, cycloheptyl, etc. Examples of the substituents in the optionally substituted cycloalkyl include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the substituents in the optionally substituted hydroxy group as the substituent for ring A and ring B include:

(1) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(2) an optionally substituted cycloalkyl which may have a heteroatom (e.g., $C_{3-7}$cycloalkyl such as cyclopropyl, cyclobutyl, cyclopentyl, cyclohexyl, cycloheptyl, etc.; saturated 5- or 6-membered heterocyclic group containing 1 to 2 heteroatoms such as tetrahydrofuranyl, tetrahydrothienyl, pyrrolidinyl, pyrazolidinyl, piperidyl, piperazinyl, morpholinyl, thiomorpholinyl, tetrahydropyranyl, tetrahydrothiopyranyl, etc. (preferably, tetrahydropyranyl, etc.); etc.);

(3) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(4) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.);

(5) an optionally substituted aralkyl (e.g., phenyl-$C_{1-4}$alkyl (e.g., benzyl, phenethyl, etc.) and the like.);

(6) formyl or an optionally substituted acyl (e.g., $C_{2-4}$alkanoyl (e.g., acetyl, propionyl, butyryl, isobutyryl, etc.), $C_{1-4}$alkylsulfonyl (e.g., methanesulfonyl, ethanesulfonyl, etc.) and the like.); and (7) an optionally substituted aryl (e.g., phenyl, naphthyl, etc.) and the like.

Examples of the substituents that the above mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl, and (7) optionally substituted aryl may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_4$ alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-6}$alkoxy (e.g., methoxy, ethoxy, propoxy, butoxy, trifluoromethoxy, trifluoroethoxy, etc.; preferably an optionally halogenated $C_{1-4}$alkoxy), formyl, $C_{2-4}$alkanoyl (e.g., acetyl, propionyl, etc.), $C_{1-4}$alkylsulfonyl (e.g., methanesulfonyl, ethanesulfonyl, etc.), an optionally substituted 5- or 6-membered aromatic heterocyclic ring [for example, 5- or 6-membered aromatic heterocyclic ring containing 1 to 4 hetero-atoms consisting of 1 or 2 kinds of hetero-atoms selected from nitrogen atom, sulfur atom and oxygen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; examples of the substituent that the heterocyclic ring may have, include halogen (e.g., fluorine, chlorine, bromine, iodine, etc.), nitro, cyano, hydroxy group, thiol group, amino group, carboxyl group, an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like and the number of the substituents is preferably 1 to 3.], etc. The number of substituents is preferably 1 to 3.

Examples of the substituents in the optionally substituted thiol group as the substituent of ring A and ring B include those similar to the above-mentioned "substituent in the optionally substituted hydroxy group as the substituent of ring A and ring B", and among them, (1) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(2) an optionally substituted cycloalkyl (e.g., $C_{3-7}$cycloalkyl such as cyclopropyl, cyclobutyl, cyclopentyl, cyclohexyl, cycloheptyl, etc.);

(3) an optionally substituted aralkyl (e.g., phenyl-$C_{1-4}$alkyl (e.g., benzyl, phenethyl, etc.) and the like.); and (4) an optionally substituted aryl (e.g., phenyl, naphthyl, etc.) and the like are preferred.

Examples of the substituent that the above mentioned (1) optionally substituted alkyl, (2) optionally substituted cycloalkyl, (3) optionally substituted aralkyl, and (4) optionally substituted aryl may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the substituent for the optionally substituted amino group as the substituent of ring A and ring B include an amino group optionally having 1 to 2 substituents similar to those of the above-mentioned "substituent in optionally substituted hydroxy group as the substituent of ring A and ring B", and among them, (1) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(2) an optionally substituted cycloalkyl (e.g., $C_{3-7}$cycloalkyl such as cyclopropyl, cyclobutyl, cyclopentyl, cyclohexyl, cycloheptyl, etc.);

(3) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(4) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.);

(5) formyl or an optionally substituted acyl (e.g., $C_{2-4}$alkanoyl (e.g., acetyl, propionyl, butyryl, isobutyryl, etc.), $C_{1-4}$alkylsulfonyl (e.g., methanesulfonyl, ethanesulfonyl, etc.) and the like; and (6) an optionally substituted aryl (e.g., phenyl, naphthyl, etc.) and the like, are preferred.

Examples of the substituents that the above mentioned (1) optionally substituted alkyl, (2) optionally substituted cycloalkyl, (3) optionally substituted alkenyl, (4) optionally substituted cycloalkenyl, (5) optionally substituted acyl, and (6) optionally substituted aryl may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

In addition, the optionally substituted amino group as the substituent of ring A and ring B may form a cyclic amino group by binding the substituents for amino group to each other (e.g., a cyclic amino group which has a bond on the nitrogen atom and is formed by eliminating one hydrogen atom from ring-constituting nitrogen of 5- or 6-membered ring such as tetrahydropyrrole, piperazine, piperidine, morpholine, thiomorpholine, pyrrole, imidazole, etc.). The cyclic amino group may have a substituent, and the examples of such substituents include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy(e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of the substituents is preferably 1 to 3.

Examples of the optionally substituted acyl group as the substituent for ring A and ring B include a group formed by binding:

(1) hydrogen;

(2) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(3) an optionally substituted cycloalkyl (e.g., $C_{3-7}$cycloalkyl such as cyclopropyl, cyclobutyl, cyclopentyl, cyclohexyl, cycloheptyl, etc.);

(4) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(5) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.); and (6) an optionally substituted 5- or 6-membered monocyclic aromatic group (e.g., phenyl, pyridyl, etc.) and the like, to carbonyl group or sulfonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl, etc.). Examples of the substituents that the above-mentioned (2) optionally substituted alkyl, (3) optionally substituted cycloalkyl, (4) optionally substituted alkenyl, (5) optionally substituted cycloalkenyl, and (6) optionally substituted 5- or 6-membered monocyclic aromatic group may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the optionally esterified carboxyl group as the substituent for ring A and ring B include a group formed by bindig:

(1) hydrogen;

(2) an optionally substituted alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.);

(3) an optionally substituted cycloalkyl (e.g., $C_{3-7}$cycloalkyl such as cyclopropyl, cyclobutyl, cyclopentyl, cyclohexyl, cycloheptyl, etc.);

(4) an optionally substituted alkenyl (e.g., $C_{2-10}$alkenyl such as allyl, crotyl, 2-pentenyl, 3-hexenyl, etc., preferably lower ($C_{2-6}$)alkenyl, etc.);

(5) an optionally substituted cycloalkenyl (e.g., $C_{3-7}$cycloalkenyl such as 2-cyclopentenyl, 2-cyclohexenyl, 2-cyclopentenylmethyl, 2-cyclohexenylmethyl, etc.); and (6) an optionally substituted aryl (e.g., phenyl, naphthyl, etc.) and the like, to carbonyloxy group, preferably carboxyl, lower ($C_{1-6}$)alkoxycarbonyl, aryloxycarbonyl (e.g., methoxycarbonyl, ethoxycarbonyl, propoxycarbonyl, phenoxycarbonyl, naphtoxycarbonyl, etc.) and the like. Examples of the substituents that the above-mentioned (2) optionally substituted alkyl, (3) optionally substituted cycloalkyl, (4) optionally substituted alkenyl, (5) optionally substituted cycloalkenyl, and (6) optionally substituted aryl may have, include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkoxy (e.g., methoxy, ethoxy, propoxy, butoxy, trifluoromethoxy, trifluoroethoxy, etc.), an optionally halogenated $C_{1-4}$alkoxy-$C_{1-4}$alkoxy (e.g., methoxymethoxy, methoxyethoxy, ethoxyethoxy, trifluoromethoxyethoxy, trifluoroethoxyethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

Examples of the aromatic group in the optionally substituted aromatic group as the substituent for ring A and ring B include 5- or 6-membered homocyclic or heterocyclic aromatic group such as phenyl, pyridyl, furyl, thienyl, pyrrolyl, imidazolyl, pyrazolyl, thiazolyl, oxazolyl, isothiazolyl, isoxazolyl, tetrazolyl, pyrazinyl, pyrimidinyl, pyridazinyl, triazolyl, etc., and condensed heterocyclic aromatic group such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc. Examples of substituents of these aromatic groups include halogen (e.g., fluorine, chlorine, bromine, iodine, etc.), nitro, cyano, hydroxy group, an optionally substituted thiol group (e.g., thiol, $C_{1-4}$alkylthio, etc.), an optionally substituted amino group (e.g., amino, mono$C_{1-4}$alkylamino, di$C_{1-4}$alkylamino, 5- or 6-membered cyclic amino such as tetrahydropyrrole, piperazine, piperidine, morpholine, thiomorpholine, pyrrole, imidazole, etc.), an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, etc.), an optionally halogenated $C_{1-4}$alkyl (e.g., trifluoromethyl, methyl, ethyl, etc.), an optionally halogenated $C_{1-4}$alkoxy (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.) and the like. The number of substituents is preferably 1 to 3.

The same or different 1 to 4 (preferably 1 to 2) substituents for ring A and ring B may substitute at any possible position on the ring. In addition, when "aromatic ring" in the "further optionally substituted aromatic ring" represented by ring A or "aromatic ring" in the "further optionally substituted aromatic ring" represented by ring B have a further 2 or more substituents, two of the substituents may bind together to form a group such as lower ($C_{1-6}$)alkylene (e.g., trimethylene, tetramethylene, etc.), lower ($C_{1-6}$)alkyleneoxy (e.g., —$CH_2$—O—$CH_2$—, —O—$CH_2$—$CH_2$—, —O—$CH_2$—$CH_2$—$CH_2$—, —O—$CH_2$—$CH_2$—$CH_2$—$CH_2$—, —O—C($CH_3$)($CH_3$)—$CH_2$—$CH_2$—, etc.), lower ($C_{1-6}$)alkylenethio (e.g., —$CH_2$—S—$CH_2$—, —S—$CH_2$—$CH_2$—, —S—$CH_2$—$CH_2$—$CH_2$—, —S—$CH_2$—$CH_2$—$CH_2$—$CH_2$—, —S—C($CH_3$)($CH_3$)—$CH_2$—$CH_2$—, etc.), lower ($C_{1-6}$)alkylenedioxy (e.g., —O—$CH_2$—O—, —O—$CH_2$—$CH_2$—O—, —O—$CH_2$—$CH_2$—$CH_2$—O—, etc.), lower ($C_{1-6}$)alkylenedithio (e.g., —S—$CH_2$—S—, —S—$CH_2$—$CH_2$—S—, —S—$CH_2$—$CH_2$—$CH_2$—S—, etc.), oxy lower ($C_{1-6}$)alkyleneamino (e.g., —O—$CH_2$—NH—, —O—$CH_2$—$CH_2$—NH—, etc.), oxy lower ($C_{1-6}$) alkylenethio (e.g., —O—$CH_2$—S—, —O—$CH_2$—$CH_2$—S—, etc.), lower ($C_{1-6}$) alkyleneamino (e.g., —NH—$CH_2$—$CH_2$—, —NH—$CH_2$—$CH_2$—$CH_2$—, etc.), lower ($C_{1-6}$) alkylenediamino (e.g., —NH—$CH_2$—NH—, —NH—$CH_2$—$CH_2$—NH—, etc.), thia lower ($C_{1-6}$)alkyleneamino (e.g., —S—$CH_2$—NH—, —S—$CH_2$—$CH_2$—NH—, etc.), lower ($C_{2-6}$)alkenylene (e.g., —$CH_2$—CH=CH—, —$CH_2$—$CH_2$—CH=CH—, —$CH_2$—CH=CH—$CH_2$—, etc.), lower ($C_{4-6}$)alkadienylene (e.g., —CH=CH—CH=CH—, etc.) and the like.

Furthermore, the divalent group formed by binding 2 substituents for ring A to each other and the divalent group formed by binding 2 substituents for ring B to each other may have 1 to 3 substituents similar to those of the "substituent" that "aromatic ring" in the "further optionally substituted aromatic ring" represented by ring A and ring B may have (a halogen atom, nitro, cyano, an optionally substituted alkyl, an optionally substituted cycloalkyl, an optionally substituted hydroxy group, an optionally substituted thiol group (the sulfur atom may be optionally oxidized, and may form an optionally substituted sulfinyl group or an optionally substituted sulfonyl group), an optionally substituted amino group, an optionally substituted acyl group, an optionally esterified or amidated carboxyl group, an optionally substituted aromatic group, etc.).

The "substituent" that "aromatic ring" in the "further optionally substituted aromatic ring" represented by ring A and ring B may have, includes, in particular, halogen atom, cyano, hydroxy group, nitro, an optionally esterified or amidated carboxyl group (e.g., carboxyl, $C_{1-4}$alkoxycarbonyl, carbamoyl, mono$C_{1-4}$alkylcarbamoyl, di$C_{1-4}$alkylcarbamoyl, pyrrolidinocarbonyl, piperidinocarbonyl, morpholinocarbonyl, thiomorpholinocarbonyl, etc.), an optionally halogenated or lower ($C_{1-4}$) alkoxylated lower ($C_{1-4}$) alkyl (e.g., methyl, ethyl, t-butyl, trifluoromethyl, methoxymethyl, ethoxymethyl, propoxymethyl, butoxymethyl, methoxyethyl, ethoxyethyl, propoxyethyl, butoxyethyl, etc.), lower ($C_{1-4}$)alkyl optionally substituted with hydroxy group or cyano group (e.g., hydroxy$C_{1-4}$ alkyl, cyano$C_{1-4}$alkyl, etc.), lower ($C_{1-4}$)alkyl optionally substituted with a optionally esterified or amidated carboxyl group (e.g., carboxyl$C_{1-4}$alkyl, $C_{1-4}$alkoxycarbonyl$C_{1-4}$ alkyl, carbamoyl$C_{1-4}$alkyl, mono$C_{1-4}$alkylcarbamoyl$C_{1-4}$ alkyl, di$C_{1-4}$alkylcarbamoyl$C_{1-4}$alkyl, pyrrolidinocarbonyl$C_{1-4}$alkyl, piperidinocarbonyl$C_{1-4}$alkyl, morpholinocarbonyl$C_{1-4}$alkyl, thiomorpholinocarbonyl$C_{1-4}$alkyl, etc.), an optionally halogenated or lower ($C_{1-4}$)alkoxylated lower ($C_{1-4}$)alkoxy (e.g., methoxy, ethoxy, propoxy, butoxy, t-butoxy, trifluoromethoxy, methoxymethoxy, ethoxymethoxy, propoxymethoxy, butoxymethoxy, methoxyethoxy, ethoxyethoxy, propoxyethoxy, butoxyethoxy, methoxypropoxy, ethoxypropoxy, propoxypropoxy, butoxypropoxy, etc.), halogen (e.g., fluorine, chlorine, etc.), nitro, cyano, amino optionally substituted with 1 to 2 lower ($C_{1-4}$)alkyl, formyl or lower ($C_{2-4}$)alkanoyl (e.g., amino, methylamino, dimethylamino, formylamino, acetylamino, etc.), 5- or 6-membered cyclic amino group (e.g., 1-pyrrolidinyl, 1-piperazinyl, 1-piperidinyl, 4-morpholino, 4-thiomorpholino, 1-imidazolyl, 4-tetrahydropyranyl, etc.) and the like. As the substituent for ring A, among them, an optionally halogenated lower ($C_{1-4}$)alkyl is preferred, and as the substituent for ring B, among them, an optionally substituted lower ($C_{1-4}$)alkyl is preferred.

In the above formula (I), examples of the divalent group represented by W include a group of the formula —$W^1$—$X^2$—$W^2$ ($W^1$ and $W^2$ are independently 0.0, S(O)$_{m1}$ (m1 is 0, 1 or 2), an optionally substituted imino group (—N($R^3$)—) or a bond, and $X^2$ is an optionally substituted alkylene group, an optionally substituted alkenylene group or a binding site), and the bonding position of $W^1$ may be at any position, but preferably at para position, when ring A is, for example, a benzene ring. Examples of the substituents ($R^3$) for the optionally substituted imino group represented by $W^1$ and $W^2$ include a hydrogen atom, an optionally substituted lower ($C_{1-6}$)alkyl [for example, methyl, ethyl, propyl, isopropyl, butyl, isobutyl, sec-butyl, tert-butyl, pentyl, isopentyl, neopentyl, hexyl, hydroxy$C_{1-6}$alkyl (e.g., hydroxyethyl, hydroxypropyl, hydroxybutyl, etc.), halogenated $C_{1-6}$alkyl (e.g., trifluoromethyl, trifluoroethyl, etc.), cyanated $C_{1-6}$alkyl (e.g., cyanoethyl, cyanopropyl, etc.), an optionally esterified or amidated carboxyl$C_{1-6}$alkyl, etc.], formyl, lower ($C_{2-5}$)alkanoyl (e.g., acetyl, propionyl, butyryl, etc.), lower ($C_{1-5}$)alkylsulfonyl(methylsulfonyl, ethylsulfonyl, etc.) and the like.

Examples of the alkylene group of the "optionally substituted alkylene group" represented by $X^2$ include an alkylene chain represented by —($CH_2$)$_{k1}$— (k1 is an integer of 1 to 4), etc. Examples of the alkenylene group of the "optionally substituted alkenylene group" represented by $X^2$ include an alkenylene chain represented by —($CH_2$)$_{k2}$—(CH=CH)—($CH_2$)$_{k3}$— (k2 and k3 are the same or different, and 0, 1 or 2, provided that the sum of k2 and k3 is 2 or less), etc. The alkylene group and the alkenylene group represented by $X^2$ may have a substituent at any position (preferably on carbon atom), and examples of such substituents include any one that may bind to the alkylene chain or alkenylene chain constituting the straight chain moiety, and for example, lower ($C_{1-6}$)alkyl (e.g., methyl, ethyl, propyl, isopropyl, butyl, isobutyl, sec-butyl, pentyl, isopentyl, neopentyl, hexyl, etc.), lower ($C_{3-7}$)cycloalkyl (e.g., cyclopropyl, cyclobutyl, cyclopentyl, cyclohexyl, cycloheptyl, etc.), formyl, lower ($C_{2-7}$)alkanoyl (e.g., acetyl, propionyl, butyryl, etc.), an optionally esterified phosphono group, an optionally esterified or amidated carboxyl group (e.g., carboxyl, $C_{1-4}$alkoxycarbonyl, carbamoyl, mono$C_{1-4}$ alkylcarbamoyl, di$C_{1-4}$alkylcarbamoyl, etc.), hydroxy group, oxo, a hydroxyimino group, an optionally substituted lower ($C_{1-6}$)alkoxyimino group, etc., and preferably, lower ($C_{1-6}$) alkyl (preferably, $C_{1-3}$alkyl), hydroxy group, oxo, hydroxyimino group, and lower ($C_{1-6}$)alkoxyimino group (optionally substituted with polar group such as hydroxy group, cyano group, an optionally esterified or amidated carboxyl group, etc.) and the like.

Examples of the optionally esterified phosphono group include a group represented by —P(O) (OR$^{7b}$) (OR$^{8b}$) [wherein, R$^{7b}$ and R$^{8b}$ are independently hydrogen, $C_{1-6}$alkyl group or $C_{3-7}$cycloalkyl group, or R$^{7b}$ and R$^{8b}$ may be bound together to form a 5- to 7-membered ring].

In the above formula, examples of the $C_{1-6}$alkyl group represented by R$^{7b}$ and R$^{8b}$ include methyl, ethyl, propyl, isopropyl, butyl, isobutyl, sec-butyl, tert-butyl, pentyl, isopentyl, neopentyl, hexyl etc., and examples of the $C_{3-7}$cycloalkyl include cyclopropyl, cyclobutyl, cyclopentyl, cyclohexyl, cycloheptyl, etc., and preferably, straight $C_{1-6}$lower alkyl, and more preferably $C_{1-3}$lower alkyl. R$^{7b}$ and R$^{8b}$ may be the same or different, but preferably the same. In addition, when R$^{7b}$ and R$^{8b}$ are bound together to form a 5- to 7-membered ring, R$^{7b}$ and R$^{8b}$ are bound to each other to form a straight $C_{2-4}$alkylene side chain represented by —(CH$_2$)$_2$—, —(CH$_2$)$_3$—, and —(CH$_2$)$_4$—. The side chain may have a substituent, and examples of such substituent include hydroxy group, halogen, etc.

Examples of the ester of the optionally esterified carboxyl group include a group formed by bondingcarboxyl group and $C_{1-6}$alkyl group or $C_{3-7}$cycloalkyl group, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, cyclopentyloxycarbonyl, cyclohexyloxycarbonyl, etc.

Examples of the amide of the optionally aminated carboxyl group include a group formed by bonding carboxyl group and $C_{1-6}$alkylamino group, $C_{3-7}$cycloalkyl amino group or 5- to 8-membered cyclic amine (e.g., pyrrolidine, piperidine, morpholine, etc.), for example carbamoyl, mono$C_{1-6}$alkylcarbamoyl, di$C_{1-6}$alkylcarbamoyl, cyclopentylaminocarbonyl, cyclohexylaminocarbonyl, pyrrolidinocarbonyl, piperidinocarbonyl, morpholinocarbonyl, thiomorpholinocarbonyl, etc.

As W, preferably, one of W$^1$ and W$^2$ is O, S(O)$_{m1}$ (m1 is 0, 1 or 2) or —N(R$^3$)— (R$^3$ is a hydrogen atom or an optionally substituted lower. $C_{1-4}$alkyl group), and the other is a bond and X$^2$ is —(CH$_2$)$_p$— (p is an integer of 1 to 3) or, W is a divalent group of —CH(OH)—, and, more preferably, one of W$^1$ and W$^2$ is O, S(O)$_{m1}$ (m1 is 0, 1 or 2), and the other is a bond and X$^2$ is —(CH$_2$)$_p$— (p is an integer of 1 to 3) or, W is a divalent group of —CH(OH)—, in particular, when W$^1$ binds to ring A, —SOCH$_2$— is preferred.

As the compound represented by the above formula (I), the compound according to claim 1 wherein ring A is benzene ring, ring B is an optionally substituted imidazole ring or an optionally substituted triazole ring, one of W$^1$ and W$^2$ is S(O)$_{m1}$ (m1 is 0, 1 or 2), and the other is a bond and X$^2$ is —(CH$_2$)$_p$— (p is an integer of 1 to 3), or W is —CH(OH)—, is preferred, and among them, the compound wherein

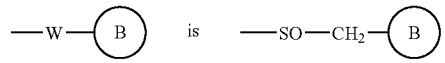

is preferable, and in that case, the steric configuration of SO is preferably (S) configuration.

As the compound represented by the above formula (I), the following compounds are specifically preferred;

7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide, 7-[4-(2-butoxyethoxy)phenyl]-1-isobutyl-N-[4-[(4-propyl-4H-1,2,4-triazol-3-yl)methoxy]phenyl]-2,3-dihydro-1H-1-benzazepine-4-carboxamide, 7-[4-(2-butoxyethoxy)phenyl]-1-isobutyl-N-[3-methyl-4-[(4-propyl-4H-1,2,4-triazol-3-yl)methylthio]phenyl]-2,3-dihydro-1H-1-benzazepine-4-carboxamide, 7-[4-(2-butoxyethoxy)phenyl]-1-isobutyl-N-[2-(4-propyl-4H-1,2,4-triazol-3-yl)methylthiopyridin-5-yl]-2,3-dihydro-1H-1-benzazepine-4-carboxamide, 7-[4-(2-butoxyethoxy)phenyl]-1-isobutyl-N-[4-[3-(4H-1,2,4-triazol-4-yl)propyl]phenyl]-2,3-dihydro-1H-1-benzazepine-4-carboxamide, 7-[4-(2-butoxyethoxy)phenyl]-1-isobutyl-N-[6-[(4-propyl-1H-1,2,4-triazol-5-3-yl)methylsulfinyl]pyridazin-3-yl]-2,3-dihydro-1H-1-benzazepine-4-carboxamide, 7-[4-(2-butoxyethoxy)phenyl]-1-isobutyl-N-[4-[(3-cyclopropylimidazol-4-yl)methylsulfinyl]phenyl]-2,3-dihydro-1H-1-benzazepine-4-carboxamide, 7-[4-(2-butoxyethoxy)phenyl]-N-[4-[(S)-hydroxy(1-oxidopyridin-2-yl)methyl]phenyl]-1-isobutyl-2,3-dihydro-1H-1-benzazepine-4-carboxamide, 7-[4-(2-butoxyethoxy)phenyl]-N-[4-[(S)-hydroxy(1-oxidopyridin-2-yl)methyl]phenyl]-1-(1-methylpyrazol-5-ylmethyl)-2,3-dihydro-1H-1-benzazepine-4-carboxamide, 7-[4-(2-butoxyethoxy)phenyl]-N-[4-(4-methyl-4H-1,2,4-triazol-3-ylthiomethyl)phenyl]-1-isobutyl-2,3-dihydro-1H-1-benzazepine-4-carboxamide, 7-[4-(2-butoxyethoxy)phenyl]-N-[4-(4-methyl-4H-1,2,4-triazol-3-ylmethylthio)phenyl]-1-isobutyl-2,3-dihydro-1H-1-benzazepine-4-carboxamide, 7-[4-(2-butoxyethoxy)phenyl]-N-[4-(4-ethyl-4H-1,2,4-triazol-3-ylmethylsulfinyl)phenyl]-1-isobutyl-2,3-dihydro-1H-benzazepine-4-carboxamide, 7-[4-(2-butoxyethoxy)phenyl]-1-propyl-N-[4-(4-propyl-4H-1,2,4-triazol-3-ylmethylsulfinyl)phenyl]-2,3-dihydro-1H-benzazepine-4-carboxamide, 7-[4-(2-butoxyethoxy)phenyl]-1-isobutyl-N-[4-[2-(4-propyl-4H-1,2,4-triazol-3-yl)ethyl]phenyl]-2,3-dihydro-1H-benzazepine-4-carboxamide, 7-[4-(2-butoxyethoxy)phenyl]-N-[4-(4H-1,2,4-triazol-4-ylethylthio)phenyl]-1-isobutyl-2,3-dihydro-1H-benzazepine-4-carboxamide, 7-[4-(2-butoxyethoxy)phenyl]-1-isobutyl-N-[4-[(3-pyridinylmethyl)sulfinyl]phenyl]-2,3-dihydro-1-benzazepine-4-carboxamide, 7-[4-(2-butoxyethoxy)phenyl]-N-[4-[[(4,6-dimethyl-2-pyrimidinyl)methyl]sulfinyl]phenyl]-1-isobutyl-2,3-dihydro-1-benzazepine-4-carboxamide, 7-[4-(2-butoxyethoxy)phenyl]-1-isobutyl-N-[3-methoxy-4-[(3-pyridinylmethyl)sulfinyl]phenyl]-2,3-dihydro-1-benzazepine-4-carboxamide, 7-[4-(2-butoxyethoxy)phenyl]-1-isobutyl-N-[4-[[(1-ethyl-tetrazol-5-yl)methyl]sulfinyl]phenyl]-2,3-dihydro-1-benzazepine-4-carboxamide, 7-[4-(2-butoxyethoxy)phenyl]-1-isobutyl-N-[4-[[(2-methyl-3-pyridinyl)methyl]sulfinyl]phenyl]-2,3-dihydro-1-benzazepine-4-carboxamide, 7-[4-(2-butoxyethoxy)phenyl]-1-isobutyl-N-[4-[(3-pyridazinylmethyl)sulfinyl]phenyl]-2,3-dihydro-1-benzazepine-4-carboxamide, 7-[4-(2-butoxyethoxy)phenyl]-1-isobutyl-N-[6-[[(2-methyl-3-pyridinyl)methyl]sulfinyl]-3-pyridinyl]-2,3-dihydro-1-benzazepine-4-carboxamide, 7-[4-(2-butoxyethoxy)phenyl]-1-isobutyl-N-[4-[[[1-(2-methoxyethyl)imidazol-5-yl]methyl]sulfinyl]phenyl]-2,3-dihydro-1-benzazepine-4-carboxamide, 7-[4-(2-butoxyethoxy)phenyl]-1-isobutyl-N-[2-[[(1-propylimidazol-5-yl)methyl]sulfinyl]benzimidazol-5-yl]-2,3-dihydro-1-benzazepine-4-carboxamide, 7-[4-(2-butoxyethoxy)phenyl]-1-isobutyl-N-[3-methyl-4-[[(1-methylimidazol-2-yl)methyl]sulfanyl]phenyl]-2,3-dihydro-1-benzazepine-4-carboxamide, N-[4-[[[1-allylimidazol-2-yl]methyl]sulfinyl]phenyl]-7-[4-(2-butoxyethoxy)phenyl]-1-isobutyl-2,3-dihydro-1-benzazepine-4-carboxamide, 7-[4-(2-butoxyethoxy)phenyl]-N-[4-[[[1-cyclopropylimidazol-2-yl]methyl]sulfanyl]phenyl]-1-isobutyl-2,3-dihydro-1-benzazepine-4-carboxamide, 7-[4-(2-butoxyethoxy)phenyl]-N-[4-[[[1-cyclopropylimidazol-2-yl]methyl]sulfinyl]phenyl]-1-isobutyl-2,3-dihydro-1-benzazepine-4-carboxamide, 7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide, 7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide, 7-[4-(2-butoxyethoxy)phenyl]-1-isobutyl-N-[4-[[[1-isopropylimidazol-5-yl]methyl]sulfanyl]phenyl]-2,3-dihydro-1-benzazepine-4-carboxamide, (−)-7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide, (−)-7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide, (−)-7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide, (−)-1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide, (+)-7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide, etc.

Examples of the salts of the compound represented by the formula (I) of the present invention include a pharmaceutically acceptable salt such as a salt with inorganic base, a salt with organic base, a salt with inorganic acid, a salt with organic acid, a salt with basic or acidic amino acid, etc. Suitable examples of the salt with the inorganic base include a salt with alkali metal such as sodium salt, potassium salt, etc.; a salt with alkaline earth metal such as calcium salt, magnesium salt, etc.); and aluminum salt, ammonium salt, etc. Suitable examples of the salt with organic base include a salt with trimethylamine, triethylamine, pyridine, picoline, ethanolamine, diethanolamine, triethanolamine, dicyclohexylamine, N,N'-dibenzylethylenediamine, etc. Suitable examples of the salt with inorganic acid include a salt with hydrochloric acid, hydrobromic acid, nitric acid, sulfuric acid, phosphoric acid, etc. Suitable examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Suitable examples of the salt with basic amino acid include a salt with arginine, lysine, ornithine, etc. Suitable examples of the salt with acidic amino acid include a salt with aspartic acid, glutamic acid, etc. The compound of the formula (I) of the present invention or a salt thereof may be hydrated or non-hydrated. When the compound of the formula (I) of the present invention or a salt thereof exists as configurational isomer, diastereomer, conformer, etc., it is possible to isolate individual isomers with a per se known separation and purification method, if desired. When the compound represented by the formula (I) or a salt thereof is racemate, it can be separated into an (S)-isomer and an (R)-isomer with usual optical resolution means, and individual optical isomers and racemates thereof are included in the scope of the present invention.

The prodrug of the compound represented by formula (I) of the present invention or a salt thereof [hereinafter, referred to as Compound (I) in some cases] refers to a compound which is converted to Compound (I) by in vivo reaction with an enzyme, a gastric acid, etc. under physiological conditions, that is, a compound which is converted to Compound (I) by an enzymatic oxidation, reduction, hydrolysis, etc.; a compound which is converted to Compound (I) by hydrolysis with a gastric acid, etc. Examples of the prodrug of Compound (I) include a compound wherein an amino group of Compound (I) is acylated, alkylated or phosphorylated (e.g. a compound wherein the amino group of Compound (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, tert-butylated, etc,); a compound wherein the hydroxy group of Compound (I) is acylated, alkylated, phosphorylated, borylated (e.g. a compound wherein the hydroxy group of Compound (I) is acetylated, palmitoylated, propanoylated, pivaloylated, succinylated, fumarylated, alanylated, dimethylaminomethylcarbonylated, etc.); a compound wherein the carboxyl group of Compound (I) is esterified or amidated (e.g. a compound wherein the carboxyl group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl) methyl esterified, cyclohexyloxycarbonylethyl esterified, methyl amidated, etc.); etc. These prodrugs can be produced from Compound (I) by methods known per se.

In addition, the prodrug of Compound (I) may be a compound which is converted into Compound (I) under a physiological condition, such as those described in "Development of Medicaments", Vol.7, Molecular. Design, pages 163 to 198, published by Hirokawashoten in 1990.

In addition, compound (I) may be labeled with an isotope (e.g., $^3H$, $^{14}C$, $^{35}S$, $^{125}I$, etc.) and the like.

The present invention is further to provide a preparation method of the compound represented by formula (I) or a salt thereof.

The compound of formula (I) or a salt thereof can be produced in accordance with methods known per se (for example, the methods described in JP-A H08-73476) or the method analogous thereto. The compound of the formula (I) or a salt thereof can also be produced in accordance with the methods described below.

As a salt of the compounds represented by the following formulas (II), (III), (IV), (V), (VI), (VII), (VIII), (I') and (I") (hereinafter, abbreviated as Compound (II), Compound (III), Compound (IV), Compound (V), Compound (VI), Compound (VII), Compound (VIII), Compound (I') and Compound (I"), respectively, in some cases), the salt similar to that with Compound (I) can be used.

In the following reactions, when the starting compounds have amino group, carboxyl group and/or hydroxy group as substituents, to these groups may be introduced a protective group that is generally used in peptide chemistry, etc. After the reaction, if necessary, the protective groups may be removed to obtain the desired compound.

Examples of the protective group for amino group include an optionally substituted $C_{1-6}$alkylcarbonyl (e.g., acetyl, propionyl, etc.), formyl, phenylcarbonyl, $C_{1-6}$alkyloxycarbonyl (e.g., methoxycarbonyl, ethoxycarbonyl, t-butoxycarbonyl, etc.), phenyloxycarbonyl (e.g., benzoxycarbonyl, etc.), $C_{7-10}$aralkyloxycarbonyl (e.g., benzyloxycarbonyl, etc.), trityl, phthaloyl, etc. As the substituent of these protective groups, halogen atom (e.g., fluorine, chlorine, bromine, iodine, etc.), $C_{1-6}$alkylcarbonyl (e.g., acetyl, propionyl, butyryl, etc.), nitro group, etc. are used, and the number of substituents is preferably 1 to 3.

Examples of the protective group for carboxyl group include an optionally substituted $C_{1-6}$alkyl (e.g., methyl, ethyl, propyl, isopropyl, butyl, tert-butyl, etc.), phenyl, trityl, silyl, etc. As the substituent of these protective groups, halogen atom (e.g., fluorine, chlorine, bromine, iodine, etc.), $C_{1-6}$alkylcarbonyl (e.g., acetyl, propionyl, butyryl, etc.), formyl, nitro group, etc. are used, and the number of substituents is preferably 1 to 3.

Examples of the protective group for hydroxy group include an optionally substituted $C_{1-6}$alkyl (e.g., methyl, ethyl, propyl, isopropyl, butyl, tert-butyl, etc.), phenyl, $C_{7-10}$aralkyl (e.g., benzyl, etc.), $C_{1-6}$alkylcarbonyl (e.g., acetyl, propionyl, etc.), formyl, phenyloxycarbonyl, $C_{7-10}$aralkyloxycarbonyl (e.g., benzyloxycarbonyl, etc.), pyranyl, furanyl, silyl, etc. As the substituent of these protective groups, halogen atom (e.g., fluorine, chlorine, bromine, iodine, etc.), $C_{1-6}$alkyl, phenyl, $C_{7-10}$aralkyl, nitro group, etc. are used, and the number of substituents is preferably 1 to 4.

These protective groups may be introduced or removed by methods known per se (e.g. a method described in Protective Groups in Organic Chemistry (J. F. W. McOmie et al.; Plenum Press Inc.) or the methods analogous thereto. For example, as a method for removing the protective groups, method of treating with an acid, a base, reduction, ultraviolet ray, hydrazine, phenylhydrazine, sodium N-methyldithiocarbamate, tetrabutylammonium fluoride, palladium acetate, etc. can be used.

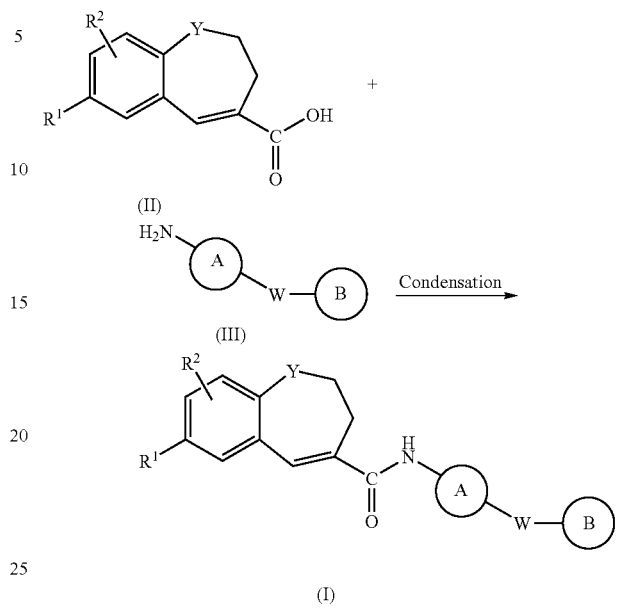

wherein, each symbol has the same meaning as defined in the above.

In this production method, anilide Compound (I) can be obtained by reacting Compound (II) with Compound (III).

The condensation reaction of Compounds (II) and (III) is carried out by usual methods for peptide synthesis. Said methods for peptide synthesis are employed according to any known methods, and for example, methods described in "Peptide Synthesis" written by M. Bodansky and M. A. Ondetti, Interscience, New York, 1966; "The Proteins", volume 2, written by F. M. Finn and K. Hofmann, H. Nenrath and R. L. Hill edition, Academic Press Inc., New York, 1976; "peputido-gosei no kiso to jikken (Basis and Experiment of Peptide Synthesis)" written by Nobuo Izumiya et al., Maruzen K. K., 1985; etc., as well as azide method, chloride method, acid anhydride method, mixed acid anhydride method, DCC method, active ester method, method using Woodward reagent K, carbonyldiimidazole method, oxidation-reduction method, DCC/HONB method, etc. and in addition WSC method, method using diethyl cyanophosphate (DEPC), etc. are exemplified. In other words, as a reactive derivative, for example, reactive derivatives such as acid halide (e.g., acid chloride, acid bromide, etc.), acid azide, acid anhydride, mixed acid anhydride (e.g., mono$C_{1-6}$alkylcarbonic acid mixed acid anhydride (e.g., mixed acid anhydride of free acid with mono-methylcarbonic acid, mono-ethylcarbonic acid, mono-isopropylcarbonic acid, mono-isobutylcarbonic acid, mono-tert-butylcarbonic acid, mono-benzylcarbonic acid, mono-(p-nitrobenzyl)carbonic acid, mono-allylcarbonic acid, or the like), $C_{1-6}$aliphatic carboxylic acid mixed acid anhydride (e.g., mixed acid anhydride of free acid with acetic acid, trichloroacetic acid, cyanoacetic acid, propionic acid, butanoic acid, isobutyric acid, valeric acid, isovaleric acid, pivalic acid, trifluoroacetic acid, trichloroacetic acid, acetoacetic acid, or the like), $C_{7-12}$aromatic carboxylic acid mixed acid anhydride (e.g., mixed acid anhydride of free acid with benzoic acid, p-toluic acid, p-chlorobenzoic acid, or the like), organic sulfonic acid mixed acid anhydride (e.g., mixed acid anhydride of free acid with methanesulfonic acid, ethanesulfonic acid, benzenesulfonic acid, p-toluenesulfonic acid, or the like) and the like, active amide, active ester (e.g., diethoxyphosphoric acid ester, diphenoxyphosphoric acid ester, p-nitrophenyl ester, 2,4-dinitrophenyl ester, etc.), active thio ester (e.g., 2-pyridylthiol ester, 2-benzothiazolylthiol ester, etc.) and the like may be used. The present condensation reaction can be carried out in a solvent. Examples of the solvent include anhydrous or hydrous N,N-dimethylformamide (DMF), dimethylsulfoxide (DMSO), pyridine, chloroform, dichloromethane, tetrahydrofuran (THF), dioxane, acetonitrile and the suitable mixture thereof.

In the present condensation reaction, about 1 to 2 moles of the Compound (III) are usually used relative to 1 mole of the Compound (II). The reaction temperature is generally about −20° C. to about 50° C., preferably about −10° C. to about 30° C. and the reaction time is generally about 1 to about 100 hours, preferably about 2 to about 40 hours. The thus obtained Compound (I) can be isolated and purified by known separation and purification methods such as concentration, concentration under reduced pressure, solvent extraction, crystallization, recrystallization, solvent conversion, chromatography, etc.

$R^a$ in Compound (I') is a hydrogen or a substituent that the optionally substituted imino group represented by $W^1$ and $W^2$ may have.

By reacting Compound (IV) with Compound (V) having ring B, for example, Compound (I) having oxy group, thio group or imino group as $W^{2a}$ like compound (I') can be prepared. Usually about 1 to 3 moles of Compound (V) is used relative to 1 mole of compound (IV). The reaction can be smoothly proceeded, if necessary, by addition of about once to thrice moles of a base such as triethylamine, diisopropylethylamine, pyridine, lithium hydride, sodium hydride, sodium methoxide, sodium ethoxide, sodium carbonate, potassium carbonate, sodium hydrogen carbonate, etc., and further sodium iodide, potassium iodide, etc. The present substitution reaction can be carried out in an inert solvent, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane,

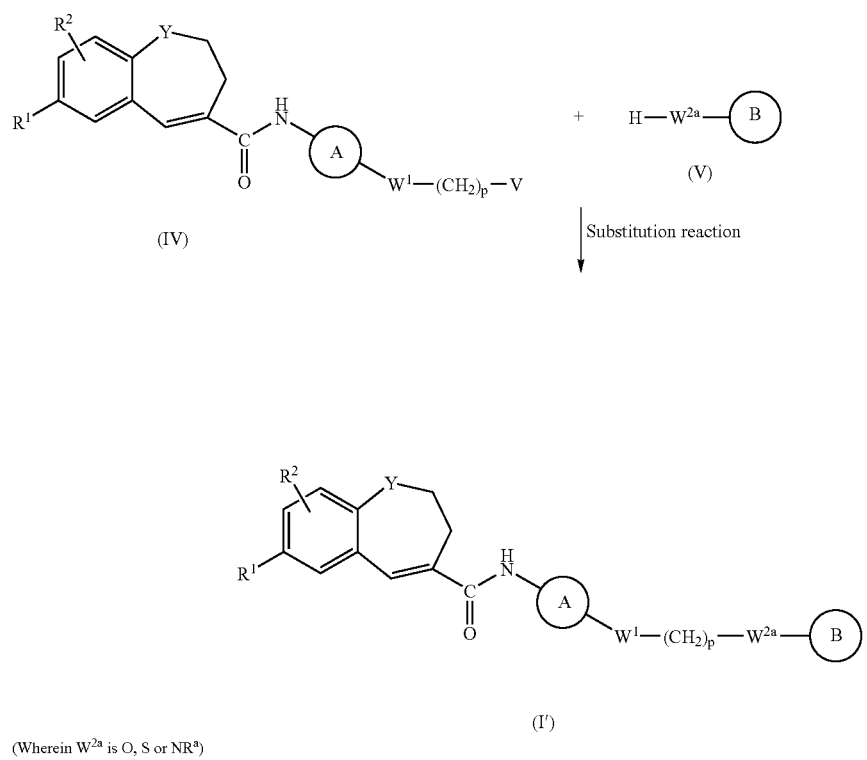

(Wherein $W^{2a}$ is O, S or $NR^a$)

V in Compound (IV) is a halogen atom (chlorine, bromine, iodine, etc.), and a sulfonyloxy group (methanesulfonyloxy group, trifluoromethanesulfonyloxy group, benzenesulfonyloxy group, toluenesulfonyloxy group, etc.), and the other symbols have the same meanings as defined in the above.

dimethylformamide (DMF), dimethyl sulfoxide (DMSO), pyridine, etc., or a mixture of these solvents. The reaction is carried out at the temperature range of about −10° C. to about 180° C., for about 1 hours to about 40 hours. In addition, the present reaction is preferably carried out under an inert gas (e.g. nitrogen, argon, etc.) atmosphere.

[Method C]

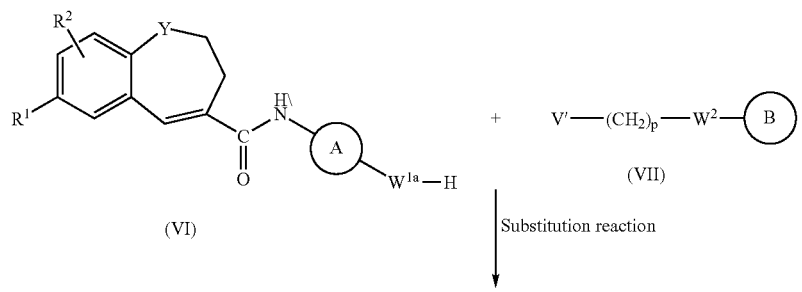

(VI)

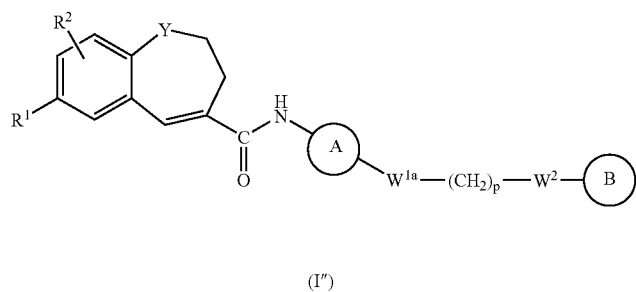

(I'')

(Wherein $W^{1a}$ is O, S, or $NR^b$)

V' in Compound (VII) is a halogen atom (chlorine, bromine, iodine, etc.), a sulfonyloxy group (methanesulfonyloxy group, trifluoromethanesulfonyloxy group, benzenesulfonyloxy group, toluenesulfonyloxy group, etc.), $R^b$ in compound (I'') is a hydrogen or the substituent that the optionally substituted imino group represented by $W^1$ and $W^2$ may have, and other symbols have the same meanings as defined in the above.

By reacting compound (VI) with compound (VII) having ring B, for example, Compound (I'') having oxy group, sulfinyl group or imino group as $W^{1a}$, can be prepared. Usually about 1 to 3 moles of compound (VII) is used relative to 1 mole of compound (VI). The reaction can be smoothly proceeded, if necessary, by addition of about once to thrice moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc. The present substitution reaction can be carried out in an inert solvent, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine, etc., or a mixture of these solvents. The reaction is carried out at the temperature range of about −10° C. to about 180° C., for about 1 hours to about 40 hours. In addition, the present reaction is preferably carried out under inert gas (e.g. nitrogen, argon, etc.) atmosphere.

[Method D]

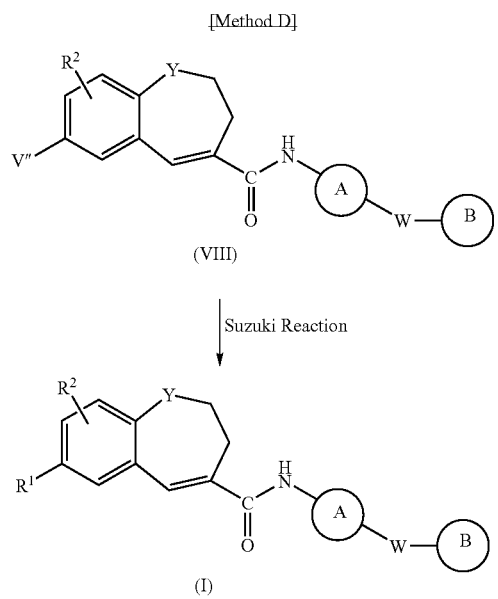

Compound (VIII) [wherein, V'' is a halogen atom (bromine, iodine, etc.), and a sulfonyloxy group (trifluoromethanesulfonyloxy group, etc.), other symbols have the same meaning as defined in the above.] is subjected to, for example, Suzuki reaction [cross condensation reaction of aryl boric acid with, for example aryl halide or aryl oxytrifluoromethane sulfonate in the presence of paradium catalyst; A. Suzuki et al., Synth. Commun. 1981, 11, 513], to prepare Compound (I) wherein $R^1$ is 5- or 6-membered ring aromatic group. Aryl boric acid is used in an amount of about 1 to 1.5 moles relative to 1 mole of Compound (VIII), to obtain Compound (I).

[E Method]

When W of compound (I) is, for example, —CO— or —S—, by a method known per se, for example, by a method described in Ojima, I., ed., Catalytic Asymmetric Synthesis, 2000, Wiley-VCH (New York) or the methods analoguous thereto, Compound (I) having optically active —CH(OH)— or —SO— can be prepared.

The resulting Compound (I) can be isolated and purified by known separation and purification methods such as concentration, concentration under reduced pressure, solvent extraction, crystallization, recrystallization, solvent conversion, chromatography, etc.

The Compound (II) used as the starting material can be produced by a known method (for example, method described in JP-A H08-73476, etc.) or methods analogous thereto, and for example, Compound (II) can be produced by a method shown in the following Reaction scheme I or II and a method described in the following Reference Examples or the methods analogous thereto.

Reaction scheme I

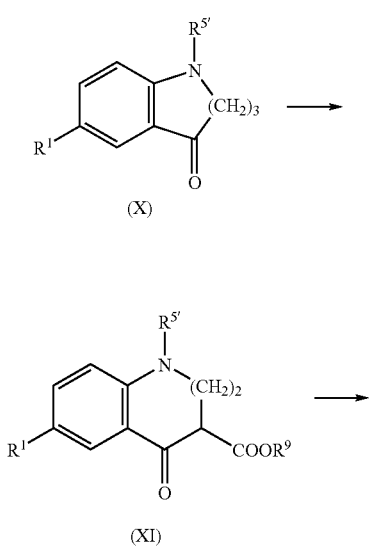

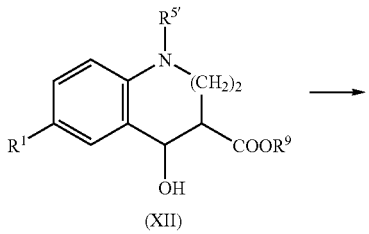

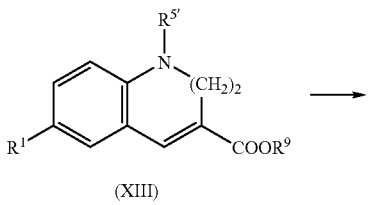

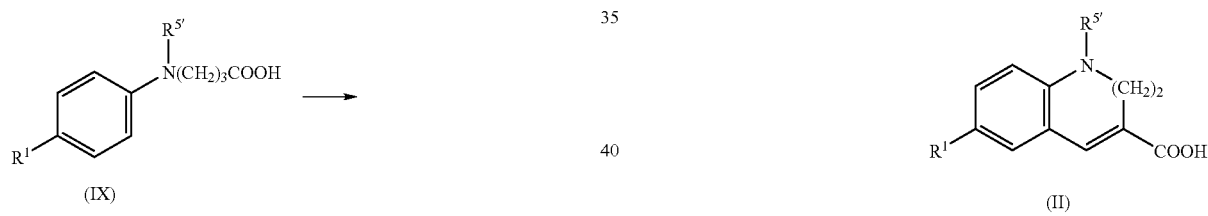

wherein, $R^9$ is $C_{1-4}$alkyl group, $R^{5'}$ has the same meaning as the substituent represented by $R^5$, and other symbols have the same meanings as defined in the above.

In the present method, first the compound represented by formula (IX) is heated together with polyphosphoric acid, or Compound (IX) is converted to acid chloride with thionyl chloride, oxalyl chloride, phosphorus oxychloride or phosphorous pentachloride, etc., followed by subjecting the acid chloride to conventional Friedel Crafts reaction and cyclizing the same to prepare Compound (X). Then, Compound (X) is reacted with carbonic acid ester in the presence of a base to prepare ketoester (XI). Compound (XI) is subjected to reduction reaction with catalytic hydrogenation or sodium boro hydride, etc. to produce Compound (XII). Compound (XII) is subjected to conventional dehydration reaction to produce Compound (XIII). Compound (XIII) is subjected to ester hydrolysis, to produce unsaturated carboxylic acid (II).

Reaction scheme II

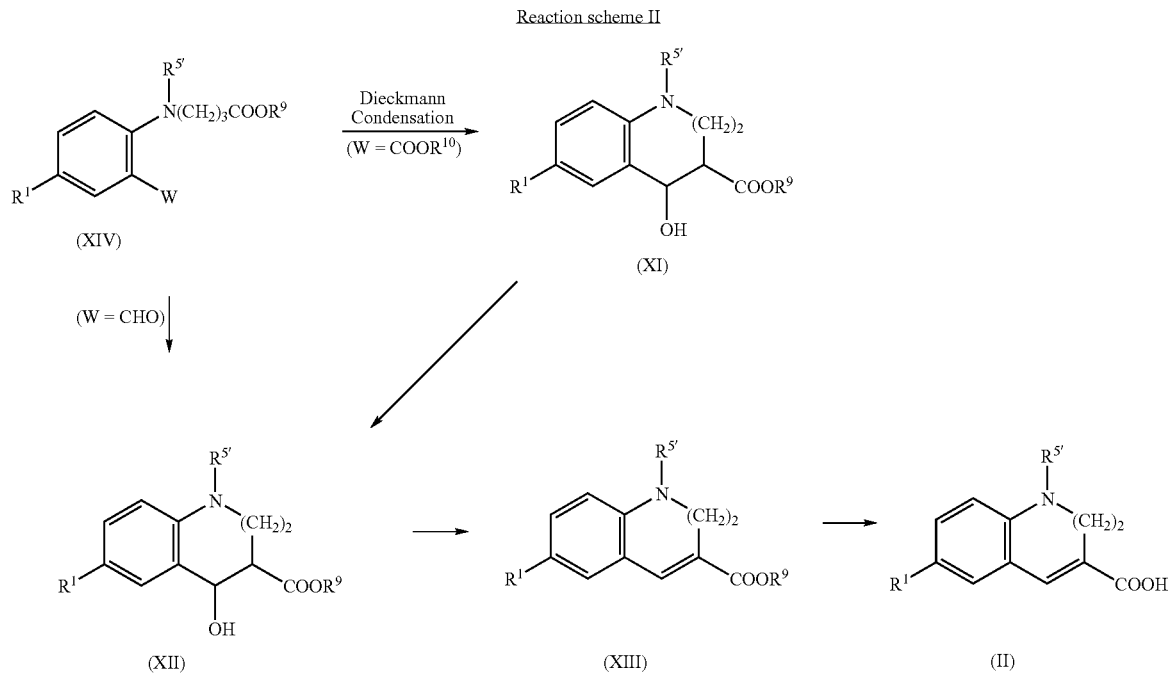

wherein, $R^{10}$ is $C_{1-4}$alkyl group, and the other symbols have the same meaning as defined in the above.

Compound (XIV) is subjected to a Dieckmann (type) condensation reaction (J. P. Schaefer and J. J. Bloomfield, Org. Reactions, 1967, 15, 1), to prepare Compound (XI) to Compound (XIII). Compound (XI) to Compound (XIII) is reacted subsequently according to the method described in the Reaction formula I to prepare unsaturated carboxylic acid compound (II).

In addition, Compound (III) also can be prepared by a known method (e.g., the method described in JP-A H08-73476, etc.) or the methods analogous thereto, and for example, can be prepared by a method shown in Reaction scheme III and a method described in the following Reference Examples, or the methods analogous thereto.

Reaction scheme III

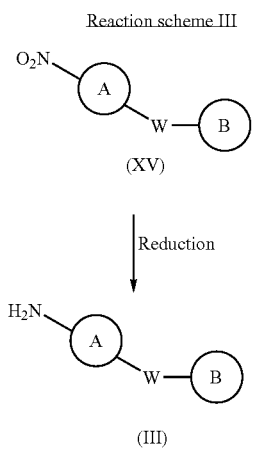

The reduction reaction of Compound (XV) can be carried out by a method known per se. For example, reduction with metal, reduction with metal hydride, reduction with metal hydrido complex compound, reduction with diborane or substituted borane, catalytic hydrogenation, etc. are used. In other words, this reaction is carried out by treating Compound (XV) with reducing agent. Examples of the reducing agent include metal such as reduced iron, zinc powder, etc., alkali metal borohydride (e.g., sodium borohydride, lithium borohydride, etc.), metal hydrido complex compound such as lithium aluminum hydride, etc., metal hydride such as sodium hydride, etc., organotin compound (triphenyl tin hydride, etc.), metal and metal salt such as nickel compound, zinc compound at the like, catalytic reducing agent using transition metal catalyst such as palladium, platinum, rhodium, etc., and hydrogen, and diborane, etc., and catalytic reduction using transition metal catalyst such as palladium, platinum, rhodium, etc., and hydrogen, and reduction with metal such as reduced iron, etc., are advantageously carried out. This reaction is carried out in organic solvent which does not affect the reaction. Examples of the solvents include benzene, toluene, xylene, chloroform, carbon tetrachloride, dichloromethane, 1,2-dichloroethane, 1,1,2,2-tetrachloroethane, diethylether, tetrahydrofuran, dioxane, methanol, ethanol, propanol, isopropanol, 2-methoxyethanol, N,N-dimethylformamide, acetic acid or the mixed solvent thereof, etc. The solvent is suitably selected and used depending on the kinds of reducing agent. Reaction temperature is about −20° C. to about 150° C., in particular, about 0° C. to about 100° C. is preferable, and reaction time is about 1 to about 24 hours.

The resulting. Compound (II) or (III) can be isolated and purified by known separation and purification methods such as concentration, concentration under reduced pressure, solvent extraction, crystallization, recrystallization, solvent conversion, chromatography, etc.

The compound represented by formula (I) of the present invention or a salt thereof including the above Compound (I') and Compound (I") (hereinafter, when briefly referred to as the compound represented by formula (I), it includes the compound represented by formula (I) and a salt thereof) may be administered orally or parenterally alone or as a pharmaceutical composition compounded with a pharmaceutically acceptable carrier such as solid formulations such as tablets, capsules, granules, powders, etc.; or liquid formulations such as syrups, injectables, etc.), Examples of parenteral formulations include injectables, drip infusions, suppositories, pessaries, etc. In particular, pessaries are useful for the prophylaxis of HIV infection.

As the pharmaceutically acceptable carriers, various organic or inorganic carriers which are generally used conventionally as preparation materials are used. For example, an excipient, a lubricant, a binder, a disintegrating agent, etc. in solid formulations; and a solvent, a solubilizer, a suspending agent, an isotonizing agent, a buffer, a soothing agent, etc. in liquid formulations are compounded. In addition, if desired, preparation additives such as a preservative, an antioxidant, a colorant, a sweetener, etc. may be used. Suitable examples of excipients include lactose, sucrose, D-mannitol, starch, crystalline cellulose, light silicic acid anhydride, etc. Suitable examples of lubricants include magnesium stearate, calcium stearate, talc, colloidal silica, etc. Suitable examples of binders include crystalline cellulose, sucrose, D-mannitol, dextrin, hydroxypropyl cellulose, hydroxypropylmethyl cellulose, polyvinyl-pyrrolidone, etc. Suitable examples of disintegrating agents include starch, carboxymethyl cellulose, carboxymethyl cellulose calcium, croscarmellose sodium, sodium carboxymethyl starch, etc. Suitable examples of solvents include water for injection, alcohol, propylene glycol, macrogol, sesame oil, corn oil, etc. Suitable examples of solubilizers include polyethylene glycol, propylene glycol, D-mannitol, benzyl benzoate, ethanol, trisaminomethane, cholesterol, triethanolamine, sodium carbonate, sodium citrate, etc. Suitable examples of suspending agents include surfactants such as stearyl triethanolamine, sodium laurylsulfate, laurylaminopropionic acid, lecithin, benzalkonium chloride, benzetonium chloride, glycerin monostearate, etc.; and hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc. Suitable examples of isotonizing agents include sodium chloride, glycerin, D-mannitol, etc. Suitable examples of buffers include a buffer solution of phosphate, acetate, carbonate, citrate, etc. Suitable examples of soothing agents include benzylacohol, etc. Suitable examples of preservatives include paraoxybenzoic esters, chlorobutanol, benzylalcohol, phenethylalcohol, dehydroacetic acid, sorbic acid, etc. Suitable examples of antioxidants include sulfite, ascorbic acid, etc.

The compound represented by formula (I) of the present invention or a salt thereof has an excellent CC chemokine receptor antagonism, especially CCR5 and/or CCR2 antagonism, in particular, potent CCR5 antagonism, and therefore, can be used for the prophylaxis or treatment of HIV infection, for example, AIDS or other various diseases in human. In addition, the compound represented by formula (I) of the present invention or a salt thereof is low toxic and can be used safely.

For example, the pharmaceutical composition comprising the compound represented by formula (I) of the present invention or a salt thereof may be used as CCR5 antagonist, for example, as an agent for prophylaxis or treatment of AIDS and as an inhibiting agent for the progression of AIDS. In addition, the pharmaceutical composition comprising the compound represented by formula (I) of the present invention or a salt thereof may be used as an agent for prophylaxis and/or treatment of various diseases such as an agent for prophylaxis or treatment of graft versus host disease and/or rejection and an agent for prophylaxis or treatment of chronic rheumatoid arthritis, autoimmune diseases, allergic diseases, ischemic brain cell disorders, myocardial infarction, chronic nephritis, arteriosclerosis, etc., and.

Examples of the subject diseases of preventive and therapeutic agent of the present invention include graft rejection (posttransplantational rejection, posttransplantational polycythaemia, hypertension, organ disorder, vascular hypertrophy, graft versus host disease, etc.,); arthritic osteopathy such as osteomeningitis, etc., (chronic rheumatoid arthritis, osteoarthritis, rheumatoid myelitis, osteoporosis, abnormal growth of cell, fracture, refracture, osteomalacia, osseous Behcet's disease, rigorous myelitis, articular tissue destruction by gonarthrosis and similar diseases thereto, etc.); autoimmune diseases (collagen disease, systemic lupus erythematosus, pachyderma, polyarteritis, myasthenia gravis, multiple sclerosis, etc.); allergic diseases (allergic nasal catarrh, conjunctivitis, gastrointestinal allergy, pollinosis, anaphylaxis, atopic dermatitis, bronchial asthma, etc.); inflammatory enteropathy diseases (ulcerative colitis, Crohn disease, gastritis, gastric ulcer, gastric cancer, postgastrotomy disorder, dyspepsia, esophageal ulcer, pancreatitis, colon polyp, cholelithiasis, hemorrhoids, peptic ulcer, situational ileitis, etc.); inflammatory diseases (retinopathy, postoperative and posttraumatic inflammation, remission of puffiness, pharyngitis, cystitis, meningitides, inflammatory ophthalmic diseases, etc.); respiratory diseases (cold syndrome, pneumonia, asthma, pulmonary hypertension, pulmonary thromboembolism, pulmonary sarcoidosis, pulmonary tuberculosis, interstitial pneumonia, silicosis, adult tachypnea syndrome, chronic obliterative pulmonary diseases, etc.); infectious diseases (virus infection by cytomegalovirus, influenzavirus, herpesvirus and the like, *rickettsia* infection, bacterial infection, sexually transmitted diseases, *carinii* pneumonia, *helicobacter pylori* infection, systemic fungal infection, tuberculosis, invasive staphylococcal infection, acute viral encephalitis, acute bacteria meningitides, AIDS encephalopathia, septicemia, sepsis, sepsis gravis, septic shock, endotoxin shock, toxin shock syndromes, et.); cancers and accompanying cachexia, cancer metastases (bladder cancer, breast cancer, cervical cancer, ovarian cancer, chronic lymphoblastic leukemia, chronic myeloid leukemia, colon cancer, rectal cancer, colic cancer, multiple myeloma, malignant myeloma, prostatic cancer, lung cancer, gastric cancer, Hodgkin disease, malignant melanoma, malignant lymphoma, etc.); non-Hodgkin's lymphoma; non-small cell lung cancer; malignant melanoma, neurodegenerative diseases (Alzheimer disease, Parkinson disease, amyotrophic lateral sclerosis (ALS), Huntington chorea, diabetic neural disorder, Creutzfeldt-Jakob disease, etc.); mental diseases (depression, epilepsy, alcoholism etc.); schizophrenia; venous dysfunction; central nerve disorders (disorder and aftereffect/complication from intracerebral breeding, brain infarction and the like, cephalic trauma, spine damage, brain edema, sensory function disorder, sensory function abnormality, autonomic nervous function disorder, autonomic nervous function abnormality, etc.); centralis damage (cephalic trauma, spiral damage, whiplash injury, etc.); vascular dementia (multiinfarct dementia, Binswanger's disease, etc.); cerebro-vascular accident (asymptomatic cerebro-vascular accident, transient cerebral ischemic attack, stroke, multiinfarct dementia, hypertensive encephalopathia, etc.); recurrence and aftereffect of cerebrovascular accident (neural sympton, mental symptom, subjective sympton, operational disorder in daily life, etc.);

multiinfarct dementia; post-cerebrovascular obliteration central hypofunction; disorder or abnormality of autoregulation of cerebral circulation and renal circulation; blood brain barrier damage; anxiety symptom; acute coronary artery syndromes including unstable angina, etc.; anxious mental state; amnesia; prosopalgia; otolaryngological disease (Menuel syndrome, buzzing, gustation disorder, dizziness, dysequilibrium, dysphagia, etc.); migraine; chronic pain; dermatoses (keloid, angioma, psoriasis, etc.); arteriosclerosis obliterans; thromboangiitis obliterans; obstruction of peripheral artery; postischemic reperfusion injury; Raynaud disease; Buerger disease; myocarditis; cardiac ischemia; cardiac infarction; progress of cardiac failure after cardiac infarction; cardiomyopathy; cardiac hypertrophy; acute cardiac failure and chronic (including estatic) cardiac failure; angina pectoris; arrhythmia; tachycardia; circadian rhythm disorder of blood pressure; abnormality in characteristic of blood haemocyte components (enhancement in platelet aggregation, abnormality of erythrocyte deformability, enhancement in leucocyte adhesiveness, increase in blood viscosity, polycythaemia, vascular peliosis, autoimmune hemolytic anemia, disseminated intravascular coagulation syndrome, multiple myelopathy, etc.); arteriosclerosis including atherosclerosis (aneurysm, coronary arteriosclerosis, cerebro arteriosclerosis, peripheral arteriosclerosis, etc.); vascular reocclusion and restenosis after bypass operation; vascular hyperplasy or occlusion and organ malfunction after intervention (transdermal coronary arterioplasty, stent detention, coronary autoscope, vascular ultrasound therapy, coronary injection thrombolytic therapy, etc.); production and enhancement of vasoactive materials and thrombi inducing materials (endothelin, thromboxan A2, etc.); arterialization (including abnormal vasculogenesis in abnormal capillary vasoganglion formation of pultaceous arteriosclerosis outer membrane); thrombosis; fat storage disease acceleration; ophthalmic diseases (glaucoma, hyper-ocular-tension disease, etc.); hypertension; hypertensive buzzing; dialysis hypotension; endothelial cell and organ disorders; endocrinopathy (Addison disease, Cushing syndrome, melanocytoma, primary aldosteronism, etc.); nephritis; renal diseases (nephritis, glomerulonephritis, glomerulosclerosis, renal failure, thrombotic microangiopathy, dialysis complications, organ disorders including nephropathia by radiation, diabetic nephropathia, etc.); diabetic diseases (insulin-dependent diabetes, diabetic complications, diabetic retinopathy, diabetic microangiopathy, diabetic neuropathy, etc.); glucose tolerance abnormality; hepatic diseases (hepatitis (including chronic hepatitis), cirrhosis, etc.); interstitial hepatic diseases; chronic pancreatitis; portal blood pressure enhancement; obesity; male sterility; gynecologic diseases (climacteric disorder, gestational toxicosis, endometriosis, hysteromyoma, ovarian disease, mammary disease, etc.); dropsy; chronic fatigue syndromes; prostatomegaly; Behcet's disease; Hodgkin's disease; lacunar infarction; consciousness disorder; psoriasis; diseases due to environmental or occupational factors (radiational disorder, disorders by ultraviolet ray/infrared ray/laser ray, altitude sickness, etc.); and intermittent claudication.

A pharmaceutical composition containing the compound of the formula (I) of the present invention or a salt thereof, may be used in combination with other medicines depending on the diseases to be treated. Examples of the other medicines include, HDL increasing drugs [squalene synthase inhibitor, CETP inhibitor, LPL activator, etc.]; preventive and therapeutic drug for HIV infectious disease [nucleic acid reverse transcriptase inhibitors such as zidovudine, didanosine, zalcitabine, lamivudine, stavudine, abacavir, adefovir, adefovir dipivoxil, fozivudine tidoxil, etc., non-nucleic acid reverse transcriptase inhibitors such as nevirapine, delavirdine, efavirenz, loviride, immuncal, oltipraz, etc., protease inhibitors such as saquinavir, ritonavir, indinavir, nelfinavir, amprenavir, palinavir, lasinavir, lopinavir, etc.]; NMG-CoA reductase inhibitors [cerivastatin, atorvastatin, pravastatin, simvastatin, itavastatin, lovastatin, fluvastatin, (+)-3R, 5S-7-[4-[4fluorophenyl]-6-isopropyl-2-(N-methyl-N-methanesulfonylamino)pyrimidin-5-yl)-3,5-dihydroxy-6 (E)heptenoic acid, etc.]; atopic dermatitis drugs [sodium cromoglicate, etc.]; allergic nasal catarrh drugs [sodium cromoglicate, chlorpheniramine maleate, alimemazine tartrate, clemastine fumarate, homochlorcyclizine hydrochloride, terfenadine, mequitazine, etc.]; imipenemcilastatin sodium; endotoxin antagonists or antibodies; oxidosqualene-lanosterol cyclase. [e.g., decalin derivatives, azadecalin derivatives and indan derivatives]; calcium antagonists (diltiazem, etc.); glycerol; cholinesterase inhibitors (e.g., Aricept (donepezil), etc.); compounds suppressing cholesterol uptake [e.g., sitosterol, neomycin, etc.]; compounds inhibiting cholesterol biosynthses [e.g., HMG-CoA reductase inhibitors such as lovastatin, simvastatin, pravastatin, etc.]; cyclooxygenase depressants [Cox-I,Cox-II depressants such as celecoxib, rofecoxib, salicylic acid derivatives such as aspirin and the like, diclofenac, indometacin, loxoprofen, etc.]; sigal transduction inhibitors, squalene epoxidase inhibitors [e.g., NB-598 and the analogous compounds, etc.]; steroidal drugs [dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone propionate, estriol, etc.]; diacerin; nicotinic acid and derivatives and analogues thereof [e.g., acipimox and probucol]; nicergoline, nephrotic syndrome drugs: prednisolone (Predonine), prednisolone sodium succinate (Predonine), methylprednisolone sodium succinate (Solu medrol), betamethasone (Rinderon), dipyridamole (Persantine), dilazep hydrochloride (Comelian), ticlopidine, clopidogrel, antiplatelet drugs an d anticoagulants such as FXa inhibitors, etc.; barbital-based anticonulsants or anaesthetic drugs (phenobarbital, mephobarbital, metharbital, etc.); Parkinson disease drugs (e.g., L-DOPA, etc.); histamine receptor blockers (cimetidine, famotidine, etc.); hidantoin-based anticonvulsant drugs (phenyloin, mephenyloin, ethotoin, etc.); pyroxicam, fibrates. [e.g., clofibrate, benzafibrate, gemfibrozil, etc.]; prostaglandins; megestrol acetate; gastric and intraduodenal ulcer drugs: antacids [e.g., histamine H2 antagonists (cimetidine, etc.), proton pump inhibitors (lansoprazole etc.,), etc.]; inflammatory mediator depressants; coronary vasodilators: nifedipine, diltiazem, nicorandil, nitrite drugs, etc.; infectious disease drugs: [e.g., antibiotic formulations (cefotiam hydrochloride, cefozopran hydrochloride, ampicillin, etc.), chemotherapeutic agents (sulfa drugs, synthetic antibacterial agents, antiviral agents, etc.), biologic formulations (vaccines, blood products including immunoglobulins) etc.] etc.; hepatic disease drugs: glycyrrhizin formulations [e.g., Stronger Minophagen, etc.]; liver hydrolysate; SH compounds [e.g., glutathione, etc.]; special amino acid formulations [e.g., aminoleban, etc.]; phospholipids [e.g., polyene-phosphatidyl choline, etc.]; vitamins [e.g., vitamin $B_1$, $B_2$, $B_6$, $B_{12}$, C, etc.]; adrenocortical hormones. [e.g., dexamethasone, betamethasone, etc.]; interferons [e.g., interferon α, β etc.]; hepatic encephalopathy drugs [e.g., lactulose, etc.]; hemostats used in cases of rapture of esophageal or gastric venous cancer [e.g., vasopressin, somatostatin, etc] etc.; arthritis drugs; muscle relaxants [pridinol, tubocurarine, pancuronium, tolperisone hydrochloride, chlorphenesin carbamate, baclofen, chlormezanone, mephenesin, chlorzoxazone, eperisone, tizanidine, etc.]; vasodilators[oxyfedrine, diltiazem, tolazoline, hexobendine, bamethan, clonidine, methyldopa, guanabenz, etc.]; vasoconstrictors [dopamine, dobutamine denopamine, etc.]; antiplatelet drugs (ozagrel, etc.); thrombogenesis preventive and therapeutic drugs: anticoagulant drugs [e.g., heparin sodium, heparin calcium, warfarin calcium (Warfarin), Xa inhibitor]; thrombolytic drugs [e.g., tPA, urokinase]; antiplatelet drugs [e.g., aspirin, sulfinpyrazone (Anturan), dipyridamole (Persantine), ticlopidine (Panaldine), cilostazol (Pletaal), GPIIb/IIIa antagonist (ReoPro)]; antidepressants [imipramine, clomipramine, noxiptiline, fenelzine, amitriptyline hydrochloride, nortriptyline hydrochloride, amoxapine, mianserin hydrochloride, maprotiline hydrochloride, sulpiride, aluvoxamine maleate, trazodone hydrochloride, etc.]; antiepileptic drugs [gavapentin, phenyloin, ethosuximide, acetazolamide, chlordiazepoxide, trimethadione, carbamazepine, phenobarbital, primidone, sultiame, sodium valproate, clonazepam, diazepam, nitrazepam, etc.]; anti-allergic drugs [diphenhydramine, chlorpheniramine, tripelennamine, metodiramine, clemizole, diphenylpyraline, methoxyphenamine, sodium cromoglicate, tranilast, repirinast, amlexanox, ibudilast, ketotifen, terfenadine, mequitazine, acelastin, epinastine, ozagrel hydrochloride, pranlukast hydrate, seratrodast, fexofenadine, ebastine, bucillamine, oxatomide, Stronger Neo-Minophagen C, tranexamic acid, ketotifen fumarate, etc.]; anticholinergic drugs (e.g., ipratropium bromide, flutropium bromide, oxitropium bromide, etc.); anti-Parkinson drugs (dopamine, levodopa, etc.); antirheumatic drugs; anti-inflammatory drugs (e.g., aspirin, acetaminophen, diclofenac sodium, ibuprofen, indometacin, loxoprofen sodium, dexamethasone, etc.); anticoagulant and antiplatelet drugs. [sodium citrate, activated protein C, tissue factor pathway inhibitors, antithrombin III, dalteparin sodium, argatroban, gabexate, ozagrel sodium, ethyl icosapentate, beraprost sodium, alprostadil, pentoxifylline, tisokinase, streptokinase, heparin, etc.]; anticoagulant therapeutic drugs [dipyridamole (Persantine), dilazep hydrochloride (Comelian), ticlopidine, clopidogrel, Xa inhibitors]; antibacterial drugs [(1) sulfa drugs [sulfamethizole, sulfisoxazole, sulfamonomethoxine, sulfamethizole, salazosulfapyridine, sulfadiazine silver, etc.], (2) quinolone-based antibacterial drugs [nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin, etc.], (3) antituberculous drugs [isoniazid, ethambutol (ethambutol hydrochloride), p-aminosalicyclic acid (calcium p-aminosalicylate), pyrazinamide, ethionamide, prothionamide, rifampicin, streptomycin sulfate, kanamycin sulfate, cycloserine, etc.], (4) anti-acid fast bacteria drugs [diaphenylsulfone, rifampicillin, etc.], (5) antiviral drugs [idoxuridine, aciclovir, vidarabine, ganciclovir, etc.], (6) anti-HIV drugs [zidovudine, didanosine, zalcitabine, indinavir sulfate ethanolate, ritonavir, etc.], (7) spirocheticide, (8) antibiotics [tetracycline hydrochloride, ampicillin, piperacillin, gentamcin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cefalexin, cefroxadine, cefadroxil, cefamandole, cefotiam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or salts thereof, griseofulvin, lankacidins [J. Antibiotics, 38, 877 to 885 (1985)], etc., cefixime, levofloxacin]; antithrombotic drugs (argatroban, etc.); antiprotozoal drugs [metronidazole, tinidazole, diethylcarbamazine citrate, quinine hydrochloride, quinine sulfate, etc.]; antitumor drugs [6-O-(N-chloroacetylcarbamoyl] fumagillol, bleomycin, methotrexate, actinomycin D, mitomycin C, daunorubicin, adriamycin, neocartinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathiopurine, mercaptopurine, tegafur, carmofur, cytarabine, methyltestosterone, testosterone propionate, testosterone enanthate, mepitiostane, fosfestrol, chlormadinone acetate, leuproline acetate, buserelin acetate, etc.; antifungal drugs [(1) polyethylene-based antibiotics (e.g., amphotericin B, nystatin, trichomycin), (2) griseofulvin, pyrrolnitrin, etc., (3) cytosine metabolism antagonists (e.g., flucytosine), (4) imidazole derivatives (e.g., econazole, clotrimazole, miconazole nitrate, bifonazole, croconazole), (5) triazole derivatives (e.g., fluconazole, itoraconazole, azole compounds [2-[(1R,2R)-2-[2,4-difluorophenyl)-2-hydroxy-1-methyl-3-(1H-1,2,4-triazol-lyl)propyl]-4-[4-(2,2,3,3-tetrafluoropropoxy)phenyl-3(2H,4H)-1,2,4-triazolone], (6) thiocarbamate derivatives [e.g., trinaphthol], (7) echinocandin-based derivatives (e.g., caspofungin, FK-463, V-echinocandin), etc.]; antipsychotic drugs [chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine, etc.]; antiulcer drugs [metoclopramide, histidine hydrochloride, lansoprazole, metoclopramide, pirenzepine, cimetidine, ranitidine, famotidine, urogastron, oxethazaine, proglumide, omeprazole, sucralfate, sulpiride, cetraxate, gefarnate, aldioxa, teprenone, prostaglandins etc.]; anti diabetic drugs [e.g., pioglitazone, nateglinide, voglibose, acarbose, etc.]; antiobese drugs [mazindol, etc.]; antirheumatic drugs; antianxiety drugs [diazepam, lorazepam, oxazepam, chlordiazepoxide, medazepam, oxazolam, cloxazolam, clotiazepam, bromazepam, etizolam, fludiazepam, hydroxyzine, etc.]; antiarrhythmic drugs. [disopyramide, lidocaine, quinidine sulfate, flecainide acetate, mexiletine hydrochloride, amiodarone hydrochloride, and p blockers, Ca antagonists, etc.; antiasthmatic drugs [isoprenaline hydrochloride, salbutamol sulfate, procaterol hydrochloride, terbutaline sulfate, trimetoquinol hydrochloride, tulobuterol hydrochloride, orciprenaline sulfate., fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlukast hydrate, seratrodast, dexamethasone, prednisolone, hydrocortisone, beclomethasone propionate, fluticasone propionate, beclomethasone propionate, procaterol, etc.]; anti-hypothyroidism drugs. [dried thyroid (Thyreoid), levothyroxine sodium (Tyradin S), liothyronine sodium (thyronine, tyronine)]; nephrotic syndrome drugs [prednisolone (Predonine), prednisolone sodium succinate (Predonine), methylprednisolone sodium succinate (Solu medrol), betamethasone (Rinderon).]; antihypertensive drugs [(1) sympathetic nerve depressants [α2 stimulating drugs (e.g., clonidine, guanabenz, guanfacine, methyldopa, etc.), ganglionic blockers (e.g., hexamethonium, trimethaphan, etc.), presynaptic blockers (e.g., Alusa-Oxylone, dimethylamino reserupinate, rescinnamine, reserpine, syrosingopine, etc.), neuronal blockers (e.g., betanidine, guanethidine, etc.), α1 blockers (e.g., bunazosin, doxazosin, prazosin, terazosin, urapidil, etc.), β blockers (e.g., propranolol, nadolol, timolol, nipladilol, bunitrolol, indenolol, penbutolol, carteolol, carvedilol, pindolol, acebutolol, atenolol, bisoprolol, metoprolol, labetalol, amosulalol, arotinolol, etc.), etc], (2) vasodilators [calcium channel antagonists (e.g., manidipine, nicardipine, nilvadipine, nisoldipine, nitrendipine, benidipine, amlodipine, aranidipine, etc.), phthalazine derivatives (e.g., budralazine, cadralazine, ecarazine, hydralazine, todralazine, etc.), etc.], (3) ACE inhibitors [alacepril, captopril, cilazapril, delapril, enalapril, lisinopril, temocapril, trandolapril, quinapril, imidapril, benazepril, perindopril, etc.)], (4) AII antagonists [losartan, candesartan, valsartan, telmisartan, irbesartan, forasartan, etc.], (5) diuretic drugs [e.g., diuretic drugs described above, etc.]; antihypertensive drugs [diuretic drugs [e.g., furosemide (Lasix), bumetanide (Lunetoron), azosemide (DIART)], antihypertensive drugs [e.g., ACE inhibitors, (enalapril maleate (RENIVACE) etc.,) and Ca antagonists (manidipine, amlodipine etc.), α or β receptor blockers, etc.], antihyperlipemia drugs. [HMG-CoA reductase inhibitors (e.g., fluvastatin, cerivastatin, atorvastatin, etc.), fibrates [e.g., simfibrate, aluminum clofibrate, clinofibrate, fenofibrate, etc.], anion exchange resin [e.g., cholestyramine, etc.], nicotinic acid drugs [e.g., nicomol, niceritrol, tocopherol nicotinate etc.], polyvalent unsaturated fatty acid derivatives [e.g., ethyl icosapentaenoic acid, polyene phosphatidyl choline, melinamide, etc.], phytosterols [e.g., gamma-oryzanol, soysterol, etc.], elastase, sodium dextran sulfate, squalene synthase inhibitors, CETP inhibitors, 2-chloro-3-[4-(2-methyl-2-phenylpropoxy)phenyl] ethyl propionate [Chem. & Pharm. Bull., 38, 2792 to 2796 (1990)], etc.]; osseous disease drugs. [calcium formulations [e.g., calcium carbonate, etc.], calcitonin formulations, activated vitamin $D_3$ formulations [e.g., alfacalcidol (Alfarol etc.), calcitriol (Rocaltrol), etc.], sex hormones [e.g., estrogen, estradiol, etc.], hormone formulations [e.g., conjugated estrogen (Premarin), etc.], ipriflavone formulations [osten, etc.], vitamin $K_2$, vitamin $K_2$ formulations [e.g., menatetrenone (Glakay), etc.], bis-phosphonate-based formulations [etidronate, etc.], prostaglandin E2, fluorine compounds [e.g., sodium fluoride, etc.], bone morphogenetic protein (BMP), fibroblast growth factor (FGF), platelet derived growth factor (PDGF), transforming growth factor (TGF-β), insulin-like growth factor-1 and -2 (IGF-1, -2), parathyroid adrenal hormones (PTH), and compounds described in EP-A1-376197, EP-A1-460488, and EP-A1-719782 [e.g., (2R, 4S)-(−)-N-[4-(diethoxyphosphorylmethyl)phenyl]-1,2,4,5-tetrahydro-4-methyl-7,8-methylenedioxy-5-oxo-3-bemzothiepin-2-carboxamide, etc.], etc.), lipid-soluble vitamin drugs [(1) vitamin A family (vitamin $A_1$, vitamin $A_2$, and retinol palmitate), (2) vitamin D family (vitamin $D_1$, $D_2$, $D_3$, $D_4$, and $D_5$), (3) vitamin E family (α-tocopherol, β-tocopherol, γ-tocopherol, δ-tocopherol, dl-α-tocopherol nicotinate.), (4) vitamin K family (vitamin $K_1$, $K_2$, $K_3$, and $K_4$,), (5) folic acids (vitamin M), etc.]; vitamin derivatives [various vitamin derivatives, e.g., vitamin $D_3$ derivatives such as 5,6-trans-cholecalciferol, 2,5-hydroxycholecalciferol, 1-α-hydroxycholecalciferol, vitamin $D_2$ derivatives such as 5,6-trans-ergocalciferol, and the like]; disease-modifying antirheumatic and immunosuppressive drugs. [e.g., methotrexate, leflunomide, prograf, sulfasalazine, D-penicillamine, the oral gold salts]; hypertensors [dopamine, dobutamine, denopamine, digitoxin, digoxin, methyldigoxin, lanatoside C, G-strophanthin, etc.]; myocardial protective drugs: heart ATP-K opener (Na-H exchange inhibitors, endothelin antagonists, urotensin antagonist, etc.), cardiac failure drugs [cardiac stimulants (e.g., digitoxin, digoxin, methyldigoxin, lanatoside C, proscillaridin, etc.), α, β stimulating drugs (e.g., epinephrine, norepinephrine, isoproterenol, dopamine, docarpamine, dobutamine, denopamine, etc.), phosphodiesterase inhibitors (e.g., amrinone, milrinone, olprinone hydrochloride, etc.), calcium channel sensibility improvers (e.g., pimobendan, etc.), nitrate drugs (e.g., nitroglycerin, isosorbide nitrate, etc.), ACE inhibitors (e.g., the ACE inhibitor described above, etc.), diuretic drugs (e.g., diuretic drugs described above, etc.), calperitide, ubidecarenone, vesnarinone, aminophylline, etc.]; neurotrophic factors; renal failure and nephropathia drugs; biologics [e.g., monoclonal antibodies (e.g., anti-TNF-α antibodies, anti-IL-12 antibodies, anti-IL-6 antibodies, anti-ICAM-1 antibodies, anti-CD4 antibodies, etc.), soluble receptors (e.g., soluble TNF-α receptors, etc.), protein ligands (IL-I receptor antagonist, etc.)]; bile acid binding resins [e.g., cholestyramine, cholestipol, etc.]; biliary tract disease drugs: cholereticcholepoietic drugs [e.g., dehydrocholic acid, etc.], cholekinetic drugs [e.g., magnesium sulfate, etc.], etc.; central nervous system agonists: antianxiety drugs, hypnotic and sedative drugs, anesthetic drugs, spasmolytic drugs, autonomic drugs, anti-Parkinson drugs and other psychoneuro drugs, etc.; antitiussive and expectorants. [ephedrine hydrochloride, noscapine hydrochloride, codeine phosphate, dihydrocodeine phosphate, isoproterenol hydrochloride, ephedrine hydrochloride, methylephedrine hydrochloride, noscapin hydrochloride, arocloramide, chlofedanol, picoperidamine, cloperastine, protoxlol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocisteine, etc.], sedative drug [chlorpromazine hydrochloride, atropine sulfate, phenobarbital, barbital, amobarbital, pentobarbital, thiopental sodium, thiamylal sodium, nitrazepam, estazolam, flurazapam, haloxazolam, triazolam, flunitrazepam, bromovalerylurea, chloral hydrate, triclofos sodium, etc.], analgesic and antiphlogistic drugs [e.g., central analgesic drugs (e.g., morphine, codeine, pentazocine etc.), steroid drugs (e.g., prednisolone, dexamethasone, betamethasone), etc., antiphlogistic enzymic drugs (e.g., bromerain, lysozymes, protease, etc.)], diabetic drugs [sulfonylurea drugs (e.g., tolbutamide, chlorpropamide, glyclopyramide, acetohexamide, tolazamide, glibenclamide, glybuzole, etc.), biguanide drugs (e.g., metformin hydrochloride, buformin hydrochloride, etc.), α-glucosidase inhibitors (e.g., voglibose, acarbose, etc.), insulin resistance improvers (e.g., pioglitazone, troglytazone, etc.), insulin, glucagon, diabetic complication drugs (e.g., epalrestat, thioctic acid, etc.), actos, rosigliatazone, kinedak, penfill, humulin, euglucon, glimicron, daonil, novolin, monotard, insulin family, glucobay, dimelin, rastinone, bacilcon, deamelin S, iszilin family, etc.]; brain function reviving agents (e.g., idebenone, vinpocetin, etc.); urinary and male genital disease drugs [e.g., prostatomegaly drugs (tamsulosin hydrochloride, prazosin hydrochloride, chlormadinone acetate, etc.), prostate cancer drugs (leuprorelin acetate, goserelin acetate, chlormadinone acetate, etc.)], etc; nonsteroidal antiinflammatory drugs [acetaminophen, phenacetin, ethenzamide, sulpyrine, antipyrine, migrenin, aspirin, mefenamic acid, fulfenamic acid, diclofenac sodium, loxoprofen sodium, phenylbutazone, indomethacin, ibuprofenn, ketoprofen, naproxen, oxaoprozin, flurbiprofen, fenbufen, pranoprofen, floctafenine, epirizole, tiaramide hydrochloride, zaltoprofen, gabexate mesilate, camostat mesilate, urinastatin, colchicine, probenecid, sulfinpyrazone, benzbromarone, allopurinol, sodium aurothiomalate, sodium hyaluronate, sodium salicylate, morphine hydrochloride, salicyclic acid, atropine, scopolamine, morphine, pethidine, levorphanol, ketoprofen, naproxen, oxymorphone or the salts thereof, etc.]; frequent urination and anischuria drugs [flavoxate hydrochloride, etc.]; unstable plague stablizers [MMP inhibitors, chymase inhibitors, etc.]; arrhythmic drugs [sodium channel blockers (e.g., quinidine, procainamide, disopyramide, ajmaline, cibenzoline, lidocaine, diphenylhydantoin, mexiletine, propafenone, flecainide, pilsicainide, phenyloin, etc.), β blockers (e.g., propranolol, alprenolol, bufetolol, oxprenolol, atenolol, acebutolol, metoprolol, bisoprolol, pindolol, carteolol, arotinolol, etc.), potassium channel blockers (e.g., amiodarone, etc.), calcium channel blockers (e.g., verapamil, diltiazem, etc.), etc.]; gynecologic disease drugs [e.g., climacteric disorder drugs (conjugated estrogen, estradiol, testosterone enanthate, estradiol valerate, etc.), breast cancer drugs (tamoxifen citrate, etc.), endometriosis and hysteromyoma drugs (leuprorelin acetate, danazol, etc.)], etc.; anesthetic drugs. [a local anaesthetic drugs [cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine], etc.]; b. general anesthetic drugs [(I) inhalation anesthetic drugs (e.g., ether, halothane, nitrous oxide, influrane, enflurane), (2) intravenous anesthetic drugs (e.g., ketamine hydrochloride, droperidol, thiopental sodium, thiamylal sodium, pentobarbital), etc.]]; anesthetic antagonists [levallorphan, nalorphine, naloxone, or the salts thereof, etc.]; chronic cardiac failure drugs: cardiac stimulants [e.g., cardiac glycoside (digoxin, etc.), β receptor stimulating drugs (catecholamine preparations such as denopamine, dobutamine.), PDE inhibitors, etc.]; diuretic drugs [e.g., furosemide (Lasix), spironolactone (Aldactone), bumetanide (Lunetoron), azosemide (Diart), etc.]; ACE inhibitors. [e.g., enalapril maleate (Renivace), etc.]; Ca antagonists [e.g., amlodipine, manidipine, etc.] and β receptor blockers, etc.; immunomodulators [cyclosporin, tacrolimus, gusperimus, azathioprine, antilymphocyte sera, dried sulfonated immunoglobulins, erythropoietins, colony stimulating factors, interleukins, interferons, etc.]; diuretic drugs. [thiazide-based diuretic drugs (benzylhydrochlorothiazide, cyclopenthiazide, ethiazide, hydrochlorothiazide, hydroflumethiazide, methylclothiazide, penflutiazide, polythiazide, trichlormethiazide, etc.), loop diuretic drugs (chlortalidone, clofenamide, indapamide, mefruside, meticrane, sotrazone, tripamide, quinethazone, metolazone, furosemide, mefruside, etc.), potassium-sparing diuretic drugs (spironolactone, triamterene, etc.)]; and erectile dysfunction drugs (Viagra, apomorphine, etc.).

These drugs, separately or simultaneously may be prepared by mixing with pharmaceutically acceptable carriers, excipients, binders, diluents or the like, and can be administered either orally or parenterally. When the drug is prepared separately, the separately prepared drugs may be administered with mixing with a diluent or the like before use, and each of the preparations separately prepared may be administered, simultaneously or separately at an interval, to the same subject. Kit products for administering the separately prepared preparations with mixing with a diluent and the like before using (for example, an injectable kit including ampoules containing each powdery drug, and a diluent for mixing to dissolve 2 or more drugs before using, and the like), kit products for administering each of the separately-prepared preparations, simultaneously or separately at an interval, to the same subject (for example, a tablet kit for administering 2 or more tablets, simultaneously or separately at an interval, wherein the tablet containing each drugs was put into the same or separate bags and, if necessary, a column wherein the drug administration time is to be indicated was provided on the bags, and the like), or the like are also included in the pharmaceutical composition of the present invention.

A dosage of the pharmaceutical composition of the present invention can be appropriately selected by taking into consideration of the administration subject, age and body weight of the administration subject, disease conditions, administration time, administration route, dosage form, etc.

The dosage for a particular patient is determined depending on the subject's age, body weight, general health condition, sex, meal, administration time, administration route, excretion rate and the degree of disease being treated at that time and by taking into consideration of these and other factors.

When the pharmaceutical composition described above is used as a preventive and therapeutic agent for AIDS and a depressant for disease progression of AIDS, the dosage of composition varies depending on the patient's condition, body weight and administration route However, in the case of oral administration, a daily dosage is in a range of about 5 to 1000 mg, preferably about 10 to 600 mg, and more preferably about 10 to 300 mg, especially preferably about 15 to 150 mg of active ingredient (i.e. as the compound of the formula (I)) per adult (body weight: 50 kg), and the composition may be administered once a day or 2 to 3 times a day.

When the pharmaceutical composition described above is used as a preventive and therapeutic agent for graft versus host disease and/or rejection associated with transplantation of organs such as heart, kidney, liver, bone marrow, etc., administration of the composition starts 3 days before the transplantation, and continues after the transplantation. A daily dosage of the pharmaceutical composition varies depending on the patient's condition, body weight and route of administration, and in the case of oral administration, about 5 to 1000 mg, preferably about 10 to 600 mg, more preferably about 10 to 300 mg, and especially preferably about 15 to 150 mg, as an active ingredient (i.e., as the compound of the formula (I)), per adult (body weight: 50 kg) and the composition may be administered, once a day, or separately 2 or 3 times a day. In this case, the composition may be used in combination with a depressant for graft versus host disease and/or rejection in other organ transplantation. Specific examples of the depressant of graft versus host disease and/or rejection in organ transplantation which are used in combination with the compound represented by the compound of the formula (I) or a salt thereof include cyclosporin, tacrolimus, rapamycin, steroids, azathioprine, mycophenolate mophetil, mizoribine, etc. When one drug affects metabolism of other drugs in the case where these drugs are used in combination, dosage of each drugs is properly adjusted, but generally dosage of each of the drugs used in combination is that of each drugs when used independently.

When the compound of formula (I) or a salt thereof described above is used for the subject disease except for suppression of the graft versus host disease and/or rejection in organ transplantation, the daily dosage varies depending on the kind of subject disease, the patient's condition and body weight, and route of administration, and is usually, in oral administration, about 5 to 1000 mg, preferably about 10 to 600 mg, more preferably about 10 to 300 mg, and especially preferably about 15 to 150 mg of active ingredient (i.e., as the compound of the formula (I)), per adult (body weight: 50 kg), and the composition may be administered, once a day, or separately 2 to 3 times a day. When the compound is used in combination with other drugs, dosage of the other drugs is properly selected in a range of about 1/200 to 1/2 or more to about 2 to 3 times or less of usual dosage. Further, when in the case where the composition is used in combination with 2 or more drugs, one of the drugs affects metabolism of the other drug, dosage of each of the drugs is properly adjusted, but generally, dosage of each of the drugs used in combination is that of each drug when used independently.

Further, the compound of formula (I) or a salt thereof can be included in or used in combination with blood for blood transfusion or blood products. The blood for blood transfusion or blood products are produced by mixing blood obtained from multiple persons and, in some cases, uninfected cells are contaminated with cells infected with HIV virus. In such a case, uninfected cells are likely to be infected with HIV virus. When the compound represented by the formula (I) of the present invention is compounded to blood for blood transfusion or blood products, infection with the virus and proliferation thereof can be prevented or controlled. Especially, when blood products are stored, infection and proliferation of the virus is effectively prevented or controlled by addition of the compound of formula (I) of the present invention. In addition, when blood for blood transfusion or blood products contaminated with HIV virus are administered, infection and proliferation of HIV in the person's body can be prevented by adding the compound of formula (I) to the blood or blood products. For example, when the compound is administered orally to an adult (body weight: 50 kg) for preventing. HIV infection upon blood transfusion or using blood products, the single dosage is usually in a range of about 0.02 to 50 mg/kg, preferably about 0.05 to 30 mg/kg, and more preferably about 0.1 to 10 mg/kg of CCR antagonist, and the dosage may be administered once to thrice a day. As a matter of course, although the dosage range can be controlled on the basis of unit dosages necessary for dividing the daily dosage, as described above, a dosage can be determined depending on the property and degree of the diseases, the patient's age, body weight, general health condition, sex, meal, administration time, administration route and excretion rate, and by taking into consideration of these and other factors. In this case, the administration route is also appropriately selected and, the agent for preventing HIV infection of the present invention may be added directly to blood or blood products for transfusion before transfusion or using blood products. In such a case, desirably, the agent is mixed immediately to 24 hours before, preferably immediately to 12 hours before, more preferably immediately to 6 hours before transfusion or using blood products.

When the agent for preventing HIV infection of the present invention is administered separately from the blood for transfusion or blood products on blood transfusion or in use of blood products, the agent is administered preferably at the same time of, or 1 hour before transfusion or using the blood products. More preferably, the agent is administered once to 3 times per day and administration is continued for 4 weeks.

Furthermore, when the compound of formula (I) or a salt thereof is used in combination with a reverse transcriptase inhibitor and/or a protease inhibitor, the dosage of the reverse transcriptase or the protease is properly selected from a range of about 1/200 to 1/2 or more, to about 2 to 3 times or less of the usual dosage.

The usual dosages of the representative reverse transcriptase inhibitor and protease inhibitor are as follows:

| | |
|---|---|
| zidovudine: | 100 mg |
| didanosine: | 125 to 200 mg |
| zalcitabine: | 0.75 mg |
| lamivudine: | 150 mg |
| stavudine: | 30 to 40 mg |
| saquinavir: | 600 mg |
| ritonavir: | 600 mg |
| indinavir: | 800 mg |
| nelfinavir: | 750 mg. |

A typical embodiment of combined use of the compound of the formula (I) or a salt thereof, and a reverse transcriptase inhibitor and/or a protease inhibitor are as follows.

(1) About 10 to 300 mg of the compound of formula (I) or the salt thereof and about 50 to 200 mg of zidovudine, per an adult (body weight, 50 kg), are administered in combination to the same subject. Each medicine may be administered simultaneously or separately in a time interval of less than 12 hours.

(2) About 10 to 300 mg of the compound of formula (I) or the salt thereof and about 300 to 1200 mg of saquinavir, per adult (body weight, 50 kg), are administered in combination to the same subject. Each medicine may be administered simultaneously or separately in a time interval of less than 12 hours.

EXAMPLES

The present invention is hereinafter illustrated in more detailed by Examples, Reference Examples, and Experiment. Examples, but the present invention is not intended to be limited to these Examples.

Example 1

(Preparation of Compound 1)

7-[4-(2-butoxyethoxy)phenyl]-N-[4-[hydroxy(4-methyl-1-oxidopyridin-2-yl)methyl]phenyl]-1-trifluoroacetyl-2,3-dihydro-1H-1-benzazepine-4-carboxamide (0.27 g) was dissolved in ethanol (30 ml), and to the solution, sodium borohydride (0.08 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(4-methyl-1-oxidopyridin-2-yl)methyl]phenyl]-2,3-dihydro-1H-1-benzazepine-4-carboxamide (compound 1) (0.26 g) as yellow crystals.

mp 198-201° C. (dec.).

¹H-NMR (δ, CDCl₃) 0.93 (3H, t, J=7.1 Hz), 1.34 to 1.45 (2H, m), 1.57 to 1.65 (2H, m), 2.28 (3H, s), 2.97 (2H, t-like), 3.47 (2H, t-like), 3.55 (2H, t, J=6.6 Hz), 3.80 (2H, t, J=4.9 Hz), 4.16 (2H, t, J=4.9 Hz), 4.61 (1H, br), 6.03 to 6.04 (1H, m), 6.69 to 6.73 (3H, m), 6.95 to 7.17 (3H, m), 7.26 to 7.34 (2H, m), 7.43 to 7.48 (5H, m), 7.63 to 7.67 (3H, m), 8.14 (1H, d, J=6.6 Hz).

IR (KBr) ν: 2926, 2843, 1651, 1601 cm⁻¹.

Anal calcd for $C_{36}H_{39}N_3O_5 \cdot 0.25H_2O$: C, 72.28; H, 6.66; N, 7.02. Found: C, 71.99; H, 6.57; N, 6.91.

Example 2

(Preparation of Compound 2)

7-[4-(2-butoxyethoxy)phenyl]-N-[4-[hydroxy(4-methyl-1-oxidopyridin-2-yl)methyl]phenyl]-2,3-dihydro-1H-1-benzazepine-4-carboxamide (0.25 g) and isobutylaldehyde (0.15 ml) were dissolved in 1,2-dichloroethane (80 ml), and to the solution, triacetoxy sodium borohydride (0.27 g) was added under ice-cooling and the mixture was stirred overnight at room temperature. To the mixture, isobutylaldehyde (1 ml) and triacetoxy sodium borohydride (1.3 g) were further added, and the mixture was stirred overnight at room temperature. The mixture was washed with sodium bicarbonate solution and water, and dried over anhydrous magnesium sulfate. The solvent was distilled off, to give 7-[4-(2-butoxyethoxy)phenyl]-N-[4-[hydroxy(4-methyl-1-oxidopyridin-2-yl)methyl]phenyl]-1-isobutyl-2,3-dihydro-1H-1-benzazepine-4-carboxamide (compound 2) (0.2 g) as yellow amorphous.

¹H-NMR (δ, CDCl₃) 0.85 to 0.99 (9H, m), 1.22 to 1.45 (2H, m), 1.54 to 1.65 (2H, m), 2.08 (1H, br), 2.28 (3H, s), 2.93 (2H, t-like), 3.19 (2H, d, J=7.4 Hz), 3.37 (2H, t-like), 3.55 (2H, t, J=6.6 Hz), 3.80 (2H, t, J=5.0 Hz), 4.16 (2H, t, J=5.0 Hz), 6.05 (1H, s), 6.65 (H, br), 6.72 to 6.73 (1H, m), 6.90 to 7.06 (5H, m), 7.38 to 7.68 (10H, m), 8.16 (1H, d, J=6.6 Hz).

IR (KBr) ν: 2957, 2934, 2870, 1653, 1607, 1514, 1499 cm⁻¹.

Anal calcd for $C_{40}H_{47}N_3O_5 \cdot 0.5H_2O$: C, 72.92; H, 7.34; N, 6.38. Found: C, 72.81; H, 7.43; N, 6.38.

Example 3

(Preparation of Compound 3)

7-[4-(2-butoxyethoxy)phenyl]-N-[4-[hydroxy(1-oxidopyridin-2-yl)methyl]-3-methoxyphenyl]-1-trifluoroacetyl-2,3-dihydro-1H-1-benzazepine-4-carboxamide (0.4 g) was dissolved in ethanol (300 ml), and to the solution, sodium borohydride (0.11 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(1-oxidopyridin-2-yl)methyl]-3-methoxyphenyl]-2,3-dihydro-1H-1-benzazepine-4-carboxamide (compound 3) (0.35 g) as yellow crystals.

mp 116 to 118° C.

¹H-NMR (δ, CDCl₃) 0.93 (3H, t, J=7.1 Hz), 1.26 to 1.57 (4H, m), 2.96 (2H, t-like), 3.48 (2H, t-like), 3.55 (2H, t, J=6.6 Hz), 3.73 to 3.90 (5H, m), 4.16 (2H, t, J=5.0 Hz), 4.61 (1H, br), 6.33 (1H, d, J=4.8 Hz), 6.67 to 6.73 (2H, m), 6.87 to 7.00 (4H, m), 7.21 to 7.48 (7H, m), 7.63 to 7.75 (3H, m), 8.22 to 8.26 (1H, m).

IR (KBr) ν: 2934, 2872, 1651, 1609, 1499 cm⁻¹.

Anal calcd for $C_{36}H_{39}N_3O_6 \cdot 0.75H_2O$: C, 69.38; H, 6.55; N, 6.74. Found :C, 69.55; H, 6.66; N, 6.38.

Example 4

(Preparation of Compound 4)

7-[4-(2-butoxyethoxy)phenyl]-N-[4-[hydroxy(1-oxidopyridin-2-yl)methyl]-3-methoxyphenyl]-2,3-dihydro-1H-1-benzazepine-4-carboxamide (0.3 g) and isobutylaldehyde (0.22 ml) were dissolved in 1,2-dichloroethane (15 ml), and to the solution, triacetoxy sodium borohydride (0.31 g) was added under ice-cooling and the mixture was stirred overnight at room temperature. The mixture was poured into water, neutralized with solution of sodium bicarbonate, and extracted with ethyl acetate. The organic layer was washed with water and saturated brine, and then, dried over anhydrous magnesium sulfate. The solvent was distilled off, to give 7-[4-(2-butoxyethoxy)phenyl]-N-[4-[hydroxy(1-oxidopyridin-2-yl)methyl]-3-methoxyphenyl]-1-isobutyl-2,3-dihydro-1H-1-benzazepine-4-carboxamide (compound 4) (0.3 g) as yellow amorphous.

¹H-NMR (δ, CDCl₃) 0.90 to 1.00 (9H, m), 1.26 to 1.65 (4H, m), 2.00 to 2.15 (1H, m), 2.93 (2H, t-like), 3.20 (2H, d, J=7.2 Hz), 3.38 (2H, t-like), 3.55 (2H, t, J=6.5 Hz), 3.74 to 3.83 (5H, m), 4.16 (2H, t, J=4.8 Hz), 6.33 (1H, d, J=4.8 Hz), 6.69 (1H, d, J=4.8 Hz), 6.88 to 7.00 (5H, m), 7.21 to 7.26 (1H, m), 7.40 to 7.52 (6H, m), 7.63 to 7.68 (2H, m), 7.77 (1H, s), 8.22 to 8.24 (1H, m).

IR (KBr) ν: 2959, 1653, 1605, 1499 cm⁻¹.

Anal calcd for $C_{40}H_{47}N_3O_6 \cdot 0.25H_2O$: C, 71.67; H, 7.14; N, 6.27. Found: C, 71.51; H, 7.24; N, 6.17.

Example 5

(Preparation of Compound 5)

7-[4-(2-butoxyethoxy)phenyl]-N-[3-chloro-4-[hydroxy(1-oxidopyridin-2-yl)methyl]phenyl]-1-trifluoroacetyl-2,3-dihydro-1H-1-benzazepine-4-carboxamide (0.24 g) was dissolved in ethanol (30 ml), and to the solution, sodium borohydride (0.065 g) was added under ice-cooling and the mixture was stirred at room temperature for 3 hours. The solvent was distilled off, and to the residue was added water, and the mixture was extracted with ethyl acetate. The organic layer was washed with water and saturated brine, and then, dried over anhydrous magnesium sulfate. The solvent was distilled off, to give 7-[4-(2-butoxyethoxy)phenyl]-N-[3-chloro-4-[hydroxy(1-oxidopyridin-2-yl)methyl]phenyl]-2,3-dihydro-1H-1-benzazepine-4-carboxamide (compound 5) (0.3 g) as yellow amorphous.

¹H-NMR (δ, CDCl₃) 0.93 (3H, t, J=7.3 Hz), 1.29 to 1.48 (2H, m), 1.54 to 1.72 (2H, m), 2.92 (2H, br), 3.43 (2H, br), 3.55 (2H, t, J=6.6 Hz), 3.80 (2H, t, J=4.8 Hz), 4.12 (2H, t, J=4.8 Hz), 4.60 (1H, br), 6.39 (1H, s), 6.69 (1H, d, J=8.4 Hz), 6.85 to 6.98 (3H, m), 7.23 to 7.55 (9H, m), 7.60 to 8.00 (3H, m), 8.26 (1H, br).

IR (KBr) ν: 2934, 2872, 1692 cm⁻¹.

Example 6

(Preparation of Compound 6)

7-[4-(2-butoxyethoxy)phenyl]-N-[3-chloro-4-[hydroxy(1-oxidopyridin-2-yl)methyl]phenyl]-2,3-dihydro-1H-1-benzazepine-4-carboxamide (0.3 g) and isobutylaldehyde (0.22 ml) were dissolved in 1,2-dichloroethane (30 ml), and to the solution, triacetoxy sodium borohydride (0.31 g) was added under ice-cooling and the mixture was stirred overnight at room temperature. To the mixture, isobutylaldehyde (0.22 ml) and triacetoxy sodium borohydride (0.31 g) were further added, and the mixture was stirred overnight at room temperature. The mixture was neutralized with solution of sodium bicarbonate, concentrated, and extracted with ethyl acetate. The organic layer was washed with water and saturated brine, and then, dried over anhydrous magnesium sulfate. The solvent was distilled off, and the residue was purified by silica gel column chromatography (elution solvent: ethyl acetate) to give crude crystals, which were recrystalized from ethyl acetate-hexane, to give 7-[4-(2-butoxyethoxy)phenyl]-N-[3-chloro-4-[hydroxy(1-oxidopyridin-2-yl)methyl]phenyl]-1-isobutyl-2,3-dihydro-1H-1-benzazepine-4-carboxamide (compound 6) (0.2 g) as yellow crystals.

mp 105 to 107° C.

$^1$H-NMR (δ, $CDCl_3$) 0.85 to 0.99 (9H, m), 1.22 to 1.68 (4H, m), 2.00 to 2.11 (1H, m), 2.92 (2H, t, J=4.6 Hz), 3.19 (2H, d, J=7.6 Hz), 3.37 (2H, t, J=4.6 Hz), 3.55 (2H, t, J=6.6 Hz), 3.80 (2H, t, J=4.9 Hz), 4.16 (2H, t, J=4.9 Hz), 6.39 (1H, d, J=3.7 Hz), 6.68 (1H, d, J=3.7 Hz), 6.82 to 7.00 (4H, m), 7.20 to 7.30 (1H, m), 7.38 to 7.51 (6H, m), 7.72 (1H, s), 7.78 (1H, d, J=8.8 Hz), 7.94 (1H, d, J=2.2 Hz), 8.26 to 8.30 (1H, m).

IR (KBr) ν: 2957, 2934, 2870, 1651, 1659, 1607, 1588, 1499 $cm^{-1}$.

Anal calcd for $C_{39}H_{44}ClN_3O_5.0.25H_2O$: C, 69.42; H, 6.65; N, 6.23. Found: C, 69.45; H, 6.52; N, 6.23.

Example 7

(Preparation of Compound 7)

7-[4-(2-butoxyethoxy)phenyl]-N-[4-[hydroxy(1-oxidopyridin-2-yl)methyl]-3-methylphenyl]-1-trifluoroacetyl-2,3-dihydro-1H-1-benzazepine-4-carboxamide (0.77 g) was dissolved in ethanol (200 ml), and to the solution, sodium borohydride (0.13 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(1-oxidopyridin-2-yl)methyl]-3-methylphenyl]-2,3-dihydro-1H-1-benzazepine-4-carboxamide (compound 7) (0.64 g) as yellow crystals.

mp 179 to 182° C. (dec.).

$^1$H-NMR (δ, $CDCl_3$) 0.93 (3H, t, J=7.3 Hz), 1.22 to 1.64 (4H, m), 2.21 (3H, s), 2.96 (2H, t, J=4.4 Hz), 3.46 (2H, t, J=4.4 Hz), 3.55 (2H, t, J=6.6 Hz), 3.80 (2H, t, J=4.9 Hz), 4.15 (2H, t, J=4.9 Hz), 4.63 (1H, br), 6.27 (2H, s), 6.68 to 6.76 (1H, m), 6.97 (2H, d, J=8.8 Hz), 7.16 to 7.33 (3H, m), 7.43 to 7.47 (4H, m), 7.56 to 7.60 (2H, m), 7.70 (1H, s), 8.30 (1H, dd, J=1.0, 5.8 Hz).

IR (KBr) ν: 2955, 2928, 2872, 1645, 1609, 1501 $cm^{-1}$.

Anal calcd for $C_{36}H_{39}N_3O_5.0.5H_2O$: C, 71.74; H, 6.69; N, 6.97. Found: C, 71.75; H, 6.65; N, 6.81.

Example 8

(Preparation of Compound 8)

7-[4-(2-butoxyethoxy)phenyl]-N-[4-[hydroxy(1-oxidopyridin-2-yl)methyl]-3-methylphenyl]-2,3-dihydro-1H-1-benzazepine-4-carboxamide (0.6 g) and isobutylaldehyde (0.46 ml) were dissolved in 1,2-dichloroethane (50 ml), and to the solution, triacetoxy sodium borohydride (0.64 g) was added under ice-cooling and the mixture was stirred overnight at room temperature. To the mixture, isobutylaldehyde (0.46 ml) and triacetoxy sodium borohydride (0.64 g) were further added, and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, and the residue was purified by silica gel column chromatography (elution solvent: ethyl acetate/methanol/triethylamine) to give 7-[4-(2-butoxyethoxy)phenyl]-N-[4-[hydroxy(1-oxidopyridin-2-yl)methyl]-3-methylphenyl]-1-isobutyl-2,3-dihydro-1H-1-benzazepine-4-carboxamide (compound 8) (0.6 g) as pale yellow amorphous.

$^1$H-NMR (δ, $CDCl_3$) 0.85 to 0.99 (9H, m), 1.26 to 1.68 (4H, m), 2.04 to 2.14 (1H, m), 2.21 (3H, s), 2.93 (2H, t-like), 3.19 (2H, d, J=7.0 Hz), 3.36 (2H, t-like), 3.55 (2H, t, J=6.6 Hz), 3.80 (2H, t, J=5.0 Hz), 4.15 (2H, t, J=5.0 Hz), 6.27 (2H, br), 6.73 (1H, dd, J=2.4, 7.8 Hz), 6.90 to 6.99 (3H, m), 7.16 to 7.30 (2H, m), 7.37 to 7.60 (7H, m), 7.72 (1H, s), 8.30 (1H, d, J=4.8 Hz).

IR (KBr) ν: 2957, 2932, 2870, 1645, 1607, 1520, 1499 $cm^{-1}$.

Anal calcd for $C_{40}H_{47}N_3O_5.0.5H_2O$: C, 72.92; H, 7.34; N, 6.38. Found: C, 72.74; H, 7.47; N, 6.18.

Example 9

(Preparation of Compound 9)

7-[4-(2-butoxyethoxy)phenyl]-N-[4-[hydroxy(4-methyl-1-oxidopyridin-2-yl)methyl]-3-methoxyphenyl]-1-trifluoroacetyl-2,3-dihydro-1H-1-benzazepine-4-carboxamide (0.77 g) was dissolved in ethanol (200 ml), and to the solution, sodium borohydride (0.12 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(4-methyl-1-oxidopyridin-2-yl)methyl]-3-methoxyphenyl]-2,3-dihydro-1H-1-benzazepine-4-carboxamide (compound 9) (0.56 g) as yellow amorphous.

$^1$H-NMR (δ, $CDCl_3$) 0.93 (3H, t, J=7.3 Hz), 1.22 to 1.57 (4H, m), 2.27 (3H, s), 2.96 (2H, t-like), 3.47 (2H, t-like), 3.55 (2H, t, J=6.6 Hz), 3.78 to 3.89 (5H, m), 4.16 (2H, t, J=4.8 Hz), 4.61 (1H, br), 6.32 (1H, s), 6.68 to 6.76 (2H, m), 6.85 to 7.02 (5H, m), 7.30 to 7.47 (5H, m), 7.62 (1H, d, J=8.6 Hz), 7.73 (1H, s), 7.80 (1H, br), 8.12 (1H, d, J=6.2 Hz).

IR (KBr) ν: 2936, 2868, 1647, 1607, 1507 $cm^{-1}$.

Anal calcd for $C_{37}H_{41}N_3O_6.1.5H_2O$: C, 68.29; H, 6.81; N, 6.46. Found: C, 68.46; H, 6.52; N, 6.39.

Example 10

(Preparation of Compound 10)

7-[4-(2-butoxyethoxy)phenyl]-N-[4-[hydroxy(4-methyl-1-oxidopyridin-2-yl)methyl]-3-methoxyphenyl]-2,3-dihydro-1H-1-benzazepine-4-carboxamide (0.5 g) and isobutylaldehyde (0.23 ml) were dissolved in 1,2-dichloroethane (30 ml), and to the solution, triacetoxy sodium borohydride (0.85 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, and the residue was purified by silica gel column chromatography (elution solvent: ethyl acetate/methanol/triethylamine) to give crude crystals, which were recrystallized from ethyl acetate-hexane, to give 7-[4-(2-butoxyethoxy)phenyl]-N-[4-[hydroxy(4-methyl-1-oxidopyridin-2-yl)methyl]-3-methoxyphenyl]-1-isobutyl-2,3-dihydro-1H-1-benzazepine-4-carboxamide (compound 10) (0.38 g) as yellow crystals.

mp 174 to 176° C.

$^1$H-NMR (δ, CDCl$_3$) 0.89 to 1.00 (9H, m), 1.23 to 1.65 (4H, m), 2.00 to 2.20 (1H, m), 2.27 (3H, s), 2.93 (2H, t-like), 3.20 (2H, d, J=6.8 Hz), 3.38 (2H, t-like), 3.55 (2H, t, J=6.5 Hz), 3.75 to 3.83 (5H, m), 4.16 (2H, t, J=5.0 Hz), 6.32 (1H, d, J=4.4 Hz), 6.74 (1H, s), 6.88 to 7.03 (6H, m), 7.39 to 7.52 (5H, m), 7.62 to 7.70 (2H, m), 7.77 (1H, d, J=1.8 Hz), 8.12 (1H, d, J=6.6 Hz).

IR (KBr) ν: 2957, 2911, 1605, 1499 cm$^{-1}$.

Anal calcd for C$_{41}$H$_{49}$N$_3$O$_6$.0.5H$_2$O: C, 71.49; H, 7.32; N, 6.10. Found: C, 71.46; H, 7.18; N, 6.12.

Example 11

(Preparation of Compound 11)

7-[4-(2-butoxyethoxy)phenyl]-N-[3-ethoxy-4-[hydroxy(4-methyl-1-oxidopyridin-2-yl)methyl]phenyl]-1-trifluoroacetyl-2,3-dihydro-1H-1-benzazepine-4-carboxamide (0.85 g) was dissolved in ethanol (200 ml), and to the solution, sodium borohydride (0.13 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[3-ethoxy-4-[hydroxy(4-methyl-1-oxidopyridin-2-yl)methyl]phenyl]-2,3-dihydro-1H-1-benzazepine-4-carboxamide (compound 11) (0.66 g) as yellow crystals.

mp 110 to 115° C.

$^1$H-NMR (δ, CDCl$_3$) 0.85 to 0.97 (6H, m), 1.23 to 1.65 (4H, m), 2.28 (3H, s), 2.96 (2H, t-like), 3.47 (2H, t-like), 3.55 (2H, t, J=6.6 Hz), 3.80 (2H, t, J=4.8 Hz), 4.02 to 4.18 (4H, m), 4.61 (1H, br), 6.27 to 6.28 (1H, m), 6.70 (1H, d, J=8.0 Hz), 6.85 to 7.03 (6H, m), 7.30 to 7.35 (2H, m), 7.43 to 7.47 (3H, m), 7.64 to 7.72 (3H, m), 8.10 (1H, d, J=6.6 Hz).

IR (KBr) ν: 2936, 2870, 1651, 1609, 1499 cm$^{-1}$.

Anal calcd for C$_{38}$H$_{43}$N$_3$O$_6$.0.5H$_2$O: C, 70.57; H, 6.86; N, 6.50. Found: C, 70.27; H, 7.00; N, 6.48.

Example 12

(Preparation of Compound 12)

7-[4-(2-butoxyethoxy)phenyl]-N-[3-ethoxy-4-[hydroxy(4-methyl-1-oxidopyridin-2-yl)methyl]phenyl]-2,3-dihydro-1H-1-benzazepine-4-carboxamide (0.6 g) and isobutylaldehyde (0.27 ml) were dissolved in 1,2-dichloroethane (50 ml), and to the solution, triacetoxy sodium borohydride (1 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, and the residue was purified by silica gel column chromatography (elution solvent: ethyl acetate) to give crude crystals, which were recrystallized from ethyl acetate-hexane, to give 7-[4-(2-butoxyethoxy)phenyl]-N-[3-ethoxy-4-[hydroxy(4-methyl-1-oxidopyridin-2-yl)methyl]phenyl]-1-isobutyl-2,3-dihydro-1H-1-benzazepine-4-carboxamide (compound 12) (0.53 g) as yellow crystals.

mp 108 to 110° C.

$^1$H-NMR (δ, CDCl$_3$) 0.85 to 0.99 (12H, m), 1.23 to 1.65 (4H, m), 2.00 to 2.15 (1H, m), 2.28 (3H, s), 2.92 (2H, t-like), 3.19 (2H, d, J=7.4 Hz), 3.38 (2H, t-like), 3.55 (2H, t, J=6.5 Hz), 3.80 (2H, t, J=5.0 Hz), 4.02 to 4.18 (4H, m), 6.29 (1H, d, J=5.6 Hz), 6.84 to 7.06 (7H, m), 7.38 to 7.53 (5H, m), 7.65 to 7.69 (2H, m), 7.75 (1H, d, J=2.0 Hz), 8.10 (1H, d, J=6.6 Hz).

IR (KBr) ν: 2959, 2870, 1651, 1605, 1499 cm$^{-1}$. Anal calcd for C$_{42}$H$_{51}$N$_3$O$_6$H$_2$O: C, 70.86; H, 7.50; N, 5.90. Found: C, 71.25; H, 7.57; N, 6.00.

Example 13

(Preparation of Compound 13)

7-[4-(2-butoxyethoxy)phenyl]-N-[4-[hydroxy(1-oxidopyridin-2-yl)methyl]-3-trifluoromethylphenyl]-2,3-dihydro-1H-1-benzazepine-4-carboxamide (0.53 g) and propionyl aldehyde (0.3 ml) were dissolved in 1,2-dichloroethane (50 ml), and to the solution, triacetoxy sodium borohydride (0.87 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, and the residue was purified by silica gel column chromatography (elution solvent: ethyl acetate/methanol/triethylamine), to give 7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide (compound 13) (0.46 g) as yellow amorphous.

$^1$H-NMR (δ, CDCl$_3$) 0.88 to 1.01 (6H, m), 1.28 to 1.78 (6H, m), 2.89 (2H, t-like), 3.24 to 3.31 (4H, m), 3.54 (2H, t, J=6.6 Hz), 3.79 (2H, t, J=4.9 Hz), 4.13 (2H, t, j=4.9 Hz), 6.43 (1H, s), 6.60 to 6.65 (2H, m), 6.84 to 6.96 (3H, m), 7.12 to 7.27 (2H, m), 7.36 to 7.44 (5H, m), 7.76 to 7.92 (2H, m), 8.05 to 8.06 (1H, m), 8.21 to 8.24 (H, m), 8.50 (1H, s).

IR (KBr) ν: 2957, 2872, 1653, 1607 cm$^{-1}$.

Anal calcd for C$_{39}$H$_{42}$F$_3$N$_3$O$_5$.0.5H$_2$O: C, 67.03; H, 6.20; N, 6.01. Found: C, 67.40; H, 6.36; N, 6.02.

Example 14

(Preparation of Compound 14 and Compound 15)

7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide (0.4 g) was optically resoluted with CHIRALPAK AD 50 mm ID×500 mL and the elution solvent (hexane/ethanol). The fractions were concentrated and dried, and the residue was dissolved in ethanol, and then, was filtered by 0.45 μm filter. The filtrate was concentrated, hexane was added and dried to a solid, to give (+)-7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide (compound 14) (160 mg, >99.9% ee), (−)-7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide (compound 15) (160 mg, >99.9% ee).

(+) isomer: $[\alpha]_D$=+18.1° (c=0.497%, ethanol solution)
(−) isomer: $[\alpha]_D$=−18.5° (c=0.500%, ethanol solution)

Example 15

(Preparation of Compound 16 Preparation)

7-[4-(2-butoxyethoxy)phenyl]-N-[4-[hydroxy(4-methyl-1-oxidopyridin-2-yl)methyl]-3-trifluoromethylphenyl]-1-trifluoroacetyl-2,3-dihydro-1H-1-benzazepine-4-carboxamide (1 g) was dissolved in ethanol (100 ml), and to the solution, sodium borohydride (0.15 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(4-methyl-1-oxidopyridin-2-yl)methyl]-3-trifluoromethylphenyl]-2,3-dihydro-1H-1-benzazepine-4-carboxamide (compound 16) (0.63 g) as yellow crystals.

mp 124 to 128° C.

$^1$H-NMR (δ, CDCl$_3$) 0.93 (3H, t, J=7.1 Hz), 1.27 to 1.68 (4H, m), 2.23 (3H, s), 2.98 (2H, t-like), 3.49 (2H, t-like), 3.55 (2H, t, J=6.6 Hz), 3.80 (2H, t, J=5.0 Hz), 4.16 (2H, t, J=5.0 Hz), 4.65 (1H, br), 6.38 to 6.43 (2H, m), 6.71 (1H, d, J=8.6 Hz), 6.95 to 7.07 (4H, m), 7.31 to 7.54 (5H, m), 7.82 to 7.95 (3H, m), 8.04 (1H, s), 8.17 (1H, d, J=6.6 Hz).

IR (KBr) ν: 2934, 2847, 1653, 1609, 1499 cm$^{-1}$.

Anal calcd. for C$_{37}$H$_{38}$F$_3$N$_3$O$_5$·H$_2$O: C, 65.38; H, 5.93; N, 6.18. Found: C, 65.16; H, 5.81; N, 6.17.

Example 16

(Preparation of Compound 17)

7-[4-(2-butoxyethoxy)phenyl]-N-[4-[hydroxy(4-methyl-1-oxidopyridin-2-yl)methyl]-3-trifluoromethylphenyl]-2,3-dihydro-1H-1-benzazepine-4-carboxamide (0.3 g) and propionyl aldehyde (0.16 ml) were dissolved in 1,2-dichloroethane (25 ml), and to the solution, triacetoxy sodium borohydride (0.48 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, to give crude crystals, which were recrystallized from ethyl acetate-hexane, to give 7-[4-(2-butoxyethoxy)phenyl]-N-[4-[hydroxy(4-methyl-1-oxidopyridin-2-yl)methyl]-3-trifluoromethylphenyl]-1-propyl-2,3-dihydro-1H-1-benzazepine-4-carboxamide (compound 17) (0.28 g) as yellow crystals.

mp 103 to 105° C.

$^1$H-NMR (δ, CDCl$_3$) 0.88 to 1.04 (6H, m), 1.22 to 1.82 (6H, m), 2.23 (3H, s), 2.94 (2H, t-like), 3.30 to 3.37 (4H, m), 3.55 (2H, t, J=6.6 Hz), 3.80 (2H, t, J=5.0 Hz), 4.16 (2H, t, J=5.0 Hz), 6.37 (1H, d, J=2.2 Hz), 6.43 (1H, s), 6.89 to 7.06 (5H, m), 7.40 to 7.52 (5H, m), 7.85 to 7.96 (3H, m), 8.05 (1H, s), 8.17 (1H, d, J=6.6 Hz).

IR (KBr) ν: 2961, 2932, 2911, 1659, 1607, 1501 cm$^{-1}$.

Anal calcd for C$_{40}$H$_{44}$F$_3$N$_3$O$_5$: C, 68.26; H, 6.30; N, 5.97. Found: C, 67.88; H, 6.27; N, 6.11.

Example 17

(Preparation of Compound 18 and Compound 19)

7-[4-(2-butoxyethoxy)phenyl]-N-[4-[hydroxy(4-methyl-1-oxidopyridin-2-yl)methyl]-3-trifluoromethylphenyl]-1-propyl-2,3-dihydro-1H-1-benzazepine-4-carboxamide (0.11 g) was optically resoluted with CHIRALPAK AD 50 mm ID×500 mL and the elution solvent (hexane/ethanol). The fractions were concentrated and dried, and the residue was dissolved in ethanol, and then, was filtered by 0.45 μm filter. The filtrate was concentrated, hexane was added and dried to a solid, to give (+)-7-[4-(2-butoxyethoxy)phenyl]-N-[4-[hydroxy(4-methyl-1-oxidopyridin-2-yl)methyl]-3-trifluoromethylphenyl]-1-propyl-2,3-dihydro-1H-1-benzazepine-4-carboxamide (compound 18) (54 mg, >99.9% ee), (−)-7-[4-(2-butoxyethoxy)phenyl]-N-[4-[hydroxy(4-methyl-1-oxidopyridin-2-yl)methyl]-3-trifluoromethylphenyl]-1-propyl-2,3-dihydro-1H-1-benzazepine-4-carboxamide (compound 19) (53 mg, >99.9% ee).

(+) isomer: $[\alpha]_D$=+36.0° (c=0.491%, ethanol solution).
(−) isomer: $[\alpha]_D$=−30.5° (c=0.118%, ethanol solution).

Example 18

(Preparation of Compound 20)

7-[4-(2-butoxyethoxy)phenyl]-N-[4-[hydroxy(4-methyl-1-oxidopyridin-2-yl)methyl]-3-trifluoromethylphenyl]-2,3-dihydro-1H-1-benzazepine-4-carboxamide (0.3 g) and isobutylaldehyde (0.22 ml) were dissolved in 1,2-dichloroethane (25 ml), and to the solution, triacetoxy sodium borohydride (0.48 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, to give 7-[4-(2-butoxyethoxy)phenyl]-1-isobutyl-N-[4-[hydroxy(4-methyl-1-oxidopyridin-2-yl)methyl]-3-trifluoromethylphenyl]-2,3-dihydro-1H-1-benzazepine-4-carboxamide (compound 20) (0.3 g) as yellow amorphous.

$^1$H-NMR (δ, CDCl$_3$) 0.85 to 1.00 (9H, m), 1.22 to 1.68 (4H, m), 2.05 to 2.12 (1H, m), 2.23 (3H, s), 2.95 (2H, t-like), 3.20 (2H, d, J=7.2 Hz), 3.38 (2H, t-like), 3.55 (2H, t, J=6.6 Hz), 3.81 (2H, t, J=4.8 Hz), 4.16 (2H, t, J=4.8 Hz), 6.37 (1H, d, J=2.2 Hz), 6.44 (1H, s), 6.91 to 7.06 (5H, m), 7.40 to 7.51 (5H, m), 7.90 to 7.93 (3H, m), 8.06 (1H, s), 8.17 (1H, d, J=6.6 Hz).

IR (KBr) ν: 2957, 2870, 1651, 1607, 1520, 1499 cm$^{-1}$.

Anal calcd for $C_{41}H_{46}F_3N_3O_5 \cdot 0.5H_2O$: C, 67.75; H, 6.52; N, 5.78. Found: C, 67.93; H, 6.74; N, 5.67.

Example 19

(Preparation of Compound 21)

7-[4-(2-butoxyethoxy)phenyl]-N-[4-[hydroxy(1-oxidopyridin-2-yl)methyl]-3-(2,2,2-trifluoroethoxy)phenyl]-1-trifluoroacetyl-2,3-dihydro-1H-1-benzazepine-4-carboxamide (1.7 g) was dissolved in ethanol (150 ml), and to the solution, sodium borohydride (0.24 g) was added under ice-cooling and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(1-oxidopyridin-2-yl)methyl]-3-(2,2,2-trifluoroethoxy)phenyl]-2,3-dihydro-1H-1-benzazepine-4-carboxamide (compound 21) (1 g) as yellow amorphous.

$^1$H-NMR (δ, CDCl$_3$) 0.93 (3H, t, J=7.3 Hz), 1.22 to 1.68 (4H, m), 2.94 (2H, t-like), 3.47 (2H, t-like), 3.55 (2H, t, J=6.6 Hz), 3.80 (2H, t, J=5.0 Hz), 4.15 (2H, t, J=5.0 Hz), 4.33 to 4.44 (2H, m), 4.63 (1H, br), 6.24 (H, d, J=6.6 Hz), 6.70 (1H, d, J=8.4 Hz), 6.89 (1H, dd, J=1.8, 8.4 Hz), 6.95 to 7.01 (3H, m), 7.14 to 7.34 (5H, m), 7.42 to 7.47 (3H, m), 7.75 to 7.79 (2H, m), 7.72 (H, d, J=1.8 Hz), 8.17-8.20 (1H, m).

IR (KBr) ν: 3326, 2934, 1651, 1609, 1501 cm$^{-1}$.

Anal calcd for $C_{37}H_{38}F_3N_3O_6 \cdot 0.5H_2O$: C, 64.71; H, 5.72; N, 6.12. Found: C, 64.70; H, 5.79; N, 5.84.

Example 20

(Preparation of Compound 22)

7-[4-(2-butoxyethoxy)phenyl]-N-[4-[hydroxy(1-oxidopyridin-2-yl)methyl]-3-(2,2,2-trifluoroethoxy)phenyl]-2,3-dihydro-1H-1-benzazepine-4-carboxamide (0.5 g) and propionyl aldehyde (0.27 ml) were dissolved in 1,2-dichloroethane (25 ml), and to the solution, triacetoxy sodium borohydride (0.78 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off, to give 7-[4-(2-butoxyethoxy)phenyl]-N-[4-[hydroxy(1-oxidopyridin-2-yl)methyl]-3-(2,2,2-trifluoroethoxy)phenyl]-1-propyl-2,3-dihydro-1H-1-benzazepine-4-carboxamide (compound 22) (0.49 g) as pale yellow amorphous.

$^1$H-NMR (δ, CDCl$_3$) 0.85 to 1.03 (6H, m), 1.22 to 1.81 (6H, m), 2.91 (2H, t-like), 3.29 to 3.36 (4H, m), 3.55 (2H, t, J=6.6 Hz), 3.80 (2H, t, J=5.0 Hz), 4.16 (2H, t, J=5.0 Hz), 4.33 to 4.45 (2H, m), 6.24 (1H, d, J=7.0 Hz), 6.85 to 7.03 (5H, m), 7.14 to 7.32 (3H, m), 7.40 to 7.50 (5H, m), 7.70 (1H, s), 7.78 (1H, d, J=8.4 Hz), 7.88 (1H, s), 8.18 to 8.20 (1H, m).

IR (KBr) ν: 2961, 2934, 2872, 1651, 1605, 1499 cm$^{-1}$.

Anal calcd for $C_{40}H_{44}F_3N_3O_6 \cdot 0.5H_2O$: C, 65.92; H, 6.22; N, 5.77. Found: C, 66.16; H, 6.00; N, 5.78.

Example 21

(Preparation of Compound 23)

7-[4-(2-butoxyethoxy)phenyl]-N-[4-[hydroxy(1-oxidopyridin-2-yl)methyl]-3-(2,2,2-trifluoroethoxy)phenyl]-2,3-dihydro-1H-1-benzazepine-4-carboxamide (0.45 g) and isobutylaldehyde (0.32 ml) were dissolved in 1,2-dichloroethane (15 ml), and to the solution, triacetoxy sodium borohydride (0.7 g) was added under ice-cooling and the mixture was stirred overnight at room temperature. The mixture was neutralized with solution of sodium bicarbonate, concentrated, and extracted with ethyl acetate. The organic layer was washed with water and saturated brine, and dried over anhydrous magnesium sulfate. The solvent was distilled off to give crude crystals, which were recrystallized from ethyl acetate-hexane, to give 7-[4-(2-butoxyethoxy)phenyl]-1-isobutyl-N-[4-[hydroxy(1-oxidopyridin-2-yl)methyl]-3-(2,2,2-trifluoroethoxy)phenyl]-2,3-dihydro-1H-1-benzazepine-4-carboxamide (compound 23) (0.44 g) as yellow crystals.

mp 118 to 123° C.

$^1$H-NMR (δ, CDCl$_3$) 0.86 to 0.99 (9H, m), 1.26 to 1.68 (4H, m), 1.95 to 2.15 (1H, m), 2.91 (2H, t-like), 3.20 (2H, d, J=6.8 Hz), 3.38 (2H, t-like), 3.55 (2H, t, J=6.6 Hz), 3.81 (2H, t, J=4.9 Hz), 4.16 (2H, t, J=4.9 Hz), 4.34 to 4.46 (2H, m), 6.25 (1H, d, J=7.0 Hz), 6.87 to 7.04 (5H, m), 7.19 to 7.30 (3H, m), 7.40 to 7.51 (5H, m), 7.70 (1H, s), 7.79 (1H, d, J=8.0 Hz), 7.89 (1H, d, J=2.2 Hz), 8.20 (1H, d, J=6.0 Hz).

IR (KBr) ν: 2955, 2870, 1651, 1605, 1499 cm$^{-1}$.

Anal calcd for $C_{41}H_{46}F_3N_3O_6$: C, 67.11; H, 6.32; N, 5.73. Found: C, 66.75; H, 6.35; N, 5.46.

Example 22

(Preparation of Compound 24)

To 7-[4-(2-butoxyethoxy)phenyl]-N-(4-hydroxyphenyl)-1-propyl-2,3-dihydro-1H-1-benzazepine-4-carboxamide (0.62 g), 3-chloromethyl-4-methyl-4H-1,2,4-triazole hydrochloride (0.24 g) and potassium carbonate (0.5 g), N,N-dimethylformamide (15 ml) was added and the mixture was stirred overnight under nitrogen atmosphere at room temperature. The mixture was poured into water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy)phenyl]-N-[4-[(4-methyl-4H-1,2,4-triazol-3-yl) methoxy]phenyl]-1-propyl-2,3-dihydro-1H-1-benzazepine-4-carboxamide (compound 24) (0.48 g) as yellow amorphous.

$^1$H-NMR (δ, CDCl$_3$) 0.85 to 1.06 (6H, m), 1.25 to 1.80 (6H, m), 2.90 (2H, t-like), 3.25 to 3.38 (4H, m), 3.55 (2H, t, J=6.6 Hz), 3.77 (3H, s), 3.80 (2H, t, J=4.8 Hz), 4.15 (2H, t, J=4.8 Hz), 5.29 (2H, s), 6.87 to 7.03 (5H, m), 7.40 to 7.58 (8H, m), 8.11 (1H, s).

IR (KBr) ν: 2957, 2930, 2872, 1501 cm$^{-1}$.

Anal calcd for $C_{36}H_{43}N_5O_4 \cdot 0.25H_2O$: C, 70.39; H, 7.14; N, 11.40. Found: C, 70.35; H, 7.46; N, 11.46.

Example 23

(Preparation of Compound 25)

To 7-[4-(2-butoxyethoxy)phenyl]-1-isobutyl-N-(4-hydroxyphenyl)-2,3-dihydro-1H-1-benzazepine-4-carboxamide (0.5 g), 2-chloromethyl-1-propylimidazole hydrochloride (0.22 g) and potassium carbonate (0.4 g), N,N-dimethylformamide (15 ml) was added, and the mixture was stirred overnight under nitrogen atmosphere at room temperature. The mixture was poured into water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/hexane) to give crude crystals, which were recrystallized from ethyl acetate-hexane, to give 7-[4-(2-butoxyethoxy)phenyl]-1-isobutyl-N-[4-[(1-propylimidazole-2-yl) methoxy]phenyl]-2,3-dihydro-1H-1-benzazepine-4-carboxamide (compound 25) (0.51 g) as pale yellow crystals.

mp 118 to 120° C.

$^1$H-NMR (δ, CDCl$_3$) 0.89 to 0.98 (12H, m), 1.30 to 1.69 (4H, m), 1.77 to 1.88 (2H, m), 2.04 to 2.10 (1H, m), 2.91 (2H, t-like), 3.18 (2H, d, J=7.2 Hz), 3.36 (2H, t-like), 3.55 (2H, t, J=6.6 Hz), 3.80 (2H, t, J=5.0 Hz), 3.97 (2H, t, J=7.3 Hz), 4.16 (2H, t, J=5.0 Hz), 5.14 (2H, s), 6.89 to 7.04 (7H, m), 7.37 to 7.51 (8H, m).

IR (KBr) ν: 2957, 2934, 2870, 1647, 1605, 1499, 1510 cm$^{-1}$

Anal calcd for C$_{40}$H$_{50}$N$_4$O$_4$.0.25H$_2$O: C, 73.31; H, 7.77; N, 8.55. Found: C, 73.07; H, 7.67; N, 8.44.

Example 24

(Preparation of Compound 26)

To 7-[4-(2-butoxyethoxy)phenyl]-1-isobutyl-N-(4-hydroxyphenyl)-2,3-dihydro-1H-1-benzazepine-4-carboxamide (0.5 g), 3-chloromethyl-4-propyl-4H-1,2,4-triazole hydrochloride (0.22 g) and potassium carbonate (0.4 g), N,N-dimethylformamide (10 ml) was added, and the mixture was stirred overnight under nitrogen atmosphere at room temperature. The mixture was poured into water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy)phenyl]-1-isobutyl-N-[4-[(4-propyl-4H-1,2,4-triazol-3-yl)methoxy]phenyl]-2,3-dihydro-1H-1-benzazepine-4-carboxamide (compound 26) (0.47 g) as pale yellow amorphous.

$^1$H-NMR (δ, CDCl$_3$) 0.89 to 1.01 (12H, m), 1.23 to 1.56 (4H, m), 1.80 to 1.91 (2H, m), 2.00 to 2.18 (1H, m), 2.91 (2H, t-like), 3.18 (2H, d, J=7.2 Hz), 3.36 (2H, t-like), 3.55 (2H, t, J=6.6 Hz), 3.81 (2H, t, J=5.0 Hz), 4.03 (2H, t, J=7.3 Hz), 4.16 (2H, t, J=5.0 Hz), 5.28 (2H, s), 6.89 to 7.03 (5H, m), 7.38 to 7.59 (8H, m), 8.15 (1H, s).

IR (KBr) ν: 2957, 2868, 1647, 1605, 1507 cm$^{-1}$.

Anal calcd for C$_{39}$H$_{49}$N$_5$O$_4$.0.25H$_2$O: C, 71.37; H, 7.60; N, 10.67. Found: C, 71.12; H, 7.58; N, 10.88.

Example 25

(Preparation of Compound 27)

To 7-[4-(2-butoxyethoxy)phenyl]-1-isobutyl-N-(4-hydroxyphenyl)-2,3-dihydro-1H-1-benzazepine-4-carboxamide (0.3 g), 3-chloromethyl-4-isobutyl-4H-1,2,4-triazole hydrochloride (0.15 g) and potassium carbonate (0.4 g), N,N-dimethylformamide (5 ml) was added, and the mixture was stirred overnight under nitrogen atmosphere at room temperature. The mixture was poured into water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy)phenyl]-1-isobutyl-N-[4-[(4-isobutyl-4H-1,2,4-triazol-3-yl)methoxy]phenyl]-2,3-dihydro-1H-1-benzazepine-4-carboxamide (compound 27) (0.31 g) as yellow amorphous.

$^1$H-NMR (δ, CDCl$_3$) 0.85 to 1.00 (15H, m), 1.26 to 1.48 (2H, m), 1.54 to 1.68 (2H, m), 2.00 to 2.16 (2H, m), 2.91 (2H, t-like), 3.17 (2H, d, J=7.2 Hz), 3.34 (2H, t-like), 3.55 (2H, t, J=6.6 Hz), 3.78 to 3.86 (4H, m), 4.13 to 4.17 (2H, m), 5.25 (2H, s), 6.88 to 7.01 (5H, m), 7.36 to 7.56 (7H, m), 7.85 (1H, br), 8.09 (1H, s).

IR (KBr) ν: 2950, 2880, 1650, 1600, 1507 cm$^{-1}$.

Example 26

(Preparation of Compound 28)

7-[4-(2-butoxyethoxy)phenyl]-1-isobutyl-2,3-dihydro-1H-1-benzazepine-4-carboxylic acid (1 g) was dissolved in tetrahydrofuran (15 ml), and to the solution, thionyl chloride (0.25 ml) and N,N-dimethylformamide (catalytic amout) were added under ice-cooling, and the mixture was stirred for 1 hour at room temperature. The solvent was distilled off, the residue was dissolved in tetrahydrofuran (25 ml), and the solution was added dropwise to a solution of S-(4-aminophenyl) O-benzyl thiocarbonate (0.6 g) and triethylamine (1 ml) in tetrahydrofuran (15 ml) under ice-cooling. The mixture was stirred overnight under nitrogen atmosphere at room temperature. To the mixture, methanol (15 ml) and 1N sodium hydroxide solution (15 ml) were added, and the mixture was stirred for 30 minutes. To the mixture, 3-chloromethyl-4-isobutyl-4H-1,2,4-triazole hydrochloride (0.53 g) was added, and the mixture was stirred for 1 hour at room temperature. The mixture was concentrated, and extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy)phenyl]-1-isobutyl-N-[4-[(4-isobutyl-4H-1,2,4-triazol-3-yl)methylthio]phenyl]-2,3-dihydro-1H-1-benzazepine-4-carboxamide (compound 28) (0.6 g) as yellow amorphous.

$^1$H-NMR (δ, CDCl$_3$) 0.88 to 1.01 (15H, m), 1.17 to 1.68 (4H, m), 1.70 to 2.15 (2H, m), 2.91 (2H, t-like), 3.18 (2H, d, J=7.0 Hz), 3.34 (2H, t-like), 3.55 (2H, t, J=6.6 Hz), 3.69 (2H, d, J=7.2 Hz), 3.80 (2H, t, J=5.0 Hz), 4.07 (2H, s), 4.16 (2H, t, J=5.0 Hz), 6.90 (1H, d, J=8.8 Hz), 6.97 (2H, d, J=8.8 Hz), 7.28 to 7.46 (7H, m), 7.60 (2H, d, J=8.8 Hz), 7.94 (1H, s), 8.37 (H, br).

IR (KBr) ν: 2959, 2932, 2870, 1651, 1607, 1588, 1497 cm$^{-1}$

Anal calcd for C$_{40}$H$_{51}$N$_5$O$_3$S.0.75H$_2$O: C, 69.08; H, 7.01; N, 10.07. Found: C, 68.84; H, 7.80; N, 10.39.

Example 27

(Preparation of Compound 29)

7-[4-(2-butoxyethoxy)phenyl]-1-isobutyl-N-[4-[(4-isobutyl-4H-1,2,4-triazol-3-yl)methylthio]phenyl]-2,3-dihydro-1H-1-benzazepine-4-carboxamide (0.45 g) was dissolved in dichloromethane (20 ml). The solution was cooled to −78° C., and a solution of 3-chloroperbenzoic acid (0.45 g) in dichloromethane (5 ml) was added dropwise to the solution. The mixture was stirred for 1 hour at −78° C., sodium thiosulfate solution was added to the mixture, and the mixture was concentrated and extracted with ethyl acetate. The organic layer was washed with sodium bicarbonate solution, water, and saturated brine, dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy)phenyl]-1-isobutyl-N-[4-[(4-isobutyl-4H-1,2,4-triazol-3-yl)methylsulfinyl]phenyl]-2,3-dihydro-1H-1-benzazepine-4-carboxamide (compound 29) (0.3 g) as yellow amorphous.

$^1$H-NMR (δ, CDCl$_3$) 0.83 to 1.09 (15H, m), 1.22 to 1.48 (2H, m), 1.54 to 1.65 (2H, m), 1.80 to 1.95 (1H, m), 1.95 to 2.15 (1H, m), 2.95 (2H, t-like), 3.20 (2H, d, J=6.6 Hz), 3.63 (2H, t-like), 3.55 (2H, t, J=6.6 Hz), 3.74 (2H, d, J=7.0 Hz), 3.80 (2H, t, J=5.0 Hz), 4.03 to 4.22 (4H, m), 6.90 to 6.99 (3H, m), 7.15 to 7.45 (7H, m), 7.84 (2H, d, J=8.8 Hz), 8.02 (1H, s), 8.51 (1H, br).

IR (KBr) ν: 2959, 2932, 2872, 1661, 1588, 1518, 1499 cm$^{-1}$.

Example 28

(Preparation of Compound 30 and Compound 31)

7-[4-(2-butoxyethoxy)phenyl]-1-isobutyl-N-[4-[(4-isobutyl-4H-1,2,4-triazol-3-yl)methylsulfinyl]phenyl]-2,3-dihydro-1H-1-benzazepine-4-carboxamide (0.27 g) was optically resolved with CHIRALPAK AD 50 mm ID×500 mL and the elution solvent (hexane/ethanol). The fractions were concentrated and dried, and the residue was dissolved in ethanol, and then, was filtered by 0.45 μm filter. The filtrate was concentrated, hexane was added and dried to a solid, to give (+)-7-[4-(2-butoxyethoxy)phenyl]-1-isobutyl-N-[4-[(4-isobutyl-4H-1,2,4-triazol-3-yl)methylsulfinyl]phenyl]-2,3-dihydro-1H-1-benzazepine-4-carboxamide (compound 30) (0.13 g, >99.9% ee), (−)-7-[4-(2-butoxyethoxy)phenyl]-1-isobutyl-N-[4-[(4-isobutyl-4H-1,2,4-triazol-3-yl)methylsulfinyl]phenyl]-2,3-dihydro-1H-1-benzazepine-4-carboxamide (compound 31) (0.12 g, >99.9% ee) was obtained.

(+) isomer: [α]$_D$=+119.2° (c=0.492%, ethanol solution).
(−) isomer: [α]$_D$=−114.1° (c=0.499%, ethanol solution)

Example 29

(Preparation of Compound 32)

7-[4-(2-butoxyethoxy)phenyl]-1-propyl-2,3-dihydro-1H-1-benzazepine-4-carboxylic acid (0.97 g) was dissolved in tetrahydrofuran (10 ml), and to the solution, thionyl chloride (0.25 ml) and N,N-dimethylformamide (catalytic amout) were added under ice-cooling, and the mixture was stirred for 1 hour at room temperature. The solvent was distilled off, the residue was dissolved in tetrahydrofuran (10 ml), and the solution was added dropwise to a solution of S-(4-aminophenyl) O-benzyl thiocarbonate (0.6 g) and triethylamine (1 ml) in tetrahydrofuran (10 ml) under ice-cooling. The mixture was stirred for 2.5 hours under nitrogen atmosphere at room temperature, methanol (15 ml) and 1N sodium hydroxide solution (15 ml) were added, and stirred for 30 minutes 3-chloromethyl-4-isobutyl-4H-1,2,4-triazole hydrochloride (0.53 g) was added to the reaction mixture, and stirred for 2 hours at room temperature. The mixture was concentrated, and extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy)phenyl]-N-[4-[(4-isobutyl-4H-1,2,4-triazol-3-yl)methylthio]phenyl]-1-propyl-2,3-dihydro-1H-1-benzazepine-4-carboxamide (compound 32) (1.2 g) as pale yellow crystals.

mp 130 to 132° C.

$^1$H-NMR (δ, CDCl$_3$) 0.85 to 1.03 (12H, m), 1.34 to 1.49 (2H, m), 1.54 to 1.80 (4H, m), 1.93 to 2.07 (1H, m), 2.91 (2H, t-like), 3.28 to 3.34 (4H, m), 3.55 (2H, t, J=6.6 Hz), 3.68 (2H, d, J=7.4 Hz), 3.80 (2H, t, J=5.0 Hz), 4.06 (2H, s), 4.16 (2H, t, J=5.0 Hz), 6.87 (1H, d, J=8.4 Hz), 6.97 (2H, d, J=8.8 Hz), 7.26 to 7.46 (7H, m), 7.60 (2H, d, J=8.8 Hz), 7.94 (1H, s), 8.41 (H, br).

IR (KBr) ν: 2961, 2932, 2872, 1655, 1605, 1588, 1499 cm$^{-1}$.

Anal calcd for C$_{39}$H$_{49}$N$_5$O$_3$S: C, 70.13; H, 7.39; N, 10.49. Found: C, 69.89; H, 7.52; N, 10.46.

Example 30

(Preparation of Compound 33)

7-[4-(2-butoxyethoxy)phenyl]-N-[4-[(4-isobutyl-4H-1,2,4-triazol-3-yl)methylthio]phenyl]-1-propyl-2,3-dihydro-1H-1-benzazepine-4-carboxamide (0.7 g) was dissolved in dichloromethane (50 ml). The solution was cooled to −78° C., and a solution of 3-chloroperbenzoic acid (0.39 g) in dichloromethane (5 ml) was added dropwise to the solution. The mixture was stirred for 1 hour at −78° C., and then, sodium thiosulfate solution was added to the mixture, and the mixture was concentrated and extracted with ethyl acetate. The organic layer was washed with sodium bicarbonate solution, water, and saturated brine, dried over anhydrous magnesium sulfate, and then, the solvent was distilled off. The residue was purified by silica gel column chromatography (extraction solvent: ethyl acetate/methanol/triethylamine) to give crude crystals, which were recrystallized from ethyl acetate-hexane, to give 7-[4-(2-butoxyethoxy)phenyl]-N-[4-((4-isobutyl-4H-1,2,4-triazol-3-yl)methylsulfinyl]phenyl]-1-propyl-2,3-dihydro-1H-1-benzazepine-4-carboxamide (compound 33) (0.57 g) as yellow crystals.

mp 186 to 190° C. (dec.).

$^1$H-NMR (δ, CDCl$_3$) 0.82 (6H, d, J=6.6 Hz), 0.93 (3H, t, J=7.1 Hz), 1.02 (3H, t, J=7.3 Hz), 1.30 to 1.48 (2H, m), 1.54 to 1.89 (5H, m), 2.96 (2H, br), 3.31 to 3.34 (4H, m), 3.55 (2H, t, J=6.6 Hz), 3.70 (2H, d, J=7.4 Hz), 3.80 (2H, t, J=4.7 Hz), 3.95 to 4.17 (4H, m), 6.89 (H, d, J=8.8 Hz), 6.95 (2H, d, J=8.8 Hz), 7.27 to 7.43 (7H, m), 7.86 (2H, d, J=8.8 Hz), 8.01 (1H, s), 8.68 (1H, br).

IR (KBr) ν: 2961, 2930, 2872, 1661, 1607, 1590, 1520, 1499 cm$^{-1}$.

Anal calcd for C$_{39}$H$_{49}$N$_5$O$_4$S: C, 68.49; H, 7.22; N, 10.24. Found: C, 68.17; H, 7.02; N, 10.17.

Example 31

(Preparation of Compound 34 and Compound 35)

7-[4-(2-butoxyethoxy)phenyl]-N-[4-[(4-isobutyl-4H-1,2,4-triazol-3-yl)methylsulfinyl]phenyl]-1-propyl-2,3-dihydro-1H-1-benzazepine-4-carboxamide (0.27 g) was optically resolved with CHIRAL PAK AD 50 mm ID×500 mL and the elution solvent (hexane/isopropanol). The fractions were concentrated and dried, and the residue was dissolved in ethanol, and then, was filtered by 0.45 μm filter. The filtrate was concentrated, hexane was added and dried to a solid, to give (+)-7-[4-(2-butoxyethoxy)phenyl]-N-[4-[(4- isobutyl-4H-1,2,4-triazol111-3-yl)methylsulfinyl]phenyl]-1-propyl-2,3-dihydro-1H-1-benzazepine-4-carboxamide (Compound 34) (0.12 g, >99.9% ee), (−)-7-[4-(2-butoxyethoxy)phenyl]-N-[4-[(4-isobutyl-4H-1,2,4-triazol-3-yl)methylsulfinyl]phenyl]-1-propyl-2,3-dihydro-1H-1-benzazepine-4-carboxamide (Compound 35) (0.12 g, 99.6% ee).

(+) isomer: [α]D=. +131.9° (c=0.457%, ethanol solution)
(−) isomer: [α]$_D$=−137.6° (c=0.493%, ethanol solution)

Example 32

(Preparation of Compound 36)
7-[4-(2-butoxyethoxy)phenyl]-1-isobutyl-2,3-dihydro-1H-1-benzazepine-4-carboxylic acid (1 g) was dissolved in tetrahydrofuran (10 ml), and to the solution, thionyl chloride (0.25 ml) and N,N-dimethylformamide (catalytic amout) were added under ice-cooling at room temperature, and the mixture was stirred for 1.5 hours. The solvent was distilled off, the residue was dissolved in tetrahydrofuran (10 ml) and the solution was added dropwise to a solution of 4-[(5,6-dimethyl-1,2,4-triazin-3-yl)methylthio]aniline (0.59 g) and triethylamine (1 ml) in tetrahydrofuran (5 ml) under ice-cooling. The mixture was stirred overnight under nitrogen atmosphere at room temperature, the solvent was distilled off. To the residue was added water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[(5,6-dimethyl-1,2,4-triazin-3-yl)methylthio]phenyl]-1-isobutyl-2,3-dihydro-1H-1-benzazepine-4-carboxamide (Compound 36) (0.46 g) as yellow amorphous.

$^1$H-NMR (δ, CDCl$_3$) 0.90 to 0.98 (9H, m), 1.29 to 1.49-(2H, m), 1.54 to 1.69 (2H, m), 2.04 to 2.10 (1H, m), 2.47 (3H, s), 2.60 (3H, s), 2.90 (2H, t-like), 3.17 (2H, d, J=7.2 Hz), 3.34 (2H, t-like), 3.55 (2H, t, J=6.6 Hz), 3.80 (2H, t, J=5.0 Hz), 4.14 (2H, t, J=5.0 Hz), 4.33 (2H, s), 6.87 to 6.99 (3H, m), 7.35 to 7.54 (9H, m), 7.85 (1H, br).
IR (KBr) ν: 2959, 2867, 1653, 1607, 1586, 1499 cm$^{-1}$.

Example 33

(Preparation of Compound 37)
7-[4-(2-butoxyethoxy)phenyl]-N-[4-[(5,6-dimethyl-1,2,4-triazin-3-yl)methylthio]phenyl]-1-isobutyl-2,3-dihydro-1H-1-benzazepine-4-carboxamide (0.25 g) was dissolved in dichloromethane (100 ml). The solution was cooled to −78° C., and to the solution, a solution of 3-chloroperbenzoic acid (0.14 g) in dichloromethane (3 ml) was added dropwise. The mixture was stirred for 1 hour at −78° C., and to the mixture was added sodium thiosulfate solution, and the mixture was concentrated and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: ethyl acetate/methanol/triethylamine) to give crude crystals, which were recrystallized from ethyl acetate-hexane, to give 7-[4-(2-butoxyethoxy)phenyl]-N-[4-[(5,6-dimethyl-1,2,4-triazin-3-yl)methylsulfinyl]phenyl]-1-isobutyl-2,3-dihydro-1H-1-benzazepine-4-carboxamide (Compound 37) (0.20 g) as yellow crystals.

mp 178 to 183° C. (dec.).

$^1$H-NMR (δ, CDCl$_3$) 0.88 to 1.09 (9H, m), 1.22 to 1.69 (4H, m), 2.00 to 2.15 (1H, m), 2.51 (3H, s), 2.67 (3H, s), 2.93 (2H, t-like), 3.20 (2H, d, J=7.2 Hz), 3.38 (2H, t-like), 3.55 (2H, t, J=6.6 Hz), 3.81 (2H, t, J=5.0 Hz), 4.16 (2H, t, J=5.0 Hz), 4.36 (1H, d, J=12.6 Hz), 4.53 (1H, d, J=12.6 Hz), 6.91 to 7.00 (3H, m), 7.37 to 7.49 (5H, m), 7.61 (2H, d, J=8.4 Hz), 7.74 to 7.82 (3H, m).
IR (KBr) ν: 2955, 2928, 2868, 1653, 1607, 1588, 1518, 1499 cm$^{-1}$.
Anal calcd for C$_{39}$H$_{49}$N$_5$O$_4$S.0.25H$_2$O: C, 68.49; H, 7.22; N, 10.24. Found: C, 68.17; H, 7.02; N, 10.17.

Example 34

(Preparation of Compound 38)
7-[4-(2-butoxyethoxy)phenyl]-1-isobutyl-2,3-dihydro-1H-1-benzazepine-4-carboxylic acid (0.9 g) was dissolved in tetrahydrofuran (15 ml), and to the solution, thionyl chloride (0.23 ml) and N,N-dimethylformamide (catalytic amout) were added under ice-cooling, and the mixture was stirred for 1 hour at room temperature. The solvent was distilled off, and the residue was dissolved in tetrahydrofuran (15 ml). The solution was added dropwise under ice-cooling to a solution of 4-[(5-methyl-1,2,4-triazin-3-yl)methylthio]aniline (0.47 g) and triethylamine (0.86 ml) in tetrahydrofuran (10 ml). The mixture was stirred overnight under nitrogen atmosphere at room temperature, the solvent was distilled off. To the residue was added water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[(5-methyl-1,2,4-triazin-3-yl)methylthio]phenyl]-1-isobutyl-2,3-dihydro-1H-1-benzazepine-4-carboxamide (Compound 38) (1.1 g) as yellow amorphous.

$^1$H-NMR (δ, CDCl$_3$) 0.89 to 0.98 (9H, m), 1.34 to 1.45 (2H, m), 1.54 to 1.72 (2H, m), 1.94 to 2.05 (1H, m), 2.51 (3H, s), 2.89 (2H, t-like), 3.17 (2H, d, J=7.4 Hz), 3.33 (2H, t-like), 3.55 (2H, t, J=6.6 Hz), 3.80 (2H, t, J=4.9 Hz), 4.14 (2H, t, J=4.9 Hz), 4.36 (2H, s), 6.90 (1H, d, J=9.6 Hz), 6.97 (2H, d, J=8.8 Hz), 7.34 to 7.55 (9H, m), 7.92 (1H, br), 8.93 (1H, s).
IR (KBr) ν: 2953, 2867, 1659 cm$^{-1}$.

Example 35

(Preparation of Compound 39)
7-[4-(2-butoxyethoxy)phenyl]-N-[4-[(5-methyl-1,2,4-triazin-3-yl)methylthio]phenyl]-1-isobutyl-2,3-dihydro-1H-1-benzazepine-4-carboxamide (0.67 g) was suspended in dichloromethane (100 ml). The suspension was cooled to −78° C. A solution of 3-chloroperbenzoic acid (0.38 g) in dichloromethane (7 ml) was added dropwise to the suspension. The mixture was stirred for 1.5 hours at −78° C. To the mixture was added sodium thiosulfate solution, and the mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: ethyl acetate/hexane) to give crude crystals, which were recrystallized from ethyl acetate-hexane, to give 7-[4-(2-butoxyethoxy)phenyl]-N-[4-[(5-methyl-1,2,4-triazin-3-yl)methylsulfinyl]phenyl]-1-isobutyl-2, 3-dihydro-1H-1-benzazepine-4-carboxamide (Compound 39) (0.50 g) as yellow crystals.

$^1$H-NMR (δ, CDCl$_3$) 0.89 to 1.05 (9H, m), 1.27 to 1.49 (2H, m), 1.54 to 1.68 (2H, m), 1.98 to 2.15 (1H, m), 2.56 (3H, s), 2.92 (2H, t-like), 3.20 (2H, d, J=7.2 Hz), 3.37 (2H, t-like), 3.55 (2H, t, J=6.6 Hz), 3.80 (2H, t, J=5.0 Hz), 4.16 (2H, t, J=5.0 Hz), 4.40 (1H, d, J=12.6 Hz), 4.58 (1H, d, J=12.6 Hz), 6.90 to 7.00 (3H, m), 7.39 to 7.49 (5H, m), 7.59 (2H, d, J=8.6 Hz), 7.76 (2H, d, J=8.6 Hz), 7.81 (1H, s), 9.03 (1H, s).

IR (KBr) ν: 2957, 2899, 1663, 1588, 1518, 1499 cm$^{-1}$.

Example 36

(Preparation of Compound 40)

7-[4-(2-butoxyethoxy)phenyl]-1-isobutyl-2,3-dihydro-1H-1-benzazepine-4-carboxylic acid (3 g) was dissolved in tetrahydrofuran (15 ml), and to the solution under ice-cooling, thionyl chloride (0.8 ml) and N,N-dimethylformamide (catalytic amout) were added at room temperature, and the mixture was stirred for 1.5 hours. The solvent was distilled off to give the acid chloride. Benzyl chloroformate (0.9 ml) was added dropwise to a solution of 4-mercapto-3-methylaniline (0.9 g) and triethylamine (4.5 ml) in tetrahydrofuran (50 ml) at −78° C., and the mixture was stirred for 1.5 hours. Then, a solution of the foremetioned acid chloride in tetrahydrofuran (15 ml) was added dropwise to the solution under ice-cooling, and the mixture was stirred for 1 hour at room temperature. To the mixture, 1N aqueous sodium hydroxide solution (40 ml) and methanol (40 ml) were added and the mixture was stirred for 30 minutes at room temperature. 3-chloromethyl-4-propyl-4H-1,2,4-triazole hydrochloride (1.3 g) was added to the mixture and the mixture was stirred overnight at room temperature. The mixture was concentrated, and extracted with ethyl acetate. The organic layer was washed with water and saturated brine, and dried over anhydrous magnesium sulfate, and then, the solvent was distilled off. The residue was purified by basic silica gel column chromatography (elution solvent: triethylamine/methanol/ethyl acetate) to give crude crystals, which were recrystallized from ethyl acetate-hexane, to give 7-[4-(2-butoxyethoxy)phenyl]-1-isobutyl-N-[3-methyl-4-[(4-propyl-4H-1,2,4-triazol-3-yl)methylthio]phenyl]-2,3-dihydro-1H-1-benzazepine-4-carboxamide (Compound 40) (1.9 g) as yellow crystals.

mp 104 to 107° C.

$^1$H-NMR (dppm, CDCl$_3$) 0.90 to 0.99 (12H, m), 1.27 to 1.45 (2H, m), 1.49 to 1.65 (2H, m), 1.72 to 1.85 (2H, m), 2.00 to 2.18 (1H, m), 2.33 (3H, s), 2.91 (2H, t-like), 3.18 (2H, d, J=7.4 Hz), 3.35 (2H, t-like), 3.56 (2H, t, J=6.6 Hz), 3.78 to 3.91 (4H, m), 4.05 (2H, s), 4.16 (2H, t, J=4.9 Hz), 6.91 (1H, d, J=9.2 Hz), 6.97 (2H, d, J=8.4 Hz), 7.29 to 7.47 (7H, m), 7.57 (1H, s), 8.01 (1H, s), 8.07(1H, br).

IR (KBr) n: 2959, 2870, 1659, 1607, 1580, 1518, 1499 cm$^{-1}$

Anal calcd for C$_{40}$H$_{51}$N$_5$O$_3$S.0.25H$_2$O: C, 69.99; H, 7.56; N, 10.20. Found: C, 69.98; H, 7.55; N, 10.00.

Example 37

(Preparation of Compound 41)

7-[4-(2-butoxyethoxy)phenyl]-1-isobutyl-N-[3-methyl-4-[(4-propyl-4H-1,2,4-triazol-3-yl)methylthio]phenyl]-2,3-dihydro-1H-1-benzazepine-4-carboxamide (0.67 g) was suspended in dichloromethane (100 ml) and the suspension was cooled to −78° C. A solution of 3-chloroperbenzoic acid (0.35 g) in dichloromethane (5 ml) was added dropwise to the suspension. The mixture was stirred for 1 hour at −78° C., and then, sodium thiosulfate solution was added to the mixture, and the mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[3-methyl-4-[(4-propyl-4H-1,2,4-triazol-3-yl)methylsulfinyl]phenyl]-2,3-dihydro-1H-1-benzazepine-4-carboxamide (Compound 41) (0.54 g) as yellow amorphous.

$^1$H-NMR (dppm, CDCl$_3$) 0.85 to 1.02 (12H, m), 1.22 to 1.75 (6H, m), 2.05 to 2.18 (1H, m), 2.29 (3H, s), 2.85 to 2.98 (2H, m), 3.18 to 3.28 (2H, m), 3.30 to 3.40 (2H, m), 3.55 (2H, t, J=6.6 Hz), 3.80 (2H, t, J=5.0 Hz), 3.89 to 3.95 (2H, m), 4.08 to 4.17 (2H, tm), 6.89 to 6.98 (3H, m), 7.31 to 7.65 (7H, m), 7.72 (1H, d, J=8.4 Hz), 8.04 (1H, s), 8.46 (1H, br).

IR (KBr) n: 2959, 2932, 2870, 1661, 1405, 1520, 1499 cm$^{-1}$.

Example 38

(Preparation of Compound 42)

7-[4-(2-butoxyethoxy)phenyl]-1-isobutyl-2,3-dihydro-1H-1-benzazepine-4-carboxylic acid (0.14 g) was dissolved in tetrahydrofuran (5 ml), and to the solution, thionyl chloride (0.05 ml) and N,N-dimethylformamide (catalytic amout) were added under ice-cooling at room temperature, and the mixture was stirred for 1.5 hours. The solvent was distilled off, the residue was dissolved in tetrahydrofuran (10 ml), and the solution was added dropwise under ice-cooling to a solution of 4-[(4-propyl-4H-1,2,4-triazol-3-yl)methylthio]-3-trifluoromethylaniline (0.1 g) and 4-dimethylaminopyridine (catalytic amout) in pyridine (5 ml). The mixture was stirred for 1.5 hours at room temperature, and the solvent was distilled off. To the residue was added water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: triethylamine/methanol/ethyl acetate) to give crude crystals, which were recrystallized from ethyl acetate-hexane, to give 7-[4-(2-butoxyethoxy)phenyl]-1-isobutyl-N-[3-trifluoromethyl-4-[(4-propyl-4H-1,2,4-triazol-3-yl)methylthio]phenyl]-2,3-dihydro-1H-1-benzazepine-4-carboxamide (Compound 42) (0.23 g) as yellow crystals.

mp 131 to 133° C.

$^1$H-NMR (dppm, CDCl$_3$) 0.84 to 1.01 (12H, m), 1.27 to 1.69 (6H, m), 2.00 to 2.15 (1H, m), 2.96 (2H, t-like), 3.20 (2H, d, J=7.0 Hz), 3.34 (2H, t-like), 3.56 (2H, t, J=6.6 Hz), 3.70 (2H, t, J=7.6 Hz), 3.81 (2H, t, J=5.0 Hz), 3.86 (2H, s), 4.15 (2H, t, J=5.0 Hz), 6.87 to 6.97 (3H, m), 7.11 (1H, s), 7.24 (1H, s), 7.36 to 7.43 (4H, m), 7.84 (1H, dd, J=2.2, 8.8 Hz), 7.90 (1H, s), 8.18 (1H, d, J=2.2 Hz), 9.46 (1H, br).

IR (KBr) n: 2963, 2934, 2870, 1661, 1607, 1518, 1499 cm$^{-1}$.

Anal calcd for C$_{40}$H$_{48}$F$_3$N$_5$O$_3$S.0.25H$_2$O: C, 64.89; H, 6.66; N, 9.46. Found: C, 64.70; H, 6.49; N, 9.65.

Example 39

(Preparation of Compound 43)

7-[4-(2-butoxyethoxy)phenyl]-1-isobutyl-N-[3-trifluoromethyl-4-[(4-propyl-4H-1,2,4-triazol-3-yl)methylthio]phenyl]-2,3-dihydro-1H-1-benzazepine-4-carboxamide (0.38 g) was dissolved in dichloromethane (50 ml), and the mixture was cooled to −78° C. A solution of 3-chloroperbenzoic acid (0.14 g) in dichloromethane (5 ml) was added dropwise to the solution. The mixture was stirred for 2 hours at −78° C., and sodium thiosulfate solution was added to the mixture, and the mixture was concentrated, and extracted with ethyl acetate. The organic layer was washed with sodium bicarbonate solution, water and saturated brine and dried over anhydrous magnesium sulfate. The solvent was distilled off, to give 7-[4-(2-butoxyethoxy)phenyl]-1-isobutyl-N-[3-trifluoromethyl-4-[(4-propyl-4H-1,2,4-triazo-3-yl)methylsulfinyl]phenyl]-2,3-dihydro-1H-1-benzazepine-4-carboxamide (Compound 43) (0.35 g) as yellow crystals.

mp 169 to 172° C.

$^1$H-NMR (dppm, CDCl$_3$) 0.82 (3H, t, J=7.3 Hz), 0.94 (3H, t, J=7.2 Hz), 1.05 (6H, d, J=6.6 Hz), 1.31 to 1.72 (6H, m), 2.06 to 2.15 (1H, m), 2.85 to 3.52 (6H, m), 3.56 (2H, t, J=6.6 Hz), 3.60 to 3.78 (2H, m), 3.80 (2H, t, J=4.8 Hz), 3.88 (2H, s), 4.14 (2H, t, J=4.8 Hz), 6.84 to 6.94 (4H, m), 7.08 (1H, s), 7.30 to 7.41 (4H, m), 7.92 (1H, s), 8.13 (1H, s), 8.28 to 8.32 (1H, m), 10.14 (1H, br).

IR (KBr) n: 2961, 2934, 2870, 1663, 1599, 1539, 1520, 1501 cm$^{-1}$.

Anal calcd for C$_{40}$H$_{48}$F$_3$N$_5$O$_4$S: C, 63.90; H, 6.43; N, 9.31. Found: C, 63.63; H, 6.31; N, 9.55.

Example 40

(Preparation of Compound 44)

7-[4-(2-butoxyethoxy)phenyl]-2,3-dihydro-1-benzazepine-4-carboxylic acid (0.5 g) was dissolved in tetrahydrofuran (5 ml), and to the solution, thionyl chloride (0.14 ml) and N,N-dimethylformamide (catalytic amount) were added under ice-cooling, and the mixture was stirred for 1 hour at room temperature. The solvent was distilled off, to obtain acid chloride. Benzyl chloroformate (0.18 ml) was added dropwise at −78° C. to a solution of 4-mercapto-3-chloroaniline (0.2 g) and triethylamine (0.87 ml) in tetrahydrofuran (10 ml), and the mixture was stirred for 1 hour. Then, a solution of the above acid chloride in tetrahydrofuran (10 ml) was added dropwise to the solution under ice-cooling, and the mixture was stirred overnight at room temperature. 1N aqueous sodium hydroxide solution (8.5 ml) and methanol (10 ml) were added to the mixture and the mixture was stirred for 30 minutes at room temperature. 3-chloromethyl-4-propyl-4H-1,2,4-triazole hydrochloride (0.25 g) was added to the mixture and the mixture was stirred overnight at room temperature. The mixture was concentrated, and extracted with ethyl acetate. The organic layer was washed with water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[3-chloro-4-[(4-propyl-4H-1,2,4-triazol-3-yl)methylthio]phenyl]-2,3-dihydro-1H-1-benzazepine-4-carboxamide (Compound 44) (0.37 g) as yellow amorphous.

$^1$H-NMR (dppm, CDCl$_3$) 0.82 to 1.00 (12H, m), 1.17 to 1.66 (6H, m), 2.04 to 2.15 (1H, m), 2.94 (2H, t-like), 3.18 (2H, d, J=7.6 Hz), 3.32 (2H, t-like), 3.56 (2H, t, J=6.5 Hz), 3.67 (2H, t, J=7.7 Hz), 3.79 to 3.83 (4H, m), 4.14 (2H, t, J=5.0 Hz), 6.85 to 7.03 (4H, m), 7.17 (1H, s), 7.31 to 7.40 (4H, m), 7.53 (1H, dd, J=2.2, 8.4 Hz), 7.84 (H, s), 8.06 (1H, d, J=2.2 Hz), 9.70 (1H, br).

IR (KBr) n: 2957, 2934, 2868, 1653, 1607, 1580, 1499 cm$^{-1}$.

Example 41

(Preparation of Compound 45)

One droplet of DMF was added to a solution of 7-[4-(2-propoxyethoxy)phenyl]-1-propyl-2,3-dihydro-1-benzazepine-4-carboxylic acid (1.5 g) in tetrahydrofuran (15 ml). Then, thionyl chloride (0.35 ml) was added under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl) O-benzyl carbonothioate (950 mg) and triethylamine (2.6 ml) in THF (15 ml) at 0° C. under argon atmosphere. After finishing the dropping, the mixture was allowed to be at room temperature, and stirred overnight under argon atmosphere, and then, methanol (30 ml) was added to the mixture. Further, 1N aqueous solution of sodium hydroxide (18.3 ml) was added to the mixture, and the mixture was stirred for 30 minutes under argon atmosphere. Then, 5-chloromethyl-1-propylimidazole hydrochloride (928 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure, and the obtained residue was isolated and purified by silica gel column chromatography (ethyl acetate), which was recrystallized from ethyl acetate, to give 7-[4-(2-propoxyethoxy)phenyl]-1-propyl-N-[4-[[[1-propylimidazol-5-yl]methyl]sulfanyl]phenyl]-2,3-dihydro-1-benzazepine-4-carboxamide (1.63 g)(Compound 45) as yellow crystals.

$^1$H-NMR (200 MHz, CDCl$_3$) δ 0.91 to 1.01 (9H, m), 1.53 to 1.93 (6H, m), 2.85 to 2.95 (2H, m), 3.19 (2H, d, J=7.0 Hz), 3.28 to 3.36 (4H, m), 3.51 (2H, t, J=6.6 Hz), 3.81 (2H, t, J=4.4 Hz), 3.93 (2H, t, J=7.4 Hz), 3.99 (2H, s), 4.16 (2H, t, J=4.4 Hz), 6.70 (1H, s), 6.90 (1H, d, J=8.8 Hz), 6.98 (2H, d, J=8.8 Hz), 7.25 to 7.30 (2H, m), 7.36 to 7.55 (8H, m), 7.63 (1H, s).

Elemental Analysis for C$_{38}$H$_{46}$N$_4$O$_3$S.0.25H$_2$ Calcd. C, 70.94; H, 7.28; N, 8.71. Found: C, 70.93; H, 7.22; N, 8.69.

Example 42

(Preparation of Compound 46, 47)

To a solution of 7-[4-(2-propoxyethoxy)phenyl]-1-propyl-N-[4-[[[1-propylimidazol-5-yl]methyl]sulfanyl]phenyl]-2,3-dihydro-1-benzazepine-4-carboxamide (1.0 g) in dichloromethane (15 ml) was added dropwise 70% solution of 3-chloroperbenzoic acid (579 mg) in dichloromethane (15 ml) was added dropwise at −78° C. Dimethylsulfide (0.1 ml) was added to the mixture, and the mixture was allowed to be at room temperature, and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure and the obtained residue was isolated and purified by silica gel column chromatography (ethyl acetate), to give 7-[4-(2-propoxyethoxy)phenyl]-1-propyl-N-[4-[[[1-propylimidazol-5-yl]methyl]sulfinyl]phenyl]-2,3-dihydro-1-benzazepine-4-carboxamide (693 mg)(Compound 46) and 7-[4-(2-propoxyethoxy)phenyl]-1-propyl-N-[4-[[[1-propylimidazol-5-yl]methyl]sulfonyl]phenyl]-2,3-dihydro-1-benzazepine-4-carboxamide (48 mg)(Compound 47) as yellow amorphous.

Compound 46

$^1$H-NMR (200 MHz, CDCl$_3$) δ 0.89 to 1.03 (9H, m), 1.56 to 1.81 (6H, m), 2.90 to 2.95 (2H, m), 3.30 to 3.40 (4H, m), 3.51 (2H, t, J=6.6 Hz), 3.74 to 3.84 (4H, m), 4.02 (1H, d, J=13.2 Hz), 4.07 to 4.19 (3H, m), 6.57 (1H, s), 6.91 (1H, d, J=8.8 Hz), 6.98 (2H, d, J=8.8 Hz), 7.37 to 7.51 (8H, m), 7.74 (2H, d, J=8.8, Hz), 7.87 (1H, s) Elemental Analysis for C$_{38}$H$_{46}$N$_4$O$_4$S.0.25H$_2$O Calcd. C, 69.22; H, 7.11; N, 8.50. Found: C, 69.03; H, 6.97; N, 8.47.

Compound 47

$^1$H-NMR (200 MHz, CDCl$_3$) δ 0.89 to 1.03 (9H, m), 1.59 to 1.81 (6H, m), 2.85 to 2.95 (2H, m), 3.25 to 3.40 (4H, m), 3.51 (2H, t, J=6.6 Hz), 3.81 (2H, t, J=4.4 Hz), 3.95 (2H, t, J=7.6 Hz), 4.16 (2H, t, J=4.4 Hz), 4.32 (2H, s), 6.53 (1H, s), 6.90 (H, d, J=8.8 Hz), 6.98 (2H, d, J=8.8 Hz), 7.40 to 7.50 (6H, m), 7.60 (2H, d, J=8.8 Hz), 7.76 (2H, d, J=8.8 Hz), 8.02 (1H, s).

Elemental Analysis for C$_{38}$H$_{46}$N$_4$O$_5$S Calcd. C, 68.03; H, 6.91; N, 8.35. Found: C, 67.73; H, 6.85; N, 8.13.

Example 43

(Preparation of Compound 48)

One droplet of DMF was added to a solution of 7-[4-(2-butoxyethoxy)phenyl]-1-isobutyl-2,3-dihydro-1-benzazepine-4-carboxylic acid (600 mg) in tetrahydrofuran (15 ml). Then, thionyl chloride (0.13 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of 4-[(1-methylimidazol-2-yl)thio]aniline (365 mg) and triethylamine (1.3 ml) in THF (15 ml) at 0° C. under nitrogen atmosphere. After finishing the dropping, the mixture was allowed to be at room temperature, and stirred overnight under nitrogen atmosphere, and water was added to the mixture, and the mixture was extracted with ethyl acetate. The organic layer was washed with saturated brine, and dried over magnesium sulfate. The solvent was distilled off under reduced pressure and the residue was isolated and purified by basic silica gel column chromatography (hexane-ethyl acetate=1:4), to give 7-[4-(2-butoxyethoxy)phenyl]-1-isobutyl-N-[4-[[1-methylimidazol-2-yl]sulfanyl]phenyl]-2,3-dihydro-1-benzazepine-4-carboxamide (716 mg) (Compound 48) as yellow amorphous.

$^1$H-NMR (200 MHz, CDCl$_3$) δ 0.89 to 0.98 (9H, m), 1.30 to 1.50 (2H, m), 1.55 to 1.75 (2H, m), 1.95 to 2.15 (1H, m), 2.85 to 2.95 (2H, m), 3.18 (2H, d, J=7.2 Hz), 3.30 to 3.40 (2H, m), 3.55 (2H, t, J=6.6 Hz), 3.63 (3H, s), 3.80 (2H, t, J=4.8 Hz), 4.16 (2H, t, J=4.8 Hz), 6.91 (1H, d, J=8.8 Hz), 6.97 (2H, d, J=8.8 Hz), 7.05 (1H, d, J=1.4 Hz), 7.16 to 7.21 (3H, m), 7.37 to 7.53 (7H, m), 7.64 (1H, s).

Elemental Analysis for C$_{37}$H$_{44}$N$_4$O$_3$S Calcd. C, 71.12; H, 7.10; N, 8.97. Found: C, 70.81; H, 7.07; N, 8.89.

Example 44

(Preparation of Compound 49)

7-[4-(2-butoxyethoxy)phenyl]-1-isobutyl-2,3-dihydro-1H-1-benzazepine-4-carboxylic acid (1.0 g) was dissolved in tetrahydrofuran (10 ml), and to the solution, thionyl chloride (0.26 ml) and N,N-dimethylformamide (catalytic amout) were added under ice-cooling, and the mixture was stirred for 1 hour at room temperature. The solvent was distilled off, the residue was dissolved in tetrahydrofuran (10 ml), and the mixture was added dropwise under ice-cooling to a solution of 4-[2-(4-propyl-4H-1,2,4-triazol-3-yl) ethylthio]aniline (0.6 g) in pyridine (10 ml). The mixture was stirred at room temperature overnight and the solvent was distilled off. To the residue was added water, and the mixture was extracted with ethyl acetate. The organic layer was washed with water and saturated brine, and dried over anhydrous magnesium sulfate, and then, the solvent was distilled off. The residue was purified by silica gel column chromatography (elutionsolvent: triethylamine/methanol/ethyl acetate), to give 7-[4-(2-butoxyethoxy)phenyl]-1-isobutyl-N-[4-[2-(4-propyl-4H-1,2,4-triazol-3-yl)ethylthio]phenyl]-2,3-dihydro-1H-1-benzazepine-4-carboxamide (Compound 49) (1.49 g) as yellow amorphous.

$^1$H-NMR (dppm, CDCl$_3$) 0.85 to 0.98 (12H, m), 1.33 to 1.45 (2H, m), 1.54 to 1.77 (4H, m), 1.98 to 2.58 (1H, m), 2.91 to 2.98 (4H, m), 3.17 (2H, d, J=7.2 Hz), 3.32 to 3.40 (4H, m), 3.55 (2H, t, J=6.6 Hz), 3.71 (2H, t, J=7.3 Hz), 3.80 (2H, t, J=4.7 Hz), 4.15 (2H, t, J=4.7 Hz), 6.88 to 6.99 (3H, m), 7.34 to 7.47 (7H, m), 7.61 (2H, d, J=8.8 Hz), 8.00 (1H, s), 8.04 (1H, s).

IR (KBr) n: 2959, 2930, 2870, 1659, 1588, 1499 cm$^{-1}$.

Example 45

(Preparation of Compound 50)

7-[4-(2-butoxyethoxy)phenyl]-1-isobutyl-N-[4-[2-(4-propyl-4H-1,2,4-triazol-3-yl)ethylthio]phenyl]-2,3-dihydro-1H-1-benzazepine-4-carboxamide (1.1 g) was dissolved in dichloromethane (40 ml), and the mixture was cooled to −78° C. A solution of 3-chloroperbenzoic acid (0.6 g) in dichloromethane (10 ml) was added dropwise to the mixture. The mixture was stirred for 1 hour at −78° C., and then, sodium thiosulfate solution was added to the mixture, and the mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[4-[2-(4-propyl-4H-1,2,4-triazol-3-yl)ethylsulfinyl]phenyl]-2,3-dihydro-1H-1-benzazepine-4-carboxamide (Compound 50) (0.94 g) as yellow amorphous.

$^1$H-NMR (dppm, CDCl$_3$) 0.86 to 0.99 (12H, m), 1.30 to 1.45 (2H, m), 1.58 to 1.77 (4H, m), 1.95 to 2.15 (1H, m), 2.87 to 3.05 (3H, m), 3.10 to 3.35 (4H, m), 3.37 (2H, t-like), 3.45 to 3.65 (3H, m), 3.78 to 3.83 (4H, m), 4.14 to 4.18 (2H, m), 6.90 to 7.00 (3H, m), 7.39 to 7.48 (5H, m), 7.61 (2H, d, J=8.6 Hz), 7.83 (2H, d, J=8.6 Hz), 8.02 (1H, s), 8.15 (1H, br).

IR (KBr) n: 2961, 2932, 2872, 1661, 1590, 1518, 1499 cm$^{-1}$.

Example 46

(Preparation of Compound 51)

7-[4-(2-butoxyethoxy)phenyl]-1-propyl-2,3-dihydro-1H-1-benzazepine-4-carboxylic acid (0.7 g) was dissolved in tetrahydrofuran (10 ml), and to the solution, thionyl chloride (0.18 ml) and N,N-dimethylformamide (catalytic amout) were added under ice-cooling, and the mixture was stirred for 1 hour at room temperature. The solvent was distilled off and the residue was dissolved in tetrahydrofuran (20 ml). To the solution, a solution of 4-[2-(4-propyl-4H-1,2,4-triazol-3-yl)ethylthio]aniline (0.43 g) in pyridine (10 ml) was added dropwise under ice-cooling. The mixture was stirred at room temperature overnight and the solvent was distilled off. To the residue was added water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-propyl-N-[4-[2-(4-propyl-4H-1,2,4-triazol-3-yl)ethylthio]phenyl]-2,3-dihydro-1H-1-benzazepine-4-carboxamide (Compound 51) (0.9 g) as yellow amorphous.

$^1$H-NMR (dppm, CDCl$_3$) 0.88 to 1.03 (9H, m), 1.30 to 1.45 (2H, m), 1.54 to 1.81 (6H, m), 2.91 to 3.02 (4H, m), 3.28 to 3.43 (6H, m), 3.55 (2H, t, J=6.6 Hz), 3.72 to 3.83 (4H, m), 4.16 (2H, t, J=4.9 Hz), 6.90 (1H, d, J=8.8 Hz), 6.98 (2H, d, J=8.8 Hz), 7.36 to 7.48 (7H, m), 7.57 (2H, d, J=8.8 Hz), 7.67 (1H, br), 8.03 (1H, s).

IR (KBr) n: 2963, 2934, 2876, 1655, 1499 cm$^{-1}$.

Example 47

(Preparation of Compound 52)

7-[4-(2-butoxyethoxy)phenyl]-1-propyl-N-[4-[2-(4-propyl-4H-1,2,4-triazol-3-yl)ethylthio]phenyl]-2,3-dihydro-1H-1-benzazepine-4-carboxamide (0.7 g) was dissolved in dichloromethane (50 ml), and the mixture was cooled to −78° C. To the mixture, a solution of 3-chloroperbenzoic acid (0.39 g) in dichloromethane (5 ml) was added dropwise. The mixture was stirred for 1 hour at −78° C., and then, sodium thiosulfate solution was added to the mixture, and the mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-propyl-N-[4-[2-(4-propyl-4H-1,2,4-triazol-3-yl)ethylsulfinyl]phenyl]-2,3-dihydro-1H-1-benzazepine-4-carboxamide (Compound 52) (0.43 g) as pale yellow crystals.

mp 93 to 101° C.

$^1$H-NMR (dppm, CDCl$_3$) 0.91 to 1.02 (9H, m), 1.36 to 1.43 (2H, m), 1.56 to 1.66 (2H, m), 1.72 to 1.80 (4H, m), 2.91 to 2.99 (3H, m), 3.19 to 3.37 (6H, m), 3.53 to 3.57 (3H, m), 3.79 to 3.86 (4H, m), 4.16 (2H, t, J=5.9 Hz), 6.90 (1H, d, J=8.4 Hz), 6.98 (2H, d, J=8.7 Hz), 7.40 to 7.49 (5H, m), 7.62 (2H, d, J=9.0 Hz), 7.81 (2H, d, J=8.7 Hz), 7.93 (1H, br), 8.04 (1H, s).

IR (KBr) n: 2963, 2932, 2870, 1661, 1590, 1520, 1499 cm$^{-1}$.

Anal calcd for C$_{39}$H$_{49}$N$_5$O$_4$S.0.25H$_2$O: C, 68.04; H, 7.25; N, 10.17. Found: C, 67.82; H, 7.24; N, 10.13.

Example 48

(Preparation of Compound 53)

7-[4-(2-butoxyethoxy)phenyl]-1-isobutyl-2,3-dihydro-1H-1-benzazepine-4-carboxylic acid (0.79 g) was dissolved in tetrahydrofuran (5 ml), and to the solution, thionyl chloride (0.2 ml) and N,N-dimethylformamide (catalytic amout) were added under ice-cooling, and the mixture was stirred for 1 hour at room temperature. The solvent was distilled off, and the residue was dissolved in tetrahydrofuran (15 ml). The solution was added dropwise under ice-cooling to a solution of 5-amino-2-(4-propyl-4H-1,2,4-triazol-3-yl) methylthiopyridine (0.45 g) in pyridine (10 ml). The mixture was stirred at room temperature overnight and the solvent was distilled off. To the residue was added water, and the mixture was extracted with ethyl acetate. The organic layer was washed with water and saturated brine, and dried over anhydrous magnesium sulfate, and then, the solvent was distilled off. The residue was purified by silica gel column chromatography (elutionsolvent: triethylamine/methanol/ethyl acetate), to give 7-[4-(2-butoxyethoxy)phenyl]-1-isobutyl-N-[2-(4-propyl-4H-1,2,4-triazol-3-yl)methylthiopyridin-5-yl]-2,3-dihydro-1H-1-benzazepine-4-carboxamide (Compound 53) (1.1 g) as yellow amorphous.

$^1$H-NMR (dppm, CDCl$_3$) 0.84 to 1.22 (12H, m), 1.54 to 1.85 (4H, m), 2.03 to 2.14 (1H, m), 2.92 (2H, t-like), 3.18 (2H, d, J=7.4 Hz), 3.34 (2H, t-like), 3.55 (2H, t, J=6.6 Hz), 3.78 to 3.90 (4H, m), 4.13 to 4.17 (2H, m), 4.54 (2H, s), 6.88 to 6.99 (3H, m), 7.18 (1H, d, J=8.8 Hz), 7.36 to 7.46 (5H, m), 7.93 (H, dd, J=2.6, 8.4 Hz), 7.98 (1H, s), 8.58 (1H, br), 8.75 (1H, s).

IR (KBr) n: 2959, 2932, 2870, 1659, 1499 cm$^{-1}$.

Example 49

(Preparation of Compound 54)

7-[4-(2-butoxyethoxy)phenyl]-1-isobutyl-N-[2-(4-propyl-4H-1,2,4-triazol-3-yl)methylthiopyridin-5-yl]-2,3-dihydro-1H-1-benzazepine-4-carboxamide (0.70 g) was dissolved in dichloromethane (50 ml), and the mixture was cooled to −78° C. To the solution, a solution of 3-chloroperbenzoic acid (0.31 g) in dichloromethane (5 ml) was added dropwise. The mixture was stirred for 2 hours at −78° C. and sodium thiosulfate solution was added to the mixture. The mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[2-(4-propyl-4H-1,2,4-triazol-3-yl)methylsulfinylpyridin-5-yl]-2,3-dihydro-1H-1-benzazepine-4-carboxamide (Compound 54) (0.70 g) as yellow crystals.

mp 135 to 138° C.

$^1$H-NMR (dppm, CDCl$_3$) 0.77 (3H, t, J=7.6 Hz), 0.93 (3H, t, J=7.1 Hz), 1.06 (6H, d, J=6.2 Hz), 1.34 to 1.68 (6H, m), 2.05 to 2.25 (1H, m), 2.85 to 3.40 (5H, m), 3.45 to 3.75 (3H, m), 3.55 (2H, t, J=6.6 Hz), 3.80 (2H, t, j=5.0 Hz), 3.82 to 4.07 (2H, m), 4.14 (2H, t, J=5.0 Hz), 6.85 to 6.94 (4H, m), 7.24 to 7.40 (5H, m), 7.92 (1H, s), 8.00 (H, d, J=8.4 Hz), 9.61 (1H, s), 10.17 (1H, br).

IR (KBr) n: 2959, 2934, 2870, 1667, 1607, 1574, 1518, 1499 cm$^{-1}$.

Anal calcd for C$_{38}$H$_{48}$N$_6$O$_4$S: C, 66.64; H, 7.06; N, 12.27. Found: C, 66.33; H, 6.88; N, 12.21.

Example 50

(Preparation of Compound 55, Compound 56)

7-[4-(2-butoxyethoxy)phenyl]-1-isobutyl-N-[2-(4-propyl-4H-1,2,4-triazol-3-yl)methylsulfinylpyridin-5-yl]-2,3-dihydro-1H-1-benzazepine-4-carboxamide (0.39 g) was optically resolved with CHIRAL PAK AD (ethanol/isopropylalcohol), to give (+)-7-[4-(2-butoxyethoxy)phenyl]-1-isobutyl-N-[2-(4-propyl-4H-1,2,4-triazol-3-yl)methylsulfinylpyridin-5-yl]-2,3-dihydro-1H-1-benzazepine-4-carboxamide (Compound 55) (0.18 g, 99.9% ee), (−)-7-[4-(2-butoxyethoxy)phenyl]-1-isobutyl-N-[2-(4-propyl-4H-1,2,4-triazol-3-yl)methylsulfinylpyridin-5-yl]-2,3-dihydro-1H-1-benzazepine-4-carboxamide (Compound 56) (0.18 g, 99.8% ee).

(+)-isomer: $[\alpha]_D$=+235.0° (C=0.500%, ethanol solution)
(−)-isomer: $[\alpha]_D$=−238.9° (C=0.493%, ethanol solution)

Example 51

(Preparation of Compound 57)

7-[4-(2-butoxyethoxy)phenyl]-1-propyl-2,3-dihydro-1H-1-benzazepine-4-carboxylic acid (0.76 g) was dissolved in tetrahydrofuran (5 ml), and to the solution, thionyl chloride (0.2 ml) and N,N-dimethylformamide (catalytic amout) were added under ice-cooling, and the mixture was stirred for 1 hour at room temperature. The solvent was distilled off, and the residue was dissolved in tetrahydrofuran (15 ml). The solution was added dropwise under ice-cooling to a solution of 5-amino-2-(4-propyl-4H-1,2,4-triazol-3-yl)methylthiopyridine (0.45 g) in pyridine (10 ml). The mixture was stirred at room temperature overnight and the solvent was distilled off. To the residue was added water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-propyl-N-[2-(4-propyl-4H-1,2,4-triazol-3-yl)methylthiopyridin-5-yl]-2,3-dihydro-1H-1-benzazepine-4-carboxamide (Compound 57) (1.1 g) as yellow amorphous.

$^1$H-NMR (dppm, CDCl$_3$) 0.86 to 1.02 (9H, m), 1.30 to 1.45 (2H, m), 1.54 to 1.80 (6H, m), 2.91 (2H, t-like), 3.28 to 3.35 (4H, m), 3.55 (2H, t, J=6.6 Hz), 3.78 to 3.91 (4H, m), 4.15 (2H, t, J=4.8 Hz), 4.56 (2H, s), 6.18 (1H, d, J=9.2 Hz), 6.97 (2H, d, J=8.8 Hz), 7.19 (1H, d, J=8.4 Hz), 7.38 to 7.46 (5H, m), 7.92 (1H, dd, J=2.6, 8.8 Hz), 8.00 (1H, br), 8.72 (1H, d, J=2.4 Hz).

IR (KBr) n: 2961, 2934, 2872, 1659, 1501 cm$^{-1}$.

Example 52

(Preparation of Compound 58)

7-[4-(2-butoxyethoxy)phenyl]-1-propyl-N-[2-(4-propyl-4H-1,2,4-triazol-3-yl)methylthiopyridin-5-yl]-2,3-dihydro-1H-1-benzazepine-4-carboxamide (0.60 g) was dissolved in dichloromethane (50 ml), and the mixture was cooled to −78° C. To the solution, a solution of 3-chloroperbenzoic acid (0.27 g) in dichloromethane (5 ml) was added dropwise. The mixture was stirred for 1.5 hours at −78° C. and sodium thiosulfate solution was added to the mixture. The mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-propyl-N-[2-(4-propyl-4H-1,2,4-triazol-3-yl)methylsulfinylpyridin-5-yl]-2,3-dihydro-1H-1-benzazepine-4-carboxamide (Compound 58) (0.50 g) as yellow crystals.

$^1$H-NMR (dppm, CDCl$_3$) 0.78 (3H, t, J=7.3 Hz), 0.93 (3H, t, J=7.3 Hz), 1.06 (3H, t, J=7.4 Hz), 1.30 to 1.88 (10H, m), 2.90 to 3.71 (8H, m), 3.55 (2H, t, J=6.6 Hz), 3.79 (2H, t, J=5.0 Hz), 3.90 (1H, d, J=14.2 Hz), 4.03 (1H, d, J=14.2 Hz), 4.13 (2H, t, J=5.0 Hz), 6.86 to 6.94 (4H, m), 7.25 to 7.46 (5H, m), 7.93 (1H, s), 7.99 (1H, dd, J=2.0, 8.8 Hz), 9.60 (1H, d, J=2.0 Hz), (1H, s), 10.06 (1H, s).

IR (KBr) n: 2959, 2932, 2872, 1669, 1607, 1518, 1499 cm$^{-1}$.

Anal calcd for $C_{37}H_{46}N_6O_4S$: C, 66.24; H, 6.91; N, 12.53. Found: C, 66.06; H, 6.96; N, 12.29.

Example 53

(Preparation of Compound 59, Compound 60)

7-[4-(2-butoxyethoxy)phenyl]-1-propyl-N-[2-(4-propyl-4H-1,2,4-triazol-3-yl)methylsulfinylpyridin-5-yl]-2,3-dihydro-1H-1-benzazepine-4-carboxamide (0.39 g) was optically resolved with CHIRALPAK AD (ethanol/isopropylalcohol), to give (+)-7-[4-(2-butoxyethoxy)phenyl]-1-propyl-N-[2-(4-propyl-4H-1,2,4-triazol-3-yl)methylsulfinylpyridin-5-yl]-2,3-dihydro-1H-1-benzazepine-4-carboxamide (Compound 59) (0.16 g, >99.9% ee), (−)-7-[4-(2-butoxyethoxy)phenyl]-1-propyl-N-[2-(4-propyl-4H-1,2,4-triazol-3-yl)methylsulfinylpyridin-5-yl]-2,3-dihydro-1H-1-benzazepine-4-carboxamide (Compound 60) (0.16 g, 99.4% ee).

(+)-isomer: $[\alpha]_D$=+245.5° (C=0.473%, ethanol solution)
(−)-isomer: $[\alpha]_D$=−254.6° (C=0.491%, ethanol solution)

Example 54

(Preparation of Compound 61)

7-[4-(2-butoxyethoxy)phenyl]-1-propyl-2,3-dihydro-1H-1-benzazepine-4-carboxylic acid (0.5 g) was dissolved in tetrahydrofuran (5 ml), and to the solution, thionyl chloride (0.13 ml) and N,N-dimethylformamide (catalytic amout) were added under ice-cooling, and the mixture was stirred for 1 hour at room temperature. The solvent was distilled off, and the residue was dissolved in tetrahydrofuran (10 ml). The solution was added dropwise under ice-cooling to a solution of 4-[2-(1-propylimidazol-2-yl)ethyl]aniline (0.27 g) and triethylamine (0.82 ml) in tetrahydrofuran (5 ml). The mixture was stirred at room temperature for 2 hours, and the solvent was distilled off. To the residue was added water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: triethylamine/methanol/ethyl acetate) and basic silica gel column chromatography (elution solvent: ethyl acetate/hexane), to give 7-[4-(2-butoxyethoxy)phenyl]-1-propyl-N-[4-[2-(1-propylimidazol-2-yl)ethyl]phenyl]-2,3-dihydro-1H-1-benzazepine-4-carboxamide (Compound 61) (0.36 g) as pale yellow amorphous.

$^1$H-NMR (dppm, CDCl$_3$) 0.85 to 1.03 (9H, m), 1.30 to 1.45 (2H, m), 1.54 to 1.81 (6H, m), 2.87 to 2.95 (4H, m), 3.05 to 3.13 (2H, m), 3.28 to 3.32 (4H, m), 3.55 (2H, t, J=6.6

Hz), 3.67 (2H, t, J=7.1 Hz), 3.80 (2H, t, J=5.0 Hz), 4.14 (2H, t, J=5.0 Hz), 6.80 (1H, s), 6.90 (1H, d, J=8.8 Hz), 6.95 to 7.01 (3H, m), 7.16 (2H, d, J=8.4 Hz), 7.38 to 7.54 (8H, m).

IR (KBr) n: 2961, 2938, 2870, 1655, 1605, 1516 cm$^{-1}$.

Example 55

(Preparation of Compound 62)

7-[4-(2-butoxyethoxy)phenyl]-1-propyl-2,3-dihydro-1H-1-benzazepine-4-carboxylic acid (0.52 g) was dissolved in tetrahydrofuran (5 ml), and to the solution, thionyl chloride (0.13 ml) and N,N-dimethylformamide (catalytic amout) were added under ice-cooling, and the mixture was stirred for 1 hour at room temperature. The solvent was distilled off, and the residue was dissolved in tetrahydrofuran (15 ml). The solution was added dropwise under ice-cooling to a solution of 4-[N-methyl-N-[(1-propylimidazol-2-yl)methyl] amino]aniline (0.3 g) and triethylamine (0.86 ml) in tetrahydrofuran (10 ml). The mixture was stirred at room temperature for 2 hours, and the solvent was distilled off. To the residue was added water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-propyl-N-[4-[N-methyl-N-[(1-propylimidazol-2-yl)methyl]amino]phenyl]-2,3-dihydro-1H-1-benzazepine-4-carboxamide (Compound 62) (0.51 g) as yellow amorphous.

$^1$H-NMR (dppm, CDCl$_3$) 0.83 to 1.02 (9H, m), 1.34 to 1.45 (2H, m), 1.54 to 1.80 (6H, m), 2.81 (3H, s), 2.85 to 2.95 (2H, m), 3.27 to 3.35 (4H, m), 3.55 (2H, t, J=6.6 Hz), 3.78 to 3.87 (4H, m), 4.13 to 4.15 (2H, m), 4.46 (2H, s), 6.86 to 6.99 (7H, m), 7.37 to 7.55 (8H, m).

IR (KBr) n: 2959, 2872, 1651, 1607, 1520, 1499 cm$^{-1}$.

Example 56

(Preparation of Compound 63)

7-[4-(2-butoxyethoxy)phenyl]-1-isobutyl-2,3-dihydro-1H-1-benzazepine-4-carboxylic acid (0.5 g) was dissolved in tetrahydrofuran (10 ml), and to the solution, thionyl chloride (0.13 ml) and N,N-dimethylformamide (catalytic amout) were added under ice-cooling, and the mixture was stirred for 1 hour at room temperature. The solvent was distilled off, and the residue was dissolved in tetrahydrofuran (25 ml). The solution was added dropwise under ice-cooling to a solution of 4-[3-(4H-1,2,4-triazol-4-yl) propyl] aniline (0.23 g) and 4-dimethylaminopyridine (catalytic amout) in pyridine (10 ml). The mixture was stirred at room temperature for 2 hours, and the solvent was distilled off. To the residue was added water, and the mixture was extracted with ethyl acetate. The organic layer was washed with 1N citric acid solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[4-[3-(4H-1,2,4-triazol-4-yl)propyl]phenyl]-2,3-dihydro-1H-1-benzazepine-4-carboxamide (Compound 63) (0.51 g) as yellow crystals.

mp 165 to 167° C.

$^1$H-NMR (dppm, CDCl$_3$) 0.89 to 0.99 (9H, m), 1.26 to 1.65 (4H, m), 2.05 to 2.19 (3H, m), 2.64 (2H, t, J=7.1 Hz), 2.92 (2H, t-like), 3.19 (2H, d, J=7.2 Hz), 3.37 (2H, t-like), 3.55 (2H, t, J=6.6 Hz), 3.80 (2H, t, J=5.1 Hz), 3.99 (2H, t, J=7.2 Hz), 4.16 (2H, t, J=5.1 Hz), 6.90 to 7.00 (3H, m), 7.13 (2H, d, J=8.4 Hz), 7.39 to 7.61 (7H, m), 8.14 (2H, s).

IR (KBr) n: 2953, 1651, 1607, 1516, 1499 cm$^{-1}$.

Anal calcd for C$_{38}$H$_{47}$N$_5$O$_3$: C, 73.40; H, 7.62; N, 11.26. Found: C, 73.10; H, 7.47; N, 11.28.

Example 57

(Preparation of Compound 64)

7-[4-(2-butoxyethoxy)phenyl]-1-propyl-2,3-dihydro-1H-1-benzazepine-4-carboxylic acid (0.5 g) was dissolved in tetrahydrofuran (7.5 ml), and to the solution under ice-cooling, thionyl chloride (0.15 ml) and N,N-dimethylformamide. (catalytic amout) were added, and the mixture was stirred for 1 hour at room temperature. The solvent was distilled off and the residue was dissolved in tetrahydrofuran (20 ml). The solution was added dropwise under ice-cooling to a solution of 4-[3-(4H-1,2,4-triazol-4-yl)propyl]aniline (0.24 g) and 4-dimethylaminopyridine (catalytic amout) in pyridine (5 ml). The mixture was stirred at room temperature for 2 hours, and the solvent was distilled off. To the residue was added water, and the mixture was extracted with ethyl acetate. The organic layer was washed with 1N citric acid solution, water and saturated brine, dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-propyl-N-[4-[3-(4H-1,2,4-triazol-4-yl)propyl]phenyl]-2,3-dihydro-1H-1-benzazepine-4-carboxamide (Compound 64) (0.53 g) as pale yellow crystals.

mp 191 to 194° C.

$^1$H-NMR (dppm, CDCl$_3$) 0.90 to 1.03 (6H, m), 1.30 to 1.48 (2H, m), 1.54 to 1.81 (4H, m), 2.09 to 2.23 (2H, m), 2.64 (2H, t, j=7.4 Hz), 2.92 (2H, t-like), 3.29 to 3.35 (4H, m), 3.55 (2H, t, J=6.6 Hz), 3.80 (2H, t, J=5.0 Hz), 4.00 (2H, t, j=7.2 Hz), 4.16 (2H, t, J=5.0 Hz), 6.90 (1H, d, J=8.8 Hz), 6.98 (2H, d, J=8.8 Hz), 7.38 to 7.57 (8H, m), 8.14 (2H, s).

IR (KBr) n: 2959, 1653, 1605, 1516, 1501 cm$^{-1}$.

Anal calcd for C$_{37}$H$_{45}$N$_5$O$_3$: C, 73.12; H, 7.46; N, 11.52. Found: C, 72.76; H, 7.53; N, 11.33.

Example 58

(Preparation of Compound 65)

7-[4-(2-butoxyethoxy)phenyl]-1-isobutyl-2,3-dihydro-1H-1-benzazepine-4-carboxylic acid (0.61 g) was dissolved in tetrahydrofuran (5 ml), and to the solution, thionyl chloride (0.15 ml) and N,N-dimethylformamide (catalytic amout) were added under ice-cooling at room temperature, and the mixture was stirred for 3 hours. The solvent was distilled off, the residue was dissolved in tetrahydrofuran (25 ml). The solution was added dropwise under ice-cooling to a solution of 4-[(4-propyl-1H-1,2,4-triazole-5-on-3-yl)methylthio]aniline (0.35 g) in pyridine (10 ml). The mixture was stirred at room temperature for 2 hours, and the solvent was distilled off. To the residue was added water, and the mixture was extracted with ethyl acetate. The organic layer was washed with 1N citric acid solution, water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-1-isobutyl-N-[4-[(4-propyl-1H-1,2,4-triazol-5-on-3-yl)methylthio]phenyl]-2,3-dihydro-1H-1-benzazepine-4-carboxamide (Compound 65) (0.69 g) as pale yellow crystals.

mp 98 to 101° C.

$^1$H-NMR (dppm, CDCl$_3$) 0.85 to 0.99 (12H, m), 1.22 to 1.48 (2H, m), 1.54 to 1.82 (4H, m), 1.95 to 2.15 (1H, m), 2.88 (2H, t-like), 3.16 (2H, d, J=7.2 Hz), 3.32 (2H, t-like), 3.55 (2H, t, J=6.6 Hz), 3.67 to 3.85 (6H, m), 4.15 (2H, t, J=5.0 Hz), 6.87 to 6.98 (3H, m), 7.31 to 7.46 (7H, m), 7.57 (2H, d, J=8.8 Hz), 7.83 (1H, s), 9.31 (1H, s).

IR (KBr) n: 2959, 2934, 2868, 1703, 1499 cm$^{-1}$.

Anal calcd for C$_{39}$H$_{49}$N$_5$O$_4$S: C, 68.49; H, 7.22; N, 10.24. Found: C, 68.21; H, 7.17; N, 10.10.

Example 59

(Preparation of Compound 66)

7-[4-(2-butoxyethoxy)phenyl]-1-isobutyl-N-[4-[(4-propyl-1H-1,2,4-triazol-5-on-3-yl)methylthio]phenyl]-2,3-dihydro-1H-1-benzazepine-4-carboxamide (0.50 g) was dissolved in dichloromethane (30 ml), and the mixture was cooled to −78° C. To the solution, 3-chloroperbenzoic acid (0.22 g) in dichloromethane solution (5 ml) was added dropwise. The mixture was stirred for 1 hour at −78° C., and then, sodium thiosulfate solution was added to the mixture. The mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[4-[(4-propyl-1H-1,2,4-triazol-5-on-3-yl)methylsulfinyl]phenyl]-2,3-dihydro-1H-1-benzazepine-4-carboxamide (Compound 66) (0.45 g) as yellow amorphous.

$^1$H-NMR (dppm, CDCl$_3$) 0.85 to 1.04 (12H, m), 1.22 to 1.70 (6H, m), 2.00 to 2.15 (1H, m), 2.90 (2H, t-like), 3.18 (2H, d, J=7.2 Hz), 3.35 (2H, t-like), 3.52 to 3.61 (4H, m), 3.80 (2H, t-like), 3.97 (2H, s), 4.15 (2H, t, J=4.9 Hz), 6.89 to 6.99 (3H, m), 7.36 to 7.52 (7H, m), 7.29 (2H, d, J=8.8 Hz), 8.03 (1H, s), 9.53 (1H, s).

IR (KBr) n: 2959, 2936, 2874, 1705 cm$^{-1}$.

Anal calcd for C$_{39}$H$_{49}$N$_5$O$_5$S.0.25H$_2$O: C, 66.50; H, 7.08; N, 9.94. Found: C, 66.18; H, 6.93; N, 9.93.

Example 60

(Preparation of Compound 67)

7-[4-(2-butoxyethoxy)phenyl]-1-isobutyl-2,3-dihydro-1H-1-benzazepine-4-carboxylic acid (0.95 g) was dissolved in tetrahydrofuran (5 ml), and to the solution, thionyl chloride (0.23 ml) and N,N-dimethylformamide (catalytic amount) were added under ice-cooling at room temperature, and the mixture was stirred for 1.5 hours. The solvent was distilled off, and the residue was dissolved in tetrahydrofuran (10 ml). The solution was added dropwise under ice-cooling to a solution of 3-amino-6-[(4-propyl-1H-1,2,4-triazol-3-yl)methylthio]pyridazine (0.52 g) in pyridine (20 ml). The mixture was stirred at room temperature overnight and the solvent was distilled off. To the residue was added water, and the mixture was extracted with ethyl acetate. The organic layer was washed with 1N citric acid solution, water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-1-isobutyl-N-[6-[(4-propyl-1H-1,2,4-triazol-3-yl)methylthio]pyridazin-3-yl]-2,3-dihydro-1H-1-benzazepine-4-carboxamide (Compound 67) (0.22 g) as yellow amorphous.

$^1$H-NMR (dppm, CDCl$_3$) 0.86 to 0.99 (12H, m), 1.34 to 1.46 (2H, m), 1.57 to 1.66 (2H, m), 1.79 to 1.89 (2H, m), 2.05 to 2.11 (1H, m), 2.93 (2H, t-like), 3.21 (2H, d, J=7.2 Hz), 3.39 (2H, t-like), 3.56 (2H, t, J=6.6 Hz), 3.81 (2H, t, J=5.0 Hz), 4.04 (2H, t, J=7.2 Hz), 4.17 (2H, t, J=5.0 Hz), 4.78 (2H, s), 6.93 (1H, d, J=8.7 Hz), 6.99 (2H, d, J=9.0 Hz), 7.41 to 7.49 (4H, m), 7.53 (1H, d, J=2.1 Hz), 7.60 (1H, s), 8.12 (1H, s), 8.46 (1H, d, J=9.6 Hz), 8.60 (1H, s).

IR (KBr) n: 2957, 2934, 2872, 1663, 1605, 1499 cm$^{-1}$.

Example 61

(Preparation of Compound 68)

7-[4-(2-butoxyethoxy)phenyl]-1-isobutyl-N-[6-[(4-propyl-1H-1,2,4-triazol-3-yl)methylthio]pyridazin-3-yl]-2,3-dihydro-1H-1-benzazepine-4-carboxamide (0.18 g) was dissolved in dichloromethane (20 ml), and the mixture was cooled to −78° C. A solution of 3-chloroperbenzoic acid (0.08 g) in dichloromethane (5 ml) was added dropwise to the solution. The mixture was stirred for 2 hours at −78° C. and sodium thiosulfate solution was added to the mixture. The mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[6-[(4-propyl-1H-1,2,4-triazol-3-yl) methylsulfinyl]pyridazin-3-yl]-2,3-dihydro-1H-1-benzazepine-4-carboxamide (Compound 68) (0.14 g) as yellow amorphous.

$^1$H-NMR (dppm, CDCl$_3$) 0.86 to 1.08 (12H, m), 1.29 to 1.48 (2H, m), 1.54 to 1.67 (2H, m), 1.72 to 1.90 (2H, m), 2.04 to 2.15 (1H, m), 2.94 (2H, br), 3.19 (2H, d, J=7.4 Hz), 3.37 (2H, br), 3.54 (2H, t, J=6.5 Hz), 3.80 (2H, t, J=4.8 Hz), 3.95 to 4.18 (4H, m), 4.44 (1H, d, J=14.2 Hz), 4.66 (H, d, J=14.2 Hz), 6.89 to 7.00 (3H, m), 7.34 to 7.51 (4H, m), 7.67 (2H, d, J=9.6 Hz), 8.14 (1H, s), 8.67 (1H, d, J=9.0 Hz), 9.62 (1H, s).

IR (KBr) n: 2950, 2872, 1671 cm$^{-1}$.

Example 62

(Preparation of Compound 69)

7-[4-(2-butoxyethoxy)phenyl]-1-isobutyl-2,3-dihydro-1H-1-benzazepine-4-carboxylic acid (0.92 g) was dissolved in tetrahydrofuran (10 ml), and to the solution, thionyl chloride (0.22 ml) and N,N-dimethylformamide (catalytic amount) were added under ice-cooling at room temperature, and the mixture was stirred for 1.5 hours. The solvent was distilled off, and the residue was dissolved in tetrahydrofuran (10 ml). The solution was added dropwise under ice-cooling to a solution of 3-amino-6-[(3-propylimidazol-4-yl) methylthio]pyridazine (0.5 g) in pyridine (15 ml). The mixture was stirred at room temperature overnight and the solvent was distilled off. To the residue was added water, and the mixture was extracted with ethyl acetate. The organic layer was washed with iN citric acid solution, water and saturated brine, and dried over anhydrous magnesium sulfate, and then, the solvent was distilled off. The residue was purified by silica gel column chromatography (elution solvent: methanol/ethyl acetate/triethylamine), to give 7-[4-(2- butoxyethoxy)phenyl]-1-isobutyl-N-[6-[(3-propylimidazol-4-yl)methylthio]pyridazin-3-yl]-2,3-dihydro-1H-1-benzazepine-4-carboxamide (Compound 69) (0.3 g) as yellow amorphous.

$^1$H-NMR (dppm, CDCl$_3$) 0.91 to 0.99 (12H, m), 1.34 to 1.46 (2H, m), 1.56 to 1.66 (2H, m), 1.78 to 1.87 (2H, m), 2.05 to 2.11 (1H, m), 2.94 (2H, t, J=4.5 Hz), 3.20 (2H, d, J=7.5 Hz), 3.39 (2H, t, J=4.5 Hz), 3.55 (2H, t, J=6.8 Hz), 3.81 (2H, t, J=5.0 Hz), 3.93 (2H, t, J=7.2 Hz), 4.16 (2H, t, J=5.0 Hz), 4.58 (2H, s), 6.91 to 7.04 (4H, m), 7.31 (1H, d, J=9.5 Hz), 7.41 to 7.53 (5H, m), 7.62 (1H, s), 8.42 (1H, d, J=9.5 Hz), 8.78 (1H, br).

IR (KBr) n: 2959, 2870, 1661, 1499 cm$^{-1}$.

Example 63

(Preparation of Compound 70)

7-[4-(2-butoxyethoxy)phenyl]-1-isobutyl-N-[6-[(3-propylimidazol-4-yl)methylthio]pyridazin-3-yl]-2,3-dihydro-1H-1-benzazepine-4-carboxamide (0.25 g) was dissolved in dichloromethane (10 ml), and the mixture was cooled to −78° C. 0.3-chloroperbenzoic acid (0.38 g) in dichloromethane solution (5 ml) was added dropwise to the solution. The mixture was stirred at −78° C. for 4 hours and sodium thiosulfate solution was added to the mixture. The mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[6-[(3-propylimidazol-4-yl)methylsulfinyl]pyridazin-3-yl]-2,3-dihydro-1H-1-benzazepine-4-carboxamide (Compound 70) (0.14 g) as yellow amorphous.

$^1$H-NMR (dppm, CDCl$_3$) 0.89 to 1.00 (12H, m), 1.34 to 1.44 (2H, m), 1.54 to 1.81 (4H, m), 2.05 to 2.13 (1H, m), 2.96 (2H, t-like), 3.21 (2H, d, J=7.4 Hz), 3.40 (2H, t-like), 3.55 (2H, t, J=6.5 Hz), 3.80 (2H, t, J=5.0 Hz), 3.88 to 4.01 (2H, m), 4.17 (2H, t, j=5.0 Hz), 4.23 (1H, d, J=7.4 Hz), 4.50 (1H, d, J=7.4 Hz), 6.52 (1H, d, J=0.6 Hz), 6.91 to 7.02 (3H, m), 7.41 to 7.53 (5H, m), 7.63 (1H, s), 7.72 (1H, d, J=9.5 Hz), 8.69 (1H, d, J=9.5 Hz), 9.37 (1H, br).

IR (KBr) n: 2961, 2930, 2870, 1667, 1607, 1559, 1499 cm$^{-1}$.

Example 64

(Preparation of Compound 71)

7-[4-(2-butoxyethoxy)phenyl]-1-isobutyl-2,3-dihydro-1H-1-benzazepine-4-carboxylic acid (0.6 g) was dissolved in tetrahydrofuran (5 ml), and to the solution, thionyl chloride (0.15 ml) and N,N-dimethylformamide (catalytic amout) were added under ice-cooling at room temperature, and the mixture was stirred for 1.5 hours. The solvent was distilled off and the residue was dissolved in tetrahydrofuran (5 ml). The solution was added dropwise under ice-cooling to a solution of S-(4-aminophenyl)-o-benzylthiocarbonate (0.36 g) and triethylamine (1 ml) in tetrahydrofuran (5 ml). The mixture was stirred at room temperature for 4 hours. 1N aqueous sodium hydroxide solution (7 ml) and methanol (7 ml) were added to the mixture and the mixture was stirred for 1 hour at room temperature. Then, 4-chloromethyl-3-methylimidazole hydrochloride (0.24 g) was added to the mixture and the mixture was stirred overnight at room temperature. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: methanol/ethyl acetate/triethylamine), to give 7-[4-(2-butoxyethoxy)phenyl]-1-isobutyl-N-[4-[(3-methylimidazol-4-yl)methylthio]phenyl]-2,3-dihydro-1H-1-benzazepine-4-carboxamide (Compound 71) (0.61 g) as pale yellow amorphous.

$^1$H-NMR (dppm, CDCl$_3$) 0.89 to 0.99 (9H, m), 1.33 to 1.48 (2H, m), 1.54 to 1.68 (2H, m), 2.00 to 2.10 (1H, m), 2.91 (2H, t-like), 3.19 (2H, d, J=7.2 Hz), 3.35 (2H, t-like), 3.55 (2H, t, J=6.8 Hz), 3.65 (3H, s), 3.80 (2H, t, J=4.8 Hz), 3.99 (2H, s), 4.16 (2H, t, J=4.9 Hz), 6.71 (1H, s), 6.89 to 7.00 (3H, m), 7.25 to 7.29 (2H, m), 7.40 to 7.56 (8H, m), 7.65 (1H, br).

IR (KBr) n: 2955, 2867, 1655, 1605, 1586, 1499 cm$^{-1}$.

Example 65

(Preparation of Compound 72)

7-[4-(2-butoxyethoxy)phenyl]-1-isobutyl-N-[4-[(3-methylimidazol-4-yl)methylthio]phenyl]-2,3-dihydro-1H-1-benzazepine-4-carboxamide (0.53 g) was dissolved in dichloromethane (5 ml), and the mixture was cooled to −78° C. 3-chloroperbenzoic acid (0.31 g) in dichloromethane solution (5 ml) was added dropwise to the solution. The mixture was stirred for 1 hour at −78° C., and then, sodium thiosulfate solution was added to the mixture. The mixture was concentrated, and extracted with ethyl acetate. The organic layer was washed with aqueous sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[4-[(3-methylimidazol-4-yl)methylsulfinyl]phenyl]-2,3-dihydro-1H-1-benzazepine-4-carboxamide (Compound 72) (0.36 g) as yellow amorphous.

$^1$H-NMR (dppm, CDCl$_3$) 0.89 to 0.99 (9H, m), 1.30 to 1.48 (2H, m), 1.54 to 1.68 (2H, m), 2.05 to 2.15 (1H, m), 2.93 (2H, t-like), 3.19 (2H, d, J=7.0 Hz), 3.36 (2H, t-like), 3.44 (3H, s), 3.55 (2H, t, J=6.6 Hz), 3.80 (2H, t, J=5.0 Hz), 3.95 (1H, d, J=7.2 Hz), 4.14 to 4.17 (3H, m), 6.60 (1H, s), 6.92 (1H, d, J=8.4 Hz), 6.97 (2H, d, J=8.4 Hz), 7.30 to 7.47 (8H, m), 7.77 (2H, d, J=8.8 Hz), 8.28 (H, br).

IR (KBr) n: 2955, 2930, 2870, 1663, 1605, 1588, 1499 cm$^{-1}$.

Example 66

(Preparation of Compound 73)

7-[4-(2-butoxyethoxy)phenyl]-1-isobutyl-2,3-dihydro-1H-1-benzazepine-4-carboxylic acid (1 g) was dissolved in tetrahydrofuran (5 ml), and to the solution, thionyl chloride (0.25 ml) and N,N-dimethylformamide (catalytic amout) were added under ice-cooling, and the mixture was stirred for 1 hour at room temperature. The solvent was distilled off and the residue was dissolved in tetrahydrofuran (10 ml). The solution was added dropwise under ice-cooling to a solution of S-(4-aminophenyl)-o-benzylthiocarbonate (0.6 g) and triethylamine (1 ml) in tetrahydrofuran (5 ml). The mixture was stirred at room temperature for 4 hours and 1N aqueous sodium hydroxide solution (12.5 ml), methanol (25 ml) and tetrahydrofuran (15 ml) were added to the mixture.

The mixture was stirred at room temperature for 4 hours. Then, 4-chloromethyl-3-cyclopropylimidazole hydrochloride (0.57 g) was added to the mixture and the mixture was stirred overnight at room temperature. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: methanol/ethyl acetate/triethylamine), to give 7-[4-(2-butoxyethoxy)phenyl]-1-isobutyl-N-[4-[(3-cyclopropylimidazol-4-yl)methylthio]phenyl]-2,3-dihydro-1H-1-benzazepine-4-carboxamide (Compound 73) (0.34 g) as yellow amorphous.

$^1$H-NMR (dppm, CDCl$_3$) 0.90 to 1.06 (13H, m), 1.30 to 1.45 (2H, m), 1.54 to 1.68 (2H, m), 2.05 to 2.10 (1H, m), 2.91 (2H, t-like), 3.19 (2H, d, J=7.6 Hz), 3.21 to 3.34 (1H, m), 3.36 (2H, t-like), 3.55 (2H, t, J=6.6 Hz), 3.80 (2H, t, J=4.8 Hz), 4.07 to 4.18 (4H, m), 6.67 (1H, s), 6.92 (1H, d, J=8.8 Hz), 6.98 (2H, d, J=8.8 Hz), 7.30 (2H, d, J=8.8 Hz), 7.38 to 7.57 (8H, m), 7.72 (1H, br).

IR (KBr) n: 2957, 2928, 2870, 1657, 1605, 1588, 1497 cm$^{-1}$.

Example 67

(Preparation of Compound 74)

7-[4-(2-butoxyethoxy)phenyl]-1-isobutyl-N-[4-[(3-cyclopropylimidazol-4-yl)methylthio]phenyl]-2,3-dihydro-1H-1-benzazepine-4-carboxamide (0.3 g) was dissolved in dichloromethane (10 ml), and the mixture was cooled to −78° C. 3-chloroperbenzoic acid (0.17 g) in dichloromethane solution (5 ml) was added dropwise to the solution. The mixture was stirred for 1 hour at −78° C., and then, sodium thiosulfate solution was added to the mixture. The mixture was concentrated, and extracted with ethyl acetate. The organic layer was washed with aqueous sodium bicarbonate solution, water and saturated brine, and dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[4-[(3-cyclopropylimidazol-4-yl)methylsulfinyl]phenyl]-2,3-dihydro-1H-1-benzazepine-4-carboxamide (Compound 74) (0.22 g) as yellow amorphous.

$^1$H-NMR (dppm, CDCl$_3$) 0.85 to 1.07 (13H, m), 1.33 to 1.46 (2H, m), 1.56 to 1.66 (2H, m), 1.98 to 2.11 (1H, m), 2.93 to 3.00 (3H, m), 3.19 (2H, d, J=6.9 Hz), 3.36 (2H, s), 3.55 (2H, t, J=6.6 Hz), 3.81 (2H, t, J=4.8 Hz), 4.09 to 4.26 (4H, m), 6.57 (1H, s), 6.92 (1H, d, J=8.7 Hz), 6.98 (2H, d, J=8.4 Hz), 7.37 to 7.48 (8H, m), 7.77 (2H, d, J=8.1 Hz), 8.06 (1H, br).

IR (KBr) n: 2959, 2930, 2870, 1663, 1607, 1588, 1518, 1499 cm$^{-1}$.

Example 68

(Preparation of Compound 75)

To a solution of 7-[4-(2-butoxyethoxy)phenyl]-1-formyl-2,3-dihydro-1H-1-benzazepine-4-carboxylic acid (280 mg) and 1-hydroxybenzotriazole (0.14 g) in DMF (10 ml), 1-ethyl-3-(3'-dimethylaminopropyl)carbodiimide hydrochloride (0.20 g) was added at room temperature, and the mixture was stirred for 1 hour. To the reaction solution, a solution of (S)-(4-aminophenyl)-(2-pyridyl) methanol (150 mg) and triethylamine (0.28 ml) in DMF (10 ml) were added dropwise. The mixture was stirred for 4 days at room temperature, water was added to the mixture and the mixture was extracted with ethyl acetate. The organic layer was washed with water and saturated brine, dried over magnesium sulfate and concentrated under reduced pressure. The obtained residue was separated and purified by column chromatography (ethyl acetate) and recrystallized from ethyl acetate-diisopropylether to give 7-[4-(2-butoxyethoxy)phenyl]-1-formyl-N-[4-[(S)-hydroxy(2-pyridyl)methyl]phenyl]-2,3-dihydro-1H-1-benzazepine-4-carboxamide (Compound 75) (247 mg) as pale yellow crystals.

m.p. 130 to 134° C.

$^1$H-NMR (200 MHz, CDCl$_3$) δ 0.93 (3H, t, J=7.3 Hz), 1.30 to 1.48 (2H, m), 1.53 to 1.68 (2H, m), 3.02 (2H, t, J=5.5 Hz), 3.56 (2H, t, J=6.4 Hz), 3.82 (2H, t, J=5.0 Hz), 3.91 (2H, t, J=5.5 Hz), 4.18 (2H, t, J=5.0 Hz), 5.32 (1H, d, J=4.1 Hz), 5.75 (1H, d, J=4.1 Hz), 7.02 (2H, d, J=8.4 Hz), 7.12 to 7.24 (3H, m), 7.36 to 7.67 (11H, m), 8.54 (1H, s), 8.56 to 8.59 (1H, m).

IR (KBr) 3343, 1664, 1601, 1597, 1514, 1497, 1360, 1314, 1248, 1190, 824 cm$^{-1}$

Elemental Analysis for C$_{36}$H$_{37}$N$_3$O$_5$ Calcd. C, 73.08; H, 6.30; N, 7.10. Found: C, 72.72; H, 6.27; N, 7.04.

Example 69

(Preparation of Compound 76)

To a solution of 7-[4-(2-butoxyethoxy)phenyl]-1-formyl-2,3-dihydro-1H-1-benzazepine-4-carboxylic acid (280 mg) and 1-hydroxybenzotriazole (0.14 g) in DMF (10 ml), 1-ethyl-3-(3'-dimethylaminopropyl)carbodiimide hydrochloride (0.20 g) was added at room temperature, and the mixture was stirred for 0.5 hour. To the reaction solution, a solution of (R)-(4-aminophenyl)-(2-pyridyl) methanol (150 mg) and triethylamine (0.28 ml) in DMF (10 ml) was added dropwise. The mixture was stirred for 3 days at room temperature, water was added to the mixture and the mixture was extracted with ethyl acetate. The organic layer was washed with water and saturated brine, dried over magnesium sulfate and concentrated under reduced pressure. The obtained residue was separated and purified with column chromatography (ethyl acetate) and recrystallized from ethyl acetate-diisopropylether to give 7-[4-(2-butoxyethoxy)phenyl]-1-formyl-N-[4-[(R)-hydroxy(2-pyridyl)methyl]phenyl]-2,3-dihydro-1H-1-benzazepine-4-carboxamide (Compound 76) (154.5 mg) as pale yellow crystals.

m.p. 110 to 112° C.

$^1$H-NMR (200 MHz, CDCl$_3$) δ 0.93 (3H, t, J=7.3 Hz), 1.30 to 1.48 (2H, m), 1.53 to 1.68 (2H, m), 3.02 (2H, t, J=5.5 Hz), 3.56 (2H, t, J=6.6 Hz), 3.82 (2H, t, J=5.0 Hz), 3.91 (2H, t, J=5.5 Hz), 4.18 (2H, t, J=5.0 Hz), 5.32 (1H, d, J=4.4 Hz), 5.75 (1H, d, J=4.4 Hz), 7.02 (2H, d, J=8.4 Hz), 7.12 to 7.24 (3H, m), 7.36 to 7.67 (11H, m), 8.54 (1H, s), 8.56 to 8.59 (1H, m).

IR (KBr) 3357, 1663, 1601, 1597, 1514, 1497, 1360, 1314, 1248, 1190, 822 cm$^{-1}$

Elemental Analysis for C$_{36}$H$_{37}$N$_3$O$_5$.0.25H$_2$O Calcd. C, 72.52; H, 6.34; N, 7.05. Found: C, 72.45; H, 6.35; N, 7.10.

Example 70

(Preparation of Compound 77)

To a solution of 7-[4-(2-butoxyethoxy)phenyl]-1-formyl-N-[4-[(S)-hydroxy (2-pyridyl)methyl]phenyl]-2,3-dihydro-1H-1-benzazepine-4-carboxamide (225.3 mg) in dichloromethane (20 ml), 3-chloroperbenzoic acid (70%, 113 mg) was added at 0° C., and the mixture was stirred at room temperature for 20 hours. To the reaction solution, sodium thiosulfate solution was added, and the mixture was stirred for several minutes, and extracted with ethyl acetate. The organic layer was washed with sodium bicarbonate solution and saturated brine, dried over magnesium sulfate and concentrated under reduced pressure. The obtained residue was purified by column chromatography (ethanol:ethyl acetate 1:4) and recrystallized from ethyl acetate-diisopropylether to give, as pale yellow crystals 7-[4-(2-butoxyethoxy)phenyl]-1-formyl-N-[4-[(S)-hydroxy(1-oxidopyridin-2-yl)methyl]phenyl]-2,3-dihydro-1H-1-benzazepine-4-carboxamide (Compound 77) (125.5 mg).

m.p. 120 to 125° C.

$^1$H-NMR (200 MHz, CDCl$_3$) δ 0.93 (3H, t, J=7.3 Hz), 1.28 to 1.47 (2H, m), 1.53 to 1.68 (2H, m), 3.03 (2H, t, J=5.5 Hz), 3.56 (2H, t, J=6.6 Hz), 3.82 (2H, t, J=5.0 Hz), 3.93 (2H, t, J=5.5 Hz), 4.18 (2H, t, J=5.0 Hz), 6.07 (1H, d, J=4.8 Hz), 6.43 (1H, d, J=4.8 Hz), 6.91 to 7.01 (1H, m), 7.03 (2H, d, J=8.8 Hz), 7.16 to 7.28 (2H, m), 7.46 to 7.79 (10H, m), 8.25 to 8.29 (1H, m), 8.55 (1H, s).

IR (KBr) 3248, 1665, 1607, 1518, 1499, 1314, 1246, 1186 cm$^{-1}$

Elemental Analysis for C$_{36}$H$_{37}$N$_3$O$_6$·1.0H$_2$O Calcd. C, 69.10; H, 6.28; N, 6.72. Found: C, 68.78; H, 6.20; N, 6.78.

Example 71

(Preparation of Compound 78)

To a solution of 7-[4-(2-butoxyethoxy)phenyl]-1-formyl-N-[4-[(R)-hydroxy(2-pyridyl)methyl]phenyl]-2,3-dihydro-1H-1-benzazepine-4-carboxamide (130 mg) in dichloromethane (20 ml) was added 3-chloroperbenzoic acid (70%, 65 mg) at 0° C., and the mixture was stirred at room temperature for 18 hours. To the reaction solution was added sodium thiosulfate solution, and the mixture was stirred for several minutes, and extracted with ethyl acetate. The organic layer was washed with sodium bicarbonate solution and saturated brine, dried over magnesium sulfate and concentrated under reduced pressure. The obtained residue was purified by column chromatography (ethanol:ethyl acetate 1:4) and recrystallized from ethyl acetate-diisopropylether to give 7-[4-(2-butoxyethoxy)phenyl]-1-formyl-N-[4-[(R)-hydroxy(1-oxidopyridin-2-yl)methyl]phenyl]-2,3-dihydro-1H-1-benzazepine-4-carboxamide (Compound 78) (68.2 mg) as pale yellow crystals.

m.p. 104 to 106° C.

$^1$H-NMR (200 MHz, CDCl$_3$) δ 0.93 (3H, t, J=7.3 Hz), 1.28 to 1.47 (2H, m), 1.53 to 1.68 (2H, m), 3.03 (2H, t, J=5.5 Hz), 3.56 (2H, t, J=6.6 Hz), 3.81 (2H, t, J=5.0 Hz), 3.91 (2H, t, J=5.5 Hz), 4.17 (2H, t, J=5.0 Hz), 6.06 (1H, d, J=4.2 Hz), 6.39 (1H, d, J=4.2 Hz), 6.91 to 7.01 (1H, m), 7.03 (2H, d, J=8.8 Hz), 7.16 to 7.28 (2H, m), 7.44 to 7.67 (9H, m), 7.75 (1H, s), 8.23-8.27 (1H, m), 8.53 (1H, s).

IR (KBr) 3263, 1667, 1607, 1518, 1497, 1316, 1248, 1188 cm$^{-1}$

Elemental Analysis for C$_{36}$H$_{37}$N$_3$O$_6$·1.0H$_2$O Calcd. C, 69.10; H, 6.28; N, 6.72. Found: C, 69.31; H, 6.17; N, 6.85.

Example 72

(Preparation of Compound 79)

To a solution of 7-[4-(2-butoxyethoxy)phenyl]-2,3-dihydro-1H-1-benzazepine-4-carboxylic acid (463 mg) and triethylamine (0.51 ml) in acetonitrile (25 ml), trifluoroacetic acid anhydride (0.43 ml) was added at 0° C., and the mixture was stirred for 1 hour. The reaction solution was concentrated under reduced pressure, water was added to the mixture and the mixture was extracted with ethyl acetate. The organic layer was washed with saturated brine, dried over magnesium sulfate and concentrated under reduced pressure. To a solution of the residue and 1-hydroxybenzotriazole (0.33 g) in DMF (10 ml) was added 1-ethyl-3-(3'-dimethylaminopropyl)carbodiimide hydrochloride (0.46 g) at room temperature, and the mixture was stirred for 1 hour. To the reaction solution, a solution of (S)-(4-aminophenyl)-(2-pyridyl)methanol (267 mg) and triethylamine (0.67 ml) in DMF (5 ml) was added dropwise. The mixture was stirred at room temperature for 20 hours, water was added to the mixture and the mixture was extracted with ethyl acetate. The organic layer was washed with water and saturated brine, dried over magnesium sulfate and concentrated under reduced pressure. The obtained residue was purified by column chromatography (ethyl acetate:hexane 2:1→ethyl acetate), which was recrystallized from ethyl acetate-hexane, to give 7-[4-(2-butoxyethoxy)phenyl]-N-[4-[(S)-hydroxy(2-pyridyl)methyl]phenyl]-1-trifluoroacetyl-2,3-dihydro-1H-1-benzazepine-4-carboxamide (Compound 79) (316 mg) as pale yellow crystals.

m.p. 100 to 102° C.

$^1$H-NMR (200 MHz, CDCl$_3$) δ 0.93 (3H, t, J=7.4 Hz), 1.32 to 1.48 (2H, m), 1.51 to 1.66 (2H, m), 2.86 to 3.27 (3H, m), 3.56 (2H, t, J=6.6 Hz), 3.82 (2H, t, J=4.9 Hz), 4.18 (2H, t, J=4.9 Hz), 4.74 to 4.89 (1H, m), 5.34 (1H, d, J=3.0 Hz), 5.75 (1H, d, J=3.0 Hz), 7.03 (2H, d, J=8.8 Hz), 7.13 to 7.27 (3H, m), 7.30 to 7.42 (4H, m), 7.51 to 7.69 (7H, m), 8.5 to 8.62 (1H, m).

IR (KBr) 3356, 1694, 1653, 1595, 1520, 1499., 1314, 1208, 1179, 1155, 826 cm$^{-1}$

Elemental Analysis for C$_{37}$H$_{36}$N$_3$O$_5$F$_3$·0.25H$_2$O Calcd. C, 66.91; H, 5.54; N, 6.33. Found: C, 66.93; H, 5.60; N, 6.32.

Example 73

(Preparation of Compound 80)

To a solution of 7-[4-(2-butoxyethoxy)phenyl]-N-[4-[(S)-hydroxy(2-pyridyl)methyl]phenyl]-1-trifluoroacetyl-2,3-dihydro-1H-1-benzazepine-4-carboxamide (285 mg) in dichloromethane (10 ml) was added 3-chloroperbenzoic acid (70%, 127 mg) was added at 0° C. and the mixture was stirred at room temperature for 20 hours. To the reaction solution was added sodium thiosulfate solution, and the mixture was stirred for several minutes, and extracted with ethyl acetate. The organic layer was washed with sodium bicarbonate solution and saturated brine, dried over magnesium sulfate and concentrated under reduced pressure. The obtained residue was purified by column chromatography (ethanol:ethyl acetate 1:4) and recrystallized from ethanol-diisopropylether to give 7-[4-(2-butoxyethoxy)phenyl]-N-[4-[(S)-hydroxy(1-oxidopyridin-2-yl)methyl]phenyl]-2,3-dihydro-1-trifluoroacetyl-1H-1-benzazepine-4-carboxamide (Compound 80) (220.9 mg) as pale yellow crystals.

m.p. 107 to 110° C.

$^1$H-NMR (200 MHz, CDCl$_3$) δ 0.93 (3H, t, J=7.2 Hz), 1.29 to 1.48 (2H, m), 1.51 to 1.67 (2H, m), 2.86 to 3.34 (3H, m), 3.56 (2H, t, J=6.6 Hz), 3.82 (2H, t, J=4.9 Hz), 4.18 (2H, t, J=4.9 Hz), 4.76 to 4.91 (1H, m), 6.07 (1H, d, J=3.8 Hz), 6.41 (H, d, J=3.8 Hz), 6.91 to 7.05 (3H, m), 7.20 to 7.38 (4H, m), 7.45 to 7.67 (9H, m), 8.24 to 8.28 (1H, m).

IR (KBr) 3044, 1696, 1650, 1607, 1499, 1435, 1316, 1252, 1206, 1181, 1155, 825 cm$^{-1}$

Elemental Analysis for $C_{37}H_{36}N_3O_6F_3 \cdot 0.5H_2O$ Calcd. C, 64.90; H, 5.45; N, 6.14. Found: C, 64.97; H, 5.37; N, 6.10.

Example 74

(Preparation of Compound 81)

To a solution of 7-[4-(2-butoxyethoxy)phenyl]-N-[4-[(S)-hydroxy(2-pyridyl)methyl]phenyl]-1-propyl-2,3-dihydro-1H-1-benzazepine-4-carboxamide (300 mg) in THF (10 ml) were added thionyl chloride (0.13 ml) and DMF (1 droplet) at room temperature and the mixture was stirred for 1 hour. The reaction solution was concentrated under reduced pressure, and a solution of the residue in THF (15 ml) was added dropwise at 0° C. to a solution of (S)-(4-aminophenyl)-(2-pyridyl)methanol (156 mg) and triethylamine (0.59 ml) in THF (5 ml). The mixture was stirred at room temperature for 18 hours, water was added to the mixture and the mixture was extracted with ethyl acetate. The organic layer was washed with saturated brine, and dried over magnesium sulfate. The solvent was removed under reduced pressure, and the obtained residue was purified by column chromatography (ethyl acetate:hexane 2:1→4:1), to give 7-[4-(2-butoxyethoxy)phenyl]-N-[4-[(S)-hydroxy(2-pyridyl)methyl]phenyl]-1-propyl-2,3-dihydro-1H-1-benzazepine-4-carboxamide (Compound 81) (316 mg) as yellow amorphous.

$^1$H-NMR (200 MHz, CDCl$_3$) δ 0.93 (3H, t, J=7.3 Hz), 0.99 (3H, t, J=7.3 Hz), 1.29 to 1.47 (2H, m), 1.50 to 1.82 (4H, m), 2.86 to 2.95 (2H, m), 3.25 to 3.39 (4H, m), 3.55 (2H, t, J=6.6 Hz), 3.80 (2H, t, J=5.0 Hz), 4.16 (2H, t, J=5.0 Hz), 5.27 to 5.37 (1H, m), 5.74 (1H, br s), 6.89 (1H, d, J=8.4 Hz), 6.98 (2H, d, J=8.8 Hz), 7.12 to 7.26 (2H, m), 7.34 to 7.67 (11H, m), 8.56 to 8.58 (1H, m).

IR (KBr) 3350, 1651, 1607, 1516, 1499, 1314, 1242, 1179 cm$^{-1}$

Elemental Analysis For $C_{38}H_{43}N_3O_4 \cdot 0.25H_2O$ Calcd. C, 74.79; H, 7.1.8; N, 6.89. Found: C, 74.82; H, 7.29; N, 6.93.

Example 75

(Preparation of Compound 82)

To a solution of 7-[4-(2-butoxyethoxy)phenyl]-N-[4-[(S)-hydroxy(1-oxidopyridin-2-yl)methyl]phenyl]-2,3-dihydro-1-trifluoroacetyl-1H-1-benzazepine-4-carboxamide (180 mg) in ethanol (30 ml) was added sodium borohydride (10.0 mg) at room temperature and stirred for 2 hours. To the reaction solution was further added sodium borohydride (10.0 mg), and the mixture was stirred for 2 hours. To the reaction solution was added water, and the mixture was extracted with ethyl acetate. The organic layer was washed with saturated brine, dried over magnesium sulfate and concentrated under reduced pressure. The obtained residue was purified by column chromatography (ethanol:ethyl acetate 1:2) to give 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (Compound 82) (141.4 mg) as yellow amorphous.

$^1$H-NMR (200 MHz, CDCl$_3$) δ 0.93 (3H, t, J=7.3 Hz), 1.28 to 1.48 (2H, m), 1.51 to 1.68 (2H, m), 2.89 to 3.01 (2H, m), 3.41 to 3.51 (2H, m), 3.55 (2H, t, J=6.6 Hz), 3.80 (2H, t, J=5.0 Hz), 4.16 (2H, t, J=5.0 Hz), 6.07 (1H, br s), 6.31-6.45 (1H, m), 6.71 (1H, d, J=8.0 Hz), 6.92-6.99 (3H, m), 7.20 to 7.36 (5H, m), 7.39 to 7.52 (4H, m), 7.62 to 7.66 (3H, m), 8.24 to 8.28 (1H, m).

IR (KBr) 3293, 1651, 1609, 1499, 1435, 1408, 1316, 1246, 1181, 820 cm$^{-1}$

Elemental Analysis for $C_{35}H_{37}N_3O_5 \cdot 1.5H_2O$ Calcd. C, 69.27; H, 6.65; N, 6.93. Found: C, 69.05; H, 6.31; N, 6.67.

Example 76

(Preparation of Compound 83)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (120 mg) and propionaldehyde (0.15 ml) in 1,2-dichloroethane (10 ml) was added sodium triacetoxyborohydride (0.13 g) at room temperature, and the mixture was stirred for 20 hours. To the reaction solution was added water, and the mixture was extracted with ethyl acetate. The organic layer was washed with saturated brine, and dried over magnesium sulfate. The solvent was removed under reduced pressure, and the obtained residue was purified by column chromatography (ethanol:ethyl acetate 1:2), to give 7-[4-(2-butoxyethoxy)phenyl]-N-[4-[(S)-hydroxy(1-oxidopyridin-2-yl)methyl]phenyl]-1-propyl-2,3-dihydro-1H-1-benzazepine-4-carboxamide (Compound 83) (105.4 mg) as yellow crystals.

m.p. 87 to 89° C.

$^1$H-NMR (200 MHz, CDCl$_3$) δ 0.93 (3H, t, J=7.1 Hz), 1.00 (3H, t, J=7.0 Hz), 1.29 to 1.48 (2H, m), 1.53 to 1.82 (4H, m), 2.86 to 2.96 (2H, m), 3.25 to 3.40 (4H, m), 3.55 (2H, t, J=6.6 Hz), 3.80 (2H, t, J=5.0 Hz), 4.16 (2H, t, J=5.0 Hz), 6.06 (1H, br s), 6.35 to 6.45 (1H, m), 6.88 to 7.00 (4H, m), 7.23 to 7.28 (2H, m), 7.38 to 7.51 (7H, m), 7.62 to 7.67 (3H, m), 8.24 to 8.28 (1H, m).

IR (KBr) 3296, 1651, 1607, 1516, 1499, 1313, 1242, 1181, 814 cm$^{-1}$

Elemental Analysis for $C_{38}H_{43}N_3O_5 \cdot 0.5H_2O$ Calcd. C, 72.36; H, 7.03; N, 6.66. Found: C, 72.07; H, 7.01; N, 6.51.

Example 77

(Preparation of Compound 84)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (142.6 mg) and cyclopropane carboxyaldehyde (0.17 g) in 1,2-dichloroethane (10 ml) was added sodium triacetoxyborohydride (0.13 g) at room temperature and the mixture was stirred for 64 hours. To the reaction solution were added cyclopropane carboxyaldehyde (0.1 g) and sodium triacetoxyborohydride (0.13 g), and the mixture was further stirred for 4 hours. To the reaction solution was added water and the mixture was extracted with ethyl acetate. The organic layer was washed with saturated brine, and dried over magnesium sulfate. The solvent was removed under reduced pressure, and the residue was purified by column chromatography (ethanol:ethyl acetate 1:4), which was recrystallized from ethyl acetate-diisopropylether, to give 7-[4-(2-butoxyethoxy)phenyl]-1-cyclopropylmethyl-N-[4-[(S)-hydroxy(1-oxidopyridin-2-yl)methyl]phenyl]-2,3-dihydro-1H-1-benzazepine-4-carboxamide (Compound 84) (120.7 mg) as yellow crystals.

m.p. 85 to 88° C.

$^1$H-NMR (200 MHz, CDCl$_3$) δ 0.24-0.35 (2H, m), 0.60 to 0.70 (2H, m), 0.93 (3H, t, J=7.1 Hz), 1.02 to 1.22 (1H, m), 1.30 to 1.46 (2H, m), 1.53 to 1.66 (2H, m), 2.91 to 3.02 (2H, m), 3.26 (2H, d, J=6.2 Hz), 3.43 to 3.50 (2H, m), 3.55 (2H, t, J=6.6 Hz), 3.80 (2H, t, J=5.0 Hz), 4.16 (2H, t, J=5.0 Hz), 6.04 to 6.09 (1H, m), 6.36 to 6.46 (1H, m), 6.91 to 7.00 (4H, m), 7.24 to 7.28 (2H, m), 7.39 to 7.52 (7H, m), 7.63 to 7.67 (3H, m), 8.25 to 8.29 (1H, m).

IR (KBr) 3270, 1653, 1605, 1516, 1499, 1244, 1181, 837 cm$^{-1}$

Elemental Analysis for $C_{39}H_{43}N_3O_5 \cdot 1.0H_2O$ Calcd. C, 71.87; H, 6.96; N, 6.45. Found: C, 72.10; H, 6.93; N, 6.50.

Example 78

(Preparation of Compound 85)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and isobutylaldehyde (0.15 g) in 1,2-dichloroethane (10 ml) was added sodium triacetoxyborohydride (0.22 g) at room temperature and the mixture was stirred for 4 days. To the reaction solution were added isobutylaldehyde (0.15 g) and sodium triacetoxyborohydride (0.22 g), and the mixture was further stirred for 5 hours. To the reaction solution was added water and the mixture was extracted with ethyl acetate. The organic layer was washed with saturated brine, dried over magnesium sulfate and concentrated under reduced pressure. The residue was purified by column chromatography (ethanol:ethyl acetate 1:4) to give 7-[4-(2-butoxyethoxy)phenyl]-N-[4-[(S)-hydroxy(1-oxidopyridin-2-yl)methyl]phenyl]-1-isobutyl-2,3-dihydro-1H-1-benzazepine-4-carboxamide (Compound 85) (155.2 mg) as yellow amorphous.

$^1$H-NMR (200 MHz, CDCl$_3$) δ 0.93 (3H, t, J=7.4 Hz), 0.98 (6H, d, J=6.6 Hz), 1.27 to 1.47 (2H, m), 1.53 to 1.68 (2H, m), 1.98 to 2.18 (1H, m), 2.89 to 2.98 (2H, m), 3.19 (2H, d, J=7.4 Hz), 3.32 to 3.42 (2H, m), 3.55 (2H, t, J=6.6 Hz), 3.80 (2H, t, J=5.0 Hz), 4.16 (2H, t, J=5.0 Hz), 6.07 (1H, d, J=4.1 Hz), 6.42 (1H, d, J=4.1 Hz), 6.90 to 7.00 (4H, m), 7.23 to 7.28 (2H, m), 7.38 to 7.52 (7H, m), 7.63 to 7.68 (3H, m), 8.24 to 8.28 (1H, m).

IR (KBr) 3230, 1653, 1605, 1516, 1499, 1240, 1181, 839 cm-1

Elemental Analysis for $C_{39}H_{45}N_3O_5 \cdot 0.75H_2O$ Calcd. C, 72.14; H, 7.22; N, 6.47. Found: C, 72.22; H, 7.29; N, 6.57.

Example 79

(Preparation of Compound 86)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and 2-formylthiazole (0.24 g) in 1,2-dichloroethane (10 ml) was added sodium triacetoxyborohydride (0.22 g) at room temperature and the mixture was stirred for 4 days. To the reaction solution were added 2-formylthiazole (0.24 g), sodium triacetoxyborohydride (0.22 g) and acetic acid (1 droplet), and the mixture was further stirred for 24 hours. To the reaction solution was added water and the mixture was extracted with ethyl acetate. The organic layer was washed with saturated brine, and dried over magnesium sulfate. The solvent was removed under reduced pressure, and the residue was purified by column chromatography (ethanol:ethyl acetate 1:4→1:3), which was recrystallized from ethyl acetate, to give 7-[4-(2-butoxyethoxy)phenyl]-N-[4-[(S)-hydroxy(1-oxidopyridin-2-yl)methyl]phenyl]-1-(thiazol-2-ylmethyl)-2,3-dihydro-1H-1-benzazepine-4-carboxamide (Compound 86) (113.6 mg) as yellow crystals.

m.p. 164 to 165° C.

$^1$H-NMR (200 MHz, CDCl$_3$) δ 0.93 (3H, t, J=7.3 Hz), 1.29 to 1.47 (2H, m), 1.54 to 1.68 (2H, m), 2.90 to 2.99 (2H, m), 3.43 to 3.50 (2H, m), 3.55 (2H, t, J=6.8 Hz), 3.80 (2H, t, J=5.0 Hz), 4.15 (2H, t, J=5.0 Hz), 4.87 (2H, s), 6.06 (H, d, J=4.4 Hz), 6.42 (1H, d, J=4.4 Hz), 6.92 to 7.03 (4H, m), 7.23 to 7.27 (2H, m), 7.32 (1H, d, J=5=3.2 Hz), 7.37 to 7.54 (7H, m), 7.65 (2H, d, J=8.4 Hz), 7.76 (1H, s), 7.79 (1H, d, J=3.2 Hz), 8.23-8.27 (1H, m).

IR (KBr) 3263, 1634, 1595, 1537, 1499, 1435, 1406, 1318, 1244, 1188, 1126, 814 cm$^{-1}$

Elemental Analysis for $C_{39}H_{40}N_4O_5S$ Calcd. C, 69.21; H, 5.96; N, 8.28. Found: C, 68.93; H, 5.84; N, 8.20.

Example 80

(Preparation of Compound 87)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and 4-formyl-1-methylpyrazole (0.4 g) in 1,2-dichloroethane (10 ml) were added sodium triacetoxyborohydride (0.22 g) and acetic acid (1 droplet) at room temperature and the mixture was stirred for 5 days. To the reaction solution was added water and the mixture was extracted with ethyl acetate. The organic layer was washed with saturated brine, dried over magnesium sulfate and concentrated under reduced pressure. The residue was purified by column chromatography (ethanol:ethyl acetate 1:3→1:2) and recrystallized from ethyl acetate-diisopropylether to give 7-[4-(2-butoxyethoxy)phenyl]-N-[4-[(S)-hydroxy(1-oxidopyridin-2-yl)methyl]phenyl]-1-(1-methylpyrazol-4-ylmethyl)-2,3-dihydro-1H-1-benzazepine-4-carboxamide (Compound 87) (96.1 mg) as yellow crystals.

m.p. 94 to 97° C.

$^1$H-NMR (200 MHz, CDCl$_3$) δ 0.93 (3H, t, J=7.1 Hz), 1.32 to 1.46 (2H, m), 1.51 to 1.68 (2H, m), 2.80 to 2.89 (2H, m), 3.29 to 3.39 (2H, m), 3.55 (2H, t, J=6.6 Hz), 3.81 (2H, t, J=5.0 Hz), 3.90 (3H, s), 4.16 (2H, t, j=5.0 Hz), 4.44 (2H, s), 6.07 (1H, d, J=4.4 Hz), 6.43 (1H, d, J=4.4 Hz), 6.91 to 7.00 (4H, m), 7.24 to 7.28 (2H, m), 7.32 (1H, s), 7.38 to 7.63 (8H, m), 7.62 to 7.67 (3H, m), 8.24 to 8.28 (1H, m).

IR (KBr) 3274, 1653, 1605, 1516, 1499, 1433, 1404, 1316, 1240, 1184, 1123, 818 cm$^{-1}$

Elemental Analysis for $C_{40}H_{43}N_5O_5 \cdot 0.75H_2O$ Calcd. C, 69.90; H, 6.53; N, 10.19. Found: C, 69.98; H, 6.77; N, 9.90.

Example 81

(Preparation of Compound 88)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and thiophene-3-carboxaldehyde (0.5 g) in 1,2-dichloroethane (10 ml) were added sodium triacetoxyborohydride (0.22 g) and acetic acid (1 droplet) at room temperature and the mixture was stirred for 20 hours. To the reaction solution was added water and the mixture was extracted with ethyl acetate. The organic layer was washed with saturated brine, dried over magnesium sulfate and concentrated under reduced pressure. The residue was purified by column chromatography (ethanol: ethyl acetate 1:4) and recrystallized from ethyl acetate-diisopropylether to give 7-[4-(2-butoxyethoxy)phenyl]-N-[4-[(S)-hydroxy(1-oxidopyridin-2-yl)methyl]phenyl]-(3-thienylmethyl)-2,3-dihydro-1-1H-1-benzazepine-4-carboxamide (Compound 88) (171.4 mg) as yellow crystals.

m.p. 110 to 112° C.

$^1$H-NMR (200 MHz, CDCl$_3$) δ 0.93 (3H, t, J=7.1 Hz), 1.29 to 1.48 (2H, m), 1.54 to 1.68 (2H, m), 2.90 to 2.90 (2H, m), 3.31 to 3.42 (2H, m), 3.55 (2H, t, J=6.8 Hz), 3.80 (2H, t, J=4.9 Hz), 4.16 (2H, t, J=4.9 Hz), 4.58 (2H, s), 6.07 (1H, d, J=4.2 Hz), 6.42 (1H, d, J=4.2 Hz), 6.91 to 7.07 (5H, m), 7.12 to 7.18 (1H, m), 7.23 to 7.27 (2H, m), 7.34 to 7.49 (7H, m), 7.54 (1H, d, J=2.2 Hz), 7.63 to 7.68 (3H, m), 8.24 to 8.28 (1H, m).

IR (KBr) 3262, 1636, 1595, 1499, 1435, 1406, 1316, 1242, 1186, 1128, 810 cm$^{-1}$

Elemental Analysis for $C_{40}H_{41}N_3O_5S.0.25H_2O$ Calcd. C, 70.62; H, 6.15; N, 6.18. Found: C, 70.61; H, 6.22; N, 6.21.

Example 82

(Preparation of Compound 89)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and 5-formyl-1-methylpyrazole (0.23 g) in 1,2-dichloroethane (10 ml) were added sodium triacetoxyborohydride (0.22 g) and acetic acid (1 droplet) at room temperature and the mixture was stirred for 5 days. To the reaction solution, 5-formyl-1-methylpyrazole (0.23 g) and sodium triacetoxyborohydride (0.22 g) and acetic acid (1 droplet) were added, and the mixture was further stirred for 24 hours. To the reaction solution was added water and the mixture was extracted with ethyl acetate. The organic layer was washed with saturated brine, dried over magnesium sulfate and concentrated under reduced pressure. The residue was separated and purified by column chromatography (ethanol:ethyl acetate 1:3) and further recrystallized from ethyl acetate to give 7-[4-(2-butoxyethoxy)phenyl]-N-[4-[(S)-hydroxy(1-oxidopyridin-2-yl)methyl]phenyl]-1-(1-methylpyrazol-5-ylmethyl)-2,3-dihydro-1H-1-benzazepine-4-carboxamide (Compound 89) (140.1 mg) as yellow crystals.

m.p. 109 to 111° C.

$^1$H-NMR (200 MHz, CDCl$_3$) δ 0.93 (3H, t, J=7.3 Hz), 1.30 to 1.48 (2H, m), 1.52 to 1.68 (2H, m), 2.62-2.70 (2H, m), 3.29 to 3.39 (2H, m), 3.56 (2H, t, J=6.6 Hz), 3.78 to 3.83 (5H, m), 4.17 (2H, t, J=5.0 Hz), 4.55 (2H, s), 6.07 (1H, d, J=4.3 Hz), 6.25 (1H, d, J=1.8 Hz), 6.43 (1H, d, J=4.3 Hz), 6.91 to 7.02 (4H, m), 7.24 to 7.28 (2H, m), 7.42 to 7.67 (11H, m), 8.25 to 8.28 (1H, m).

IR (KBr) 3260, 1636, 1597, 1499, 1437, 1406, 1318, 1246, 1188, 1128, 810 cm$^{-1}$

Elemental Analysis for $C_{40}H_{43}N_5O_5.1.0H_2O$ Calcd. C, 69.44; H, 6.56; N, 10.12. Found: C, 69.34; H, 6.72; N, 10.07.

Example 83

(Preparation of Compound 90)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and benzaldehyde (0.22 g) in 1,2-dichloroethane (10 ml) were added sodium triacetoxyborohydride (0.22 g) and acetic acid (1 droplet) at room temperature and the mixture was stirred for 24 hours. To the reaction solution were added benzaldehyde (0.22 g) and sodium triacetoxyborohydride (0.22 g), and the mixture was further stirred for 24 hours. To the reaction solution was added water and the mixture was extracted with ethyl acetate. The organic layer was washed with saturated brine, dried over magnesium sulfate and concentrated under reduced pressure. The residue was separated and purified by column chromatography (ethanol:ethyl acetate 1:4) and further recrystallized from ethyl acetate-diisopropylether to give 1-benzyl-7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (Compound 90) (168.0 mg) as yellow crystals.

m.p. 89 to 93° C.

$^1$H-NMR (200 MHz, CDCl$_3$) δ 0.93 (3H, t, J=7.1 Hz), 1.28 to 1.48 (2H, m), 1.51 to 1.67 (2H, m), 2.81 to 2.89 (2H, m), 3.32 to 3.42 (2H, m), 3.55 (2H, t, J=6.6 Hz), 3.80 (2H, t, J=4.9 Hz), 4.16 (2H, t, J=4.9 Hz), 4.62 (2H, s), 6.07 (1H, d, J=4.3 Hz), 6.41 (1H, d, J=4.9 Hz), 6.88 to 7.06 (4H, m), 7.24 to 7.67 (17H, m), 8.25 to 8.28 (1H, m).

IR (KBr) 3275, 1653, 1603, 1499, 1454, 1433, 1406, 1314, 1244, 1184, 1123, 812 cm$^{-1}$

Elemental Analysis for $C_{42}H_{43}N_3O_5.1.0H_2O$ Calcd. C, 73.34; H, 6.59; N, 6.11. Found: C, 73.70; H, 6.66; N, 5.99.

Example 84

(Preparation of Compound 91)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and 2-furaldehyde (0.2 g) in 1,2-dichloroethane (10 ml) were added sodium triacetoxyborohydride (0.22 g) and acetic acid (1 droplet) at room temperature and the mixture was stirred for 20 hours. To the reaction solution were added 2-furaldehyde (0.2 g) and sodium triacetoxyborohydride (0.22 g), and the mixture was further stirred for 3 days. To the reaction solution was added water and the mixture was extracted with ethyl acetate. The organic layer was washed with saturated brine, dried over magnesium sulfate and concentrated under reduced pressure. The residue was separated and purified by column chromatography (ethanol:ethyl acetate 1:4) and further recrystallized from ethyl acetate-diisopropylether to give 7-[4-(2-butoxyethoxy)phenyl]-1-(2-furyl)-N-[4-[(S)-hydroxy(1-oxidopyridin-2-yl)methyl]phenyl]-2,3-dihydro-1H-1-benzazepine-4-carboxamide (Compound 91) (150.0 mg) as yellow crystals.

m.p. 117 to 119° C.

$^1$H-NMR (200 MHz, CDCl$_3$) δ 0.93 (3H, t, J=7.1 Hz), 1.29 to 1.48 (2H, m), 1.54 to 1.68 (2H, m), 2.81 to 2.88 (2H, m), 3.31 to 3.41 (2H, m), 3.55 (2H, t, J=6.6 Hz), 3.80 (2H, t, J=5.0 Hz), 4.16 (2H, t, J=5.0 Hz), 4.51 (2H, s), 6.06 (1H, d, J=4.4 Hz), 6.30 (H, d, J=3.6 Hz), 6.37 to 6.42 (2H, m), 6.91 to 7.06 (3H, m), 7.08 (H, d, J=8.4 Hz), 7.23 to 7.27 (2H, m), 7.40 to 7.53 (8H, m), 7.64 (2H, d, J=8.4 Hz), 7.68 (1H, s), 8.23-8.27 (1H, m).

IR (KBr) 3281, 1644, 1597, 1499, 1435, 1408, 1316, 1244, 1186, 1123, 812 cm$^{-1}$

Elemental Analysis for $C_{40}H_{41}N_3O_6.0.25H_2O$ Calcd. C, 72.32; H, 6.30; N, 6.33. Found: C, 72.36; H, 6.33; N, 6.10.

Example 85

(Preparation of Compound 92)

To a solution of 7-[4-(2-butoxyethoxy)phenyl]-N-[4-[(S)-hydroxy(1-oxidopyridin-2-yl)methyl]phenyl]-2,3-dihydro-1H-1-benzazepine-4-carboxamide (200 mg) and 5-formyl-3-methyl isothiazole (0.44 g) in 1,2-dichloroethane (10 ml) were added sodium triacetoxyborohydride (0.22 g) and acetic acid (1 droplet) at room temperature and the mixture was stirred for 24 hours. To the reaction solution was added sodium triacetoxyborohydride (0.22 g) was added to the mixture, and the mixture was further stirred for 3 days. To the reaction solution was added water and the mixture was extracted with ethyl acetate. The organic layer was washed with saturated brine, dried over magnesium sulfate and concentrated under reduced pressure. The residue was separated and purified by column chromatography (ethanol:ethyl acetate 1:4) and further recrystallized from ethyl acetate-diisopropylether to give 7-[4-(2-butoxyethoxy)phenyl]-1-(3-methyl-isothiazol-5-ylmethyl)-N-[4-[(S)-hydroxy(1-oxidopyridin-2-yl)methyl]phenyl]-2,3-dihydro-1H-1-benzazepine-4-carboxamide (Compound 92) (154.0 mg) as yellow crystals.

m.p. 93 to 96° C.

$^1$H-NMR (200 MHz, CDCl$_3$) δ 0.93 (3H, t, J=7.1 Hz), 1.29 to 1.47 (2H, m), 1.52 to 1.68 (2H, m), 2.49 (3H, s), 2.88 to 2.98 (2H, m), 3.35 to 3.45 (2H, m), 3.55 (2H, t, J=6.6 Hz), 3.81 (2H, t, J=4.8 Hz), 4.16 (2H, t, J=4.8 Hz), 4.79 (2H, s), 6.07 (1H, d, J=4.4 Hz), 6.43 (1H, d, J=4.4 Hz), 6.91 to 7.01 (5H, m), 7.24 to 7.28 (2H, m), 7.39 to 7.49 (6H, m), 7.52 to 7.58 (1H, m), 7.63 to 7.68 (3H, m), 8.25 to 8.29 (1H, m).

IR (KBr) 3314, 1655, 1605, 1514, 1499, 1433, 1406, 1314, 1244, 1182, 1120, 814 cm$^{-1}$

Elemental Analysis for C$_{40}$H$_{42}$N$_4$O$_5$S.1.0H$_2$O Calcd. C, 67.77; H, 6.26; N, 7.90. Found: C, 67.73; H, 6.12; N, 7.90.

Example 86

(Preparation of Compound 93)

To a solution of 7-[4-(2-butoxyethoxy)phenyl]-1-methanesulfonyl-2,3-dihydro-1H-1-benzazepine-4-carboxylic acid (0.50 g) in THF (10 ml) were added thionyl chloride (0.12 ml) and DMF (1 droplet) at room temperature and the mixture was stirred for 2 hours. The reaction solution was concentrated under reduced pressure, a solution of the residue in THF (20 ml) was added dropwise at 0° C. to a solution of (S)-(+)-(4-aminophenyl)(2-pyridyl)methanol (0.24 g) and triethylamine (0.6 ml) in THF (5 ml), and the mixture was stirred for 18 hours at room temperature. To the reaction solution was added water, and the mixture was extracted with ethyl acetate. The organic layer was washed with saturated brine, dried over magnesium sulfate and concentrated under reduced pressure. The residue was recrystallized from ethyl acetate-diisopropylether to give 7-[4-(2-butoxyethoxy)phenyl]-N-[4-[(S)-hydroxy(2-pyridyl)methyl]phenyl]-1-methanesulfonyl-2,3-dihydro-1H-1-benzazepine-4-carboxamide (Compound 93) (542.7 mg) as colorless crystals.

m.p. 158 to 160° C.

$^1$H-NMR (200 MHz, CDCl$_3$) δ 0.93 (3H, t, J=7.3 Hz), 1.32 to 1.45 (2H, m), 1.52 to 1.67 (2H, m), 2.88 (3H, s), 3.05 to 3.15 (2H, m), 3.56 (2H, t, J=6.6 Hz), 3.81 (2H, t, J=4.9 Hz), 3.88 to 3.94 (2H, m), 4.17 (2H, t, J=4.9 Hz), 5.29-5.36 (1H, m), 5.72-5.79 (1H, m), 7.01 (2H, d, J=8.8 Hz), 7.12 to 7.26 (2H, m), 7.39 (2H, d, J=8.8 Hz), 7.48 to 7.68 (10H, m), 8.56 to 8.59 (1H, m).

IR (KBr) 3362, 1651, 1597, 1518, 1493, 1341, 1242, 1154, 966, 822 cm$^{-1}$

Elemental Analysis for C$_{36}$H$_{39}$N$_3$O$_6$S Calcd. C, 67.37; H, 6.13; N, 6.55. Found: C, 67.21; H, 5.85; N, 6.67.

Example 87

(Preparation of Compound 94)

To a solution of 7-[4-(2-butoxyethoxy)phenyl]-N-[4-[(S)-hydroxy(2-pyridyl)methyl]phenyl]-1-methanesulfonyl-2,3-dihydro-1H-1-benzazepine-4-carboxamide (0.45 g) in dichloromethane (10 ml) was added 3-chloroperbenzoic acid (70%, 0.21 g) at 0° C. and the mixture was stirred for 20 hours at room temperature. To the reaction solution was added sodium thiosulfate solution, and the mixture was stirred for several minutes and extracted with ethyl acetate. The organic layer was washed with sodium bicarbonate solution and saturated brine, dried over magnesium sulfate and concentrated under reduced pressure. The obtained residue was separated and purified by column chromatography (ethanol:ethyl acetate 1:4) and further recrystallized from ethyl acetate-diisopropylether to give 7-[4-(2-butoxyethoxy)phenyl]-N-[4-[(S)-hydroxy(1-oxidopyridin-2-yl)methyl]phenyl]-1-methanesulfonyl-2,3-dihydro-1H-1-benzazepine-4-carboxamide (Compound 94) (292.1 mg) as colorless crystals.

m.p. 118 to 120° C.

$^1$H-NMR (200 MHz, CDCl$_3$) δ 0.93 (3H, t, J=7.2 Hz), 1.29 to 1.46 (2H, m), 1.51 to 1.68 (2H, m), 2.90 (3H, s), 3.08 to 3.19 (2H, m), 3.56 (2H, t, J=6.6 Hz), 3.82 (2H, t, J=4.9 Hz), 3.86 to 3.96 (2H, m), 4.18 (2H, t, J=4.9 Hz), 6.03 to 6.09 (1H, m), 6.38 to 6.45 (1H, m), 6.94 to 7.00 (1H, m), 7.02 (2H, d, J=8.6 Hz), 7.25 to 7.29 (2H, m), 7.46 to 7.57 (6H, m), 7.63 to 7.72 (5H, m), 8.25 to 8.28 (1H, m).

IR (KBr) 3250, 1657, 1607, 1518, 1493, 1341, 1246, 1154, 1103, 1061, 966, 824 cm$^{-1}$

Elemental Analysis for C$_{36}$H$_{39}$N$_3$O$_7$S.0.75H$_2$O Calcd. C, 64.41; H, 6.08; N, 6.26. Found: C, 64.39; H, 6.22; N, 6.05.

Example 88

(Preparation of Compound 95)

To a solution of 7-[4-(2-butoxyethoxy)phenyl]-1-trifluoroacetyl-2,3-dihydro-1H-1-benzazepine-4-carboxylic acid 0.5 g (1.05 mmole) and 1-hydroxybenzotriazole (0.35 g) in DMF (10 ml) was added 1-ethyl-3-(3'-dimethylaminopropyl)carbodiimide hydrochloride (0.50 g) at room temperature, and the mixture was stirred for 1 hour. To the reaction solution were added a solution of (4-aminophenyl)(6-methylpyridin-2-yl)methanol (0.29 g) and triethylamine (0.60 ml) in DMF (5 ml) and 4-dimethylaminopyridine (1 flake) and the mixture was stirred for 20 hours. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1→2:1) to give 7-[4-(2-butoxyethoxy)phenyl]-N-[4-[hydroxy(6-methylpyridin-2-yl)methyl]phenyl]-1-trifluoroacetyl-2,3-dihydro-1H-1-benzazepine-4-carboxamide (Compound 95) (378.9 mg) as pale yellow amorphous.

$^1$H-NMR (200 MHz, CDCl$_3$) δ 0.93 (3H, t, J=7.1 Hz), 1.29 to 1.48 (2H, m), 1.52 to 1.70 (2H, m), 2.60 (3H, s), 2.88 to 3.26 (3H, m), 3.56 (2H, t, J=6.6 Hz), 3.82 (2H, t, J=4.9 Hz), 4.18 (2H, t, J=4.9 Hz), 4.74 to 4.89 (1H, m), 5.64 to 5.76 (2H, m), 6.89 (1H, d, J=7.6 Hz), 7.00 to 7.07 (3H, m), 7.30 to 7.65 (12H, m).

IR (KBr) 3343, 1692, 1597, 1518, 1497, 1460, 1406, 1314, 1250, 1208, 1179, 1155, 828 cm$^{-1}$

Elemental Analysis for C$_{38}$H$_{38}$N$_3$O$_5$F$_3$.0.25H$_2$O Calcd. C, 67.29; H, 5.72; N, 6.20. Found: C, 67.25; H, 5.58; N, 6.35.

Example 89

(Preparation of Compound 96)

To a solution of 7-[4-(2-butoxyethoxy)phenyl]-N-[4-[hydroxy(6-methylpyridin-2-yl)methyl]phenyl]-1-trifluoroacetyl-2,3-dihydro-1H-1-benzazepine-4-carboxamide (340 mg) in dichloromethane (10 ml) was added 3-chloroperbenzoic acid (70%, 0.15 g) at 0° C. and the mixture was stirred at room temperature for 20 hours. To the reaction solution was added sodium thiosulfate solution and the mixture was stirred for several minutes. The mixture was extracted with ethyl acetate, and the organic layer was washed with saturated brine, dried over magnesium sulfate and concentrated under reduced pressure. The obtained residue was separated and purified by column chromatography (ethanol:ethyl acetate 1:19) and further recrystallized from ethyl acetate-diisopropylether to give 7-[4-(2-butoxyethoxy)phenyl]-N-[4-[hydroxy(6-methyl-1-oxidopyridin-2-yl)methyl]phenyl]-1-trifluoroacetyl-2,3-dihydro-1H-1-benzazepine-4-carboxamide (Compound 96) (262 mg) as colorless crystals.

m.p. 170 to 173° C.

$^1$H-NMR (200 MHz, CDCl$_3$) δ 0.94 (3H, t, J=7.2 Hz), 1.29 to 1.48 (2H, m), 1.54 to 1.68 (2H, m), 2.57 (3H, s), 2.93 to 3.27 (3H, m), 3.56 (2H, t, J=6.8 Hz), 3.82 (2H, t, J=4.9 Hz), 4.18 (2H, t, J=4.9 Hz), 4.76 to 4.91 (1H, m), 6.06 (1H, d, J=4.6 Hz), 6.68 (1H, d, J=4.6 Hz), 6.78 to 6.84 (1H, m), 7.03 (2H, d, J=8.8 Hz), 7.13 to 7.36 (3H, m), 7.46 to 7.66 (10H, m).

IR (KBr) 3296, 1694, 1647, 1597, 1530, 1497, 1316, 1248, 1206, 1179, 1154, 847, 828 cm$^{-1}$

Elemental Analysis for C$_{38}$H$_{38}$N$_3$O$_6$F$_3$ Calcd. C, 66.17; H, 5.55; N, 6.09. Found: C, 65.97; H, 5.48; N, 6.10.

Example 90

(Preparation of Compound 97)

To a solution of 7-[4-(2-butoxyethoxy)phenyl]-1-trifluoroacetyl-N-[4-[hydroxy(6-methyl-1-oxidopyridin-2-yl)methyl]phenyl]-2,3-dihydro-1H-1-benzazepine-4-carboxamide (230 mg) in ethanol (20 ml) was added sodium borohydride (63 mg) at room temperature and the mixture was stirred for 3 hours. To the reaction solution was added water and the mixture was extracted with ethyl acetate. The organic layer was washed with saturated brine, dried over magnesium sulfate and concentrated under reduced pressure. The obtained residue was separated and purified by column chromatography (ethanol:ethyl acetate 1:4) and further recrystallized from ethyl acetate-diisopropylether to give 7-[4-(2-butoxyethoxy)phenyl]-N-[4-[hydroxy(6-methyl-1-oxidopyridin-2-yl)methyl]phenyl]-2,3-dihydro-1H-1-benzazepine-4-carboxamide (Compound 97) (120.5 mg) as yellow crystals.

m.p. 175 to 177° C.

$^1$H-NMR (200 MHz, CDCl$_3$) δ 0.93 (3H, t, J=7.1 Hz), 1.28 to 1.44 (2H, m), 1.48 to 1.68 (2H, m), 2.56 (3H, s), 2.92 to 3.01 (2H, m), 3.41 to 3.49 (2H, m), 3.55 (2H, t, J=6.8 Hz), 3.80 (2H, t, t, J=5.0 Hz), 4.16 (2H, t, J=5.0 Hz), 4.46 to 4.72 (H, m), 6.06 (1H, s), 6.70 (1H, d, J=8.4 Hz), 6.78 to 6.84 (1H, m), 6.97 (2H, d, J=8.8 Hz), 7.11 to 7.18 (1H, m), 7.20 to 7.34 (3H, m), 7.43 to 7.47 (5H, m), 7.61 to 7.65 (3H, m).

IR (KBr) 3283, 1661, 1645, 1599, 1499, 1321, 1248, 1181, 826 cm$^{-1}$

Elemental Analysis for C$_{36}$H$_{39}$N$_3$O$_5$·1.0H$_2$O Calcd. C, 70.68; H, 6.76; N, 6.87. Found: C, 70.53; H, 6.15; N, 6.93.

Example 91

(Preparation of Compound 98)

To a solution of 7-[4-(2-butoxyethoxy)phenyl]-N-[4-[hydroxy(6-methyl-1-oxidopyridin-2-yl)methyl]phenyl]-2,3-dihydro-1H-1-benzazepine-4-carboxamide (154 mg) and isobutylaldehyde (0.12 g) in 1,2-dichloroethane (10 ml) were added sodium triacetoxyborohydride (0.17 g) and acetic acid (1 droplet) at room temperature and the mixture was stirred for 24 hours. To the reaction solution were further added isobutylaldehyde (0.12 g) and sodium triacetoxyborohydride (0.17 g), and the mixture was further stirred for 4 days. To the reaction solution was added water and the mixture was extracted with ethyl acetate. The organic layer was washed with saturated brine, dried over magnesium sulfate and concentrated under reduced pressure. The obtained residue was separated and purified by basic silica gel column chromatography (ethanol:ethyl acetate 1:4) and further recrystallized from ethyl acetate-diisopropylether to give 7-[4-(2-butoxyethoxy)phenyl]-N-[4-[hydroxy(6-methyl-1-oxidopyridin-2-yl)methyl]phenyl]-1-isobutyl-2,3-dihydro-1H-1-benzazepine-4-carboxamide (Compound 98) (122.3 mg) as yellow crystals.

m.p. 114 to 116° C.

$^1$H-NMR (200 MHz, CDCl$_3$) δ 0.93 (3H, t, J=7.2 Hz), 0.98 (6H, d, J=6.6 Hz), 1.30 to 1.46 (2H, m), 1.50 to 1.71 (2H, m), 1.98 to 2.16 (1H, m), 2.57 (3H, s), 2.88 to 2.97 (2H, m), 3.19 (2H, d, J=6.6 Hz), 3.33 to 3.43 (2H, m), 3.55 (2H, t, J=6.6 Hz), 3.80 (2H, t, J=5.0 Hz), 4.16 (2H, t, J=5.0 Hz), 6.07 (1H, s), 6.77 to 6.84 (1H, m), 6.91 to 7.00 (3H, m), 7.15 (1H, t, J=7.7 Hz), 7.37 to 7.51 (8H, m), 7.63 to 7.70 (3H, m).

IR (KBr) 3282, 1641, 1598, 1499, 1315, 1246, 1182, 1065, 838, 815 cm$^{-1}$

Elemental Analysis for C$_{40}$H$_{47}$N$_3$O$_5$ Calcd. C, 73.93; H, 7.29; N, 6.47. Found: C, 73.83; H, 7.21; N, 6.45.

Example 92

(Preparation of Compound 99)

To a solution of 7-[4-(2-butoxyethoxy)phenyl]-1-trifluoroacetyl-2,3-dihydro-1H-1-benzazepine-4-carboxylic acid (0.5 g) and 1-hydroxybenzotriazole (0.28 g) in DMF (10 ml), was added 1-ethyl-3-(3'-dimethylaminopropyl)carbodiimide hydrochloride (0.40 g) at room temperature, and the mixture was stirred for 1 hour. To the reaction solution were added a solution of (4-aminophenyl)(3-methylpyridin-2-yl)methanol (0.27 g) and triethylamine (0.60 ml) in DMF (5 ml) and 4-dimethylaminopyridine (1 flake), and the mixture was stirred for 3 days. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:3→1:2→1:1) to give 7-[4-(2-butoxyethoxy)phenyl]-N-[4-[hydroxy(3-methylpyridin-2-yl)methyl]phenyl]-1-trifluoroacetyl-2,3-dihydro-1H-1-benzazepine-4-carboxamide (Compound 99) (319.2 mg) as colorless amorphous.

$^1$H-NMR (200 MHz, CDCl$_3$) δ 0.93 (3H, t, J=7.4 Hz), 1.30 to 1.48 (2H, m), 1.51 to 1.68 (2H, m), 2.09 (3H, s), 2.87 to 3.34 (3H, m), 3.56 (2H, t, J=6.6 Hz), 3.82 (2H, t, J=4.9 Hz), 4.18 (2H, t, J=4.9 Hz), 4.75 to 4.88 (1H, m), 5.73 (1H, d, J=5.9 Hz), 6.06 (1H, d, J=5.9 Hz), 7.02 (2H, d, J=8.8 Hz), 7.17 to 7.35 (5H, m), 7.42 to 7.43 (1H, m), 7.47 to 7.54 (6H, m), 7.62 to 7.66 (1H, m), 8.45 to 8.50 (1H, m).

IR (KBr) 3314, 1693, 1607, 1520, 1497, 1414, 1314, 1250, 1206, 1179, 1155, 1042, 828 cm$^{-1}$

Elemental Analysis for C$_{38}$H$_{38}$N$_3$O$_5$ F$_3$ 0.25H$_2$O Calcd. C, 67.29; H, 5.72; N, 6.20. Found: C, 67.13; H, 5.56; N, 6.05.

Example 93

(Preparation of Compound 100)

To a solution of 7-[4-(2-butoxyethoxy)phenyl]-1-trifluoroacetyl-N-[4-[hydroxy(3-methylpyridin-2-yl)methyl]phenyl]-2,3-dihydro-1H-1-benzazepine-4-carboxamide (291 mg) in dichloromethane (10 ml) was added 3-chloroperbenzoic acid (70%, 128 mg) at 0° C. and the mixture was stirred at room temperature for 20 hours. To the reaction solution was added sodium thiosulfate solution and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethanol:ethyl acetate 1:9) and further recrystallized from ethyl acetate-diisopropylether, to give 7-[4-(2-butoxyethoxy)phenyl]-N-[4-[hydroxy(3-methyl-1-oxidopyridin-2-yl)methyl]phenyl]-1-trifluoroacetyl-2,3-dihydro-1H-1-benzazepine-4-carboxamide (Compound 100) (210.9 mg) as pale yellow crystals.

m.p. 109 to 112° C.

$^1$H-NMR (200 MHz, CDCl$_3$) δ 0.93 (3H, t, J=7.2 Hz), 1.29 to 1.48 (2H, m), 1.55 to 1.68 (2H, m), 2.46 (3H, s), 2.88 to 3.30 (3H, m), 3.56 (2H, t, J=6.6 Hz), 3.81 (2H, t, J=4.9 Hz), 4.18 (2H, t, J=4.9 Hz), 4.72 to 4.88 (1H, m), 6.03 (1H, d, J=10.2 Hz), 7.02 (2H, d, J=8.8 Hz), 7.15 to 7.64 (13H, m), 7.90 to 8.02 (1H, m), 8.08 to 8.11 (1H, m).

IR (KBr) 3284, 1696, 1609, 1520, 1499, 1248, 1206, 1181, 1155, 1061, 1040, 828 cm$^{-1}$

Elemental Analysis for $C_{38}H_{38}N_3O_6F_3$·1.0H$_2$O Calcd. C, 64.49; H, 5.70; N, 5.94. Found: C, 64.75; H, 5.42; N, 5.75.

Example 94

(Preparation of Compound 101)

To a solution of 7-[4-(2-butoxyethoxy)phenyl]-N-[4-[hydroxy(3-methyl-1-oxidopyridin-2-yl)methyl]phenyl]-1-trifluoroacetyl-2,3-dihydro-1H-1-benzazepine-4-carboxamide (180 mg) in ethanol (10 ml) was added sodium borohydride (49 mg) at room temperature and the mixture was stirred for 2 hours. To the reaction solution was further added sodium borohydride (49 mg), and the mixture was stirred for 2 hours. To the reaction solution was added water and the mixture was extracted with ethyl acetate. The organic layer was washed with saturated brine, and dried over magnesium sulfate. After the organic layer was concentrated under reduced pressure, the obtained residue was separated and purified by column chromatography (ethanol:ethyl acetate 1:4) and further recrystallized from ethyl acetate-diisopropylether to give 7-[4-(2-butoxyethoxy)phenyl]-N-[4-[hydroxy(3-methyl-1-oxidopyridins-2-yl)methyl]phenyl]-2,3-dihydro-1H-1-benzazepine-4-carboxamide (Compound 101) (86.1 mg) as yellow crystals.

m.p. 101 to 104° C.

$^1$H-NMR (200 MHz, CDCl$_3$) δ 0.93 (3H, t, J=7.1 Hz), 1.28 to 1.47 (2H, m), 1.52 to 1.89 (2H, m), 2.46 (3H, s), 2.90 to 2.97 (2H, m), 3.39 to 3.49 (2H, m), 3.55 (2H, t, J=6.6 Hz), 3.80 (2H, t, J=4.9 Hz), 4.15 (2H, t, J=4.9 Hz), 4.52 to 4.64 (1H, m), 6.03 (1H, d, J=11.2 Hz), 6.69 (1H, d, J=8.4 Hz), 6.97 (2H, d, J=8.8 Hz), 7.15 to 7.58 (12H, m), 8.00 (1H, d, J=11.2 Hz), 8.08 to 8.11 (1H, m).

IR (KBr) 3295, 1651, 1609, 1499, 1454, 1316, 1246, 1179, 1121, 1040, 824 cm$^{-1}$

Elemental Analysis for $C_{36}H_{39}N_3O_5$·1.0H$_2$O Calcd. C, 70.68; H, 6.76; N, 6.87. Found: C, 70.72; H, 6.43; N, 6.86.

Example 95

(Preparation of Compound 102)

To a solution of 7-[4-(2-butoxyethoxy)phenyl]-N-[4-[hydroxy(3-methyl-1-oxidopyridin-2-yl)methyl]phenyl]-2,3-dihydro-1H-1-benzazepine-4-carboxamide (70 mg) and isobutylaldehyde (0.09 ml) in 1,2-dichloroethane (10 ml) were added sodium triacetoxyborohydride (64 mg) and acetic acid (1 droplet) at room temperature and the mixture was stirred for 18 hours. To the reaction solution were further added isobutylaldehyde (0.09 ml) and sodium triacetoxyborohydride (64 mg) and the mixture was stirred for 24 hours. To the reaction solution was added water and the mixture was extracted with ethyl acetate. The organic layer was washed with saturated brine, dried over magnesium sulfate and concentrated under reduced pressure. The residue was separated and purified by column chromatography (ethanol:ethyl acetate 1:4) to give 7-[4-(2-butoxyethoxy)phenyl]-N-[4-[hydroxy(3-methyl-1-oxidopyridin-2-yl)methyl]phenyl]-1-isobutyl-2,3-dihydro-1H-1-benzazepine-4-carboxamide (Compound 102) (28.5 mg) as yellow amorphous.

$^1$H-NMR (200 MHz, CDCl$_3$) δ 0.93 (3H, t, J=7.3 Hz), 0.97 (6H, d, J=6.6 Hz), 1.30 to 1.48 (2H, m), 1.50 to 1.70 (2H, m), 1.96 to 2.17 (1H, m), 2.46 (3H, s), 2.84 to 2.95 (2H, m), 3.18 (2H, d, J=7.4 Hz), 3.29 to 3.40 (2H, m), 3.55 (2H, t, J=6.6 Hz), 3.80 (2H, t, J=5.0 Hz), 4.16 (2H, t, J=5.0 Hz), 6.03 (1H, d, J=10.8 Hz), 6.91 (1H, d, J=8.8 Hz), 6.98 (2H, d, J=9.2 Hz), 7.15 to 7.24 (2H, m), 7.38 to 7.58 (10H, m), 8.01 (1H, d, J=10.8 Hz), 8.08 to 8.11 (1H, m).

IR (KBr) 3295, 1657, 1607, 1514, 1499, 1454, 1244, 1181, 1117, 1061, 816 cm$^{-1}$

Elemental Analysis for $C_{40}H_{47}N_3O_5$·1.25H$_2$O Calcd. C, 71.46; H, 7.42; N, 6.25. Found: C, 71.50; H, 7.32; N, 6.00.

Example 96

(Preparation of Compound 103)

To a solution of 7-[4-(2-butoxyethoxy)phenyl]-1-trifluoroacetyl-2,3-dihydro-1H-1-benzazepine-4-carboxylic acid (0.5 g), 1-hydroxybenzotriazole (0.28 g), (4-aminophenyl)(5-methylpyridin-2-yl)methanol (0.29 g) and triethylamine (0.60 ml) in DMF (10 ml) were added 1-ethyl-3-(3'-dimethylaminopropyl)carbodiimide hydrochloride (0.40 g) and 4-dimethylaminopyridine (1 flake) at room temperature and the mixture was stirred for 3 days. To the reaction solution was added water, and the mixture was extracted with ethyl acetate. The organic layer was washed with water and saturated brine, dried over magnesium sulfate and concentrated under reduced pressure. The obtained residue was separated and purified by column chromatography (ethyl acetate:hexane 1:1→2:1) and further recrystallized to give 7-[4-(2-butoxyethoxy)phenyl]-N-[4-[hydroxy(5-methylpyridin-2-yl)methyl]phenyl]-1-trifluoroacetyl-2,3-dihydro-1H-1-benzazepine-4-carboxamide (Compound 103) (529.9 mg) as pale yellow crystals.

m.p. 110 to 113° C.

$^1$H-NMR (200 MHz, CDCl$_3$) δ 0.93 (3H, t, J=7.3 Hz), 1.28 to 1.48 (2H, m), 1.53 to 1.68 (2H, m), 2.33 (3H, s), 2.85 to 3.31 (3H, m), 3.56 (2H, t, J=6.6 Hz), 3.82 (2H, t, J=4.8 Hz), 4.18 (2H, t, J=4.8 Hz), 4.74 to 4.89 (1H, m), 5.31 (1H, d, J=4.2 Hz), 5.71 (1H, d, J=4.2 Hz), 7.01 to 7.05 (3H, m), 7.31 to 7.57 (11H, m), 7.62 to 7.67 (1H, m), 8.36 to 8.42 (1H, m).

IR (KBr) 3364, 1692, 1651, 1609, 1518, 1499, 1314, 1250, 1208, 1181, 1154, 828 cm$^{-1}$

Elemental Analysis for $C_{38}H_{38}N_3O_5F_3$ Calcd. C, 67.74; H, 5.69; N, 6.24. Found: C, 67.43; H, 5.76; N, 6.01.

Example 97

(Preparation of Compound 104)

To a solution of 7-[4-(2-butoxyethoxy)phenyl]-N-[4-[hydroxy(1-oxido-5-methylpyridin-2-yl)methyl]phenyl]-1-trifluoroacetyl-2,3-dihydro-1H-1-benzazepine-4-carboxamide (480 mg) in dichloromethane (15 ml) was added 3-chloroperbenzoic acid (70%, 0.21 g) at 0° C. and the mixture was stirred at room temperature for 18 hours. To the reaction solution was added sodium thiosulfate solution and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethanol:ethyl acetate 1:4) and further recrystallized from ethyl acetate-diisopropylether to give 7-[4-(2-butoxyethoxy)phenyl]-N-[4-[hydroxy(5-methyl-1-oxideopyridin-2-yl)methyl]phenyl]-1-trifluoroacetyl-2,3-dihydro-1H-1-benzazepine-4-carboxamide (Compound 104) (386.8 mg) as colorless crystals.

m.p. 201 to 204° C.

$^1$H-NMR (200 MHz, CDCl$_3$) δ 0.94 (3H, t, J=7.2 Hz), 1.30 to 1.49 (2H, m), 1.54 to 1.70 (2H, m), 2.32 (3H, s), 2.89 to 3.35 (3H, m), 3.56 (2H, t, J=6.6 Hz), 3.82 (2H, t, J=4.9 Hz), 4.18 (2H, t, J=4.9 Hz), 4.78 to 4.97 (H, m), 6.03 (1H, d, J=4.2 Hz), 6.52 (1H, d, J=4.2 Hz), 6.81 (1H, d, J=8.2 Hz), 7.01 to 7.10 (3H, m), 7.26 to 7.36 (1H, m), 7.44 to 7.66 (10H, m), 8.11 (1H, s).

IR (KBr) 3248, 1686, 1647, 1609, 1597, 1314, 1250, 1209, 1181, 1157, 1144, 826 cm$^{-1}$

Elemental Analysis for C$_{38}$H$_{38}$N$_3$O$_6$F$_3$. Calcd. C, 66.17; H, 5.55; N, 6.09. Found: C, 66.11; H, 5.40; N, 6.21.

Example 98

(Preparation of Compound 105)

To a solution of 7-[4-(2-butoxyethoxy)phenyl]-N-[4-[hydroxy(5-methyl-1-oxidopyridin-2-yl)methyl]phenyl]-1-trifluoroacetyl-2,3-dihydro-1H-1-benzazepine-4-carboxamide (320 mg) in ethanol (10 ml) was added sodium borohydride (88 mg) at room temperature and the mixture was stirred for 2 hours. To the reaction solution was added sodium borohydride (88 mg), and the mixture was stirred for 1 hour. Sodium borohydride (88 mg) was further added to the mixture and the mixture was stirred for 13 hours. Water was added to the mixture and the mixture was extracted with ethyl acetate. The organic layer was washed with saturated brine, and dried over magnesium sulfate. The organic layer was concentrated under reduced pressure, the obtained residue was separated and purified by column chromatography (ethanol:ethyl acetate 1:4) and further recrystallized from ethyl acetate-diisopropylether to give 7-[4-(2-butoxyethoxy)phenyl]-N-[4-[hydroxy(5-methyl-1-oxidpyridin-2-yl)methyl]phenyl]-2,3-dihydro-1H-1-benzazepine-4-carboxamide (Compound 105) (256.8 mg) as yellow crystals.

m.p. 119 to 121° C.

$^1$H-NMR (200 MHz, CDCl$_3$) δ 0.93 (3H, t, J=7.3 Hz), 1.29 to 1.46 (2H, m), 1.53 to 1.70 (2H, m), 2.30 (3H, s), 2.90 to 3.01 (2H, m), 3.21 to 3.50 (2H, m), 3.55 (2H, t, J=6.6 Hz), 3.80 (2H, t, J=4.9 Hz), 4.15 (2H, t, J=4.9 Hz), 4.56 to 4.65 (1H, m), 6.03 (1H, br s), 6.45 to 6.54 (1H, m), 6.70 (1H, d, J=8.0 Hz), 6.79 (1H, d, J=8.0 Hz), 6.97 (1H, d, J=8.8 Hz), 6.99 to 7.07 (1H, m), 7.29 to 7.33 (2H, m), 7.41 to 7.47 (5H, m), 7.64 (2H, d, J=8.4 Hz), 7.74 (1H, s), 8.10 (1H, s).

IR (KBr) 3252, 1647, 1599, 1499, 1318, 1250, 1181, 1123, 822 cm$^{-1}$

Elemental Analysis for C$_{36}$H$_{39}$N$_3$O$_5$.0.5H$_2$O Calcd. C, 71.74; H, 6.69; N, 6.97. Found: C, 71.76; H, 6.98; N, 6.91.

Example 99

(Preparation of Compound 106)

To a solution of 7-[4-(2-butoxyethoxy)phenyl]-N-[4-[hydroxy(5-methyl-1-oxidopyridin-2-yl)methyl]phenyl]-2,3-dihydro-1H-1-benzazepine-4-carboxamide (180 mg) and isobutylaldehyde (0.17 ml) in 1,2-dichloroethane (10 ml) were added sodium triacetoxyborohydride (0.19 g) and acetic acid (1 droplet) at room temperature and the mixture was stirred for 16 hours. To the reaction solution were further added isobutylaldehyde (0.17 ml) and sodium triacetoxyborohydride (0.19 g), and the mixture was further stirred for 24 hours. To the reaction solution was added water and the mixture was extracted with ethyl acetate. The organic layer was washed with saturated brine, dried over magnesium sulfate and concentrated under reduced pressure. The residue was separated and purified by column chromatography (ethanol:ethyl acetate 1:4) to give 7-[4-(2-butoxyethoxy)phenyl]-N-[4-[hydroxy(5-methyl-1-oxidopyridin-2-yl)methyl]phenyl]-1-isobutyl-2,3-dihydro-1H-1-benzazepine-4-carboxamide (Compound 106) (130.6 mg) as yellow amorphous.

$^1$H-NMR (200 MHz, CDCl$_3$) δ 0.93 (3H, t, J=7.2 Hz), 0.98 (6H, d, J=6.6 Hz), 1.30 to 1.46 (2H, m), 1.52 to 1.68 (2H, m), 1.98 to 2.16 (H, m), 2.31 (3H, s), 2.89 to 2.97 (2H, m), 3.19 (2H, d, J=7.0 Hz), 3.31 to 3.42 (2H, m), 3.55 (2H, t, J=6.6 Hz), 3.80 (2H, t, J=5.0 Hz), 4.16 (2H, t, J=5.0 Hz), 6.03 (1H, s), 6.79 (1H, d, J=8.0 Hz), 6.90 to 7.08 (4H, m), 7.38 to 7.52 (7H, m), 7.64 (2H, d, J=8.4 Hz), 7.65 (1H, s), 8.11 (1H, s).

IR (KBr) 3250, 1647, 1607, 1499, 1314, 1244, 1182, 1119, 1065, 1049, 818 cm$^{-1}$

Elemental Analysis for C$_{40}$H$_{47}$N$_3$O$_5$.0.5H$_2$O Calcd. C, 71.94; H, 7.40; N, 6.29. Found: C, 71.90; H, 7.53; N, 6.13.

Example 100

(Preparation of Compound 107)

To a solution of 7-[4-(2-butoxyethoxy)phenyl]-1-trifluoroacetyl-2,3-dihydro-1H-1-benzazepine-4-carboxylic acid (0.5 g), 1-hydroxybenzotriazole (0.28 g), (4-aminophenyl)(5-chloropyridin-2-yl)methanol (0.32 g) and triethylamine (0.60 ml) in DMF (10 ml) were added 1-ethyl-3-(3'-dimethylaminopropyl)carbodiimide hydrochloride (0.40 g) and 4-dimethylaminopyridine (1 flake) at room temperature and the mixture was stirred for 24 hours. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1) and further separated and purified by basic silica gel column chromatography (ethyl acetate:hexane 1:1→2:1→3:1), and the residue was recrystallized from ethyl acetate-diisopropylether to give 7-[4-(2-butoxyethoxy)phenyl]-N-[4-[hydroxy(5-chloropyridin-2-yl)methyl]phenyl]-1-trifluoroacetyl-2,3-dihydro-1H-1-benzazepine-4-carboxamide (Compound 106) (365.8 mg) as pale yellow crystals.

m.p. 144 to 146° C.

¹H-NMR (200 MHz, CDCl₃) δ 0.93 (3H, t, J=7.4 Hz), 1.29 to 1.47 (2H, m), 1.54 to 1.68 (2H, m), 2.90 to 3.25 (3H, m), 3.56 (2H, t, J=6.8 Hz), 3.82 (2H, t, J=4.9 Hz), 4.18 (2H, t, J=4.9 Hz), 4.75 to 4.89 (2H, m), 5.75 (H, d, J=4.0 Hz), 7.02 (2H, d, J=8.8 Hz), 7.14 (H, d, J=8.4 Hz), 7.32 to 7.43 (4H, m), 7.50 to 7.65 (8H, m), 8.53 (1H, d, J=2.6 Hz).

IR (KBr) 3343, 1694, 1651, 1595, 1518, 1497, 1312, 1244, 1213, 1182, 1152, 1111, 828 cm⁻¹

Elemental Analysis for $C_{37}H_{35}N_3O_5ClF_3$ Calcd. C, 64.02; H, 5.08; N, 6.05. Found: C, 64.02; H, 5.20; N, 6.03.

Example 101

(Preparation of Compound 108)

To a solution of 7-[4-(2-butoxyethoxy)phenyl]-N-[4-[hydroxy(5-chloropyridin-2-yl)methyl]phenyl]-1-trifluoroacetyl-2,3-dihydro-1H-1-benzazepine-4-carboxamide (682 mg) in dichloromethane (15 ml) was added 3-chloroperbenzoic acid (70%, 0.29 g) at 0° C. and the mixture was stirred for 24 hours at room temperature. 3-chloroperbenzoic acid (70%, 0.29 g) was further added to the mixture at room temperature and the mixture was stirred for 18 hours. To the reaction solution was added sodium thiosulfate solution and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethyl acetate) to give 7-[4-(2-butoxyethoxy)phenyl]-N-[4-[hydroxy(5-chloro-1-oxidopyridin-2-yl)methyl]phenyl]-1-trifluoroacetyl-2,3-dihydro-1H-1-benzazepine-4-carboxamide (Compound 108) (233.8 mg) as colorless crystals.

m.p. 200 to 203° C.

¹H-NMR (200 MHz, CDCl₃) δ 0.93 (3H, t, J=7.4 Hz), 1.34 to 1.45 (2H, m), 1.52 to 1.67 (2H, m), 2.86 to 3.34 (3H, m), 3.56 (2H, t, J=6.6 Hz), 3.82 (2H, t, J=4.8 Hz), 4.18 (2H, t, J=4.8 Hz), 4.78 to 4.92 (1H, m), 5.75 (1H, d, J=4.2 Hz), 6.05 (1H, d, J=4.2 Hz), 6.91 (H, d, J=8.6 Hz), 7.03 (2H, d, J=8.4 Hz), 7.22 to 7.37 (2H, m), 7.43 to 7.67 (10H, m), 8.16 (1H, d, J=1.6 Hz).

IR (KBr) 3279, 1688, 1651, 1597, 1497, 1408, 1314, 1252, 1211, 1181, 1142, 924, 828 cm⁻¹

Elemental Analysis for $C_{37}H_{35}N_3O_6ClF_3$ Calcd. C, 62.58; H, 4.97; N, 5.92. Found: C, 62.36; H, 5.01; N, 5.89.

Example 102

(Preparation of Compound 109)

To a solution of 7-[4-(2-butoxyethoxy)phenyl]-N-[4-[hydroxy(5-chloro-1-oxidopyridin-2-yl)methyl]phenyl]-1-trifluoroacetyl-2,3-dihydro-1H-1-benzazepine-4-carboxamide (0.20 g) in ethanol (30 ml), sodium borohydride (50 mg) was added at room temperature and the mixture was stirred for 2.5 hours. To the reaction solution was added sodium borohydride (50 mg), and the mixture was stirred for 2.5 hours. Sodium borohydride (50 mg) was further added to the mixture and the mixture was stirred for 1 hour. Sodium borohydride (50 mg) was further added to the mixture, and the mixture was stirred for 13 hours. Water was added to the mixture and the mixture was extracted with ethyl acetate. The organic layer was washed with saturated brine, dried over magnesium sulfate and concentrated under reduced pressure. The obtained residue was separated and purified by column chromatography (ethyl acetate:hexane 4:1→ethyl acetate) to give 7-[4-(2-butoxyethoxy)phenyl]-N-[4-[hydroxy(5-chloro-1-oxidopyridin-2-yl)methyl]phenyl]-2,3-dihydro-1H-1-benzazepine-4-carboxamide (Compound 109) (53 mg) as yellow amorphous.

¹H-NMR (200 MHz, CDCl₃) δ 0.93 (3H, t, J=7.1 Hz), 1.34 to 1.49 (2H, m), 1.51 to 1.68 (2H, m), 2.91 to 3.00 (2H, m), 3.42 to 3.50 (2H, m), 3.55 (2H, t, J=6.6 Hz), 3.80 (2H, t, J=5.0 Hz), 4.16 (2H, t, J=5.0 Hz), 4.45 to 4.69 (1H, m), 5.71-5.78 (1H, m), 6.02-6.06 (1H, m), 6.71 (1H, d, J=8.4 Hz), 6.88 (1H, d, J=8.4 Hz), 6.98 (2H, d, J=8.8 Hz), 7.17 to 7.22 (1H, m), 7.28 to 7.36 (2H, m), 7.42 to 7.48 (5H, m), 7.50 to 7.67 (2H, m), 8.30 (1H, d, J=1.8 Hz).

Example 103

(Preparation of Compound 110)

To a solution of 7-[4-(2-butoxyethoxy)phenyl]-N-[4-[hydroxy(5-chloro-1-oxidopyridin-2-yl)methyl]phenyl]-2,3-dihydro-1H-1-benzazepine-4-carboxamide (40 mg) and isobutylaldehyde (0.1 ml) in 1,2-dichloroethane (5 ml) were added sodium triacetoxyborohydride (60 mg) and acetic acid (1 droplet) at room temperature and the mixture was stirred for 14 hours. To the reaction solution was further added sodium triacetoxyborohydride (40 mg), and the mixture was stirred for 6 hours. To the reaction solution was added water and the mixture was extracted with ethyl acetate. The organic layer was washed with saturated brine, dried over magnesium sulfate and concentrated under reduced pressure. The residue was recrystallized from ethyl acetate-diisopropylether to give 7-[4-(2-butoxyethoxy)phenyl]-N-[4-[hydroxy(5-chloro-1-oxidopyridin-2-yl)methyl]phenyl]-1-isobutyl-2,3-dihydro-1H-1-benzazepine-4-carboxamide (Compound 110) (26.6 mg) as yellow crystals.

m.p. 137-139° C.

¹H-NMR (200 MHz, CDCl₃) δ 0.93 (3H, t, J=7.2 Hz), 0.98 (6H, d, J=6.6 Hz), 1.29 to 1.46 (2H, m), 1.52 to 1.68 (2H, m), 1.94 to 2.17 (1H, m), 2.86 to 2.99 (2H, m), 3.19 (2H, d, J=7.4 Hz), 3.31 to 3.41 (2H, m), 3.55 (2H, t, J=6.6 Hz), 3.80 (2H, t, J=4.9 Hz), 4.16 (2H, t, J=4.9 Hz), 5.76 (1H, d, J=3.9 Hz), 6.04 (1H, d, J=3.9 Hz), 6.87 to 6.94 (2H, m), 6.98 (2H, d, J=8.8 Hz), 7.20 to 7.26 (1H, m), 7.35 to 7.52 (7H, m), 7.63 to 7.67 (3H, m), 8.29 (1H, d, J=1.8 Hz).

IR (KBr) 3290, 1644, 1597, 1499, 1318, 1244, 1182, 924, 813 cm⁻¹.

Example 104

(Preparation of Compound 111)

To a solution of 7-[4-(2-butoxyethoxy)phenyl]-1-trifluoroacetyl-2,3-dihydro-1H-1-benzazepine-4-carboxylic acid (0.5 g) and 1-hydroxybenzotriazole (0.30 g), (4-aminophenyl)(3-propoxypyridin-2-yl)methanol (0.30 g) in DMF (10 ml) were added 1-ethyl-3-(3'-dimethylaminopropyl)carbodiimide hydrochloride (0.40 g), triethylamine (0.6 ml) and 4-dimethylaminopyridine (1 flake) at room temperature and the mixture was stirred for 24 hours. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1) to give 7-[4-(2-butoxyethoxy)phenyl]-N-[4-[hydroxy(3-propoxypyridin-2-yl)methyl]phenyl]-1-trifluoroacetyl-2,3-dihydro-1H-1-benzazepine-4-carboxamide (Compound 111) (528.7 mg) as pale yellow crystals.

m.p. 154 to 157° C.

¹H-NMR (200 MHz, CDCl₃) δ 0.93 (3H, t, J=7.6 Hz), 0.99 (3H, t, J=7.4 Hz), 1.31 to 1.48 (2H, m), 1.51 to 1.66 (2H, m), 1.71 to 1.83 (2H, m), 2.83 to 3.26 (3H, m), 3.56 (2H, t, J=6.6 Hz), 3.79 to 3.89 (2H, m), 4.18 (2H, t, J=4.8 Hz), 4.74 to 4.95 (H, m), 5.59 (1H, d, J=6.6 Hz), 5.93 (1H, d, J=6.6 Hz), 7.02 (2H, d, J=8.8 Hz), 7.08 to 7.24 (2H, m), 7.29 to 7.41 (4H, m), 7.46 to 7.58 (6H, m), 7.64 (1H, br s), 8.16 to 8.18 (1H, m).

IR (KBr) 3324, 1698, 1671, 1609, 1522, 1499, 1453, 1406, 1316, 1281, 1250, 1208, 1179, 1144, 1042, 828 cm⁻¹

Elemental Anaylsis for $C_{40}H_{42}N_3O_6F_3$ Calcd. C, 66.93; H, 5.90; N, 5.85. Found: C, 66.72; H, 6.09; N, 5.80.

Example 105

(Preparation of Compound 112)

To a solution of 7-[4-(2-butoxyethoxy)phenyl]-N-[4-[hydroxy(3-propoxypyridin-2-yl)methyl]phenyl]-1-trifluoroacetyl-2,3-dihydro-1H-1-benzazepine-4-carboxamide (480 mg) in dichloromethane (10 ml) was added 3-chloroperbenzoic acid (70%, 0.2 g) at 0° C. and the mixture was stirred for 30 hours at room temperature. To the reaction solution was added sodium thiosulfate solution and the mixture was stirred for several minutes. The mixture was extracted with ethyl acetate, and the organic layer was washed with saturated brine, dried over magnesium sulfate and concentrated under reduced pressure. The obtained residue was separated and purified by column chromatography (ethanol:ethyl acetate 1:9) to give 7-[4-(2-butoxyethoxy)phenyl]-N-[4-[hydroxy(1-oxido-3-propoxypyridin-2-yl)methyl]phenyl]-1-trifluoroacetyl-2,3-dihydro-1H-1-benzazepine-4-carboxamide (Compound 112) (370 mg) as colorless crystals.

m.p. 144 to 146° C.

¹H-NMR (200 MHz, CDCl₃) δ 0.93 (3H, t, J=7.2 Hz), 1.09 (3H, t, J=7.3 Hz), 1.31 to 1.47 (2H, m), 1.51 to 1.67 (2H, m), 1.82 to 1.97 (2H, m), 2.86 to 3.24 (3H, m), 3.56 (2H, t, J=6.6 Hz), 3.81 (2H, t, J=5.0 Hz), 3.93 to 4.13 (2H, m), 4.18 (2H, t, J=5.0 Hz), 4.72 to 4.89 (1H, m), 6.36 (1H, d, J=11.0 Hz), 6.95 (1H, d, J=7.6 Hz), 7.02 (2H, d, J=8.8 Hz), 7.12 to 7.19 (1H, m), 7.28 to 7.41 (2H, m), 7.45 to 7.64 (9H, m), 7.81 to 7.84 (1H, m), 7.90 to 7.96 (1H, m).

IR (KBr) 3318, 1694, 1674, 1599, 1532, 1514, 1499, 1319, 1291, 1250, 1181, 1146, 1074, 1042, 826 cm⁻¹

Elemental Analysis for $C_{40}H_{42}N_3O_7F_3$ Calcd. C, 65.47; H, 5.77; N, 5.73. Found: C, 65.23; H, 5.60; N, 5.51.

Example 106

(Preparation of Compound 113)

To a solution of 7-[4-(2-butoxyethoxy)phenyl]-1-trifluoroacetyl-N-[4-[hydroxy(1-oxido-3-propoxypyridin-2-yl)methyl]phenyl]-2,3-dihydro-1H-1-benzazepine-4-carboxamide (330 mg) in ethanol (20 ml) was added sodium borohydride (85 mg) at room temperature and the mixture was stirred for 2 hours. To the reaction solution was further added sodium borohydride (85 mg), and the mixture was stirred for 2 hours. To the reaction solution was further added sodium borohydride (85 mg), and the mixture was stirred for 2 hours. To the reaction solution was further added sodium borohydride (85 mg), and the mixture was stirred for 14 hours. Water was added to the mixture and the mixture was extracted with ethyl acetate. The organic layer was washed with saturated brine, dried over magnesium sulfate and concentrated under reduced pressure. The residue was recrystallized from ethyl acetate to give 7-[4-(2-butoxyethoxy)phenyl]-N-[4-[hydroxy(1-oxido-3-propoxypyridine-2-yl)methyl]phenyl]-2,3-dihydro-1H-1-benzazepine-4-carboxamide (Compound 113) (230.7 mg) as yellow crystals.

m.p. 148 to 149° C.

¹H-NMR (200 MHz, CDCl₃) δ 0.93 (3H, t, J=7.3 Hz), 1.09 (3H, t, J=7.3 Hz), 1.28 to 1.49 (2H, m), 1.52 to 1.67 (2H, m), 1.81 to 2.00 (2H, m), 2.88 to 2.97 (2H, m), 3.41 to 3.52 (2H, m), 3.55 (2H, t, J=6.6 Hz), 3.80 (2H, t, t, J=4.9 Hz), 3.95 to 4.10 (2H, m), 4.15 (2H, t, J=4.9 Hz), 4.48 to 4.67 (1H, m), 6.31-6.41 (1H, m), 6.92-6.99 (3H, m), 7.11 to 7.19 (1H, m), 7.26 to 7.33 (3H, m), 7.43 to 7.47 (3H, m), 7.50 to 7.56 (4H, m), 7.82 (1H, m, J=6.6 Hz), 7.84 to 8.02 (1H, m).

IR (KBr) 3308, 1657, 1601, 1507, 1498, 1317, 1244, 1181, 1040, 831 cm⁻¹

Elemental Analysis for $C_{38}H_{43}N_3O_6$ Calcd. C, 71.56; H, 6.80; N, 6.59. Found: C, 71.37; H, 6.82; N, 6.42.

Example 107

(Preparation of Compound 114)

To a solution of 7-[4-(2-butoxyethoxy)phenyl]-N-[4-[hydroxy(1-oxido-3-propoxypyridin-2-yl)methyl]phenyl]-2,3-dihydro-1H-1-benzazepine-4-carboxamide (190 mg) and isobutylaldehyde (0.27 ml) in 1,2-dichloroethane (10 ml) were added sodium triacetoxyborohydride (0.19 g) and acetic acid (1 droplet) at room temperature and the mixture was stirred for 15 hours. To the reaction solution were further added isobutylaldehyde (0.27 ml) and sodium triacetoxyborohydride (0.19 g), and the mixture was stirred for 6 hours. To the reaction solution was added water and the mixture was extracted with ethyl acetate. The organic layer was washed with saturated brine, dried over magnesium sulfate and concentrated under reduced pressure. The obtained residue was separated and purified by column chromatography (ethanol:ethyl acetate 1:4) to give 7-[4-(2-butoxyethoxy)phenyl]-N-[4-[hydroxy(1-oxido-3-propoxypyridin-2-yl)methyl]phenyl]-1-isobutyl-2,3-dihydro-1H-1-benzazepine-4-carboxamide (Compound 114) (143.3 mg) as yellow amorphous.

¹H-NMR (200 MHz, CDCl₃) δ 0.93 (3H, t, J=7.1 Hz), 0.97 (6H, d, J=6.6 Hz), 1.09 (3H, t, J=7.3 Hz), 1.32 to 1.72 (4H, m), 1.81 to 2.13 (3H, m), 2.84 to 2.93 (2H, m), 3.18 (2H, d, J=7.8 Hz), 3.30 to 3.38 (2H, m), 3.55 (2H, t, J=6.6 Hz), 3.80 (2H, t, J=5.0 Hz), 3.98 to 4.11 (2H, m), 4.16 (2H, t, J=5.0 Hz), 6.36 (1H, s), 6.89 to 7.00 (4H, m), 7.12 to 7.19 (1H, m), 7.37 to 7.60 (11H, m), 7.81 to 7.84 (1H, m).

IR (KBr) 3301, 1653, 1607, 1514, 1499, 1468, 1314, 1244, 1181, 1073, 818 cm⁻¹

Elemental Analysis for $C_{42}H_{51}N_3O_6 \cdot 1.0H_2O$ Calcd. C, 70.86; H, 7.50; N, 5.90. Found: C, 70.87; H, 7.33; N, 5.80.

Example 108

(Preparation of Compound 115)

To a solution of 7-[4-(2-butoxyethoxy)phenyl]-N-(4-hydroxymethylphenyl)-2,3-dihydro-1-isobutyl-1H-1-benzazepine-4-carboxamide (0.50 g) in THF (10 ml) were added thionyl chloride (0.1 ml) and pyridine (1 droplet) at room temperature and the mixture was stirred for 1.5 hours. The solvent was removed under reduced pressure, to a solution of the residue in ethanol (20 ml) was added triethylamine (2.0 ml) and 2-mercapto-1,3,4-thiadiazole (0.12 g) at 50° C. and the mixture was stirred for 2 hours. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:2→1:1) and further recrystallized from ethyl acetate-hexane to give 7-[4-(2-butoxyethoxy)phenyl]-N-[4-(1,3,4-thiadiazol-2-ylthiomethyl)phenyl]-1-isobutyl-2,3-dihydro-1H-1-benzazepine-4-carboxamide (Compound 115) (373.1 mg) as yellow crystals.

m.p. 77 to 79° C.

$^1$H-NMR (200 MHz, CDCl$_3$) δ 0.93 (3H, t, J=7.3 Hz), 0.97 (6H, d, J=6.6 Hz), 1.30 to 1.46 (2H, m), 1.52 to 1.68 (2H, m), 1.96 to 2.11 (1H, m), 2.86 to 2.97 (2H, m), 3.19 (2H, d, J=7.4 Hz), 3.30 to 3.41 (2H, m), 3.55 (2H, t, J=6.6 Hz), 3.80 (2H, t, J=5.0 Hz), 4.16 (2H, t, J=5.0 Hz), 4.58 (2H, s), 6.92 (1H, d, J=8.8 Hz), 6.98 (2H, d, J=8.8 Hz), 7.34 to 7.61 (10H, m), 9.00 (1H, s).

IR (KBr) 3299, 1640, 1605, 1595, 1516, 1499, 1408, 1368, 1316, 1246, 1181, 1123, 1061, 816 cm$^{-1}$

Elemental Analysis for C$_{36}$H$_{42}$N$_4$O$_3$S$_2$ Calcd. C, 67.26; H, 6.59; N, 8.72. Found: C, 67.07; H, 6.37; N, 8.53.

Example 109

(Preparation of Compound 116)

To a solution of 7-[4-(2-butoxyethoxy)phenyl]-N-(4-hydroxymethylphenyl)-2,3-dihydro-1-isobutyl-1H-1-benzazepine-4-carboxamide (0.50 g) in THF (10 ml) were added thionyl chloride (0.1 ml) and pyridine (1 droplet) at room temperature and the mixture was stirred for 1.5 hours. The reaction solution was concentrated under reduced pressure, and to a solution of the residue in DMF (10 ml) was added potassium carbonate (0.51 g) and potassium 5-methyl-2-mercapto-1,3,4-oxadiazole (0.18 g), and the mixture was stirred at 50° C. for 1 hour. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1) and further recrystallized from ethyl acetate-hexane to give 7-[4-(2-butoxyethoxy)phenyl]-N-[4-(5-methyl-1,3,4-oxadiazol-2-ylthiomethyl)phenyl]-1-isobutyl-2,3-dihydro-1H-1-benzazepine-4-carboxamide (Compound 116) (469.8 mg) as yellow crystals.

m.p. 107 to 109° C.

$^1$H-NMR (200 MHz, CDCl$_3$) δ 0.93 (3H, t, J=7.1 Hz), 0.97 (6H, d, J=6.6 Hz), 1.29 to 1.48 (2H, m), 1.54 to 1.67 (2H, m), 1.97 to 2.16 (1H, m), 2.49 (3H, s), 2.85 to 2.95 (2H, m), 3.18 (2H, d, J=7.4 Hz), 3.33 to 3.37 (2H, m), 3.55 (2H, t, J=6.6 Hz), 3.80 (2H, t, J=5.0 Hz), 4.15 (2H, t, J=5.0 Hz), 4.43 (2H, s), 6.91 (1H, d, J=8.8 Hz), 6.97 (2H, d, J=8.8 Hz), 7.37 to 7.50 (7H, m), 7.57 (2H, d, J=8.4 Hz), 7.63 (1H, s).

IR (KBr) 3345, 1645, 1605, 1591, 1518, 1499, 1487, 1246, 1161, 808 cm$^{-1}$

Elemental Analysis for C$_{37}$H$_{44}$N$_4$O$_4$S Calcd. C, 69.35; H, 6.92; N, 8.74. Found: C, 69.12; H, 6.84; N, 8.93.

Example 110

(Preparation of Compound 117)

To a solution of 7-[4-(2-butoxyethoxy)phenyl]-N-(4-hydroxymethylphenyl)-2,3-dihydro-1-isobutyl-1H-1-benzazepine-4-carboxamide (0.50 g) in THF (10 ml) were added thionyl chloride (0.1 ml) and pyridine (1 droplet) at room temperature and the mixture was stirred for 1.5 hours. The reaction solution was concentrated under reduced pressure, and a solution of the residue in ethanol (20 ml) was added to triethylamine (2.0 ml) and 2-mercapto-4-methyl-1,2,4-triazole (0.14 g) at 50° C. and the mixture was stirred for 16 hours. To the reaction solution was added 1,8-diazabicyclo [5,4,0]-7-undecene (1.0 ml), and the mixture was further stirred at 60° C. for 4 hours. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 2:1→ethanol:ethyl acetate 1:10) to give 7-[4-(2-butoxyethoxy)phenyl]-N-[4-(4-methyl-4H-1,2,4-triazol-3-ylthiomethyl)phenyl]-1-isobutyl-2,3-dihydro-1H-1-benzazepine-4-carboxamide (Compound 117) (312.9 mg) as yellow amorphous.

$^1$H-NMR (200 MHz, CDCl$_3$) δ 0.93 (3H, t, J=7.1 Hz), 0.97 (6H, d, =6.6 Hz), 1.31 to 1.46 (2H, m), 1.51 to 1.66 (2H, m), 1.93 to 2.15 (1H, m), 2.85 to 2.94 (2H, m), 3.18 (2H, d, J=7.2 Hz), 3.30 to 3.38 (5H, m), 3.55 (2H, t, J=6.6 Hz), 3.80 (2H, t, J=5.0 Hz), 4.16 (2H, t, J=5.0 Hz), 4.34 (2H, s), 6.91 (1H, d, J=8.8 Hz), 6.97 (2H, d, J=8.8 Hz), 7.22 to 7.26 (2H, m), 7.37 to 7.54 (7H, m), 7.62 (1H, s), 8.08 (1H, s).

IR (KBr) 3275, 1655, 1605, 1516, 1499, 1408, 1316, 1244, 1181, 1123, 1065, 835, 816 cm$^{-1}$

Elemental Analysis for C$_{37}$H$_{45}$N$_5$O$_3$S.0.5H$_2$O Calcd. C, 68.49; H, 7.15; N, 10.79. Found: C, 68.45; H, 7.22; N, 10.68.

Example 111

(Preparation of Compound 118)

To a solution of 7-[4-(2-butoxyethoxy)phenyl]-N-[4-(4-methyl-4H-1,2,4-triazol-3-ylthiomethyl)phenyl]-1-isobutyl-2,3-dihydro-1H-1-benzazepine-4-carboxamide (0.26 g) in dichloromethane (10 ml) was added a solution of 3-chloroperbenzoic acid (70%, 0.26 g) in dichloromethane (10 ml) at −78° C. and the mixture was stirred at −10 to −15° C. for 1.5 hours. To the reaction solution was added magnesium thiosulfate solution at room temperature and the mixture was stirred for several minutes. The mixture was extracted with ethyl acetate. The organic layer was washed with sodium bicarbonate solution and saturated brine, dried over magnesium sulfate and concentrated under reduced pressure. The obtained residue was separated and purified by column chromatography (ethanol:ethyl acetate 1:9→1:4) to give 7-[4-(2-butoxyethoxy)phenyl]-N-[4-(4-methyl-4H-1,2,4-triazol-3-ylsulfinylmethyl)phenyl]-1-isobutyl-2,3-dihydro-1H-1-benzazepine-4-carboxamide (Compound 118) (73.8 mg) as yellow crystals.

m.p. 87 to 89° C.

$^1$H-NMR (200 MHz, CDCl$_3$) δ 0.93 (3H, t, J=7.1 Hz), 0.97 (6H, d, J=6.6 Hz), 1.26 to 1.45 (2H, m), 1.48 to 1.67 (2H, m), 1.98 to 2.12 (1H, m), 2.85 to 2.96 (2H, m), 3.19 (2H, d, J=7.0 Hz), 3.30 to 3.43 (5H, m), 3.55 (2H, t, J=6.6 Hz), 3.80 (2H, t, J=5.0 Hz), 4.16 (2H, t, J=5.0 Hz), 4.37 (1H, d, J=13.4 Hz), 4.65 (1H, d, J=13.4 Hz), 6.92 (1H, d, J=8.8 Hz), 6.98 (2H, d, J=8.8 Hz), 7.09 (2H, d, J=8.6 Hz), 7.34 to 7.64 (8H, m), 8.05 (1H, s).

IR (KBr) 3267, 1655, 1607, 1516, 1499, 1410, 1314, 1246, 1182, 1125, 1063, 820 cm$^{-1}$

Elemental Analysis for C$_{37}$H$_{45}$N$_5$O$_4$S.1.0H$_2$O Calcd. C, 65.95; H, 7.03; N, 10.39. Found: C, 65.55; H, 6.79; N, 10.34.

Example 112

(Preparation of Compound 119)

To a solution of 7-[4-(2-butoxyethoxy)phenyl]-N-[4-(1,3,4-thiadiazol-2-ylthiomethyl)phenyl]-1-isobutyl-2,3-dihydro-1H-1-benzazepine-4-carboxamide (480 mg) in dichloromethane (20 ml) was added dropwise a solution of 3-chloroperbenzoic acid (70%, 0.28 g) in dichloromethane (10 ml) at −78° C. The mixture was stirred at −10° C. for 4 hours, and to the reaction solution was added sodium thiosulfate solution and the mixture was further stirred at room temperature for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetate:hexane 1:2→1:1) to give 7-[4-(2-butoxyethoxy)phenyl]-N-[4-(1,3,4-thiadiazol-2-ylsulfinylmethyl)phenyl]-1-isobutyl-2,3-dihydro-1H-1-benzazepine-4-carboxamide (Compound 119) (33 mg) as yellow crystals.

$^1$H-NMR (200 MHz, CDCl$_3$) δ 0.93 (3H, t, J=7.1 Hz), 0.97 (6H, d, J=6.6 Hz), 1.30 to 1.49 (2H, m), 1.53 to 1.68 (2H, m), 1.98 to 2.13 (1H, m), 2.85 to 2.96 (2H, m), 3.19 (2H, d, J=7.2 Hz), 3.30 to 3.38 (2H, m), 3.55 (2H, t, J=6.6 Hz), 3.80 (2H, t, J=5.0 Hz), 4.16 (2H, t, J=5.0 Hz), 4.31 (1H, d, J=13.2 Hz), 4.54 (1H, d, J=13.2 Hz), 6.92 (1H, d, J=8.8 Hz), 6.98 (2H, d, J=8.4 Hz), 7.07 (2H, d, J=8.4 Hz), 7.35 to 7.56 (7H, m), 7.62 (H, s), 9.21 (1H, s).

IR (KBr) 3306, 1653, 1607, 1516, 1499, 1410, 1316, 1244, 1182, 1117, 1071, 820 cm$^{-1}$

Elemental Analysis for C$_{36}$H$_{42}$N$_4$O$_4$S$_2$.0.5H$_2$O Calcd. C, 64.74; H, 6.49; N, 8.39. Found: C, 64.75; H, 6.48; N, 8.50.

Example 113

(Preparation of Compound 120)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, to the solution was added thionyl chloride (0.15 ml) at 0° C., and the mixture was allowed to be at room temperature and stirred for 1 hour under nitrogen atmosphere. This solution was added to a solution of 4-[[(1-isopropylimidazol-2-yl)methyl]sulfanyl]aniline (515 mg) and triethylamine (5.8 ml) in tetrahydrofuran (15 ml) at 0° C. The mixture was stirred for 1 hour at room temperature under nitrogen atmosphere, water was added to the mixture, and the mixture was extracted with ethyl acetate. The organic layer was washed with saturated brine and dried over magnesium sulfate. The solvent was distilled off under reduced pressure and the obtained residue was purified by silica gel column chromatography (hexane:ethyl acetate=1:3→ethyl acetate), which was recrystallized from ethanol-hexane, to give 7-[4-(2-butoxyethoxy)phenyl]-1-isobutyl-N-[4-[[(1-isopropylimidazol-2-yl)methyl]sulfanyl]phenyl]-2,3-dihydro-1-benzazepine-4-carboxamide (417 mg) (Compound 120) as yellow crystals.

$^1$H-NMR (200 MHz, CDCl$_3$) δ 0.90 to 0.99 (9H, m), 1.30 to 1.45 (8H, m), 1.55 to 1.70 (2H, m), 1.95 to 2.10 (1H, m), 2.90 (2H, t, J=4.8 Hz), 3.18 (2H, d, J=7.0 Hz), 3.35 (2H, t, J=4.8 Hz), 3.56 (2H, t, J=7.0 Hz), 3.80 (2H, t, J=4.4 Hz), 4.13 to 4.18 (4H, m), 4.40 to 4.60 (1H, m), 6.89 to 7.00 (5H, m), 7.32 to 7.55 (9H, m), 7.75 (1H, s).

Elemental Analysis for C$_{40}$H$_{50}$N$_4$O$_3$S.0.25H$_2$O Calcd. C, 71.55; H, 7.58; N, 8.34. Found: C, 71.32; H, 7.52; N, 8.17.

Example 114

(Preparation of Compound 121, Compound 122)

To a solution of 7-[4-(2-butoxyethoxy)phenyl]-1-isobutyl-N-[4-[[(1-isopropylimidazol-2-yl)methyl]sulfanyl]phenyl]-2,3-dihydro-1-benzazepine-4-carboxamide (200 mg) in dichloromethane (10 ml) was added dropwise 70% solution of 3-chloroperbenzoic acid (111 mg) in dichloromethane (10 ml) at −78° C. After finishing the dropping, the mixture was stirred for 1 hour at −10° C. to −25° C. To the mixture was added sodium thiosulfate solution, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure and the obtained residue was separated and purified by silica gel column chromatography (methanol:ethyl acetate=1:9) to give 7-[4-(2-butoxyethoxy)phenyl]-1-isobutyl-N-[4-[[(1-isopropylimidazol-2-yl)methyl]sulfonyl]phenyl]-2,3-dihydro-1-benzazepine-4-carboxamide (89.0 mg)(Compound 121) as yellow amorphous, and was recrystallized from hexane-ethyl acetate, to give 7-[4-(2-butoxyethoxy)phenyl]-1-isobutyl-N-[4-[[(1-isopropylimidazol-2-yl)methyl]sulfanyl]phenyl]-2,3-dihydro-1-benzazepine-4-carboxamide (29 mg)(Compound 122) as yellow crystals.

Compound 121

1H-NMR (200 MHz, CDCl$_3$) δ 0.90 to 0.99 (9H, m), 1.22 to 1.49 (8H, m), 1.54 to 1.75 (2H, m), 2.00 to 2.20 (H, m), 2.90 to 3.00 (2H, m), 3.20 (2H, d, J=7.6 Hz), 3.30 to 3.40 (2H, m), 3.55 (2H, t, J=7.6 Hz), 3.80 (2H, t, J=4.4 Hz), 4.10 to 4.30 (4H, m), 4.40 to 4.50 (1H, m), 6.90 to 7.02 (5H, m), 7.38 to 7.48 (7H, m), 7.73 (2H, d, J=8.8 Hz), 7.88 (1H, s).

Elemental Analysis for C$_{40}$H$_{50}$N$_4$O$_4$S.0.3H$_2$O Calcd. C, 69.80; H, 7.41; N, 8.14. Found: C, 69.56; H, 7.18; N, 7.91.

Compound 122

$^1$H-NMR (200 MHz, CDCl$_3$) δ 0.90 to 1.02 (9H, m), 1.34 to 1.65 (10H, m), 2.00 to 2.20 (1H, m), 2.90 to 3.00 (2H, m), 3.21 (2H, d, J=7.4 Hz), 3.30 to 3.40 (2H, m), 3.55 (2H, t, J=7.0 Hz), 3.80 (2H, t, J=5.2 Hz), 4.15 (2H, t, J=5.2 Hz), 4.42 (2H, s), 4.60 to 4.70 (1H, m), 6.89 to 7.03 (5H, m), 7.31 to 7.38 (5H, m), 7.55 (2H, d, J=8.8 Hz), 7.74 (2H, d, J=8.8 Hz), 8.52 (1H, s).

Elemental Analysis for C$_{40}$H$_{50}$N$_4$O$_5$S.0.5H$_2$O Calcd. C, 67.86; H, 7.26; N, 7.91. Found: C, 67.61; H, 7.07; N, 7.76.

Example 115

(Preparation of Compound 123)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature and the mixture was stirred for 1 hour. The mixture was concentrated under reduced pressure to obtain acid chloride. To a solution of 4-aminothiophenol (0.29 g) and triethylamine (1.6 ml) in THF (10 ml) was added benzyl chlorocarbonate (0.35 ml) at 0° C., and the mixture was stirred at 0° C. for 0.5 hour and at room temperature for 0.5 hour. To the mixture was added a solution of the previously prepared acid chloride in THF (20 ml) dropwise at 0° C., and the mixture was stirred at room temperature for 2 hours. To the reaction solution was added water, and the mixture was extracted with ethyl acetate. The organic layer was washed with saturated brine, dried over magnesium sulfate and concentrated under reduced pressure. A solution of the residue in THF-methanol (30-30 ml) was added to 1N aqueous solution of sodium hydroxide (10 ml) at room temperature, and the mixture was stirred for 0.5 hour. To the reaction solution was added 5-chloromethyl-1-methyl-1H-1,2,4-triazole hydrochloride (0.39 g), and the mixture was stirred for 16 hours. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethyl acetate:hexane 1:1→3:2→2:1), to give 7-[4-(2-butoxyethoxy)phenyl]-N-[4-(1-methyl-1H-1,2,4-triazol-5-ylmethylthio)phenyl]-1-isobutyl-2,3-dihydro-1H-1-benzazepine-4-carboxamide (Compound 123) (639 mg) as yellow amorphous.

$^1$H-NMR (200 MHz, CDCl$_3$) δ 0.93 (3H, t, J=7.1 Hz), 0.97 (6H, d, J=6.6 Hz), 1.30 to 1.48 (2H, m), 1.51 to 1.68 (2H, m), 1.98 to 2.16 (1H, m), 2.85 to 2.95 (2H, m), 3.19 (2H, d, J=7.2 Hz), 3.33 to 3.78 (2H, m), 3.55 (2H, t, J=6.6 Hz), 3.74 (3H, s), 3.80 (2H, t, J=5.0 Hz), 4.12 (2H, s), 4.16 (2H, t, J=5.0 Hz), 6.92 (1H, d, J=8.4 Hz), 6.98 (2H, d, J=8.8 Hz), 7.31 to 7.49 (7H, m), 7.55 (2H, d, J=8.8 Hz), 7.62 (1H, s), 7.76 (1H, s).

IR (KBr) 3300, 1651, 1607, 1586, 1497, 1395, 1312, 1285, 1244, 1181, 1119, 822 cm$^{-1}$

Elemental Analysis for C$_{37}$H$_{45}$N$_5$O$_3$S0.5H$_2$O Calcd. C, 68.49; H, 7.15; N, 10.79. Found: C, 68.62; H, 7.14; N, 11.00.

Example 116

(Preparation of Compound 124)

To a solution of 7-[4-(2-butoxyethoxy)phenyl]-N-[4-(1-methyl-1H-1,2,4-triazol-5-ylmethylthio)phenyl]-1-isobutyl-2,3-dihydro-1H-1-benzazepine-4-carboxamide (565 mg) in dichloromethane (10 ml) was added dropwise a solution of 3-chloroperbenzoic acid (70%, 0.32 g) in dichloromethane (10 ml) at −78° C. The mixture was stirred for 1 hour at −78° C., sodium thiosulfate solution was added to the reaction solution at room temperature and the mixture was stirred for several minutes. The mixture was extracted with ethyl acetate and the organic layer was washed with sodium bicarbonate solution and saturated brine, dried over magnesium sulfate and concentrated under reduced pressure. The obtained residue was separated and purified by column chromatography (ethanol:ethyl acetate 1:19→1:9) and further recrystallized from ethyl acetate-hexane to give 7-[4-(2-butoxyethoxy)phenyl]-N-[4-(1-methyl-1H-1,2,4-triazol-5-ylmethylsulfinyl)phenyl]-1-isobutyl-2,3-dihydro-1H-1-benzazepine-4-carboxamide (Compound 124) (515 mg) as yellow crystals.

m.p. 135 to 138° C.

$^1$H-NMR (200 MHz, CDCl$_3$) δ 0.93 (3H, t, J=7.2 Hz), 0.98 (6H, d, J=6.6 Hz), 1.35 to 1.47 (2H, m), 1.52 to 1.68 (2H, m), 1.96 to 2.17 (1H, m), 2.87 to 2.97 (2H, m), 3.20 (2H, d, J=7.4 Hz), 3.32 to 3.41 (2H, m), 3.55 (2H, t, J=6.6 Hz), 3.76 (3H, s), 3.81 (2H, t, J=4.9 Hz), 4.16 (2H, t, J=4.9 Hz), 4.19 (H, d, J=13.6 Hz), 4.28 (1H, d, J=13.6 Hz), 6.91 to 7.01 (3H, m), 7.36 to 7.52 (7H, m), 7.74 (1H, br s), 7.78 (2H, d, J=8.8 Hz), 7.83 (1H, s).

IR (KBr) 3382, 1655, 1613, 1591, 1520, 1497, 1393, 1318, 1246, 1184, 1121, 1036, 820 cm$^{-1}$

Elemental Analysis for C$_{37}$H$_{45}$N$_5$O$_4$S Calcd. C, 67.76; H, 6.92; N, 10.68. Found: C, 67.52; H, 6.76; N, 10.43.

Example 117

(Preparation of Compound 125)

To a solution of 7-[4-(2-butoxyethoxy)phenyl]-1-isobutyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1 hour. The reaction solution was concentrated under reduced pressure, and a solution of the residue in THF (30 ml), was added dropwise to a solution of S-(4-aminophenyl)O-benzyl thiocarbonate (0.64 g) and triethylamine (1.3 ml) in THF (5 ml) at 0° C. The mixture was stirred at room temperature for 2 hours, methanol (50 ml) and 1N aqueous solution of sodium hydroxide (15 ml) were added to the mixture and the mixture was stirred for 0.5 hour. To the reaction solution was added 3-chloromethyl-1-methyl-1H-1,2,4-triazole hydrochloride (0.44 g), and the mixture was stirred for 1 hour. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethyl acetate:hexane 2:1→ethyl acetate) to give 7-[4-(2-butoxyethoxy)phenyl]-1-isobutyl-N-[4-(1-methyl-1H-1,2,4-triazol-3-ylmethylthio)phenyl]-2,3-dihydro-1H-benzazepine-4-carboxamide (Compound 125) (1.00 g) as yellow amorphous.

$^1$H-NMR (200 MHz, CDCl$_3$) δ 0.93 (3H, t, J=7.3 Hz), 0.97 (6H, d, J=6.6 Hz), 1.32 to 1.50 (2H, m), 1.53 to 1.69 (2H, m), 1.96 to 2.15 (1H, m), 2.85 to 2.95 (2H, m), 3.18 (2H, d, J=7.0 Hz), 3.33 to 3.38 (2H, m), 3.55 (1H, t, J=6.6 Hz), 3.80 (2H, t, J=5.0 Hz), 3.86 (3H, s), 4.13 to 4.18 (4H, m), 6.92 (1H, d, J=8.8 Hz), 6.98 (2H, d, J=8.8 Hz), 7.38 to 7.55 (10H, m), 7.94 (1H, s).

IR (KBr) 3300, 1653, 1605, 1586, 1499, 1312, 1285, 1244, 1181, 1123, 820 cm$^{-1}$

Elemental Analysis for C$_{37}$H$_{45}$N$_5$O$_3$S.0.5H$_2$O Calcd. C, 68.49; H, 7.15; N, 10.79. Found: C, 68.18; H, 6.85; N, 11.09.

Example 118

(Preparation of Compound 126, Compound 127)

To a solution of 7-[4-(2-butoxyethoxy)phenyl]-1-isobutyl-N-[4-(1-methyl-1H-1,2,4-triazol-3-ylmethylthio)phenyl]-2,3-dihydro-1H-benzazepine-4-carboxamide (0.8 g) in dichloromethane (20 ml) was added dropwise a solution of 3-chloroperbenzoic acid (70%, 0.46 g) in dichloromethane (10 ml) at −78° C., and the mixture was stirred at −78° C. for 0.5 hour. To the reaction solution was added sodium thiosulfate solution at room temperature and the mixture was stirred for several minutes. The mixture was extracted with ethyl acetate and the organic layer was washed with sodium bicarbonate solution and saturated brine, dried over magnesium sulfate and concentrated under reduced pressure. The obtained residue was purified by column chromatography (ethanol:ethyl acetate 1:5→1:3), and was further recrystalized from ethyl acetate-hexane, to give 7-[4-(2-butoxyethoxy)phenyl]-1-isobutyl-N-[4-(1-methyl-1H-1,2,4-triazol-3-ylmethylsulfinyl)phenyl]-2,3-dihydro-1H-benzazepine-4-carboxamide (Compound 126) (678.9 mg) as yellow crystals.

In addition, at the same time, 7-[4-(2-butoxyethoxy)phenyl]-1-isobutyl-N-[4-(1-methyl-1H-1,2,4-triazol-3-ylmethylsulfonyl)phenyl]-2,3-dihydro-1H-benzazepine-4-carboxamide (Compound 127) (22.2 mg) was obtained.

Compound 126 m.p. 112 to 114° C.

$^1$H-NMR (200 MHz, CDCl$_3$) δ 0.93 (3H, t, J=7.2 Hz), 0.98 (6H, d, J=6.6 Hz), 1.30 to 1.44 (2H, m), 1.50 to 1.66 (2H, m), 1.96 to 2.15 (1H, m), 2.86 to 2.97 (2H, m), 3.20 (2H, d, J=7.0 Hz), 3.32 to 3.41 (2H, m), 3.55 (1H, t, J=6.6 Hz), 3.81 (2H, t, J=4.8 Hz), 3.89 (3H, s), 4.09 (1H, d, J=13.2 Hz), 4.16 (2H, t, J=4.8 Hz), 4.28 (1H, d, J=13.2 Hz), 6.93 (1H, d, J=8.4 Hz), 6.98 (2H, d, J=9.2 Hz), 7.36 to 7.50 (5H, m), 7.58 (2H, d, J=8.8 Hz), 7.69 (1H, s), 7.75 (2H, d, J=8.8 Hz), 7.97 (1H, s).

IR (KBr) 3104, 1661, 1607, 1590, 1518, 1499, 1314, 1246, 1179, 1125, 1046, 835 cm$^{-1}$

Elemental Analysis for C$_{37}$H$_{45}$N$_5$O$_4$S.0.25H$_2$O Calcd. C, 67.30; H, 6.94; N, 10.61. Found: C, 67.16; H, 6.89; N, 10.61.

Compound 127 m.p. 205 to 208° C.

$^1$H-NMR (200 MHz, CDCl$_3$) δ 0.93 (3H, t, J=7.2 Hz), 0.97 (6H, d, J=6.6 Hz), 1.28 to 1.46 (2H, m), 1.52 to 1.68 (2H, m), 1.96 to 2.13 (H, m), 2.86 to 2.96 (2H, m), 3.20 (2H, d, J=7.0 Hz), 3.31 to 3.42 (2H, m), 3.55 (1H, t, J=6.6 Hz), 3.80 (2H, t, J=4.8 Hz), 3.89 (3H, s), 4.16 (2H, t, J=4.8 Hz), 4.52 (2H, s), 6.91 to 7.00 (3H, m), 7.39 to 7.50 (5H, m), 7.77 to 7.81 (5H, m), 7.95 (H, s).

IR (KBr) 3240, 1672, 1609, 1590, 1520, 1501, 1402, 1318, 1240, 1182, 1146, 808 cm$^{-1}$

Elemental Analysis for C$_{37}$H$_{45}$N$_5$O$_5$S.0.5H$_2$O Calcd. C, 65.27; H, 6.81; N, 10.29. Found: C, 65.17; H, 6.72; N, 10.16.

Example 119

(Preparation of Compound 128)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.21 ml) and DMF (1 droplet) at room temperature, and the mixture was stirred for 1.5 hours. The reaction mixture was concentrated under reduced pressure, and a solution of the residue in THF (20 ml) was added dropwise to a solution of 4-(1,2,4-oxadiazol-3-ylmethylthio) aniline (0.43 g) and triethylamine (1.6 ml) in THF (2 ml) at 0° C. The mixture was stirred at room temperature for 4 hours, water was added to the mixture and the mixture was extracted with ethyl acetate. The organic layer was washed with saturated brine, dried over magnesium sulfate and concentrated under reduced pressure. The obtained residue was purified by column chromatography (ethyl acetate:hexane 1:2→1:1), and was further recrystalized from ethanol, to give 7-[4-(2-butoxyethoxy)phenyl]-1-isobutyl-N-[4-(1,2,4-oxadiazol-3-ylmethylthio)phenyl]-2,3-dihydro-1H-benzazepine-4-carboxamide (Compound 128) (855.7 mg) as yellow crystals.

m.p. 112 to 115° C.

$^1$H-NMR (200 MHz, CDCl$_3$) δ 0.93 (3H, t, J=7.3 Hz), 0.97 (6H, d, J=6.6 Hz), 1.28 to 1.48 (2H, m), 1.54 to 1.68 (2H, m), 1.94 to 2.18 (1H, m), 2.84 to 2.95 (2H, m), 3.19 (2H, d, J=7.2 Hz), 3.33 to 3.38 (2H, m), 3.55 (2H, t, J=6.6 Hz), 3.81 (2H, t, J=5.0 Hz), 4.13 to 4.18 (4H, m), 6.92 (H, d, J=8.4 Hz), 6.98 (2H, d, J=8.8 Hz), 7.38 to 7.58 (10H, m), 8.67 (1H, s).

IR (KBr) 3337, 1647, 1605, 1584, 1551, 1501, 1397, 1337, 1310, 1240, 1109, 828, 810 cm$^{-1}$

Elemental Analysis for C$_{36}$H$_{42}$N$_4$O$_4$S Calcd. C, 68.98; H, 6.75; N, 8.94. Found: C, 68.95; H, 6.94; N, 8.97.

Example 120

(Preparation of Compound 129)

To a solution of 7-[4-(2-butoxyethoxy)phenyl]-1-isobutyl-N-[4-(1,2,4-oxadiazol-3-ylmethylthio)phenyl]-2,3-dihydro-1H-benzazepine-4-carboxamide (0.60 g) in dichloromethane (15 ml) was added dropwise a solution of 3-chloroperbenzoic acid (70%, 0.35 g) in dichloromethane (5 ml) at –78° C., and the mixture was stirred at –78° C. for 1 hour. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethyl acetate:hexane 1:1→4:1), and was further recrystalized from ethyl acetate-hexane, to give 7-[4-(2-butoxyethoxy)phenyl]-1-isobutyl-N-[4-(1,2,4-oxadiazol-3-ylmethylsulfinyl)phenyl]-2,3-dihydro-1H-benzazepine-4-carboxamide (Compound 129) (534.9 mg) as yellow crystals.

m.p. 142 to 144° C.

$^1$H-NMR (200 MHz, CDCl$_3$) δ 0.93 (3H, t, J=7.2 Hz), 0.97 (6H, d, J=6.6 Hz), 1.34 to 1.49 (2H, m), 1.54 to 1.71 (2H, m), 1.96 to 2.16 (1H, m), 2.86 to 2.95 (2H, m), 3.20 (2H, d, J=7.2 Hz), 3.31 to 3.41 (2H, m), 3.55 (2H, t, J=6.6 Hz), 3.81 (2H, t, J=5.0 Hz), 4.16 (2H, t, J=5.0 Hz), 4.21 (1H, d, J=13.2 Hz), 4.32 (1H, d, J=13.2 Hz), 6.91 to 7.00 (3H, m), 7.39 to 7.50 (5H, m), 7.59 (2H, d, J=8.8 Hz), 7.77 to 7.81 (3H, m), 8.71 (1H, s).

IR (KBr) 3222, 1649, 1607, 1588, 1499, 1397, 1343, 1314, 1246, 1181, 1128, 1047, 828, 808 cm$^{-1}$

Elemental Analysis for C$_{36}$H$_{42}$N$_4$O$_5$S Calcd. C, 67.26; H, 6.59; N, 8.72. Found: C, 67.24; H, 6.60; N, 8.66.

Example 121

(Preparation of Compound 130)

To a solution of 7-[4-(2-butoxyethoxy)phenyl]-1-isobutyl-2,3-dihydro-1H-1-benzazepine-4-carboxylic acid (0.50 g) in THF (10 ml) were added thionyl chloride (0.13 ml) and DMF (1 droplet) at room temperature, and the mixture was stirred for 1 hour. The mixture was concentrated under reduced pressure to obtain acid chloride. Separately, to a solution of 4-aminothiophenol (0.16 g) and triethylamine (0.70 ml) in THF (10 ml) was added benzyl chlorocarbonate (0.19 ml) at –78° C., and the mixture was stirred at –78° C. for 10 minutes, at 0° C. for 0.5 hour and at room temperature for 0.5 hour. A solution of the previously prepared acid chloride in THF (10 ml) was added dropwise to the solution at 0° C., and the mixture was stirred for 1 hour at room temperature. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:4→1:3) to give yellow amorphous. To a solution of the obtained compound (0.54 g) in THF-methanol (10$^{-10}$ ml) was added 1N aqueous solution of sodium hydroxide (32 ml) at room temperature, and the mixture was stirred for 1 hour. To the reaction solution was added 3-chloromethyl-4-methyl-4H-1,2,4-triazole hydrochloride (0.15 g), and the mixture was stirred for 0.5 hour. The mixture was concentrated under reduced pressure and extracted with ethyl acetate. The organic layer was washed with saturated brine, dried over magnesium sulfate and concentrated under reduced pressure. The obtained residue was purified by column chromatography (ethyl acetate→ethanol:ethyl acetate 1:10→1:4), to give 7-[4-(2-butoxyethoxy)phenyl]-N-[4-(4-methyl-4H-1,2,4-triazol-3-ylmethylthio)phenyl]-1-isobutyl-2,3-dihydro-1H-1-benzazepine-4-carboxamide (Compound 130) (352.8 mg) as yellow amorphous.

$^1$H-NMR (200 MHz, CDCl$_3$) δ 0.93 (3H, t, J=7.4 Hz), 0.98 (6H, d, J=6.6 Hz), 1.29 to 1.48 (2H, m), 1.51 to 1.68 (2H, m), 1.97 to 2.18 (1H, m), 2.86 to 2.96 (2H, m), 3.19 (2H, d, J=6.6 Hz), 3.28 to 3.39 (2H, m), 3.56 (2H, t, J=6.6 Hz), 3.60 (3H, s), 3.81 (2H, t, J=5.0 Hz), 4.11 (2H, s), 4.16 (2H, t, J=5.0 Hz), 6.89 to 7.00 (3H, m), 7.29 to 7.43 (6H, m), 7.46 (2H, d, J=8.4 Hz), 7.57 (2H, d, J=8.4 Hz), 7.97 (1H, s), 806 (1H, br s).

IR (KBr) 3282, 1655, 1607, 1586, 1499, 1312, 1242, 1181, 1123, 820 cm$^{-1}$

Example 122

(Preparation of Compound 131)

To a solution of 7-[4-(2-butoxyethoxy)phenyl]-N-[4-(4-methyl-4H-1,2,4-triazol-3-ylmethylthio)phenyl]-1-isobutyl-2,3-dihydro-1H-1-benzazepine-4-carboxamide (0.30 g) in dichloromethane (10 ml) was added dropwise a solution of 3-chloroperbenzoic acid (70%, 0.17 g) in dichloromethane (10 ml) at −78° C. The mixture was stirred for 0.5 hour at −78° C. and to the reaction solution was added sodium thiosulfate solution at room temperature and the mixture was stirred for several minutes. The mixture was extracted with ethyl acetate and the organic layer was washed with sodium bicarbonate solution and saturated brine, dried over magnesium sulfate and concentrated under reduced pressure. The obtained residue was separated and purified by column chromatography (ethanol:ethyl acetate 1:4→1:2), to give 7-[4-(2-butoxyethoxy)phenyl]-N-[4-(4-methyl-4H-1,2,4-triazol-3-ylmethylsulfinyl)phenyl]-1-isobutyl-2,3-dihydro-1H-1-benzazepine-4-carboxamide (Compound 131) (204 mg) as yellow crystals.

m.p. 103 to 105° C.

$^1$H-NMR (200 MHz, CDCl$_3$) δ 0.93 (3H, t, J=7.2 Hz), 1.01 (6H, d, J=6.2 Hz), 1.29 to 1.47 (2H, m), 1.53 to 1.72 (2H, m), 1.96 to 2.17 (1H, m), 2.89 to 3.01 (2H, m), 3.22 (2H, d, J=7.8 Hz), 3.30 to 3.40 (2H, m), 3.53 to 3.61 (5H, m), 3.81 (2H, t, J=4.9 Hz), 3.96 (1H, d, J=14.0 Hz), 4.11 (1H, d, J=14.0 Hz), 4.16 (2H, t, J=4.9 Hz), 6.89 to 6.99 (3H, m), 7.16 to 7.22 (2H, m), 7.34 to 7.48 (5H, m), 7.85 (2H, d, J=8.4 Hz), 8.00 (1H, s), 8.64 (1H, br s).

IR (KBr) 3298, 1655, 1607, 1588, 1520, 1499, 1314, 1246, 1181, 1125, 1090, 1047, 833 cm$^{-1}$

Example 123

(Preparation of Compound 132)

To a solution of 7-[4-(2-butoxyethoxy)phenyl]-1-propyl-2,3-dihydro-1H-1-benzazepine-4-carboxylic acid (1.0 g) in THF (10 ml) were added thionyl chloride (0.26 ml) and DMF (1 droplet) at room temperature and the mixture was stirred for 1 hour. The mixture was concentrated under reduced pressure to obtain acid chloride. In addition, to a solution of 4-aminothiophenol (0.30 g) and triethylamine (2.0 ml) in THF (5 ml) was added benzyl chlorocarbonate (0.36 ml) at −78° C. and the mixture was stirred at −78° C. for 20 minutes and at 0° C. for 20 minutes. To the mixture was added dropwise a solution of the previously prepared acid chloride in THF (20 ml) at 0° C., and the mixture was stirred at room temperature for 2 hours. To the reaction solution were added methanol (50 ml) and 1N aqueous solution of sodium hydroxide (15 ml), and the mixture was stirred for 20 minutes. To the reaction solution was added 3-chloromethyl-4-methyl-4H-1,2,4-triazole hydrochloride (0.41 g), and the mixture was stirred for 0.5 hour. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:10→1:4), to give 7-[4-(2-butoxyethoxy)phenyl]-N-[4-(4-methyl-4H-1,2,4-triazol-3-ylmethylthio)phenyl]-1-propyl-2,3-dihydro-1H-1-benzazepine-4-carboxamide (Compound 132) (836.4 mg) as yellow amorphous.

$^1$H-NMR (200 MHz, CDCl$_3$) δ 0.93 (3H, t, J=7.1 Hz), 1.00 (3H, t, J=7.3 Hz), 1.30 to 1.46 (2H, m), 1.51 to 1.82 (4H, m), 2.85 to 2.96 (2H, m), 3.24 to 3.38 (4H, m), 3.56 (2H, t, J=6.6 Hz), 3.57 (3H, s), 3.81 (2H, t, J=4.9 Hz), 4.07 (2H, s), 4.16 (2H, t, J=4.9 Hz), 6.88 (1H, d, J=8.4 Hz), 6.97 (2H, d, J=9.2 Hz), 7.31 to 7.47 (7H, m), 7.58 (2H, d, J=8.8 Hz), 7.94 (1H, s), 8.26 (1H, s).

IR (KBr) 3268, 1655, 1605, 1586, 1499, 1397, 1310, 1242, 1179, 1119, 816 cm$^{-1}$

Example 124

(Preparation of Compound 133)

To a solution of 7-[4-(2-butoxyethoxy)phenyl]-N-[4-(4-methyl-4H-1,2,4-triazol-3-ylmethylthio)phenyl]-1-propyl-2,3-dihydro-1H-1-benzazepine-4-carboxamide (0.70 mg) in dichloromethane (20 ml) was added dropwise a solution of 3-chloroperbenzoic acid (70%, 0.41 g) in dichloromethane (5 ml) at −78° C. The mixture was stirred for 1 hour at −78° C., and to the reaction solution was added sodium thiosulfate solution at room temperature and the mixture was stirred for several minutes. The mixture was extracted with ethyl acetate and the organic layer was washed with sodium bicarbonate solution and saturated brine, dried over magnesium sulfate and concentrated under reduced pressure. The residue was separated and purified by basic silica gel column chromatography (ethanol:ethyl acetate ~1:9), and was further recrystalized from ethyl acetate-hexane, to give 7-[4-(2-butoxyethoxy)phenyl]-N-[4-(4-methyl-4H-1,2,4-triazol-3-ylmethylsulfinyl)phenyl]-1-propyl-2,3-dihydro-1H-1-benzazepine-4-carboxamide (Compound 133) (613.2 mg) as yellow crystals.

m.p. 101 to 103° C.

$^1$H-NMR (200 MHz, CDCl$_3$) δ 0.93 (3H, t, J=7.3 Hz), 1.03 (3H, t, J=7.3 Hz), 1.30 to 1.46 (2H, m), 1.52 to 1.88 (4H, m), 2.89 to 3.00 (2H, m), 3.28 to 3.41 (4H, m), 3.48 (3H, s), 3.55 (2H, t, J=6.6 Hz), 3.80 (2H, t, J=4.8 Hz), 3.87 (1H, d, J=14.0 Hz), 4.04 (1H, d, J=14.0 Hz), 4.13 (2H, t, J=4.8 Hz), 6.89 (1H, d, J=8.6 Hz), 6.96 (2H, d, J=8.8 Hz), 7.16 (2H, d, J=8.4 Hz), 7.30 to 7.43 (5H, m), 7.86 (2H, d, J=8.8 Hz), 7.96 (1H, s), 8.88 (1H, br s).

IR (KBr) 3262, 1653, 1590, 1520, 1501, 1316, 1246, 1179, 1123, 1051, 835 cm$^{-1}$

Example 125

(Preparation of Compound 134)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.26 ml) and DMF (1 droplet) at room temperature and the mixture was stirred for 1 hour. The mixture was concentrated under reduced pressure, and a solution of the residue in THF (35 ml), was added dropwise to a solution of S-(4-aminophenyl) O-benzylcarbonate (0.59 g) and triethylamine (2.0 ml) in THF (5 ml) at 0° C. The mixture was stirred at room temperature for 18 hours, methanol (50 ml) and 1N aqueous solution of sodium hydroxide (15 ml) were added to the mixture and the mixture was stirred for 0.5 hour. To the reaction solution was added 3-chloromethyl-4-ethyl-4H-1,2,4-triazole hydrochloride (0.46 g), and the mixture was stirred for 1 hour. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:9→1:5), to give 7-[4-(2-butoxyethoxy)phenyl]-N-[4-(4-ethyl-4H-1,2,4-triazol-3-ylmethylthio)phenyl]-1-isobutyl-2,3-dihydro-1H-benzazepine-4-carboxamide (Compound 134) (1.14 g) as yellow amorphous.

$^1$H-NMR (200 MHz, CDCl$_3$) δ 0.93 (3H, t, J=7.1 Hz), 0.97 (6H, d, J=6.6 Hz), 1.31 to 1.46 (5H, m), 1.55 to 1.67 (2H, m), 1.97 to 2.17 (1H, m), 2.85 to 2.95 (2H, m), 3.18 (2H, d, J=7.4 Hz), 3.27 to 3.36 (2H, m), 3.55 (2H, t, J=6.6 Hz), 3.80 (2H, t, J=5.0 Hz), 3.92 (2H, q, J=7.5 Hz), 4.06 (2H, s), 4.16 (2H, t, J=5.0 Hz), 6.89 (1H, d, J=8.8 Hz), 6.97 (2H, d, J=8.8 Hz), 7.26 to 7.41 (5H, m), 7.43 (2H, d, J=8.8 Hz), 7.60 (2H, d, J=8.8 Hz), 8.00 (1H, s), 8.43 (1H, s).

IR (KBr) 3264, 1659, 1605, 1588, 1514, 1499, 1244, 1182, 1125, 818 cm$^{-1}$

Elemental Analysis for C$_{38}$H$_{47}$N$_5$O$_3$S.0.25H$_2$O Calcd. C, 69.32; H, 7.27; N, 10.64. Found: C, 69.28; H, 7.49; N, 10.50.

Example 126

(Preparation of Compound 135)

To a solution of 7-[4-(2-butoxyethoxy)phenyl]-N-[4-(4-ethyl-4H-1,2,4-triazol-3-ylmethylthio)phenyl]-1-isobutyl-2,3-dihydro-1H-benzazepine-4-carboxamide (0.94 g) in dichloromethane (20 ml) was added dropwise a solution of 3-chloroperbenzoic acid (70%, 0.53 g) in dichloromethane (10 ml) at −78° C., and the mixture was stirred at −78° C. for 1 hour. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethanol:ethyl acetate 1:9), and was recrystalized from ethyl acetate, to give 7-[4-(2-butoxyethoxy)phenyl]-N-[4-(4-ethyl-4H-1,2,4-triazol-3-ylmethylsulfinyl)phenyl]-1-isobutyl-2,3-dihydro-1H-benzazepine-4-carboxamide (Compound 135) (858.7 mg) as yellow crystals.

m.p. 102 to 104° C.

$^1$H-NMR (200 MHz, CDCl$_3$) δ 0.93 (3H, t, J=7.2 Hz), 0.99 (6H, d, J=6.6 Hz), 1.30 to 1.48 (5H, m), 1.51 to 1.68 (2H, m), 1.96 to 2.19 (1H, m), 2.89 to 2.99 (2H, m), 3.21 (2H, d, J=6.6 Hz), 3.32 to 3.42 (2H, m), 3.56 (2H, t, J=6.6 Hz), 3.81 (2H, t, J=4.8 Hz), 3.93 to 4.26 (6H, m), 6.90 to 7.00 (3H, m), 7.37 to 7.46 (7H, m), 7.81 (2H, d, J=8.8 Hz), 8.09 to 8.17 (2H, m).

IR (KBr) 3218, 1655, 1605, 1590, 1520, 1499, 1314, 1244, 1181, 1090, 1053, 835 cm$^{-1}$

Elemental Analysis for C$_{38}$H$_{47}$N$_5$O$_4$S.0.5H$_2$O Calcd. C, 67.23; H, 7.13; N, 10.32. Found: C, 66.91; H, 7.06; N, 10.03.

Example 127

(Preparation of Compound 136)

To a solution of 7-[4-(2-butoxyethoxy)phenyl]-1-propyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1.5 hours. The reaction mixture was concentrated under reduced pressure, and a solution of the residue in THF (35 ml) was added dropwise to a solution of S-(4-aminophenyl)O-benzylcarbonate (0.62 g) and triethylamine (2.0 ml) in THF (5 ml) at 0° C. The mixture was stirred for 16 hours at room temperature, methanol (50 ml) and 1N aqueous solution of sodium hydroxide (15 ml) were added to the mixture and the mixture was stirred for 0.5 hour. To the reaction solution was added 3-chloromethyl-4-ethyl-4H-1,2,4-triazole hydrochloride (0.47 g), and the mixture was stirred for 2 hours. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:9→1:5), to give 7-[4-(2-butoxyethoxy)phenyl]-N-[4-(4-ethyl-4H-1,2,4-triazol-3-ylmethylthio)phenyl]-1-propyl-2,3-dihydro-1H-benzazepine-4-carboxamide (Compound 136) (1.15 g) as yellow amorphous.

$^1$H-NMR (200 MHz, CDCl$_3$) δ 0.93 (3H, t, J=7.2 Hz), 1.00 (3H, t, J=7.3 Hz), 1.26 to 1.47 (5H, m), 1.52 to 1.82 (4H, m), 2.85 to 2.96 (2H, m), 3.27 to 3.37 (4H, m), 3.56 (2H, t, J=6.6 Hz), 3.81 (2H, t, J=5.0 Hz), 3.92 (2H, q, J=7.4 Hz), 4.05 (2H, s), 4.16 (2H, t, J=5.0 Hz), 6.87 (1H, d, J=8.4 Hz), 6.97 (2H, d, J=8.8 Hz), 7.27 to 7.32 (4H, m), 7.36 to 7.46 (3H, m), 7.60 (2H, d, J=8.4 Hz), 8.00 (1H, s), 8.45 (1H, br s).

IR (KBr) 3223, 1657, 1605, 1588, 1499, 1310, 1240, 1181, 1121, 816 cm$^{-1}$

Elemental Analysis for C$_{37}$H$_{45}$N$_5$O$_3$S.0.5H$_2$O Calcd. C, 68.49; H, 7.15; N, 10.79. Found: C, 68.52; H, 7.20; N, 11.14.

Example 128

(Preparation of Compound 137)

To a solution of 7-[4-(2-butoxyethoxy)phenyl]-N-[4-(4-ethyl-4H-1, 2, 4-triazol-3-ylmethylthio) phenyl]-1-propyl-2, 3-dihydro-1H-benzazepine-4-carboxamide (0.93 g) in dichloromethane (20 ml) was added dropwise a solution of 3-chloroperbenzoic acid (70%, 0.54 g) in dichloromethane (10 ml) at −78° C., and the mixture was stirred at −78° C. for 1 hour. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethanol:ethyl acetate 1:5→1:3→1:2), to give 7-[4-(2-butoxyethoxy)phenyl]-N-[4-(4-ethyl-4H-1,2,4-triazol-3-ylmethylsulfinyl)phenyl]-1-propyl-2,3-dihydro-1H-benzazepine-4-carboxamide (Compound 137) (694.7 mg) as yellow amorphous.

$^1$H-NMR (200 MHz, CDCl$_3$) δ 0.93 (3H, t, J=7.3 Hz), 1.02 (3H, t, J=7.3 Hz), 1.29 to 1.50 (5H, m), 1.53 to 1.86

(4H, m), 2.92-2.99 (2H, m), 3.25 to 3.40 (4H, m), 3.55 (2H, t, J=6.6 Hz), 3.80 (2H, t, J=4.9 Hz), 3.87 to 4.01 (3H, m), 4.08 to 4.17 (3H, m), 6.89 (1H, d, J=8.8 Hz), 6.96 (2H, d, J=8.8 Hz), 7.23 to 7.43 (7H, m), 7.85 (2H, d, J=8.8 Hz), 8.08 (1H, s), 8.62 (1H, br s).

IR (KBr) 3104, 1661, 1607, 1588, 1518, 1499, 1397, 1314, 1244, 1179, 1123, 1090, 833 cm$^{-1}$

Elemental Analysis for $C_{37}H_{45}N_5O_4S$—$H_2O$ Calcd. C, 65.95; H, 7.03; N, 10.39. Found: C, 65.78; H, 7.10; N, 10.52.

Example 129

(Preparation of Compound 138)

To a solution of 7-[4-(2-butoxyethoxy)phenyl]-1-isobutyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1 hour. The reaction mixture was concentrated under reduced pressure, and a solution of the residue in THF (30 ml) was added dropwise to a solution of S-(4-aminophenyl)O-benzylcarbonate (0.64 g) and triethylamine (1.3 ml) in THF (5 ml) at 0° C. The mixture was stirred at room temperature for 2 hours, and methanol (50 ml) and 1N aqueous solution of sodium hydroxide (15 ml) were added to the mixture and the mixture was stirred for 0.5 hour. To the reaction solution was added 3-chloromethyl-4-propyl-4H-1,2,4-triazole hydrochloride (0.51 g), and the mixture was stirred for 1 hour. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:9→1:5), to give 7-[4-(2-butoxyethoxy)phenyl]-1-isobutyl-N-[4-(4-propyl-4H-1,2,4-triazol-3-ylmethylthio)phenyl]-2,3-dihydro-1H-benzazepine-4-carboxamide (Compound 138) (987 mg) as yellow amorphous.

$^1$H-NMR (200 MHz, CDCl$_3$) δ 0.89 to 2.99 (12H, m), 1.29 to 1.49 (2H, m), 1.53 to 1.85 (4H, m), 1.96 to 2.17 (1H, m), 2.86 to 2.96 (2H, m), 3.18 (2H, d, J=7.0 Hz), 3.28 to 3.38 (2H, m), 3.56 (2H, t, J=6.6 Hz), 3.79 to 3.86 (4H, m), 4.06 (2H, s), 4.16 (2H, t, J=4.9 Hz), 6.90 (1H, d, J=8.8 Hz), 6.97 (2H, d, J=8.8 Hz), 7.31 to 7.46 (7H, m), 7.60 (2H, d, J=8.8 Hz), 7.97 (1H, s), 8.42 (1H, br s).

IR (KBr) 3264, 1659, 1607, 1588, 1497, 1397, 1312, 1242, 1181, 1123, 816 cm$^{-1}$

Elemental Analysis for $C_{39}H_{49}N_5O_3S\cdot0.5H_2O$ Calcd. C, 69.20; H, 7.45; N, 10.35. Found: C, 69.12; H, 7.58; N, 10.41.

Example 130

(Preparation of Compound 139)

To a solution of 7-[4-(2-butoxyethoxy)phenyl]-1-isobutyl-N-[4-(4-propyl-4H-1,2,4-triazol-3-ylmethylthio)phenyl]-2,3-dihydro-1H-benzazepine-4-carboxamide (826 mg) in dichloromethane (20 ml) was added dropwise a solution of 3-chloroperbenzoic acid (70%, 0.46 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The residue was purified by basic silica gel column chromatography (ethanol:ethyl acetate 1:5→1:3), to give 7-[4-(2-butoxyethoxy)phenyl]-1-isobutyl-N-[4-(4-propyl-4H-1,2,4-triazol-3-ylmethylsulfinyl)phenyl]-2,3-dihydro-1H-benzazepine-4-carboxamide (Compound 139) (628.7 mg) as yellow amorphous.

$^1$H-NMR (200 MHz, CDCl$_3$) δ 0.88 (3H, t, J=7.3 Hz), 0.93 (3H, t, J=7.1 Hz), 1.01 (6H, d, J=6.6 Hz), 1.28 to 1.47 (2H, m), 1.51 to 1.78 (4H, m), 1.95 to 2.18 (1H, m), 2.90 to 3.01 (2H, m), 3.21 (2H, d, J=7.2 Hz), 3.31 to 3.41 (2H, m), 3.55 (2H, t, J=6.6 Hz), 3.76 to 3.86 (4H, m), 3.97 (1H, d, J=14.2 Hz), 4.11 (1H, d, J=14.2 Hz), 4.15 (2H, t, J=4.9 Hz), 6.91 (1H, d, J=8.8 Hz), 6.96 (2H, d, J=8.4 Hz), 7.27 to 7.43 (7H, m), 7.85 (2H, d, J=8.8 Hz), 8.04 (1H, s), 8.70 (1H, br s).

IR (KBr) 3282, 1661, 1607, 1588, 1518, 1499, 1397, 1314, 1244, 1181, 1125, 1051, 835 cm$^{-1}$

Elemental Analysis for $C_{39}H_{49}N_5O_4S\cdot0.5H_2O$ Calcd. C, 67.60; H, 7.27; N, 10.11. Found: C, 67.25; H, 7.28; N, 9.82.

Example 131

(Preparation of Compound 140)

To a solution of 7-[4-(2-butoxyethoxy)phenyl]-1-propyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1.5 hours. The reaction mixture was concentrated under reduced pressure, and a solution of the residue in THF (30 ml) was added dropwise to a solution of S-(4-aminophenyl)O-benzylcarbonate (0.64 g) and triethylamine (2.0 ml) in THF (5 ml) at 0° C. The mixture was stirred at room temperature for 2 hours, and methanol (50 ml) and 1N aqueous solution of sodium hydroxide (15 ml) were added to the mixture and the mixture was stirred for 0.5 hour. To the reaction solution was added 3-chloromethyl-4-propyl-4H-1,2,4-triazole hydrochloride (0.50 g), and the mixture was stirred for 1 hour. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:9→1:5), to give 7-[4-(2-butoxyethoxy)phenyl]-1-propyl-N-[4-(4-propyl-4H-1,2,4-triazol-3-ylmethylthio)phenyl]-2,3-dihydro-1H-benzazepine-4-carboxamide (Compound 140) (1.00 g) as yellow amorphous.

$^1$H-NMR (200 MHz, CDCl$_3$) δ 0.89 to 1.03 (9H, m), 1.28 to 1.47 (2H, m), 1.51 to 1.88 (6H, m), 2.85 to 2.96 (2H, m), 3.23 to 3.36 (4H, m), 3.56 (2H, t, J=6.6 Hz), 3.77 to 3.84 (4H, m), 4.04 (2H, s), 4.16 (2H, t, J=4.8 Hz), 6.87 (1H, d, J=8.8 Hz), 6.97 (2H, d, J=8.8 Hz), 7.26 to 7.45 (7H, m), 7.60 (2H, d, J=8.8 Hz), 7.96 (1H, s), 8.52 (1H, s).

IR (KBr) 3280, 1655, 1607, 1588, 1499, 1456, 1397, 1310, 1287, 1242, 1181, 1121, 818 cm$^{-1}$

Elemental Analysis for $C_{38}H_{47}N_5O_3S$ Calcd. C, 68.85; H, 7.30; N, 10.56. Found: C, 68.54; H, 7.41; N, 10.70.

Example 132

(Preparation of Compound 141)

To a solution of 7-[4-(2-butoxyethoxy)phenyl]-1-propyl-N-[4-(4-propyl-4H-1,2,4-triazol-3-ylmethylthio)phenyl]-2,3-dihydro-1H-benzazepine-4-carboxamide (843.7 mg) in dichloromethane (20 ml) was added dropwise a solution of 3-chloroperbenzoic acid (70%, 0.48 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was purified by column chromatography (ethanol:ethyl acetate 1:5→1:4), to give 7-[4-(2-butoxyethoxy)phenyl]-1-propyl-N-[4-(4-propyl-4H-1,2,4-triazol-3-ylmethylsulfinyl)phenyl]-2,3-dihydro-1H-benzazepine-4-carboxamide (Compound 141) (490.8 mg) as yellow amorphous.

$^1$H-NMR (200 MHz, CDCl$_3$) δ 0.89 (3H, t, J=7.2 Hz), 0.93 (3H, t, J=7.4 Hz), 1.02 (3H, d, J=7.3 Hz), 1.27 to 1.48 (2H, m), 1.51 to 1.86 (6H, m), 2.89 to 3.00 (2H, m), 3.28 to 3.41 (4H, m), 3.55 (2H, t, J=6.6 Hz), 3.78 to 3.89 (4H, m), 4.00 (1H, d, J=14.4 Hz), 4.12 to 4.19 (3H, m), 6.90 (1H, d, J=8.4 Hz), 6.96 (2H, d, J=9.2 Hz), 7.27 to 7.44 (7H, m), 7.84 (2H, d, J=8.4 Hz), 8.06 (1H, s), 8.54 (1H, br s).

IR (KBr) 3284, 1661, 1607, 1588, 1518, 1499, 1397, 1314, 1244, 1179, 1088, 1051, 835 cm$^{-1}$

Elemental Analysis for $C_{38}H_{47}N_5O_4S$ Calcd. C, 66.35; H, 7.18; N, 10.18. Found: C, 65.95; H, 7.23; N, 10.53.

Example 133

(Preparation of Compound 142)

To a solution of 7-[4-(2-butoxyethoxy)phenyl]-1-isobutyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1 hour. The reaction mixture was concentrated under reduced pressure, and a solution of the residue in THF (30 ml) was added dropwise to a solution of S-(4-aminophenyl)O-benzylcarbonate (0.59 g) and triethylamine (2.0 ml) in THF (5 ml) at 0° C. The mixture was stirred at room temperature for 18 hours, methanol (50 ml) and 1N aqueous solution of sodium hydroxide (15 ml) were added to the mixture and the mixture was stirred for 0.5 hour. To the reaction solution was added 4-n-butyl-3-chloromethyl-4H-1,2,4-triazole hydrochloride (0.51 g), and the mixture was stirred for 2 hours. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:9), to give 7-[4-(2-butoxyethoxy)phenyl]-N-[4-(4-n-butyl-4H-1,2,4-triazol-3-ylmethylthio)phenyl]-1-isobutyl-2,3-dihydro-1H-benzazepine-4-carboxamide (Compound 142) (1.34 g) as yellow amorphous.

$^1$H-NMR (200 MHz, CDCl$_3$) δ 0.90 to 0.99 (12H, m), 1.22 to 1.48 (4H, m), 1.52 to 1.83 (4H, m), 1.98 to 2.18 (1H, m), 2.85 to 2.95 (2H, m), 3.18 (2H, d, J=7.6 Hz), 3.29 to 3.39 (2H, m), 3.55 (2H, t, J=6.6 Hz), 3.80 (2H, t, J=4.8 Hz), 3.89 (2H, t. J=7.5 Hz), 4.09 (2H, s), 4.16 (2H, t, J=4.8 Hz), 6.88 to 6.99 (3H, m), 7.29 to 7.47 (7H, m), 7.58 (2H, d, J=8.8 Hz), 8.00 (1H, s), 8.21 (1H, s).

IR (KBr) 3227, 1653, 1605, 1588, 1518, 1497, 1312, 1242, 1181, 1121, 820 cm$^{-1}$

Elemental Analysis for $C_{40}H_{51}N_5O_3S.0.5H_2O$ Calcd. C, 69.53; H, 7.59; N, 10.14. Found: C, 69.29; H, 7.57; N, 10.41.

Example 134

(Preparation of Compound 143)

To a solution of 7-[4-(2-butoxyethoxy)phenyl]-N-[4-(4-n-butyl-4H-1,2,4-triazol-3-ylmethylthio)phenyl]-1-isobutyl-2,3-dihydro-1H-benzazepine-4-carboxamide (1.01 g) in dichloromethane (20 ml) was added dropwise a solution of 3-chloroperbenzoic acid (70%, 0.55 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethanol:ethyl acetate 1:9→1:4), and was recrystallized from ethyl acetate, to give 7-[4-(2-butoxyethoxy)phenyl]-N-[4-(4-n-butyl-4H-1,2,4-triazol-3-ylmethylsulfinyl)phenyl]-1-isobutyl-2,3-dihydro-1H-benzazepine-4-carboxamide (Compound 143) (794.5 mg) as yellow crystals.

m.p. 178 to 180°

$^1$H-NMR (200 MHz, CDCl$_3$) δ 0.88 to 1.07 (12H, m), 1.20 to 1.69 (8H, m), 1.99 to 2.19 (1H, m), 2.91 to 2.99 (2H, m), 3.20 (2H, d, J=7.0 Hz), 3.31 to 3.40 (2H, m), 3.55 (2H, t, J=6.6 Hz), 3.78 to 3.93 (4H, m), 4.03 (1H, d, J=14.0 Hz), 4.12 to 4.18 (3H, m), 6.90 to 6.99 (3H, m), 7.27 to 7.45 (7H, m), 7.83 (2H, d, J=8.8 Hz), 8.06 (1H, s), 8.46 (1H, s).

IR (KBr) 3297, 1653, 1607, 1588, 1520, 1499, 1397, 1310, 1240, 1181, 1028, 833 cm$^{-1}$

Elemental Analysis for $C_{40}H_{51}N_5O_4S.0.25H_2O$ Calcd. C, 68.39; H, 7.39; N, 9.97. Found: C, 68.22; H, 7.34; N, 10.04.

Example 135

(Preparation of Compound 144)

To a solution of 7-[4-(2-butoxyethoxy)phenyl]-1-propyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1.5 hours. The reaction mixture was concentrated under reduced pressure, and a solution of the residue in THF (30 ml) was added dropwise to a solution of S-(4-aminophenyl)O-benzylcarbonate (0.61 g) and triethylamine (2.0 ml) in THF (5 ml) at 0° C. The mixture was stirred for 64 hours at room temperature, methanol (50 ml) and 1N aqueous solution of sodium hydroxide (15 ml) were added to the mixture and the mixture was stirred for 0.5 hour. To the reaction solution was added 4-n-butyl-3-chloromethyl-4H-1,2,4-triazole hydrochloride (0.52 g), and the mixture was stirred for 2 hours. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethanol:ethyl acetate 1:9→1:5), to give 7-[4-(2-butoxyethoxy)phenyl]-N-[4-(4-n-butyl-4H-1,2,4-triazol-3-ylmethylthio)phenyl]-1-propyl-2,3-dihydro-1H-benzazepine-4-carboxamide (Compound 144) (1.23 g) as yellow amorphous.

$^1$H-NMR (200 MHz, CDCl$_3$) δ 0.90 to 1.03 (9H, m), 1.23 to 1.45 (4H, m), 1.53 to 1.82 (6H, m), 2.87 to 2.96 (2H, m), 3.25 to 3.36 (4H, m), 3.56 (2H, t, J=6.6 Hz), 3.81 (2H, t, J=5.0 Hz), 3.87 (2H, t, J=7.3 Hz), 4.08 (2H, s), 4.16 (2H, t,

J=5.0 Hz), 6.88 (1H, d, J=8.6 Hz), 6.97 (2H, d, J=8.4 Hz), 7.26 to 7.46 (7H, m), 7.59 (2H, d, J=8.4 Hz), 7.98 (1H, s), 8.32 (1H, br s).

IR (KBr) 3218, 1655, 1605, 1587, 1499, 1397, 1310, 1242, 1179, 1119, 833 cm$^{-1}$

Elemental Analysis for $C_{39}H_{49}N_5O_3S.0.75H_2O$. Calcd. C, 68.74; H, 7.47; N, 10.28. Found: C, 68.79; H, 7.15; N, 10.68.

Example 136

(Preparation of Compound 145)

To a solution of 7-[4-(2-butoxyethoxy)phenyl]-N-[4-(4-n-butyl-4H-1,2,4-triazol-3-ylmethylthio)phenyl]-1-propyl-2,3-dihydro-1H-benzazepine-4-carboxamide (1.00 g) in dichloromethane (20 ml) was added dropwise a solution of 3-chloroperbenzoic acid (70%, 0.55 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethanol:ethyl acetate 1:5→1:4), and was recrystalized from ethyl acetate, to give 7-[4-(2-butoxyethoxy)phenyl]-N-[4-(4-n-butyl-4H-1,2,4-triazol-3-ylmethylsulfinyl)phenyl]-1-propyl-2,3-dihydro-1H-benzazepine-4-carboxamide (Compound 145) (614.2 mg) as yellow crystals.

m.p. 157 to 160° C.

$^1$H-NMR (200 MHz, CDCl$_3$) δ 0.86 to 0.97 (6H, m), 1.02 (3H, t, J=7.3 Hz), 1.18 to 1.84 (10H, m), 2.89 to 2.99 (2H, m), 3.26 to 3.40 (4H, m), 3.55 (2H, t, J=6.6 Hz), 3.78 to 3.97 (5H, m), 4.06 to 4.17 (3H, m), 6.89 (H, d, J=8.8 Hz), 6.95 (2H, d, J=8.8 Hz), 7.24 to 7.42 (7H, m), 7.85 (2H, d, J=8.8 Hz), 8.03 (1H, s), 8.73 (1H, s).

IR (KBr) 3295, 1655, 1607, 1588, 1518, 1499, 1318, 1242, 1181, 1028, 835 cm$^{-1}$

Elemental Analysis for $C_{39}H_{49}N_5O_4S.0.5H_2O$ Calcd. C, 67.60; H, 7.27; N, 10.11. Found: C, 67.46; H, 7.03; N, 10.33.

Example 137

(Preparation of Compound 146)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.21 ml) and DMF (1 droplet) at room temperature and the mixture was stirred for 1.5 hours. The reaction mixture was concentrated under reduced pressure, and a solution of the residue in THF (30 ml) was added dropwise to a solution of S-(4-aminophenyl)O-benzylcarbonate (0.48 g) and triethylamine (1.5 ml) in THF (5 ml) at 0° C. The mixture was stirred at room temperature for 2 hours, methanol (50 ml) and 1N aqueous solution of sodium hydroxide (9 ml) were added and the mixture was stirred for 0.5 hour. To the reaction solution was added 3-chloromethyl-5-ethylthio-4-isobutyl-4H-1,2,4-triazole hydrochloride (0.54 g), and the mixture was stirred for 2 hours. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethyl acetate:hexane 1:1→2:1), to give 7-[4-(2-butoxyethoxy)phenyl]-N-[4-(5-ethylthio-4-isobutyl-4H-1,2,4-triazol-3-ylmethylthio)phenyl]-1-isobutyl-2,3-dihydro-1H-benzazepine-4-carboxamide (Compound 146) (845.4 mg) as yellow amorphous.

$^1$H-NMR (200 MHz, CDCl$_3$) δ 0.89 (6H, d, J=7.0 Hz), 0.93 (3H, t, J=7.1 Hz), 0.97 (6H, d, J=6.6 Hz), 1.26 to 1.44 (5H, m), 1.54 to 1.68 (2H, m), 1.94 to 2.16 (2H, m), 2.84 to 2.95 (2H, m), 3.18 (2H, d, J=7.0 Hz), 3.21 (2H, q, J=7.4 Hz), 3.28 to 3.38 (2H, m), 3.55 (2H, t, J=6.6 Hz), 3.74 (2H, d, J=8.0 Hz), 3.80 (2H, t, J=5.0 Hz), 4.12 (2H, s), 4.16 (2H, t, J=5.0 Hz), 6.90 (1H, d, J=8.8 Hz), 6.97 (2H, d, J=8.8 Hz), 7.31 to 7.47 (7H, m), 7.56 (2H, d, J=8.4 Hz), 7.93 (1H, s).

IR (KBr) 3083, 1659, 1607, 1588, 1499, 1468, 1397, 1312, 1242, 1181, 1125, 831 cm$^{-1}$

Elemental Analysis for $C_{42}H_{55}N_5O_3S_2.0.25H_2O$ Calcd. C, 67.57; H, 7.49; N, 9.38. Found: C, 67.37; H, 7.50; N, 9.30.

Example 138

(Preparation of Compound 147)

To a solution of 7-[4-(2-butoxyethoxy)phenyl]-N-[4-(5-ethylthio-4-isobutyl-4H-1,2,4-triazol-3-ylmethylthio)phenyl]-1-isobutyl-2,3-dihydro-1H-benzazepine-4-carboxamide (697 mg) in dichloromethane (15 ml) was added dropwise a solution of 3-chloroperbenzoic acid (70%, 0.35 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (ethyl acetate:hexane 4:1→9:1 →ethyl acetate→ethanol:ethyl acetate 1:19), to give 7-[4-(2-butoxyethoxy)phenyl]-N-[4-(5-ethylthio-4-isobutyl-4H-1,2,4-triazol-3-ylmethylsulfinyl)phenyl]-1-isobutyl-2,3-dihydro-1H-benzazepine-4-carboxamide (Compound 147) (574.6 mg) as yellow amorphous.

$^1$H-NMR (200 MHz, CDCl$_3$) δ 0.84 to 1.00 (15H, m), 1.28 to 1.48 (5H, m), 1.52 to 1.68 (2H, m), 1.84 to 2.18 (2H, m), 2.89 to 2.98 (2H, m), 3.16 to 3.31 (4H, m), 3.34 to 3.41 (2H, m), 3.55 (2H, t, J=6.6 Hz), 3.66 to 3.84 (4H, m), 4.08 to 4.28 (4H, m), 6.91 to 7.00 (3H, m), 7.35 to 7.52 (7H, m), 7.79 (2H, d, J=8.8 Hz), 7.92 (1H, s).

IR (KBr) 3268, 1663, 1607, 1588, 1518, 1499, 1468, 1397, 1312, 1244, 1179, 1125, 1090, 835 cm$^{-1}$

Elemental Analysis for $C_{42}H_{55}N_5O_4S_2.0.5H_2O$ Calcd. C, 65.76; H, 7.36; N, 9.13. Found: C, 65.85; H, 7.47; N, 9.19.

Example 139

(Preparation of Compound 148)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.21 ml) and DMF (1 droplet) at room temperature and the mixture was stirred for 1.5 hours. The reaction mixture was concentrated under reduced pressure, and a solution of the residue in THF (30 ml) was added dropwise to a solution of S-(4-aminophenyl)O-benzylcarbonate (0.48 g) and triethylamine (1.5 ml) in THF (5 ml) at 0° C. The mixture was stirred at room temperature for 4 hours, methanol (50 ml) and 1N aqueous solution of sodium hydroxide (12 ml) were added to the mixture, and the mixture was stirred for 0.5 hour. To the reaction solution was added 3-chloromethyl-5-methylthio- 4-propyl-4H-1,2,4-triazole hydrochloride (0.47 g), and the mixture was stirred for 1 hour. The mixture was concentrated under reduced pressure and extracted with ethyl acetate. The organic layer was washed with saturated brine, dried over magnesium sulfate and concentrated under reduced pressure. The obtained residue was separated and purified by column chromatography (ethyl acetate:hexane 2:1→ethyl acetate), to give 7-[4-(2-butoxyethoxy)phenyl]-1-isobutyl-N-[4-(5-methylthio-4-propyl-4H-1,2,4-triazol-3-ylmethylthio)phenyl]-2,3-dihydro-1H-benzazepine-4-carboxamide (Compound 148) (931 mg) as yellow amorphous.

$^1$H-NMR (200 MHz, CDCl$_3$) δ 0.90 to 0.99 (12H, m), 1.25 to 1.48 (2H, m), 1.52 to 1.81 (4H, m), 1.94 to 2.17 (1H, m), 2.68 (3H, s), 2.85 to 2.95 (2H, m), 3.18 (2H, d, J=7.4 Hz), 3.29 to 3.39 (2H, m), 3.55 (2H, t, J=6.6 Hz), 3.78 to 3.86 (4H, m), 4.11 (2H, s), 4.16 (2H, t, J=4.9 Hz), 6.91 (1H, d, J=8.4 Hz), 6.98 (2H, d, J=8.8 Hz), 7.32 to 7.47 (7H, m), 7.57 (2H, d, J=8.8 Hz), 7.97 (1H, s).

IR (KBr) 3270, 1659, 1607, 1588, 1499, 1470, 1397, 1312, 1244, 1181, 1125, 816 cm$^{-1}$

Elemental Analysis for C$_{40}$H$_{51}$N$_5$O$_3$S$_2$.0.25H$_2$O Calcd. C, 66.87; H, 7.22; N, 9.75. Found: C, 66.82; H, 7.11; N, 9.82.

Example 140

(Preparation of Compound 149)

To a solution of 7-[4-(2-butoxyethoxy)phenyl]-1-isobutyl-N-[4-(5-methylthio-4-propyl-4H-1,2,4-triazol-3-ylmethylthio)phenyl]-2,3-dihydro-1H-benzazepine-4-carboxamide (0.80 g) in dichloromethane (10 ml) was added dropwise a solution of 3-chloroperbenzoic acid (70%, 0.41 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetate), which was further recrystalized from ethyl acetate-hexane, to give 7-[4-(2-butoxyethoxy)phenyl]-1-isobutyl-N-[4-(5-methylthio-4-propyl-4H-1,2,4-triazol-3-ylmethylsulfinyl)phenyl]-2,3-dihydro-1H-benzazepine-4-carboxamide (Compound 149) (617.6 mg) as yellow crystals.

m.p. 150 to 152° C.

$^1$H-NMR (200 MHz, CDCl$_3$) δ 0.88 (3H, t, J=7.3 Hz), 0.93 (3H, t, J=7.3 Hz), 0.99 (6H, d, J=6.6 Hz), 1.29 to 1.45 (2H, m), 1.48 to 1.73 (4H, m), 1.96 to 2.19 (1H, m), 2.70 (3H, s), 2.89 to 3.01 (2H, m), 3.20 (2H, d, J=7.0 Hz), 3.31 to 3.43 (2H, m), 3.55 (2H, t, J=6.6 Hz), 3.78 to 3.89 (4H, m), 4.02 (1H, d, J=13.8 Hz), 4.13 to 4.20 (3H, m), 6.89 to 6.99 (3H, m), 7.36 to 7.47 (7H, m), 7.83 (2H, d, J=8.8 Hz), 8.22 (1H, s).

IR (KBr) 3164, 1659, 1603, 1590, 1518, 1499, 1476, 1395, 1312, 1242, 1179, 1125, 1053, 833 cm$^{-1}$

Elemental Analysis for C$_{40}$H$_{51}$N$_5$O$_4$S$_2$ Calcd. C, 65.81; H, 7.04; N, 9.59. Found: C, 65.64; H, 7.00; N, 9.52.

Example 141

(Preparation of Compound 150)

To a solution of 7-[4-(2-butoxyethoxy)phenyl]-1-isobutyl-2,3-dihydro-1H-benzazepine-4-carboxylic acid (0.30 g) in THF (10 ml) were added thionyl chloride (0.075 ml) and DMF (1 droplet) at room temperature and the mixture was stirred for 1.5 hours. The reaction mixture was concentrated under reduced pressure, and a solution of the residue in THF (10 ml) was added dropwise to a solution of 4-[methyl(4-propyl-4H-1,2,4-triazol-3-ylmethyl)amino]aniline (0.18 g) in pyridine (2 ml) at 0° C. The mixture was stirred at room temperature for 18 hours. To the reaction solution was added water and the mixture was extracted with ethyl acetate. The organic layer was washed with saturated brine, dried over magnesium sulfate and concentrated under reduced pressure. The obtained residue was separated and purified by column chromatography (basic silica gel, ethyl acetate), and was further recrystallized from ethyl acetate-hexane, to give 7-[4-(2-butoxyethoxy)phenyl]-1-isobutyl-N-[4-[methyl(4-propyl-4H-1,2,4-triazol-3-ylmethyl)amino]phenyl]-2,3-dihydro-1H-benzazepine-4-carboxamide (Compound 150) (210.4 mg) as yellow crystals.

m.p. 134 to 136° C.

$^1$H-NMR (200 MHz, CDCl$_3$) δ 0.84-0.98 (12H, m), 1.31 to 1.46 (2H, m), 1.52 to 1.86 (4H, m), 1.95 to 2.13 (1H, m), 2.84 (3H, s), 2.85 to 2.95 (2H, m), 3.18 (2H, d, J=7.2 Hz), 3.28 to 3.38 (2H, m), 3.55 (2H, t, J=6.5 Hz), 3.78 to 3.90 (4H, m), 4.10 to 4.17 (2H, m), 4.56 (2H, s), 6.88 to 7.00 (5H, m), 7.36 to 7.54 (7H, m), 7.62 to 7.81 (1H, m), 8.10 (1H, s).

IR (KBr) 3287, 1655, 1605, 1518, 1499, 1248, 1186, 1121, 1067, 820 cm$^{-1}$

Elemental Analysis for C$_{40}$H$_{52}$N$_6$O$_3$ Calcd. C, 72.26; H, 7.88; N, 12.64. Found: C, 71.96; H, 7.89; N, 12.49.

Example 142

(Preparation of Compound 151)

To a solution of 7-[4-(2-butoxyethoxy)phenyl]-1-propyl-2,3-dihydro-1H-benzazepine-4-carboxylic acid (0.30 g) in THF (10 ml) were added thionyl chloride (0.077 ml) and DMF (1 droplet) at room temperature and the mixture was stirred for 1.5 hours. The reaction mixture was concentrated under reduced pressure, and a solution of the residue in THF (10 ml) was added dropwise to a solution of 4-[methyl(4-propyl-4H-1,2,4-triazol-3-ylmethyl)amino]aniline (0.19 g) in pyridine (7 ml) at 0° C. The mixture was stirred at room temperature for 20 hours, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethanol:ethyl acetate 1:4), and was further recrystallized from ethyl acetate-hexane, to give 7-[4-(2-butoxyethoxy)phenyl]-N-[4-[methyl (4-propyl-4H-1,2,4-triazol-3-ylmethyl)amino]phenyl]-1-propyl-2,3-dihydro-1H-benzazepine-4-carboxamide (Compound 151) (240.2 mg) as yellow crystals.

m.p. 131 to 133° C.

$^1$H-NMR (200 MHz, CDCl$_3$) δ 0.90 (3H, t, J=7.3 Hz), 0.93 (3H, t, J=7.1 Hz), 0.99 (3H, t, J=7.3 Hz), 1.28 to 1.47 (2H, m), 1.52 to 1.80 (6H, m), 2.85 (3H, s), 2.86 to 2.95 (2H, m), 3.26 to 3.38 (4H, m), 3.55 (2H, t, J=6.6 Hz), 3.80 (2H, t, J=5.0 Hz), 3.89 (2H, t, J=7.3 Hz), 4.16 (2H, t, J=5.0 Hz), 4.59 (2H, s), 6.88 to 7.00 (5H, m), 7.34 to 7.52 (8H, m), 8.11 (1H, s).

IR (KBr) 3303, 1640, 1605, 1518, 1501, 1306, 1246, 119, 1175, 1128, 833, 821 cm$^{-1}$

Elemental Analysis for C$_{39}$H$_{50}$N$_6$O$_3$.0.25H$_2$O Calcd. C, 71.48; H, 7.77; N, 12.82. Found: C, 71.51; H, 7.74; N, 12.54.

Example 143

(Preparation of Compound 152)

To a solution of 7-[4-(2-butoxyethoxy)phenyl]-1-isobutyl-2,3-dihydro-1H-benzazepine-4-carboxylic acid (0.30 g) in THF (10 ml) were added thionyl chloride (0.075 ml) and DMF (1 droplet) at room temperature and the mixture was stirred for 1.5 hours. The reaction mixture was concentrated under reduced pressure, and a solution of the residue in THF (20 ml) was added dropwise to a solution of 4-[2-(4-propyl-4H-1,2,4-triazol-3-yl)ethyl]aniline (0.17 g) and pyridine (2 ml) in THF (7 ml) at 0° C. The mixture was stirred at room temperature for 64 hours, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethanol:ethyl acetate 1:9→1:4), to give 7-[4-(2-butoxyethoxy)phenyl]-1-isobutyl-N-[4-[2-(4-propyl-4H-1,2,4-triazol-3-yl)ethyl]phenyl]-2,3-dihydro-1H-benzazepine-4-carboxamide (Compound 152) (219.5 mg) as yellow amorphous.

$^1$H-NMR (200 MHz, CDCl$_3$) δ 0.86 to 0.98 (12H, m), 1.33 to 1.48 (2H, m), 1.51 to 1.79 (2H, m), 1.96 to 2.15 (1H, m), 2.82 to 3.03 (4H, m), 3.05 to 3.22 (4H, m), 3.27 to 3.41 (2H, m), 3.55 (2H, t, J=6.6 Hz), 3.63 (2H, t, J=7.2 Hz), 3.80 (2H, t, J=4.9 Hz), 4.15 (2H, t, J=4.9 Hz), 6.91 (1H, d, J=8.8 Hz), 6.97 (2H, d, J=8.8 Hz), 7.16 (2H, d, J=8.4 Hz), 7.37 to 7.55 (7H, m), 7.65 to 7.86 (1H, m), 8.03 (1H, s).

IR (KBr) 3090, 1655, 1605, 1516, 1499, 1246, 1182, 1123, 1067, 820 cm$^{-1}$

Elemental Analysis for C$_{40}$H$_{51}$N$_5$O$_3$.0.5H$_2$O Calcd. C, 72.92; H, 7.95; N, 10.63. Found: C, 72.88; H, 7.78; N, 10.56.

Example 144

(Preparation of Compound 153)

To a solution of 7-[4-(2-butoxyethoxy)phenyl]-1-propyl-2,3-dihydro-1H-benzazepine-4-carboxylic acid (0.30 g) in THF (10 ml) were added thionyl chloride (0.077 ml) and DMF (1 droplet) at room temperature and the mixture was stirred for 1.5 hours. The reaction mixture was concentrated under reduced pressure, and a solution of the residue in THF (10 ml) was added dropwise to a solution of 4-[2-(4-propyl-4H-1,2,4-triazol-3-yl)ethyl]aniline (0.18 g) in pyridine (7 ml) at 0° C. The mixture was stirred at room temperature for 20 hours, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethyl acetate→ethanol:ethyl acetate 1:9→1:4), to give 7-[4-(2-butoxyethoxy)phenyl]-N-[4-[4-[2-(4-propyl-4H-1,2,4-triazol-3-yl)ethyl]phenyl]-1-propyl-2,3-dihydro-1H-benzazepine-4-carboxamide (Compound 153) (378.3 mg) as yellow amorphous.

$^1$H-NMR (200 MHz, CDCl$_3$) δ 0.90 (3H, t, J=7.2 Hz), 0.93 (3H, t, J=7.4 Hz), 0.99 (3H, t, J=7.4 Hz), 1.28 to 1.48 (2H, m), 1.54 to 1.81 (6H, m), 2.86 to 3.03 (4H, m), 3.10 to 3.22 (2H, m), 3.24 to 3.39 (4H, m), 3.55 (2H, t, J=6.6 Hz), 3.65 (2H, t, J=7.3 Hz), 3.80 (2H, t, J=5.0 Hz), 4.16 (2H, t, J=5.0 Hz), 6.90 (1H, d, J=8.8 Hz), 6.98 (2H, d, J=8.8 Hz), 7.17 (2H, d, J=8.8 Hz), 7.35 to 7.54 (7H, m), 7.62 (1H, s), 8.03 (1H, s).

IR (KBr) 3260, 1655, 1605, 1516, 1499, 1454, 1408, 1316, 1244, 1179, 1123, 1067, 818 cm$^{-1}$

Elemental Analysis for C$_{39}$H$_{49}$N$_5$O$_3$.0.5H$_2$O Calcd. C, 72.64; H, 7.82; N, 10.86. Found: C, 72.70; H, 7.74; N, 10.74.

Example 145

(Preparation of Compound 154)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.20 ml) and DMF (1 droplet) at room temperature and the mixture was stirred for 1 hour. The reaction mixture was concentrated under reduced pressure, and a solution of the residue in THF (20 ml) was added dropwise to a solution of 4-[2-(4-aminophenylthio)ethyl]-4H-1,2,4-triazole (0.44 g) in pyridine (20 ml) at 1° C. The mixture was stirred at room temperature for 2 days, water was added to the mixture and the mixture was extracted with ethyl acetate. The organic layer was washed with saturated brine, dried over magnesium sulfate and concentrated under reduced pressure. The obtained residue was separated and purified by column chromatography (ethyl acetate→ethanol:ethyl acetate 1:4→1:3), to give 7-[4-(2-butoxyethoxy)phenyl]-N-[4-(4H-1,2,4-triazol-4-ylethylthio)phenyl]-1-isobutyl-2,3-dihydro-1H-benzazepine-4-carboxamide (Compound 154) (1.06 g) as yellow amorphous.

$^1$H-NMR (200 MHz, CDCl$_6$) δ 0.93 (3H, t, J=7.1 Hz), 0.97 (6H, d, J=6.6 Hz), 1.28 to 1.48 (2H, m), 1.51 to 1.67 (2H, m), 1.92 to 2.18 (1H, m), 2.86 to 2.96 (2H, m), 3.15 to 3.22 (4H, m), 3.31 to 3.41 (2H, m), 3.55 (2H, t, J=6.6 Hz), 3.80 (2H, t, J=5.0 Hz), 4.10 to 4.19 (4H, m), 6.92 (1H, d, J=8.8 Hz), 6.98 (2H, d, J=8.8 Hz), 7.35 to 7.50 (7H, m), 7.61 (2H, d, J=8.4 Hz), 7.73 (1H, s), 8.15 (2H, s).

IR (KBr) 3092, 1659, 1607, 1497, 1456, 1395, 1310, 1285, 1242, 1182, 1123, 1071, 818 cm$^{-1}$

Elemental Analysis for C$_{37}$H$_{45}$N$_5$O$_3$S.0.25H$_2$O Calcd. C, 68.97; H, 7.12; N, 10.87. Found: C, 68.94; H, 7.12; N, 11.03.

Example 146

(Preparation of Compound 155)

To a solution of 7-[4-(2-butoxyethoxy)phenyl]-N-[4-(4H-1,2,4-triazol-4-ylethylthio)phenyl]-1-isobutyl-2,3-dihydro-1H-benzazepine-4-carboxamide (0.80 g) in dichloromethane (20 ml) was added dropwise a solution of 3-chloroperbenzoic acid (70%, 0.37 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethanol:ethyl acetate 1:20→1:19), and was recrystallized from ethyl acetate, to give 7-[4-(2-butoxyethoxy)phenyl]-N-[4-(4H-1,2,4-triazol-4-ylethylsulfinyl)phenyl]-1-isobutyl-2,3-dihydro-1H-benzazepine-4-carboxamide (Compound 155) (681.4 mg) as yellow crystals.

m.p. 168 to 170° C.

$^1$H-NMR (200 MHz, CDCl$_3$) δ 0.92 (3H, t, J=7.4 Hz), 0.97 (6H, d, J=6.2 Hz), 1.25 to 1.48 (2H, m), 1.53 to 1.68 (2H, m), 1.95 to 2.19 (1H, m), 2.86 to 2.95 (2H, m), 2.97 to 3.41 (6H, m), 3.55 (2H, t, J=6.6 Hz), 3.80 (2H, t, J=4.9 Hz), 4.15 (2H, t, J=4.9 Hz), 4.22 to 4.37 (1H, m), 4.47 to 4.61

(1H, m), 6.90 to 6.99 (3H, m), 7.38 to 7.57 (7H, m), 7.83 (2H, d, J=8.6 Hz), 8.06 (1H, s), 8.17 (2H, s).

IR (KBr) 3225, 1663, 1605, 1590, 1534, 1501, 1316, 1246, 1182, 1040, 828 cm$^{-1}$

Elemental Analysis for $C_{37}H_{45}N_5O_4S$ Calcd. C, 67.76; H, 6.92; N, 10.68. Found: C, 67.49; H, 6.89; N, 10.51.

Example 147

(Preparation of Compound 156)

To a solution of 7-[4-(2-butoxyethoxy)phenyl]-1-propyl-2,3-dihydro-1H-benzazepine-4-carboxylic acid (1.0 g) in THF (10 ml) were added thionyl chloride (0.26 ml) and DMF (1 droplet) at room temperature and the mixture was stirred for 1 hour. The reaction mixture was concentrated under reduced pressure, and a solution of the residue in THF (30 ml) was added dropwise to a solution of 4-[2-(4-aminophenylthio)ethyl]-4H-1,2,4-triazole (0.57 g) in pyridine (20 ml) at 0° C. The mixture was stirred at room temperature for 18 hours, water was added to the mixture and the mixture was extracted with ethyl acetate. The organic layer was washed with saturated brine, dried over magnesium sulfate and concentrated under reduced pressure. The obtained residue was separated and purified by column chromatography (ethyl acetate→ethanol:ethyl acetate 1:5→1:3), and was further recrystallized from ethyl acetate-hexane, to give 7-[4-(2-butoxyethoxy)phenyl]-N-[4-(4H-1,2,4-triazol-4-ylethylthio)phenyl]-1-propyl-2,3-dihydro-1H-benzazepine-4-carboxamide (Compound 156) (1.34 g) as yellow crystals.

m.p. 114 to 115° C.

$^1$H-NMR (200 MHz, CDCl$_3$) δ 0.93 (3H, t, J=7.2 Hz), 1.00 (3H, t, J=7.4 Hz), 1.31 to 1.45 (2H, m), 1.52 to 1.84 (4H, m), 2.87 to 2.96 (2H, m), 3.20 (2H, t, J=6.6 Hz), 3.26 to 3.40 (4H, m), 3.55 (2H, t, J=6.6 Hz), 3.81 (2H, t, J=5.0 Hz), 4.14 (4H, m), 6.91 (1H, d, J=8.8 Hz), 6.98 (2H, d, J=8.8 Hz), 7.36 to 7.49 (7H, m), 7.57 to 7.62 (3H, m), 8.16 (2H, s).

IR (KBr) 3243, 1647, 1609, 1591, 1526, 1501, 1397, 1319, 1275, 1246, 1182, 1123, 808 cm$^{-1}$

Elemental Analysis for $C_{36}H_{43}N_5O_3S.0.5H_2O$ Calcd. C, 68.11; H, 6.99; N, 11.03. Found: C, 67.98; H, 7.07; N, 10.95.

Example 148

(Preparation of Compound 157)

To a solution of 7-[4-(2-butoxyethoxy)phenyl]-N-[4-(4H-1,2,4-triazol-4-ylethylthio)phenyl]-1-propyl-2,3-dihydro-1H-benzazepine-4-carboxamide (1.0 g) in dichloromethane (20 ml) was added dropwise a solution of 3-chloroperbenzoic acid (70%, 0.43 g) in dichloromethane (10 ml) at −78° C., and the mixture was stirred for 1 hour at −78° C. To the reaction solution was added sodium thiosulfate solution at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethanol:ethyl acetate 1:20→1:9), to give 7-[4-(2-butoxyethoxy)phenyl]-N-[4-(4H-1,2,4-triazol-4-ylethylsulfinyl)phenyl]-1-propyl-2,3-dihydro-1H-benzazepine-4-carboxamide (Compound 157) (0.90 g) as yellow amorphous.

$^1$H-NMR (200 MHz, CDCl$_3$) δ 0.93 (3H, t, J=7.0 Hz), 0.99 (3H, t, J=7.2 Hz), 1.29 to 1.47 (2H, m), 1.52 to 1.86 (4H, m), 2.84 to 2.95 (2H, m), 2.98 to 3.39 (6H, m), 3.55 (2H, t, J=6.6 Hz), 3.80 (2H, t, J=4.9 Hz), 4.15 (2H, t, J=4.9 Hz), 4.21 to 4.36 (1H, m), 4.46 to 4.61 (1H, m), 6.90 (1H, d, J=8.8 Hz), 6.97 (2H, d, J=8.8 Hz), 7.39 to 7.55 (7H, m), 7.82 (2H, d, J=8.8 Hz), 8.09 (1H, s), 8.16 (2H, s).

IR (KBr) 3112, 1661, 1607, 1588, 1516, 1499, 1397, 1312, 1242, 1181, 1046, 836 cm$^{-1}$

Elemental Analysis for $C_{36}H_{43}N_5O_4S.0.5H_2$ Calcd. C, 66.44; H, 6.81; N, 10.76. Found: C, 66.34; H, 6.80; N, 10.62.

Example 149

(Preparation of Compound 158)

To a solution of 7-[4-(2-butoxyethoxy)phenyl]-1-isobutyl-2,3-dihydro-1H-benzazepine-4-carboxylic acid (0.50 g) in THF (10 ml) were added thionyl chloride (0.13 ml) and DMF (1 droplet) at room temperature and the mixture was stirred for 1.5 hours. The reaction mixture was contcentrated under reduced pressure, and a solution of the residue in THF (20 ml) was added dropwise to a solution of 3-[(4-aminobenzyl)methylamino]-4-propyl-4H-1,2,4-triazole (0.34 g) in pyridine (10 ml) at 0° C. The mixture was stirred at room temperature for 18 hours, water was added to the mixture and the mixture was extracted with ethyl acetate. The organic layer was washed with saturated brine, dried over magnesium sulfate and concentrated under reduced pressure. The obtained residue was separated and purified by column chromatography (ethyl acetate→ethanol:ethyl acetate 1:4), to give 7-[4-(2-butoxyethoxy)phenyl]-1-isobutyl-N-[4-[methyl(4-n-propyl-4H-1,2,4-triazol-3-yl)aminomethyl]phenyl]-2,3-dihydro-1H-benzazepine-4-carboxamide (Compound 158) (243 mg) as yellow amorphous.

$^1$H-NMR (200 MHz, CDCl$_3$) δ 0.90 to 0.99 (12H, m), 1.29 to 1.50 (2H, m), 1.52 to 1.68 (2H, m), 1.71 to 1.90 (2H, m), 1.97 to 2.18 (1H, m), 2.77 (3H, s), 2.87 to 2.96 (2H, m), 3.19 (2H, d, J=7.4 Hz), 3.30 to 3.42 (2H, m), 3.55 (2H, d, J=6.6 Hz), 3.71 to 3.83 (4H, m), 4.16 (2H, t, J=4.9 Hz), 4.24 (2H, s), 6.92 (1H, d, J=8.8 Hz), 6.98 (2H, d, J=8.8 Hz), 7.27 to 7.50 (7H, m), 7.58 (2H, d, J=8.6 Hz), 7.66 (1H, s), 7.93 (1H, s).

IR (KBr) 3163, 1657, 1603, 1516, 1499, 1406, 1314, 1244, 1181, 1119, 816 cm$^{-1}$

Elemental Analysis for $C_{40}H_{52}N_6O_3.0.25H_2O$ Calcd. C, 71.77; H, 7.91; N, 12.55. Found: C, 71.66; H, 7.91; N, 12.37.

Example 150

(Preparation of Compound 159)

To a solution of 7-[4-(2-butoxyethoxy)phenyl]-1-propyl-2,3-dihydro-1H-benzazepine-4-carboxylic acid (0.48 g) in THF (10 ml) were added thionyl chloride (0.12 ml) and DMF (1 droplet) at room temperature and the mixture was stirred for 1.5 hours. The reaction mixture was concentrated under reduced pressure, and a solution of the residue in THF (20 ml) was added dropwise to a solution of 3-[(4-aminobenzyl)methylamino]-4-propyl-4H-1,2,4-triazole (0.31 g) in pyridine (10 ml) at 0° C. The mixture was stirred at room temperature for 16 hours, water was added to the mixture and the mixture was extracted with ethyl acetate. The organic layer was washed with saturated brine, dried over magnesium sulfate and concentrated under reduced pressure. The obtained residue was separated and purified by column chromatography (ethyl acetate→ethanol:ethyl acetate 1:4), to give 7-[4-(2-butoxyethoxy)phenyl]-N-[4-[methyl(4-n-propyl-4H-1,2,4-triazol-3-yl)aminomethyl]

phenyl]-1-propyl-2,3-dihydro-1H-benzazepine-4-carboxamide (Compound 159) (120 mg) as yellow amorphous.

$^1$H-NMR (200 MHz, CDCl$_3$) δ 0.90 to 1.03 (9H, m), 1.31 to 1.49 (2H, m), 1.51 to 1.85 (6H, m), 2.77 (3H, s), 2.86 to 2.97 (2H, m), 3.25 to 3.39 (4H, m), 3.55 (2H, t, J=6.6 Hz), 3.72 to 3.83 (4H, m), 4.16 (2H, t, J=4.9 Hz), 4.24 (2H, s), 6.90 (1H, d, J=8.4 Hz), 6.98 (2H, d, J=8.8 Hz), 7.29 to 7.55 (7H, m), 7.57 (2H, d, J=8.6 Hz), 7.62 (1H, s), 7.94 (1H, s).

IR (KBr) 3036, 1657, 1605, 1516, 1499, 1454, 1406, 1314, 1244, 1177, 818 cm$^{-1}$

Elemental Analysis for C$_{39}$H$_{50}$N$_6$O$_3$.0.25H$_2$O Calcd. C, 71.48; H, 7.77; N, 12.82. Found: C, 71.29; H, 7.63; N, 12.53.

Example 151

(Preparation of Compound 160)

To a solution of 7-[4-(2-butoxyethoxy)phenyl]-1-isobutyl-N-[4-[[1-methylimidazol-2-yl]sulfanyl]phenyl]-2,3-dihydro-1-benzazepine-4-carboxamide (600 mg) in dichloromethane (15 ml) was added dropwise 70% solution of 3-chloroperbenzoic acid (355 mg) in dichloromethane (15 ml) at −78° C. The reaction vessel was removed from a dry ice-acetone bath, and sodium thiosulfate solution was added to the reaction vessel with strongly stirring. The mixture was allowed to be at room temperature, stirred for 30 minutes, and extracted with ethyl acetate. The organic layer was washed with an aqueous solution of saturated sodium bicarbonate and saturated brine, dried over magnesium sulfate. The solvent was distilled off under reduced pressure and the obtained residue was separated and purified by silica gel column chromatography (ethyl acetate), to give 7-[4-(2-butoxyethoxy)phenyl]-1-isobutyl-N-[4-[[1-methylimidazol-2-yl]sulfinyl]phenyl]-2,3-dihydro-1-benzazepine-4-carboxamide (246 mg) (Compound 160) as yellow amorphous.

$^1$H-NMR (200 MHz, CDCl$_3$) δ 0.89 to 0.98 (9H, m), 1.30 to 1.50 (2H, m), 1.55 to 1.75 (2H, m), 1.95 to 2.15 (1H, m), 2.85 to 2.95 (2H, m), 3.18 (2H, d, J=7.2 Hz), 3.30 to 3.40 (2H, m), 3.55 (2H, t, J=6.6 Hz), 3.63 (3H, s), 3.80 (2H, t, J=4.8 Hz), 4.16 (2H, t, J=4.8 Hz), 6.91 (H, d, J=8.8 Hz), 6.97 (2H, d, J=8.8 Hz), 7.05 (1H, d, J=1.4 Hz), 7.16 to 7.21 (3H, m), 7.37 to 7.53 (7H, m), 7.64 (1H, s).

Elemental Analysis for C$_{37}$H$_{44}$N$_4$O$_4$S Calcd. C, 71.12; H, 7.10; N, 8.97. Found: C, 70.81; H, 7.07; N, 8.89.

Example 152

(Preparation of Compound 161)

To a solution of 7-[4-(2-butoxyethoxy)phenyl]-1-isobutyl-2,3-dihydro-1-benzazepine-4-carboxylic acid (400 mg) in tetrahydrofuran (15 ml) was added one droplet of DMF. Then, thionyl chloride (0.09 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of 4-[(4-methyl-1,2,4-triazol-3-yl)thio]aniline (189 mg) in pyridine (15 ml) at 0° C. under nitrogen atmosphere. After finishing the dropping, the mixture was allowed to be at room temperature under nitrogen atmosphere. The mixture was stirred for 1.5 hours, and water was added to the mixture, and the mixture was extracted with ethyl acetate. The organic layer was washed with saturated brine, and dried over magnesium sulfate. The solvent was distilled off under reduced pressure, and the obtained residue was separated and purified by basic silica gel column chromatography (hexane-ethyl acetate=1:3), to give 7-[4-(2-butoxyethoxy)phenyl]-1-isobutyl-N-[4-[(4-methyl-1,2,4-triazol-3-yl)sulfanyl]phenyl]-2,3-dihydro-1-benzazepine-4-carboxamide (376 mg) (Compound 161) as yellow amorphous.

$^1$H-NMR (200 MHz, CDCl$_3$) δ 0.90 to 0.99 (9H, m), 1.34 to 1.45 (2H, m), 1.50 to 1.70 (2H, m), 1.95 to 2.15 (1H, m), 2.90 to 3.00 (2H, m), 3.20 (2H, d, J=7.2 Hz), 3.30 to 3.45 (2H, m), 3.55 (2H, t, J=6.6 Hz), 3.66 (3H, s), 3.81 (2H, t, J=4.8 Hz), 4.16 (2H, t, J=4.8 Hz), 6.93 (1H, d, J=8.8 Hz), 6.98 (2H, d, J=8.6 Hz), 7.39 to 7.53 (5H, m), 7.67 to 7.76 (3H, m), 7.90 (1H, s), 8.00 (2H, d, J=8.8 Hz).

Elemental Analysis for C$_{36}$H$_{43}$N$_5$O$_3$S.0.25H$_2$O Calcd. C, 68.86; H, 6.95; N, 8.68. Found: C, 68.82; H, 6.98; N, 8.55.

Example 153

(Preparation of Compound 162)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.20 ml) and DMF (1 droplet) at room temperature and the mixture was stirred for 1.5 hours. The reaction mixture was concentrated under reduced pressure, and a solution of the residue in THF (20 ml) was added dropwise to a solution of 3-(4-aminophenylthiomethyl)-2-methylimidazol[1,2-a]pyridine (0.54 g) in pyridine (7 ml) at 0° C. The mixture was stirred at room temperature for 20 hours, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1→ethyl acetate), to give 7-[4-(2-butoxyethoxy)phenyl]-1-isobutyl-N-[4-(2-methylimidazol[1,2-a]pyridin-3-ylmethylthio)phenyl]-2,3-dihydro-1H-benzazepine-4-carboxamide (Compound 162) (1.03 g) as yellow amorphous.

$^1$H-NMR (200 MHz, CDCl$_3$) δ 0.93 (3H, t, J=7.3 Hz), 0.96 (6H, d, J=6.6 Hz), 1.29 to 1.48 (2H, m), 1.52 to 1.69 (2H, m), 1.94 to 2.17 (4H, m), 2.84 to 2.95 (2H, m), 3.18 (2H, d, J=7.2 Hz), 3.32 to 3.37 (2H, m), 3.56 (2H, t, J=6.6 Hz), 3.81 (2H, t, J=5.0 Hz), 4.16 (2H, t, J=5.0 Hz), 4.25 (2H, s), 6.81 to 6.85 (1H, m), 6.90 (1H, d, J=8.8 Hz), 6.97 (2H, d, J=8.8 Hz), 7.12 to 7.23 (3H, m), 7.36 to 7.55 (8H, m), 7.83 (1H, s), 8.00 to 8.06 (1H, m).

IR (KBr) 3032, 1655, 1607, 1586, 1499, 1397, 1350, 1285, 1242, 1179, 912, 818, 743 cm$^{-1}$

Elemental Analysis for C$_{42}$H$_{48}$N$_4$O$_3$S.0.5H$_2$O Calcd. C, 72.28; H, 7.08; N, 8.03. Found: C, 72.45; H, 7.58; N, 7.95.

Example 154

(Preparation of Compound 163)

To a solution of 7-[4-(2-butoxyethoxy)phenyl]-1-isobutyl-N-[4-(2-methylimidazol[1,2-a]pyridin-3-ylmethylthio)phenyl]-2,3-dihydro-1H-benzazepine-4-carboxamide (0.80 g) in dichloromethane (10 ml) was added dropwise a solution of 3-chloroperbenzoic acid (70%, 0.43 g) in dichloromethane (10 ml) at −78° C. The mixture was stirred for 1 hour at −78° C., sodium thiosulfate solution was added to the mixture at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetatehexane 3:1→ethyl acetate), and was recrystallized from ethyl acetate-diisopropylether, to give 7-[4-(2-butoxyethoxy)phenyl]-1-isobutyl-N-[4-(2-methylimidazol[1,2-a]pyridin-3-ylmethylsulfinyl)phenyl]-2,3-dihydro-1H-benzazepine-4-carboxamide (Compound 163) (456.5 mg) as yellow crystals.

m.p. 130 to 133° C.

$^1$H-NMR (200 MHz, CDCl$_3$) δ 0.93 (3H, t, J=7.4 Hz), 0.97 (6H, d, J=6.6 Hz), 1.29 to 1.49 (2H, m), 1.53 to 1.68 (2H, m), 1.90 (3H, s), 1.95 to 2.18 (1H, m), 2.84 to 2.96 (2H, m), 3.19 (2H, d, J=7.0 Hz), 3.30 to 3.40 (2H, m), 3.56 (2H, d, J=6.8 Hz), 3.81 (2H, t, J=4.9 Hz), 4.16 (2H, t, J=4.9 Hz), 4.27 (1H, d, J=14.1 Hz), 4.45 (1H, d, J=14.1 Hz), 6.72 to 6.79 (1H, m), 6.91 (1H, d, J=8.8 Hz), 6.97 (2H, d, J=8.8 Hz), 7.12 to 7.21 (1H, m), 7.31 (1H, s), 7.38 to 7.50 (7H, m), 7.71 (2H, d, H=8.8 Hz), 8.04 (1H, s), 8.07 to 8.11 (1H, m).

IR (KBr) 3032, 1661, 1607, 1588, 1518, 1499, 13797, 1350, 1312, 1244, 1179, 912, 747 cm$^{-1}$

Elemental Analysis for C$_{42}$H$_{48}$N$_4$O$_4$S.0.5H$_2$O Calcd. C, 70.66; H, 6.92; N, 7.85. Found: C, 70.79; H, 6.87; N, 7.78.

Example 155

(Preparation of Compound 164)

To a solution of 7-[4-(2-butoxyethoxy)phenyl]-1-propyl-2,3-dihydro-1H-benzazepine-4-carboxylic acid (0.80 g) in THF (10 ml) were added thionyl chloride (0.21 ml) and DMF (1 droplet) at room temperature and the mixture was stirred for 1.5 hours. The reaction mixture was concentrated under reduced pressure, and a solution of the residue in THF (20 ml) was added dropwise to a solution of 3-(4-aminophenylthiomethyl)-2-methylimidazol[1,2-a]pyridine (0.56 g) in pyridine (7 ml) at 0° C. The mixture was stirred for 3 days at room temperature, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethyl acetate:hexane 2:1→ethyl acetate), to give 7-[4-(2-butoxyethoxy)phenyl]-N-[4-(2-methylimidazol[1,2-a]pyridin-3-ylmethylthio)phenyl]-1-propyl-2,3-dihydro-1H-benzazepine-4-carboxamide (Compound 164) (1.17 g) as yellow amorphous.

$^1$H-NMR (200 MHz, CDCl$_3$) δ 0.93 (3H, t, J=7.2 Hz), 0.99 (3H, t, J=7.5 Hz), 1.28 to 1.48 (2H, m), 1.53 to 1.84 (4H, m), 2.07 (3H, s), 2.84 to 2.93 (2H, m), 3.25 to 3.36 (4H, m), 3.56 (2H, t, J=6.6 Hz), 3.81 (2H, t, J=4.7 Hz), 4.16 (2H, t, J=4.7 Hz), 4.26 (2H, s), 6.81 to 6.95 (2H, m), 6.97 (2H, d, J=8.8 Hz), 7.13 to 7.23 (3H, m), 7.39 to 7.54 (8H, m), 7.72 (1H, s), 8.03 to 8.07 (1H, m).

IR (KBr) 3077, 1659, 1607, 1586, 1499, 1397, 1352, 1308, 1242, 1177, 1119, 818, 737 cm$^{-1}$

Elemental Analysis for C$_{41}$H$_{46}$N$_4$O$_3$S.0.5H$_2$O Calcd. C, 72.00; H, 6.93; N, 8.19. Found: C, 72.18; H, 6.89; N, 8.03.

Example 156

(Preparation of Compound 165)

To a solution of 7-[4-(2-butoxyethoxy)phenyl]-N-[4-(2-methylimidazo[1,2-a]pyridin-3-ylmethylthio)phenyl]-1-propyl-2,3-dihydro-1H-benzazepine-4-carboxamide (0.96 g) in dichloromethane (10 ml) was added dropwise a solution of 3-chloroperbenzoic acid (70%, 0.52 g) in dichloromethane (10 ml) at −78° C. The mixture was stirred for 1 hour at −78° C., sodium thiosulfate solution was added to the mixture at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetate:hexane 3:1→ethyl acetate), and was further recrystallized from ethyl acetate-diisopropylether, to give 7-[4-(2-butoxyethoxy)phenyl]-N-[4-(2-methylimidazo[1,2-a]pyridin-3-ylmethylsulfinyl)phenyl]-1-propyl-2,3-dihydro-1H-benzazepine-4-carboxamide (Compound 165) (663.1 mg) as yellow crystals.

m.p. 134 to 137° C.

$^1$H-NMR (200 MHz, CDCl$_3$) δ 0.93 (3H, t, J=7.2 Hz), 1.00 (3H, t, J=7.3 Hz), 1.28 to 1.49 (2H, m), 1.51 to 1.84 (4H, m), 1.94 (3H, s), 2.86 to 2.96 (2H, m), 3.27 to 3.39 (4H, m), 3.56 (2H, t, J=6.6 Hz), 3.81 (2H, t, J=5.0 Hz), 4.16 (2H, t, J=5.0 Hz), 4.30 (1H, d, J=14.4 Hz), 4.47 (1H, d, J=14.4 Hz), 6.73-6.79 (1H, m), 6.90 (H, d, J=8.8 Hz), 6.98 (2H, d, J=8.8 Hz), 7.13 to 7.21 (1H, m), 7.30 (2H, d, J=8.8 Hz), 7.40 to 7.53 (1H, m), 7.69 (2H, d, J=8.8 Hz), 7.73 to 7.79 (1H, m), 8.09 (1H, d, J=7.0 Hz).

IR (KBr) 3228, 1661, 1607, 1588, 1518, 1499, 1312, 1244, 1179, 1042, 833 cm$^{-1}$

Elemental Analysis for C$_{41}$H$_{46}$N$_4$O$_4$S.0.5H$_2$O Calcd. C, 70.36; H, 6.77; N, 8.00. Found: C, 70.63; H, 6.96; N, 8.06.

Example 157

(Preparation of Compound 166)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.20 ml) and DMF (1 droplet) at room temperature and the mixture was stirred for 1.5 hours. The reaction mixture was concentrated under reduced pressure, and a solution of the residue in THF (20 ml) was added dropwise to a solution of 3-(4-aminophenylthiomethyl)imidazo[1,2-a]pyridine (0.51 g) in pyridine (7 ml) at 0° C. The mixture was stirred at room temperature for 18 hours, water was added to the reaction solution and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1→2:1→ethyl acetate), to give 7-[4-(2-butoxyethoxy)phenyl]-1-isobutyl-N-[4-(imidazo[1,2-a]pyridin-3-ylmethylthio)phenyl]-2,3-dihydro-1H-benzazepine-4-carboxamide (Compound 166) (0.98 g) as yellow amorphous.

$^1$H-NMR (200 MHz, CDCl$_3$) δ 0.93 (3H, t, J=7.3 Hz), 0.97 (6H, d, J=6.6 Hz), 1.30 to 1.47 (2H, m), 1.55 to 1.76 (2H, m), 1.96 to 2.17 (1H, m), 2.84 to 2.96 (2H, m), 3.18 (2H, d, J=7.4 Hz), 3.32 to 3.37 (2H, m), 3.55 (2H, t, J=6.6 Hz), 3.81 (2H, t, J=5.0 Hz), 4.16 (2H, t, J=5.0 Hz), 4.32 (2H, s), 6.86 to 6.93 (2H, m), 6.97 (2H, d, J=8.8 Hz), 7.18 to 7.29 (5H, m), 7.37 to 7.52 (6H, m), 7.58 to 7.64 (1H, m), 7.72 (1H, s), 8.13 to 8.17 (1H, m).

IR (KBr) 3165, 1657, 1607, 1588, 1499, 1310, 1242, 1181, 1128, 741, cm$^{-1}$

Elemental Analysis for C$_{41}$H$_{46}$N$_4$O$_3$S.0.25H$_2$O Calcd. C, 72.48; H, 6.90; N, 8.25. Found: C, 72.36; H, 6.98; N, 8.31.

Example 158

(Preparation of Compound 167)

To a solution of 7-[4-(2-butoxyethoxy)phenyl]-1-isobutyl-N-[4-(imidazo[1,2-a]pyridin-3-ylmethylthio)phenyl]-2, 3-dihydro-1H-benzazepine-4-carboxamide (0.80 g) in dichloromethane (10 ml) was added dropwise a solution of 3-chloroperbenzoic acid (70%, 0.44 g) in dichloromethane (10 ml) at −78° C. The mixture was stirred for 1 hour at −78° C., sodium thiosulfate solution was added to the mixture at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetate:hexane 3:1→ethyl acetate), to give 7-[4-(2-butoxyethoxy)phenyl]-1-isobutyl-N-[4-(imidazo[1,2-a]pyridin-3-ylmethylsulfinyl)phenyl]-2,3-dihydro-1H-benzazepine-4-carboxamide (Compound 167) (642 mg) as yellow amorphous.

$^1$H-NMR (200 MHz, CDCl$_3$) δ 0.93 (3H, t, J=7.3 Hz), 0.97 (6H, d, J=6.6 Hz), 1.29 to 1.48 (2H, m), 1.52 to 1.74 (2H, m), 1.96 to 2.15 (1H, m), 2.88 to 2.98 (2H, m), 3.20 (2H, d, J=7.8 Hz), 3.30 to 3.42 (2H, m), 3.56 (2H, d, J=6.6 Hz), 3.81 (2H, t, J=4.9 Hz), 4.16 (2H, t, J=4.9 Hz), 4.29 (1H, d, J=14.3 Hz), 4.48 (1H, d, J=14.3 Hz), 6.76 to 6.85 (1H, m), 6.92 (1H, d, J=8.8 Hz), 6.98 (2H, d, J=8.8 Hz), 7.13 to 7.23 (2H, m), 7.32 to 7.48 (7H, m), 7.56 to 7.60 (1H, m), 7.71 (2H, d, H=8.8 Hz), 7.92 (1H, s), 8.15-8.18 (1H, m).

IR (KBr) 3088, 1661, 1607, 1588, 1518, 1499, 1397, 1312, 1244, 1179, 1123, 833 cm$^{-1}$

Elemental Analysis for C$_{41}$H$_{46}$N$_4$O$_4$S.0.5H$_2$O Calcd. C, 70.36; H, 6.77; N, 8.00. Found: C, 70.1; H, 6.80; N, 7.94.

Example 159

(Preparation of Compound 168)

To a solution of 7-[4-(2-butoxyethoxy)phenyl]-1-isobutyl-2,3-dihydro-1H-benzazepine-4-carboxylic acid (1.0 g) in THF (10 ml) were added thionyl chloride (0.25 ml) and DMF (1 droplet) at room temperature and the mixture was stirred for 1.5 hours. The reaction mixture was concentrated under reduced pressure, and a solution of the residue in THF (20 ml) was added dropwise to a solution of 5-(4-aminophenylthio)imidazo[1,2-a]pyridine (0.61 g) in pyridine (7 ml) at 0° C. The mixture was stirred at room temperature for 20 hours, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1→ethyl acetate), to give 7-[4-(2-butoxyethoxy)phenyl]-1-isobutyl-N-[4-(imidazo[1,2-a]pyridin-5-ylthio)phenyl]-2,3-dihydro-1H-benzazepine-4-carboxamide (Compound 168) (1.27 g) as yellow amorphous.

$^1$H-NMR (200 MHz, CDCl$_3$) δ 0.93 (3H, t, J=7.3 Hz), 0.96 (6H, d, J=6.6 Hz), 1.30 to 1.48 (2H, m), 1.51 to 1.69 (2H, m), 1.94 to 2.13 (1H, m), 2.86 to 2.96 (2H, m), 3.18 (2H, d, J=7.0 Hz), 3.30 to 3.40 (2H, m), 3.55 (2H, d, J=6.8 Hz), 3.80 (2H, t, J=4.9 Hz), 4.16 (2H, t, J=4.9 Hz), 6.89 to 7.00 (4H, m), 7.12 to 7.20 (1H, m), 7.31 to 7.49 (7H, m), 7.58 to 7.68 (6H, m).

IR (KBr) 3223, 1655, 1609, 1588, 1499, 1397, 1310, 1289, 1244, 1179, 1121, 820 cm$^{-1}$

Elemental Analysis for C$_{40}$H$_{44}$N$_4$O$_3$S.0.25H$_2$O Calcd. C, 72.20; H, 6.74; N, 8.42. Found: C, 72.14; H, 6.67; N, 8.35.

Example 160

(Preparation of Compound 169)

To a solution of 7-[4-(2-butoxyethoxy)phenyl]-1-isobutyl-N-[4-(imidazo[1,2-a]pyridin-5-ylthio)phenyl]-2,3-dihydro-1H-benzazepine-4-carboxamide (1.0 g) in dichloromethane (10 ml) was added dropwise a solution of 3-chloroperbenzoic acid (70%, 0.56 g) in dichloromethane (10 ml) at −78° C. The mixture was stirred for 5 hours at −20° C., sodium thiosulfate solution was added to the mixture at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetate:hexane 1:1→3:1), to give 7-[4-(2-butoxyethoxy)phenyl]-1-isobutyl-N-[4-(imidazo[1,2-a]pyridin-5-ylsulfinyl)phenyl]-2,3-dihydro-1H-benzazepine-4-carboxamide (Compound 169) (259 mg) as yellow crystals.

m.p. 162 to 164° C.

$^1$H-NMR (200 MHz, CDCl$_3$) δ 0.93 (3H, t, J=7.4 Hz), 0.96 (6H, d, J=6.6 Hz), 1.28 to 1.50 (2H, m), 1.52 to 1.70 (2H, m), 1.94 to 2.15 (1H, m), 2.84 to 2.93 (2H, m), 3.18 (2H, d, J=7.4 Hz), 3.28 to 3.39 (2H, m), 3.55 (2H, d, J=6.6 Hz), 3.80 (2H, t, J=5.0 Hz), 4.15 (2H, t, J=5.0 Hz), 6.91 (1H, d, J=8.8 Hz), 6.97 (2H, d, J=8.6 Hz), 7.31 to 7.53 (7H, m), 7.63 to 7.83 (8H, m).

IR (KBr) 3297, 1672, 1609, 1593, 1534, 1497, 1393, 1321, 1289, 1246, 1184, 1140, 138, 820 cm$^{-1}$

Elemental Analysis for C$_{40}$H$_{44}$N$_4$O$_4$S Calcd. C, 70.98; H, 6.55; N, 8.28. Found: C, 70.72; H, 6.26; N, 8.30.

Example 161

(Preparation of Compound 170)

To a solution of 7-[4-(2-butoxyethoxy)phenyl]-1-isobutyl-2,3-dihydro-1H-benzazepine-4-carboxylic acid (0.80 g) in THF (10 ml) were added thionyl chloride (0.20 ml) and DMF (1 droplet) at room temperature and the mixture was stirred for 1.5 hours. The reaction mixture was concentrated under reduced pressure, and a solution of the residue in THF (25 ml) was added dropwise to a solution of 5-(4-aminophenylthio)-2-methylimidazo[1,2-a]pyridine (0.52 g) in pyridine (10 ml) at 0° C. The mixture was stirred at room temperature for 3 days, and water was added to the reaction solution and the mixture was extracted with ethyl acetate. The organic layer was washed with saturated brine, dried over magnesium sulfate and concentrated under reduced pressure. The obtained residue was separated and purified by column chromatography (ethyl acetate:hexane 1:1→ethyl acetate), to give 7-[4-(2-butoxyethoxy)phenyl]-1-isobutyl-N-[4-(2-methylimidazo[1,2-a]pyridin-5-ylthio)phenyl]-2,3-dihydro-1H-benzazepine-4-carboxamide (Compound 170) (574 mg) as yellow crystals.

m.p. 164 to 166° C.

$^1$H-NMR (200 MHz, CDCl$_3$) δ 0.93 (3H, t, J=7.1 Hz), 0.97 (6H, d, J=6.6 Hz), 1.27 to 1.46 (2H, m), 1.51 to 1.67 (2H, m), 1.96 to 2.14 (1H, m), 2.43 (3H, s), 2.85 to 2.94 (2H, m), 3.19 (2H, d, J=7.2 Hz), 3.30 to 3.40 (2H, m), 3.55 (2H, d, J=6.6 Hz), 3.80 (2H, t, J=5.0 Hz), 4.16 (2H, t, J=5.0 Hz), 6.87-6.94 (2H, m), 6.97 (2H, d, J=8.8 Hz), 7.07 to 7.15 (1H, m), 7.30 (2H, d, J=8.8 Hz), 7.38 to 7.62 (10H, m).

IR (KBr) 3274, 1638, 1607, 1586, 1499, 1397, 1314, 1244, 1181, 1121, 814 cm$^{-1}$

Example 162

(Preparation of Compound 171)

To a solution of 7-[4-(2-butoxyethoxy)phenyl]-1-isobutyl-N-[4-(2-methylimidazo[1,2-a]pyridin-5-ylthio)phenyl]-2,3-dihydro-1H-benzazepine-4-carboxamide (0.50 g) in dichloromethane (10 ml) was added dropwise a solution of 3-chloroperbenzoic acid (70%, 0.27 g) in dichloromethane (10 ml) at −78° C. The mixture was stirred at −20° C. for 18 hours, sodium thiosulfate solution was added to the mixture at room temperature and the mixture was stirred for several minutes. The mixture was extracted with ethyl acetate, and the organic layer was washed with sodium bicarbonate solution and saturated brine, dried over magnesium sulfate and concentrated under reduced pressure. The obtained residue was separated and purified by column chromatography (basic silica gel, ethyl acetate:hexane 1:1→2:1), to give 7-[4-(2-butoxyethoxy)phenyl]-1-isobutyl-N-[4-(2-methylimidazo[1,2-a]pyridin-5-ylsulfinyl)phenyl]-2,3-dihydro-1H-benzazepine-4-carboxamide (Compound 171) (110.5 mg) as yellow crystals.

$^1$H-NMR (200 MHz, CDCl$_3$) δ 0.93 (3H, t, J=7.2 Hz), 0.96 (6H, d, J=6.6 Hz), 1.38 to 1.48-(2H, m), 1.51 to 1.67 (2H, m), 1.93 to 2.14 (1H, m), 2.40 (3H, s), 2.83 to 2.92 (2H, m), 3.18 (2H, d, J=7.4 Hz), 3.30 to 3.40 (2H,), 3.55 (2H, t, J=6.6 Hz), 3.80 (2H, t, J=5.0 Hz), 4.15 (2H, t, J=5.0 Hz), 6.91 (1H, d, J=9.2 Hz), 6.97 (2H, d, J=8.8 Hz), 7.26 to 7.34 (1H, m), 7.35 to 7.47 (6H, m), 7.58 to 7.78 (7H, m).

IR (KBr) 3300, 1671, 1609, 1591, 1532, 1499, 1318, 1246, 1184, 1121, 1042, 808 cm$^{-1}$

Elemental Analysis for C$_{41}$H$_{46}$N$_4$O$_4$S.0.25H$_2$O Calcd. C, 70.81; H, 6.74; N, 8.06. Found: C, 70.75; H, 6.53; N, 7.73.

Example 163

(Preparation of Compound 172, Compound 173)

7-[4-(2-butoxyethoxy)phenyl]-N-[4-(4-methyl-4H-1,2,4-triazol-3-ylmethylsulfinyl)phenyl]-1-propyl-2,3-dihydro-1H-1-benzazepine-4-carboxamide (Compound 133) was optically resolved with CHIRALPAK AD(50 mm ID×500 mmL, hexane:ethanol), to give (+)-7-[4-(2-butoxyethoxy)phenyl]-N-[4-(4-methyl-4H-1,2,4-triazol-3-ylmethylsulfinyl)phenyl]-1-propyl-2,3-dihydro-1H-1-benzazepine-4-carboxamide (Compound 172) (141 mg, 99.9% ee) and (−)-7-[4-(2-butoxyethoxy)phenyl]-N-[4-(4-methyl-4H-1,2,4-triazol-3-ylmethylsulfinyl)phenyl]-1-propyl-2,3-dihydro-1H-1-benzazepine-4-carboxamide (Compound 173) (142 mg, 99.9% ee).

Compound 172
[α]$_D$=+137.5° (C=0.504, ethanol solution)
Compound 173
[α]$_D$=−137.9° (C=0.504, ethanol solution)

Example 164

(Preparation of Compound 174, Compound 175)

7-[4-(2-butoxyethoxy)phenyl]-1-isobutyl-N-[4-(4-propyl-4H-1,2,4-triazol-3-ylmethylsulfinyl)phenyl]-2,3-dihydro-1H-1-benzazepine-4-carboxamide (Compound 139) (387 mg) was optically resolved with CHIRALPAK AD(50 mm ID×500 mmL, hexane:ethanol), to give (+)-7-[4-(2-butoxyethoxy)phenyl]-1-isobutyl-N-[4-(4-propyl-4H-1,2,4-triazol-3-ylmethylsulfinyl)phenyl]-2,3-dihydro-1H-1-benzazepine-4-carboxamide (Compound 174) (170 mg, 99.9% ee) and (−)-7-[4-(2-butoxyethoxy)phenyl]-1-isobutyl-N-[4-(4-propyl-4H-1,2,4-triazol-3-ylmethylsulfinyl)phenyl]-2,3-dihydro-1H-1-benzazepine-4-carboxamide (Compound 175) (171 mg, 99.9% ee).

Compound 174
[α]$_D$=+146.6° (C=0.498, ethanol solution)
Compound 175
[α]$_D$=−147.0° (C=0.506, ethanol solution)

Example 165

(Preparation of Compound 176, Compound 177)

7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide (Compound 141) was optically resolved with CHIRALPAK AD(50 mm ID×500 mmL, hexane:ethanol), to give (+)-7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide (Compound 176) (6.61 g, 99.9% ee) and (−)-7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide (Compound 177) (6.85 g, 99.8% ee).

Compound 176
[α]$_D$=+141.8° (C=0.495, ethanol solution)
Compound 177
[α]$_D$=−140.8° (C=0.504, ethanol solution)

Example 166

(Preparation of Compound 178, Compound 179)

7-[4-(2-butoxyethoxy)phenyl]-N-[4-(4-n-butyl-4H-1,2,4-triazol-3-ylmethylsulfinyl)phenyl]-1-isobutyl-2,3-dihydro-1H-1-benzazepine-4-carboxamide (Compound 143) was optically resolved with CHIRALPAK AD(50 mm ID×500 mmL, hexane:ethanol), to give (+)-7-[4-(2-butoxyethoxy)phenyl]-N-[4-(4-n-butyl-4H-1,2,4-triazol-3-ylmethylsulfinyl)phenyl]-1-isobutyl-2,3-dihydro-1H-1-benzazepine-4-carboxamide (Compound 178) (220 mg, 99.9% ee) and (−)-7-[4-(2-butoxyethoxy)phenyl]-N-[4-(4-n-butyl-4H-1,2,4-triazol-3-ylmethylsulfinyl)phenyl]-1-isobutyl-2,3-dihydro-1H-1-benzazepine-4-carboxamide (Compound 179) (200 mg, 99.8% ee).

Compound 178
[α]$_D$=+133.1° (C=0.504, ethanol solution)
Compound 179
[α]$_D$=−132.4° (C=0.5005, ethanol solution)

Example 167

(Preparation of Compound 180)

7-[4-(2-butoxyethoxy)phenyl]-1-propyl-2,3-dihydro-1-benzazepine-4-carboxylic acid (1.0 g) was dissolved in THF (20 ml), DMF (2 droplets) was added to the solution, thionyl chloride (0.34 ml) was added to the solution, and the solution was stirred at room temperature for 1 hour. The solution was added dropwise to the solution of 4-[(2-pyridinylsulfanyl)methyl]aniline (0.56 g) and triethylamine (1.97 ml) in THF (20 ml) under ice-cooling at room temperature and the mixture was stirred for 2 hours. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[(2-pyridinylsulfanyl)methyl]phenyl]-2,3-dihydro-1-benzazepine-4-carboxamide (Compound 180) (0.56 g).

$^1$H-NMR (200 MHz, CDCl$_3$) δ 0.93 (3H, t, J=6.8 Hz), 0.98(3H, t, J=7.4 Hz), 1.33 to 1.45 (2H, m), 1.54 to 1.80 (4H, m), 2.89 (2H, m), 3.26 to 3.34(4H, m), 3.55 (2H, t, J=6.6 Hz), 3.77 to 3.83 (2H, m), 4.12 to 4.18 (2H, m), 4.41 (2H, s), 6.88 (1H, d, J=8.4 Hz), 6.94 to 7.02 (2H, m), 6.97 (2H, d, J=8.8 Hz), 7.15 (1H, d, J=8.0 Hz), 7.35 to 7.56 (10H, m), 8.45 (1H, d, J=5.2 Hz).

IR (KBr) 3339, 2959, 1642, 1607, 1497, 1412, 1250, 1127, 924, 829 cm$^{-1}$

Example 168

(Preparation of Compound 181)

7-[4-(2-butoxyethoxy)phenyl]-1-propyl-N-[4-[(2-pyridinylsulfanyl)methyl]phenyl]-2,3-dihydro-1-benzazepine-4-carboxamide (0.30 g) was dissolved in methylene chloride (15 ml), m-chloroperbenzoic acid (83 mg) was added to the solution at −30° C., and the mixture was stirred for 1 hour at 0° C. The reaction mixture was added to an aqueous solution of saturated sodium thiosulfate, and extracted with ethyl acetate. The organic layer washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[(2-pyridinylsulfinyl)methyl]phenyl]-2,3-dihydro-1-benzazepine-4-carboxamide (Compound 181) (97 mg).

$^1$H-NMR (200 MHz, CDCl$_3$) δ 0.93 (3H, t, J=7.2 Hz), 0.98 (3H, t, J=7.4 Hz), 1.33 to 1.45 (2H, m), 1.55 to 1.76 (4H, m), 2.89 (2H, m), 3.26 to 3.34 (4H, m), 3.55 (2H, t, J=6.6 Hz), 3.78 (2H, t, J=4.8 Hz), 4.05 (1H, d, J=13.2 Hz), 4.12 to 4.18 (2H, m), 4.34 (H, d, J=13.2 Hz), 6.86 to 6.89 (5H, m), 7.32 to 7.59 (9H, m), 7.70 to 7.76 (2H, m), 8.64 to 8.68 (H, m)

IR (KBr) 2955, 1655, 1607, 1499, 1246, 1181, 1125, 1038 cm$^{-1}$

Example 169

(Preparation of Compound 182)

7-[4-(2-butoxyethoxy)phenyl]-1-propyl-2,3-dihydro-1-benzazepine-4-carboxylic acid (1.0 g) was dissolved in THF (20 ml), DMF (2 droplets) was added to the mixture, and thionyl chloride (0.34 ml) was added to the mixture. The mixture was stirred at room temperature for 1 hour, and the mixture was added dropwise to the solution of 4-(2-pyridinylsulfanyl) aniline (0.53 g) and triethylamine (1.97 ml) in THF (20 ml) under ice-cooling, and the mixture was stirred at room temperature for 2 hours. The reaction solution was added to water, and extracted with ethyl acetate. The organic layer washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-(2-pyridinylsulfanyl)phenyl]-2,3-dihydro-1-benzazepine-4-carboxamide (Compound 182) (0.57 g).

$^1$H-NMR (200 MHz, CDCl$_3$) δ 0.93 (3H, t, J=7.0 Hz), 1.00 (3H, t, J=7.2 Hz), 1.33 to 1.45 (2H, m), 1.57 to 1.77 (4H, m), 2.93 (2H, m), 3.28 to 3.36 (4H, m), 3.51 to 3.59 (2H, m), 3.80 (2H, t, J=4.8 Hz), 4.13 to 4.18 (2H, m), 6.85 (1H, d, J=8.0 Hz), 6.90 (2H, t, J=8.8 Hz), 6.95 to 7.00 (3H, m), 7.40 to 7.50 (6H, m), 7.58 (2H, d, J=8.8 Hz), 7.66 to 7.71 (10H, m), 8.40 to 8.43 (1H, m).

IR (KBr) 3283, 2957, 1651, 1607, 1499, 1242, 1177, 1127, 833, 733 cm$^{-1}$

Example 170

(Preparation of Compound 183)

7-[4-(2-butoxyethoxy)phenyl]-1-propyl-N-[4-(2-pyridinylsulfanyl)phenyl]-2,3-dihydro-1-benzazepine-4-carboxamide (0.15 g) was dissolved in methylene chloride (7.5 ml), m-chloroperbenzoic acid (95 mg) was added to the solution at 0° C., and the mixture was stirred for 15 minutes at 0° C. To the mixture was m-chloroperbenzoic acid (95 mg) was added, and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-(2-pyridinylsulfinyl)phenyl]-2,3-dihydro-1-benzazepine-4-carboxamide (Compound 183) (30 mg).

$^1$H-NMR (200 MHz, CDCl$_3$) δ 0.92 (3H, t, J=7.6 Hz), 0.96 (3H, t, J=7.6 Hz), 1.33 to 1.44 (2H, m), 1.43 to 1.82 (4H, m), 2.85 (2H, m), 3.23 to 3.31 (2H, m), 3.54 (2H, t, J=6.6 Hz), 3.76 to 3.82 (2H, m), 3.76 to 3.82 (2H, m), 4.13 (2H, t, J=6.6 Hz), 6.86 (1H, d, J=8.8 Hz), 6.93 (2H, d, J=8.8 Hz), 7.24 to 8.09 (13H, m), 8.52 (1H, d, J=4.0 Hz)

IR (KBr) 3268, 2957, 1663, 1588, 1499, 1244, 1123, 1036, 824, 735 cm$^{-1}$

Example 171

(Preparation of Compound 184)

7-[4-(2-butoxyethoxy)phenyl]-1-isobutyl-2,3-dihydro-1-benzazepine-4-carboxylic acid (1.0 g) was dissolved in THF (20 ml), DMF (2 droplets) was added to the mixture, oxalyl chloride (0.40 ml) was added to the mixture, and the mixture was stirred at room temperature for 1 hour. The solvent was removed under reduced pressure, and a solution of the obtained residue in THF (20 ml) was added dropwise to a solution of 4-[(2-pyridinylsulfanyl)methyl]aniline (0.54 g) and triethylamine (1.91 ml) in THF (16.2 ml) under ice-cooling and the mixture was stirred for 1 hour at room temperature. The reaction solution was added to water, and extracted with ethyl acetate. The organic layer washed with saturated brine, and dried over magnesium sulfate. The solvent was removed under reduced pressure, and the obtained residue washed with hexane/ethyl acetate, to give 7-[4-(2-butoxyethoxy)phenyl]-1-isobutyl-N-[4-[(2-pyridinylsulfanyl)methyl]phenyl]-2,3-dihydro-1-benzazepine-4-carboxamide (Compound 184) (0.65 g).

$^1$H-NMR (200 MHz, CDCl$_3$) δ 0.93 (3H, t, J=7.0 Hz), 0.96 (6H, t, J=6.6 Hz), 1.33 to 1.44 (2H, m), 1.54 to 1.69 (2H, m), 2.06 (1H, m), 2.90 (2H, m), 3.18 (2H, d, J=7.4 Hz), 3.32 to 3.37 (2H, m), 3.55 (2H, t, J=6.6 Hz), 3.80 (2H, t, J=4.6 Hz), 4.41 (2H, s), 6.91 (1H, d, J=8.8 Hz), 6.95 to 7.02 (3H, m), 7.15 (1H, d, J=8.0 Hz), 7.36 to 7.54 (11H, m), 8.44 to 8.47 (1H, m).

Elemental Analysis for C$_{39}$H$_{45}$N$_3$O$_3$S Cald. C, 73.67; N, 6.61; H, 7.13. Found: C, 73.50; N, 6.60; H, 7.09

Example 172

(Preparation of Compound 185)

7-[4-(2-butoxyethoxy)phenyl]-1-isobutyl-N-[4-[(2-pyridinylsulfanyl)methyl]phenyl]-2,3-dihydro-1-benzazepine-4-carboxamide (0.40 g) was dissolved in methylene chloride (12 ml), and m-chloroperbenzoic acid (217 mg) was added to the solution at 0° C., and the mixture was stirred at 0° C. for 20 minutes. The reaction mixture was added to an aqueous solution of saturated sodium thiosulfate, and extracted with ethyl acetate. The organic layer washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[(2-pyridinylsulfinyl)methyl]phenyl]-2,3-dihydro-1-benzazepine-4-carboxamide (Compound 185) (70 mg).

$^1$H-NMR (200 MHz, CDCl$_3$) δ 0.93 (3H, t, J=7.2 Hz), 0.97 (6H, t, J=6.6 Hz), 1.26 to 1.49 (2H, m), 1.54 to 1.69 (2H, m), 2.06 (1H, m), 2.90 (2H, m), 3.18 (2H, d, J=7.4 Hz), 3.35 (2H, m), 3.55 (2H, t, J=6.6 Hz), 3.80 (2H, t, J=4.8 Hz), 4.07 (1H, d, J=13.2 Hz), 4.16 (2H, t, J=4.6 Hz), 4.35 (1H, d, J=13.0 Hz), 6.89 (1H, m), 6.91 (2H, d, J=8.8 Hz), 6.96 (2H, d, J=8.8 Hz), 7.31 to 7.60 (10H, m), 7.78 (1H, td, J=7.8, 1.6 Hz), 8.66 to 8.69 (1H, m).

Example 173

(Preparation of Compound 186)

7-[4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.21 ml) was added to the mixture, and the mixture was stirred at room temperature for 1 hour. The solvent was removed under reduced pressure, and a solution of the obtained residue in THF (14 ml) was added dropwise to a solution of 4-(benzenesulfanylmethyl) aniline (0.36 g) and triethylamine (1.34 ml) in THF (10.7 ml) under ice-cooling and the mixture was stirred at room temperature for 2 hours. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give N-[4-(benzenesulfanylmethyl)phenyl]-7-[4-(2-butoxyethoxy)phenyl]-1-isobutyl-2,3-dihydro-1-benzazepine-4-carboxamide (Compound 186) (0.42 g).

$^1$H-NMR (200 MHz, CDCl$_3$) δ 0.93 (3H, t, J=7.0 Hz), 0.97 (6H, d, J=6.6 Hz), 1.33 to 1.45 (2H, m), 1.44 to 1.67 (2H, m), 2.06 (1H, m), 2.90 (2H, m), 3.18 (2H, d, J=7.4 Hz), 3.32 to 3.38 (2H, m), 3.55 (2H, t, J=6.6 Hz), 3.77 to 3.83 (2H, m), 4.10 (2H, m), 4.12 to 4.18 (2H, m), 6.88 to 7.00 (5H, m), 7.14 to 7.31 (8H, m), 7.36 to 7.56 (5H, m)

Example 174

(Preparation of Compound 187)

N-[4-(benzenesulfanylmethyl)phenyl]-7-[4-(2-butoxyethoxy)phenyl]-1-isobutyl-2,3-dihydro-1-benzazepine-4-carboxamide (0.35 g) was dissolved in methylene chloride (10.5 ml), m-chloroperbenzoic acid (99 mg) was added to the mixture at 0° C., and the mixture was stirred at 0° C. for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, and recrystallized from ethyl acetate, to give N-[4-(benzenesulfinylmethyl)phenyl]-7-[4-(2-butoxyethoxy)phenyl]-1-isobutyl-2,3-dihydro-1-benzazepine-4-carboxamide (Compound 187) (164 mg).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.65 (2H, m), 2.06 (1H, m), 2.90 (2H, m), 3.18 (2H, d, J=5.6 Hz), 3.20 to 3.37 (2H, m), 3.55 (2H, t, J=6.6 Hz), 3.78 to 3.83 (2H, m), 4.02 (2H, d, J=5.2 Hz), 4.13 to 4.18 (2H, m), 6.89 to 7.00 (5H, m), 7.37 to 7.53 (12H, m), 7.56 (1H, s).

IR (KBr) 3337, 2955, 1644, 1609, 1499, 1242, 1040, 831 cm$^{-1}$

Elemental Analysis for C$_{40}$H$_{46}$N$_2$O$_4$S Cald. C, 73.81; N, 4.30; H, 7.12. Found: C, 73.60; N, 4.06; H, 7.21

Example 175

(Preparation of Compound 188)

7-[4-(2-butoxyethoxy)phenyl]-1-isobutyl-2,3-dihydro-1-benzazepine-4-carboxylic acid (1.0 g) was dissolved in THF (20 ml), DMF (2 droplets) was added to the mixture, oxalyl chloride (0.30 ml) was added to the mixture, and the mixture was stirred for 1 hour at room temperature. The solvent was removed under reduced pressure, and a solution of the obtained residue in THF (20 ml) was added dropwise to a solution of 4-[(2-pyrimidinylsulfanyl)methyl]aniline (0.55 g) and triethylamine (1.91 ml) in THF (16.5 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyrimidylsulfanyl)methyl]phenyl]-2,3-dihydro-1-benzazepine-4-carboxamide (Compound 188) (0.30 g).

$^1$H-NMR (200 MHz, CDCl$_3$) δ 0.93 (3H, t, J=7.0 Hz), 0.96 (6H, d, J=6.6 Hz), 1.33 to 1.45 (2H, m), 1.54 to 1.65 (2H, m), 2.06 (1H, m), 2.90 (2H, m), 3.18 (2H, d, J=7.2 Hz), 3.35 (2H, m), 3.55 (2H, t, J=6.6 Hz), 3.77 to 3.83 (2H, m), 4.12 to 4.18 (2H, m), 4.40 (2H, s), 6.89 to 7.00 (4H, m), 7.36 to 7.56 (10H, m), 8.53 (2H, d, J=5.0 Hz).

Example 176

(Preparation of Compound 189)

7-[4-(2-butoxyethoxy)phenyl]-1-isobutyl-N-[4-[(2-pyrimidylsulfanyl)methyl]phenyl]-2,3-dihydro-1-benzazepine-4-carboxamide (0.23 g) was dissolved in methylene chloride (7.5 ml), m-chloroperbenzoic acid (68 mg) was added to the mixture at 0° C., and the mixture was stirred for 15 minutes at 0° C. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyrimidylsulfinyl)methyl]phenyl]-2,3-dihydro-1-benzazepine-4-carboxamide (Compound 189) (90 mg).

$^1$H-NMR (200 MHz, CDCl$_3$) δ 0.93 (3H, t, J=7.4 Hz), 0.96 (6H, d, J=6.6 Hz), 1.33 to 1.47 (2H, m), 1.55 to 1.69 (2H, m), 2.04 (1H, m), 2.89 (2H, m), 3.17 (2H, d, J=7.4 Hz), 3.30 to 3.36 (2H, m), 3.55 (2H, t, J=6.6 Hz), 3.80 (2H, t, J=4.8 Hz), 4.13 to 4.18 (2H, m), 4.22 (1H, d, J=13.2 Hz), 4.37 (1H, d, J=13.2 Hz), 6.89 (1H, d, J=8.8 Hz), 6.97 (2H, d, J=8.8 Hz), 7.07 (2H, d, J=8.4 Hz), 7.31 to 7.55 (8H, m), 7.82 (1H, s), 8.79 (2H, d, J=4.8 Hz).

IR (KBr) 3293, 2957, 1653, 1607, 1499, 1381, 1181, 1065, 816 cm$^{-1}$

Example 177

(Preparation of Compound 190)

7-[4-(2-butoxyethoxy)phenyl]-1-isobutyl-2,3-dihydro-1-benzazepine-4-carboxylic acid (1.0 g) was dissolved in THF (20 ml), DMF (2 droplets) was added to the mixture, oxalyl chloride (0.40 ml) was added to the mixture, and the mixture was stirred for 1 hour at room temperature. The solvent was removed under reduced pressure, and a solution of the obtained residue in THF (20 ml) was added dropwise to a solution of 4-[[[5-(trifluoromethyl)-2-pyridinyl]sulfanyl]methyl]aniline (0.68 g) and triethylamine (1.91 ml) in THF (20.4 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[[5-(trifluoromethyl)-2-pyridinyl]sulfanyl]methyl]phenyl]-2,3-dihydro-1-benzazepine-4-carboxamide (Compound 0.190) (1.08 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.68 (2H, m), 2.06 (1H, m), 2.90 (2H, m), 3.18 (2H, d, J=7.2 Hz), 3.32 to 3.37 (2H, m), 3.55 (2H, t, J=6.6 Hz), 3.80 (2H, t, J=4.8 Hz), 4.15 (2H, t, J=4.8 Hz), 4.45 (2H, s), 6.91 (1H, d, J=8.8 Hz), 6.97 (2H, d, J=8.8 Hz), 7.22 to 7.26 (1H, m), 7.37 to 7.56 (10H, m), 7.66 (1H, dd, J=8.0, 2.2 Hz), 8.69(1H, s).

Example 178

(Preparation of Compound 191)

7-[4-(2-butoxyethoxy)phenyl]-1-isobutyl-N-[4-[[[5-(trifluoromethyl)-2-pyridinyl]sulfanyl]methyl]phenyl]-2,3-dihydro-1-benzazepine-4-carboxamide (0.51 g) was dissolved in methylene chloride (20.4 ml), m-chloroperbenzoic acid (125 mg) was added to the mixture at 0° C., and the mixture was stirred at 0° C. for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[[5-(trifluoromethyl)-2-pyridinyl]sulfinyl]methyl]phenyl]-2,3-dihydro-1-benzazepine-4-carboxamide (Compound 191) (136 mg).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.48 to 1.65 (2H, m), 2.06 (1H, m), 2.91 (2H, m), 3.18 (2H, d, J=7.0 Hz), 3.35 (2H, m), 3.55 (2H, t, J=6.6 Hz), 3.81 (2H, t, J=4.8 Hz), 4.09 (1H, d, J=13.4 Hz), 4.13 to 4.18 (2H, m), 4.04 (1H, d, J=13.2 Hz), 6.88 to 7.00 (3H, m), 6.99 (2H, d, J=8.8 Hz), 7.37 to 7.33 (7H, m), 7.63 (1H, s), 7.75 (H, d, J=8.0 Hz), 8.02 (1H, m), 8.92 to 8.94 (H, m).

Example 179

(Preparation of Compound 192)

7-[4-(2-butoxyethoxy)phenyl]-1-propyl-2,3-dihydro-1-benzazepine-4-carboxylic acid (0.80 g) was dissolved in THF (16 ml), DMF (2 droplets) was added to the mixture, oxalyl chloride (0.25 ml) was added to the mixture, and the mixture was stirred for 1 hour at room temperature. The solvent was removed under reduced pressure, and a solution of the obtained residue in THF (16 ml) was added dropwise to a solution of 4-[(2-pyridinylmethyl)sulfanyl]aniline (0.45 g) and triethylamine (2.1 ml) in THF (13.5 ml) under ice-cooling and the mixture was stirred for 1 hour at room temperature. The reaction solution was added to water, and extracted with ethyl acetate. The organic layer was washed with saturated brine, and dried over magnesium sulfate. The solvent was removed under reduced pressure, and the obtained residue was washed with hexane/ethyl acetate, to give 7-[4-(2-butoxyethoxy)phenyl]-1-propyl-N-[4-[(2-pyridinylmethyl)sulfanyl]phenyl]-2,3-dihydro-1-benzazepine-4-carboxamide (Compound 192) (0.68 g).

$^1$H-NMR (200 MHz, CDCl$_3$) δ 0.93 (3H, t, J=7.4 Hz), 0.98 (3H, t, J=6.8 Hz), 1.33 to 1.45 (2H, m), 1.57 to 1.76 (4H, m), 2.88 (2H, m), 3.26 to 3.35 (4H, m), 3.51 to 3.58 (2H, m), 3.77 to 3.83 (2H, m), 4.12 to 4.18 (2H, m), 4.21 (2H, s), 6.89 (H, d, J=8.8 Hz), 6.97 (2H, d, J=8.8 Hz), 7.14 to 7.60 (13H, m), 8.51 to 8.55 (1H, m).

Example 180

(Preparation of Compound 193)

7-[4-(2-butoxyethoxy)phenyl]-1-propyl-N-[4-[(2-pyridinylmethyl)sulfanyl]phenyl]-2,3-dihydro-1-benzazepine-4-carboxamide (0.40 g) was dissolved in methylene chloride (12 ml), m-chloroperbenzoic acid (111 mg) was added to the mixture at 0° C., and the mixture was stirred for 20 minutes at 0° C. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[(2-pyridinylmethyl)sulfinyl]phenyl]-2,3-dihydro-1-benzazepine-4-carboxamide (Compound 193) (181 mg).

$^1$H-NMR (200 MHz, CDCl$_3$) δ 0.93 (3H, t, J=7.0 Hz), 0.99 (3H, t, J=7.0 Hz), 1.33 to 1.45 (2H, m), 1.57 to 1.76 (4H, m), 2.90 (2H, m), 3.27 to 3.35 (4H, m), 3.55 (2H, t, J=6.6 Hz), 3.80 (2H, t, J=4.8 Hz), 4.13 (1H, d, J=12.2 Hz), 4.15 (2H, m), 4.25 (1H, d, J=12.2 Hz), 6.89 (1H, d, J=8.8 Hz), 6.97 (2H, d, J=8.8 Hz), 7.12 to 7.25 (2H, m), 7.38 to 7.49 (7H, m), 7.61 (1H, td, J=7.6, 1.8 Hz), 7.71 (2H, d, J=8.8 Hz), 7.90 (1H, s).

IR (KBr) 3312, 2932, 2870, 1655, 1615, 1503, 1246, 1181, 1036, 824 cm$^{-1}$

Elemental Analysis for C$_{31}$H$_{43}$N$_3$O$_4$S Cald. C, 71.56; N, 6.59; H, 6.80. Found: C, 71.38; N, 6.44; H, 7.06

Example 181

(Preparation of Compound 194)

7-[4-(2-butoxyethoxy)phenyl]-1-isobutyl-2,3-dihydro-1-benzazepine-4-carboxylic acid (1.2 g) was dissolved in THF (24 ml), DMF (2 droplets) was added to the mixture, oxalyl chloride (0.48 ml) was added to the mixture, and the mixture was stirred for 1 hour at room temperature. The solvent was removed under reduced pressure, and a solution of the obtained residue in THF (24 ml) was added dropwise to a solution of 4-[(2-pyridinylmethyl)sulfanyl]aniline (0.65 g) and triethylamine (2.3 ml) in THF (19.5 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyridinylmethyl)sulfanyl]phenyl]-2,3-dihydro-1-benzazepine-4-carboxamide (Compound 194) (0.98 g).

$^1$H-NMR (200 MHz, CDCl$_3$) δ 0.93 (3H, t, J=7.2 Hz), 0.96 (6H, d, J=6.6 Hz), 1.33 to 1.45 (2H, m), 1.57 to 1.68 (2H, m), 2.05 (1H, m), 2.89 (2H, m), 3.17 (2H, d, J=7.4 Hz), 3.31 to 3.36 (2H, m), 3.55 (2H, t, J=6.2 Hz), 3.80 (2H, t, J=4.8 Hz), 4.15 (2H, t, J=4.8 Hz), 4.21 (2H, s), 6.91 (1H, d, J=8.8 Hz), 6.97 (2H, d, J=8.8 Hz), 7.10 to 7.17 (1H, m), 7.22 to 7.63 (13H, m), 8.51 to 8.54 (1H, m).

Elemental Analysis for C$_{39}$H$_{45}$N$_3$O$_3$S Cald. C, 73.67; N, 6.61; H, 7.13. Found: C, 73.78; N, 6.62; H, 7.37

Example 182

(Preparation of Compound 195 and Compound 196)

7-[4-(2-butoxyethoxy)phenyl]-1-isobutyl-N-[4-[(2-pyridinylmethyl)sulfanyl]phenyl]-2,3-dihydro-1-benzazepine-4-carboxamide (0.85 g) was dissolved in methylene chloride (25.5 ml), m-chloroperbenzoic acid (277 mg) was added to the mixture at 0° C., and the mixture was stirred for 90 minutes at 0° C. M-chloroperbenzoic acid (230 mg) was further added to the mixture, and the mixture was stirred at 0° C. for 30 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyridinylmethyl)sulfinyl]phenyl]-2,3-dihydro-1-benzazepine-4-carboxamide (Compound 195) (300 mg) and 7-[4-(2-butoxyethoxy)phenyl]-1-isobutyl-N-[4-[(2-pyridinylmethyl)sulfonyl]phenyl]-2,3-dihydro-1-benzazepine-4-carboxamide (Compound 196) (150 mg).

Compound 195: $^1$H-NMR (200 MHz, CDCl$_3$) δ 0.93 (3H, t, J=7.2 Hz), 0.97 (6H, d, J=6.2 Hz), 1.33 to 1.45 (2H, m), 1.54 to 1.62 (2H, m), 2.08 (1H, m), 2.92 (2H, m), 3.19 (2H, d, J=7.0 Hz), 3.36 (2H, m), 3.55 (2H, t, J=6.2 Hz), 3.78 to 3.83 (2H, m), 4.13 to 4.19 (2H, m), 4.15 (1H, d, J=12.2 Hz), 4.26 (1H, d, J=12.4 Hz), 6.92 (1H, d, J=8.8 Hz), 6.98 (2H, d, J=8.8 Hz), 7.14 to 7.26 (2H, m), 7.38 to 7.51 (7H, m), 7.63 (1H, td, J=7.6, 1.8 Hz), 7.69 to 7.78 (3H, m), 8.54 to 8.57 (1H, m).

IR (KBr) 3328, 2955, 1645, 1499, 1246, 1042, 829 cm$^{-1}$

Compound 196: $^1$H-NMR (200 MHz, CDCl$_3$) δ 0.93 (3H, t, J=6.8 Hz), 0.97 (6H, d, J=6.6 Hz), 1.33 to 1.45 (2H, m), 1.57 to 1.65 (2H, m), 2.08 (1H, m), 2.97 (2H, m), 3.20 (2H, d, J=6.8 Hz), 3.34 to 3.37 (2H, m), 3.55 (2H, t, J=6.6 Hz), 3.80 (2H, m), 4.16 (2H, m), 4.54 (2H, s), 6.93 (1H, d, J=8.8 Hz), 6.98 (2H, d, J=8.8 Hz), 7.20 to 7.26 (2H, m), 7.40 to 7.49 (5H, m), 7.59 to 7.77 (6H, m), 8.43 to 8.46 (1H, m).

IR (KBr) 3310, 2955, 1649, 1501, 1242, 1163, 810 cm$^{-1}$

Elemental Analysis for C$_{39}$H$_{45}$N$_3$O$_5$S Cald. C, 70.14; N, 6.29; H, 6.79. Found: C, 70.10; N, 6.39; H, 7.06

Example 183

(Preparation of Compound 197 and Compound 198)

7-[4-(2-butoxyethoxy)phenyl]-1-isobutyl-N-[4-[(2-pyridinylmethyl)sulfinyl]phenyl]-2,3-dihydro-1-benzazepine-4-carboxamide (200 mg) was optically resolved with CHIRALCEL OJ(5 cmφ×50 cm), to give (+)-(7-[4-(2-butoxyethoxy)phenyl]-1-isobutyl-N-[4-[(2-pyridinylmethyl)sulfinyl]phenyl]-2,3-dihydro-1-benzazepine-4-carboxamide (Compound 197) (78 mg, [α]$_D$=+95.4°) and (−)-7-[4-(2-butoxyethoxy)phenyl]-1-isobutyl-N-[4-[(2-pyridinylmethyl)sulfinyl]phenyl]-2,3-dihydro-1-benzazepine-4-carboxamide (Compound 198) (95 mg).

Example 184

(Preparation of Compound 199)

7-[4-(2-butoxyethoxy)phenyl]-1-(trifluoroacetyl)-2,3-dihydro-1-benzazepine-4-carboxylic acid (0.50 g) was dissolved in DMF (10 ml), 4-[(2-pyridinylsulfanyl)methyl]aniline (272 mg) and 1-hydroxybenzotriazole (321 mg) were added to the mixture, 1-ethyl-3-(3-dimethylaminopropyl)carbodiimide chloride (401 mg) and triethylamine (0.44 ml) were added to the mixture, and the mixture was stirred for 16 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[(2-pyridinylsulfanyl)methyl]phenyl]-1-(trifluoroacetyl)-2,3-dihydro-1-benzazepine-4-carboxamide (Compound 199) (0.36 g).

$^1$H-NMR (200 MHz, CDCl$_3$) δ 0.93 (3H, t, J=7.0 Hz), 1.33 to 1.46 (2H, m), 1.54 to 1.68 (2H, m), 2.87 to 3.25 (3H, m), 3.55 (2H, t, J=6.6 Hz), 3.82 (2H, t, J=4.8 Hz), 4.10 (2H, s), 4.18 (2H, t, J=4.8 Hz), 4.86 (1H, m), 7.02 (2H, d, J=8.8 Hz), 7.10 to 7.34 (7H, m), 7.42 (1H, s), 7.48 to 7.55 (6H, m), 7.65 (1H, d, J=1.8 Hz).

Example 185

(Preparation of Compound 200 and Compound 201)

7-[4-(2-butoxyethoxy)phenyl]-N-[4-[(2-pyridinylsulfanyl)methyl]phenyl]-1-(trifluoroacetyl)-2,3-dihydro-1-benzazepine-4-carboxamide (0.35 g) was dissolved in methylene chloride (10.5 ml), m-chloroperbenzoic acid (0.28 g) was added to the mixture at 0° C., and the mixture was stirred for 2 hours at room temperature. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[(2-pyridinylsulfonyl)methyl]phenyl]-1-(trifluoroacetyl)-2,3-dihydro-1-benzazepine-4-carboxamide (Compound 200) (61 mg) and 7-[4-(2-butoxyethoxy)phenyl]-N-[4-[[(1-oxido-2-pyridinyl)sulfonyl]methyl]phenyl]-1-(trifluoroacetyl)-2,3-dihydro-1-benzazepine-4-carboxamide (Compound 201) (151 mg).

Compound 200: ¹H-NMR (200 MHz, CDCl₃) δ 0.93 (3H, t, J=7.0 Hz), 1.33 to 1.49 (2H, m), 1.58 to 1.69 (2H, m), 2.91 to 3.24 (3H, m), 3.56 (2H, t, J=6.6 Hz), 3.82 (2H, t, J=4.8 Hz), 4.15 to 4.21 (2H, m), 4.29 (2H, s), 4.75 to 4.88 (1H, m), 7.02 (2H, d, J=8.8 Hz), 7.08 (2H, d, J=8.8 Hz), 7.31 to 7.67 (11H, m).

Compound 201: ¹H-NMR (200 MHz, CDCl₃) δ 0.94 (3H, t, J=7.0 Hz), 1.29 to 1.45 (2H, m), 1.54 to 1.68 (2H, m), 2.85 to 3.26 (3H, m), 3.56 (2H, t, J=6.6 Hz), 3.82 (2H, t, J=4.6 Hz), 4.02 (2H, s), 4.18 (2H, t, J=4.8 Hz), 4.75 to 4.89 (1H, m), 6.96 (2H, d, J=8.4 Hz), 7.02 (2H, d, J=8.8 Hz), 7.30 to 7.57 (11H, m), 7.63 (1H, s), 7.83 (1H, s).

Example 186

(Preparation of Compound 202)

7-[4-(2-butoxyethoxy)phenyl]-N-[4-[[(1-oxido-2-pyridinyl)sulfonyl]methyl]phenyl]-1-(trifluoroacetyl)-2,3-dihydro-1-benzazepine-4-carboxamide (137 mg) was dissoved in ethanol (4.0 ml), sodium borohydride (36 mg) was added to the mixture, and the mixture was stirred at room temperature for 3 hours. Sodium borohydride (36 mg) was further added to the mixture, and the mixture was stirred at room temperature for 3 hours. The solvent was removed under reduced pressure and the obtained residue was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[(1-oxido-2-pyridinyl)sulfonyl]methyl]phenyl]-2,3-dihydro-1-benzazepine-4-carboxamide (Compound 202) (85 mg).

¹H-NMR (200 MHz, CDCl₃) 0.93 (3H, t, J=7.2 Hz), 1.33 to 1.45 (2H, m), 1.54 to 1.65 (2H, m), 2.9.4 (2H, m), 3.46 (2H, m), 3.55 (2H, t, J=6.6 Hz), 3.78 to 3.83 (2H, m), 3.98 (1H, d, J=12.8 Hz), 4.07 (1H, d, J=12.4 Hz), 4.13 to 4.18 (2H, m), 4.61 (1H, m), 6.70 (1H, d, J=8.4 Hz), 6.94 (2H, d, J=8.4 Hz), 6.97 (2H, d, J=8.8 Hz), 7.29 to 7.52 (11H, m), 7.64 (1H, s).

IR (KBr) 3318, 2957, 1651, 1609, 1516, 1318, 1246, 1181, 1038, 820 cm⁻¹

Examples 187

(Preparation of Compound 203)

In 1,2-dichloromethane (7.0 ml) was dissolved 7-[4-(2-butoxyethoxy)phenyl]-N-[4-[[(1-oxido-2-pyridinyl)sulfonyl]methyl]phenyl]-2,3-dihydro-1-benzazepine-4-carboxamide (70 mg), and isobutylaldehyde (51 μl), sodium triacetoxyborohydride (118 mg) and acetic acid (3 droplets) were added to the mixture, and the mixture was stirred for 60 hours at room temperature. Sodium triacetoxyborohydride (118 mg) was added to the mixture, and the mixture was stirred at 50° C. for 40 hours. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-oxido-2-pyridinyl)sulfonyl]methyl]phenyl]-2,3-dihydro-1-benzazepine-4-carboxamide (Compound 203) (52 mg).

¹H-NMR (200 MHz, CDCl₃) 0.93 (3H, t, J=7.2 Hz), 0.97 (6H, d, J=6.4 Hz), 1.33 to 1.45 (2H, m), 1.57 to 1.65 (2H, m), 2.05 (1H, m), 2.91 (2H, m), 3.18 (2H, d, J=7.4 Hz), 3.32 to 3.37 (2H, m), 3.55 (2H, t, J=6.6 Hz), 3.78 to 3.83 (2H, m), 3.98 (1H, d, J=12.2 Hz), 4.07 (1H, d, J=12.6 Hz), 4.13 to 4.18 (2H, m), 6.89 to 6.94 (3H, m), 6.98 (2H, d, J=8.4 Hz), 7.37 to 7.53 (11H, m), 7.66 (1H, s).

IR (KBr) 3337, 2951, 1640, 1518, 1499, 1246, 1038, 808 cm⁻¹

Example 188

(Preparation of Compound 204)

In ethanol (4.9 ml) was dissolved 7-[4-(2-butoxyethoxy)phenyl]-N-[4-[(2-pyridinylsulfonyl)methyl]phenyl]-1-(trifluoroacetyl)-2,3-dihydro-1-benzazepine-4-carboxamide (49 mg), and sodium borohydride (13 mg) was added to the mixture, and the mixture was stirred at room temperature for 3 hours. Sodium borohydride (13 mg) was further added to the mixture, and the mixture was stirred at room temperature for 3 hours. The solvent was removed under reduced pressure and the obtained residue was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[(2-pyridinylsulfonyl)methyl]phenyl]-2,3-dihydro-1-benzazepine-4-carboxamide (Compound 204) (23 mg).

¹H-NMR (200 MHz, CDCl₃). δ 0.93 (3H, t, J=7.4 Hz), 1.33 to 1.45 (2H, m), 1.57 to 1.62 (2H, m), 2.95 (2H, m), 3.46 (2H, t, J=4.6 Hz), 3.55 (2H, t, J=6.6 Hz), 3.80 (2H, t, J=4.8 Hz), 4.07 to 4.20 (2H, m) 4.29 (2H, s), 6.55 (1H, d, J=8.6 Hz), 6.70 (1H, d, J=8.2 Hz), 6.85 (1H, d, J=8.4 Hz), 6.97 (2H, d, J=8.8 Hz), 7.05 (2H, d, J=8.4 Hz), 7.31 to 7.35 (2H, m), 7.41 to 7.67 (7H, m).

IR (KBr) 3387, 2945, 2861, 1663, 1611, 1526, 1319, 829 cm⁻¹

Example 189

(Preparation of Compound 205)

In 1,2-dichloromethane (0.85 ml) was dissolved 7-[4-(2-butoxyethoxy)phenyl]-N-[4-[(2-pyridinylsulfonyl)methyl]phenyl]-2,3-dihydro-1-benzazepine-4-carboxamide (17 mg), and isobutylaldehyde (13 μl), sodium triacetoxyborohydride (29 mg) and acetic acid (3 droplets) were added to the mixture, and the mixture was stirred at 50° C. for 40 hours. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-oxido-2-pyridinyl)sulfonyl]methyl]phenyl]-2,3-dihydro-1-benzazepine-4-carboxamide (Compound 205) (6 mg).

¹H-NMR (200 MHz, CDCl₃). δ 0.93 (3H, t, J=6.6 Hz), 0.97 (6H, d, J=7.2 Hz), 1.33 to 1.45 (2H, m), 1.54 to 1.65 (2H, m), 2.05 (1H, m), 2.91 (2H, m), 3.18 (2H, d, J=7.4 Hz), 3.36 (2H, m), 3.55 (2H, t, J=6.6 Hz), 3.78 to 3.83 (2H, m), 4.13 to 4.19 (2H, m), 4.29 (2H, s), 6.92 (1H, d, J=8.8 Hz), 6.98 (2H, d, J=9.2 Hz), 7.05 (2H, d, J=8.6 Hz), 7.38 to 7.67 (12H, m).

Example 190

(Preparation of Compound 206)

7-(4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.28 ml) was added to the mixture, and the mixture was stirred for 1 hour at room temperature. The solvent was removed under reduced pressure, and a solution of the obtained residue in THF (14 ml) was added dropwise to a solution of 4-(benzylsulfanyl) aniline (0.38 g) and triethylamine (1.34 ml) in THF (11.4 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure and the obtained residue was washed with hexane/ethyl acetate, to give. N-[4-(benzylsulfanyl)phenyl]-7-[4-(2-butoxyethoxy)phenyl]-1-isobutyl-2,3-dihydro-1-benzazepine-4-carboxamide (Compound 206) (0.70 g).

$^1$H-NMR (200 MHz, CDCl$_3$) δ 0.93 (3H, t, J=7.2 Hz), 0.97 (6H, d, J=6.4 Hz), 1.33 to 1.45 (2H, m), 1.54 to 1.65 (2H, m), 2.05 (1H, m), 2.90 (2H, m), 3.18 (2H, d, J=7.0 Hz), 3.32 to 3.37 (2H, m), 3.55 (2H, t, J=6.6 Hz), 3.80 (2H, t, J=4.8 Hz), 4.06 (2H, s), 4.16 (2H, t, J=4.6 Hz), 6.91 (1H, d, J=8.8 Hz), 6.97 (2H, d, J=8.8 Hz), 7.25 to 7.32 (7H, m), 7.37 to 7.56 (8H, m).

Example 191

(Preparation of Compound 207, Compound 208)

In methylene chloride (11.4 ml) was dissolved m-chloroperbenzoic acid (0.23 g), and this solution was added dropwise to a solution of 7-[4-(2-butoxyethoxy)phenyl]-1-isobutyl-N-[4-(benzylsulfanyl)phenyl]-2,3-dihydro-1-benzazepine-4-carboxamide (0.57 g) in methylene chloride (17.1 ml) at 0° C. The mixture was stirred for 20 minutes at 0° C., m-chloroperbenzoic acid (0.23 g) was further added to the mixture, and the mixture was stirred for 20 minutes at 0° C. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give. N-[4-(benzylsulfinyl)phenyl]-7-[4-(2-butoxyethoxy)phenyl]-1-isobutyl-2,3-dihydro-1-benzazepine-4-carboxamide (Compound 207) (135 mg) and N-[4-(benzylsulfonyl)phenyl]-7-[4-(2-butoxyethoxy)phenyl]-1-isobutyl-2,3-dihydro-1-benzazepine-4-carboxamide (Compound 208) (35 mg).

Compound 207: $^1$H-NMR (200 MHz, CDCl$_3$) 0.93 (3H, t, J=7.2 Hz), 0.97 (6H, d, J=6.6 Hz), 1.33 to 1.45 (2H, m), 1.54 to 1.65: (2H, m), 2.06 (1H, m), 2.90 (2H, m), 3.17 (2H, d, J=7.0 Hz), 3.34 (2H, m), 3.54 (2H, t, J=6.6 Hz), 3.77 to 3.82 (2H, m), 3.95 (1H, d, J=12.4 Hz), 4.04 to 4.11 (1H, m), 4.11 to 4.17 (2H, m), 6.89 to 6.99 (3H, m), 6.96 (2H, d, J=8.6 Hz), 7.24 to 7.51 (10H, m), 7.69 (2H, d, J=8.8 Hz), 7.92 to 8.15 (1H, m).

IR (KBr) 3331, 2957, 1651, 1499, 1312, 1242, 1038, 828 cm$^{-1}$

Compound 208: $^1$H-NMR (200 MHz, CDCl$_3$) δ 0.93 (3H, t, J=7.0 Hz), 0.97 (6H, d, J=6.6 Hz), 1.33 to 1.45 (2H, m), 1.55 to 1.65 (2H, m), 2.08 (1H, m), 2.92 (2H, m), 3.20 (2H, d, J=7.6 Hz), 3.36 (2H, m), 3.55 (2H, t, J=6.6 Hz), 3.78 to 3.83 (2H, m), 4.16 (2H, t, J=4.6 Hz), 4.30 (2H, s), 6.90 to 6.95 (1H, m), 6.98 (2H, d, J=8.8 Hz), 7.24 to 7.33 (4H, m), 7.40 to 7.76 (9H, m).

IR (KBr) 3314, 2957, 1647, 1499, 1244, 1167, 787 cm$^{-1}$

Example 192

(Preparation of Compound 209)

7-[4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.28 ml) was added to the mixture, and the mixture was stirred for 1 hour at room temperature. The solvent was removed under reduced pressure, and a solution of the obtained residue in THF (14 ml) was added dropwise to a solution of 4-[(3-pyridinylmethyl)sulfanyl]aniline (0.38 g) and triethylamine (1.34 ml) in THF (11.4 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(3-pyridinylmethyl)sulfanyl]phenyl]-2,3-dihydro-1-benzazepine-4-carboxamide (Compound 209) (0.33 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.68 (2H, m), 2.07 (1H, m), 2.90 (2H, m), 3.18 (2H, d, J=7.8 Hz), 3.32 to 3.38 (2H, m), 3.55 (2H, t, J=6.2 Hz), 3.80 (2H, t, J=4.8 Hz), 4.01 (2H, s), 4.15 (2H, t, J=4.8 Hz), 6.91 (1H, d, J=8.8 Hz), 6.97 (2H, d, J=8.8 Hz), 7.15 to 7.29 (3H, m), 7.37 to 7.60 (9H, m), 8.38 (1H, d, J=2.2 Hz), 8.46 (1H, dd, J=4.6, 1.8 Hz).

Example 193

(Preparation of Compound 210)

7-[4-(2-butoxyethoxy)phenyl]-1-isobutyl-N-[4-[(3-pyridinylmethyl)sulfanyl]phenyl]-2,3-dihydro-1-benzazepine-4-carboxamide (0.32 g) was dissolved in methylene chloride (9.6 ml), m-chloroperbenzoic acid (87 mg) was added to the mixture at 0° C., and the mixture was stirred for 20 minutes at 0° C. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(3-pyridinylmethyl)sulfinyl]phenyl]-2,3-dihydro-1-benzazepine-4-carboxamide (Compound 210) (98 mg).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.68 (2H, m), 2.08 (1H, m), 2.92 (2H, m), 3.19 (2H, d, J=7.2 Hz), 3.36 (2H, m), 3.55 (2H, t, J=6.6 Hz), 3.80 (2H, t, J=4.8 Hz), 3.91 (1H, d, J=12.8 Hz), 4.05 to 4.12 (1H, m), 4.16 (2H, t, J=4.8 Hz), 6.92 (1H, d, J=8.8 Hz), 6.98 (2H, d, J=8.8 Hz), 7.19 to 7.31 (3H, m), 7.39 to 7.51 (6H, m), 7.70 (2H, d, J=8.8 Hz), 7.83 (1H, m), 8.12 (1H, m), 8.52 (0.1H, dd, J=4.8, 1.6 Hz).

IR (KBr) 3333, 2957, 1651, 1499, 1242, 1036, 818 cm$^{-1}$

Example 194

(Preparation of Compound 211)

7-[4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.28 ml) was added to the mixture, and the mixture was stirred for 1 hour at room temperature. The solvent was removed under reduced pressure, and a solution of the obtained residue in THF (14 ml) was added dropwise to a solution of 4-[(4-pyridinylmethyl)sulfanyl]aniline (0.38 g) and triethylamine (1.34 ml) in THF (11.4 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(4-pyridinylmethyl)sulfanyl]phenyl]-2,3-dihydro-1-benzazepine-4-carboxamide (Compound 211) (0.27 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.65 (2H, m), 2.06 (1H, m), 2.90 (2H, m), 3.18 (2H, d, J=7.4 Hz), 3.35 (2H, t, J=4.8 Hz), 3.55 (2H, t, J=6.6 Hz), 3.78 to 3.82 (2H, m), 3.98 (2H, s), 4.12 to 4.18 (2H, m), 6.91 (1H, d, J=8.8 Hz), 6.97 (2H, d, J=8.8 Hz), 7.27 (2H, d, J=8.8 Hz), 7.38 to 7.58 (8H, m), 8.47 to 8.51 (2H, m).

Example 195

(Preparation of Compound 212)

7-[4-(2-butoxyethoxy)phenyl]-1-isobutyl-N-[4-[(3-pyridinylmethyl)sulfanyl]phenyl]-2,3-dihydro-1-benzazepine-4-carboxamide (0.24 g) was dissolved in methylene chloride (7.2 ml), m-chloroperbenzoic acid (65 mg) was added to the mixture at 0° C., and the mixture was stirred for 20 minutes at 0° C. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(4-pyridinylmethyl)sulfinyl]phenyl]-2,3-dihydro-1-benzazepine-4-carboxamide (Compound 212) (101 mg).

H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.68 (2H, m), 2.05 (1H, m), 2.92 (2H, m), 3.19 (2H, d, J=7.2 Hz), 3.44 to 3.50 (2H, m), 3.55 (2H, t, J=6.6 Hz), 3.80 (2H, t, J=4.8 Hz), 3.92 (1H, d, J=12.4 Hz), 4.05 (1H, d, J=12.8 Hz), 4.13 to 4.18 (2H, m), 6.88 to 6.92 (3H, m), 6.98 (2H, d, J=8.8 Hz), 7.31 to 7.49 (7H, m), 7.69 to 7.82 (3H, m), 8.50 (2H, d, 5.8 Hz).

IR (KBr) 3335, 2957, 1649, 1499, 1242, 1036, 829 cm$^{-1}$

Elemental Analysis for C$_{39}$H$_{45}$N$_3$O$_4$S. Cald. C, 71.86; N, 6.45; H, 6.96. Found: C, 71.65; N, 6.56; H, 7.04

Example 196

(Preparation of Compound 213)

7-[4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.28 ml) was added to the mixture, and the mixture was stirred for 1 hour at room temperature. The solvent was removed under reduced pressure, and a solution of the obtained residue in THF (14 ml) was added dropwise to a solution of 4-[(3-pyridinylmethyl)sulfanyl]aniline (0.39 g) and triethylamine (1.34 ml) in THF (11.4 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(6-methyl-2-pyridinyl)methyl]sulfanyl]phenyl]-2,3-dihydro-1-benzazepine-4-carboxamide (Compound 213) (0.52 g).

$^1$H-NMR (200 MHz, CDCl$_3$) δ 0.93 (3H, t, J=7.0 Hz), 0.96 (6H, d, J=6.6 Hz), 1.36 to 1.45 (2H, m), 1.57 to 1.64 (2H, m), 2.05 (1H, m), 2.54 (3H, s), 2.89 (2H, m), 3.17 (2H, t, J=7.2 Hz), 3.34 (2H, t, J=4.4 Hz), 3.55 (2H, t, J=6.6 Hz), 3.77 to 3.83 (2H, m), 4.12 to 4.18 (2H, m), 4.19 (2H, s), 6.91 (1H, d, J=8.6 Hz), 6.97 (2H, d, J=8.8 Hz), 6.95 to 7.07 (2H, m), 7.29 to 7.57 (11H, m).

Example 197

(Preparation of Compound 214)

7-[4-(2-butoxyethoxy)phenyl]-1-isobutyl-N-[4-[[(6-methyl-2-pyridinyl)methyl]sulfanyl]phenyl]-2,3-dihydro-1-benzazepine-4-carboxamide (0.46 g) was dissolved in methylene chloride (13.8 ml), m-chloroperbenzoic acid (87 mg) was added to the mixture at 0° C., and the mixture was stirred for 20 minutes at 0° C. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(6-methyl-2-pyridinyl)methyl]sulfinyl]phenyl]-2,3-dihydro-1-benzazepine-4-carboxamide (Compound 214) (157 mg).

$^1$H-NMR (200 MHz, CDCl$_3$) δ 0.92 (3H, t, J=7.2 Hz), 0.97 (6H, d, J=6.6 Hz), 1.33 to 1.45 (2H, m), 1.54 to 1.65 (2H, m), 2.08 (1H, m), 2.52 (3H, s), 2.92 (2H, m), 3.19 (2H, t, J=7.4 Hz), 3.34 to 3.40 (2H, m), 3.51 to 3.58 (2H, m), 3.78 to 3.83 (2H, m), 4.09 (1H, d, J=12.0 Hz), 4.13 to 4.18 (2H, m), 4.23 (1H, d, J=12.4 Hz), 6.92 (1H, d, J=8.8 Hz), 6.98 (2H, d, J=8.8 Hz), 6.98 to 7.09 (2H, m), 7.38 to 7.55 (8H, m), 7.69 to 7.79 (3H, m).

IR (KBr) 3322, 2965, 1644, 1588, 1499, 1244, 1184, 1044, 924, 829, 750 cm$^{-1}$

Example 198

(Preparation of Compound 215)

7-[4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.28 ml) was added to the mixture, and the mixture was stirred for 1 hour at room temperature. The solvent was removed under reduced pressure, and a solution of the obtained residue in THF (14 ml) was added dropwise to a solution of 4-[[(4-chloro-2-pyridinyl)methyl]sulfanyl]aniline (0.42 g) and triethylamine (1.34 ml) in THF (12.6 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[(4-chloro-2-pyridinyl)methyl]sulfanyl]phenyl]-1-isobutyl-2,3-dihydro-1-benzazepine-4-carboxamide (Compound 215) (0.51 g).

$^1$H-NMR (200 MHz, CDCl$_3$) δ 0.92 (3H, t, J=7.4 Hz), 0.95 (6H, d, J=6.6 Hz), 1.33 to 1.45 (2H, m), 1.53 to 1.64 (2H, m), 2.04 (1H, m), 2.87 (2H, m), 3.15 (2H, d, J=7.0 Hz), 3.29 to 3.34 (2H, m), 3.54 (2H, t, 6.6 Hz), 3.77 to 3.82 (2H, m), 4.09 to 4.15 (2H, m), 4.16 (2H, s), 6.89 (1H, d, J=8.8 Hz), 6.95 (2H, d, J=8.4 Hz), 7.23 to 7.54 (11H, m), 7.73 (1H, s), 8.40 (1H, d, J=5.2 Hz).

Example 199

(Preparation of Compound 216)

7-[4-(2-butoxyethoxy)phenyl]-1-isobutyl-N-[4-[[(6-methyl-2-pyridinyl)methyl]sulfanyl]phenyl]-2,3-dihydro-1-benzazepine-4-carboxamide (0.51 g) was dissolved in methylene chloride (15.3 ml), and to the mixture was added dropwise a solution of m-chloroperbenzoic acid (0.20 g) in methylene chloride (10.2 ml) at −78° C., and the mixture was stirred for 15 minutes. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[(6-chloro-2-pyridinyl)methyl]sulfinyl]phenyl]-1-isobutyl-2,3-dihydro-1-benzazepine-4-carboxamide (Compound 216) (0.34 g).

$^1$H-NMR (200 MHz, CDCl$_3$) δ0.93 (3H, t, J=7.2 Hz), 0.97 (6H, d, J=6.6 Hz), 1.33 to 1.45 (2H, m), 1.54 to 1.63 (2H, m), 2.08 (1H, m), 2.92 (2H, m), 3.19 (2H, m), 3.34 to 3.39 (2H, m), 3.55 (2H, m), 3.77 to 3.83 (2H, m), 4.13 to 4.18 (2H, m), 6.92 (1H, d, J=8.8 Hz), 6.98 (2H, d, J=8.8 Hz), 7.23 to 7.26 (2H, m), 7.38 to 7.53 (7H, m), 7.72 to 7.81 (3H, m), 8.41 to 8.45 (1H, m).

IR (KBr) 3320, 2957, 1645, 1499, 1244, 1127, 1042, 826 cm$^{-1}$

Elemental Analysis for C$_{39}$H$_{44}$N$_3$O$_4$SCl Cald. C, 68.25; N, 6.12; H, 6.46; Cl, 5.17. Found: C, 68.04; N, 6.16; H, 6.43; Cl, 5.05

Example 200

(Preparation of Compound 217)

7-[4-(2-butoxyethoxy)phenyl]-1-isobutyl-2,3-dihydro-1-benzazepine-4-carboxylic acid (0.70 g) was dissolved in THF (14 ml), DMF (2 droplets) was added to the mixture, oxalyl chloride (0.28 ml) was added to the mixture, and the mixture was stirred for 1 hour at room temperature. The solvent was removed under reduced pressure, and a solution of the obtained residue in THF (14 ml) was added dropwise to a solution of 4-[[(4-methyl-2-pyridinyl)methyl]sulfanyl]aniline (0.41 g) and triethylamine (1.78 ml) in THF (12.3 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(6-methyl-2-pyridinyl)methyl]sulfanyl]phenyl]-2,3-dihydro-1-benzazepine-4-carboxamide (Compound 217) (0.40 g).

$^1$H-NMR (200 MHz, CDCl$_3$) δ0.93 (3H, t, J=7.2 Hz), 0.96 (6H, d, J=6.6 Hz), 1.33 to 1.45 (2H, m), 1.57 to 1.65 (2H, m), 2.05 (1H, m), 2.30 (3H, s), 2.89 (2H, m), 3.17 (2H, d, J=7.4 Hz), 3.31 to 3.37 (2H, m), 3.51 to 3.59 (2H, m), 3.77 to 3.83 (2H, m), 4.10 to 4.15 (2H, m), 4.18 (2H, s), 6.91 (1H, d, J=8.8 Hz), 6.97 (2H, d, J=8.4 Hz), 7.11 (1H, s), 7.27 to 7.52 (10H, m), 7.63 (1H, s), 7.38 (1H, d, J=5.2 Hz).

Example 201

(Preparation of Compound 218)

A solution of 7-[4-(2-butoxyethoxy)phenyl]-1-isobutyl-N-[4-[[(6-methyl-2-pyridinyl)methyl]sulfanyl]phenyl]-2,3-dihydro-1-benzazepine-4-carboxamide (0.39 g) in methylene chloride (7.8 ml) was added dropwise to a solution of m-chloroperbenzoic acid (0.21 g) in methylene chloride (7.8 ml) at −40° C., and the mixture was stirred for 20 minutes. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(6-methyl-2-pyridinyl)methyl]sulfinyl]phenyl]-2,3-dihydro-1-benzazepine-4-carboxamide (Compound 218) (146 mg).

$^1$H-NMR (200 MHz, CDCl$_3$) δ 0.93 (3H, t, J=6.8 Hz), 0.97 (6H, d, J=6.6 Hz), 1.33 to 1.45 (2H, m), 1.54 to 1.68 (2H, m), 2.07 (1H, m), 2.31 (3H, s), 2.91 (2H, m), 3.19 (2H, d, J=7.0 Hz), 3.33 to 3.38 (2H, m), 3.55 (2H, t, J=6.6 Hz), 3.77 to 3.83 (2H, m), 4.15 to 4.18 (2H, m), 4.15 (2H, s), 6.92 (1H, d, J=8.8 Hz), 6.97 (2H, d, J=8.8 Hz), 6.95 to 7.05 (2H, m), 7.37 to 7.52 (7H, m), 7.73 (2H, d, J=8.4 Hz), 7.92 (1H, s), 8.40 (1H, d, J=5.2 Hz).

IR (KBr) 3322, 2959, 1644, 1501, 1242, 1184, 828 cm$^{-1}$

Elemental Analysis for C$_{40}$H$_{47}$N$_3$O$_4$S.0.3H$_2$O. Cald. C, 72.57; N, 6.26; H, 7.15. Found: C, 71.69; N, 6.22; H, 7.28

Example 202

(Preparation of Compound 219)

7-[4-(2-butoxyethoxy)phenyl]-1-isobutyl-2,3-dihydro-1-benzazepine-4-carboxylic acid (1.2 g) was dissolved in THF (24 ml), DMF (3 droplets) was added to the mixture, oxalyl chloride (0.48 ml) was added to the mixture, and the mixture was stirred for 1 hour at room temperature. The solvent was removed under reduced pressure, and a solution of the obtained residue in THF (24 ml) was added dropwise to a solution of 4-[[2-(methoxymethoxy)benzyl]sulfanyl]aniline (0.83 g) and triethylamine (2.29 ml) in THF (24.9 ml) under ice-cooling and the mixture was stirred at room temperature for 16 hours. The reaction solution was added to water, and extracted with ethyl acetate. The organic layer was washed with saturated brine, and dried over magnesium sulfate. The solvent was removed under reduced pressure, and the obtained residue was purified by silica gel column chromatography, and washed with hexane/ethyl acetate, to give 7-[4-(2-butoxyethoxy)phenyl]-1-isobutyl-N-[4-[[2-(methoxymethoxy)benzyl]sulfanyl]phenyl]-2,3-dihydro-1-benzazepine-4-carboxamide (Compound 219) (1.09 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.55 to 1.65 (2H, m), 2.07 (1H, m), 2.91 (2H, m), 3.19 (2H, d, J=7.2 Hz), 3.33 to 3.38 (2H, m), 3.50 (3H, s), 3.55 (2H, t, J=6.6 Hz), 3.80 (2H, t, J=4.4 Hz), 4.12 (2H, S), 4.13 to 4.19 (2H, m), 5.19 (2H, s), 6.84 to 7.52(17H, m).

Example 203

(Preparation of Compound 220)

A solution of 7-[4-(2-butoxyethoxy)phenyl]-1-isobutyl-N-[4-[[2-(methoxymethoxy)benzyl]sulfanyl]phenyl]-2,3-dihydro-1-benzazepine-4-carboxamide (1.02 g) in methylene chloride (20.4 ml), was added dropwise to a solution of m-chloroperbenzoic acid (0.51 g) in methylene chloride (40.8 ml) at −78° C., and the mixture was stirred for 20 minutes. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[2-(methoxymethoxy)benzyl]sulfinyl]phenyl]-2,3-dihydro-1-benzazepine-4-carboxamide (Compound 220) (820 mg).

$^1$H-NMR (200 MHz, CDCl$_3$) δ 0.93 (3H, t, J=7.0 Hz), 0.97 (6H, d, J=6.6 Hz), 1.33 to 1.45 (2H, m), 1.53 to 1.67 (2H, m), 2.07 (1H, m), 2.91 (2H, m), 3.18 (2H, d, J=7.0 Hz), 3.35 (2H, d, J=7.0 Hz), 3.45 (3H, s), 3.54 (2H, t, J=6.6 Hz), 3.80 (2H, t, J=4.8 Hz), 4.01 (1H, d, J=12.0 Hz), 4.12 to 4.18 (2H, m), 4.29 (1H, d, J=12.2 Hz), 5.06 (2H, s), 6.86 to 7.08 (6H, m), 7.20 to 7.43 (8H, m), 7.68 (2H, d, J=8.8 Hz), 7.87 to 7.98 (1H, m).

IR (KBr) 3335, 2957, 1645, 1588, 1499, 1242, 1182, 926, 828, 760 cm$^{-1}$

Elemental Analysis for C$_{42}$H$_{50}$N$_2$O$_6$S Cald. C, 70.96; N, 3.94; H, 7.09. Found: C, 70.93; N, 3.88; H, 7.01

Example 204

(Preparation of Compound 221)

7-[4-(2-butoxyethoxy)phenyl]-1-isobutyl-N-[4-[[2-(methoxymethoxy)benzyl]sulfinyl]phenyl]-2,3-dihydro-1-benzazepine-4-carboxamide (0.69 g) was dissolved in methanol (13.8 ml), 4N hydrochloric acid/ethyl acetate (3.45 ml) was added to the mixture at room temperature, and the mixture was stirred for 15 minutes. The reaction mixture was added to an aqueous solution of saturated sodium bicarbonate, and extracted with ethyl acetate. The solvent was removed under reduced pressure, and the obtained residue was purified by silica gel column chromatography, to give 7-[4-(2-butoxyethoxy)phenyl]-N-[4-[(2-hydroxybenzyl)sulfinyl]phenyl]-1-isobutyl-2,3-dihydro-1-benzazepine-4-carboxamide (Compound 221) (0.30 g).

$^1$H-NMR (200 MHz, CDCl$_3$) δ 0.93 (3H, t, J=7.2 Hz), 0.96 (6H, d, J=6.6 Hz), 1.33 to 1.45 (2H, m), 1.53 to 1.64 (2H, m), 2.05 (1H, m), 2.89 (2H, m), 3.17 (2H, d, J=7.4 Hz), 3.31 to 3.35 (2H, d, J=6.6 Hz), 3.55 (2H, t, J=6.6 Hz), 3.80 (2H, t, J=4.8 Hz), 3.96 (1H, d, J=13.8 Hz), 4.10 to 4.17 (2H, m), 4.37 (1H, d, J=13.6 Hz), 6.63-6.72 (2H, m), 6.89 to 7.00 (4H, m), 7.12 to 7.18 (1H, m), 7.37 to 7.48 (7H, m), 7.72 (2H, d, J=7.0 Hz), 7.92 (1H, s), 9.08 (1H, s).

IR (KBr) 2957, 1649, 1607, 1499, 1397, 1246, 1179, 818, 756 cm$^{-1}$

Example 205

(Preparation of Compound 222)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, oxalyl chloride (0.24 ml) was added to the mixture, and the mixture was stirred for 1 hour at room temperature. The solvent was removed under reduced pressure, and a solution of the obtained residue in methylene chloride (12 ml) was added dropwise to a solution of 4-amino-N-(2-pyrimidinyl)benzenesulfonamide (0.38 g) and triethylamine (1.53 ml) in methylene chloride (11.4 ml) under ice-cooling and the mixture was stirred for 20 hours at room temperature. The reaction solution was added to water, and extracted with methylene chloride. The organic layer was washed with saturated brine, and dried over magnesium sulfate. The solvent was removed under reduced pressure, and the obtained residue was purified by silica gel column chromatography, and recrystallized from ethyl acetate, to give 7-[4-(2-butoxyethoxy)phenyl]-1-isobutyl-N-[4-[(2-pyrimidinylamino)sulfonyl]phenyl]-2,3-dihydro-1-benzazepine-4-carboxamide (Compound 222) (113 mg).

$^1$H-NMR (200 MHz, CDCl$_3$) δ 0.93 (3H, t, J=6.8 Hz), 0.93 (6H, d, J=6.6 Hz), 1.33 to 1.45 (2H, m), 1.54 to 1.61 (2H, m), 2.05 (1H, m), 2.83 (2H, m), 3.22 (2H, d, J=7.4 Hz), 3.26 (2H, m), 3.55 (2H, t, J=6.6 Hz), 3.80 (2H, t, J=4.4 Hz), 4.14 (2H, d, J=4.4 Hz), 6.85 to 7.00 (4H, m), 7.35 to 7.44 (5H, m), 7.74 (2H, d, J=8 Hz), 7.96 to 8.02 (3H, m), 8.64 (2H, d, J=5.0 Hz), 11.33 (1H, br).

IR (KBr) 3312, 2953, 1647, 1581, 1499, 1246, 1165, 941, 839 cm$^{-1}$

Elemental Analysis for C$_{37}$H$_{43}$N$_5$O$_5$S Cald. C, 66.34; N, 10.46; H, 6.47. Found: C, 66.18; N, 10.44; H, 6.77

Example 206

(Preparation of Compound 223)

7-[4-(2-butoxyethoxy)phenyl]-1-isobutyl-2,3-dihydro-1-benzazepine-4-carboxylic acid (0.50 g) was dissolved in THF (10 ml), DMF (3 droplets) was added to the mixture, oxalyl chloride (0.20 ml) was added to the mixture, and the mixture was stirred for 1 hour at room temperature. The solvent was removed under reduced pressure, and a solution of the obtained residue in THF (10 ml) was added dropwise to a solution of 3-methyl-4-[(2-pyridinylmethyl)sulfanyl]aniline (0.29 g) and triethylamine (0.96 ml) in THF (8.7 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[3-methyl-4-[(2-pyridinylmethyl)sulfanyl]phenyl]-2,3-dihydro-1-benzazepine-4-carboxamide (Compound 223) (0.46 g).

$^1$H-NMR (200 MHz, CDCl$_3$) δ 0.93 (3H, t, J=7.2 Hz), 0.96 (6H, d, J=6.6 Hz), 1.33 to 1.45 (2H, m), 1.57 to 1.65 (2H, m), 2.05 (1H, m), 2.34 (3H, s), 2.89 (2H, m), 3.18 (2H, d, J=7.4 Hz), 3.32 to 3.37 (2H, m), 3.52 to 3.59 (2H, m), 3.80 (2H, t, J=4.6 Hz), 4.13 to 4.18 (2H, m), 4.16 (2H, s), 6.91 (1H, d, J=8.8 Hz), 6.97 (2H, d, J=8.6 Hz), 7.14 to 7.18 (12H, m), 8.51 to 8.55 (1H, m).

Example 207

(Preparation of Compound 224)

To a solution of 7-[4-(2-butoxyethoxy)phenyl]-1-isobutyl-N-[3-methyl-4-[(2-pyridinylmethyl)sulfanyl]phenyl]-2,3-dihydro-1-benzazepine-4-carboxamide (0.45 g) in methylene chloride (13.5 ml) was added dropwise a solution of m-chloroperbenzoic acid (0.16 g) in methylene chloride (9.0 ml) at −78° C., and the mixture was stirred for 15 minutes. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[3-methyl-4-[(2-pyridinylmethyl)sulfinyl]phenyl]-2,3-dihydro-1-benzazepine-4-carboxamide (Compound 224) (185 mg).

$^1$H-NMR (200 MHz, CDCl$_3$) δ 0.93 (3H, t, J=7.4 Hz), 0.97 (6H, d, J=6.6 Hz), 1.29 to 1.45 (2H, m), 1.57 to 1.65 (2H, m), 2.07 (1H, m), 2.22 (3H, s), 2.91 (2H, m), 3.19 (2H, d, J=7.4 Hz), 3.34 (2H, m), 3.55 (2H, t, J=6.6 Hz), 3.77 to 3.83 (2H, m), 4.13 to 4.18 (2H, m), 4.18 (2H, s), 6.89 to 6.95 (1H, m), 6.97 (2H, d, J=8.8 Hz), 7.12 to 7.24 (2H, m), 7.38 to 7.79 (10H, m), 8.53 (1H, d, J=4.4 Hz).

IR (KBr) 3287, 2957, 1661, 1499, 1244, 1180, 910, 818, 733 cm$^{-1}$

Elemental Analysis for C$_{40}$H$_{47}$N$_3$O$_4$S Cald. C, 72.15; N, 6.31; H, 7.11. Found: C, 72.20; N, 6.45; H, 7.08

Example 208

(Preparation of Compound 225)

7-[4-(2-butoxyethoxy)phenyl]-1-isobutyl-2,3-dihydro-1-benzazepine-4-carboxylic acid (0.50 g) was dissolved in THF (10 ml), DMF (3 droplets) was added to the mixture, oxalyl chloride (0.20 ml) was added to the mixture, and the mixture was stirred for 1 hour at room temperature. The solvent was removed under reduced pressure, and a solution of the obtained residue in THF (10 ml) was added dropwise to a solution of 4-[[(4-ethoxy-2-pyridinyl)methyl]sulfanyl]-3-methylaniline (0.33 g) and triethylamine (0.96 ml) in THF (9.9 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[3-methyl-4-[[(4-ethoxy-2-pyridinyl)methyl]sulfanyl]phenyl]-1-isobutyl-2,3-dihydro-1-benzazepine-4-carboxamide (Compound 225) (0.18 g).

$^1$H-NMR (200 MHz, CDCl$_3$) δ 0.93 (3H, t, J=7.0 Hz), 0.96 (6H, d, J=6.6 Hz), 1.33 to 1.45 (5H, m), 1.54 to 1.65 (2H, m), 2.05 (1H, m), 2.36 (3H, s), 2.89 (2H, m), 3.18 (2H, d, J=7.4 Hz), 3.36 (2H, m), 3.51 to 3.59 (2H, m), 3.80 (2H, t, J=4.8 Hz), 4.12 (2H, s), 4.12 (2H, q, J=7.0 Hz), 6.66 (1H, dd, J=5.6, 2.2 Hz), 6.76 (1H, d, J=2.6 Hz), 6.91 (1H, d, J=8 Hz), 6.98 (2H, d, J=8.8 Hz), 7.30 to 7.48 (8H, m), 8.33 (1H, d, J=5.8 Hz).

Example 209

(Preparation of Compound 226)

To a solution of 7-[4-(2-butoxyethoxy)phenyl]-N-[3-methyl-4-[[(4-ethoxy-2-pyridinyl)methyl]sulfanyl]phenyl]-1-isobutyl-2,3-dihydro-1-benzazepine-4-carboxamide (0.17 g) in methylene chloride (5.1 ml) was added dropwise a solution of m-chloroperbenzoic acid (55 mg) in methylene chloride (3.4 ml) at −78° C., and the mixture was stirred for 15 minutes. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[3-methyl-4-[[(4-ethoxy-2-pyridinyl)methyl]sulfinyl]phenyl]-1-isobutyl-2,3-dihydro-1-benzazepine-4-carboxamide (Compound 226) (32 mg).

$^1$H-NMR (200 MHz, CDCl$_3$) δ 0.89 to 1.00 (6H, m), 0.97 (6H, d, J=6.6 Hz), 1.33 to 1.44 (5H, m), 1.54 to 1.65 (2H, m), 2.08 (1H, m), 2.27 (3H, s), 2.91 (2H, m), 3.19 (2H, d, J=7.0 Hz), 3.36 (2H, m), 3.55 (2H, t, J=6.6 Hz), 3.80 (2H, t, J=4.8 Hz), 4.01 to 4.18 (4H, m), 4.10 (2H, s), 6.69 to 6.73 (2H, m), 6.90 to 6.95 (2H, d, J=8.8 Hz), 6.98 (2H, d, J=8.8 Hz), 7.26 to 7.58 (8H, m), 7.77 (1H, d, J=8.2 Hz), 8.31 (1H, d, J=5.2 Hz).

IR (KBr) 3268, 2957, 1661, 1599, 1497, 1238, 1125, 1044, 816, 731 cm$^{-1}$

Example 210

(Preparation of Compound 227)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, oxalyl chloride (0.24 ml) was added to the mixture, and the mixture was stirred for 1 hour at room temperature. The solvent was removed under reduced pressure, and a solution of the obtained residue in THF (12 ml) was added dropwise to a solution of 4-[(3-pyridinylmethyl)sulfanyl]-3-methylaniline (0.33 g) and triethylamine (1.15 ml) in THF (9.9 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[3-methyl-4-[(3-pyridinylmethyl)sulfanyl]phenyl]-2,3-dihydro-1-benzazepine-4-carboxamide (Compound 227) (0.51 g).

$^1$H-NMR (200 MHz, CDCl$_3$) δ 0.93 (3H, t, J=7.0 Hz), 0.96 (6H, d, J=6.6 Hz), 1.33 to 1.45 (2H, m), 1.57 to 1.65 (2H, m), 2.05 (1H, m), 2.29 (3H, s), 2.89 (2H, t, J=4.0 Hz), 3.17 (2H, d, J=7.2 Hz), 3.31 to 3.36 (2H, m), 3.55 (2H, t, J=6.6 Hz), 3.77 to 3.83 (2H, m), 3.94 (2H, s), 4.10 to 4.18 (2H, m), 6.91 (1H, d, J=8.8 Hz), 6.97 (2H, d, J=8.8 Hz), 7.14 to 7.25 (2H, m), 7.34 to 7.51 (8H, m), 7.63 (1H, s), 8.36 (1H, d, J=2.2 Hz), 8.43 to 8.47 (1H, m).

Example 211

(Preparation of Compound 228)

To a solution of 7-[4-(2-butoxyethoxy)phenyl]-1-isobutyl-N-[3-methyl-4-[(3-pyridinylmethyl)sulfanyl]phenyl]-2, 3-dihydro-1-benzazepine-4-carboxamide (0.50 g) in methylene chloride (15 ml) was added dropwise a solution of m-chloroperbenzoic acid (0.17 g) in methylene chloride (10 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-1-isobutyl-N-[3-methyl-4-[(3-pyridinylmethyl)sulfinyl]phenyl]-2,3-dihydro-1-benzazepine-4-carboxamide (Compound 228) (151 mg).

$^1$H-NMR (200 MHz, CDCl$_3$) δ 0.93 (3H, t, J=7.4 Hz), 0.97 (6H, d, J=6.6 Hz), 1.33 to 1.45 (2H, m), 1.54 to 1.65 (2H, m), 2.06 (1H, m), 2.18 (3H, s), 2.90 (2H, m), 3.18 (2H, d, J=7.4 Hz), 3.34 (2H, m), 3.55 (2H, t, J=6.6 Hz), 3.82 (2H, t, J=4.8 Hz), 3.90 (1H, d, J=13.0 Hz), 4.02 (1H, d, J=12.8 Hz), 4.12 to 4.17 (2H, m), 6.89 to 6.94 (1H, m), 6.96 (2H, d, J=8.8 Hz), 7.15 to 7.49 (10H, m), 7.71 (1H, s), 8.02 (1H, s), 8.48 to 8.52 (1H, m).

IR (KBr) 3287, 2957, 1655, 1499, 1244, 910, 816, 731 cm$^{-1}$

Example 212

(Preparation of Compound 229)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(4,6-dimethyl-2-pyrimidinyl)methyl]sulfanyl]aniline (0.37 g) and triethylamine (1.53 ml) in THF (11.1 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[(4,6-dimethyl-2-pyrimidinyl)methyl]sulfanyl]phenyl]-1-isobutyl-2,3-dihydro-1-benzazepine-4-carboxamide (Compound 229) (0.57 g).

$^1$H-NMR (200 MHz, CDCl$_3$) δ 0.93 (3H, t, J=7.4 Hz), 0.97 (6H, d, J=6.6 Hz), 1.36 to 1.45 (2H, m), 1.57 to 1.65 (2H, m), 2.05 (1H, m), 2.40 (6H, s), 2.90 (2H, m), 3.18 (2H, d, J=7.2 Hz), 3.32 to 3.38 (2H, m), 3.55 (2H, t, J=6.6 Hz), 3.78 to 3.83 (2H, m), 4.13 (2H, s), 6.69 (1H, s), 6.91 (1H, d, J=9.2 Hz), 6.97 (2H, d, J=8.8 Hz), 7.36 to 7.55 (10H, m).

Example 213

(Preparation of Compound 230)

To a solution of 7-[4-(2-butoxyethoxy)phenyl]-N-[4-[[(4,6-dimethyl-2-pyrimidinyl)methyl]sulfanyl]phenyl]-1-isobutyl-2,3-dihydro-1-benzazepine-4-carboxamide (0.56 g) in methylene chloride (16.8 ml) was added dropwise a solution of m-chloroperbenzoic acid (0.22 g) in methylene chloride (10 ml) at −78° C., and the mixture was stirred for 15 minutes. The mixture was allowed to be warmed up to 0° C., and an aqueous solution of saturated sodium thiosulfate was added to the reaction mixture. The mixture was extracted with ethyl acetate, and the organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[(4,6-dimethyl-2-pyrimidinyl)methyl]sulfinyl]phenyl]-1-isobutyl-2,3-dihydro-1-benzazepine-4-carboxamide (Compound 230) (165 mg).

$^1$H-NMR (200 MHz, CDCl$_3$) δ0.93 (3H, t, J=7.2 Hz), 0.97 (6H, d, J=6.6 Hz), 1.33 to 1.45 (2H, m), 1.54 to 1.65 (2H, m), 2.05 (1H, m), 2.54 (6H, s), 2.90 (2H, m), 3.18 (2H, d, J=7.4 Hz), 3.35 (2H, t, J=4.4 Hz), 3.55 (2H, t, J=6.6 Hz), 3.80 (2H, t, J=4.8 Hz), 4.16 (2H, t, J=4.6 Hz), 4.16 to 4.24 (1H, m), 4.35 (1H, d, J=12.8 Hz), 6.91 (1H, d, J=8.8 Hz), 6.97 (1H, d, J=8.8 Hz), 7.02 (1H, d, J=8.8 Hz), 7.14 (1H, d, J=8.8 Hz), 7.36 to 7.56 (7H, m), 7.71 (1H, s).

IR (KBr) 3285, 2957, 1651, 1582, 1499, 1244, 1180, 910, 816, 733 cm$^{-1}$

Elemental Analysis for C$_{40}$H$_{48}$N$_4$O$_4$S Cald. C, 70.56; N, 8.23; H, 7.11. Found: C, 70.39; N, 8.04; H, 7.08

Example 214

(Preparation of Compound 231)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(1-methyl-1,2,3,4-tetrazol-5-yl)methyl]sulfanyl]aniline (0.31 g) and triethylamine (1.53 ml) in THF (9.3 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-methyl-tetrazol-5-yl)methyl]sulfanyl]phenyl]-2,3-dihydro-1-benzazepine-4-carboxamide (Compound 231) (0.59 g).

$^1$H-NMR (200 MHz, CDCl$_3$) 0.93 (3H, t, J=7.2 Hz), 0.97 (6H, d, J=6.6 Hz), 1.33 to 1.45 (2H, m), 1.57 to 1.65 (2H, m), 2.04 (1H, m), 2.89 (2H, m), 3.17 (2H, d, J=7.4 Hz), 3.32 (2H, m), 3.55 (2H, t, J=6.6 Hz), 3.78 to 3.83 (2H, m), 4.10 (2H, s), 4.12 to 4.18 (2H, m), 6.89 (1H, d, J=9.0 Hz), 6.96 (2H, d, J=8.8 Hz), 7.21 to 7.41 (7H, m), 7.58 (2H, d, J=8.8 Hz), 8.08(1H, s).

IR (KBr) 3310, 2957, 1651, 1607, 1499, 1244, 1180, 910, 816, 733 cm$^{-1}$

Example 215

(Preparation of Compound 232)

To a solution of 7-[4-(2-butoxyethoxy)phenyl]-1-isobutyl-N-[4-[[(1-methyl-tetrazol-5-yl)methyl]sulfanyl]phenyl]-2,3-dihydro-1-benzazepine-4-carboxamide (0.60 g) in methylene chloride (18 ml) was added dropwise a solution of m-chloroperbenzoic acid (0.19 g) in methylene chloride (12 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-methyl-tetrazol-5-yl)methyl]sulfinyl]phenyl]-2,3-dihydro-1-benzazepine-4-carboxamide (Compound 232) (350 mg).

$^1$H-NMR (200 MHz, CDCl$_3$) δ 0.93 (3H, t, J=7.8 Hz), 0.99 (6H, d, J=7.0 Hz), 1.33 to 1.45 (2H, m), 1.52 to 1.64 (2H, m), 2.08 (1H, m), 2.92 (2H, m), 3.18 (2H, d, J=6.6 Hz), 3.34 (2H, m), 3.55 (2H, t, J=6.6 Hz), 3.77 to 3.83 (2H, m), 3.91 to 4.23 (2H, m), 3.92 (3H, s), 4.11 to 4.17 (2H, m), 6.88 to 6.93 (1H, m), 6.95 (2H, d, J=8.4 Hz), 7.30 to 7.40 (7H, m), 7.83 (2H, d, J=8.4 Hz), 8.50 (1H, br).

IR (KBr) 2957, 1647, 1607, 1507, 1316, 1244, 910, 735 cm$^{-1}$

Example 216

(Preparation of Compound 233)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(2-methyl-1,2,3,4-tetrazol-5-yl)methyl]sulfanyl]aniline (0.31 g) and triethylamine (1.53 ml) in THF (9.3 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(2-methyl-tetrazol-5-yl)methyl]sulfanyl]phenyl]-2,3-dihydro-1-benzazepine-4-carboxamide (Compound 233) (0.59 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.57 to 1.65 (2H, m), 2.05 (1H, m), 2.90 (2H, m), 3.18 (2H, d, J=7.2 Hz), 3.35 (2H, m), 3.55 (2H, t, J=6.6 Hz), 3.80 (2H, t, J=4.8 Hz), 4.15 (2H, t, 4.8 Hz), 4.27 (2H, s), 4.29 (3H, s), 6.91 (1H, d, J=8.8 Hz), 6.97 (2H, d, J=8.8 Hz), 7.36 to 7.62 (10H, m).

IR (KBr) 3285, 2957, 1651, 1607, 1497, 1242, 1181, 1123, 818, 733: cm$^{-1}$

Example 217

(Preparation of Compound 234)

To a solution of 7-[4-(2-butoxyethoxy)phenyl]-1-isobutyl-N-[4-[[(2-methyl-tetrazol-5-yl)methyl]sulfanyl]phenyl]-2,3-dihydro-1-benzazepine-4-carboxamide (0.58 g) in methylene chloride (17.4 ml) was added dropwise a solution of m-chloroperbenzoic acid (0.19 g) in methylene chloride (11.6 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(2-methyl-tetrazol-5-yl)methyl]sulfinyl]phenyl]-2,3-dihydro-1-benzazepine-4-carboxamide (Compound 234) (420 mg).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.64 (2H, m), 2.04 (1H, m), 2.92 (2H, m), 3.19 (2H, d, J=7.2 Hz), 3.34 to 3.39 (2H, m), 3.55 (2H, t, J=6.6 Hz), 3.80 (2H, t, J=4.8 Hz), 4.16 (2H, t, 4.6 Hz), 4.32 (2H, s), 4.33 (3H, s), 6.93 (1H, d, J=8.8 Hz), 6.98 (2H, d, J=8.8 Hz), 7.38 to 7.56 (7H, m), 7.74 to 7.79 (3H, m).

IR (KBr) 3283, 2957, 1661, 1497, 1314, 1124, 1180, 835, 731 cm$^{-1}$

Elemental Analysis for $C_{36}H_{44}N_6O_4S$ Cald. C, 65.83; N, 12.79; H, 6.75. Found: C, 65.69; N, 12.56; H, 6.76

Example 218

(Preparation of Compound 235)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[(3-pyridinylmethyl)sulfanyl]-3-(trifluoromethyl)aniline (0.43 g) and triethylamine (1.53 ml) in THF (12.9 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(3-pyridinylmethyl)sulfanyl]-3-(trifluoromethyl)phenyl]-2,3-dihydro-1-benzazepine-4-carboxamide (Compound 235) (0.47 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.65 (2H, m), 2.05 (1H, m), 2.91 (2H, m), 3.19 (2H, d, J=7.4 Hz), 3.36 (2H, m), 3.55 (2H, t, J=6.6 Hz), 3.80 (2H, t, J=4.8 Hz), 4.05 (2H, s), 4.13 to 4.18 (2H, m), 6.92 (1H, d, J=8.6 Hz), 6.97 (2H, d, J=8.8 Hz), 7.18 to 7.61 (8H, m), 7.71 (1H, s), 7.73 to 7.79 (1H, m), 7.88 (1H, d, J=2.2 Hz), 8.37 (1H, d, J=2.2 Hz), 8.47 (1H, dd, J=4.6, 1.4 Hz).

Example 219

(Preparation of Compound 236)

To a solution of 7-[4-(2-butoxyethoxy)phenyl]-1-isobutyl-N-[4-[(3-pyridinylmethyl)sulfanyl]-3-(trifluoromethyl)phenyl]-2,3-dihydro-1-benzazepine-4-carboxamide (0.36 g) in methylene chloride (10.8 ml) was added dropwise a solution of m-chloroperbenzoic acid (0.11 g) in methylene chloride (7.2 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(3-pyridinylmethyl)sulfinyl]-3-(trifluoromethyl)phenyl]-2,3-dihydro-1-benzazepine-4-carboxamide (Compound 236) (100 mg).

$^1$H-NMR (200 MHz, CDCl$_3$) δ0.93 (3H, t, J=7.0 Hz), 0.97 (6H, d, J=6.6 Hz), 1.33 to 1.45 (2H, m), 1.54 to 1.68 (2H, m), 2.08 (1H, m), 2.92 (2H, m), 3.20 (2H, d, J=7.8 Hz), 3.37 (2H, m), 3.55 (2H, t, J=6.2 Hz), 3.80 (2H, t, J=4.8 Hz), 3.80 to 3.87 (1H, m), 4.16 (2H, t, J=4.6 Hz), 4.17 to 4.23 (1H, m), 6.90 to 6.95 (1H, m), 6.98 (2H, d, J=8.8 Hz), 7.22 to 7.28 (1H, m), 7.39 to 7.51 (7H, m), 7.61 to 7.67 (1H, m), 7.96 (1H, s), 8.06 (1H, d, J=1.4 Hz), 8.26 (1H, d, J=2.2 Hz), 8.34 (1H, dd, J=4.8, 1.6 Hz).

IR (KBr) 2959, 1667, 1607, 1499, 1321, 1240, 1175, 1127, 910, 816, 733 cm$^{-1}$

Example 220

(Preparation of Compound 237)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(5-methyl-1,3,4-oxadiazol-2-yl)methyl]sulfanyl]aniline (0.33 g) and triethylamine (1.53 ml) in THF (9.9 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(5-methyl-1,3,4-oxadiazol-2-yl)methyl]sulfanyl]phenyl]-2,3-dihydro-1-benzazepine-4-carboxamide (Compound 237) (0.37 g).

$^1$H-NMR (200 MHz, CDCl$_3$) δ 0.93 (3H, t, J=7.4 Hz), 0.96 (6H, d, J=6.6 Hz), 1.33 to 1.45 (2H, m), 1.54 to 1.65 (2H, m), 2.04 (1H, m), 2.46 (3H, s), 2.90 (2H, m), 3.17 (2H, d, J=7.2 Hz), 3.34 (2H, m), 3.55 (2H, t, J=6.6 Hz), 3.77 to 3.83 (2H, m), 4.08 (2H, s), 4.13 (2H, t, J=4.8 Hz), 6.90 (1H, d, J=8.8 Hz), 6.97 (2H, d, J=8.8 Hz), 7.33 to 7.45 (7H, m), 7.57 (2H, d, J=8.4 Hz), 7.82 (1H, s).

Example 221

(Preparation of Compound 238)

To a solution of 7-[4-(2-butoxyethoxy)phenyl]-1-isobutyl-N-[4-[[(5-methyl-1,3,4-oxadiazol-2-yl)methyl]sulfanyl]phenyl]-2,3-dihydro-1-benzazepine-4-carboxamide (0.36 g) in methylene chloride (10.8 ml) was added dropwise a solution of m-chloroperbenzoic acid (0.12 g) in methylene chloride (7.2 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(5-methyl-1,3,4-oxadiazol-2-yl)methyl]sulfinyl]phenyl]-2,3-dihydro-1-benzazepine-4-carboxamide (Compound 238) (230 mg).

$^1$H-NMR (200 MHz, CDCl$_3$) δ 0.93 (3H, t, J=7.4 Hz), 0.98 (6H, d, J=6.2 Hz), 1.33 to 1.45 (2H, m), 1.54 to 1.68 (2H, m), 2.08 (1H, m), 2.48 (3H, s), 2.92 (2H, m), 3.19 (2H, d, J=6.6 Hz), 3.36 (2H, m), 3.55 (2H, t, J=6.6 Hz), 3.78 to 3.83 (2H, m), 4.13 to 4.17 (2H, m), 4.12 (2H, s), 6.92 (1H, d, J=8.8 Hz), 6.98 (2H, d, J=8.8 Hz), 7.38 to 7.57 (7H, m), 7.80 (2H, d, J=8.8 Hz), 7.91 (1H, br).

IR (KBr) 3285, 2955, 1661, 1588, 1497, 1242, 817, 733 cm$^{-1}$

Elemental Analysis for C$_{37}$H$_{44}$N$_4$O$_5$S Cald. C, 67.66; N, 8.53; H, 6.75. Found: C, 67.39; N, 8.36; H, 6.66

Example 222

(Preparation of Compound 239)

7-[4-(2-butoxyethoxy)phenyl]-1-isobutyl-2,3-dihydro-1-benzazepine-4-carboxylic acid (0.62 g) was dissolved in THF (12.4 ml), DMF (2 droplets) was added to the mixture, thionyl chloride (0.21 ml) was added to the mixture, and the mixture was stirred for 1 hour at room temperature. The solvent was removed under reduced pressure, and a solution of the obtained residue in THF (12 ml) was added dropwise to a solution of 3-methoxy-4-[(3-pyridinylmethyl)sulfanyl]aniline (0.38 g) and triethylamine (1.58 ml) in THF (11.4 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[3-methoxy-4-[(3-pyridinylmethyl)sulfanyl]phenyl]-2,3-dihydro-1-benzazepine-4-carboxamide (Compound 239) (0.39 g).

$^1$H-NMR (200 MHz, CDCl$_3$) δ 0.93 (3H, t, J=7.2 Hz), 0.97 (6H, d, J=6.4 Hz), 1.33 to 1.45 (2H, m), 1.57 to 1.68 (2H, m), 2.05 (1H, m), 2.91 (2H, m), 3.19 (2H, d, J=7.2 Hz), 3.33 to 3.38 (2H, m), 3.55 (2H, t, J=6.6 Hz), 3.78 to 3.83 (2H, m), 3.91 (3H, s), 3.99 (2H, s), 4.13 to 4.18 (2H, m), 6.75 (1H, dd, J=8.4, 2.2 Hz), 6.92 (1H, d, J=8 Hz), 6.98 (2H, d, J=8.8 Hz), 7.12 (1H, d, J=8.2 Hz), 7.16 to 7.18 (1H, m), 7.37 to 7.55 (6H, m), 7.63 to 7.66 (2H, m), 8.36 (1H, d, J=2.2 Hz), 8.40 to 8.44 (1H, m).

IR (KBr) 2957, 1655, 1590, 1499, 1242, 1181, 816, 733 cm$^{-1}$

Example 223

(Preparation of Compound 240)

7-[4-(2-butoxyethoxy)phenyl]-1-isobutyl-N-[3-methoxy-4-[(3-pyridinylmethyl)sulfanyl]phenyl]-2,3-dihydro-1-benzazepine-4-carboxamide (0.39 g) was dissolved in methylene chloride (7.8 ml), a solution of m-chloroperbenzoic acid (152 mg) in methylene chloride (15.6 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[3-methoxy-4-[(3-pyridinylmethyl)sulfinyl]phenyl]-2,3-dihydro-1-benzazepine-4-carboxamide (Compound 240) (0.26 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.57 to 1.65 (2H, m), 2.04 (1H, m), 2.91 (2H, m), 3.19 (2H, d, J=7.4 Hz), 3.36 (2H, m), 3.55 (2H, m), 3.70 to 3.83 (2H, m), 3.95 (3H, s), 3.99 (2H, s), 4.01 (1H, d, J=13.2 Hz), 4.13 to 4.21 (3H, m), 6.75 (1H, dd, J=8.4, 1.8 Hz), 6.94 to 7.10 (4H, m), 7.39 to 7.49 (6H, m), 7.94 (1H, d, J=1.4 Hz), 8.02 (1H, d, J=1.4 Hz), 8.47 (1H, dd, J=4.6, 1.4 Hz).

IR (KBr) 3281, 2957, 1661, 1593, 1499, 1402, 1242, 1181, 1030, 816, 733 cm$^{-1}$

Example 224

(Preparation of Compound 241)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(1-ethyl-1,2,3,4-tetrazol-5-yl)methyl]sulfanyl]aniline (0.36 g) and triethylamine (1.53 ml) in THF (10.7 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-ethyl-tetrazol-5-yl)methyl]sulfanyl]phenyl]-2,3-dihydro-1-benzazepine-4-carboxamide (Compound 241) (0.46 g).

$^1$H-NMR (200 MHz, CDCl$_3$) δ 0.93 (3H, t, J=7.0 Hz), 0.97 (6H, d, J=6.6 Hz), 1.33 to 1.65 (4H, m), 1.52 (3H, t, J=7.4 Hz), 2.04 (1H, m), 2.90 (2H, m), 3.17 (2H, d, J=7.2 Hz), 3.33 (2H, m), 3.55 (2H, t, J=6.6 Hz), 3.80 (2H, t, J=4.6 Hz), 4.12 to 4.17 (2H, s), 4.14 (2H, s), 4.27 (2H, q, J=7.4 Hz), 6.90 (1H, d, J=9.0 Hz), 6.96 (2H, d, J=8.6 Hz), 7.24 to 7.56 (5H, m), 7.58 (2H, d, J=7.0 Hz), 8.01 (1H, s).

Example 225

(Preparation of Compound 242)

To a solution of 7-[4-(2-butoxyethoxy)phenyl]-1-isobutyl-N-[4-[[(1-ethyl-tetrazol-5-yl)methyl]sulfanyl]phenyl]-2,3-dihydro-1-benzazepine-4-carboxamide (0.45 g) in methylene chloride (13.5 ml) was added dropwise a solution of m-chloroperbenzoic acid (0.12 g) in methylene chloride (9.0 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-ethyl-tetrazol-5-yl)methyl]sulfinyl]phenyl]-2,3-dihydro-1-benzazepine-4-carboxamide (Compound 242) (221 mg).

$^1$H-NMR (200 MHz, CDCl$_3$) δ 0.93 (3H, t, J=7.2 Hz), 0.99 (6H, d, J=6.6 Hz), 1.33 to 1.65 (4H, m), 1.51 (3H, t, J=7.0 Hz), 2.05 (1H, m), 2.93 (2H, m), 3.20 (2H, d, J=7.2 Hz), 3.35 (2H, m), 3.55 (2H, t, J=6.6 Hz), 3.80 (2H, t, J=4.8 Hz), 4.06 to 4.12 (2H, s) 4.23 to 4.41(4H, m), 6.89 to 6.94 (1H, m), 6.96 (2H, d, J=9.2 Hz), 7.33 to 7.44 (7H, m), 7.82 (2H, d, J=8.6 Hz), 7.82 (2H, d, J=8.6 Hz), 8.19 (1H, s).

IR (KBr) 2957, 1661, 1607, 1588, 1499, 1242, 1179, 1051, 835, 733 cm$^{-1}$

Example 226

(Preparation of Compound 243)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 3-chloro-4-[(3-pyridinylmethyl)sulfanyl]aniline (0.36 g) and triethylamine (1.53 ml) in THF (10.7 ml) under ice-cooling and the mixture was stirred for 1 hour at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[3-chloro-4-[(3-pyridinylmethyl)sulfanyl]phenyl]-1-isobutyl-2,3-dihydro-1-benzazepine-4-carboxamide (Compound 243) (0.31 g).

$^1$H-NMR (200 MHz, CDCl$_3$) δ 0.93 (3H, t, J=7.2 Hz), 0.96 (6H, d, J=6.6 Hz), 1.33 to 1.45 (2H, m), 1.57 to 1.69 (2H, m), 2.05 (1H, m), 2.89 (2H, m), 3.18 (2H, d, J=7.4 Hz), 3.35 (2H, m), 3.55 (2H, t, J=6.6 Hz), 3.80 (2H, m), 4.06 (2H, s), 4.10 to 4.17 (2H, m), 6.91 (1H, d, J=8.8 Hz), 6.97 (2H, d, J=8.8 Hz), 7.17 to 7.67 (10H, m), 7.83 (1H, d, J=2.2 Hz), 7.83 (1H, d, J=2.2 Hz), 8.41 (1H, d, J=2.2 Hz), 8.46 (1H, dd, J=4.6, 1.4 Hz).

Example 227

(Preparation of Compound 244)

To a solution of 7-[4-(2-butoxyethoxy)phenyl]-N-[3-chloro-4-[(3-pyridinylmethyl)sulfanyl]phenyl]-1-isobutyl-2,3-dihydro-1-benzazepine-4-carboxamide (0.30 g) in methylene chloride (9.0 ml) was added dropwise a solution of m-chloroperbenzoic acid (93 g) in methylene chloride (6.0 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-N-[3-chloro-4-[(3-pyridinylmethyl)sulfinyl]phenyl]-1-isobutyl-2,3-dihydro-1-benzazepine-4-carboxamide (Compound 244) (94 mg).

$^1$H-NMR (200 MHz, CDCl$_3$) δ 0.93 (3H, t, J=7.0 Hz), 0.97 (6H, d, J=6.6 Hz), 1.32 to 1.45 (2H, m), 1.57 to 1.65 (2H, m), 2.05 (1H, m), 2.90 (2H, m), 3.19 (2H, d, J=7.2 Hz), 3.34 (2H, m), 3.55 (2H, t, J=6.6 Hz), 4.03 to 4.18 (4H, m), 6.92 (1H, d, J=8.8 Hz), 6.97 (2H, d, J=8.8 Hz), 7.03 to 7.21 (3H, m), 7.39 to 7.49 (6H, m), 7.92 to 8.13 (3H, m), 8.49 (1H, m).

IR (KBr) 3281, 2957, 1667, 1582, 1381, 1242, 1181, 910, 816, 731 cm$^{-1}$

Example 228

(Preparation of Compound 245)

In THF (12 ml) was dissolved 7-[4-(2-butoxyethoxy)phenyl]-N-[4-(hydroxymethyl)phenyl]-1-isobutyl-2,3-dihydro-1-benzazepine-4-carboxamide (0.60 g), and pyridine (3 droplets) and thionyl chloride (0.16 ml) were added to the mixture. The solution was stirred at room temperature for 1 hour, and added dropwise to a solution of 1-methyl-1,2,3,4-tetrazole-5-thiol (154 mg) and triethylamine (1.23 ml) in THF (12 ml) at 0° C. The mixture was stirred at room temperature for 2 hours, and stirred for 16 hours at 50° C.

After allowing to be cooled to room temperature, the reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-methyl-1,2,3,4-tetrazol-5-yl)sulfanyl]methyl]phenyl]-2,3-dihydro-1-benzazepine-4-carboxamide (Compound 245) (520 mg).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.56 to 1.65 (2H, m), 2.05 (1H, m), 2.91 (2H, m), 3.19 (2H, d, J=7.2 Hz), 3.36 (2H, m), 3.55 (2H, t, J=6.6 Hz), 3.78 to 3.81 (2H, m), 3.80 (3H, s), 4.16 (2H, m), 4.51 (2H, s), 6.92 (1H, d, J=8.4 Hz), 6.98 (2H, d, J=8.8 Hz), 7.32 to 7.59 (10H, m).

IR (KBr) 2957, 1653, 1607, 1518, 1499, 1242, 1181, 1167, 818, 733 cm$^{-1}$

Example 229

(Preparation of Compound 246)

7-[4-(2-butoxyethoxy)phenyl]-1-propyl-2,3-dihydro-1-benzazepine-4-carboxylic acid (0.60 g) was dissolved in THF (12 ml), DMF (3 droplets) was added to the mixture, thionyl chloride (0.21 ml) was added to the mixture, and the mixture was stirred for 1 hour at room temperature. The solvent was removed under reduced pressure, and a solution of the obtained residue in THF (12 ml) was added dropwise to a solution of 4-[(3-pyridinylmethyl)sulfanyl]aniline (0.34 g) and triethylamine (1.58 ml) in THF (10.2 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[(3-pyridinylmethyl)sulfanyl]phenyl]-2,3-dihydro-1-benzazepine-4-carboxamide (Compound 246) (0.30 g).

$^1$H-NMR (200 MHz, CDCl$_3$) δ 0.93 (3H, t, J=7.2 Hz), 0.98 (3H, t, J=7.2 Hz), 1.33 to 1.45 (2H, m), 1.57 to 1.80 (4H, m), 2.89 (2H, t, J=4.0 Hz), 3.26 to 3.35 (4H, m), 3.55 (2H, t, J=6.6 Hz), 3.77 to 3.84 (2H, m), 4.00 (2H, s), 4.15 (2H, t, J=4.8 Hz), 6.89 (1H, d, J=8.8 Hz), 6.97 (2H, d, J=8.8 Hz), 7.20 to 7.57 (11H, m), 7.64 (1H, s), 8.39 (1H, d, J=1.8 Hz), 8.46 (1H, dd, J=4.6, 1.4 Hz).

Example 230

(Preparation of Compound 247)

To a solution of 7-[4-(2-butoxyethoxy)phenyl]-1-propyl-N-[4-[(3-pyridinylmethyl)sulfanyl]phenyl]-2,3-dihydro-1-benzazepine-4-carboxamide (0.29 g) in methylene chloride (8.7 ml) was added dropwise a solution of m-chloroperbenzoic acid (120 g) in methylene chloride (5.8 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[(3-pyridinylmethyl)sulfinyl]phenyl]-2,3-dihydro-1-benzazepine-4-carboxamide (Compound 247) (125 mg).

$^1$H-NMR (200 MHz, CDCl$_3$) δ 0.93 (3H, t, J=7.0 Hz), 0.99 (3H, t, J=7.4 Hz), 1.33 to 1.45 (2H, m), 1.54 to 1.85 (4H, m), 2.91 (2H, m), 3.28 to 3.36 (4H, m), 3.55 (2H, t, J=6.6 Hz), 3.77 to 3.83 (2H, m), 3.90 (1H, d, J=13.2 Hz), 4.08 (1H, d, J=13.2 Hz), 4.12 to 4.18 (2H, m), 6.90 (1H, d, J=8.6 Hz), 6.97 (2H, d, J=8.4 Hz), 7.18 to 7.26 (2H, m), 7.29 to 7.49 (6H, s), 7.69 (2H, d, J=8.8 Hz), 7.91 to 8.02 (2H, m), 8.49 to 8.53 (1H, m).

IR (KBr) 3277, 2961, 1661, 1607, 1501, 1246, 910, 818, 731 cm$^{-1}$

Example 231

(Preparation of Compound 248)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(2-methoxy-3-pyridinyl)methyl]sulfanyl]aniline (0.37 g) and triethylamine (1.53 ml) in THF (11.1 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(2-methoxy-3-pyridinyl)methyl]sulfanyl]phenyl]-2,3-dihydro-1-benzazepine-4-carboxamide (Compound 248) (0.49 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.55 to 1.66 (2H, m), 2.05 (1H, m), 2.90 (2H, m), 3.18 (2H, d, J=7.8 Hz), 3.35 (2H, t, J=4.4 Hz), 3.55 (2H, t, J=6.2 Hz), 3.77 to 3.83 (2H, m), 3.96 (3H, s), 4.02 (2H, s), 4.15 (2H, t, J=4.8 Hz), 6.76 (1H, dd, J=7.2, 5.0 Hz), 6.91 (1H, d, J=8.4 Hz), 6.97 (2H, d, J=8.8 Hz), 7.27 to 7.56 (11H, m), 8.04 (1H, dd, J=5.0, 1.8 Hz).

Example 232

(Preparation of Compound 249)

To a solution of 7-[4-(2-butoxyethoxy)phenyl]-1-isobutyl-N-[4-[[(2-methoxy-3-pyridinyl)methyl]sulfanyl]phenyl]-2,3-dihydro-1-benzazepine-4-carboxamide (0.48 g) in methylene chloride (14.4 ml) was added dropwise a solution of m-chloroperbenzoic acid (187 g) in methylene chloride (9.6 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine, and dried over magnesium sulfate. The solvent was removed under reduced pressure, and the obtained residue was purified by silica gel column chromatography, and recrystallized from ethanol, to give 7-[4-(2-butoxyethoxy)phenyl]-1-isobutyl-N-[4-[[(2-methoxy-3-pyridinyl)methyl]sulfinyl]phenyl]-2,3-dihydro-1-benzazepine-4-carboxamide (Compound 249) (267 mg).

$^1$H-NMR (200 MHz, CDCl$_3$) δ 0.93 (3H, t, J=7.2 Hz), 0.98 (6H, d, J=6.6 Hz), 1.30 to 1.45 (2H, m), 1.52 to 1.65 (2H, m), 2.08 (1H, m), 2.92 (2H, m), 3.20 (2H, d, J=7.4 Hz), 3.37 (2H, m), 3.55 (2H, t, J=6.4 Hz), 3.78 (3H, s), 3.78 to 3.83 (2H, m), 3.98 (1H, d, J=12.0 Hz), 4.13 (1H, d, J=12.0

Hz), 4.13 to 4.19 (2H, m), 6.79 to 7.00 (3H, m), 6.98 (2H, d, J=8.8 Hz), 7.30 to 7.53 (8H, m), 7.70 (2H, d, J=8.8 Hz), 7.74 (1H, s), 8.04 (1H, dd, J=5.2, 1.8 Hz).

IR (KBr) 2955, 1661, 1587, 1499, 1310, 1242, 1179, 1032, 816, 733 cm$^{-1}$

Elemental Analysis for $C_{40}H_{47}N_3O_5S$ Cald. C, 70.46; N, 6.16; H, 6.95. Found: C, 70.37; N, 6.00; H, 6.73.

Example 233

(Preparation of Compound 250)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 4-[[(2-methyl-3-pyridinyl)methyl]sulfanyl] aniline (0.35 g) and triethylamine (1.53 ml) in THF (10.5 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(2-methyl-3-pyridinyl)methyl]sulfanyl]phenyl]-2,3-dihydro-1-benzazepine-4-carboxamide (Compound 250) (0.28 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.57 to 1.66 (2H, m), 2.04 (1H, m), 2.59 (3H, s), 2.91 (2H, m), 3.18 (2H, d, J=7.4 Hz), 3.32 to 3.38 (2H, m), 3.55 (2H, t, J=6.6 Hz), 3.77 to 3.83 (2H, m), 4.00 (2H, s), 4.12 to 4.18 (2H, m), 6.89 to 7.03 (4H, m), 7.27 (2H, d, J=8.8 Hz), 7.37 to 7.54 (8H, m), 7.65 (1H, s), 8.38 (1H, dd, J=4.8, 1.8 Hz).

Example 234

(Preparation of Compound 251)

To a solution of 7-[4-(2-butoxyethoxy)phenyl]-1-isobutyl-N-[4-[[(2-methyl-3-pyridinyl)methyl]sulfanyl]phenyl]-2,3-dihydro-1-benzazepine-4-carboxamide (0.27 g) in methylene chloride (8.1 ml) was added dropwise a solution of m-chloroperbenzoic acid (86 mg) in methylene chloride (5.4 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, and recrystallized from ethanol, to give 7-[4-(2-butoxyethoxy)phenyl]-1-isobutyl-N-[4-[[(2-methyl-3-pyridinyl)methyl]sulfinyl]phenyl]-2,3-dihydro-1-benzazepine-4-carboxamide (Compound 251) (148 mg).

$^1$H-NMR (200 MHz, CDCl$_3$) δ 0.93 (3H, t, J=7.0 Hz), 0.97 (6H, d, J=6.2 Hz), 1.30 to 1.48 (2H, m), 1.54 to 1.65 (2H, m), 2.08 (1H, m), 2.35 (3H, s), 2.92 (2H, m), 3.19 (2H, d, J=7.4 Hz), 3.37 (2H, m), 3.55 (2H, t, J=6.6 Hz), 3.78 to 3.83 (2H, m), 4.02 (1H, d, J=12.8 Hz), 4.10 to 4.18 (3H, m), 6.90 to 7.09 (5H, m), 7.20 to 7.51 (7H, m), 7.71 (2H, d, J=8.8 Hz), 7.83 (1H, s), 8.43 (1H, dd, J=4.8, 1.8 Hz).

IR (KBr) 2957, 1651, 1499, 1464, 1242, 1167, 816, 733 cm$^{-1}$

Elemental Analysis for $C_{40}H_{47}N_3O_4S$ Cald. C, 72.15; N, 6.31; H, 7.11. Found: C, 72.11; N, 6.24; H, 7.10.

Example 235

(Preparation of Compound 252)

7-[4-(2-butoxyethoxy)phenyl]-1-isobutyl-2,3-dihydro-1-benzazepine-4-carboxylic acid (0.70 g) was dissolved in THF (14 ml), DMF (3 droplets) was added to the mixture, thionyl chloride (0.23 ml) was added to the mixture, and the mixture was stirred for 1 hour at room temperature. The solvent was removed under reduced pressure, and a solution of the obtained residue in THF (14 ml) was added dropwise to a solution of 4-[[(6-methyl-3-pyridinyl)methyl]sulfanyl] aniline (0.41 g) and triethylamine (1.78 ml) in THF (12.3 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(6-methyl-3-pyridinyl)methyl]sulfanyl]phenyl]-2,3-dihydro-1-benzazepine-4-carboxamide (Compound 252) (0.21 g).

$^1$H-NMR (200 MHz, CDCl$_3$) δ 0.93 (3H, t, J=7.2 Hz), 0.96 (6H, d, J=6.2 Hz), 1.33 to 1.45 (2H, m), 1.54 to 1.65 (2H, m), 2.05 (1H, m), 2.52 (3H, s), 2.89 (2H, m), 3.17 (2H, d, J=7.2 Hz), 3.34 (2H, m), 3.55 (2H, t, J=6.6 Hz), 3.80 (2H, t, J=4.4 Hz), 3.98 (2H, s), 4.10 to 4.17 (2H, m), 6.88 to 7.08 (4H, m), 7.27 (2H, d, J=8.8 Hz), 7.29 to 7.54 (8H, m), 7.68 (1H, s), 8.27 (1H, dd, J=2.2 Hz).

Example 236

(Preparation of Compound 253)

To a solution of 7-[4-(2-butoxyethoxy)phenyl]-1-isobutyl-N-[4-[[(6-methyl-3-pyridinyl)methyl]sulfanyl]phenyl]-2,3-dihydro-1-benzazepine-4-carboxamide (0.20 g) in methylene chloride (6.0 ml) was added dropwise a solution of m-chloroperbenzoic acid (80 mg) in methylene chloride (4.0 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography and recrystallized from ethanol, to give 7-[4-(2-butoxyethoxy)phenyl]-1-isobutyl-N-[4-[[(6-methyl-3-pyridinyl)methyl]sulfinyl]phenyl]-2,3-dihydro-1-benzazepine-4-carboxamide (Compound 253) (104 mg).

$^1$H-NMR (200 MHz, CDCl$_3$) δ 0.93 (3H, t, J=7.2 Hz), 0.98 (6H, d, J=6.6 Hz), 1.33 to 1.45 (2H, m), 1.54 to 1.68 (2H, m), 2.05 (1H, m), 2.53 (3H, s), 2.93 (2H, m), 3.20 (2H, d, J=7.4 Hz), 3.37 (2H, m), 3.55 (2H, t, J=6.6 Hz), 3.78 to 3.84 (2H, m), 3.91 (1H, d, J=13.2 Hz), 4.06 (1H, d, J=13.2 Hz), 4.16 (2H, t, J=4.6 Hz), 6.90 to 6.95 (1H, m), 6.98 (2H, d, J=8.8 Hz), 7.09 (1H, d, J=8.2 Hz), 7.26 to 7.53 (8H, m), 7.68 to 7.73 (3H, m), 7.91 (1H, s).

IR (KBr) 327.3, 2957, 1661, 1499, 1246, 833, 733 cm$^{-1}$

Elemental Analysis for $C_{40}H_{47}N_3O_4S$ Cald. C, 72.15; N, 6.21; H, 7.11. Found: C, 72.07; N, 6.46; H, 7.26.

Example 237

(Preparation of Compound 254)

7-[4-(2-butoxyethoxy)phenyl]-1-propyl-2,3-dihydro-1-benzazepine-4-carboxylic acid (0.60 g) was dissolved in THF (12 ml), DMF (2 droplets) was added to the mixture, thionyl chloride (0.21 ml) was added to the mixture and the solution was stirred at room temperature for 1 hour. The solution was added dropwise to a solution of 3-methoxy-4-[(3-pyridinylmethyl)sulfanyl]aniline (0.37 g) and triethylamine (2.96 ml) in THF (11.1 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[3-methoxy-4-[(3-pyridinylmethyl)sulfanyl]phenyl]-1-propyl-2,3-dihydro-1-benzazepine-4-carboxamide (Compound 254) (0.50 g).

$^1$H-NMR (200 MHz, CDCl$_3$) δ 0.93 (3H, t, J=7.0 Hz), 0.98 (3H, t, J=7.4 Hz), 1.33 to 1.45 (2H, m), 1.57 to 1.77 (4H, m), 2.90 (2H, m), 3.28 to 3.36 (4H, m), 3.55 (2H, t, J=6.6 Hz), 3.78 to 3.83 (2H, m), 3.91 (3H, s), 3.99 (2H, s), 4.13 to 4.18 (2H, m), 6.74 (1H, dd, J=8.0, 1.8 Hz), 6.89 (1H, d, J=8.8 Hz), 6.98 (2H, d, J=8.8 Hz), 7.10 to 7.20 (2H, m), 7.39 to 7.55 (6H, m), 7.62 to 7.65 (2H, m), 8.36 (1H, d, J=2.2 Hz), 8.42 (1H, dd, J=4.6, 1.4 Hz).

IR (KBr) 3295, 2957, 1655, 1591, 1499, 1242, 812, 733 cm$^{-1}$

Example 238

(Preparation of Compound 255)

7-[4-(2-butoxyethoxy)phenyl]-N-[3-methoxy-4-[(3-pyridinylmethyl)sulfanyl]phenyl]-1-propyl-2,3-dihydro-1-benzazepine-4-carboxamide (0.42 g) was dissolved in methylene chloride (12.6 ml), and a solution of m-chloroperbenzoic acid (133 mg) in methylene chloride (8.4 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[3-methoxy-4-[(3-pyridinylmethyl)sulfinyl]phenyl]-1-propyl-2,3-dihydro-1-benzazepine-4-carboxamide (Compound 255) (0.18 g).

$^1$H-NMR (200 MHz, CDCl$_3$) δ 0.93 (3H, t, J=7.2 Hz), 0.99 (3H, t, J=7.2 Hz), 1.33 to 1.45 (2H, m), 1.54 to 1.81 (4H, m), 2.90 (2H, m), 3.28 to 3.33 (4H, m), 3.55 (2H, t, J=6.6 Hz), 3.80 (2H, t, J=4.8 Hz), 3.94 (3H, s), 4.00 (1H, d, J=13.2 Hz), 4.13 to 4.20 (3H, m), 6.74 (1H, dd, J=8.2, 2.0 Hz), 6.89 to 7.22 (5H, m), 7.40 to 7.50 (6H, m), 7.83 (1H, m), 7.94 (1H, d, J=1.8 Hz), 8.03 (1H, d, J=1.8 Hz), 8.47 (1H, dd, J=4.6, 1.4 Hz).

IR (KBr) 3285, 2957, 1653, 1593, 1499, 1321, 1236, 1030, 910, 814, 733 cm$^{-1}$

Elemental Analysis for C$_{40}$H$_{47}$N$_3$O$_5$S.H$_2$O Cald. C, 68.30; N, 6.13; H, 6.91. Found: C, 68.54; N, 5.93; H, 6.92.

Example 239

(Preparation of Compound 256)

7-[4-(2-butoxyethoxy)phenyl]-1-isobutyl-2,3-dihydro-1-benzazepine-4-carboxylic acid (0.60 g) was dissolved in THF (12 ml), DMF (2 droplets) was added to the mixture, thionyl chloride (0.20 ml) was added to the mixture and the solution was stirred at room temperature for 1 hour. The solution was added dropwise to a solution of 4-[(2-pyradinylmethyl)sulfanyl]aniline (0.33 g) and triethylamine (2.87 ml) in THF (9.8 ml) under ice-cooling and the mixture was stirred at room temperature for 40 hours. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyradinylmethyl)sulfanyl]phenyl]-2,3-dihydro-1-benzazepine-4-carboxamide (Compound 256) (0.43 g).

$^1$H-NMR (200 MHz, CDCl$_3$) δ 0.93 (3H, t, J=7.2 Hz), 0.96 (6H, d, J=6.6 Hz), 1.33 to 1.45 (2H, m), 1.54 to 1.68 (2H, m), 2.04 (1H, m), 2.89 (2H, m), 3.18 (2H, d, J=7.2 Hz), 3.32 to 3.37 (2H, m), 3.55 (2H, t, J=6.6 Hz), 3.80 (2H, t, J=4.8 Hz), 4.12 to 4.15 (2H, m), 4.19 (2H, s), 6.91 (1H, d, J=8.8 Hz), 6.97 (2H, d, J=8.8 Hz), 7.28 to 7.61 (1H, m), 8.41 to 8.50 (2H, m).

IR (KBr) 3301, 2957, 1651, 1607, 1589, 1499, 1397, 1242, 1181, 1123, 818, 733 cm$^{-1}$

Example 240

(Preparation of Compound 257)

7-[4-(2-butoxyethoxy)phenyl]-1-isobutyl-N-[4-[(2-pyradinylmethyl)sulfanyl]phenyl]-2,3-dihydro-1-benzazepine-4-carboxamide (0.43 g) was dissolved in methylene chloride (12.9 ml), and a solution of m-chloroperbenzoic acid (0.14 g) in methylene chloride (8.6 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyradinylmethyl)sulfinyl]phenyl]-2,3-dihydro-1-benzazepine-4-carboxamide (Compound 257) (226 mg).

$^1$H-NMR (200 MHz, CDCl$_3$) δ 0.93 (3H, t, J=7.0 Hz), 0.97 (6H, d, J=6.6 Hz), 1.33 to 1.45 (2H, m), 1.54 to 1.64 (2H, m), 2.08 (1H, m), 2.92 (2H, m), 3.19 (2H, d, J=7.4 Hz), 3.37 (2H, m), 3.55 (2H, t, J=6.6 Hz), 3.80 (2H, t, J=4.8 Hz), 4.16 (2H, t, J=4.8 Hz), 4.32 (2H, s), 6.92 (1H, d, J=8.8 Hz), 6.98 (2H, d, J=8.8 Hz), 7.38 to 7.59 (7H, m), 7.72 to 7.80 (3H, m), 8.36 (1H, s), 8.49 (2H, d, J=2.6 Hz).

IR (KBr) 3289, 2957, 1661, 1588, 1499, 1397, 1312, 1244, 1179, 833, 733 cm$^{-1}$

Elemental Analysis for C$_{38}$H$_{44}$N$_3$O$_5$S Cald. C, 69.91; N, 8.58; H, 6.79. Found: C, 69.78; N, 8.67; H, 6.98.

Example 241

(Preparation of Compound 258)

7-[4-(2-butoxyethoxy)phenyl]-1-isobutyl-2,3-dihydro-1-benzazepine-4-carboxylic acid (0.80 g) was dissolved in THF (16 ml), DMF (2 droplets) was added to the mixture, thionyl chloride (0.20 ml) was added to the mixture, and the solution was stirred at room temperature for 1 hour. The solution was added dropwise to a solution of 4-[(3-pyridazinylmethyl)sulfanyl]aniline (0.44 g) and triethylamine (2.55 ml) in THF (13.2 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified with silica gel column chromatography, to give 7-[4-(2-butoxyethoxy)phenyl]-1-isobutyl-N-[4-[(3-pyridazinylmethyl)sulfanyl]phenyl]-2,3-dihydro-1-benzazepine-4-carboxamide (Compound 258) (0.16 g).

$^1$H-NMR (200 MHz, CDCl$_3$) δ 0.93 (3H, t, J=7.2 Hz), 0.96 (6H, d, J=6.6 Hz), 1.33 to 1.45 (2H, m), 1.55 to 1.65 (2H, m), 2.04 (1H, m), 2.89 (2H, m), 3.18 (2H, d, J=6.8 Hz), 3.34 (2H, m), 3.55 (2H, t, J=6.6 Hz), 3.78 to 3.83 (2H, m), 4.13 to 4.18 (2H, m), 4.38 (2H, s), 6.91 (1H, d, J=8.8 Hz), 6.97 (2H, d, J=8.8 Hz), 7.31 to 7.54 (11H, m), 7.70 (1H, s), 9.01-9.05 (1H, m).

Example 242

(Preparation of Compound 259)

7-[4-(2-butoxyethoxy)phenyl]-1-isobutyl-N-[4-[(3-pyridazinylmethyl)sulfanyl]phenyl]-2,3-dihydro-1-benzazepine-4-carboxamide (0.15 g) was dissolved in methylene chloride (6.0 ml), and a solution of m-chloroperbenzoic acid (61 mg) in methylene chloride (4.5 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(3-pyridazinylmethyl)sulfinyl]phenyl]-2,3-dihydro-1-benzazepine-4-carboxamide (Compound 259) (62 mg).

$^1$H-NMR (200 MHz, CDCl$_3$) δ 0.93 (3H, t, J=7.2 Hz), 0.98 (6H, d, J=6.6 Hz), 1.33 to 1.43 (2H, m), 1.54 to 1.62 (2H, m), 2.04 (1H, m), 2.92 (2H, m), 3.20 (2H, d, J=7.6 Hz), 3.36 (2H, m), 3.55 (2H, t, J=6.6 Hz), 3.78 to 3.83 (2H, m), 4.13 to 4.19 (2H, m), 4.27 (1H, d, J=13.2 Hz), 4.38 (1H, d, J=13.2 Hz), 6.89 to 7.00 (3H, m), 7.36 to 7.46 (9H, m), 7.72 (2H, d, J=8.4 Hz), 8.01 (1H, m), 9.08 (1H, dd, J=4.4, 1.8 Hz).

IR (KBr) 3291, 2955, 1661, 1588, 1499, 1244, 1181, 816, 733 cm$^{-1}$

Example 243

(Preparation of Compound 260)

7-[4-(2-butoxyethoxy)phenyl]-1-isobutyl-2,3-dihydro-1-benzazepine-4-carboxylic acid (1.0 g) was dissolved in THF (10 ml), DMF (2 droplets) was added to the mixture, thionyl chloride (0.25 ml) was added to the mixture, and the mixture was stirred for 1 hour at room temperature. The solvent was removed under reduced pressure, and a solution of the obtained residue in THF (20 ml) was added dropwise to a solution of S-(4-aminophenyl)O-carbonothioate (0.59 g) and triethylamine (1.91 ml) in THF (17.7 ml) under ice-cooling and the mixture was stirred for 2 hours at room temperature. Methanol (40 ml) and 1N sodium hydroxide (15 ml) were added to the mixture, the mixture was stirred for 30 minutes, 2-(chloromethyl)pyrimidine (0.35 g) was added to the mixture, and the mixture was stirred for 30 minutes at room temperature. The solvent was removed under reduced pressure, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyrimidinylmethyl)sulfanyl]phenyl]-2,3-dihydro-1-benzazepine-4-carboxamide (Compound 260) (0.94 g).

$^1$H-NMR (200 MHz, CDCl$_3$) δ 0.93 (3H, t, J=7.4 Hz), 0.96 (6H, d, J=6.6 Hz), 1.33 to 1.45 (2H, m), 1.55 to 1.68 (2H, m), 2.04 (1H, m), 2.89 (2H, m), 3.17 (2H, d, J=7.4 Hz), 3.30 to 3.36 (2H, m), 3.55 (2H, t, J=6.6 Hz), 3.77 to 3.83 (2H, m), 4.15 (2H, t, J=4.8 Hz), 4.34 (2H, s), 6.91 (1H, d, J=8.4 Hz), 6.97 (2H, d, J=8.8 Hz), 7.15 (1H, t, J=4.8 Hz), 7.34 to 7.60 (10H, m), 8.68 (2H, d, J=4.6 Hz).

IR (KBr) 3285, 2957, 1653, 1586, 1497, 1420, 1242, 1181, 1123, 816, 731 cm$^{-1}$

Example 244

(Preparation of Compound 261)

7-[4-(2-butoxyethoxy)phenyl]-1-isobutyl-N-[4-[(2-pyrimidinylmethyl)sulfanyl]phenyl]-2,3-dihydro-1-benzazepine-4-carboxamide (0.77 g) was dissolved in methylene chloride (23.1 ml), and a solution of m-chloroperbenzoic acid (0.31 g) in methylene chloride (15.4 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(2-pyrimidinylmethyl)sulfinyl]phenyl]-2,3-dihydro-1-benzazepine-4-carboxamide (Compound 261) (485 mg).

$^1$H-NMR (200 MHz, CDCl$_3$) δ 0.93 (3H, t, J=7.0 Hz), 0.97 (6H, d, J=6.6 Hz), 1.33 to 1.45 (2H, m), 1.57 to 1.67 (2H, m), 2.08 (1H, m), 2.92 (2H, m), 3.19 (2H, d, J=7.4 Hz), 3.33 to 3.39 (2H, m), 3.55 (2H, t, J=6.2 Hz), 3.78 to 3.83 (2H, m), 4.13 to 4.18 (2H, m), 4.35 (1H, d, J=12.4 Hz), 4.52 (1H, d, J=12.4 Hz), 6.92 (1H, d, J=8.4 Hz), 6.98 (2H, d, J=8.8 Hz), 7.22 (1H, t, J=4.8 Hz), 7.38 to 7.51 (5H, m), 7.58 (2H, d, J=8.8 Hz), 7.74 (2H, d, J=8.8 Hz), 7.83 (1H, m), 8.71 (2H, d, J=5.2 Hz).

IR (KBr) 3287, 2957, 1661, 1499, 1422, 1244, 1040, 833, 733 cm$^{-1}$

Example 245

(Preparation of Compound 262)

7-[4-(2-butoxyethoxy)phenyl]-1-isobutyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (16 ml) was added dropwise to a solution of 4-[2-(1-propylimidazol-2-yl)ethyl]aniline (0.39 g) and triethylamine (2.04 ml) in THF (11.7 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[2-(1-propylimidazol-2-yl)ethyl]phenyl]-2,3-dihydro-1-benzazepine-4-carboxamide (Compound 262) (0.60 g).

$^1$H-NMR (200 MHz, CDCl$_3$) δ 0.89 (3H, t, J=7.2 Hz), 0.93 (3H, t, J=7.2 Hz), 0.97 (6H, d, J=6.6 Hz), 1.33 to 1.45 (2H, m), 1.54 to 1.73 (4H, m), 2.06 (1H, m), 2.87 to 2.96 (4H, m), 3.06 to 3.11 (2H, m), 3.19 (2H, d, J=6.8 Hz), 3.33 to 3.40 (2H, m), 3.55 (2H, t, J=6.6 Hz), 3.66 (2H, t, J=7.0 Hz), 3.78 to 3.83 (2H, m), 4.16 (2H, t, J=4.8 Hz), 6.80 (1H, d, J=1.4 Hz), 6.89 to 7.00 (4H, m), 7.16 (2H, d, J=8.4 Hz), 7.36 to 7.56 (8H, m).

IR (KBr) 2959, 1651, 1605, 1499, 1244, 1181, 1124, 816, 733 cm$^{-1}$

Example 246

(Preparation of Compound 263)
7-[4-(2-butoxyethoxy)phenyl]-1-isobutyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (16 ml) was added dropwise to a solution of 2-[(E)-2-(4-nitrophenyl)ether]-1-propylimidazole (0.38 g) and triethylamine (2.04 ml) in THF (7.6 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[(E)-2-(1-propylimidazol-2-yl)ether]phenyl]-2,3-dihydro-1-benzazepine-4-carboxamide (Compound 263) (0.43 g).

$^1$H-NMR (200 MHz, CDCl$_3$) δ 0.83 (3H, t, J=7.2 Hz), 0.93 (3H, t, J=6.8 Hz), 0.97 (6H, d, J=6.6 Hz), 1.33 to 1.45 (2H, m), 1.57 to 1.70 (4H, m), 2.06 (1H, m), 2.89 (2H, m), 3.18 (2H, d, J=7.2 Hz), 3.31 to 3.38 (2H, m), 3.55 (2H, t, J=6.6 Hz), 3.66 (2H, t, J=7.0 Hz), 3.80 (2H, t, J=4.8 Hz), 4.13 to 4.18 (2H, m), 6.29 (1H, d, J=12.2 Hz), 6.73 (1H, d, J=12.4 Hz), 6.86 to 7.00 (5H, m), 7.12 (1H, m), 7.28 to 7.81 (9H, m).

IR (KBr) 2957, 1657, 1605, 1499, 1244, 1181, 1121, 723, 542 cm$^{-1}$

Example 247

(Preparation of Compound 264)
7-[4-(2-butoxyethoxy)phenyl]-1-isobutyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (16 ml) was added dropwise to a solution of N-methyl-N-[(1-propylimidazol-2-yl)methyl]-1,4-benzodiamine (0.38 g) and triethylamine (2.04 ml) in THF (7.6 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[methyl[(1-propylimidazol-2-yl)methyl]amino]phenyl]-2,3-dihydro-1-benzazepine-4-carboxamide (Compound 264) (0.92 g).

$^1$H-NMR (200 MHz, CDCl$_3$) δ 0.86 (3H, t, J=7.2 Hz), 0.93 (3H, t, J=7.2 Hz), 0.97 (6H, d, J=6.6 Hz), 1.33 to 1.45 (2H, m), 1.54 to 1.77 (4H, m), 2.06 (1H, m), 2.82 (3H, m), 2.91 (2H, m), 3.17 (2H, d, J=7.2 Hz), 3.32 to 3.37 (2H, M), 3.55 (2H, t, J=6.6 Hz), 3.77 to 3.87 (4H, m), 4.15 (2H, t, J=4.8 Hz), 4.46 (2H, s), 6.86 to 7.01 (7H, m), 7.35 to 7.52 (8H, m).

IR (KBr) 2961, 1645, 1607, 1497, 1244, 1121, 922, 816, 731 cm$^{-1}$

Example 248

(Preparation of Compound 265)
7-[4-(2-butoxyethoxy)phenyl]-1-isobutyl-2,3-dihydro-1-benzazepine-4-carboxylic acid (0.70 g) was dissolved in THF (7.0 ml), DMF (3 droplets) was added to the mixture, thionyl chloride (0.18 ml) was added to the mixture, and the mixture was stirred for 1 hour at room temperature. The solvent was removed under reduced pressure, and a solution of the obtained residue in THF (14 ml) was added dropwise to a solution of 4-[[2-(imidazol-1-yl)ethyl]sulfanyl]phenylamine (0.39 g) and triethylamine. (1.78 ml) in THF (7.8 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[2-(imidazol-1-yl)ethyl]sulfanyl]phenyl]-1-isobutyl-2,3-dihydro-1-benzazepine-4-carboxamide (Compound 265) (0.56 g).

$^1$H-NMR (200 MHz, CDCl$_3$) δ 0.93 (3H, t, J=7.2 Hz), 0.97 (6H, d, J=6.6 Hz), 1.33 to 1.45 (2H, m), 1.54 to 1.67 (2H, m), 2.07 (1H, m), 2.92 (2H, m), 3.16 (2H, d, J=7.0 Hz), 3.16 to 3.20 (2H, m), 3.33 to 3.38 (2H, m), 3.55 (2H, t, J=6.6 Hz), 3.80 (2H, t, J=4.6 Hz), 4.08 (2H, t, J=6.6 Hz), 4.12 to 4.18 (2H, m), 6.89 (1H, s), 6.93 to 7.00 (3H, m), 7.05 (H, s), 7.34 to 7.48 (8H, m), 7.58 (1H, s), 7.62 (1H, s), 7.83 (1H, s).

Example 249

(Preparation of Compound 266)
7-[4-(2-butoxyethoxy)phenyl]-N-[4-[[2-(imidazol-1-yl)ethyl]sulfanyl]phenyl]-1-isobutyl-2,3-dihydro-1-benzazepine-4-carboxamide (0.50 g) was dissolved in methylene chloride (15 ml), and a solution of m-chloroperbenzoic acid (0.20 g) in methylene chloride (10 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[2-(imidazol-1-yl)ethyl]sulfinyl]phenyl]-1-isobutyl-2,3-dihydro-1-benzazepine-4-carboxamide (Compound 266) (60 mg).

¹H-NMR (200 MHz, CDCl₃) δ 0.92 (3H, t, J=7.4 Hz), 0.96 (6H, d, J=6.6 Hz), 1.33 to 1.44 (2H, m), 1.53 to 1.64 (2H, m), 2.04 (1H, m), 2.91 (2H, m), 3.04 to 3.11 (2H, m), 3.18 (2H, d, J=7.4 Hz), 3.35 (2H, m), 3.54 (2H, t, J=6.4 Hz), 3.77 to 3.83 (2H, m), 4.06 to 4.22 (3H, m), 4.36 to 4.56 (1H, m), 6.89 to 6.99 (4H, m), 7.07 (1H, s), 7.37 to 7.56 (8H, m), 7.37 to 7.56 (8H, m), 7.79 (1H, s), 7.83 (1H, s), 8.16 (1H, s).

Example 250

(Preparation of Compound 267)

7-[4-(2-butoxyethoxy)phenyl]-1-isobutyl-2,3-dihydro-1-benzazepine-4-carboxylic acid (0.60 g) was dissolved in THF (12 ml), DMF (3 droplets) was added to the mixture, oxalyl chloride (0.24 ml) was added to the mixture, and the mixture was stirred for 1 hour at room temperature. The solvent was removed under reduced pressure, and a solution of the obtained residue in THF (12 ml) was added dropwise to a solution of 6-[(2-pyridinylmethyl)sulfanyl]-3-pyridineamine (0.33 g) and triethylamine (1.15 ml) in THF (9.9 ml) under ice-cooling and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[(2-pyridinylmethyl)sulfanyl]-3-pyridinyl]-2,3-dihydro-1-benzazepine-4-carboxamide (Compound 267) (0.51 g).

¹H-NMR (200 MHz, CDCl₃) δ 0.93 (3H, t, J=7.4 Hz), 0.96 (6H, d, J=6.6 Hz), 1.33 to 1.44 (2H, m), 1.57 to 1.67 (2H, m), 2.05 (1H, m), 2.90 (2H, m), 3.18 (2H, d, J=7.2 Hz), 3.32 to 3.37 (2H, m), 3.51 to 3.58 (2H, m), 3.80 (2H, t, J=4.8 Hz), 4.05 (2H, d, J=4.6 Hz), 4.55 (2H, s), 6.91 (1H, d, J=8.4 Hz), 6.96 (2H, d, J=8.8 Hz), 7.12 to 7.22 (2H, m), 7.37 to 7.59 (7H, m), 7.71 (1H, s), 7.97 (1H, dd, J=8.4, 2.6 Hz), 8.52 to 8.56 (2H, m).

Example 251

(Preparation of Compound 268)

To a solution of 7-[4-(2-butoxyethoxy)phenyl]-1-isobutyl-N-[6-[(2-pyridinylmethyl)sulfanyl]-3-pyridinyl]-2,3-dihydro-1-benzazepine-4-carboxamide (0.50 g) in methylene chloride (15 ml) was added dropwise a solution of m-chloroperbenzoic acid (0.16 g) in methylene chloride (10 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-1-isobutyl-N-[6-[(2-pyridinylmethyl)sulfinyl]-3-pyridinyl]-2,3-dihydro-1-benzazepine-4-carboxamide (Compound 268) (275 mg).

¹H-NMR (200 MHz, CDCl₃) δ 0.93 (3H, t, J=7.4 Hz), 0.98 (6H, d, J=6.6 Hz), 1.33 to 1.48 (2H, m), 1.54 to 1.63 (2H, m), 2.08 (1H, m), 2.93 (2H, m), 3.20 (2H, d, J=7.0 Hz), 3.38 (2H, m), 3.55 (2H, t, J=6.2 Hz), 3.80 (2H, t, J=4.8 Hz), 4.13 to 4.18 (2H, m), 4.24 (1H, d, J=12.8 Hz), 4.51 (1H, d, J=13.0 Hz), 6.90 to 6.95 (1H, m), 6.98 (2H, d, J=9.0 Hz), 7.16 to 7.23 (2H, m), 7.36 to 7.48 (5H, m), 7.58 to 7.66 (2H, m), 8.02 (1H, m), 8.27 to 8.33 (1H, m), 8.50 (1H, d, J=4.8 Hz), 8.76 (1H, d, J=2.2 Hz).

IR (KBr) 3297, 2955, 1645, 1501, 1242, 1049, 812 cm⁻¹

Elemental Analysis for C₃₈H₄₄N₄O₄S Cald. C, 69.91; N, 8.58; H, 6.65. Found: C, 69.93; N, 8.52; H, 6.51.

Example 252

(Preparation of Compound 269)

7-[4-(2-butoxyethoxy)phenyl]-1-isobutyl-2,3-dihydro-1-benzazepine-4-carboxylic acid (0.60 g) was dissolved in THF (12 ml), DMF (2 droplets) was added to the mixture, thionyl chloride (0.20 ml) was added to the mixture, and the mixture was stirred for 1 hour at room temperature. The solvent was removed under reduced pressure, and a solution of the obtained residue in THF (12 ml) was added dropwise to a solution of 6-[(3-pyridinylmethyl)sulfanyl]-3-pyridinylamine (0.33 g) and triethylamine (1.53 ml) in THF (9.9 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[(3-pyridinylmethyl)sulfanyl]-3-pyridinyl]-2,3-dihydro-1-benzazepine-4-carboxamide (Compound 269) (0.33 g).

¹H-NMR (200 MHz, CDCl₃) δ 0.93 (3H, t, J=7.2 Hz), 0.96 (6H, d, J=6.6 Hz), 1.36 to 1.45 (2H, m), 1.54 to 1.64 (2H, m), 2.05 (1H, m), 2.89 (2H, m), 3.17 (2H, d, J=7.2 Hz), 3.34 (2H, m), 3.55 (2H, t, J=6.6 Hz), 3.80 (2H, m), 4.10 (2H, m), 4.35 (2H, s), 6.91 (1H, d, J=8.8 Hz), 6.94 to 6.99 (2H, m), 7.11 to 7.23 (2H, m), 7.26 to 7.46 (5H, m), 7.72 (1H, m), 7.87 (1H, s), 8.00 (1H, dd, J=8.4, 2.2 Hz), 8.44 (1H, dd, J=4.6, 1.4 Hz), 8.56 (1H, m), 8.62 (1H, d, J=2.0 Hz).

Example 253

(Preparation of Compound 270)

7-[4-(2-butoxyethoxy)phenyl]-1-isobutyl-N-[6-[(3-pyridinylmethyl)sulfanyl]-3-pyridinyl]-2,3-dihydro-1-benzazepine-4-carboxamide (0.32 g) was dissolved in methylene chloride (9.6 ml), and a solution of m-chloroperbenzoic acid (130 mg) in methylene chloride (6.4 ml) was added to the mixture at −78° C., and the mixture was stirred for 15 minutes. The reaction mixture was added to an aqueous solution of saturated sodium thiosulfate, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[(3-pyridinylmethyl)sulfinyl]-3-pyridinyl]-2,3-dihydro-1-benzazepine-4-carboxamide (Compound 270) (180 mg).

¹H-NMR (200 MHz, CDCl₃) δ 0.93 (3H, t, J=7.2 Hz), 0.98 (6H, d, J=6.2 Hz), 1.33 to 1.45 (2H, m), 1.57 to 1.65 (2H, m), 2.05 (1H, m), 2.92 (2H, m), 3.20 (2H, d, J=7.0 Hz), 3.37 (2H, m), 3.55 (2H, t, J=6.4 Hz), 3.80 (2H, t, J=4.8 Hz), 4.10 (1H, d, J=13.6 Hz), 4.18 (2H, t, J=4.4 Hz), 4.30 (1H, d, J=13.4 Hz), 6.90 to 6.95 (1H, m), 6.97 (2H, d, J=8.8 Hz), 7.17 to 7.26 (1H, m), 7.40 to 7.50 (7H, m), 7.98 to 8.04 (2H, m), 8.12 (1H, dd, J=8.0, 2.2 Hz), 8.45 to 8.49 (1H, m), 8.90 (1H, dd, J=2.6 Hz).

IR (KBr) 3266, 2959, 1651, 1607, 1499, 1464, 1366, 1242, 1115, 922, 816, 731 cm⁻¹

Example 254

(Preparation of Compound 271)

7-[4-(2-butoxyethoxy)phenyl]-1-isobutyl-2,3-dihydro-1-benzazepine-4-carboxylic acid (0.70 g) was dissolved in THF (14 ml), DMF (3 droplets) was added to the mixture, thionyl chloride (0.23 ml) was added to the mixture, and the mixture was stirred for 1 hour at room temperature. The solvent was removed under reduced pressure, and a solution of the obtained residue in THF (14 ml) was added dropwise to a solution of 6-[[(2-methyl-3-pyridinyl)methyl]sulfanyl]-3-pyridinylamine (0.40 g) and triethylamine (2.68 ml) in THF (16.0 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[[(2-methyl-3-pyridinyl)methyl]sulfanyl]-3-pyridinyl]-2,3-dihydro-1-benzazepine-4-carboxamide (Compound 271) (0.67 g).

$^1$H-NMR (200 MHz, CDCl$_3$) δ 0.93 (3H, t, J=7.0 Hz), 0.97 (6H, d, J=6.6 Hz), 1.33 to 1.45 (2H, m), 1.57 to 1.68 (2H, m), 2.0.5 (1H, m), 2.65 (3H, s), 2.91 (2H, m), 3.19 (2H, d, J=7.0 Hz), 3.36 (2H, m), 3.55 (2H, t, J=6.6 Hz), 3.77 to 3.83 (2H, m), 4.13 to 4.18 (2H, m), 4.41 (2H, s), 6.90 to 7.08 (4H, m), 7.17 (1H, d, J=8.8 Hz), 7.38 to 7.48 (5H, m), 7.63 to 7.68 (2H, m), 7.98 (1H, dd, J=8.4, 2.2 Hz), 8.37 (1H, dd, J=4.8, 1.6 Hz), 8.57 to 8.59 (1H, m).

Example 255

(Preparation of Compound 272)

To a solution of 7-[4-(2-butoxyethoxy)phenyl]-1-isobutyl-N-[6-[[(2-methyl-3-pyridinyl)methyl]sulfanyl]-3-pyridinyl]-2,3-dihydro-1-benzazepine-4-carboxamide (0.61 g) in methylene chloride (18.3 ml) was added dropwise a solution of m-chloroperbenzoic acid (243 g) in methylene chloride (4.0 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[[(2-methyl-3-pyridinyl)methyl]sulfinyl]-3-pyridinyl]-2,3-dihydro-1-benzazepine-4-carboxamide (Compound 272) (277 mg).

$^1$H-NMR (200 MHz, CDCl$_3$) δ 0.93 (3H, t, J=7.6 Hz), 0.98 (6H, d, J=6.6 Hz), 1.33 to 1.44 (2H, m), 1.49 to 1.69 (2H, m), 2.07 (1H, m), 2.53 (3H, s), 2.92 (2H, m), 3.20 (2H, d, J=7.0 Hz), 3.37 (2H, m), 3.55 (2H, t, J=6.6 Hz), 3.81 (2H, t, J=4.8 Hz), 3.91 (1H, d, J=13.2 Hz), 4.06 (1H, d, J=13.2 Hz), 4.123 to 4.19 (2H, m), 6.90 to 7.11 (5H, m), 7.26 to 7.53 (7H, m), 7.71 (2H, d, J=8.2 Hz), 7.91 (1H, s).

IR (KBr) 2957, 1667, 1501, 1242, 1182, 1042, 909, 814, 731 cm$^{-1}$

Example 256

(Preparation of Compound 273)

In THF (50 ml) was dissolved 7-[4-(2-butoxyethoxy)phenyl]-1-propyl-2,3-dihydro-1-benzazepine-4-carboxylic acid (2.5 g), and DMF (5 droplets) was added to the mixture, thionyl chloride (0.86 ml) was added to the mixture, and the mixture was stirred at room temperature for 1 hour. The solution was added dropwise to a solution of 6-[(3-pyridinylmethyl)sulfanyl]-3-pyridinylamine (1.41 g) and triethylamine (12.3 ml) in THF (42.3 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[6-[(3-pyridinylmethyl)sulfanyl]-3-pyridinyl]-2,3-dihydro-1-benzazepine-4-carboxamide (Compound 273) (0.92 g).

$^1$H-NMR (200 MHz, CDCl$_3$) δ 0.93 (3H, t, J=7.4 Hz), 0.98 (3H, t, J=7.2 Hz), 1.33 to 1.44 (2H, m), 1.54 to 1.79 (4H, m), 2.88 (2H, m), 3.26 to 3.34 (4H, m), 3.55 (2H, t, J=6.6 Hz), 3.80 (2H, t, J=4.8 Hz), 4.12 to 4.17 (2H, m), 4.38 (2H, s), 6.88 (1H, d, J=8.4 Hz), 6.96 (2H, d, J=8.8 Hz), 7.14 (2H, d, J=8.0 Hz), 7.37 to 7.48 (4H, m), 7.68 to 7.79 (2H, m), 7.98 (1H, dd, J=8.8, 2.6 Hz), 8.44 (1H, dd, J=4.8, 1.8 Hz), 8.55 (1H, d, J=1.8 Hz), 8.62 (1H, d, J=1.8 Hz).

Example 257

(Preparation of Compound 274)

To a solution of 7-[4-(2-butoxyethoxy)phenyl]-1-propyl-N-[6-[(3-pyridinylmethyl)sulfanyl]-3-pyridinyl]-2,3-dihydro-1-benzazepine-4-carboxamide (0.91 g) in methylene chloride (27.3 ml) was added dropwise a solution of m-chloroperbenzoic acid (303 mg) in methylene chloride (18.2 ml) at −78° C., and the mixture was stirred for 15 minutes. To the reaction mixture was added an aqueous solution of saturated sodium thiosulfate. The mixture was extracted with ethyl acetate, and the organic layer was washed with saturated brine and dried over magnesium sulfate. The solvent was removed under reduced pressure, and the obtained residue was purified by silica gel column chromatography, to give 7-[4-(2-butoxyethoxy)phenyl]-1-propyl-N-[6-[(3-pyridinylmethyl)sulfinyl]-3-pyridinyl]-2,3-dihydro-1-benzazepine-4-carboxamide (Compound 274) (258 mg).

$^1$H-NMR (200 MHz, CDCl$_3$) δ 0.92 (3H, t, J=7.4 Hz), 0.98 (3H, t, J=7.2 Hz), 1.26 to 1.44 (2H, m), 1.53 to 1.75 (4H, m), 2.90 (2H, m), 3.32 (4H, m), 3.54 (2H, t, J=6.6 Hz), 3.76 to 3.82 (2H, m), 4.01 to 4.26 (4H, m), 6.86 to 6.98 (3H, m), 7.15 to 7.23 (1H, m), 7.26 to 7.45 (7H, m), 7.99 (1H, s), 8.06 to 8.12 (1H, m), 8.44 to 8.46 (2H, m), 8.44 to 8.46 (2H, m), 8.89 (1H, d, J=2.6 Hz).

IR (KBr) 2959, 1661, 1607, 1499, 1462, 1240, 1181, 1121, 1046, 910, 812, 731 cm$^{-1}$

Example 258

(Preparation of Compound 275)

7-[4-(2-butoxyethoxy)phenyl]-1-isobutyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture at 0° C., and the mixture was stirred for 1 hour at room temperature. The solvent was removed under reduced pressure, and a solution of the obtained residue in THF (16.0 ml) was added dropwise to a solution of S-(4-aminophenyl)O-benzylthiocarbonate (0.47 g) and triethylamine (1.53 ml) in THF (14.1 ml) at 0° C. The mixture was stirred for 2 hours at room temperature, methanol (28.2 ml) and 1N sodium hydroxide (14.6 ml) were added to the mixture, and the mixture was stirred for 15 minutes. 4-chloromethyl-2-propyl-1,2,3-triazole (0.35 g) was added to the mixture at room temperature and the mixture was stirred for 15 minutes. The solvent was concentrated to half under reduced pressure, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(2-propyl-1,2,3-triazol-4-yl)methyl]sulfanyl]phenyl]-2,3-dihydro-1-benzazepine-4-carboxamide (Compound 275) (0.50 g).

$^1$H-NMR (200 MHz, CDCl$_3$) δ 0.89 (3H, t, J=7.2 Hz), 0.93 (3H, t, J=7.2 Hz), 0.96 (6H, d, J=7.2 Hz), 1.33 to 1.45 (2H, m), 1.57 to 1.66 (2H, m), 1.87 to 2.08 (3H, m), 2.90 (2H, m), 3.18 (2H, d, J=7.4 Hz), 3.32 to 3.37 (2H, m), 3.55 (2H, t, J=6.6 Hz), 3.77 to 3.83 (2H, m), 4.11 (2H, s), 4.10 to 4.18 (2H, m), 4.31 (2H, t, J=6.8 Hz), 6.91 (1H, d, J=8.8 Hz), 6.97 (2H, d, J=8.2 Hz), 7.31 to 7.58 (11H, m).

Example 259

(Preparation of Compound 276)

7-[4-(2-butoxyethoxy)phenyl]-1-isobutyl-N-[4-[[(2-propyl-1,2,3-triazol-4-yl)methyl]sulfanyl]phenyl]-2,3-dihydro-1-benzazepine-4-carboxamide (0.45 g) was dissolved in methylene chloride (9.0 ml), and to the solution was added dropwise a solution of m-chloroperbenzoic acid (174 mg) in methylene chloride (9.0 ml) at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(2-propyl-1,2,3-triazol-4-yl)methyl]sulfinyl]phenyl]-2,3-dihydro-1-benzazepine-4-carboxamide (Compound 276) (0.39 g).

$^1$H-NMR (200 MHz, CDCl$_3$) δ 0.88 (3H, t, J=7.2 Hz), 0.93 (3H, t, J=7.2 Hz), 0.98 (6H, d, J=6.6 Hz), 1.33 to 1.45 (2H, m), 1.54 to 1.68 (2H, m), 1.85 to 1.97 (2H, m), 2.04 (1H, m), 2.92 (2H, m), 3.19 (2H, d, J=7.4 Hz), 3.36 (2H, t, J=4.6 Hz), 3.55 (2H, t, J=6.6 Hz), 3.80 (2H, d, J=4.8 Hz), 4.14 (2H, s), 4.13 to 4.18 (2H, m), 4.31 (2H, t, J=7.0 Hz), 6.92 (1H, d, J=8.8 Hz), 6.98 (2H, d, J=9.2 Hz), 7.31 (1H, s), 7.38 to 7.72 (7H, m), 7.74 (2H, d, J=7.0 Hz), 7.82 (1H, s).

IR (KBr) 2959, 2870, 1661, 1590, 1499, 1246, 1122, 1033, 835, 733 cm$^{-1}$

Elemental Analysis for C$_{39}$H$_{49}$N$_5$O$_4$S Cald. C, 68.49; N, 10.24; H, 7.22. Found: C, 68.40; N, 10.21; H, 7.22.

Example 260

(Preparation of Compound 277)

7-[4-(2-butoxyethoxy)phenyl]-1-isobutyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture at 0° C. and the mixture was stirred for 1 hour at room temperature. The solvent was removed under reduced pressure, and a solution of the obtained residue in THF (16 ml) was added dropwise to S-(4-aminophenyl)O-benzylthiocarbonate (0.47 g) and triethylamine (1.53 ml) in THF (14.1 ml) at 0° C. The mixture was stirred for 2 hours at room temperature, methanol (28.2 ml) and 1N sodium hydroxide (14.6 ml) were added to the mixture, and the mixture was stirred for 15 minutes. 5-chloromethyl-1-propyl-1,2,3-triazole hydrochloride (0.43 g) was added to the mixture, and the mixture was stirred at room temperature for 15 minutes. The solvent was concentrated to half under reduced pressure, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-propyl-1,2,3-triazol-5-yl)methyl]sulfanyl]phenyl]-2,3-dihydro-1-benzazepine-4-carboxamide ((Compound 277) (0.61 g).

$^1$H-NMR (200 MHz, CDCl$_3$) δ 0.93 (3H, t, J=7.2 Hz), 0.97 (3H, t, J=7.4 Hz), 0.97 (6H, d, J=6.6 Hz), 1.33 to 1.45 (2H, m), 1.57 to 1.66 (2H, m), 1.89 to 2.05 (3H, m), 2.91 (2H, m), 3.18 (2H, d, J=7.4 Hz), 3.33 to 3.38 (2H, m), 3.55 (2H, t, J=6.6 Hz), 3.77 to 3.83 (2H, m), 3.89 (2H, s), 4.15 (2H, t, J=4.8 Hz), 4.24 (2H, t, J=7.2 Hz), 6.91 (1H, d, J=8.8 Hz), 6.97 (2H, d, J=8.8 Hz), 7.24 to 7.29 (2H, m), 7.38 to 7.58 (8H, m), 7.72 (1H, s).

Example 261

(Preparation of Compound 278)

7-[4-(2-butoxyethoxy)phenyl]-1-isobutyl-N-[4-[[(1-propyl-1,2,3-triazol-5-yl)methyl]sulfanyl]phenyl]-2,3-dihydro-1-benzazepine-4-carboxamide (0.54 g) was dissolved in methylene chloride (16.2 ml), and a solution of m-chloroperbenzoic acid (209 mg) in methylene chloride (10.8 ml) was added dropwise to the solution at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-propyl-1,2,3-triazol-5-yl)methyl]sulfinyl]phenyl]-2,3-dihydro-1-benzazepine-4-carboxamide (Compound 278) (0.35 g).

$^1$H-NMR (200 MHz, CDCl$_3$) δ 0.90 (3H, t, J=7.4 Hz), 0.93 (3H, t, J=7.0 Hz), 0.97 (6H, d, J=6.6 Hz), 1.33 to 1.45 (2H, m), 1.54 to 1.65 (2H, m), 1.54 to 1.65 (2H, m), 1.77 to 1.91 (2H, m), 2.07 (1H, m), 2.93 (2H, m), 3.19 (2H, d, J=7.4 Hz), 3.36 (2H, m), 3.55 (2H, t, J=6.6 Hz), 3.80 (2H, t, J=4.8 Hz), 3.97 (1H, d, J=14.2 Hz), 4.08 to 4.16 (4H, m), 4.21 (1H, d, J=13.8 Hz), 6.92 (1H, d, J=8 Hz), 6.97 (2H, d, J=8.8 Hz), 7.31 (2H, d, J=8.8 Hz), 7.32 to 7.50 (6H, m), 7.78 (2H, d, J=8.8 Hz), 8.07 (1H, s).

IR (KBr) 2957, 2870, 1661, 1588, 1499, 1244, 1123, 1047, 833, 733 cm$^{-1}$

Elemental Analysis for C$_{39}$H$_{49}$N$_5$O$_4$S.0.2H$_2$O Cald. C, 68.13; N, 10.19; H, 7.24. Found: C, 68.04; N, 10.19; H, 7.08.

Example 262

(Preparation of Compound 279)

7-[4-(2-butoxyethoxy)phenyl]-1-isobutyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture at 0° C., and the mixture was stirred for 1 hour at room temperature. The solvent was removed under reduced pressure, and a solution of the obtained residue in THF (16.0 ml) was added dropwise to a solution of S-(4-aminophenyl)O-benzylthiocarbonate (0.47 g) and triethylamine (1.53 ml) in THF (14.1 ml) at 0° C. The mixture was stirred for 2 hours at room temperature, methanol (28.2 ml) and 1N sodium hydroxide (14.6 ml) were added to the mixture, and the mixture was stirred for 15 minutes. 4-chloromethyl-1-propyl-1,2,3-triazole (0.35 g) was added to the mixture, and the mixture was stirred at room temperature for 15 minutes. The solvent was concentrated to half under reduced pressure, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-propyl-1,2,3-triazol-4-yl)methyl]sulfanyl]phenyl]-2,3-dihydro-1-benzazepine-4-carboxamide (Compound 279) (0.60 g).

$^1$H-NMR (200 MHz, CDCl$_3$) δ 0.90 (3H, t, J=7.2 Hz), 0.93 (3H, t, J=7.4 Hz), 0.97 (6H, d, J=6.6 Hz), 1.33 to 1.45 (2H, m), 1.57 to 1.67 (2H, m), 1.78 to 1.94 (2H, m), 2.04 (1H, m), 2.90 (2H, m), 3.18 (2H, d, J=7.2 Hz), 3.32 to 3.37 (2H, m), 3.55 (2H, t, J=6.6 Hz), 3.80 (2H, t, J=4.8 Hz), 4.12 to 4.19 (2H, m), 4.18 (2H, s), 4.23 (2H, t, J=7.0 Hz), 6.91 (1H, d, J=8.8 Hz), 6.97 (2H, d, J=8.8 Hz), 7.27 to 7.55 (10H, m), 7.70 (1H, s).

Example 263

(Preparation of Compound 280)

7-[4-(2-butoxyethoxy)phenyl]-1-isobutyl-N-[4-[[(1-propyl-1,2,3-triazol-4-yl)methyl]sulfanyl]phenyl]-2,3-dihydro-1-benzazepine-4-carboxamide (0.55 g) was dissolved in methylene chloride (16.5 ml), and a solution of m-chloroperbenzoic acid (213 mg) in methylene chloride (11 ml) was added dropwise to the solution at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[(1-propyl-1,2,3-triazol-4-yl)methyl]sulfinyl]phenyl]-2,3-dihydro-1-benzazepine-4-carboxamide (Compound 280) (0.39 g).

$^1$H-NMR (200 MHz, CDCl$_3$) δ 0.90 (3H, t, J=7.2 Hz), 0.94 (3H, t, J=7.2 Hz), 0.98 (6H, d, J=6.6 Hz), 1.33 to 1.45 (2H, m), 1.54 to 1.65 (2H, m), 1.85 to 1.97 (2H, m), 2.08 (1H, m), 2.92 (2H, m), 3.19 (2H, d, J=7.2 Hz), 3.30 to 3.39 (2H, m), 3.55 (2H, t, J=6.6 Hz), 3.80 (2H, t, J=4.8 Hz), 4.06 to 4.32 (6H, m), 6.92 (1H, d, J=8.8 Hz), 6.98 (2H, d, J=8.8 Hz), 7.38 to 7.53 (8H, m), 7.73 (2H, d, J=8.8 Hz), 7.83 (1H, br).

IR (KBr) 2959, 2870, 1661, 1607, 1499, 1244, 1044, 816, 733 cm$^{-1}$

Elemental Analysis for $C_{39}H_{49}N_5O_4S$ Cald. C, 68.49; N, 10.24; H, 7.22. Found: C, 68.23; N, 10.20; H, 7.12.

Example 264

(Preparation of Compound 281)

7-[4-(2-butoxyethoxy)phenyl]-1-propyl-2,3-dihydro-1-benzazepine-4-carboxylic acid (0.78 g) was dissolved in THF (7.8 ml), DMF (3 droplets) was added to the mixture, thionyl chloride (0.20 ml) was added to the mixture at 0° C., and the mixture was stirred for 1 hour at room temperature. The solvent was removed under reduced pressure, and a solution of the obtained residue in THF (16 ml) was added dropwise to a solution of S-(4-aminophenyl)O-benzylthiocarbonate (0.48 g) and triethylamine (1.54 ml) in THF (14.4 ml) at 0° C. The mixture was stirred for 2 hours at room temperature, methanol (28.8 ml) and 1N sodium hydroxide (14.7 ml) were added to the mixture, and the mixture was stirred for 15 minutes. 5-chloromethyl-1-propyl-1,2,3-triazole hydrochloride (0.43 g) was added to the mixture, and the mixture was stirred at room temperature for 15 minutes. The solvent was concentrated to half under reduced pressure, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[[(1-propyl-1,2,3-triazol-5-yl)methyl]sulfanyl]phenyl]-2,3-dihydro-1-benzazepine-4-carboxamide (Compound 281) (0.60 g).

$^1$H-NMR (200 MHz, CDCl$_3$) δ 0.84-103 (9H, m), 1.33 to 1.45 (2H, m), 1.54 to 1.77 (4H, m), 1.90 to 2.02 (2H, m), 2.90 (2H, m), 3.32 (4H, m), 3.55 (2H, t, J=6.6 Hz), 3.80 (2H, t, J=4.4 Hz), 4.13 to 4.29 (4H, m), 6.90 (1H, d, J=8.4 Hz), 6.98 (2H, d, J=8.8 Hz), 7.23 to 7.29 (3H, m), 7.39 to 7.57 (7H, m), 7.67 (1H, s).

IR (KBr) 2961, 2872, 1659, 1586, 1497, 1240, 1123, 1067, 818, 733 cm$^{-1}$

Example 265

(Preparation of Compound 282)

7-[4-(2-butoxyethoxy)phenyl]-1-propyl-N-[4-[[(1-propyl-1,2,3-triazol-5-yl)methyl]sulfanyl]phenyl]-2,3-dihydro-1-benzazepine-4-carboxamide (0.53 g) was dissolved in methylene chloride (15.9 ml), and to the solution was added dropwise a solution of m-chloroperbenzoic acid (0.21 g) in methylene chloride (10.6 ml) at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[[(1-propyl-1,2,3-triazol-5-yl)methyl]sulfinyl]phenyl]-2,3-dihydro-1-benzazepine-4-carboxamide (Compound 282) (0.25 g).

$^1$H-NMR (200 MHz, CDCl$_3$) δ 0.85 to 1.03 (9H, m), 1.33 to 1.45 (2H, m), 1.57 to 1.89 (6H, m), 2.92 (2H, m), 3.32 (4H, m), 3.55 (2H, t, J=6.6 Hz), 3.80 (2H, t, J=4.8 Hz), 3.93 to 4.22 (6H, m), 6.90 (1H, d, J=8.2 Hz), 6.97 (0.2H, d, J=8.4 Hz), 7.13 (1H, s), 7.29 to 7.49 (7H, m), 7.76 (2H, d, J=8.8 Hz), 7.97 (1H, br).

IR (KBr) 2961, 2874, 1661, 1588, 1505, 1242, 1177, 1049, 833, 731 cm$^{-1}$

Elemental Analysis for $C_{38}H_{47}N_5O_4S.0.2H_2O$ Cald. C, 67.77; N, 10.40; H, 7.09. Found: C, 67.81; N, 10.41; H, 7.06.

Example 266

(Preparation of Compound 283)

7-[4-(2-butoxyethoxy)phenyl]-1-propyl-2,3-dihydro-1-benzazepine-4-carboxylic acid (0.70 g) was dissolved in THF (7.0 ml), DMF (3 droplets) was added to the mixture, thionyl chloride (0.18 ml) was added to the mixture, and the mixture was stirred for 1 hour at room temperature. The solvent was removed under reduced pressure, and a solution of the obtained residue in THF (14 ml) was added dropwise to a solution of 4-[[2-(1,2,4-triazol-1-yl)ethyl]sulfanyl]phenylamine (0.39 g) and triethylamine (1.78 ml) in THF (7.8 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[[2-(1,2,4-triazol-1-yl)ethyl]sulfanyl]phenyl]-2,3-dihydro-1-benzazepine-4-carboxamide (Compound 283) (0.56 g).

$^1$H-NMR (200 MHz, CDCl$_3$) δ 0.93 (3H, t, J=7.2 Hz), 0.99 (3H, t, J=7.2 Hz), 1.33 to 1.45 (2H, m), 1.57 to 1.78 (4H, m), 2.91 (2H, m), 3.28 to 3.35 (4H, m), 3.55 (2H, t, J=6.6 Hz), 3.78 to 3.84 (2H, m), 4.13 to 4.19 (2H, m), 4.32 (2H, t, J=6.6 Hz), 6.90 (1H, d, J=8.8 Hz), 6.98 (2H, d, J=8.8 Hz), 7.34 to 7.63 (10H, m), 7.94 (1H, s), 8.04 (1H, s).

IR (KBr) 2957, 2872, 1651, 1586, 1499, 1242, 1179, 818, 733 cm$^{-1}$

Example 267

(Preparation of Compound 284)

7-[4-(2-butoxyethoxy)phenyl]-1-propyl-N-[4-[[2-(1,2,4-triazol-1-yl)ethyl]sulfanyl]phenyl]-2,3-dihydro-1-benzazepine-4-carboxamide (0.86 g) was dissolved in methylene chloride (25.8 ml), and to the mixture was added dropwise a solution of m-chloroperbenzoic acid (0.36 g) in methylene chloride (17.2 ml) at −78° C., and the mixture was stirred for 15 minutes. To the reaction mixture was added an aqueous solution of saturated sodium thiosulfate, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[[2-(1,2,4-triazol-1-yl)ethyl]sulfinyl]phenyl]-2,3-dihydro-1-benzazepine-4-carboxamide (Compound 284) (0.57 g).

$^1$H-NMR (200 MHz, CDCl$_3$) δ 0.93 (3H, t, J=6.8 Hz), 0.99 (3H, t, J=6.8 Hz), 1.33 to 1.45 (2H, m), 1.53 to 1.82 (4H, m), 2.91 (2H, m), 3.18 to 3.46 (4H, m), 3.55 (2H, t, J=6.6 Hz), 3.80 (2H, t, J=4.6 Hz), 4.13 (2H, t, J=5.0 Hz), 4.41 to 4.51 (1H, m), 4.61 to 4.80 (1H, m), 6.90 (1H, d, J=8.4 Hz), 6.97 (2H, d, J=8.4 Hz), 7.40 to 7.57 (7H, m), 7.78 (2H, d, J=8.8 Hz), 7.81 to 7.91 (1H, m), 7.93 (1H, s), 8.10 (1H, s).

IR (KBr) 2959, 2870, 1661, 15.88, 1501, 1242, 1044, 833, 733 cm$^{-1}$

Elemental Analysis for C$_{36}$H$_{44}$N$_5$O$_4$S Cald. C, 67.26; N, 10.89; H, 6.90. Found: C, 67.12; N, 10.81; H, 6.71.

Example 268

(Preparation of Compound 285)

7-[4-(2-butoxyethoxy)phenyl]-1-propyl-2,3-dihydro-1-benzazepine-4-carboxylic acid (0.60 g) was dissolved in THF (6.0 ml), DMF (3 droplets) was added to the mixture, thionyl chloride (0.16 ml) was added to the mixture, and the mixture was stirred for 1 hour at room temperature. The solvent was removed under reduced pressure, and a solution of the obtained residue in THF (12 ml) was added dropwise to a solution of 4-[2-(1,2,4-triazol-1-yl)ethoxy]aniline (0.32 g) and triethylamine (1.18 ml) in THF (12.0 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[2-(1,2,4-triazol-1-yl)ethoxy]phenyl]-2,3-dihydro-1-benzazepine-4-carboxamide (Compound 285) (0.56 g).

$^1$H-NMR (200 MHz, CDCl$_3$) δ 0.93 (3H, t, J=7.2 Hz), 0.98 (3H, t, J=7.2 Hz), 1.33 to 1.45 (2H, m), 1.57 to 1.79 (6H, m), 2.89 (2H, m), 3.26 to 3.35 (4H, m), 3.55 (2H, t, J=6.2 Hz), 3.79 to 3.83 (2H, m), 4.12 to 4.18 (2H, m), 4.29 to 4.32 (2H, m), 4.56 (2H, t, J=4.8 Hz), 6.83 (2H, d, J=8.8 Hz), 6.89 (1H, d, J=8.8 Hz), 6.97 (2H, d, J=8.8 Hz), 7.38 to 7.48 (8H, m), 7.96 (1H, s), 8.22 (1H, s).

IR (KBr) 2959, 2872, 1651, 1605, 1510, 1238, 831, 733 cm$^{-1}$

Elemental Analysis for C$_{36}$H$_{43}$N$_5$O$_4$·0.2H$_2$O Cald. C, 70.49; N, 11.42; H, 7.13. Found: C, 70.48; N, 11.41; H, 7.04.

Example 269

(Preparation of Compound 286)

7-[4-(2-butoxyethoxy)phenyl]-1-propyl-2,3-dihydro-1-benzazepine-4-carboxylic acid (0.57 g) was dissolved in THF (5.7 ml), DMF (3 droplets) was added to the mixture, thionyl chloride (0.15 ml) was added to the mixture, and the mixture was stirred for 1 hour at room temperature. The solvent was removed under reduced pressure, and a solution of the obtained residue in THF (12 ml) was added dropwise to a solution of 4-[2-(imidazol-1-yl)ethoxy]aniline (0.30 g) and triethylamine (1.12 ml) in THF (11.4 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, and recrystallized from ethanol, to give 7-[4-(2-butoxyethoxy)phenyl]-N-[4-[2-(imidazol-1-yl)ethoxy]phenyl]-1-propyl-2,3-dihydro-1-benzazepine-4-carboxamide (Compound 286) (0.41 g).

$^1$H-NMR (200 MHz, CDCl$_3$) δ 0.93 (3H, t, J=7.0 Hz), 0.99 (3H, t, J=7.0 Hz), 1.33 to 1.45 (2H, m), 1.54 to 1.80 (6H, m), 2.90 (2H, m), 3.27 to 3.36 (4H, m), 3.55 (2H, t, J=6.6 Hz), 3.80 (2H, t, J=4.6 Hz), 4.15 (2H, t, J=4.8 Hz), 4.21 (2H, t, J=4.8 Hz), 4.32 (2H, t, J=4.8 Hz), 6.82 to 7.08 (7H, m), 7.37 to 7.60 (9H, m).

IR (KBr) 2957, 2872, 1651, 1605, 1510, 1240, 831 cm$^{-1}$

Example 270

(Preparation of Compound 287)

7-[4-(2-butoxyethoxy)phenyl]-1-propyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (16 ml) was added dropwise to a solution of 4-[3-(imidazol-1-yl)propyl]aniline (0.42 g) and triethylamine (2.1 ml) in THF (12.6 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[imidazol-1-yl]propyl]phenyl]-1-propyl-2,3-dihydro-1-benzazepine-4-carboxamide (Compound 287) (0.80 g).

$^1$H-NMR (200 MHz, CDCl$_3$) δ 0.93 (3H, t, J=7.2 Hz), 0.99 (3H, t, J=7.2 Hz), 1.33 to 1.42 (2H, m), 1.54 to 1.85 (4H, m), 2.03 to 2.18 (2H, m), 2.59 (2H, m), 2.91 (4H, m), 3.55 (2H, t, J=6.6 Hz), 3.80 (2H, t, J=4.4 Hz), 3.92 (2H, t, J=7.0 Hz), 4.12 to 4.18 (2H, m), 6.89 (1H, d, J=8.4 Hz), 6.91 (1H, s), 6.97 (2H, d, J=8.8 Hz), 7.08 (1H, m), 7.13 (2H, d, J=8.4 Hz), 7.37 to 7.68 (9H, m).

IR (KBr) 2957, 2870, 1651, 1605, 1505, 1244, 816, 733 cm$^{-1}$

Elemental Analysis for C$_{38}$H$_{46}$N$_4$O$_3$ Cald. C, 75.22; N, 9.23; H, 7.64. Found: C, 75.07; N, 9.35; H, 7.62.

Example 271

(Preparation of Compound 288)

7-[4-(2-butoxyethoxy)phenyl]-1-propyl-2,3-dihydro-1-benzazepine-4-carboxylic acid (0.80 g) was dissolved in THF (8.0 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (16 ml) was added dropwise to a solution of 4-[3-(1,2,4-triazol-1-yl)propyl]aniline (0.42 g) and triethylamine (2.10 ml) in THF (12.6 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[4-[3-(1,2,4-triazol-1-yl)propyl]phenyl]-2,3-dihydro-1-benzazepine-4-carboxamide (Compound 288) (0.52 g).

$^1$H-NMR (200 MHz, CDCl$_3$) δ 0.93 (3H, t, J=6.8 Hz), 0.99 (3H, t, J=7.2 Hz), 1.33 to 1.45 (2H, m), 1.54 to 1.82 (4H, m), 2.17 to 2.31 (2H, m), 2.61 (2H, d, J=6.6 Hz), 2.91 (2H, m), 3.28 to 3.42 (4H, m), 3.55 (2H, t, J=6.2 Hz), 3.80 (2H, t, J=4.8 Hz), 4.12 to 4.22 (4H, m), 6.90 (1H, d, J=8.8 Hz), 6.98 (2H, d, J=8.8 Hz), 7.15 (2H, d, J=8.4 Hz), 7.37 to 7.56 (8H, m), 7.97 (1H, s), 8.02 (1H, s).

IR (KBr) 2957, 2870, 1651, 1605, 1501, 1244, 818 cm$^{-1}$

Elemental Analysis for C$_{37}$H$_{45}$N$_5$O$_3$.0.3H$_2$O Cald. C, 72.47; N, 11.42; H, 7.50. Found: C, 72.45; N, 11.61; H, 7.47.

Example 272

(Preparation of Compound 289)

7-[4-(2-butoxyethoxy)phenyl]-1-propyl-2,3-dihydro-1-benzazepine-4-carboxylic acid (0.80 g) was dissolved in THF (8.0 ml), DMF (3 droplets) was added to the mixture, thionyl chloride (0.21 ml) was added to the mixture, and the mixture was stirred for 1 hour at room temperature. The solvent was removed under reduced pressure, and a solution of the obtained residue in THF (16 ml) was added dropwise to a solution of N-(4-aminobenzyl)-N-methyl-1-propylimidazole-2-amine (0.51 g) in pyridine (10.2 ml) under ice-cooling and the mixture was stirred at room temperature for 3 hours. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-N-[4-[[methyl(1-propylimidazol-2-yl)amino]methyl]phenyl]-1-propyl-2,3-dihydro-1-benzazepine-4-carboxamide (Compound 289) (0.27 g).

$^1$H-NMR (200 MHz, CDCl$_3$) δ 0.91 (3H, t, J=7.2 Hz), 0.93 (3H, t, J=7.2 Hz), 0.98 (3H, t, J=7.2 Hz), 1.33 to 1.45 (2H, m), 1.57 to 1.80 (6H, m), 2.66 (3H, s), 2.91 (2H, m), 3.28 to 3.35 (4H, m), 3.55 (2H, t, J=6.2 Hz), 3.87 (2H, t, J=7.4 Hz), 3.80 (2H, t, J=4.8 Hz), 4.10 (2H, s), 4.16 (2H, t, J=4.8 Hz), 6.67 (1H, d, J=1.4 Hz), 6.84 (1H, d, J=1.6 Hz), 6.90 (1H, d, J=8.4 Hz), 6.98 (2H, d, J=8.8 Hz), 7.27 to 7.39 (9H, m), 7.91 (1H, dd, J=8.4, 2.6 Hz), 8.38 (1H, s), 8.62 (1H, d, J=2.6 Hz).

IR (KBr) 2959, 2872, 1655, 1605, 1499, 1244, 833, 733 cm$^{-1}$

Elemental Analysis for C$_{40}$H$_{51}$N$_5$O$_3$.0.2H$_2$O Cald. C, 73.52; N, 10.72; H, 7.93. Found: C, 73.46; N, 10.73; H, 7.79.

Example 273

(Preparation of Compound 290)

7-[4-(2-butoxyethoxy)phenyl]-1-propyl-2,3-dihydro-1-benzazepine-4-carboxylic acid (1.0 g) was dissolved in THF (10.0 ml), DMF (3 droplets) was added to the mixture, thionyl chloride (0.26 ml) was added to the mixture, and the mixture was stirred for 1 hour at room temperature. The solvent was removed under reduced pressure, and a solution of the obtained residue in THF (20 ml) was added dropwise to a solution of 6-[[(1-propylimidazol-2-yl)methyl]sulfanyl]pyridine-3-amine (0.65 g) and triethylamine (2.6 ml) in THF (19.5 ml) under ice-cooling and the mixture was stirred at room temperature for 3 hours. Water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[6-[[(1-propylimidazol-2-yl)methyl]sulfanyl]-3-pyridinyl]-2,3-dihydro-1-benzazepine-4-carboxamide (Compound 290) (0.76 g).

$^1$H-NMR (200 MHz, CDCl$_3$) δ 0.89 (3H, t, J=7.4 Hz), 0.93 (3H, t, J=7.2 Hz), 0.98 (3H, t, J=6.8 Hz), 1.33 to 1.42 (2H, m), 1.57 to 1.83 (6H, m), 2.90 (2H, m), 3.26 to 3.34 (4H, m), 3.55 (2H, t, J=6.4 Hz), 3.80 (2H, t, J=4.4 Hz), 3.86 (2H, t, J=7.2 Hz), 4.15 (2H, t, J=4.8 Hz), 4.50 (2H, s), 6.80 (1H, d, J=1.6 Hz), 6.87 (1H, d, J=9.2 Hz), 6.92 to 6.98 (3H, m), 7.17 (1H, d, J=8.8 Hz), 7.37 to 7.45 (5H, m), 7.91 (1H, dd, J=8.4, 2.6 Hz), 8.38 (1H, s), 8.62 (1H, d, J=2.6 Hz).

Example 274

(Preparation of Compound 291)

7-[4-(2-butoxyethoxy)phenyl]-1-propyl-N-[6-[[(1-propylimidazol-2-yl)methyl]sulfanyl]-3-pyridinyl]-2,3-dihydro-1-benzazepine-4-carboxamide (0.70 g) was dissolved in methylene chloride (21 ml), and a solution of m-chloroperbenzoic acid (0.28 g) in methylene chloride (14 ml) was added dropwise to the solution at –78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[6-[[(1-propylimidazol-2-yl)methyl]sulfinyl]-3-pyridinyl]-2,3-dihydro-1-benzazepine-4-carboxamide (Compound 291) (0.32 g).

$^1$H-NMR (200 MHz, CDCl$_3$) δ 0.84 (3H, t, J=7.2 Hz), 0.93 (3H, t, J=7.2 Hz), 1.02 (3H, t, J=7.4 Hz), 1.33 to 1.48 (2H, m), 1.54 to 1.83 (6H, m), 3.00 (2H, m), 3.30 to 3.38 (4H, m), 3.55 (2H, t, J=6.6 Hz), 3.67 to 3.75 (2H, m), 3.80 (2H, t, J=4.8 Hz), 4.07 to 4.18 (3H, m), 4.25 (1H, d, J=14.2 Hz), 6.81 to 7.12 (7H, m), 7.34 to 7.41 (3H, m), 7.49 (1H, d, J=8.8 Hz), 8.12 (1H, dd, J=8.4, 1.8 Hz), 8.96 (1H, d, J=1.8 Hz), 9.58 (1H, br).

IR (KBr) 2959, 2872, 1663, 1607, 1499, 1240, 1033, 731 cm$^{-1}$

Example 275

(Preparation of Compound 292)

7-[4-(2-butoxyethoxy)phenyl]-1-isobutyl-2,3-dihydro-1-benzazepine-4-carboxylic acid (1.0 g) was dissolved in THF (10.0 ml), DMF (3 droplets) was added to the mixture, thionyl chloride (0.25 ml) was added to the mixture, and the mixture was stirred for 1 hour at room temperature. The solvent was removed under reduced pressure, and a solution of the obtained residue in THF (20 ml) was added dropwise to a solution of 6-[[(1-propylimidazol-2-yl)methyl]sulfanyl]pyridine-3-amine (0.62 g) and triethylamine (2.6 ml) in THF (19.5 ml) under ice-cooling and the mixture was stirred at room temperature for 3 hours. Water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[[(1-propylimidazol-2-yl)methyl]sulfanyl]-3-pyridinyl]-2,3-dihydro-1-benzazepine-4-carboxamide (Compound 292) (0.73 g).

$^1$H-NMR (200 MHz, CDCl$_3$) δ 0.91 (3H, t, J=7.2 Hz), 0.93 (3H, t, J=7.2 Hz), 0.97 (6H, d, J=6.6 Hz), 1.33 to 1.45 (2H, m), 1.57 to 1.78 (6H, m), 2.04 (1H, m), 2.92 (2H, m), 3.18 (2H, t, J=7.4 Hz), 3.32 to 3.38 (2H, m), 3.55 (2H, t, J=6.6 Hz), 3.80 (2H, t, J=4.8 Hz), 3.89 (2H, t, J=7.4 Hz), 4.13 to 4.18 (2H, m), 4.54 (2H, s), 6.82 (1H, d, J=1.0 Hz), 6.89 to 7.00 (5H, m), 7.20 (1H, d, J=8.4 Hz), 7.37 to 7.48 (5H, m), 7.93 (1H, dd, J=8.8, 2.6 Hz), 8.08 (1H, s), 8.62 (1H, d, J=1.8 Hz).

Example 276

(Preparation of Compound 293)

7-[4-(2-butoxyethoxy)phenyl]-1-isobutyl-N-[6-[[(1-propylimidazol-2-yl)methyl]sulfanyl]-3-pyridinyl]-2,3-dihydro-1-benzazepine-4-carboxamide (0.66 g) was dissolved in methylene chloride (20 ml), and a solution of m-chloroperbenzoic acid (0.26 g) in methylene chloride (13 ml) was added dropwise to the solution at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[[(1-propylimidazol-2-yl)methyl]sulfinyl]-3-pyridinyl]-2,3-dihydro-1-benzazepine-4-carboxamide (Compound 293) (0.39 g).

$^1$H-NMR (200 MHz, CDCl$_3$) δ 0.81 (3H, t, J=7.2 Hz), 0.93 (3H, t, J=7.2 Hz), 1.01 (6H, d, J=6.6 Hz), 1.26 to 1.65 (6H, m), 2.02 to 2.13 (1H, m), 3.01 (2H, m), 3.19 (2H, t, J=7.2 Hz), 3.33 (2H, m), 3.55 (2H, t, J=6.6 Hz), 3.62 to 3.74 (2H, m), 3.80 (2H, t, J=4.6 Hz), 4.09 to 4.17 (4H, m), 6.79 to 7.15 (7H, m), 7.32 to 7.51 (4H, m), 8.06 to 8.12 (1H, m), 8.95 to 9.01 (1H, m), 10.06 (1H, br).

IR (KBr) 2959, 2870, 1667, 1607, 1499, 1242, 1111, 731 cm$^{-1}$

Example 277

(Preparation of Compound 294)

7-[4-(2-butoxyethoxy)phenyl]-1-propyl-2,3-dihydro-1-benzazepine-4-carboxylic acid (0.80 g) was dissolved in THF (8.0 ml), DMF (3 droplets) was added to the mixture, thionyl chloride (0.21 ml) was added to the mixture, and the mixture was stirred for 1 hour at room temperature. The solvent was removed under reduced pressure, and a solution of the obtained residue in THF (16 ml) was added dropwise to a solution of 6-[[(1-propylimidazol-5-yl)methyl]sulfanyl]pyridine-3-amine (0.52 g) in pyridine (10.4 ml) under ice-cooling and the mixture was stirred at room temperature for 3 hours. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy) phenyl]-1-propyl-N-[6-[[(1-propylimidazol-5-yl)methyl]sulfanyl]-3-pyridinyl]-2,3-dihydro-1-benzazepine-4-carboxamide (Compound 294) (0.96 g).

$^1$H-NMR (200 MHz, CDCl$_3$) δ 0.90 (3H, t, J=7.4 Hz), 0.93 (3H, t, J=7.4 Hz), 0.98 (3H, t, J=7.2 Hz), 1.33 to 1.45 (2H, m), 1.54 to 1.81 (6H, m), 2.90 (2H, m), 3.26 to 3.34 (4H, m), 3.55 (2H, t, J=6.6 Hz), 3.80 (2H, t, J=4.8 Hz), 3.84 (2H, t, J=7.0 Hz), 4.12 to 4.17 (2H, m), 4.39 (2H, s), 6.85 to 6.99 (4H, m), 7.13 (1H, d, J=8.2 Hz), 7.35 to 7.46 (6H, m), 8.01 (1H, dd, J=8.8, 2.6 Hz), 8.42 (1H, s), 8.62 (1H, d, J=2.2 Hz).

Example 278

(Preparation of Compound 295)

7-[4-(2-butoxyethoxy)phenyl]-1-propyl-N-[6-[[(1-propylimidazol-5-yl)methyl]sulfanyl]-3-pyridinyl]-2,3-dihydro-1-benzazepine-4-carboxamide (0.96 g) was dissolved in methylene chloride (29 ml), and a solution of m-chloroperbenzoic acid (0.38 g) in methylene chloride (14 ml) was added dropwise to the solution at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-propyl-N-[6-[[(1-propylimidazol-5-yl)methyl]sulfinyl]-3-pyridinyl]-2,3-dihydro-1-benzazepine-4-carboxamide (Compound 295) (0.23 g).

$^1$H-NMR (200 MHz, CDCl$_3$) δ 0.88 (3H, t, J=7.8 Hz), 0.93 (3H, t, J=7.2 Hz), 0.98 (3H, t, J=7.2 Hz), 1.33 to 1.45 (2H, m), 1.54 to 1.80 (6H, m), 2.92 (2H, m), 3.27 to 3.35 (4H, m), 3.55 (2H, t, J=6.6 Hz), 3.77 to 3.83 (2H, m), 3.87 to 3.95 (2H, m), 4.06 to 4.17 (3H, m), 4.36 (1H, d, J=14.8 Hz), 6.42 (1H, s), 6.82 (1H, d, J=9.2 Hz), 6.96 (2H, d, J=8.4 Hz), 7.38 to 7.56 (6H, m), 7.81 to 8.06 (1H, m), 8.12 (1H, dd, J=8.8, 2.6 Hz), 8.73 to 8.94 (1H, m), 9.01 (1H, s).

IR (KBr) 2961, 2872, 1661, 1607, 1499, 1240, 733 cm$^{-1}$

Example 279

(Preparation of Compound 296)

7-[4-(2-butoxyethoxy)phenyl]-1-isobutyl-2,3-dihydro-1-benzazepine-4-carboxylic acid (1.28 g) was dissolved in THF (12.8 ml), DMF (3 droplets) was added to the mixture, thionyl chloride (0.32 ml) was added to the mixture, and the mixture was stirred for 1 hour at room temperature. The solvent was removed under reduced pressure, and a solution of the obtained residue in THF (26 ml) was added dropwise to a solution of 6-[[(1-propylimidazol-5-yl)methyl]sulfanyl]pyridine-3-amine (0.80 g) in pyridine (16 ml) under ice-cooling and the mixture was stirred at room temperature for 3 hours. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[[(1-propylimidazol-5-yl)methyl]sulfanyl]-3-pyridinyl]-2,3-dihydro-1-benzazepine-4-carboxamide (Compound 296) (1.4 g).

$^1$H-NMR (200 MHz, CDCl$_3$) δ 0.92 (3H, t, J=7.4 Hz), 0.93 (3H, t, J=7.0 Hz), 0.97 (6H, d, J=6.2 Hz), 1.33 to 1.45 (2H, m), 1.53 to 1.84 (4H, m), 2.06 (1H, m), 2.92 (2H, m), 3.19 (2H, d, J=7.4 Hz), 3.55 (2H, t, J=6.6 Hz), 3.81 (2H, t, J=4.8 Hz), 3.87 (2H, t, J=7.2 Hz), 4.16 (2H, t, J=4.4 Hz), 4.42 (2H, s), 6.90 to 7.00 (4H, m), 7.15 (1H, d, J=8.8 Hz), 7.39 to 7.48 (6H, m), 7.99 to 8.05 (1H, m), 8.05 (1H, s), 8.61 (1H, d, J=1.8 Hz).

Example 280

(Preparation of Compound 297)

7-[4-(2-butoxyethoxy)phenyl]-1-isobutyl-N-[6-[[(1-propylimidazol-5-yl)methyl]sulfanyl]-3-pyridinyl]-2,3-dihydro-1-benzazepine-4-carboxamide (1.4 g) was dissolved in methylene chloride (42 ml), and a solution of m-chloroperbenzoic acid (0.65 g) in methylene chloride (28 ml) was added dropwise to the solution at −78° C. The mixture was stirred for 15 minutes, and an aqueous solution of saturated sodium thiosulfate was added to the mixture. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[6-[[(1-propylimidazol-5-yl)methyl]sulfinyl]-3-pyridinyl]-2,3-dihydro-1-benzazepine-4-carboxamide (Compound 297) (0.41 g).

$^1$H-NMR (200 MHz, CDCl$_3$) δ 0.90 (3H, t, J=7.2 Hz), 0.93 (3H, t, J=6.8 Hz), 0.97 (6H, d, J=6.6 Hz), 1.33 to 1.45 (2H, m), 1.54 to 1.81 (4H, m), 2.06 (1H, m), 2.93 (2H, m), 3.19 (2H, d, J=7.4 Hz), 3.36 (2H, m), 3.55 (2H, t, J=6 Hz), 3.80 (2H, t, J=4.4 Hz), 3.89 to 4.00 (2H, m), 4.08 to 4.18 (3H, m), 4.38 (1H, d, J=14.4 Hz), 6.42 (1H, s), 6.89 to 7.00 (3H, m), 7.38 to 7.59 (7H, m), 8.14 (1H, dd, J=8.4, 2.2 Hz), 8.50 (1H, m), 8.94 (1H, d, J=2.2 Hz).

IR (KBr) 2959, 2872, 1663, 1607, 1499, 1242, 733 cm$^{-1}$

Example 281

(Preparation of Compound 298, Compound 299)

7-[4-(2-butoxyethoxy)phenyl]-1-isobutyl-N-[6-[[(1-propylimidazol-2-yl)methyl]sulfinyl]-3-pyridinyl]-2,3-dihydro-1-benzazepine-4-carboxamide was optically resolved with CHIRALCEL AD(5 cmφ×50 cm), to give (+)-7-[4-(2-butoxyethoxy)phenyl]-1-isobutyl-N-[6-[[(1-propylimidazol-2-yl)methyl]sulfinyl]-3-pyridinyl]-2,3-dihydro-1-benzazepine-4-carboxamide (Compound 298) (64 mg, [α]$_D$=+203.2°) and (−)-7-[4-(2-butoxyethoxy)phenyl]-1-isobutyl-N-[6-[[(1-propylimidazol-2-yl)methyl]sulfinyl]-3-pyridinyl]-2,3-dihydro-1-benzazepine-4-carboxamide (Compound 299) (72 mg).

Example 282

(Preparation of Compound 300, Compound 301)

7-[4-(2-butoxyethoxy)phenyl]-1-propyl-N-[6-[[(1-propylimidazol-5-yl)methyl]sulfinyl]-3-pyridinyl]-2,3-dihydro-1-benzazepine-4-carboxamide was optically resolved with CHIRALCEL AD(5 cmφ×50 cm), to give (+)-7-[4-(2-butoxyethoxy)phenyl]-1-propyl-N-[6-[[(1-propylimidazol-5-yl)methyl]sulfinyl]-3-pyridinyl]-2,3-dihydro-1-benzazepine-4-carboxamide (Compound 300) (107 mg, [α]$_D$=+181.6°) and (−)-7-[4-(2-butoxyethoxy)phenyl]-1-propyl-N-[6-[[(1-propylimidazol-5-yl)methyl]sulfinyl]-3-pyridinyl]-2,3-dihydro-1-benzazepine-4-carboxamide (Compound 301) (103 mg).

Example 283

(Preparation of Compound 302, Compound 303)

7-[4-(2-butoxyethoxy)phenyl]-1-isobutyl-N-[6-[[(1-propylimidazol-5-yl)methyl]sulfinyl]-3-pyridinyl]-2,3-dihydro-1-benzazepine-4-carboxamide was optically resolved with CHIRALCEL AD(5 cmφ×50 cm), to give (+)-7-[4-(2-butoxyethoxy)phenyl]-1-isobutyl-N-[6-[[(1-propylimidazol-5-yl)methyl]sulfinyl]-3-pyridinyl]-2,3-dihydro-1-benzazepine-4-carboxamide (Compound 302) (80 mg, [α]$_D$=+225.8°) and (−)-7-[4-(2-butoxyethoxy)phenyl]-1-isobutyl-N-[6-[[(1-propylimidazol-5-yl)methyl]sulfinyl]-3-pyridinyl]-2,3-dihydro-1-benzazepine-4-carboxamide (Compound 303) (100 mg).

Example 284

(Preparation of Compound 304)

7-[4-(2-butoxyethoxy)phenyl]-1-propyl-2,3-dihydro-1-benzazepine-4-carboxylic acid (1.0 g) was dissolved in THF (10 ml), DMF (3 droplets) was added to the mixture, thionyl chloride (0.25 ml) was added to the mixture, and the mixture was stirred for 1 hour at room temperature. The solvent was removed under reduced pressure, and a solution of the obtained residue in THF (13.2 ml) was added dropwise to a solution of 4-[[2-(2-propylimidazol-1-yl)ethyl]sulfanyl]aniline (0.66 g) in pyridine (13.2 ml) under ice-cooling, and the mixture was stirred for 2 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[2-(2-propylimidazol-1-yl)ethyl]sulfanyl]phenyl]-2,3-dihydro-1-benzazepine-4-carboxamide (Compound 304) (0.86 g).

$^1$H-NMR (200 MHz, CDCl$_3$) δ 0.93 (3H, t, J=7.4 Hz), 0.95 (3H, t, J=7.2 Hz), 0.97 (6H, d, J=7.2 Hz), 1.33 to 1.45 (2H, m), 1.57 to 1.75 (4H, m), 2.03 (1H, m), 2.47 to 2.56 (2H, m), 2.92 (2H, m), 3.19 (2H, d, J=7.0 Hz), 3.33 to 3.40

(2H, m), 3.55 (2H, t, J=6.6 Hz), 3.80 (2H, t, J=4.8 Hz), 3.95 to 4.03 (2H, m), 4.13 to 4.18 (2H, m), 6.78 (1H, s), 6.78 to 7.00 (4H, m), 7.35 to 7.48 (7H, m), 7.61 (2H, d, J=8.8 Hz), 7.78 (1H, s).

Example 285

(Preparation of Compound 305)

7-[4-(2-butoxyethoxy)phenyl]-1-isobutyl-N-[4-[[2-(2-propylimidazol-1-yl)ethyl]sulfanyl]phenyl]-2,3-dihydro-1-benzazepine-4-carboxamide (0.78 g) was dissolved in methylene chloride (23.4 ml), and a solution of metachloroperbenzoic acid (0.34 g) in methylene chloride (15.6 ml) was added dropwise to the solution at −78° C. The mixture was stirred for 15 minutes, and to the mixture was added an aqueous solution of saturated sodium thiosulfate, and the mixture was allowed to be warmed to room temperature. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[2-(2-propylimidazol-1-yl)ethyl]sulfinyl]phenyl]-2,3-dihydro-1-benzazepine-4-carboxamide (Compound 305) (345 mg).

$^1$H-NMR (200 MHz, CDCl$_3$) δ 0.88 (3H, t, J=7.4 Hz), 0.92 to 1.01 (9H, m), 1.32 to 1.44 (2H, m), 1.54 to 1.81 (4H, m), 2.04 (1H, m), 2.61 to 2.69 (2H, m), 2.92 (2H, m), 3.00 to 3.12 (2H, m), 3.18 (2H, d, J=7.2 Hz), 3.35 (2H, m), 3.55 (2H, t, J=6.6 Hz), 4.12 to 4.18 (2H, m), 4.25 to 4.41 (2H, m), 6.78 (1H, s), 6.88 to 6.98 (4H, m), 7.38 to 7.46 (8H, m), 7.53 (2H, d, J=7.6 Hz), 7.81 (2H, d, J=8.0 Hz), 8.20 (1H, s).

IR (KBr) 2959, 1499, 1244, 733 cm$^{-1}$

Example 286

(Preparation of Compound 306)

7-[4-(2-butoxyethoxy)phenyl]-1-propyl-2,3-dihydro-1-benzazepine-4-carboxylic acid (0.79 g) was dissolved in THF (7.9 ml), DMF (3 droplets) was added to the mixture, thionyl chloride (0.20 ml) was added to the mixture, and the mixture was stirred for 1 hour at room temperature. The solvent was removed under reduced pressure, and a solution of the obtained residue in THF (10 ml) was added dropwise to a solution of 1-methyl-5-[[(1-propylimidazol-5-yl)methyl]thio]-1,2,4-triazole-3-amine (0.50 g) in pyridine (10 ml) under ice-cooling, and the mixture was stirred for 2 hours at room temperature. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[1-methyl-5-[[(1-propylpropylimidazol-5-yl)methyl]sulfanyl]-1,2,4-triazol-3-yl]-2,3-dihydro-1-benzazepine-4-carboxamide (Compound 306) (0.40 g).

$^1$H-NMR (200 MHz, CDCl$_3$) δ 0.93 (3H, t, J=6.8 Hz), 0.96 (6H, d, J=6.6 Hz), 0.96 (3H, t, J=7.4 Hz), 1.30 to 1.45 (2H, m), 1.54 to 1.67 (2H, m), 1.74 to 1.89 (2H, m), 2.04 (1H, m), 2.93 (2H, m), 3.19 (2H, d, J=7.2 Hz), 3.33 to 3.38 (2H, m), 3.55 (2H, t, J=6.6 Hz), 3.65 to 3.74 (2H, m), 3.69 (3H, s), 3.91 (2H, t, J=7.0 Hz), 4.13 to 4.19 (2H, m), 4.43 (2H, s), 6.89 to 7.01 (4H, m), 7.37 to 7.50 (6H, m), 8.10 (1H, s).

IR (KBr) 2959, 1667, 1499, 1242, 733 cm$^{-1}$

Example 287

(Preparation of Compound 307)

7-[4-(2-butoxyethoxy)phenyl]-1-propyl-2,3-dihydro-1-benzazepine-4-carboxylic acid (1.0 g) was dissolved in THF (10 ml), DMF (3 droplets) was added to the mixture, thionyl chloride (0.25 ml) was added to the mixture, and the mixture was stirred for 1 hour at room temperature. The solvent was removed under reduced pressure, and a solution of the obtained residue in THF (13.2 ml) was added dropwise to a solution of S-(4-aminophenyl)O-benzylthiocarbonate (0.59 g) and triethylamine (1.91 ml) in THF (17.8 ml) under ice-cooling, and the mixture was stirred for 2 hours at room temperature. To the reaction mixture, methanol (35.6 ml) and 1N sodium hydroxide (18.3 ml) were added and the mixture was stirred at room temperature for 20 minutes. 5-chloromethyl-1-(2-methoxyethyl)imidazole hydrochloride (0.58 g) was added to the mixture, and the mixture was stirred for 20 minutes at room temperature. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[[1-(2-methoxyethyl)imidazol-5-yl]methyl]sulfanyl]phenyl]-2,3-dihydro-1-benzazepine-4-carboxamide (Compound 307) (550 mg).

$^1$H-NMR (200 MHz, CDCl$_3$) δ 0.93 (3H, t, J=7.0 Hz), 0.96 (6H, d, J=6.6 Hz), 1.33 to 1.45 (2H, m), 1.54 to 1.65 (2H, m), 2.03 (1H, m), 2.90 (2H, m), 3.32 (3H, s), 3.55 (2H, t, J=6.6 Hz), 3.61 to 3.67 (2H, m), 3.76 to 3.83 (2H, m), 4.02 (2H, s), 4.09 to 4.18 (4H, m), 6.68 (1H, s), 6.91 (1H, d, J=8.4 Hz), 6.97 (2H, d, J=8.8 Hz), 7.22 (1H, s), 7.37 to 7.56 (9H, m), 7.91 (1H, s).

IR (KBr) 2955, 1651, 1497, 1244, 733 cm$^{-1}$

Example 288

(Preparation of Compound 308)

7-[4-(2-butoxyethoxy)phenyl]-1-isobutyl-N-[4-[[[1-(2-methoxyethyl)imidazol-5-yl]methyl]sulfanyl]phenyl]-2,3-dihydro-1-benzazepine-4-carboxamide (0.49 g) was dissolved in methylene chloride (14.7 ml), and a solution of metachloroperbenzoic acid (0.25 g) in methylene chloride (9.8 ml) was added dropwise to the solution at −78° C. The mixture was stirred for 15 minutes, and to the mixture was added an aqueous solution of saturated sodium thiosulfate, and the mixture was allowed to be warmed to room temperature. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[[1-(2-methoxyethyl)imidazol-5-yl]methyl]sulfinyl]phenyl]-2,3-dihydro-1-benzazepine-4-carboxamide (Compound 308) (0.26 g).

$^1$H-NMR (200 MHz, CDCl$_3$) δ 0.93 (3H, t, J=7.4 Hz), 0.97 (6H, d, J=6.6 Hz), 1.33 to 1.45 (2H, m), 1.57 to 1.68 (2H, m), 2.04 (1H, m), 2.93 (2H, m), 3.19 (2H, d, J=7.4 Hz), 3.28 (3H, s), 3.36 (2H, m), 3.54 to 3.58 (4H, m), 3.78 to 3.83 (2H, m), 3.99 to 4.06 (3H, m), 4.12 to 4.20 (3H, m), 6.56 (1H, s), 6.92 (1H, d, J=9.2 Hz), 6.97 (2H, d, J=8.8 Hz), 7.32 to 7.56 (9H, m), 7.74 (2H, d, J=8.6 Hz), 7.99 (1H, s).

IR (KBr) 2959, 1653, 1497, 1246, 1119 cm$^{-1}$

Example 289

(Preparation of Compound 309)

7-[4-(2-butoxyethoxy)phenyl]-1-propyl-2,3-dihydro-1-benzazepine-4-carboxylic acid (1.0 g) was dissolved in THF (10 ml), DMF (3 droplets) was added to the mixture, thionyl chloride (0.25 ml) was added to the mixture, and the mixture was stirred for 1 hour at room temperature. The solvent was removed under reduced pressure, and a solution of the obtained residue in THF (13.4 ml) was added dropwise to a solution of 4-[[2-[(1-methylimidazol-2-yl)thio]ethyl]thio]aniline (0.67 g) in pyridine (13.4 ml) under ice-cooling, and the mixture was stirred for 2 hours at room temperature. The solvent was removed under reduced pressure, and to the obtained residue was added water and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[2-[(1-methylimidazol-2-yl)sulfanyl]ethyl]sulfanyl]phenyl]-2,3-dihydro-1-benzazepine-4-carboxamide (Compound 309) (1.2 g).

$^1$H-NMR (200 MHz, CDCl$_3$) δ 0.93 (3H, t, J=7.2 Hz), 0.96 (6H, d, J=6.6 Hz), 1.33 to 1.47 (2H, m), 1.54 to 1.68 (2H, m), 2.07 (1H, m), 2.89 (2H, m), 3.15 (3H, s), 3.17 (2H, d, J=7.0 Hz), 3.30 to 3.35 (2H, m), 3.55 (2H, t, J=7.0 Hz), 3.58 (3H, s), 3.77 to 3.83 (2H, m), 4.12 to 4.17 (2H, m), 6.87 to 7.07 (4H, m), 7.18 to 7.47 (8H, m), 7.54 (2H, d, J=8.8 Hz), 7.84 (1H, s).

Example 290

(Preparation of Compound 310)

7-[4-(2-butoxyethoxy)phenyl]-1-isobutyl-N-[4-[[2-[(1-methylimidazol-2-yl)sulfanyl]ethyl]sulfanyl]phenyl]-2,3-dihydro-1-benzazepine-4-carboxamide (1.20 g) was dissolved in methylene chloride (24.0 ml), and a solution of metachloroperbenzoic acid (0.52 g) in methylene chloride (24.0 ml) was added dropwise to the solution at −78° C. The mixture was stirred for 15 minutes, and to the mixture was added an aqueous solution of saturated sodium thiosulfate, and the mixture was allowed to be warmed to room temperature. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[4-[[2-[(1-methylimidazol-2-yl)sulfanyl]ethyl]sulfinyl]phenyl]-2,3-dihydro-1-benzazepine-4-carboxamide (Compound 310) (0.68 g).

$^1$H-NMR (200 MHz, CDCl$_3$) δ 0.93 (3H, t, J=7.4 Hz), 0.96 (6H, d, J=6.6 Hz), 1.32 to 1.47 (2H, m), 1.54 to 1.65 (2H, m), 2.08 (1H, m), 2.92 (2H, m), 3.18 to 3.30 (4H, m), 3.19 (2H, d, J=7.2 Hz), 3.36 (2H, m), 3.55 (2H, t, J=6.6 Hz), 3.57 (3H, s), 3.77 to 3.83 (2H, m), 4.12 to 4.18 (2H, m), 6.89 to 6.95 (3H, m), 7.01 (2H, d, J=88.8 Hz), 7.38 to 7.56 (7H, m), 7.77 (2H, d, J=8.8 Hz), 8.11 (1H, s).

IR (KBr) 2955, 1661, 1497, 1246 cm$^{-1}$

Example 291

(Preparation of Compound 311)

7-[4-(2-butoxyethoxy)phenyl]-1-propyl-2,3-dihydro-1-benzazepine-4-carboxylic acid (0.57 g) was dissolved in THF (5.7 ml), DMF (3 droplets) was added to the mixture, thionyl chloride (0.14 ml) was added to the mixture, and the mixture was stirred for 1 hour at room temperature.

The solvent was removed under reduced pressure, and a solution of the obtained residue in THF (7.6 ml) was added dropwise to a solution of 4-[[2-[(4-methyl-1,2,4-triazol-3-yl)thio]ethyl]thio]aniline (0.38 g) in pyridine (7.6 ml) under ice-cooling, and the mixture was stirred for 2 hours at room temperature. The solvent was removed under reduced pressure, and water was added to the obtained residue and extracted with ethyl acetate. The organic layer was washed with saturated brine, and dried over magnesium sulfate.

The solvent was removed under reduced pressure, and the obtained residue was purified by silica gel column chromatography, to give 7-[4-(2-butoxyethoxy)phenyl]-1-isobutyl-N-[4-[[2-[(4-methyl-1,2,4-triazol-3-yl)sulfanyl]ethyl]sulfanyl]phenyl]-2,3-dihydro-1-benzazepine-4-carboxamide (Compound 311) (0.60 g).

$^1$H-NMR (200 MHz, CDCl$_3$) δ 0.93 (3H, t, J=7.0 Hz), 0.97 (6H, d, J=6.6 Hz), 1.33 to 1.47 (2H, m), 1.53 to 1.65 (2H, m), 2.06 (1H, m), 2.89 (2H, m), 3.17 (2H, d, J=7.4 Hz), 3.17 (2H, d, J=7.0 Hz), 3.29 to 3.36 (4H, m), 3.52 (3H, s), 3.55 (2H, t, J=6.6 Hz), 3.77 to 3.83 (2H, m), 4.12 to 4.17 (2H, m), 4.38 (2H, t, J=6.6 Hz), 6.91 (1H, d, J=8.8 Hz), 6.97 (2H, d, J=8.8 Hz), 7.14 to 7.23 (1H, m), 7.36 to 7.56 (8H, m), 7.67 (1H, s).

IR (KBr) 2959, 1651, 1497, 1242, 733 cm$^{-1}$

Example 292

(Preparation of Compound 312)

7-[4-(2-butoxyethoxy)phenyl]-1-propyl-2,3-dihydro-1-benzazepine-4-carboxylic acid (0.65 g) was dissolved in THF (6.5 ml), DMF (3 droplets) was added to the mixture, thionyl chloride (0.16 ml) was added to the mixture, and the mixture was stirred for 1 hour at room temperature. The solvent was removed under reduced pressure, and a solution of the obtained residue in THF (9.4 ml) was added dropwise to a solution of 2-[[(1-propylimidazol-5-yl)methyl]thio]benzimidazole-5-amine (0.47 g) in pyridine (9.4 ml) under ice-cooling, and the mixture was stirred for 2 hours at room temperature. The solvent was removed under reduced pressure, and to the obtained residue was added water and the mixture was extracted with ethyl acetate. The organic layer was washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[2-[[(1-propylimidazol-5-yl)methyl]sulfanyl]benzimidazol-5-yl]-2,3-dihydro-1-benzazepine-4-carboxamide (Compound 312) (0.64 g).

$^1$H-NMR (200 MHz, CDCl$_3$) δ 0.83 (3H, t, J=7.6 Hz), 0.92 ((3H, m), 0.94 (6H, d, J=7.0 Hz), 1.33 to 1.45 (2H, m), 1.54 to 1.68 (2H, m), 2.04 (1H, m), 2.89 (2H, m), 3.13 (2H, d, J=6.8 Hz), 3.30 (2H, m), 3.54 (2H, t, J=6.6 Hz), 3.76 to 3.84 (2H, m), 4.13 (2H, t, J=4.8 Hz), 4.49 (2H, s), 6.85 to 6.96 (4H, m), 7.35 to 7.47 (8H, m), 8.04 (1H, br), 8.23 (1H, s).

Example 293

(Preparation of Compound 313)

7-[4-(2-butoxyethoxy)phenyl]-1-isobutyl-N-[2-[[(1-propylimidazol-5-yl)methyl]sulfanyl]benzimidazol-5-yl]-2,3-dihydro-1-benzazepine-4-carboxamide (0.64 g) was dissolved in methylene chloride (19.2 ml), and a solution of metachloroperbenzoic acid (0.27 g) in methylene chloride (12.8 ml) was added dropwise to the solution at −78° C. The mixture was stirred for 15 minutes, and to the mixture was added an aqueous solution of saturated sodium thiosulfate, and the mixture was allowed to be warmed to room temperature. The mixture was extracted with ethyl acetate, washed with saturated brine, and dried over magnesium sulfate. The solvent was removed under reduced pressure, and the obtained residue was purified by silica gel column chromatography, to give 7-[4-(2-butoxyethoxy)phenyl]-1-isobutyl-N-[2-[[(1-propylimidazol-5-yl)methyl]sulfinyl]benzimidazol-5-yl]-2,3-dihydro-1-benzazepine-4-carboxamide (Compound 313) (0.21 g).

$^1$H-NMR (200 MHz, CDCl$_3$) δ 0.87 (3H, t, J=7.4 Hz), 0.92 (3H, t, J=7.4 Hz), 0.98 (6H, d, J=7.2 Hz), 1.32 to 1.45 (2H, m), 1.53 to 1.70 (2H, m), 2.04 (1H, m), 2.84 (2H, m), 3.07 to 3.12 (2H, m), 3.2 (2H, m), 3.54 (2H, t, J=6.6 Hz), 3.66 to 3.81 (4H, m), 4.08 to 4.13 (2H, m), 4.31 (1H, d, J=14.6 Hz), 4.56 (1H, d, J=14.6 Hz), 6.37 (1H, s), 6.85 (1H, d, J=8.4 Hz), 6.93 (2H, d, J=8.8 Hz), 7.32 to 7.45 (8H, m), 7.82 (1H, s).

IR (KBr) 2959, 1653, 1499, 1244 cm$^{-1}$

Example 294

(Preparation of Compound 314)

To a solution of 7-[4-(2-butoxyethoxy)phenyl]-N-[2-ethoxy-4-[hydroxy(1-oxidopyridin-2-yl)methyl]phenyl]-2,3-dihydro-1-benzazepine-4-carboxamide (120 mg), isobutylaldehyde (140 mg) and sodium triacetoxy borohydride (410 mg) in 1,2-dichloroethane (10 ml) was added acetic acid (0.06 ml) and the mixture was stirred overnight. To the mixture was added water, and the mixture was extracted with ethyl acetate. The organic layer was washed with saturated brine, and dried over magnesium sulfate. The solvent was distilled off under reduced pressure. The obtained residue was purified by silica gel column chromatography (methanol:ethyl acetate=1:8), to give 7-[4-(2-butoxyethoxy)phenyl]-N-[2-ethoxy-4-[hydroxy(1-oxidopyridin-2-yl)methyl]phenyl]-1-isobutyl-2,3-dihydro-1-benzazepine-4-carboxamide (63 mg) (Compound 314) as yellow amorphous.

$^1$H-NMR (200 MHz, CDCl$_3$) δ 0.89 to 1.00 (9H, m), 1.30 to 1.70 (7H, m), 2.00 to 2.20 (1H, m), 2.90 to 3.00 (2H, m), 3.20 (2H, d, J=7.2 Hz), 3.30 to 3.45 (2H, m), 3.55 (2H, t, J=6.2 Hz), 3.81 (2H, t, J=5.0 Hz), 4.10 to 4.30 (4H, m), 6.02 to 6.10 (1H, m), 6.45 to 6.55 (1H, m), 6.70 (1H, s), 6.90 to 7.05 (5H, m), 7.17 (1H, s), 7.24 to 7.28 (1H, m), 7.35 to 7.60 (5H, m), 8.22 to 8.32 (1H, m), 8.36 (1H, s), 8.48 (1H, d. J=8.8 Hz)

Elemental Analysis for C$_{41}$H$_{49}$N$_3$O$_6$.0.4H$_2$O Calcd. C, 71.67; H, 7.31; N, 6.12. Found: C, 71.39; H, 7.22; N, 5.83.

Example 295

(Preparation of Compound 315)

To a solution of 7-[4-(2-butoxyethoxy)phenyl]-N-[4-[hydroxy(1-oxidopyridin-2-yl)methyl]-3-trifluoromethylphenyl]-2,3-dihydro-1-benzazepine-4-carboxamide (80 mg), isobutylaldehyde (100 mg) and sodium triacetoxy borohydride (286 mg) in 1,2-dichloroethane (10 ml) was added acetic acid (0.04 ml) and the mixture was stirred overnight. To the mixture was added water, and the mixture was extracted with ethyl acetate. The organic layer was washed with saturated brine, and dried over magnesium sulfate. The solvent was distilled off under reduced pressure. The obtained residue was purified by silica gel column chromatography (ethyl acetate), to give 7-[4-(2-butoxyethoxy)phenyl]-N-[4-[hydroxy(1-oxidopyridin-2-yl)methyl]-3-trifluoromethylphenyl]-1-isobutyl-2,3-dihydro-1-benzazepine-4-carboxamide (30 mg) (Compound 315) as yellow amorphous.

$^1$H-NMR (200 MHz, CDCl$_3$) δ 0.90 to 1.00 (9H, m), 1.26 to 1.70 (4H, m), 2.00 to 2.20 (1H, m), 2.90 to 3.00 (2H, m), 3.21 (1H, d, J=7.4 Hz), 3.35 to 3.45 (2H, m), 3.56 (2H, t, J=7.0 Hz), 3.81 (2H, t, J=5.2 Hz), 4.16 (2H, t, J=5.2 Hz), 6.45 to 6.49 (1H, m), 6.57 to 6.63 (1H, m), 6.71 (1H, d, J=2.6 Hz), 6.92 to 7.01 (3H, m), 7.17 to 7.53 (7H, m), 7.77 (1H, s), 7.93 (2H, s), 8.04 (1H, s), 8.31 (1H, d, J=5.8 Hz).

Elemental Analysis for C$_{40}$H$_{44}$N$_3$O$_5$F$_3$.0.3H$_2$O Calcd. C, 67.74; H, 6.34; N, 5.93. Found: C, 67.58; H, 6.28; N, 5.85.

Example 296

(Preparation of Compound 316)

To a solution of 7-[4-(2-butoxyethoxy)phenyl]-1-isobutyl-2,3-dihydro-1-benzazepine-4-carboxylic acid (438 mg) in tetrahydrofuran (10 ml) was added one droplet of DMF. Then, thionyl chloride (0.095 ml) was added to the mixture at 0° C., and the mixture was allowed to be at room temperature under nitrogen atmosphere and the mixture was stirred for 1 hour. This solution was added to a solution of 4-[(thiazol-2-ylmethyl)sulfanyl]aniline (265 mg) and triethylamine (3.6 ml) in tetrahydrofuran (10 ml) at 0° C. The mixture was stirred overnight at room temperature under nitrogen atmosphere, water was added to the mixture, and the mixture was extracted with ethyl acetate. The organic layer was washed with saturated brine, and dried over magnesium sulfate. The solvent was distilled off under reduced pressure. The obtained residue was purified by silica gel column chromatography (hexane:ethyl acetate=2:1) and was recrystallized from hexane-ethyl acetate, to give 7-[4-(2-butoxyethoxy)phenyl]-1-isobutyl-N-[4-[(thiazol-2-ylmethyl)sulfanyl]phenyl]-2,3-dihydro-1-benzazepine-4-carboxamide (424 mg) (Compound 316) as yellow crystals.

$^1$H-NMR (200 MHz, CDCl$_3$) δ 0.90 to 0.98 (9H, m), 1.34 to 1.70 (4H, m), 1.95 to 2.20 (1H, m), 2.90 (2H, t, J=4.4 Hz), 3.18 (2H, d, J=7.2 Hz), 3.36 (2H, t, J=4.4 Hz), 3.55 (2H, t, J=6.6 Hz), 3.80 (2H, t, J=4.8 Hz), 4.16 (2H, t, J=4.8 Hz), 4.40 (2H, s), 6.92 (1H, d, J=8.8 Hz), 6.98 (2H, d, J=8.8 Hz), 7.24 (1H, d, J=3.2 Hz), 7.35 to 7.55 (10H, m), 7.67 (1H, d, J=3.2 Hz).

Elemental Analysis for C$_{37}$H$_{43}$N$_3$O$_3$S$_2$ Calcd. C, 69.23; H, 6.75; N, 6.55. Found: C, 69.34; H, 6.79; N, 6.60.

Example 297

(Preparation of Compound 317)

To a solution of 7-[4-(2-butoxyethoxy)phenyl]-1-isobutyl-N-[4-[(thiazol-2-ylmethyl)sulfanyl]phenyl]-2,3-dihydro-1-benzazepine-4-carboxamide (150 mg) in dichloromethane (10 ml) was added dropwise 70% solution of 3-chloroperbenzoic acid (57.6 mg) in dichloromethane (10 ml) at −78° C. After finishing the dropping, an aqueous solution of sodium thiosulfate was added to the mixture, and the mixture was allowed to be at room temperature, and stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated purified by silica gel column chromatography (hexane:ethyl acetate=1:3→ethyl acetate), and was recrystallized from hexane-ethyl acetate, to give 7-[4-(2-butoxyethoxy)phenyl]-1-isobutyl-N-[4-[(thiazol-2-ylmethyl)sulfinyl]phenyl]-2,3-dihydro-1-benzazepine-4-carboxamide (110 mg) (Compound 317) as yellow crystals.

$^1$H-NMR (200 MHz, CDCl$_3$) δ 0.89 to 0.99 (9H, m), 1.30 to 1.70 (4H, m), 2.00 to 2.20 (1H, m), 2.92 (2H, t, J=5.2 Hz), 3.19 (2H, d, J=7.2 Hz), 3.37 (2H, t, J=5.2 Hz), 3.55 (2H, t, J=6.6 Hz), 3.80 (2H, t, J=4.8 Hz), 4.16 (2H, t, J=4.8 Hz), 4.40 (1H, d, J=13.2 Hz), 4.48 (1H, d, J=13.2 Hz), 6.93 (1H, d, J=8.8 Hz), 6.98 (2H, d, J=8.8 Hz), 7.31 (1H, d, J=3.4 Hz), 7.39 to 7.49 (7H, m), 7.71 to 7.78 (4H, m).

Elemental Analysis for C$_{37}$H$_{43}$N$_3$O$_4$S$_2$ Calcd. C, 67.55; H, 6.59; N, 6.39. Found: C, 67.46; H, 6.39; N, 6.39.

Example 298

(Preparation of Compound 318)

To a solution of 7-[4-(2-butoxyethoxy)phenyl]-1-isobutyl-2,3-dihydro-1-benzazepine-4-carboxylic acid (385 mg) in tetrahydrofuran (10 ml) was added one droplet of DMF. Then, thionyl chloride (0.084 ml) was added to the mixture at 0° C., and the mixture was allowed to be at room temperature and stirred for 1 hour under nitrogen atmosphere. This solution was added to a solution of 4-[[(3-methyl isothiazol-2-yl)methyl]sulfanyl]aniline (250 mg) and triethylamine (3.2 ml) in tetrahydrofuran (10 ml) at 0° C. The mixture was stirred for 1.5 hours at room temperature under nitrogen atmosphere, water was added to the mixture, and the mixture was extracted with ethyl acetate. The organic layer was washed with saturated brine, and dried over magnesium sulfate. The solvent was distilled off under reduced pressure. The obtained residue was purified by silica gel column chromatography (hexane:ethyl acetate=3:1) and recrystallized from hexane-ether, to give 7-[4-(2-butoxyethoxy)phenyl]-1-isobutyl-N-[4-[[(3-methyl isothiazol-5-yl)methyl]sulfanyl]phenyl]-2,3-dihydro-1-benzazepine-4-carboxamide (343 mg) (Compound 318) as yellow crystals.

$^1$H-NMR (200 MHz, CDCl$_3$) δ 0.90 to 0.99 (9H, m), 1.34 to 1.70 (4H, m), 1.95 to 2.20 (1H, m), 2.42 (3H, s), 2.85 to 2.95 (2H, m), 3.19 (2H, d, J=6.6 Hz), 3.32 to 3.43 (2H, m), 3.55 (2H, t, J=7.0 Hz), 3.80 (2H, t, J=5.4 Hz), 4.16 (2H, t, J=5.4 Hz), 4.25 (2H, s), 6.79 (1H, s), 6.90 to 7.00 (3H, m), 7.34 to 7.57 (10H, m).

Example 299

(Preparation of Compound 319)

To a solution of 7-[4-(2-butoxyethoxy)phenyl]-1-isobutyl-N-[4-[[(3-methyl isothiazol-2-yl)methyl]sulfanyl]phenyl]-2,3-dihydro-1-benzazepine-4-carboxamide (150 mg) in dichloromethane (10 ml) was added dropwise 70% solution of 3-chloroperbenzoic acid (56.5 mg) in dichloromethane (10 ml) at −78° C. After finishing the dropping, an aqueous solution of sodium thiosulfate was added to the mixture, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate), and was recrystallized from hexane-ethyl acetate, to give 7-[4-(2-butoxyethoxy)phenyl]-1-isobutyl-N-[4-[[(3-methyl isothiazol-5-yl)methyl]sulfinyl]phenyl]-2,3-dihydro-1-benzazepine-4-carboxamide (132 mg) (Compound 319) as yellow crystals.

$^1$H-NMR (200 MHz, CDCl$_3$) δ 0.90 to 0.99 (9H, m), 1.34 to 1.69 (4H, m), 2.00 to 2.20 (1H, m), 2.44 (3H, s), 2.85 to 3.00 (2H, m), 3.20 (2H, d, J=7.4 Hz), 3.35 to 3.45 (2H, m), 3.55 (2H, t, J=6.6 Hz), 3.81 (2H, t, J=4.8 Hz), 4.13 to 4.31 (3H, m), 4.34 (1H, d, J=13.8 Hz), 6.79 (1H, s), 6.91 to 7.00 (3H, m), 7.40 to 7.51 (7H, m), 7.52 to 7.76 (3H, m).

Elemental Analysis for C$_{38}$H$_{45}$N$_3$O$_4$S$_2$ Calcd. C, 67.93; H, 6.75; N, 6.25. Found: C, 67.78; H, 6.67; N, 6.27.

Example 300

(Preparation of Compound 320)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 4-[[(1-methylpyrazol-2-yl)methyl]sulfanyl]aniline (456 mg) and triethylamine (5.8 ml) in tetrahydrofuran (15 ml) at 0° C. The mixture was stirred for 1 hour at room temperature under nitrogen atmosphere, water was added to the mixture, and the mixture was extracted with ethyl acetate. The organic layer was washed with saturated brine, and dried over magnesium sulfate. The solvent was distilled off under reduced pressure. The obtained residue was purified by silica gel column chromatography (hexane:ethyl acetate=1:1), to give 7-[4-(2-butoxyethoxy)phenyl]-1-isobutyl-N-[[(1-methylpyrazol-5-yl)methyl]sulfanyl]phenyl]-2,3-dihydro-1-benzazepine-4-carboxamide (827 mg) (Compound 320) as yellow amorphous.

$^1$H-NMR (200 MHz, CDCl$_3$) δ 0.89 to 0.99 (9H, m), 1.34 to 1.45 (2H, m), 1.54 to 1.64 (2H, m), 2.00 to 2.20 (1H, m), 2.90 (2H, t, J=4.2 Hz), 3.19 (2H, d, J=7.0 Hz), 3.36 (2H, t, J=4.4 Hz), 3.55 (2H, t, J=6.6 Hz), 3.78 to 3.83 (5H, m), 4.01 (2H, s), 4.16 (2H, t, J=5.0 Hz), 5.97 (1H, d, J=1.8 Hz), 6.90 to 7.00 (3H, m), 7.27 to 7.33 (3H, m), 7.37 to 7.58 (8H, m).

Example 301

(Preparation of Compound 321)

To a solution of 7-[4-(2-butoxyethoxy)phenyl]-1-isobutyl-N-[4-[[(1-methylpyrazol-2-yl)methyl]sulfanyl]phenyl]-2,3-dihydro-1-benzazepine-4-carboxamide (200 mg) in dichloromethane (10 ml) was added dropwise 70% solution of 3-chloroperbenzoic acid (116 mg) in dichloromethane (10 ml) at −78° C. After finishing the dropping, an aqueous solution of sodium thiosulfate was added to the mixture, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate), to give 7-[4-(2-butoxyethoxy)phenyl]-1-isobutyl-N-[4-[[(1-methylpyrazol-5-yl)methyl]sulfinyl]phenyl]-2,3-dihydro-1-benzazepine-4-carboxamide (139 mg) (Compound 321) as yellow amorphous.

$^1$H-NMR (200 MHz, CDCl$_3$) δ 0.88 to 0.99 (9H, m), 1.34 to 1.70 (4H, m), 2.00 to 2.20 (1H, m), 2.90 to 2.97 (2H, m), 3.20 (2H, d, J=7.2 Hz), 3.30 to 3.45 (2H, m), 3.52 to 3.58 (5H, m), 3.81 (2H, t, J=4.6 Hz), 4.12 to 4.18 (4H, m), 5.98 (1H, d, J=2.2 Hz), 6.91 to 7.02 (3H, m), 7.34 to 7.52 (8H, m), 7.72 to 7.76 (3H, m).

Elemental Analysis for $C_{38}H_{46}N_4O_4S \cdot 0.3H_2O$ Calcd. C, 69.12; H, 7.11; N, 8.49. Found: C, 68.94; H, 6.96; N, 8.15.

Example 302

(Preparation of Compound 322)

To a solution of 7-[4-(2-butoxyethoxy)phenyl]-1-isobutyl-2,3-dihydro-1-benzazepine-4-carboxylic acid (700 mg) in tetrahydrofuran (15 ml): was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 4-[[(1-methylimidazol-2-yl)methyl]sulfanyl]aniline (456 mg) and triethylamine (5.8 ml) in tetrahydrofuran (15 ml) at 0° C. The mixture was stirred overnight at room temperature under nitrogen atmosphere, water was added to the mixture, and the mixture was extracted with ethyl acetate. The organic layer was washed with saturated brine, and dried over magnesium sulfate. The solvent was distilled off under reduced pressure. The obtained residue was purified by silica gel column chromatography (ethyl acetate), to give 7-[4-(2-butoxyethoxy)phenyl]-1-isobutyl-N-[4-[[(1-methylimidazol-2-yl)methyl]sulfanyl]phenyl]-2,3-dihydro-1-benzazepine-4-carboxamide (576 mg) (Compound 322) as yellow amorphous.

$^1$H-NMR (200 MHz, CDCl$_3$) δ 0.90 to 0.99 (9H, m), 1.34 to 1.45 (2H, m), 1.54 to 1.80 (2H, m), 2.00 to 2.15 (1H, m), 2.91 (2H, t, J=5.6 Hz), 3.18 (2H, d, J=7.0 Hz), 3.36 (2H, t, J=5.6 Hz), 3.52 to 3.59 (5H, m), 3.80 (2H, t, J=4.8 Hz), 4.11 (2H, s), 4.16 (2H, t, J=4.8 Hz), 6.78 (1H, d, J=1.0 Hz), 6.89 (1H, d, J=1.4 Hz), 6.93 to 7.00 (3H, m), 7.31 to 7.55 (9H, m), 7.80 (1H, s).

Elemental Analysis for $C_{38}H_{46}N_4O_3S$ Calcd. C, 71.44; H, 7.26; N, 8.77. Found: C, 71.28; H, 7.29; N, 8.38.

Example 303

(Preparation of Compound 323 and Compound 324)

To a solution of 7-[4-(2-butoxyethoxy)phenyl]-1-isobutyl-N-[4-[[(1-methylimidazol-2-yl)methyl]sulfanyl]phenyl]-2,3-dihydro-1-benzazepine-4-carboxamide (200 mg) in dichloromethane (20 ml) was added dropwise 70% solution of 3-chloroperbenzoic acid (116 mg) in dichloromethane (20 ml) at −78° C. After finishing the dropping, an aqueous solution of sodium thiosulfate was added to the mixture, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (methanol:ethyl acetate=1:8), and was recrystallized from hexane-ethyl acetate, to give 7-[4-(2-butoxyethoxy)phenyl]-1-isobutyl-N-[4-[[(1-methylimidazol-2-yl)methyl]sulfinyl]phenyl]-2,3-dihydro-1-benzazepine-4-carboxamide (118 mg) (Compound 323) as yellow crystals, and was recrystallized from hexane-ethyl acetate, to give 7-[4-(2-butoxyethoxy)phenyl]-1-isobutyl-N-[4-[[(1-methylimidazol-2-yl)methyl]sulfonyl]phenyl]-2,3-dihydro-1-benzazepine-4-carboxamide (33.5 mg) (Compound 324) as yellow crystals.

Compound 323

$^1$H-NMR (200 MHz, CDCl$_3$) δ 0.90 to 1.00 (9H, m), 1.34 to 1.50 (2H, m), 1.55 to 1.65 (2H, m), 2.00 to 2.20 (1H, m), 2.90 to 3.00 (2H, m), 3.20 (2H, d, J=7.4 Hz), 3.33 to 3.43 (2H, m), 3.46 (3H, s), 3.55 (2H, t, J=6.6 Hz), 3.80 (2H, t, J=4.8 Hz), 4.05 to 4.28 (4H, m), 6.81 (1H, d, J=1.2 Hz), 6.90 to 7.00 (4H, m), 7.40 to 7.48 (7H, m), 7.74 (2H, d, J=8.8 Hz), 7.91 (1H, s).

Elemental Analysis for $C_{38}H_{46}N_4O_4S \cdot 0.1H_2O$ Calcd. C, 68.19; H, 7.17; N, 8.37. Found: C, 68.13; H, 6.92; N, 7.97.

Compound 324

$^1$H-NMR (200 MHz, CDCl$_3$) δ 0.90 to 1.02 (9H, m), 1.30 to 1.65 (4H, m), 1.90 to 2.20 (1H, m), 2.90 to 3.00 (2H, m), 3.21 (2H, d, J=7.4 Hz), 3.32 to 3.42 (2H, m), 3.55 (2H, t, J=6.6 Hz), 3.64 (3H, s), 3.81 (2H, t, J=4.4 Hz), 4.16 (2H, t, J=4.8 Hz), 4.34 (2H, s), 6.85 to 6.99 (5H, m), 7.23 to 7.29 (2H, m), 7.39 to 7.43 (3H, m), 7.55 (2H, d, J=8.8 Hz), 7.75 (2H, d, J=8.8 Hz), 8.48 (1H, s).

Elemental Analysis for $C_{38}H_{46}N_4{}_5S \cdot 0.1H_2O$ Calcd. C, 67.85; H, 6.92; N, 8.33. Found: C, 67.62; H, 6.87; N, 8.03.

Example 304

(Preparation of Compound 325 and Compound 326)

7-[4-(2-butoxyethoxy)phenyl]-1-isobutyl-N-[4-[[(1-methylimidazol-2-yl)methyl]sulfinyl]phenyl]-2,3-dihydro-1-benzazepine-4-carboxamide (600 mg) was optically resoluted with CHIRAKPAK AD 50 mm ID×500 mmL (hexane/ethanol), to give (+)-7-[4-(2-butoxyethoxy)phenyl]-1-isobutyl-N-[4-[[(1-methylimidazol-2-yl)methyl]sulfinyl]phenyl]-2,3-dihydro-1-benzazepine-4-carboxamide (270 mg) (Compound 325), (−)-7-[4-(2-butoxyethoxy)phenyl]-1-isobutyl-N-[4-[[(1-methylimidazol-2-yl)methyl]sulfinyl]phenyl]-2,3-dihydro-1-benzazepine-4-carboxamide (280 mg) (Compound 326).

Compound 325
$[\alpha]_D$=+7.71° (C=5.00% ethanol solution, >99.9% ee)
Compound 326
$[\alpha]_D$=−8.20° (C=4.80% ethanol solution, >99.9% ee)

Example 305

(Preparation of Compound 327)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 4-[(isoxazol-5-ylmethyl)sulfanyl]aniline (429 mg) and triethylamine (5.8 ml) in tetrahydrofuran (15 ml) at 0° C. The mixture was stirred for 1.5 hours at room temperature under nitrogen atmosphere, water was added to the mixture, and the mixture was extracted with ethyl acetate. The organic layer was washed with saturated brine, and dried over magnesium sulfate. The solvent was distilled off under reduced pressure. The obtained residue was purified by silica gel column chromatography (hexane:ethyl acetate=3:1) and was recrystallized from hexane-ethyl acetate, to give 7-[4-(2-butoxyethoxy)phenyl]-1-isobutyl-N-[4-[(isoxazol-5-ylmethyl)sulfanyl]phenyl]-2,3-dihydro-1-benzazepine-4-carboxamide (557 mg) (Compound 327) as yellow crystals.

$^1$H-NMR (200 MHz, CDCl$_3$) δ 0.89 to 0.99 (9H, m), 1.20 to 1.70 (4H, m), 1.98 to 2.20 (1H, m), 2.85 to 2.95 (2H, m), 3.19 (2H, d, J=7.0 Hz), 3.30 to 3.41 (2H, m), 3.55 (2H, t, J=6.6 Hz), 3.80 (2H, t, J=4.4 Hz), 4.12 to 4.18 (4H, m), 6.00 (1H, s), 6.90 to 7.00 (3H, m), 7.34 to 7.57 (10H, m), 8.12 (1H, s)

Elemental Analysis for $C_{37}H_{43}N_3O_4S$ Calcd. C, 71.01; H, 6.93; N, 6.71. Found: C, 70.90; H, 6.96; N, 6.64.

Example 306

(Preparation of Compound 328 and Compound 329)

To a solution of 7-[4-(2-butoxyethoxy)phenyl]-1-isobutyl-N-[4-[(isoxazol-5-ylmethyl)sulfanyl]phenyl]-2,3-dihydro-1-benzazepine-4-carboxamide (200 mg) in dichloromethane (20 ml) was added dropwise 70% solution of 3-chloroperbenzoic acid (118 mg) in dichloromethane (20 ml) at −78° C. After finishing the dropping, water was added to the mixture, an aqueous solution of saturated sodium bicarbonate was added to the mixture and the mixture was extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (hexane:ethyl acetate=1:1→1:4), and was recrystallized from hexane-ethyl acetate, to give 7-[4-(2-butoxyethoxy)phenyl]-1-isobutyl-N-[4-[(isoxazol-5-ylmethyl) sulfinyl]phenyl]-2,3-dihydro-1-benzazepine-4-carboxamide (103 mg) (Compound 328) as yellow crystals, and was recrystallized from hexane-ethyl acetate, to give 7-[4-(2-butoxyethoxy)phenyl]-1-isobutyl-N-[4-[(isoxazol-5-ylmethyl) sulfonyl]phenyl]-2,3-dihydro-1-benzazepine-4-carboxamide (72.8 mg) (Compound 329) as yellow crystals.

Compound 328

$^1$H-NMR (200 MHz, CDCl$_3$) δ 0.90 to 0.99 (9H, m), 1.34 to 1.65 (4H, m), 2.00 to 2.20 (1H, m), 2.88 to 2.98 (2H, m), 3.20 (2H, d, J=7.4 Hz), 3.35 to 3.40 (2H, m), 3.55 (2H, t, J=7.0 Hz), 3.80 (2H, t, J=4.8 Hz), 4.16 (2H, t, J=4.8 Hz), 4.23 (2H, s), 6.21 (1H, d, J=1.8 Hz), 6.91 to 7.00 (3H, m), 7.39 to 7.52 (7H, m), 7.74 to 7.78 (3H, m), 8.18 (1H, d, J=1.8 Hz).

Elemental Analysis for $C_{37}H_{43}N_3O_5S \cdot 0.2H_2O$ Calcd. C, 68.85; H, 6.78; N, 6.51. Found: C, 68.71; H, 6.60; N, 6.47.

Compound 329

$^1$H-NMR (200 MHz, CDCl$_3$) δ 0.90 to 0.99 (9H, m), 1.30 to 1.70 (4H, m), 1.90 to 2.10 (1H, m), 2.90 to 3.00 (2H, m), 3.20 (2H, d, J=7.4 Hz), 3.32 to 3.42 (2H, m), 3.55 (2H, t, J=6.6 Hz), 3.80 (2H, t, J=4.4 Hz), 4.16 (2H, t, J=5.2 Hz), 4.57 (2H, s), 6.40 (1H, d, J=1.8 Hz), 6.91 to 7.00 (3H, m), 7.40 to 7.51 (5H, m), 7.69 to 7.81 (5H, m), 8.23 (1H, d, J=2.0 Hz).

Elemental Analysis for $C_{37}H_{43}N_3O_6S$ Calcd. C, 67.56; H, 6.59; N, 6.39. Found: C, 67.28; H, 6.49; N, 6.35.

Example 307

(Preparation of Compound 330)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 4-[(pyrazol-1-ylmethyl)sulfanyl]aniline (427 mg) and triethylamine (5.8 ml) in tetrahydrofuran (15 ml) at 0° C. The mixture was stirred for 15 minutes at room temperature under nitrogen atmosphere, water was added to the mixture, and the mixture was extracted with ethyl acetate. The organic layer was washed with saturated brine and dried over magnesium sulfate. The solvent was distilled off under reduced pressure. The obtained residue was purified by silica gel column chromatography (hexane:ethyl acetate=1:1), to give 7-[4-(2-butoxyethoxy)phenyl]-1-isobutyl-N-[4-[(pyrazol-1-ylmethyl)sulfanyl]phenyl]-2,3-dihydro-1-benzazepine-4-carboxamide (384 mg) (Compound 330) as yellow amorphous.

$^1$H-NMR (200 MHz, CDCl$_3$) δ 0.90 to 0.99 (9H, m), 1.30 to 1.65 (4H, m), 1.95 to 2.20 (1H, m), 2.91 (2H, t, J=5.0 Hz), 3.19 (2H, d, J=7.4 Hz), 3.36 (2H, t, J=5.0 Hz), 3.55 (2H, t, J=6.6 Hz), 3.80 (2H, t, J=4.8 Hz), 4.16 (2H, t, J=4.8 Hz), 5.38 (2H, s), 6.21 (1H, t, J=1.8 Hz), 6.92 (1H, d, J=8.8 Hz), 6.98 (2H, d, J=8.8 Hz), 7.26 to 7.56 (12H, m).

Example 308

(Preparation of Compound 331)

To a solution of 7-[4-(2-butoxyethoxy)phenyl]-1-isobutyl-N-[4-[(pyrazol-1-ylmethyl)sulfanyl]phenyl]-2,3-dihydro-1-benzazepine-4-carboxamide (150 mg) in dichloromethane (10 ml) was added dropwise 70% solution of 3-chloroperbenzoic acid (59.2 mg) in dichloromethane (10 ml) at −78° C. After finishing the dropping, an aqueous solution of sodium thiosulfate was added to the mixture, and the mixture was allowed to be at room temperature and stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (hexane:ethyl acetate=1:2→ethyl acetate), and was recrystallized from hexane-ethyl acetate, to give 7-[4-(2-butoxyethoxy)phenyl]-1-isobutyl-N-[4-[(pyrazol-1-ylmethyl) sulfinyl]phenyl]-2,3-dihydro-1-benzazepine-4-carboxamide (80 mg) (Compound 331) as yellow crystals.

$^1$H-NMR (200 MHz, CDCl$_3$) δ 0.90 to 0.99 (9H, m), 1.34 to 1.45 (2H, m), 1.55 to 1.67 (2H, m), 2.00 to 2.15 (1H, m), 2.50 to 2.80 (2H, m), 3.20 (2H, d, J=6.8 Hz), 3.30 to 3.43 (2H, m), 3.55 (2H, t, J=6.6 Hz), 3.81 (2H, t, J=5.2 Hz), 4.16 (2H, t, J=5.2 Hz), 5.15 (2H, s), 6.29 (1H, t, J=1.8 Hz), 6.91 to 7.01 (3H, m), 7.40 to 7.57 (9H, m), 7.72 to 7.79 (3H, m)

Elemental Analysis for $C_{37}H_{44}N_4O_4S$ Calcd. C, 69.35; H, 6.92; N, 8.74. Found: C, 69.13; H, 6.91; N, 8.59.

Example 309

(Preparation of Compound 332)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 4-[[(1-ethylimidazol-2-yl)methyl]sulfanyl]aniline (485 mg) and triethylamine (5.8 ml) in tetrahydrofuran (15 ml) at 0° C. The mixture: was stirred for 1 hour at room temperature under nitrogen atmosphere, water was added to the mixture, and the mixture was extracted with ethyl acetate. The organic layer was washed with saturated brine and dried over magnesium sulfate. The solvent was distilled off under reduced pressure. The obtained residue was purified by silica gel column chromatography (ethyl acetate), to give 7-[4-(2-butoxyethoxy)phenyl]-N-[4-[[(1-ethylimidazol-2-yl)methyl]sulfanyl]phenyl]-1-isobutyl-2,3-dihydro-1-benzazepine-4-carboxamide (471 mg) (Compound 332) as yellow amorphous.

$^1$H-NMR (200 MHz, CDCl$_3$) δ 0.90 to 0.98 (9H, m), 1.34 to 1.50 (5H, m), 1.55 to 1.70 (2H, m), 1.95 to 2.15 (1H, m), 2.85 to 2.95 (2H, m), 3.18 (2H, d, J=7.4 Hz), 3.30 to 3.40 (2H, m), 3.55 (2H, t, J=6.6 Hz), 3.80 (2H, t, J=4.8 Hz), 3.94

(2H, q, J=7.2 Hz), 4.10 to 4.18 (4H, m), 6.86 (1H, d, J=1.4 Hz), 6.89 to 7.00 (4H, m), 7.31 to 7.55 (9H, m), 7.81 (1H, s).

Example 310

(Preparation of Compound 333)

To a solution of 7-[4-(2-butoxyethoxy)phenyl]-N-[4-[[(1-ethylimidazol-2-yl)methyl]sulfanyl]phenyl]-1-isobutyl-2,3-dihydro-1-benzazepine-4-carboxamide (150 mg) in dichloromethane (10 ml) was added dropwise 70% solution of 3-chloroperbenzoic acid (55.3 mg) in dichloromethane (10 ml) at −78° C. After finishing the dropping, an aqueous solution of sodium thiosulfate was added to the mixture, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (hexane:ethyl acetate=1:1), and was recrystallized from hexane-ethyl acetate, to give 7-[4-(2-butoxyethoxy)phenyl]-N-[4-[[(1-ethylimidazol-2-yl)methyl]sulfinyl]phenyl]-1-isobutyl-2,3-dihydro-1-benzazepine-4-carboxamide (82 mg) (Compound 333) as yellow crystals.

$^1$H-NMR (200 MHz, CDCl$_3$) δ 0.90 to 1.00 (9H, m), 1.29 to 1.68 (7H, m), 2.00 to 2.15 (1H, m), 2.90 to 2.98 (2H, m), 3.20 (2H, d, J=7.6 Hz), 3.30 to 3.42 (2H, m), 3.55 (2H, t, J=6.4 Hz), 3.78 to 3.91 (4H, m), 4.07 to 4.30 (4H, m), 6.90 to 7.02 (5H, m), 7.39 to 7.48 (7H, m), 7.72 to 7.81 (3H, m).

Elemental Analysis for C$_{39}$H$_{48}$N$_4$O$_4$S .0.2H$_2$O Calcd. C, 69.65; H, 7.25; N, 8.33. Found: C, 69.51; H, 7.11; N, 8.23.

Example 311

(Preparation of Compound 334)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 4-[[(1-propylimidazol-2-yl)methyl]sulfanyl]aniline (515 mg) and triethylamine (5.8 ml) in tetrahydrofuran (15 ml) at 0° C. The mixture was stirred for 1 hour at room temperature under nitrogen atmosphere, water was added to the mixture, and the mixture was extracted with ethyl acetate. The organic layer was washed with saturated brine and dried over magnesium sulfate. The solvent was distilled off under reduced pressure. The obtained residue was purified by silica gel column chromatography (hexane:ethyl acetate=1:4), and was recrystallized from ethanol-hexane, to give 7-[4-(2-butoxyethoxy)phenyl]-1-isobutyl-N-[4-[[(1-propylimidazol-2-yl)methyl]sulfanyl]phenyl]-2,3-dihydro-1-benzazepine-4-carboxamide (483 mg) (Compound 334) as yellow crystals.

$^1$H-NMR (200 MHz, CDCl$_3$) δ 0.90 to 0.99 (12H, m), 1.34 to 1.45 (2H, m), 1.50 to 1.65 (2H, m), 1.75 to 1.85 (2H, m), 1.95 to 2.15 (1H, m), 2.85 to 2.95 (2H, m), 3.19 (2H, d, J=7.2 Hz), 3.30 to 3.40 (2H, m), 3.56 (2H, t, J=6.6 Hz), 3.78 to 3.89 (4H, m), 4.14 to 4.19 (4H, m), 6.85 to 7.00 (5H, m), 7.33 to 7.56 (9H, m), 7.64 (1H, s).

Elemental Analysis for C$_{40}$H$_{50}$N$_4$O$_3$S 0.1H$_2$O Calcd. C, 71.84; H, 7.57; N, 8.38. Found: C, 71.59; H, 7.59; N, 8.18.

Example 312

(Preparation of Compound 335 and Compound 336)

To a solution of 7-[4-(2-butoxyethoxy)phenyl]-1-isobutyl-N-[4-[[(1-propylimidazol-2-yl)methyl]sulfanyl]phenyl]-2,3-dihydro-1-benzazepine-4-carboxamide (200 mg) in dichloromethane (10 ml) was added dropwise 70% solution of 3-chloroperbenzoic acid (111 mg) in dichloromethane (10 ml) at −78° C. After finishing the dropping, the mixture was stirred for 1 hour at −10° C. to −25° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-1-isobutyl-N-[4-[[(1-propylimidazol-2-yl)methyl]sulfinyl]phenyl]-2,3-dihydro-1-benzazepine-4-carboxamide (73.5 mg) (Compound 335) as yellow amorphous, and to give 7-[4-(2-butoxyethoxy)phenyl]-1-isobutyl-N-[4-[[(1-propylimidazol-2-yl)methyl]sulfonyl]phenyl]-2,3-dihydro-1-benzazepine-4-carboxamide (18.8 mg) (Compound 336) as yellow amorphous.

Compound 335

$^1$H-NMR (200 MHz, CDCl$_3$) δ 0.84 to 1.00 (12H, m), 1.22 to 1.80 (6H, m), 2.00 to 2.20 (1H, m), 2.85 to 3.00 (2H, m), 3.20 (2H, d, J=7.2 Hz), 3.30 to 3.45 (2H, m), 3.55 (2H, t, J=7.0 Hz), 3.58 to 3.83 (4H, m), 4.06 to 4.30 (4H, m), 6.87 (1H, d, J=1.4 Hz), 6.90 to 7.00 (4H, m), 7.39 to 7.48 (7H, m), 7.73 (2H, d, J=8.4 Hz), 7.89 (1H, s).

Elemental Analysis for C$_{40}$H$_{50}$N$_4$O$_4$S.0.3H$_2$O Calcd. C, 69.80; H, 7.41; N, 8.14. Found: C, 69.56; H, 7.19; N, 7.92.

Compound 336

$^1$H-NMR (200 MHz, CDCl$_3$) δ 0.89 to 1.01 (12H, m), 1.30 to 1.80 (6H, m), 2.00 to 2.20 (1H, m), 2.90 to 3.00 (2H, m), 3.20 (2H, d, J=7.4 Hz), 3.30 to 3.40 (2H, m), 3.56 (2H, t, J=6.6 Hz), 3.81 (2H, t, J=5.2 Hz), 3.95 (2H, t, J=7.8 Hz), 4.16 (2H, t, J=5.2 Hz), 4.41 (2H, s), 6.89 to 6.99 (5H, m), 7.29 to 7.32 (2H, m), 7.38 to 7.44 (3H, m), 7.55 (2H, d, J=9.2 Hz), 7.72 (2H, d, J=9.2 Hz), 8.39 (1H, s).

Example 313

(Preparation of Compound 337, 338)

7-[4-(2-butoxyethoxy)phenyl]-1-isobutyl-N-[4-[[(1-propylimidazol-2-yl)methyl]sulfinyl]phenyl]-2,3-dihydro-1-benzazepine-4-carboxamide (680 mg) was optically resoluted with CHIRAL CEL OD 50 mm ID×500 mmL (hexane/ethanol/diethylamine), to give (+)-7-[4-(2-butoxyethoxy)phenyl]-1-isobutyl-N-[4-[[(1-propylimidazol-2-yl)methyl]sulfinyl]phenyl]-2,3-dihydro-1-benzazepine-4-carboxamide (250 mg) (Compound 337), (−)-7-[4-(2-butoxyethoxy)phenyl]-1-isobutyl-N-[4-[[(1-propylimidazol-2-yl)methyl]sulfinyl]phenyl]-2,3-dihydro-1-benzazepine-4-carboxamide (280 mg) (Compound 338).

Compound 337

[α]$_D$=+79.6° (C=0.501% ethanol solution, >99.9% ee)

Compound 338

[α]$_D$=−76.0° (C=0.468% ethanol solution, 99.0% ee)

Example 314

(Preparation of Compound 339)

To a solution of 7-[4-(2-butoxyethoxy)phenyl]-1-propyl-2,3-dihydro-1-benzazepine-4-carboxylic acid (1.5 g) in tetrahydrofuran (20 ml) was added one droplet of DMF. Then, thionyl chloride (0.34 ml) was added to the mixture at 0° C., and the mixture was allowed to be at room temperature and stirred for 1 hour under nitrogen atmosphere. The solvent and excess thionyl chloride were distilled off under reduced pressure, and the residue was dissolved in THF (20 ml), and the solution was added dropwise to a solution of S-(4-aminophenyl)O-benzyl carbonothioate (918 mg) and triethylamine (2.47 ml) in THF (20 ml) at 0° C. under argon atmosphere. After finishing the dropping, the mixture was allowed to be at room temperature, the mixture was stirred for 3 hours, and methanol (40 ml) was added to the mixture. Further, 1N aqueous solution of sodium hydroxide (17.7 ml) was added to the mixture, and the mixture was stirred for 30 minutes under argon atmosphere. Then, 2-chloromethyl-1-propylimidazole hydrochloride (760 mg) was added to the mixture under argon atmosphere and the mixture was stirred overnight. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=1:4), to give 7-[4-(2-butoxyethoxy)phenyl]-1-propyl-N-[4-[[(1-propylimidazol-2-yl)methyl]sulfanyl]phenyl]-2,3-dihydro-1-benzazepine-4-carboxamide (1.65 g) (Compound 339) as yellow amorphous.

$^1$H-NMR (200 MHz, CDCl$_3$) δ 0.90 to 1.03 (9H, m), 1.26 to 1.84 (8H, m), 2.85 to 2.95 (2H, m), 3.28 to 3.35 (4H, m), 3.55 (2H, t, J=7.0 Hz), 3.80 to 3.87 (4H, m), 4.12 to 4.18 (4H, m), 6.83 (1H, d, J=1.0 Hz), 6.86 to 7.00 (4H, m), 7.31 to 7.55 (9H, m), 7.83 (1H, s).

Example 315

(Preparation of Compound 340)

To a solution of 7-[4-(2-butoxyethoxy)phenyl]-1-propyl-N-[4-[[(1-propylimidazol-2-yl)methyl]sulfanyl]phenyl]-2,3-dihydro-1-benzazepine-4-carboxamide (1.52 g) in dichloromethane (20 ml) was added dropwise 70% solution of 3-chloroperbenzoic acid (861 mg) in dichloromethane (20 ml) at −78° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:8), to give 7-[4-(2-butoxyethoxy)phenyl]-1-propyl-N-[4-[[(1-propylimidazol-2-yl)methyl]sulfinyl]phenyl]-2,3-dihydro-1-benzazepine-4-carboxamide (1.01 g) (Compound 340) as yellow amorphous.

$^1$H-NMR (200 MHz, CDCl$_3$) δ 0.84 to 1.04 (9H, m), 1.34 to 1.85 (8H, m), 2.85 to 2.97 (2H, m), 3.29 to 3.40 (4H, m), 3.55 (2H, t, J=6.6 Hz), 3.70 to 3.83 (4H, m), 4.06 to 4.31 (4H, m), 6.87 (1H, d, J=1.6 Hz), 6.93 to 7.01 (4H, m), 7.40 to 7.48 (7H, m), 7.73 (2H, d, J=8.8 Hz), 7.84 (1H, s)

Elemental Analysis for C$_{39}$H$_{48}$N$_4$O$_4$S.0.4H$_2$O Calcd. C, 69.28; H, 7.28; N, 8.29. Found: C, 68.99; H, 7.32; N, 8.01.

Example 316

(Preparation of Compound 341 and Compound 342)

7-[4-(2-butoxyethoxy)phenyl]-1-propyl-N-[4-[[(1-propylimidazol-2-yl)methyl]sulfinyl]phenyl]-2,3-dihydro-1-benzazepine-4-carboxamide (800 mg) was optically resolved with CHIRAL PAK AD 50 mm ID×500 mmL. (hexane/ethanol/methanol), to give (+)-7-[4-(2-butoxyethoxy)phenyl]-1-propyl-N-[4-[[(1-propylimidazol-2-yl)methyl]sulfinyl]phenyl]-2,3-dihydro-1-benzazepine-4-carboxamide (306 mg) (Compound 341), and (−)-7-[4-(2-butoxyethoxy)phenyl]-1-propyl-N-[4-[[(1-propylimidazol-2-yl)methyl]sulfinyl]phenyl]-2,3-dihydro-1-benzazepine-4-carboxamide (328 mg) (Compound 342).

Compound 341

[α]$_D$=+64.3° (C=0.501% ethanol solution, >99.9% ee)

Compound 342

[α]$_D$=67.9° (C=0.502% ethanol solution, 99.1% ee)

Example 317

(Preparation of Compound 343)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added dropwise to a solution of. S-(4-aminophenyl)O-benzyl carbonothioate (415 mg) and triethylamine (3.35 ml) in THF (10 ml) at 0° C. under argon atmosphere. After finishing the dropping, the mixture was allowed to be at room temperature and stirred for 30 minutes, and methanol (30 ml) was added to the mixture. Further, 1N aqueous solution of sodium hydroxide (8 ml) was added to the mixture, and the mixture was stirred for 30 minutes under argon atmosphere. Then, 2-chloromethyl-1-(2,2,2-trifluoroethyl) imidazolehydrochloride (414 mg) was added to the mixture under argon atmosphere and the mixture was stirred overnight. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure. The residue was separated and purified by silica gel column chromatography (hexane:ethyl acetate=1:1→hexane:ethyl acetate=2:7), to give 7-[4-(2-butoxyethoxy)phenyl]-1-isobutyl-N-[4-[[1-(2,2,2-trifluoroethylimidazol-2-yl)methyl]sulfanyl]phenyl]-2,3-dihydro-1-benzazepine-4-carboxamide (235 mg) (Compound 343) as yellow amorphous.

$^1$H-NMR (200 MHz, CDCl$_3$) δ 0.90 to 0.99 (9H, m), 1.34 to 1.80 (4H, m), 2.00 to 2.20 (1H, m), 2.85 to 2.95 (2H, m), 3.18 (2H, d, J=7.4 Hz), 3.30 to 3.40 (2H, m), 3.55 (2H, t, J=6.6 Hz), 3.80 (2H, t, J=4.8 Hz), 410 to 4.20 (4H, m), 4.60 (2H, q, J=8.4 Hz), 6.89 to 7.00 (5H, m), 7.28 to 7.59 (10H, m).

Example 318

(Preparation of Compound 344)

To a solution of 7-[4-(2-butoxyethoxy)phenyl]-1-isobutyl-N-[4-[[1-(2,2,2-trifluoroethylimidazol-2-yl)methyl]sulfanyl]phenyl]-2,3-dihydro-1-benzazepine-4-carboxamide (150 mg) in dichloromethane (10 ml) was added dropwise 70% solution of 3-chloroperbenzoic acid (79 mg) in dichloromethane (10 ml) at −78° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (hexane:ethyl acetate=1:1→ethyl acetate), to give 7-[4-(2-butoxyethoxy)phenyl]-1-isobutyl-N-[4-[[1-(2,2,2-trifluoroethylimidazol-2-yl)methyl]sulfinyl]phenyl]-2,3-dihydro-1-benzazepine-4-carboxamide (60 mg) (Compound 344) as yellow amorphous.

$^1$H-NMR (200 MHz, CDCl$_3$) δ 0.90 to 0.99 (9H, m), 1.34 to 1.45 (2H, m), 1.50 to 1.70 (2H, m), 2.00 to 2.15 (1H, m), 2.88 to 2.98 (2H, m), 3.20 (2H, d, J=5.8 Hz), 3.30 to 3.42 (2H, m), 3.55 (2H, t, J=6.6 Hz), 3.81 (2H, t, J=4.8 Hz), 4.12 to 4.36 (4H, m), 4.60 to 5.00 (2H, m), 6.91 to 7.03 (5H, m), 7.39 to 7.50 (7H, m), 7.75 to 7.80 (3H, m).

Elemental Analysis for C$_{39}$H$_{45}$N$_4$O$_4$SF$_3$ Calcd. C, 64.80; H, 6.27; N, 7.75. Found: C, 64.40; H, 6.14; N, 7.63.

Example 319

(Preparation of Compound 345)

To a solution of 7-[4-(2-butoxyethoxy)phenyl]-1-isobutyl-2,3-dihydro-1-benzazepine-4-carboxylic acid (700 mg) in tetrahydrofuran (10 ml) was added one droplet of DMF. Then, thionyl chloride (0.15 ml) was added to the mixture at 0° C., and the mixture was allowed to be at room temperature and stirred for 1 hour under nitrogen atmosphere. This solution was added dropwise to a solution of S-(4-aminophenyl)O-benzyl carbonothioate (415 mg) and, triethylamine (1.34 ml) in THF (10 ml) at 0° C. under argon atmosphere. After finishing the dropping, the mixture was allowed to be at room temperature and stirred for 3 hours, and methanol (20 ml) was added to the mixture. Further, 1N aqueous solution of sodium hydroxide (8 ml) was added to the mixture, and the mixture was stirred for 30 minutes under argon atmosphere. Then, 1-butyl-2-chloromethylimidazole hydrochloride (368 mg) was added to the mixture under argon atmosphere and the mixture was stirred overnight. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure. The residue was separated and purified by silica gel column chromatography (hexane:ethyl acetate=1:4→ethyl acetate), to give 7-[4-(2-butoxyethoxy)phenyl]-N-[4-[[(1-butylimidazol-2-yl)methyl]sulfanyl]phenyl]-1-isobutyl-2,3-dihydro-1-benzazepine-4-carboxamide (258 mg) (Compound 345) as yellow amorphous.

$^1$H-NMR (200 MHz, CDCl$_3$) δ 0.90 to 0.99 (12H, m), 1.33 to 1.78 (8H, m), 2.00 to 2.10 (1H, m), 2.85 to 2.95 (2H, m), 3.19 (2H, d, J=6.8 Hz), 3.30 to 3.40 (2H, m), 3.55 (2H, t, J=6.6 Hz), 3.78 to 3.92 (4H, m), 4.07 to 4.18 (4H, m), 6.84 (1H, d, J=1.2 Hz), 6.89 to 7.00 (4H, m), 7.32 to 7.55 (9H, m), 7.65 (1H, s).

Elemental Analysis for C$_{41}$H$_{52}$N$_4$O$_3$S.0.25H$_2$O Calcd. C, 71.84; H, 7.72; N, 8.17. Found: C, 71.61; H, 7.85; N, 8.21.

Example 320

(Preparation of Compound 346)

To a solution of 7-[4-(2-butoxyethoxy)phenyl]-N-[4-[[(1-butylimidazol-2-yl)methyl]sulfanyl]phenyl]-1-isobutyl-2,3-dihydro-1-benzazepine-4-carboxamide (200 mg) in dichloromethane (10 ml) was added dropwise 70% solution of 3-chloroperbenzoic acid (108 mg) in dichloromethane (10 ml) at −78° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-N-[4-[[(1-butylimidazol-2-yl)methyl]sulfinyl]phenyl]-1-isobutyl-2,3-dihydro-1-benzazepine-4-carboxamide (140 mg) (Compound 346) as yellow amorphous.

$^1$H-NMR (200 MHz, CDCl$_3$) δ 0.86 to 1.00 (12H, m), 1.17 to 1.70 (8H, m), 1.95 to 2.20 (1H, m), 2.90 to 3.00 (2H, m), 3.17 (2H, d, J=7.2 Hz), 3.30 to 3.43 (2H, m), 3.55 (2H, t, J=7.0 Hz), 3.70 to 3.95 (4H, m), 4.03 to 4.25 (4H, m), 6.85 (1H, d, J=1.2 Hz), 6.89 to 6.99 (4H, m), 7.38 to 7.46 (7H, m), 7.73 (2H, d, J=8.8 Hz), 8.18 (1H, s).

Example 321

(Preparation of Compound 347)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added dropwise to a solution of. S-(4-aminophenyl)O-benzyl carbonothioate (415 mg) and triethylamine (3.35 ml) in THF (15 ml) at 0° C. under argon atmosphere. After finishing the dropping, the mixture was allowed to be at room temperature under argon atmosphere and stirred for 3 hours, and methanol (30 ml) was added to the mixture. Further, 1N aqueous solution of sodium hydroxide (18 ml) was added to the mixture, and the mixture was stirred for 30 minutes under argon atmosphere. Then, 2-chloromethyl-1-cyclopropylmethylimidazole hydrochloride (365 mg) was added to the mixture under argon atmosphere and the mixture was stirred overnight. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure. The residue was separated and purified by silica gel column chromatography (hexane:ethyl acetate=1:1→ethyl acetate), to give 7-[4-(2-butoxyethoxy)phenyl]-N-[4-[[(1-cyclopropylmethylimidazol-2-yl)methyl]sulfanyl]phenyl]-1-isobutyl-2,3-dihydro-1-benzazepine-4-carboxamide (152 mg) (Compound 347) as yellow amorphous.

¹H-NMR (200 MHz, CDCl₃) δ 0.30 to 0.36 (2H, m), 0.62 to 0.71 (2H, m), 0.90 to 0.99 (9H, m), 1.10 to 1.20 (1H, m), 1.34 to 1.45 (2H, m), 1.55 to 1.65 (2H, m), 1.95 to 2.15 (1H, m), 2.85 to 2.95 (2H, d, J=7.0 Hz), 3.30 to 3.40 (2H, m), 3.56 (2H, t, J=6.6 Hz), 3.74 to 3.83 (4H, m), 4.13 to 4.18 (4H, m), 6.89 to 7.01 (5H, m), 7.31 to 7.56 (9H, m), 7.89 (1H, s).

Elemental Analysis for $C_{41}H_{50}N_4O_3S \cdot 0.1H_2O$ Calcd. C, 72.34; H, 7.43; N, 8.23. Found: C, 72.12; H, 7.42; N, 8.09.

Example 322

(Preparation of Compound 348)

To a solution of 7-[4-(2-butoxyethoxy)phenyl]-N-[4-[[(1-cyclopropylmethylimidazol-2-yl)methyl]sulfanyl]phenyl]-1-isobutyl-2,3-dihydro-1-benzazepine-4-carboxamide (125 mg) in dichloromethane (10 ml) was added dropwise 70% solution of 3-chloroperbenzoic acid (68 mg) in dichloromethane (10 ml) at −78° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified with silica gel column chromatography (ethyl acetate→methanol:ethyl acetate=1:9), to give 7-[4-(2-butoxyethoxy)phenyl]-N-[4-[[(1-cyclopropylmethylimidazol-2-yl)methyl]sulfinyl]phenyl]-1-isobutyl-2,3-dihydro-1-benzazepine-4-carboxamide (65.9 mg) (Compound 348) as yellow amorphous.

¹H-NMR (200 MHz, CDCl₃) δ 0.30 to 0.38 (2H, m), 0.55 to 0.70 (2H, m), 0.90 to 1.15 (10H, m), 1.30 to 1.50 (2H, m), 1.55 to 1.75 (2H, m), 1.95 to 2.15 (1H, m), 2.90 to 2.98 (2H, m), 3.20 (2H, d, J=7.0 Hz), 3.30 to 3.40 (2H, m), 3.55 (2H, t, J=6.6 Hz), 3.67 (2H, dd, J=7.0, 2.8 Hz), 3.81 (2H, t, J=4.6 Hz), 4.09 to 4.18 (3H, m), 4.26 (1H, d, J=13.6), 6.90 to 7.06 (5H, m), 7.42 to 7.48 (7H, m), 7.74 (2H, d, J=8.8 Hz), 7.89 (1H, s).

Elemental Analysis for $C_{41}H_{50}N_4O_4S$ Calcd. C, 70.86; H, 7.25; N, 8.06. Found: C, 70.51; H, 7.15; N, 7.86.

Example 323

(Preparation of Compound 349)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. The solvent and excess thionyl chloride were distilled off under reduced pressure. The obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature under argon atmosphere and stirred for 3 hours, and methanol (30 ml) was added to the mixture. Further, 1N aqueous solution of sodium hydroxide (8 ml) was added to the mixture, and the mixture was stirred for 30 minutes under argon atmosphere. Then, 2-chloromethyl-1-isobutylimidazole hydrochloride (368 mg) was added to the mixture under argon atmosphere and the mixture was stirred overnight. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=1:4→ethyl acetate), to give 7-[4-(2-butoxyethoxy)phenyl]-1-isobutyl-N-[4-[[(1-isobutylimidazol-2-yl)methyl]sulfanyl]phenyl]-2,3-dihydro-1-benzazepine-4-carboxamide (653 mg) (Compound 349) as yellow amorphous.

¹H-NMR (200 MHz, CDCl₃) δ 0.90 to 0.99 (15H, m), 1.34 to 1.45 (2H, m), 1.54 to 1.70 (2H, m), 1.95 to 2.10 (2H, m), 2.85 to 2.95 (2H, m), 3.18 (2H, d, J=7.6 Hz), 3.30 to 3.42 (2H, m), 3.55 (2H, t, J=6.6 Hz), 3.70 (2H, d, J=7.8 Hz), 3.80 (2H, t, J=4.8 Hz), 4.14 to 4.18 (4H, m), 6.81 (1H, d, J=1.6 Hz), 6.89 to 7.00 (4H, m), 7.32 to 7.55 (9H, m), 7.71 (1H, s).

Elemental Analysis for $C_{41}H_{52}N_4O_3S$ Calcd. C, 72.32; H, 7.70; N, 8.23. Found: C, 71.99; H, 7.64; N, 8.24.

Example 324

(Preparation of Compound 350)

To a solution of 7-[4-(2-butoxyethoxy)phenyl]-1-isobutyl-N-[4-[[(1-isobutylimidazol-2-yl)methyl]sulfanyl]phenyl]-2,3-dihydro-1-benzazepine-4-carboxamide (600 mg) in dichloromethane (15 ml) was added dropwise 70% solution of 3-chloroperbenzoic acid (326 mg) in dichloromethane (15 ml) at −78° C. To the mixture was added an aqueous solution of sodium thiosulfate, and the mixture was allowed to be at room temperature, and stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-1-isobutyl-N-[4-[[(1-isobutylimidazol-2-yl)methyl]sulfinyl]phenyl]-2,3-dihydro-1-benzazepine-4-carboxamide (415 mg) (Compound 350) as yellow amorphous.

¹H-NMR (200 MHz, CDCl₃) δ 0.86 (6H, d, J=6.6 Hz), 0.89 to 0.99 (9H, m), 1.34 to 1.45 (2H, m), 1.54 to 1.65 (2H, m), 1.80 to 2.20 (2H, m), 2.90 to 2.98 (2H, m), 3.20 (2H, d, J=7.2 Hz), 3.35 to 3.40 (2H, m), 3.45 to 3.70 (4H, m), 3.80 (2H, t, J=44 Hz), 4.07 to 4.18 (3H, m), 4.29 (1H, d, J=13.4 Hz), 6.81 (1H, d, J=1.6 Hz), 6.90 to 7.00 (4H, m), 7.38 to 7.48 (7H, m), 7.73 (2H, d, J=8.6 Hz), 7.88 (1H, s).

Elemental Analysis for $C_{41}H_{52}N_4O_4S \cdot 0.4H_2O$ Calcd. C, 69.93; H, 7.56; N, 7.96. Found: C, 69.79; H, 7.31; N, 7.66.

Example 325

(Preparation of Compound 351)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. The solvent and excess thionyl chloride were distilled off under reduced pressure. The obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature under argon atmosphere and stirred for 3 hours, and methanol (30 ml) was added to the mixture. Further, 1N aqueous solution of sodium hydroxide (8 ml) was added to the mixture, and the mixture was stirred for 30 minutes under argon atmosphere. Then, 1-(2-butyl)-2-chloromethylimidazole hydrochloride (368 mg) was added to the mixture under argon atmosphere and the mixture was stirred overnight. The solvent was distilled off under reduced pressure, water was added to the mixture, and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=1:4), to give 7-[4-(2-butoxyethoxy)phenyl]-N-[4-[[[1-(2-butyl)imidazol-2-yl]methyl]sulfanyl]phenyl]-1-isobutyl-2,3-dihydro-1-benzazepine-4-carboxamide (633 mg) (Compound 351) as yellow amorphous.

$^1$H-NMR (200 MHz, CDCl$_3$) δ 0.85 (3H, t, J=7.8 Hz), 0.90 to 0.99 (9H, m), 1.30 to 1.50 (5H, m), 1.55 to 1.83 (4H, m), 1.95 to 2.15 (1H, m), 2.85 to 2.95 (2H, m), 3.18 (2H, d, J=7.2 Hz), 3.30 to 3.40 (2H, m), 3.55 (2H, t, J=6.6 Hz), 3.81 (2H, t, J=4.4 Hz), 4.09 to 4.30 (5H, m), 6.88 to 7.00 (5H, m), 7.33 to 7.56 (9H, m), 7.74 (1H, s).

Elemental Analysis for C$_{41}$H$_{52}$N$_4$O$_3$S Calcd. C, 72.32; H, 7.70; N, 8.23. Found: C, 72.06; H, 7.61; N, 8.10.

Example 326

(Preparation of Compound 352)

To a solution of 7-[4-(2-butoxyethoxy)phenyl]-N-[4-[[[1-(2-butyl)imidazol-2-yl]methyl]sulfanyl]phenyl]-1-isobutyl-2,3-dihydro-1-benzazepine-4-carboxamide (550 mg) in dichloromethane (1.5 ml) was added dropwise 70% solution of 3-chloroperbenzoic acid (299 mg) in dichloromethane (15 ml) at −78° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-N-[4-[[[1-(2-butyl)imidazol-2-yl]methyl]sulfinyl]phenyl]-1-isobutyl-2,3-dihydro-1-benzazepine-4-carboxamide (350 mg) (Compound 352) as yellow amorphous.

$^1$H-NMR (200 MHz, CDCl$_3$) δ 0.73 to 1.00 (12H, m), 1.23 to 1.80 (9H, m), 2.00 to 2.20 (1H, m), 2.88 to 2.98 (2H, m), 3.19 (2H, d, J=7.4 Hz), 3.38 to 3.43 (2H, m), 3.55 (2H, t, J=6.6 Hz), 3.80 (2H, t, J=4.4 Hz), 4.10 to 4.35 (5H, m), 6.90 to 7.04 (5H, m), 7.40 to 7.55 (7H, m), 7.69 to 7.84 (4H, m).

Elemental Analysis for C$_{41}$H$_{52}$N$_4$O$_4$S .0.4H$_2$O Calcd. C, 69.93; H, 7.56; N, 7.96. Found: C, 69.66; H, 7.30; N, 7.71.

Example 327

(Preparation of Compound 353)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature under argon atmosphere and stirred for 3 hours, and methanol (30 ml) was added to the mixture. Further, 1N aqueous solution of sodium hydroxide (8 ml) was added to the mixture, and the mixture was stirred for 30 minutes under argon atmosphere. Then, 2-chloromethyl-1-pentylimidazole hydrochloride (393 mg) was added to the mixture under argon atmosphere and the mixture was stirred overnight. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure. The obtained residue was separated and separated and purified by silica gel column chromatography (hexane:ethyl acetate=1:4), to give 7-[4-(2-butoxyethoxy)phenyl]-1-isobutyl-N-[4-[[[(1-pentylimidazol-2-yl)methyl]sulfanyl]phenyl]-2,3-dihydro-1-benzazepine-4-carboxamide (737 mg) (Compound 353) as yellow amorphous.

$^1$H-NMR (200 MHz, CDCl$_3$) δ 0.87 to 0.99 (12H, m), 1.25 to 1.49 (6H, m), 1.54 to 1.90 (4H, m), 2.00 to 2.15 (1H, m), 2.85 to 2.95 (2H, m), 3.18 (2H, d, J=7.4 Hz), 3.30 to 3.40 (2H, m), 3.55 (2H, t, J=6.6 Hz), 3.78 to 3.90 (4H, m), 4.13 to 4.18 (4H, m), 6.84 (1H, d, J=1.6 Hz), 6.89 to 7.00 (4H, m), 7.32 to 7.55 (9H, m), 7.75 (1H, s).

Example 328

(Preparation of Compound 354)

To a solution of 7-[4-(2-butoxyethoxy)phenyl]-1-isobutyl-N-[4-[[[(1-pentylimidazol-2-yl)methyl]sulfanyl]phenyl]-2,3-dihydro-1-benzazepine-4-carboxamide (680 mg) in dichloromethane (15 ml) was added dropwise 70% solution of 3-chloroperbenzoic acid (362 mg) in dichloromethane (15 ml) at −78° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-1-isobutyl-N-[4-[[[(1-pentyl-imidazole-2-yl)methyl]sulfinyl]phenyl]-2,3-dihydro-1-benzazepine-4-carboxamide (411 mg) (Compound 354) as yellow amorphous.

$^1$H-NMR (200 MHz, CDCl$_3$) δ 0.84 to 1.00 (12H, m), 1.15 to 1.50 (6H, m), 1.55 to 1.75 (4H, m), 1.95 to 2.20 (1H, m), 2.85 to 2.95 (2H, m), 3.19 (2H, d, J=7.4 Hz), 3.30 to 3.40 (2H, m), 3.55 (2H, t, J=6.6 Hz), 3.71 to 3.83 (4H, m), 4.08 to 4.18 (3H, m), 4.27 (1H, d, J=13.6 Hz), 6.87 (1H, d, J=1.0 Hz), 6.90 to 7.00 (4H, m), 7.37 to 7.48 (7H, m), 7.74 (2H, d, J=8.8 Hz), 7.97 (1H, s).

Elemental Analysis for C$_{42}$H$_{54}$N$_4$O$_4$S Calcd. C, 70.95; H, 7.66; N, 7.88. Found: C, 70.75; H, 7.79; N, 7.55.

Example 329

(Preparation of Compound 355)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture at 0° C., and the mixture was allowed to be at room temperature and stirred for 1 hour under nitrogen atmosphere. This solution was added to a solution of 3-methyl-4-[[(1-methylimidazol-2-yl)methyl]sulfanyl]aniline (448 mg) and triethylamine (5.8 ml) in tetrahydrofuran (15 ml) at 0° C. The mixture was stirred overnight at room temperature under nitrogen atmosphere, water was added to the mixture, and the mixture was extracted with ethyl acetate. The organic layer was washed with saturated brine and dried over magnesium sulfate. The solvent was distilled off under reduced pressure. The obtained residue was purified by silica gel column chromatography (ethyl acetate), to give 7-[4-(2-butoxyethoxy)phenyl]-1-isobutyl-N-[3-methyl-4-[[(1-methylimidazol-2-yl)methyl]sulfanyl]phenyl]-2,3-dihydro-1-benzazepine-4-carboxamide (335 mg) (Compound 355) as yellow amorphous.

$^1$H-NMR (200 MHz, CDCl$_3$) δ 0.90 to 0.99 (9H, m), 1.30 to 1.45 (2H, m), 1.55 to 1.75 (2H, m), 2.00 to 2.20 (1H, m), 2.32 (3H, s), 2.85 to 2.95 (2H, m), 3.19 (2H, d, J=7.0 Hz), 3.30 to 3.40 (2H, m), 3.52 to 3.59 (5H, m), 3.81 (2H, t, J=5.0 Hz), 4.04 (2H, s), 4.16 (2H, t, J=5.0 Hz), 6.78 (1H, d, J=1.0 Hz), 6.89 (1H, d, J=1.0 Hz), 6.93 to 7.00 (3H, m), 7.36 to 7.51 (8H, m), 7.75 (1H, s).

Elemental Analysis for C$_{39}$H$_{48}$N$_4$O$_3$S Calcd. C, 71.75; H, 7.41; N, 8.58. Found: C, 71.48; H, 7.68; N, 8.43.

Example 330

(Preparation of Compound 356 and Compound 357)

To a solution of 7-[4-(2-butoxyethoxy)phenyl]-1-isobutyl-N-[3-methyl-4-[[(1-methylimidazol-2-yl)methyl]sulfanyl]phenyl]-2,3-dihydro-1-benzazepine-4-carboxamide (200 mg) in dichloromethane (10 ml) was added dropwise 70% solution of 3-chloroperbenzoic acid (113 mg) in dichloromethane (10 ml) at −78° C. After finishing the dropping, the mixture was stirred for 1 hour at −10° C. to −25° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:8), and was recrystallized from hexane-ethyl acetate to give 7-[4-(2-butoxyethoxy)phenyl]-1-isobutyl-N-[3-methyl-4-[[(1-methylimidazol-2-yl)methyl]sulfinyl]phenyl]-2,3-dihydro-1-benzazepine-4-carboxamide (104 mg) (Compound 356) as yellow crystals, and was recrystallized from hexane-ethyl acetate to give 7-[4-(2-butoxyethoxy)phenyl]-1-isobutyl-N-[3-methyl-4-[[(1-methylimidazol-2-yl)methyl]sulfonyl]phenyl]-2,3-dihydro-1-benzazepine-4-carboxamide (10 mg) (Compound 357) as yellow crystals.

Compound 356

$^1$H-NMR (200 MHz, CDCl$_3$) δ 0.90 to 1.00 (9H, m), 1.34 to 1.45 (2H, m), 1.55 to 1.73 (2H, m), 2.00 to 2.15 (1H, m), 2.18 (3H, s), 2.90 to 2.98 (2H, m), 3.20 (2H, d, J=6.8 Hz), 3.30 to 3.40 (2H, m), 3.49 (3H, s), 3.56 (2H, t, J=6.6 Hz), 3.81 (2H, t, J=4.4 Hz), 4.06 to 4.22 (4H, m), 6.82 (1H, s), 6.90 to 7.00 (4H, m), 7.39 to 7.62 (7H, m), 7.76 (1H, d, J=8.8 Hz), 7.96 (1H, s).

Elemental Analysis for C$_{39}$H$_{48}$N$_4$O$_4$S.0.2H$_2$O Calcd. C, 69.65; H, 7.25; N, 8.33. Found: C, 69.53; H, 7.39; N, 8.43.

Compound 357

$^1$H-NMR (200 MHz, CDCl$_3$) δ 0.90 to 1.02 (9H, m), 1.34 to 1.45 (2H, m), 1.49 to 1.66 (2H, m), 2.00 to 2.15 (1H, m), 2.38 (3H, s), 2.90 to 3.00 (2H, m), 3.21 (2H, d, J=7.0 Hz), 3.30 to 3.40 (2H, m), 3.53 to 3.59 (5H, m), 3.81 (2H, t, J=5.2 Hz), 4.17 (2H, t, J=5.2 Hz), 4.29 (2H, s), 6.80 (1H, s), 6.90 to 6.99 (4H, m), 7.09 to 7.26 (2H, m), 7.37 to 7.50 (4H, m), 7.60 (1H, d, J=9.2 Hz), 7.71 to 7.76 (1H, m), 8.70 to 8.81 (1H, m).

Example 331

(Preparation of Compound 358)

To a solution of 7-[4-(2-butoxyethoxy)phenyl]-N-[4-(hydroxymethyl)phenyl]-1-isobutyl-2,3-dihydro-1-benzazepine-4-carboxamide (500 mg) in THF (10 ml) was added 1 droplet of pyridine, and thionyl chloride (0.09 ml) was added to the mixture at 0° C. The mixture was allowed to be at room temperature under nitrogen atmosphere, and stirred for 1 hour. The solvent and excess thionyl chloride were distilled off under reduced pressure, and the residue was dissolved in THF (10 ml). This solution was added to a solution of 2-mercapto-1-methylimidazole (137 mg) and triethylamine (1.67 ml) in THF (10 ml) at 0° C., and the mixture was heated overnight under nitrogen atmosphere at 50° C. The mixture was allowed to be cooled, water was added to the mixture and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=0.1:2), to give 7-[4-(2-butoxyethoxy)phenyl]-1-isobutyl-N-[4-[[(1-methylimidazol-2-yl)sulfanyl]methyl]phenyl]-2,3-dihydro-1-benzazepine-4-carboxamide (437 mg) (Compound 358) as yellow amorphous.

$^1$H-NMR (200 MHz, CDCl$_3$) δ 0.90 to 0.99 (9H, m), 1.30 to 1.45 (2H, m), 1.50 to 1.70 (2H, m), 1.95 to 2.20 (1H, m), 2.90 to 2.97 (2H, m), 3.19 (2H, d, J=7.4 Hz), 3.28 (3H, s), 3.30 to 3.40 (2H, m), 3.55 (2H, t, J=6.6 Hz), 3.80 (2H, t, J=4.6 Hz), 4.13 to 4.18 (4H, m), 6.87 to 7.11 (7H, m), 7.37 to 7.56 (8H, m).

Elemental Analysis for C$_{38}$H$_{46}$N$_4$O$_3$S.0.3H$_2$O Calcd. C, 70.84; H, 7.29; N, 8.70. Found: C, 70.62; H, 7.49; N, 8.91.

Example 332

(Preparation of Compound 359)

To a solution of 7-[4-(2-butoxyethoxy)phenyl]-1-isobutyl-N-[4-[[(1-methylimidazol-2-yl)sulfanyl]methyl]phenyl]-2,3-dihydro-1-benzazepine-4-carboxamide (200 mg) in dichloromethane (10 ml) was added dropwise 70% solution of 3-chloroperbenzoic acid (116 mg) in dichloromethane (10 ml) at −78° C. After finishing the dropping, the mixture was stirred for 1 hour at −10° C. to −25° C. To the mixture was added an aqueous solution of sodium thiosulfate, and the mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:8), to give 7-[4-(2-butoxyethoxy)phenyl]-1-isobutyl-N-[4-[[(1-methylimidazol-2-yl)sulfinyl]methyl]phenyl]-2,3-dihydro-1-benzazepine-4-carboxamide (122 mg) (Compound 359) as yellow amorphous.

$^1$H-NMR (200 MHz, CDCl$_3$) δ 0.90 to 0.99 (9H, m), 1.33 to 1.45 (2H, m), 1.58 to 1.80 (2H, m), 2.00 to 2.20 (1H, m), 2.85 to 2.95 (2H, m), 3.19 (2H, d, J=7.4 Hz), 3.34 to 3.40 (5H, m), 3.55 (2H, t, J=7.0 Hz), 3.81 (2H, t, J=5.2 Hz), 4.16 (2H, t, J=5.2 Hz), 4.37 (1H, d, J=12.4 Hz), 4.61 (1H, d, J=12.4 Hz), 6.87 to 7.06 (6H, m), 7.22 (1H, s), 7.39 to 7.57 (8H, m).

Example 333

(Preparation of Compound 360)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature under argon atmosphere and stirred for 3 hours, and methanol (30 ml) was added to the mixture. Further, 1N aqueous solution of sodium hydroxide (8 ml) was added to the mixture, and the mixture was stirred for 30 minutes under argon atmosphere. Then, 2-chloromethyl-1-cyclobutylmethylimidazole hydrochloride (389 mg) was added to the mixture under argon atmosphere and the mixture was stirred overnight. To the mixture was added water and the mixture was extracted with ethyl acetate. The organic layer was washed with saturated brine, and dried over magnesium sulfate. The solvent was distilled off under reduced pressure. The obtained residue was separated and, purified by silica gel column chromatography (hexane:ethyl acetate=1:4) and was recrystallized from hexane-ethyl acetate, to give 7-[4-(2-butoxyethoxy)phenyl]-N-[4-[[[1-cyclobutylmethylimidazol-2-yl]methyl]sulfanyl]phenyl]-1-isobutyl-2,3-dihydro-1-benzazepine-4-carboxamide (700 mg) (Compound 360).

$^1$H-NMR (200 MHz, CDCl$_3$) δ 0.90 to 1.05 (9H, m), 1.20 to 2.20 (11H, m), 2.60 to 2.80 (1H, m), 2.85 to 2.95 (2H, m), 3.10 to 3.25 (2H, m), 3.30 to 3.40 (2H, m), 3.50 to 3.65 (2H, m), 3.75 to 3.95 (4H, m), 4.10 to 4.22 (4H, m), 6.79 to 6.99 (5H, m), 7.26 to 7.55 (9H, m), 7.83 (1H, s).

Elemental Analysis for C$_{42}$H$_{52}$N$_4$O$_3$S Calcd. C, 72.80; H, 7.56; N, 8.09. Found: C, 72.53; H, 7.57; N, 7.97.

Example 334

(Preparation of Compound 361)

To a solution of 7-[4-(2-butoxyethoxy)phenyl]-N-[4-[[[1-cyclobutylmethylimidazol-2-yl]methyl]sulfanyl]phenyl]-1-isobutyl-2,3-dihydro-1-benzazepine-4-carboxamide (640 mg) in dichloromethane (15 ml) was added dropwise 70% solution of 3-chloroperbenzoic acid (342 mg) in dichloromethane (15 ml) at −78° C. The reaction vessel was removed from a dry ice-acetone bath, and an aqueous solution of sodium thiosulfate was added to the reaction vessel with strongly stirring. The mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-N-[4-[[[1-cyclobutylmethylimidazol-2-yl]methyl]sulfinyl]phenyl]-1-isobutyl-2,3-dihydro-1-benzazepine-4-carboxamide (439 mg) (Compound 361) as yellow amorphous.

$^1$H-NMR (200 MHz, CDCl$_3$) δ 0.90 to 1.00 (9H, m), 1.30 to 2.15 (11H, m), 2.50 to 2.65 (1H, m), 2.90 to 3.00 (2H, m), 3.20 (2H, d, J=7.2 Hz), 3.35 to 3.45 (2H, m), 3.56 (2H, t, J=6.6 Hz), 3.77 to 3.83 (4H, m), 4.07 to 4.19 (3H, m), 4.27 (1H, d, J=13.4 Hz), 6.84 (1H, d, J=1.2 Hz), 6.90 to 7.00 (4H, m), 7.40 to 7.48 (7H, m), 7.74 (2H, d, J=8.8 Hz), 7.96 (1H, s).

Elemental Analysis for C$_{42}$H$_{52}$N$_4$O$_4$S.0.5H$_2$O Calcd. C, 70.26; H, 7.44; N, 7.80. Found: C, 69.97; H, 7.22; N, 7.54.

Example 335

(Preparation of Compound 362)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature under argon atmosphere and stirred for 3 hours, and methanol (30 ml) was added to the mixture. Further, 1N aqueous solution of sodium hydroxide (8 ml) was added to the mixture, and the mixture was stirred for 30 minutes under argon atmosphere. Then, 1-aryl-2-chloromethylimidazole hydrochloride (340 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=1:4) N-[4-[[[1-arylimidazol-2-yl]methyl]sulfanyl]phenyl]-7-[4-(2-butoxyethoxy)phenyl]-1-isobutyl-2,3-dihydro-1-benzazepine-4-carboxamide (609 mg) (Compound 362) as yellow amorphous.

$^1$H-NMR (200 MHz, CDCl$_3$) δ 0.90 to 0.99 (9H, m), 1.26 to 1.48 (2H, m), 1.54 to 1.70 (2H, m), 2.00 to 2.20 (1H, m), 2.85 to 2.95 (2H, m), 3.18 (2H, d, J=7.2 Hz), 3.30 to 3.40 (2H, m), 3.55 (2H, t, J=6.6 Hz), 3.80 (2H, t, J=5.4 Hz), 4.11 (2H, s), 4.16 (2H, t, J=5.4 Hz), 4.54 (2H, d, J=5.6 Hz), 5.01 to 5.26 (2H, m), 5.80 to 6.00 (1H, m), 6.82 (1H, d, J=0.8 Hz), 6.89 to 7.00 (4H, m), 7.31 to 7.55 (9H, m), 7.82 (1H, s).

Elemental Analysis for C$_{40}$H$_{48}$N$_4$O$_3$S Calcd. C, 72.26; H, 7.28; N, 8.43. Found: C, 71.88; H, 7.22; N, 8.14.

Example 336

(Preparation of Compound 363)

To a solution of N-[4-[[[1-arylimidazol-2-yl]methyl]sulfanyl]phenyl]-7-[4-(2-butoxyethoxy)phenyl]-1-isobutyl-2,3-dihydro-1-benzazepine-4-carboxamide (500 mg) in dichloromethane (15 ml) was added dropwise 70% solution of 3-chloroperbenzoic acid (204 mg) in dichloromethane (15 ml) at −78° C. The reaction vessel was removed from a dry ice-acetone bath, and an aqueous solution of sodium thiosulfate was added to the reaction vessel with strongly stirring. The mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give. N-[4-[[[1-arylimidazol-2-yl]methyl]sulfinyl]phenyl]-7-[4-(2-butoxyethoxy)phenyl]-1-isobutyl-2,3-dihydro-1-benzazepine-4-carboxamide (382 mg) (Compound 363) as yellow amorphous.

$^1$H-NMR (200 MHz, CDCl$_3$) δ 0.90 to 1.00 (9H, m), 1.30 to 1.50 (2H, m), 1.5.5 to 1.75 (2H, m), 2.00 to 2.20 (1H, m), 2.90 to 3.00 (2H, m), 3.20 (2H, d, J=7.2 Hz), 3.30 to 3.45 (2H, m), 3.55 (2H, t, J=6.6 Hz), 3.80 (2H, t, J=4.4 Hz), 4.07 to 4.24 (4H, m), 4.30 to 4.65 (2H, m), 4.93 to 5.22 (2H, m), 5.70 to 5.95 (1H, m), 6.87 (1H, d, J=1.0 Hz), 6.90 to 7.02 (4H, m), 7.40 to 7.48 (7H, m), 7.74 (2H, d, J=8.8 Hz), 7.96 (1H, s).

Example 337

(Preparation of Compound 364)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature and stirred under argon atmosphere, and methanol (30 ml) was added to the mixture. Further, 1N aqueous solution of sodium hydroxide (8 ml) was added to the mixture, and the mixture was stirred for 30 minutes under argon atmosphere. Then, 2-chloromethyl-5-methyl-1-propylimidazole hydrochloride (368 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=1:4), to give 7-[4-(2-butoxyethoxy)phenyl]-1-isobutyl-N-[4-[[[5-methyl-1-propylimidazol-2-yl]methyl]sulfanyl]phenyl]-2,3-dihydro-1-benzazepine-4-carboxamide (573 mg) (Compound 364) as yellow amorphous.

$^1$H-NMR (200 MHz, CDCl$_3$) δ 0.90 to 0.99 (12H, m), 1.30 to 1.50 (2H, m), 1.55 to 1.80 (4H, m), 2.00 to 2.20 (4H, m), 2.85 to 2.95 (2H, m), 3.18 (2H, d, J=7.4 Hz), 3.30 to 3.40 (2H, m), 3.56 (2H, t, J=7.0 Hz), 3.72 to 4.07 (4H, m), 4.08 (2H, s), 4.16 (2H, t, J=5.6 Hz), 6.64 (1H, s), 6.88 to 7.00 (3H, m), 7.31 to 7.56 (9H, m), 8.05 (1H, s).

Elemental Analysis for C$_{41}$H$_{52}$N$_4$O$_3$S Calcd. C, 72.32; H, 7.70; N, 8.23. Found: C, 72.13; H, 7.75; N, 8.08.

Example 338

(Preparation of Compound 365)

To a solution of 7-[4-(2-butoxyethoxy)phenyl]-1-isobutyl-N-[4-[[[5-methyl-1-propylimidazol-2-yl]methyl]sulfanyl]phenyl]-2,3-dihydro-1-benzazepine-4-carboxamide (450 mg) in dichloromethane (15 ml) was added dropwise 70% solution of 3-chloroperbenzoic acid (244 mg) in dichloromethane (15 ml) at −78° C. The reaction vessel was removed from a dry ice-acetone bath, and an aqueous solution of sodium thiosulfate was added to the reaction vessel with strongly stirring. The mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate→methanol:ethyl acetate=1:9), to give 7-[4-(2-butoxyethoxy)phenyl]-1-isobutyl-N-[4-[[[5-methyl-1-propylimidazol-2-yl]methyl]sulfinyl]phenyl]-2,3-dihydro-1-benzazepine-4-carboxamide (340 mg) (Compound 365) as yellow amorphous.

$^1$H-NMR (200 MHz, CDCl$_3$) δ 0.84 to 1.22 (12H, m), 1.30 to 1.50 (2H, m), 1.55 to 1.70 (4H, m), 2.00 to 2.20 (4H, m), 2.85 to 2.95 (2H, m), 3.19 (2H, d, J=7.0 Hz), 3.35 to 3.45 (2H, m), 3.52 to 3.83 (6H, m), 4.03 to 4.24 (4H, m), 6.74 (1H, d, J=1.2 Hz), 6.89 to 6.99 (3H, m), 7.39 to 7.47 (7H, m), 7.73 (2H, d, J=8.8 Hz), 8.12 (1H, s).

Elemental Analysis for C$_{41}$H$_{52}$N$_4$O$_4$S.0.5H$_2$O Calcd. C, 69.76; H, 7.57; N, 7.94. Found: C, 69.76; H, 7.54; N, 7.66.

Example 339

(Preparation of Compound 366)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.12 ml) in THF (15 ml) at 0° C. under argon atmosphere. After finishing the dropping, the mixture was allowed to be at room temperature and stirred under argon atmosphere, and methanol (30 ml) was added to the mixture. Further, 1N aqueous solution of sodium hydroxide (8 ml) was added to the mixture, and the mixture was stirred for 30 minutes under argon atmosphere. Then, 2-chloromethyl-1-cyclopropylimidazole hydrochloride (340 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The obtained residue was separated and purified by silica gel column chromatography (hexane:ethyl acetate=1:4), to give 7-[4-(2-butoxyethoxy) phenyl]-N-[4-[[[1-cyclopropylimidazol-2-yl]methyl]sulfanyl]phenyl]-1-isobutyl-2,3-dihydro-1-benzazepine-4-carboxamide (841 mg) (Compound 366) as yellow amorphous.

$^1$H-NMR (200 MHz, CDCl$_3$) δ 0.80 to 1.05 (13H, m), 1.30 to 1.50 (2H, m), 1.55 to 1.70 (2H, m), 1.95 to 2.20 (1H, m), 2.85 to 2.95 (2H, m), 3.10 to 3.25 (3H, m), 3.30 to 3.40 (2H, m), 3.56 (2H, t, J=6.6 Hz), 3.81 (2H, t, J=4.8 Hz), 4.16 (2H, t, J=4.8 Hz), 4.20 (2H, s), 6.80 (1H, d, J=1.2 Hz), 6.84 (1H, d, J=1.2 Hz), 6.91 (1H, d, J=9.6 Hz), 6.98 (2H, d, J=8.8 Hz), 7.33 to 7.56 (9H, m), 7.99 (1H, s).

Elemental Analysis for C$_{40}$H$_{48}$N$_4$O$_3$S.0.25H$_2$O Calcd. C, 71.77; H, 7.30; N, 8.37. Found: C, 71.71; H, 7.35; N, 8.45.

Example 340

(Preparation of Compound 367)

To a solution of 7-[4-(2-butoxyethoxy)phenyl]-N-[4-[[[1-cyclopropylimidazol-2-yl]methyl]sulfanyl]phenyl]-1-isobutyl-2,3-dihydro-1-benzazepine-4-carboxamide (700 mg) in dichloromethane (15 ml) was added dropwise 70% solution of 3-chloroperbenzoic acid (389 mg) in dichloromethane (15 ml) at −78° C. The reaction vessel was removed from a dry ice-acetone bath, and an aqueous solution of sodium thiosulfate was added to the reaction vessel with strongly stirring. The mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (ethyl acetate), and was recrystallized from hexane-ethyl acetate, to give 7-[4-(2-butoxyethoxy)phenyl]-N-[4-[[[1-cyclopropylimidazol-2-yl]methyl]sulfinyl]phenyl]-1-isobutyl-2,3-dihydro-1-benzazepine-4-carboxamide (526 mg) (Compound 367) as yellow crystals.

$^1$H-NMR (200 MHz, CDCl$_3$) δ 0.66 to 1.00 (13H, m), 1.30 to 1.49 (2H, m), 1.54 to 1.69 (2H, m), 2.00 to 2.20 (1H, m), 2.90 to 3.05 (3H, m), 3.20 (2H, d, J=7.4 Hz), 3.30 to 3.45 (2H, m), 3.55 (2H, t, J=6.6 Hz), 3.80 (2H, t, J=4.4 Hz), 4.13 to 4.24 (3H, m), 4.39 (1H, d, J=13.2 Hz), 6.84 (1H, d, J=1.6 Hz), 6.90 to 7.00 (4H, m), 7.39 to 7.46 (7H, m), 7.74 (2H, d, J=8.4 Hz), 8.03 (1H, s).

Elemental Analysis for C$_{40}$H$_{48}$N$_4$O$_4$S Calcd. C, 70.56; H, 7.11; N, 8.23. Found: C, 70.21; H, 7.13; N, 7.97.

Example 341

(Preparation of Compounds 368 and 369)

7-[4-(2-butoxyethoxy)phenyl]-N-[4-[[[1-cyclopropylimidazol-2-yl]methyl]sulfinyl]phenyl]-1-isobutyl-2,3-dihydro-1-benzazepine-4-carboxamide (400 mg) was optically resoluted with CHIRAL PAK AD 50 mm ID×500 mmL (hexane/isopropanol), to give (+)-7-[4-(2-butoxyethoxy)phenyl]-N-[4-[[[1-cyclopropylimidazol-2-yl]methyl]sulfinyl]phenyl]-1-isobutyl-2,3-dihydro-1-benzazepine-4-carboxamide (176 mg) (Compound 368) and (−)-7-[4-(2-butoxyethoxy)phenyl]-N-[4-[[[1-cyclopropylimidazol-2-yl]methyl]sulfinyl]phenyl]-1-isobutyl-2,3-dihydro-1-benzazepine-4-carboxamide (175 mg) (Compound 369).

Compound 368

[α]$_D$=+79.5° (C=0.499% ethanol solution, >99.9% ee)

Compound 369

[α]$_D$=−81.5° (C=0.497% ethanol solution, 99.8% ee)

Example 342

(Preparation of Compound 370)

To a solution of 7-[4-(2-butoxyethoxy)phenyl]-1-isobutyl-2,3-dihydro-1-benzazepine-4-carboxylic acid (25.0 g) in tetrahydrofuran (250 ml) was added DMF (0.5 ml). Then, thionyl chloride (5.4 ml) was added to the mixture under nitrogen atmosphere and the mixture was stirred for 1 hour. The solvent and excess thionyl chloride were distilled off under reduced pressure, and the residue was dissolved in THF (250 ml). This solution was added dropwise to a solution of S-(4-aminophenyl)O-benzyl carbonothioate (14.8 g) and triethylamine (39.8 ml) in THF (250 ml) at 0° C. under argon atmosphere. After finishing the dropping, the mixture was allowed to be at room temperature and stirred under argon atmosphere, and methanol (500 ml) was added to the mixture. Further, 2N aqueous solution of sodium hydroxide (143 ml) was added to the mixture, and the mixture was stirred for 30 minutes under argon atmosphere. Then, 5-chloromethyl-1-propylimidazole hydrochloride (12.3 g) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by basic silica gel column chromatography (hexane: ethyl acetate=1:1), to give 7-[4-(2-butoxyethoxy)phenyl]-1-isobutyl-N-[4-[[[1-propylimidazol-5-yl]methyl]sulfanyl]phenyl]-2,3-dihydro-1-benzazepine-4-carboxamide (34.6 g) (Compound 370) as yellow amorphous.

$^1$H-NMR (200 MHz, CDCl$_3$) δ 0.90 to 1.00 (12H, m), 1.30 to 1.48 (2H, m), 1.54 to 1.68 (2H, m), 1.75 to 1.89 (2H, m), 2.00 to 2.20 (1H, m), 2.88 to 2.98 (2H, m), 3.19 (2H, d, J=7.4 Hz), 3.35 to 3.45 (2H, m), 3.55 (2H, t, J=7.4 Hz), 3.81 (2H, t, J=4.8 Hz), 3.92 (2H, t, J=7.6 Hz), 3.99 (2H, s), 4.16 (2H, t, J=4.8 Hz), 6.70 (1H, s), 6.92 (1H, d, J=8.8 Hz), 6.98 (2H, d, J=8.8 Hz), 7.25 to 7.29 (2H, m), 7.38 to 7.56 (8H, m), 7.66 (1H, s).

Elemental Analysis for C$_{40}$H$_{50}$N$_4$O$_3$S Calcd. C, 72.04; H, 7.56; N, 8.40. Found: C, 71.76; H, 7.63; N, 8.16.

Example 343

(Preparation of Compound 371)

To a solution of 7-[4-(2-butoxyethoxy)phenyl]-1-isobutyl-N-[4-[[[1-propylimidazol-5-yl]methyl]sulfanyl]phenyl]-2,3-dihydro-1-benzazepine-4-carboxamide (35.7 g) in dichloromethane (350 ml) was added dropwise 70% solution of 3-chloroperbenzoic acid (19.8 g) in dichloromethane (200 ml) at −78° C. Dimethylsulfide (10 ml) was added to the mixture, and the mixture was allowed to be at room temperature and stirred for 30 minutes. To the mixture was added water, and the organic layer was washed with an aqueous solution of saturated sodium bicarbonate and saturated brine, and dried over magnesium sulfate. The solvent was distilled off under reduced pressure. The obtained residue was separated and purified by silica gel column chromatography (ethyl acetate), which was recrystallized from diisopropyl ether-ethyl acetate to give 7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide (30.5 g) (Compound 371) as yellow crystals.

$^1$H-NMR (200 MHz, CDCl$_3$) δ 0.86 to 0.99 (12H, m), 1.29 to 1.50 (2H, m), 1.55 to 1.77 (4H, m), 1.95 to 2.20 (1H, m), 2.90 to 3.00 (2H, m), 3.20 (2H, d, J=7.4 Hz), 3.30 to 3.45

(2H, m), 3.55 (2H, t, J=6.6 Hz), 3.74 to 3.83 (4H, m), 4.02 (1H, d, J=14.4 Hz), 4.07 to 4.18 (3H, m), 6.56 (1H, s), 6.92 (1H, d, J=8.8 Hz), 6.98 (2H, d, J=8.8 Hz), 7.32 to 7.50 (8H, m), 7.75 (2H, d, J=8.8 Hz), 7.97 (1H, s).

Elemental Analysis for $C_{40}H_{50}N_4O_4S$ Calcd. C, 70.35; H, 7.38; N, 8.20. Found: C, 70.03; H, 7.40; N, 8.06.

Example 344

(Preparation of Compounds 372 and 373)

7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide (1.33 g) was optically resolved with CHIRAL. PAK AD 50 mm ID×500 mmL (ethanol→isopropanol), to give (+)-7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide (0.58 g) (Compound 372) and (−)-7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide (0.60 g) (Compound 373).

Compound 372
$[\alpha]_D$=+131.8° (C=0.498% ethanol solution, >99.9% ee)
Compound 373
$[\alpha]_D$=−126.9° (C=0.497% ethanol solution, 99.6% ee)

Example 345

(Preparation of Compound 374)

To a solution of 7-[4-(2-butoxyethoxy)phenyl]-1-propyl-2,3-dihydro-1-benzazepine-4-carboxylic acid (1.0 g) in tetrahydrofuran (15 ml) was added one droplet of DMF. Then, thionyl chloride (0.23 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (612 mg) and triethylamine (1.65 ml) in THF (15 ml) at 0° C. under argon atmosphere. After finishing the dropping, the mixture was allowed to be at room temperature and stirred under argon atmosphere, and methanol (30 ml) was added to the mixture. Further, 1N aqueous solution of sodium hydroxide (11.8 ml) was added to the mixture, and the mixture was stirred for 30 minutes under argon atmosphere. Then, 5-chloromethyl-1-propylimidazole hydrochloride (506 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The obtained residue was separated and purified by silica gel column chromatography (methanol-ethyl acetate=1:19), to give 7-[4-(2-butoxyethoxy)phenyl]-1-propyl-N-[4-[[[1-propylimidazol-5-yl]methyl]sulfanyl]phenyl]-2,3-dihydro-1-benzazepine-4-carboxamide (988 mg) (Compound 374) as yellow amorphous.

$^1$H-NMR (200 MHz, CDCl$_3$) δ 0.89 to 1.03 (9H, m), 1.27 to 1.50 (2H, m), 1.55 to 1.95 (6H, m), 2.85 to 2.95 (2H, m), 3.25 to 3.40 (4H, m), 3.55 (2H, t, J=6.6 Hz), 3.80 (2H, t, J=4.8 Hz), 3.92 (2H, t, J=7.4 Hz), 3.99 (2H, s), 4.16 (2H, t, J=4.8 Hz), 6.70 (1H, s), 6.90 (1H, d, J=7.8 Hz), 6.98 (2H, d, J=8.4 Hz), 7.25 to 7.30 (2H, m), 7.39 to 7.55 (8H, m), 7.62 (1H, s).

Elemental Analysis for $C_{39}H_{48}N_4O_3S$ Calcd. C, 71.75; H, 7.41; N, 8.58. Found: C, 71.54; H, 7.37; N, 8.53.

Example 346

(Preparation of Compounds 375 and 376)

To a solution of 7-[4-(2-butoxyethoxy)phenyl]-1-propyl-N-[4-[[[1-propylimidazol-5-yl]methyl]sulfanyl]phenyl]-2,3-dihydro-1-benzazepine-4-carboxamide (900 mg) in dichloromethane (15 ml) was added dropwise 70% solution of 3-chloroperbenzoic acid (510 mg) in dichloromethane (15 ml) at −78° C. The reaction vessel was removed from a dry ice-acetone bath, and an aqueous solution of sodium thiosulfate was added to the reaction vessel with strongly stirring. The mixture was allowed to be at room temperature and stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide (529 mg) (Compound 375) and 7-[4-(2-butoxyethoxy)phenyl]-1-propyl-N-[4-[[[1-propylimidazol-5-yl]methyl]sulfonyl]phenyl]-2,3-dihydro-1-benzazepine-4-carboxamide (37 mg) (Compound 376) as yellow amorphous.

Compound 375
$^1$H-NMR (300 MHz, CDCl$_3$) δ 0.88 to 1.025 (9H, m), 1.33 to 1.46 (2H, m), 1.56 to 1.79 (6H, m), 2.90 to 2.95 (2H, m), 3.31 to 3.37 (4H, m), 3.55 (2H, t, J=6.3 Hz), 3.76 to 3.82 (4H, m), 4.02 (1H, d, J=14.1 Hz), 4.09 (1H, d, J=14.1 Hz), 4.16 (2H, t, J=4.8 Hz), 6.57 (1H, s), 6.91 (1H, d, J=9.0 Hz), 6.98 (2H, d, J=8.7 Hz), 7.33 to 7.51 (8H, m), 7.74 (2H, d, J=9.0 Hz), 7.84 (1H, s).

Elemental Analysis for $C_{39}H_{48}N_4O_4S \cdot 0.25H_2O$ Calcd. C, 69.56; H, 7.26; N, 8.32. Found: C, 69.49; H, 7.23; N, 8.18.

Compound 376
$^1$H-NMR (200 MHz, CDCl$_3$) δ 0.89 to 1.03 (9H, m), 1.30 to 1.50 (2H, m), 1.55 to 1.85 (6H, m), 2.85 to 2.95 (2H, m), 3.25 to 3.40 (4H, m), 3.55 (2H, t, J=6.6 Hz), 3.81 (2H, t, J=4.8 Hz), 3.95 (2H, t, J=7.4 Hz), 4.16 (2H, t, J=4.8 Hz), 4.32 (2H, s), 6.53 (1H, s), 6.90 (1H, d, J=8.8 Hz), 6.98 (2H, d, J=8.8 Hz), 7.41 to 7.50 (6H, m), 7.60 (2H, d, J=8.8 Hz), 7.76 (2H, d, J=8.8 Hz), 8.06 (1H, s).

Elemental Analysis for $C_{39}H_{48}N_4O_5S \cdot 0.75H_2O$ Calcd. C, 67.07; H, 7.14; N, 8.02. Found: C, 67.12; H, 6.97; N, 7.70.

Example 347

(Preparation of Compounds 377 and 378)

7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide (413 mg) was optically resolved with CHIRAL PAK AD 50 mm ID×500 mmL (ethanol→isopropanol), to give (+)-7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide (140 mg) (Compound 377) and (−)-7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide (155 mg) (Compound 378).

Compound 377
$[\alpha]_D$=+136.0° (C=0.495% ethanol solution, >99.9% ee)
Compound 378
$[\alpha]_D$=−138.2° (C=0.499% ethanol solution, 99.9% ee)

Example 348

(Preparation of Compound 379)

To a solution of 7-[4-(2-butoxyethoxy)phenyl]-1-isobutyl-2,3-dihydro-1-benzazepine-4-carboxylic acid (1.0 g) in tetrahydrofuran (15 ml) was added one droplet of DMF. Then, thionyl chloride (0.22 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (594 mg) and triethylamine (1.6 ml) in THF (15 ml) at 0° C. under argon atmosphere. After finishing the dropping, the mixture was allowed to be at room temperature and stirred under argon atmosphere overnight, and methanol (30 ml) was added to the mixture. Further, 1N aqueous solution of sodium hydroxide (11.5 ml) was added to the mixture, and the mixture was stirred for 30 minutes under argon atmosphere. Then, 5-chloromethyl-1-ethylimidazole hydrochloride (435 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by basic silica gel column chromatography (hexane:ethyl acetate=1:1), to give 7-[4-(2-butoxyethoxy)phenyl]-N-[4-[[[1-ethylimidazol-5-yl]methyl]sulfanyl]phenyl]-1-isobutyl-2,3-dihydro-1-benzazepine-4-carboxamide (960 mg) (Compound 379) as yellow amorphous.

$^1$H-NMR (200 MHz, CDCl$_3$) δ 0.90 to 0.99 (9H, m), 1.34 to 1.65 (7H, m), 1.95 to 2.15 (1H, m), 2.85 to 2.95 (2H, m), 3.19 (2H, d, J=7.4 Hz), 3.35 to 3.45 (2H, m), 3.55 (2H, t, J=6.6 Hz), 3.80 (2H, t, J=4.8 Hz), 4.01 to 4.08 (4H, m), 4.16 (2H, t, J=4.8 Hz), 6.70 (1H, s), 6.92 (1H, d, J=8.8 Hz), 6.98 (2H, d, J=8.8 Hz), 7.28 (2H, d, J=8.8 Hz), 7.39 to 7.56 (8H, m), 7.60 (1H, s).

Elemental Analysis for $C_{39}H_{48}N_4O_3S\cdot0.25H_2O$ Calcd. C, 71.25; H, 7.44; N, 8.52. Found: C, 71.10; H, 7.42; N, 8.59.

Example 349

(Preparation of Compound 380)

To a solution of 7-[4-(2-butoxyethoxy)phenyl]-N-[4-[[[1-ethylimidazol-5-yl]methyl]sulfanyl]phenyl]-1-isobutyl-2,3-dihydro-1-benzazepine-4-carboxamide (900 mg) in dichloromethane (15 ml) was added dropwise 70% solution of 3-chloroperbenzoic acid (365 mg) in dichloromethane (15 ml) at −78° C. Dimethylsulfide (0.1 ml) was added to the mixture, and the mixture was allowed to be at room temperature and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-N-[4-[[[1-ethylimidazol-5-yl]methyl]sulfinyl]phenyl]-1-isobutyl-2,3-dihydro-1-benzazepine-4-carboxamide (516 mg) (Compound 380) as yellow amorphous.

$^1$H-NMR (200 MHz, CDCl$_3$) δ 0.90 to 0.99 (9H, m), 1.30 to 1.45 (5H, m), 1.50 to 1.70 (2H, m), 1.95 to 2.15 (1H, m), 2.90 to 3.00 (2H, m), 3.20 (2H, d, J=7.6 Hz), 3.33 to 3.43 (2H, m), 3.55 (2H, t, J=6.6 Hz), 3.78 to 3.93 (4H, m), 4.01 (1H, d, J=13.8 Hz), 4.14 (1H, d, J=13.8 Hz), 4.16 (2H, t, J=4.8 Hz), 6.58 (1H, s), 6.91 to 7.00 (3H, m), 7.34 to 7.55 (8H, m), 7.75 (2H, d, J=8.8 Hz), 7.83 (1H, s).

Elemental Analysis for $C_{39}H_{48}N_4O_4S\cdot0.25H_2O$ Calcd. C, 69.56; H, 7.26; N, 8.32. Found: C, 69.37; H, 7.13; N, 8.20.

Example 350

(Preparation of Compound 381)

To a solution of 7-[4-(2-butoxyethoxy)phenyl]-1-isobutyl-2,3-dihydro-1-benzazepine-4-carboxylic acid (1.0 g) in tetrahydrofuran (15 ml) was added one droplet of DMF. Then, thionyl chloride (0.22 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (594 mg) and triethylamine (1.6 ml) in THF (15 ml) at 0° C. under argon atmosphere. After finishing the dropping, the mixture was allowed to be at room temperature and stirred under argon atmosphere overnight, and methanol (30 ml) was added to the mixture. Further, 1N aqueous solution of sodium hydroxide (11.5 ml) was added to the mixture, and the mixture was stirred for 30 minutes under argon atmosphere. Then, 5-chloromethyl-1-isobutylimidazole hydrochloride (503 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The obtained residue was separated and purified by silica gel column chromatography (ethyl acetate), to give 7-[4-(2-butoxyethoxy)phenyl]-1-isobutyl-N-[4-[[[1-isobutylimidazol-5-yl]methyl]sulfanyl]phenyl]-2,3-dihydro-1-benzazepine-4-carboxamide (1.0 g) (Compound 381) as yellow amorphous.

$^1$H-NMR (200 MHz, CDCl$_3$) δ 0.90 to 0.99 (15H, m), 1.30 to 1.45 (2H, m), 1.50 to 1.70 (2H, m), 2.00 to 2.20 (2H, m), 2.85 to 2.95 (2H, m), 3.19 (2H, d, J=7.8 Hz), 3.30 to 3.40 (2H, m), 3.55 (2H, t, J=6.6 Hz), 3.76 to 3.83 (4H, m), 3.99 (2H, s), 4.16 (2H, t, J=4.8 Hz), 6.70 (1H, s), 6.92 (1H, d, J=8.8 Hz), 6.98 (2H, d, J=8.8 Hz), 7.26 to 7.30 (2H, m), 7.38 to 7.57 (8H, m), 7.73 (1H, s).

Elemental Analysis for $C_{41}H_{52}N_4O_3S$ Calcd. C, 72.32; H, 7.70; N, 8.23. Found: C, 71.93; H, 7.67; N, 8.29.

Example 351

(Preparation of Compound 382)

To a solution of 7-[4-(2-butoxyethoxy)phenyl]-1-isobutyl-N-[4-[[[1-isobutylimidazol-5-yl]methyl]sulfanyl]phenyl]-2,3-dihydro-1-benzazepine-4-carboxamide (900 mg) in dichloromethane (15 ml) was added dropwise 70% solution of 3-chloroperbenzoic acid (358 mg) in dichloromethane (15 ml) at −78° C. Dimethylsulfide (0.1 ml) was added to the mixture, and the mixture was allowed to be at room temperature, and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-1-isobutyl-N-[4-[[[1-isobutylimidazol-5-yl]

methyl]sulfinyl]phenyl]-2,3-dihydro-1-benzazepine-4-carboxamide (619 mg) (Compound 382) as yellow amorphous.

$^1$H-NMR (200 MHz, CDCl$_3$) δ 0.85 to 0.99 (15H, m), 1.34 to 1.50 (2H, m), 1.55 to 1.70 (2H, m), 1.80 to 2.20 (2H, m), 2.90 to 3.00 (2H, m), 3.20 (2H, d, J=6.8 Hz), 3.30 to 3.45 (2H, m), 3.55 (2H, t, J=6.6 Hz), 3.63 (2H, d, J=7.8 Hz), 3.80 (2H, t, J=4.4 Hz), 3.95 to 4.18 (4H, m), 6.55 (1H, s), 6.93 (1H, d, J=8.8 Hz), 6.98 (2H, d, J=8.8 Hz), 7.37 to 7.52 (8H, m), 7.75 (2H, d, J=8.8 Hz), 7.93 (1H, s).

Elemental Analysis for C$_{41}$H$_{52}$N$_4$O$_4$S.0.25H$_2$O Calcd. C, 70.20; H, 7.54; N, 7.99. Found: C, 70.13; H, 7.50; N, 7.87.

Example 352

(Preparation of Compound 383)

To a solution of 7-[4-(2-butoxyethoxy)phenyl]-1-isobutyl-2,3-dihydro-1-benzazepine-4-carboxylic acid (1.0 g) in tetrahydrofuran (15 ml) was added one droplet of DMF. Then, thionyl chloride (0.22 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (594 mg) and triethylamine (1.6 ml) in THF (15 ml) at 0° C. under argon atmosphere. After finishing the dropping, the mixture was allowed to be at room temperature and stirred under argon atmosphere overnight, and methanol (30 ml) was added to the mixture. Further, 1N aqueous solution of sodium hydroxide (11.5 ml) was added to the mixture, and the mixture was stirred for 30 minutes under argon atmosphere. Then, 5-chloromethyl-1-isopropylimidazole hydrochloride (491 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by basic silica gel column chromatography (hexane-ethyl acetate=1:1→hexane-ethyl acetate=1:3), to give 7-[4-(2-butoxyethoxy)phenyl]-1-isobutyl-N-[4-[[[1-isopropylimidazol-5-yl]methyl]sulfanyl]phenyl]-2,3-dihydro-1-benzazepine-4-carboxamide (1.1 g) (Compound 383) as yellow amorphous.

$^1$H-NMR (200 MHz, CDCl$_3$) δ 0.90 to 0.99 (9H, m), 1.30 to 1.65 (10H, m), 2.00 to 2.20 (1H, m), 2.85 to 2.95 (2H, m), 3.19 (2H, d, J=7.0 Hz), 3.30 to 3.40 (2H, m), 3.55 (2H, t, J=6.6 Hz), 3.80 (2H, t, J=4.8 Hz), 4.00 (2H, s), 4.16 (2H, t, J=4.8 Hz), 4.35 to 4.50 (1H, m), 6.69 (1H, s), 6.92 (1H, d, J=8.8 Hz), 6.98 (2H, d, J=8.8 Hz), 7.28 (2H, d, J=8.8 Hz), 7.38 to 7.56 (8H, m), 7.65 (1H, s).

Elemental Analysis for C$_{40}$H$_{50}$N$_4$O$_3$S.0.25H$_2$O Calcd. C, 71.55; H, 7.58; N, 8.34. Found: C, 71.30; H, 7.45; N, 8.69.

Example 353

(Preparation of Compound 384)

To a solution of 7-[4-(2-butoxyethoxy)phenyl]-1-isobutyl-N-[4-[[[1-isopropylimidazol-5-yl]methyl]sulfanyl]phenyl]-2,3-dihydro-1-benzazepine-4-carboxamide (1.0 g) in dichloromethane (15 ml) was added dropwise 70% solution of 3-chloroperbenzoic acid (388 mg) in dichloromethane (15 ml) at −78° C. Dimethylsulfide (0.1 ml) was added to the mixture, and the mixture was allowed to be at room temperature, and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-1-isobutyl-N-[4-[[[1-isopropylimidazol-5-yl]methyl]sulfinyl]phenyl]-2,3-dihydro-1-benzazepine-4-carboxamide (634 mg) (Compound 384) as yellow amorphous.

$^1$H-NMR (300 MHz, CDCl$_3$) δ 0.91 to 0.99 (9H, m), 1.36 to 1.45 (8H, m), 1.55 to 1.65 (2H, m), 2.00 to 2.15 (1H, m), 2.90 to 2.95 (2H, m), 3.20 (2H, d, J=7.5 Hz), 3.35 to 3.40 (2H, m), 3.55 (2H, t, J=6.6 Hz), 3.81 (2H, t, J=4.8 Hz), 4.01 (1H, d, J=14.1 Hz), 4.11 (1H, d, J=14.1 Hz), 4.16 (2H, t, J=4.8 Hz), 4.25 to 4.35 (1H, m), 6.54 (1H, s), 6.93 (1H, d, J=8.7 Hz), 6.98 (2H, d, J=8.7 Hz), 7.34 to 7.51 (7H, m), 7.59 (1H, s), 7.75 (2H, d, J=8.7 Hz), 7.93 (1H, s).

Elemental Analysis for C$_{40}$H$_{50}$N$_4$O$_4$S.0.25H$_2$O Calcd. C, 69.89; H, 7.40; N, 8.15. Found: C, 69.79; H, 7.58; N, 7.88.

Example 354

(Preparation of Compound 385)

To a solution of 7-[4-(2-butoxyethoxy)phenyl]-1-isobutyl-2,3-dihydro-1-benzazepine-4-carboxylic acid (1.0 g) in tetrahydrofuran (15 ml) was added one droplet of DMF. Then, thionyl chloride (0.22 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (594 mg) and triethylamine (1.6 ml) in THF (15 ml) at 0° C. under argon atmosphere. After finishing the dropping, the mixture was allowed to be at room temperature and stirred overnight under argon atmosphere, and methanol (30 ml) was added to the mixture. Further, 1N aqueous solution of sodium hydroxide (11.5 ml) was added to the mixture, and the mixture was stirred for 30 minutes under argon atmosphere. Then, 5-chloromethyl-1-cyclopropylmethylimidazole hydrochloride (497 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by basic silica gel column chromatography (hexane-ethyl acetate=1:1), to give 7-[4-(2-butoxyethoxy)phenyl]-N-[4-[[[1-cyclopropylmethylimidazol-5-yl]methyl]sulfanyl]phenyl]-1-isobutyl-2,3-dihydro-1-benzazepine-4-carboxamide (1.2 g) (Compound 385) as yellow amorphous.

$^1$H-NMR (200 MHz, CDCl$_3$) δ 0.34 to 0.42 (2H, m), 0.66 to 0.75 (2H, m), 0.90 to 0.99 (9H, m), 1.20 to 1.50 (3H, m), 1.55 to 1.70 (2H, m), 1.95 to 2.15 (1H, m), 2.85 to 2.95 (2H, m), 3.19 (2H, d, J=7.4 Hz), 3.29 to 3.37 (2H, m), 3.55 (2H, t, J=6.6 Hz), 3.78 to 3.84 (4H, m), 4.02 (2H, s), 4.16 (2H, t, J=4.4 Hz), 6.72 (1H, s), 6.92 (1H, d, J=8.8 Hz), 6.98 (2H, d, J=8.8 Hz), 7.27 (2H, d, J=8.8 Hz), 7.38 to 7.60 (8H, m), 7.65 (1H, s).

Elemental Analysis for C$_{41}$H$_{50}$N$_4$O$_3$S.0.25H$_2$O Calcd. C, 72.05; H, 7.45; N, 8.20. Found: C, 71.93; H, 7.43; N, 8.34.

Example 355

(Preparation of Compound 386)

To a solution of 7-[4-(2-butoxyethoxy)phenyl]-N-[4-[[[1-cyclopropylmethylimidazol-5-yl]methyl]sulfanyl]phenyl]-1-isobutyl-2,3-dihydro-1-benzazepine-4-carboxamide (1.1 g) in dichloromethane (15 ml) was added dropwise 70% solution of 3-chloroperbenzoic acid (440 mg) in dichloromethane (15 ml) at −78° C. Dimethylsulfide (0.1 ml) was added to the mixture, and the mixture was allowed to be at room temperature, and stirred for 30 minutes. To the mixture was added water and the mixture was extracted with ethyl acetate. The organic layer was washed with an aqueous solution of saturated sodium bicarbonate and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-N-[4-[[[1-cyclopropylmethylimidazol-5-yl]methyl]sulfinyl]phenyl]-1-isobutyl-2,3-dihydro-1-benzazepine-4-carboxamide (614 mg) (Compound 386) as yellow amorphous.

$^1$H-NMR (300 MHz, CDCl$_3$) δ 0.29 to 0.34 (2H, m), 0.63 to 0.69 (2H, m), 0.91 to 0.99 (9H, m), 1.05 to 1.20 (1H, m), 1.36 to 1.43 (2H, m), 1.56 to 1.66 (2H, m), 2.00 to 2.20 (1H, m), 2.90 to 2.95 (2H, m), 3.20 (2H, d, J=7.2 Hz), 3.35 to 3.39 (2H, m), 3.55 (2H, t, J=6.6 Hz), 3.66 (2H, t, J=4.5 Hz), 3.81 (2H, t, J=6.6 Hz), 4.02 (1H, d, J=14.1 Hz), 4.10 to 4.17 (3H, m), 6.58 (1H, s), 6.92 (1H, d, J=8.7 Hz), 6.98 (2H, d, J=8.7 Hz), 7.34 to 7.56 (7H, m), 7.63 (1H, s), 7.75 (2H, d, J=8.7 Hz), 7.97 (1H, s).

Elemental Analysis for C$_{41}$H$_{50}$N$_4$O$_4$S .0.2H$_2$O Calcd. C, 70.50; H, 7.27; N, 8.02. Found: C, 70.35; H, 7.32; N, 7.94.

Example 356

(Preparation of Compound 387)

To a solution of 7-[4-(2-butoxyethoxy)phenyl]-1-isobutyl-2,3-dihydro-1-benzazepine-4-carboxylic acid (1.0 g) in tetrahydrofuran (15 ml) was added one droplet of DMF. Then, thionyl chloride (0.22 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (594 mg) and triethylamine (1.6 ml) in THF (15 ml) at 0° C. under argon atmosphere. After finishing the dropping, the mixture was allowed to be at room temperature and stirred overnight under argon atmosphere, and methanol (30 ml) was added to the mixture. Further, 1N aqueous solution of sodium hydroxide (11.5 ml) was added to the mixture, and the mixture was stirred for 30 minutes under argon atmosphere. Then, a solution of 5-chloromethyl-4-methyl-1-propylimidazole hydrochloride (599 mg) in methanol (10 ml) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by basic silica gel column chromatography (hexane-ethyl acetate=1:1→1:3), to give 7-[4-(2-butoxyethoxy)phenyl]-1-isobutyl-N-[4-[[[4-methyl-1-propylimidazol-5-yl]methyl]sulfanyl]phenyl]-2,3-dihydro-1-benzazepine-4-carboxamide (529 mg) (Compound 387) as yellow amorphous.

$^1$H-NMR (200 MHz, CDCl$_3$) δ 0.90 to 1.26 (12H, m), 1.30 to 1.48 (2H, m), 1.54 to 1.65 (2H, m), 1.70 to 1.90 (5H, m), 1.95 to 2.15 (1H, m), 2.85 to 2.95 (2H, m), 3.19 (2H, d, J=7.0 Hz), 3.34 to 3.38 (2H, m), 3.55 (2H, t, J=6.6 Hz), 3.78 to 3.90 (4H, m), 3.95 (2H, s), 4.16 (2H, t, J=4.8 Hz), 6.92 (1H, d, J=8.4 Hz), 6.98 (2H, d, J=8.4 Hz), 7.24 (2H, d, J=8.4 Hz), 7.36 to 7.55 (8H, m), 7.67 (1H, s).

Example 357

(Preparation of Compound 388)

To a solution of 7-[4-(2-butoxyethoxy)phenyl]-1-isobutyl-N-[4-[[[4-methyl-1-propylimidazol-5-yl]methyl]sulfanyl]phenyl]-2,3-dihydro-1-benzazepine-4-carboxamide (460 mg) in dichloromethane (15 ml) was added dropwise 70% solution of 3-chloroperbenzoic acid (175 mg) in dichloromethane (15 ml) at −78° C. Dimethylsulfide (0.1 ml) was added to the mixture, and the mixture was allowed to be at room temperature and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-1-isobutyl-N-[4-[[[4-methyl-1-propylimidazol-5-yl]methyl]sulfinyl]phenyl]-2,3-dihydro-1-benzazepine-4-carboxamide (236 mg) (Compound 388) as yellow amorphous.

$^1$H-NMR (300 MHz, CDCl$_3$) δ 0.87 to 0.98 (12H, m), 1.30 to 1.45 (2H, m), 1.55 to 1.75 (7H, m), 2.00 to 2.15 (1H, m), 2.90 to 2.95 (2H, m), 3.19 (2H, d, J=7.5 Hz), 3.37 to 3.42 (2H, m), 3.55 (2H, t, J=6.9 Hz), 3.75 (2H, t, J=6.9 Hz), 3.81 (2H, t, J=5.4 Hz), 4.04 (2H, s), 4.16 (2H, t, J=5.4 Hz), 6.92 (1H, d, J=8.7 Hz), 6.98 (2H, d, J=9.0 Hz), 7.31 (2H, d, J=8.7 Hz), 7.39 to 7.49 (6H, m), 7.74 (2H, d, J=8.7 Hz), 7.97 (1H, s).

Elemental Analysis for C$_{41}$H$_{52}$N$_4$O$_4$S.0.25H$_2$O Calcd. C, 70.20; H, 7.54; N, 7.99. Found: C, 70.00; H, 7.50; N, 7.97.

Example 358

(Preparation of Compound 389)

To a solution of 1-isobutyl-7-[4-(2-propoxyethoxy)phenyl]-2,3-dihydro-1-benzazepine-4-carboxylic acid (820 mg) in tetrahydrofuran (15 ml) was added one droplet of DMF. Then, thionyl chloride (0.18 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (503 mg) and triethylamine (1.4 ml) in THF (15 ml) at 0° C. under argon atmosphere. After finishing the dropping, the mixture was allowed to be at room temperature and stirred overnight under argon atmosphere, and methanol (30 ml) was added to the mixture. Further, 1N aqueous solution of sodium hydroxide (9.7 ml) was added to the mixture, and the mixture was stirred for 30 minutes under argon atmosphere. Then, 5-chloromethyl-1-propylimidazole hydrochloride (492 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by basic silica gel column chromatography (hexane-ethyl acetate=1:1→ethyl acetate), to give 1-isobutyl-7-[4-(2-propoxyethoxy)phenyl]-N-[4-[[[1-propylimidazol-5-yl]methyl]sulfanyl]phenyl]-2,3-dihydro-1-benzazepine-4-carboxamide (685 mg) (Compound 389) as yellow amorphous.

$^1$H-NMR (200 MHz, CDCl$_3$) δ 0.91 to 1.01 (12H, m), 1.50 to 1.70 (2H, m), 1.79 to 1.90 (2H, m), 2.00 to 2.20 (1H, m), 2.85 to 2.95 (2H, m), 3.19 (2H, d, J=7.0 Hz), 3.30 to 3.40 (2H, m), 3.51 (2H, t, J=6.6 Hz), 3.81 (2H, t, J=4.6 Hz), 3.93 (2H, t, J=7.6 Hz), 4.00 (2H, s), 4.16 (2H, t, J=4.6 Hz), 6.70 (1H, s), 6.92 (1H, d, J=8.8 Hz), 6.98 (2H, d, J=8.8 Hz), 7.26 to 7.30 (2H, m), 7.38 to 7.58 (9H, m).

Elemental Analysis for C$_{39}$H$_{48}$N$_4$O$_3$S.0.25H$_2$O Calcd. C, 71.25; H, 7.44; N, 8.52. Found: C, 70.96; H, 7.55; N, 8.43.

Example 359

(Preparation of Compound 390)

To a solution of 1-isobutyl-7-[4-(2-propoxyethoxy)phenyl]-N-[4-[[[1-propylimidazol-5-yl]methyl]sulfanyl]phenyl]-2,3-dihydro-1-benzazepine-4-carboxamide (600 mg) in dichloromethane (15 ml) was added dropwise 70% solution of 3-chloroperbenzoic acid (272 mg) in dichloromethane (15 ml) at −78° C. Dimethylsulfide (0.1 ml) was added to the mixture, and the mixture was allowed to be at room temperature and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide (433 mg) (Compound 390) as yellow amorphous.

$^1$H-NMR (200 MHz, CDCl$_3$) δ 0.87 to 0.99 (12H, m), 1.55 to 1.80 (4H, m), 1.95 to 2.15 (1H, m), 2.90 to 3.00 (2H, m), 3.20 (2H, d, J=7.2 Hz), 3.35 to 3.45 (2H, m), 3.51 (2H, t, J=6.4 Hz), 3.75 to 3.84 (4H, m), 4.02 (1H, d, J=14.2 Hz), 4.08 to 4.19 (3H, m), 6.57 (1H, s), 6.93 (1H, d, J=8.8 Hz), 6.98 (2H, d, J=8.8 Hz), 7.38 to 7.53 (8H, m), 7.76 (2H, d, J=8.8 Hz), 7.95 (1H, s).

Elemental Analysis for C$_{39}$H$_{48}$N$_4$O$_4$S.0.25H$_2$O Calcd. C, 69.56; H, 7.26; N, 8.32. Found: C, 69.19; H, 7.21; N, 8.34.

Example 360

(Preparation of Compounds 391 and 392)

1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide (320 mg) was optically resoluted with CHIRAL PAK AD 50 mm ID×500 mmL (ethanol→isopropanol), to give (+)-1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide (136 mg) (Compound 391) and (−)-1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide (123 mg) (Compound 392).

Compound 391
[α]$_D$=+131.4° (C=0.499% ethanol solution, 99.7% ee)
Compound 392
[α]$_D$=−135.3° (C=0.499% ethanol solution, 99.8% ee)

Example 361

(Preparation of Compound 393)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.1 ml) in THF (15 ml) at 0° C. under argon atmosphere. After finishing the dropping, the mixture was allowed to be at room temperature and stirred overnight under argon atmosphere, and methanol (30 ml) was added to the mixture. Further, 1N aqueous solution of sodium hydroxide (8 ml) was added to the mixture, and the mixture was stirred for 30 minutes under argon atmosphere. Then, 4-chloromethyl-1-propylimidazole hydrochloride (406 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by silica gel column chromatography (hexane-ethyl acetate=1:4→ethyl acetate), and was recrystallized from hexane-diisopropyl ether-ethyl acetate to give 7-[4-(2-butoxyethoxy)phenyl]-1-isobutyl-N-[4-[[[1-propylimidazol-4-yl]methyl]sulfanyl]phenyl]-2,3-dihydro-1-benzazepine-4-carboxamide (200 mg) (Compound 393) as yellow crystals.

$^1$H-NMR (200 MHz, CDCl$_3$) δ 0.85 to 0.99 (12H, m), 1.30 to 1.48 (2H, m), 1.54 to 1.80 (4H, m), 1.95 to 2.15 (1H, m), 2.85 to 2.95 (2H, m), 3.19 (2H, d, J=7.2 Hz), 3.30 to 3.40 (2H, m), 3.55 (2H, t, J=6.6 Hz), 3.76 to 3.83 (4H, m), 4.07 (2H, s), 4.16 (2H, t, J=5.2 Hz), 6.69 (1H, s), 6.92 (1H, d, J=9.2 Hz), 6.98 (2H, d, J=8.8 Hz), 7.32 to 7.55 (11H, m).

Elemental Analysis for C$_{40}$H$_{50}$N$_4$O$_3$S Calcd. C, 72.04; H, 7.56; N, 8.40. Found: C, 71.78; H, 7.41; N, 8.48.

Example 362

(Preparation of Compound 394)

To a solution of 7-[4-(2-butoxyethoxy)phenyl]-1-isobutyl-N-[4-[[[1-propylimidazol-4-yl]methyl]sulfanyl]phenyl]-2,3-dihydro-1-benzazepine-4-carboxamide (140 mg) in dichloromethane (15 ml) was added dropwise 70% solution of 3-chloroperbenzoic acid (78 mg) in dichloromethane (15 ml) at −78° C. The reaction vessel was removed from a dry ice-acetone bath, and an aqueous solution of sodium thiosulfate was added to the reaction vessel with strongly stirring. The mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by silica gel column chromatography (methanol-ethyl acetate=1:9), to give 7-[4-(2-butoxyethoxy)phenyl]-1-isobutyl-N-[4-[[[1-propylimidazol-4-yl]methyl]sulfinyl]phenyl]-2,3-dihydro-1-benzazepine-4-carboxamide (103 mg) (Compound 394) as yellow amorphous.

$^1$H-NMR (200 MHz, CDCl$_3$) δ 0.88 to 0.99 (12H, m), 1.30 to 1.50 (2H, m), 1.55 to 1.85 (4H, m), 1.95 to 2.20 (1H, m), 2.85 to 2.95 (2H, m), 3.20 (2H, d, J=7.6 Hz), 3.30 to 3.45

(2H, m), 3.55 (2H, t, J=7.2 Hz), 3.78 to 3.87 (4H, m), 3.98 (1H, d, J=12.8 Hz), 4.09 (1H, d, J=12.8 Hz), 4.16 (2H, t, J=4.8 Hz), 6.80 (1H, s), 6.93 (1H, d, J=8.4 Hz), 6.98 (2H, d, J=8.8 Hz), 7.39 to 7.53 (8H, m), 7.70 to 7.75 (3H, m).

Elemental Analysis for $C_{40}H_{50}N_4O_4S$ Calcd. C, 70.35; H, 7.38; N, 8.20. Found: C, 70.10; H, 7.34; N, 8.12.

Example 363

(Preparation of Compound 395)

To a solution of 7-[4-(2-butoxyethoxy)phenyl]-1-isobutyl-2,3-dihydro-1-benzazepine-4-carboxylic acid (700 mg) in tetrahydrofuran (15 ml) was added one droplet of DMF. Then, thionyl chloride (0.15 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of S-(4-aminophenyl)O-benzyl carbonothioate (415 mg) and triethylamine (1.1 ml) in THF (15 ml) at 0° C. under argon atmosphere. After finishing the dropping, the mixture was allowed to be at room temperature and stirred overnight under argon atmosphere, and methanol (30 ml) was added to the mixture. Further, 1N aqueous solution of sodium hydroxide (8 ml) was added to the mixture, and the mixture was stirred for 30 minutes under argon atmosphere. Then, 2-(1-chloroethyl)-1-propylimidazole hydrochloride (368 mg) was added to the mixture, and the mixture was stirred for 1.5 hours under argon atmosphere. To the mixture was added water and the mixture was extracted with ethyl acetate. The organic layer was washed with saturated brine, and dried over magnesium sulfate. The solvent was distilled off under reduced pressure. The residue was separated and purified by silica gel column chromatography (hexane-ethyl acetate=1:4), to give 7-[4-(2-butoxyethoxy)phenyl]-1-isobutyl-N-[4-[[1-[1-propylimidazol-2-yl]ethyl]sulfanyl]phenyl]-2,3-dihydro-1-benzazepine-4-carboxamide (223 mg) (Compound 395) as yellow amorphous.

$^1$H-NMR (200 MHz, CDCl$_3$) δ 0.90 to 0.99 (12H, m), 1.30 to 1.50 (2H, m), 1.55 to 1.65 (2H, m), 1.70 to 1.84 (5H, m), 1.95 to 2.15 (1H, m), 2.85 to 2.95 (2H, m), 3.19 (2H, d, J=7.4 Hz), 3.30 to 3.40 (2H, m), 3.55 (2H, t, J=7.0 Hz), 3.75 to 3.95 (4H, m), 4.16 (2H, t, J=4.8 Hz), 4.27 (1H, q, J=6.8 Hz), 6.84 (1H, d, J=1.4 Hz), 6.96 to 7.00 (4H, m), 7.26 (2H, d, J=8.8 Hz), 7.39 to 7.58 (8H, m).

Elemental Analysis for $C_{41}H_{52}N_4O_3S \cdot 0.25H_2O$ Calcd. C, 71.84; H, 7.72; N, 8.17. Found: C, 71.67; H, 7.76; N, 8.15.

Example 364

(Preparation of Compound 396)

To a solution of 7-[4-(2-butoxyethoxy)phenyl]-1-isobutyl-N-[4-[[1-[1-propylimidazol-2-yl]ethyl]sulfanyl]phenyl]-2,3-dihydro-1-benzazepine-4-carboxamide (170 mg) in dichloromethane (10 ml) was added dropwise 70% solution of 3-chloroperbenzoic acid (92 mg) in dichloromethane (10 ml) at −78° C. The reaction vessel was removed from a dry ice-acetone bath, and an aqueous solution of sodium thiosulfate was added to the reaction vessel with strongly stirring. The mixture was allowed to be at room temperature, stirred for 30 minutes, and extracted with ethyl acetate. The organic layer was washed with an aqueous solution of saturated sodium bicarbonate, and saturated brine, and dried over magnesium sulfate. The solvent was distilled off under reduced pressure. The obtained residue was separated and purified by basic silica gel column chromatography (ethyl acetate), to give 7-[4-(2-butoxyethoxy)phenyl]-1-isobutyl-N-[4-[[1-[1-propylimidazol-2-yl]ethyl]sulfinyl]phenyl]-2,3-dihydro-1-benzazepine-4-carboxamide (142 mg) (Compound 396) as yellow amorphous.

$^1$H-NMR (200 MHz, CDCl$_3$) δ 0.90 to 1.02 (12H, m), 1.30 to 1.90 (9H, m), 1.95 to 2.15 (1H, m), 2.90 to 2.95 (2H, m), 3.05 (2H, d, J=7.4 Hz), 3.35 to 3.45 (2H, m), 3.55 (2H, t, J=7.0 Hz), 3.80 (2H, t, J=4.8 Hz), 3.91 to 4.24 (5H, m), 6.73 to 7.75 (15H, m).

Elemental Analysis for $C_{41}H_{52}N_4O_4S \cdot 0.25H_2O$ Calcd. C, 70.20; H, 7.54; N, 7.99. Found: C, 70.21; H, 7.61; N, 7.86.

Example 365

(Preparation of Compound 397)

To a solution of 7-[4-(2-butoxyethoxy)phenyl]-1-isobutyl-2,3-dihydro-1-benzazepine-4-carboxylic acid (300 mg) in tetrahydrofuran (15 ml) was added one droplet of DMF. Then, thionyl chloride (0.07 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of (4-aminophenyl) (1-methylimidazol-2-yl) methanol (181 mg) and triethylamine (0.6 ml) in THF (15 ml) at 0° C. under nitrogen atmosphere. After finishing the dropping, the mixture was allowed to be at room temperature and stirred overnight under nitrogen atmosphere, and water was added to the mixture, and the mixture was extracted with ethyl acetate. The organic layer was washed with saturated brine, and dried over magnesium sulfate. The solvent was distilled off under reduced pressure. The residue was separated and purified by basic silica gel column chromatography (ethyl acetate→methanol:ethyl acetate=1:8), to give 7-[4-(2-butoxyethoxy)phenyl]-1-isobutyl-N-[4-[hydroxy[1-methylimidazol-2-yl]methyl]]-2,3-dihydro-1-benzazepine-4-carboxamide (122 mg) (Compound 397) as yellow amorphous.

$^1$H-NMR (200 MHz, CDCl$_3$) δ 0.89 to 0.98 (9H, m), 1.30 to 1.50 (2H, m), 1.55 to 1.70 (2H, m), 1.95 to 2.15 (1H, m), 2.85 to 2.95 (2H, m), 3.18 (2H, d, J=7.8 Hz), 3.30 to 3.39 (2H, m), 3.40 (3H, s), 3.55 (2H, t, J=6.6 Hz), 3.80 (2H, t, J=4.8 Hz), 4.15 (2H, t, J=4.8 Hz), 5.87 (1H, s), 6.83 to 7.01 (5H, m), 7.28 to 7.60 (10H, m).

Example 366

(Preparation of Compound 398)

To a solution of 7-[4-(2-butoxyethoxy)phenyl]-1-isobutyl-2,3-dihydro-1-benzazepine-4-carboxylic acid (600 mg) in tetrahydrofuran (15 ml) was added one droplet of DMF. Then, thionyl chloride (0.13 ml) was added to the mixture under nitrogen atmosphere and the mixture was stirred for 1 hour. The solvent and excess thionyl chloride were distilled off under reduced pressure, and the obtained residue was dissolved in THF (15 ml). This solution was added dropwise to a solution of (4-aminophenyl)(1-propylimidazol-2-yl) methanol (412 mg) and triethylamine (1.2 ml) in THF (15 ml) at 0° C. under nitrogen atmosphere. After finishing the dropping, the mixture was allowed to be at room temperature, stirred under nitrogen atmosphere, and water was added to the mixture, and the mixture was extracted with ethyl acetate. The organic layer was washed with saturated brine, and dried over magnesium sulfate. The solvent was distilled off under reduced pressure. The obtained residue was separated and purified by basic silica gel column chromatography (ethyl acetate), and was recrystallized from hexane-ethyl acetate to give 7-[4-(2-butoxyethoxy)phenyl]-1-isobutyl-N-[4-[hydroxy[1-propylimidazol-2-yl]methyl]phenyl]-2,3-dihydro-1-benzazepine-4-carboxamide (167 mg) (Compound 398) as yellow crystals.

$^1$H-NMR (200 MHz, CDCl$_3$) δ 0.79 (3H, t, J=7.4 Hz), 0.89 to 0.98 (9H, m), 1.30 to 1.80 (6H, m), 1.95 to 2.15 (1H, m), 2.85 to 2.95 (2H, m), 3.18 (2H, d, J=8.2 Hz), 3.30 to 3.40 (2H, m), 3.55 (2H, t, J=6.6 Hz), 3.64 (2H, t, J=7.4 Hz), 3.80 (2H, t, J=4.8 Hz), 4.16 (2H, t, J=4.8 Hz), 5.81 (1H, s), 6.88 to 7.02 (5H, m), 7.28 to 7.61 (10H, m).

Elemental Analysis for C$_{40}$H$_{50}$N$_4$O$_4$ Calcd. C, 73.82; H, 7.74; N, 8.61. Found: C, 73.52; H, 7.53; N, 8.73.

Example 367

(Preparation of Compound 399)

To a solution of 7-[4-(2-butoxyethoxy)phenyl]-1-isobutyl-N-[4-[[[1-propylimidazol-5-yl]methyl]sulfanyl]phenyl]-2,3-dihydro-1-benzazepine-4-carboxamide (300 mg) in dichloromethane (10 ml) was added dropwise 70% solution of 3-chloroperbenzoic acid (221 mg) in dichloromethane (10 ml) at −78° C. The mixture was stirred for 1 hour at −15° C., dimethylsulfide (0.1 ml) was added to the mixture, and the mixture was allowed to be at room temperature and stirred for 30 minutes. To the mixture was added water, and the organic layer was washed with an aqueous solution of saturated sodium bicarbonate and saturated brine, dried over magnesium sulfate. The solvent was distilled off under reduced pressure and the obtained residue was separated and purified by basic silica gel column chromatography (hexane:ethyl acetate=1:1), and was recrystallized from hexane-ethyl acetate to give 7-[4-(2-butoxyethoxy)phenyl]-1-isobutyl-N-[4-[[[1-propylimidazol-5-yl]methyl]sulfonyl]phenyl]-2,3-dihydro-1-benzazepine-4-carboxamide (122 mg) (Compound 399) as yellow crystals.

$^1$H-NMR (200 MHz, CDCl$_3$) δ 0.85 to 0.99 (12. H, m), 1.30 to 1.50 (2H, m), 1.55-1.85 (4H, m), 1.95 to 2.15 (1H, m), 2.90 to 3.00 (2H, m), 3.20 (2H, d, J=7.0 Hz), 3.35 to 3.45 (2H, m) 3.56 (2H, t, J=7.0 Hz), 3.81 (2H, t, J=4.4 Hz), 3.95 (2H, t, J=7.8 Hz), 4.16 (2H, t, J=4.4 Hz), 4.32 (2H, s), 6.53 (1H, d, J=0.8 Hz), 6.92 (1H, d, J=8.4 Hz), 6.98 (2H, d, J=8.8 Hz), 7.39 to 7.50 (6H, m), 7.60 (2H, d, J=8.8 Hz), 7.77 (2H, d, J=8.8 Hz), 8.05 (1H, s).

Example 368

(Preparation of Compound 400)

7-[4-(2-butoxyethoxy)phenyl]-1-isobutyl-2,3-dihydro-1H-1-benzazepine-4-carboxylic acid (1 g) was dissolved in tetrahydrofuran (7 ml), and to the solution, thionyl chloride (0.25 ml) and N,N-dimethylformamide (catalytic amout) were added under ice-cooling, and the mixture was stirred for 1 hour at room temperature. The solvent was distilled off and the residue was dissolved in tetrahydrofuran (20 ml), and the solution was added dropwise to a solution of S-(4-aminophenyl)-o-benzylthiocarbonate (0.71 g) and triethylamine (1 ml) in tetrahydrofuran (10 ml) under ice-cooling. The mixture was stirred at room temperature for 2 hours, 1N aqueous solution of sodium hydroxide (15 ml), methanol (15 ml) and tetrahydrofuran (15 ml) were added to the mixture, and the mixture was stirred for 1 hour at room temperature. Then, 4-chloromethyl-3-dibutylimidazole hydrochloride (0.6 g) was added to the mixture and the mixture was stirred for 2 hours at room temperature. The mixture was concentrated and extracted with ethyl acetate. The organic layer was washed with water and saturated brine, dried over anhydrous magnesium sulfate, and then, the solvent was distilled off. The residue was purified by silica gel column chromatography (elution solvent: methanol/ethyl acetate/triethylamine), to give 7-[4-(2-butoxyethoxy)phenyl]-1-isobutyl-N-[4-[(3-butylimidazol-4-yl)methylthio]phenyl]-2,3-dihydro-1H-1-benzazepine-4-carboxamide (Compound 400) (1.36 g) as yellow amorphous.

$^1$H-NMR (dppm, CDCl$_3$) 0.85 to 1.07 (12H, m), 1.22 to 1.48 (4H, m), 1.54 to 1.86 (4: H, m), 2.00 to 2.11 (1H, m), 2.91 (2H, t, J=4.5 Hz), 3.19 (2H, d, J=7.2 Hz), 3.36 (2H, t, J=4.5 Hz), 3.55 (2H, t, J=6.6 Hz), 3.80 (2H, t, J=4.9 Hz), 3.92 to 3.99 (4H, m), 4.16 (2H, t, J=4.9 Hz), 6.70 (1H, s), 6.89 to 7.00 (3H, m), 7.26 to 7.56 (10H, m), 7.66 (1H, s).

IR (KBr) n: 2959, 2930, 2868, 1657, 1588, 1499 cm$^{-1}$.

Example 369

(Preparation of Compound 401)

7-[4-(2-butoxyethoxy)phenyl]-1-isobutyl-N-[4-[(3-butylimidazol-4-yl)methylthio]phenyl]-2,3-dihydro-1H-1-benzazepine-4-carboxamide (1.15 g) was dissolved in dichloromethane (40 ml), and the mixture was cooled to −78° C. A solution of 3-chloroperbenzoic acid (0.62 g) in dichloromethane (10 ml) was added dropwise to the solution. The mixture was stirred for 1 hour at −78° C., and then, an aqueous solution of sodium thiosulfate was added to the mixture. The mixture was concentrated, and extracted with ethyl acetate. The organic layer was washed with sodium bicarbonate solution, water and saturated brine, dried over anhydrous magnesium sulfate, and then, the solvent was distilled off. The residue was purified by silica gel column chromatography (elution solvent: triethylamine/methanol/ethyl acetate), to give 7-[4-(2-butoxyethoxy)phenyl]-1-isobutyl-N-[4-[(3-butylimidazol-4-yl)methylsulfinyl]phenyl]-2,3-dihydro-1H-1-benzazepine-4-carboxamide (Compound 401) (0.72 g) as yellow amorphous.

$^1$H-NMR (dppm, CDC13) 0.90 to 0.98 (12H, m), 1.24 to 1.46 (6H, m), 1.56 to 1.66 (2H, m), 2.04 to 2.10 (1H, m), 2.93 (2H, t to like), 3.19 (2H, d, J=7.5 Hz), 3.36 (2H, t to like), 3.55 (2H, t, J=6.8 Hz), 3.79 to 3.81 (2H, m), 3.81 (2H, t, J=5.0 Hz), 3.98 to 4.11 (2H, m), 4.16 (2H, t, J=5.0 Hz), 6.56 (1H, s), 6.92 (1H, d, J=8.4 Hz), 6.98 (2H, d, J=8.7 Hz), 7.33 to 7.48 (8H, m), 7.75 (2H, d, J=7.8 Hz), 8.10 (1H, br).

IR (KBr) n: 2957, 2932, 2870, 1661, 1607, 1590, 1518, 1499 cm$^{-1}$.

Example 370

(Preparation of Compound 402, 403)

7-[4-(2-butoxyethoxy)phenyl]-N-[4-[hydroxy(1-oxidepyridin-2-yl)methyl]-3-trifluoromethylphenyl]-1-isobutyl-2,3-dihydro-1H-1-benzazepine-4-carboxamide (0.6 g) was optically resoluted with CHIRALPAK AD 50 mm ID×500 mmL and the elution solvent (hexane/ethanol). The fractions were concentrated and dried, and the residue was dissolved in ethanol, and then, was filtered by 0.45 μm filter. The filtrate was concentrated, hexane was added and evaporated to dryness, to give (+)-7-[4-(2-butoxyethoxy)phenyl]-N-[4-[hydroxy(1-oxidepyridin-2-yl)methyl]-3-trifluoromethylphenyl]-1-isobutyl-2,3-dihydro-1H-1-benzazepine-4-carboxamide (Compound 402) (275 mg, >99.9% ee), (−)-7-[4-(2-butoxyethoxy)phenyl]-N-[4-[hydroxy(1-oxidepyridin-2-yl)methyl]-3-trifluoromethylphenyl]-1-isobutyl-2,3-dihydro-1H-1-benzazepine-4-carboxamide (Compound 403) (260 mg, 99.6% ee).

Compound 402 [α]$_D$=+13.66° (c=0.30%, ethanol solution)

Compound 403 [α]$_D$=−13.78° (c=0.26%, ethanol solution)

Example 371

(Preparation of Compound 177)

To a solution of (S)-(−)-1,1'-bi-2-naphtol (87.5 mg) in toluene (10 ml) were added titanium tetraisopropoxide (45.2 μl) and water (55 μl) at room temperature and the mixture was stirred for 1 hour. To the reaction solution were added 7-[4-(2-butoxyethoxy)phenyl]-1-propyl-N-[4-(4-propyl-4H-1,2,4-triazol-3-ylmethylthio)phenyl]-2,3-dihydro-1H-1-benzazepine-4-carboxamide (1.0 g) and cummene hyperoxide (80%, 0.31 ml) and the mixture was stirred for 20 hours at room temperature Cumene hydroperoxide (80%, 0.14 ml) was added to the mixture, and the mixture was further stirred for 10 hours. To the reaction solution was added an aqueous solution of sodium thiosulfate and the mixture was stirred for several minutes and extracted with ethyl acetate. The organic layer was washed with sodium bicarbonate solution and saturated brine, and dried over magnesium sulfate and concentrated under reduced pressure. The obtained residue was separated and purified by column chromatography (basic silica gel, ethyl acetate→ethanol:ethyl acetate 1:19), to give (−)-7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide (Compound 177) (860.9 mg) as yellow amorphous.

Optical purify analyzed with CHIRALPAK AD (4 mm ID×25 mmL, hexane:2-propanol) was 96% ee.

Elemental Analysis for $C_{38}H_{47}N_5O_4S.0.5H_2O$ Calcd. C, 67.23; H, 7.13; N, 10.32. Found: C, 67.52; H, 7.04; N, 10.23.

Example 372

(Preparation of Compound 404)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature and the mixture was stirred for 1 hour at room temperature. The reaction mixture was concentrated under reduced pressure, and a solution of the residue in THF (20 ml) was added dropwise to a solution of S-(4-aminophenyl)O-benzyl thiocarbonate (0.59 g) and triethylamine (2.0 ml) in THF (5 ml) at 0° C. The mixture was stirred at room temperature for 20 hours. To the reaction solution, 1N aqueous solution of sodium hydroxide (15 ml) and methanol (50 ml) were added, and the mixture was stirred for 0.5 hour. To the reaction solution, 3-(chloromethyl)-5,6,7,8-tetrahydroimidazo[1,2-a]pyridine hydrochloride (0.48 g) was added, and the mixture was further stirred for 2 hours. Methanol was distilled off under reduced pressure and the residue was extracted with ethyl acetate. The organic layer was washed with saturated brine, and dried over magnesium sulfate, and concentrated under reduced pressure. The obtained residue was separated and purified by column chromatography (basic silica gel, ethyl acetate:hexane 3:1→4:1→ethanol:ethyl acetate 1:4), to give 7-[4-(2-butoxyethoxy)phenyl]-1-isobutyl-N-[4-[[(5,6,7,8-tetrahydroimidazo[1,2-a]pyridin-3-yl)methyl]thio]phenyl]-2,3-dihydro-1H-1-benzazepine-4-carboxamide (Compound 404) (529.0 mg) as yellow amorphous.

$^1$H-NMR (200 MHz, CDCl$_3$) δ 0.93 (3H, t, J=7.1 Hz), 0.97 (6H, d, J=6.6 Hz), 1.28 to 1.46 (2H, m), 1.51 to 1.73 (2H, m), 1.80 to 2.16 (5H, m), 2.80 to 2.91 (4H, m), 3.19 (2H, d, J=7.2 Hz), 3.29 to 3.40 (2H, m), 3.55 (2H, t, J=6.6 Hz), 3.81 (2H, t, J=4.9 Hz), 3.90 (2H, t, J=5.8 Hz), 3.95 (2H, s), 4.16 (2H, t, J=4.9 Hz), 6.66 (1H, s), 6.91 (1H, d, J=8.4 Hz), 6.98 (2H, d, J=8.8 Hz), 7.26 to 7.48 (7H, m), 7.55 (2H, d, J=8.8 Hz), 7.81 (1H, s).

IR (KBr) 3031, 1651, 1607, 1588, 1520, 1497, 1312, 1242, 1181, 1125, 816 cm$^{-1}$

Elemental Analysis for $C_{41}H_{50}N_4O_3.0.5H_2O$ Calcd. C, 71.58; H, 7.47; N, 8.14. Found: C, 71.71; H, 7.52; N, 8.20.

Example 373

(Preparation of Compound 405)

To a solution of 7-[4-(2-butoxyethoxy)phenyl]-1-isobutyl-N-[4-[[(5,6,7,8-tetrahydroimidazo[1,2-a]pyridin-3-yl)methyl]thio]phenyl]-2,3-dihydro-1H-1-benzazepine-4-carboxamide (460 mg) in dichloromethane (10 ml) was added a solution of 3-chloroperbenzoic acid (70%, 0.25 g) in dichloromethane (10 ml) at −78° C. The mixture was stirred for 1 hour at −78° C., an aqueous solution of sodium thiosulfate was added to the mixture and the mixture was stirred at room temperature for 10 minutes. The mixture was extracted with ethyl acetate, and the organic layer was washed with sodium bicarbonate solution and saturated brine, and dried over magnesium sulfate, and concentrated under reduced pressure. The obtained residue was separated and purified by column chromatography (basic silica gel, ethyl acetate:hexane 9:1→ethyl acetate), and was recrystallized from ethyl acetate-diisopropyl ether, to give 7-[4-(2-butoxyethoxy)phenyl]-1-isobutyl-N-[4-[[(5,6,7,8-tetrahydroimidazo[1,2-a]pyridin-3-yl)methyl]sulfinyl]phenyl]-2,3-dihydro-1H-1-benzazepine-4-carboxamide (Compound 405) (311.3 mg) as yellow crystals.

mp 184 to 186° C.

$^1$H-NMR (200 MHz, CDCl$_3$) δ 0.93 (3H, t, J=7.3 Hz), 0.97 (6H, d, J=6.6 Hz), 1.29 to 1.47 (2H, m), 1.53 to 1.67 (2H, m), 1.72 to 1.94 (4H, m), 1.97 to 2.18 (1H, m), 2.74 to 2.84 (2H, m), 2.89 to 2.98 (2H, m), 3.19 (2H, d, J=7.2 Hz), 3.30 to 3.41 (2H, m), 3.56 (2H, t, J=6.6 Hz), 3.61 to 3.70 (2H, m), 3.81 (2H, t, J=4.8 Hz), 3.92 (1H, d, J=14.3 Hz), 4.02 (1H, d, J=14.3 Hz), 4.16 (2H, t, J=4.8 Hz), 6.57 (1H, s), 6.92 (1H, d, J=9.2 Hz), 6.98 (2H, d, J=8.8 Hz), 7.35 to 7.47 (7H, m), 7.78 (2H, d, J=8.8 Hz), 8.25 (1H, s).

IR (KBr) 3075, 1655, 1605, 1588, 1520, 1499, 1312, 1244, 1179, 1127, 822 cm$^{-1}$

Elemental Analysis for $C_{41}H_{50}N_4O_4.0.5H_2O$ Calcd. C, 69.96; H, 7.30; N, 7.96. Found: C, 69.84; H, 7.43; N, 7.82.

Example 374

(Preparation of Compound 406)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature and the mixture was stirred for 1 hour at room temperature. The reaction mixture was concentrated under reduced pressure, and a solution of the residue in THF (20 ml) was added dropwise to a solution of 4-[[(5-methylimidazo[1,2-a]pyridin-3-yl)methyl]thio]aniline (0.74 g) in pyridine (7.0 ml) at 0° C. The mixture was stirred at room temperature for 20 hours, and water was added to the reaction solution, and the mixture was extracted with ethyl acetate. The organic layer was washed with saturated brine, and dried over magnesium sulfate, and concentrated under reduced pressure. The obtained residue was separated and purified by column chromatography (basic silica gel, ethyl acetate:hexane 1:1→2:1), to give 7-[4-(2-butoxyethoxy)phenyl]-1-isobutyl-N-[4-[[(5-methylimidazo[1,2-a]pyridin-3-yl)methyl]thio]phenyl]-2,3-dihydro-1H-1-benzazepine-4-carboxamide (Compound 406) (1.41 g) as yellow amorphous.

$^1$H-NMR (200 MHz, CDCl$_3$) δ 0.93 (3H, t, J=7.3 Hz), 0.97 (6H, d, J=6.6 Hz), 1.29 to 1.47 (2H, m), 1.51 to 1.69 (2H, m), 1.97 to 2.17 (1H, m), 2.85 to 2.95 (2H, m), 3.02 (3H, s), 3.18 (2H, d, J=7.4 Hz), 3.33 to 3.38 (2H, m), 3.55 (2H, t, J=6.6 Hz), 3.80 (2H, t, J=5.0 Hz), 4.16 (2H, t, J=5.0 Hz), 4.48 (2H, s), 6.55 (1H, d, J=7.0 Hz), 6.91 (1H, d, J=8.4 Hz), 6.97 (2H, d, J=8.8 Hz), 7.07 (1H, dd, J=8.8, 7.0 Hz), 7.14 (1H, s), 7.21 (2H, d, J=8.4 Hz), 7.37 to 7.56 (8H, m), 7.79 (1H, s).

IR (KBr) 3031, 1653, 1607, 1586, 1497, 1312, 1289, 1242, 1179, 1123, 816 cm$^{-1}$

Elemental Analysis for C$_{42}$H$_{48}$N$_4$O$_3$S.0.5H$_2$O Calcd. C, 72.28; H, 7.08; N, 8.03. Found: C, 72.43; H, 7.03; N, 8.01.

Example 375

(Preparation of Compound 407)

To a solution of 7-[4-(2-butoxyethoxy)phenyl]-1-isobutyl-N-[4-[[(5-methylimidazo[1,2-a]pyridin-3-yl)methyl]thio]phenyl]-2,3-dihydro-1H-1-benzazepine-4-carboxamide (1.157 g) in dichloromethane (10 ml) was added 3-chloroperbenzoic acid (70%, 0.50 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with sodium bicarbonate solution and saturated brine, dried over magnesium sulfate, and concentrated under reduced pressure. The obtained residue was separated and purified by column chromatography (basic silica gel, ethyl acetate:hexane 3:1→ethyl acetate), to give 7-[4-(2-butoxyethoxy)phenyl]-1-isobutyl-N-[4-[[(5-methylimidazo[1,2-a]pyridin-3-yl)methyl]sulfinyl]phenyl]-2,3-dihydro-1H-1-benzazepine-4-carboxamide (Compound 407) (1.05 g) as yellow amorphous.

$^1$H-NMR (200 MHz, CDCl$_3$) δ 0.93 (3H, t, J=7.4 Hz), 0.98 (6H, d, J=6.6 Hz), 1.32 to 1.46 (2H, m), 1.52 to 1.66 (2H, m), 1.99 to 2.14 (1H, m), 2.88 to 2.97 (5H, m), 3.20 (2H, d, J=7.5 Hz), 3.36 to 3.39 (2H, m), 3.56 (2H, t, J=6.8 Hz), 3.81 (2H, t, J=5.0 Hz), 4.16 (2H, t, J=5.0 Hz), 4.56 (1H, d, J=14.9 Hz), 4.63 (1H, d, J=14.9 Hz), 6.58 (1H, d, J=6.9 Hz), 6.91 to 7.00 (4H, m), 7.09 to 7.15 (1H, m), 7.28 to 7.31 (2H, m), 7.40 to 7.50 (6H, m), 7.74 (2H, d, J=8.4 Hz), 7.89 (1H, s).

IR (KBr) 3031, 1661, 1607, 1588, 1520, 1499, 1312, 1242, 1177, 835 cm$^{-1}$

Elemental Analysis for C$_{42}$H$_{41}$N$_4$O$_4$S.0.5H$_2$O Calcd. C, 70.66; H, 6.92; N, 7.85. Found: C, 70.39; H, 7.08; N, 7.85.

Example 376

(Preparation of Compound 408)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature and the mixture was stirred for 1 hour at room temperature. The reaction mixture was concentrated under reduced pressure, and a solution of the residue in THF (20 ml) was added dropwise to a solution of 4-[[(6-methylimidazo[1,2-a]pyridin-3-yl)methyl]thio] aniline (0.68 g) in pyridine (7.0 ml) at 0° C. The mixture was stirred at room temperature for 20 hours, and water was added to the reaction solution, and the mixture was extracted with ethyl acetate. The organic layer was washed with saturated brine, dried over magnesium sulfate, and concentrated under reduced pressure. The residue was separated and purified by basic silica gel column chromatography (ethyl acetate:hexane 1:1→2:1), to give 7-[4-(2-butoxyethoxy)phenyl]-1-isobutyl-N-[4-[[(6-methylimidazo[1,2-a]pyridin-3-yl)methyl]thio]phenyl]-2,3-dihydro-1H-1-benzazepine-4-carboxamide (Compound 408) (1.29 g) as yellow amorphous.

$^1$H-NMR (200 MHz, CDCl$_3$) δ 0.93 (3H, t, J=7.1 Hz), 0.97 (6H, d, J=6.6 Hz), 1.31 to 1.50 (2H, m), 1.52 to 1.71 (2H, m), 1.95 to 2.16 (1H, m), 2.39 (3H, s), 2.85 to 2.94 (2H, m), 3.19 (2H, d, J=7.2 Hz), 3.31 to 3.40 (2H, m), 3.55 (2H, t, J=6.6 Hz), 3.80 (2H, t, J=5.0 Hz), 4.16 (2H, t, J=5.0 Hz), 4.30 (2H, s), 6.91 (1H, d, J=9.2 Hz), 6.98 (2H, d, J=8.8 Hz), 7.07 (1H, dd, J=9.4, 1.6 Hz), 7.17 to 7.24 (3H, m), 7.36 to 7.54 (8H, m), 7.61 (1H, s), 7.88 (1H, br s).

IR (KBr) 3031, 1653, 1607, 1588, 1499, 1312, 1242, 1181, 1125, 816 cm$^{-1}$

Elemental Analysis for C$_{42}$H$_{48}$N$_4$O$_3$S 0.5H$_2$O Calcd. C, 72.28; H, 7.08; N, 8.03. Found: C, 72.40; H, 7.08; N, 8.10.

Example 377

(Preparation of Compound 409)

To a solution of 7-[4-(2-butoxyethoxy)phenyl]-1-isobutyl-N-[4-[(6-methylimidazo[1,2-a]pyridin-3-yl)methylthio] phenyl]-2,3-dihydro-1H-1-benzazepine-4-carboxamide (1.13 g) in dichloromethane (10 ml) was added dropwise a solution of 3-chloroperbenzoic acid (70%, 0.49 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with sodium bicarbonate solution and saturated brine, dried over magnesium sulfate, and concentrated under reduced pressure. The obtained residue was separated and purified by Column chromatography (basic silica gel, ethyl acetate: hexane 2:1→ethyl acetate), to give 7-[4-(2-butoxyethoxy) phenyl]-1-isobutyl-N-[4-[[(6-methylimidazo[1,2-a]pyridin,-3-yl)methyl]sulfinyl]phenyl]-2,3-dihydro-1H-1-benzazepine-4-carboxamide (Compound 409) (926 mg) as yellow amorphous.

$^1$H-NMR (300 MHz, CDCl$_3$) δ 0.93 (3H, t, J=7.2 Hz), 0.98 (6H, d, J=6.6 Hz), 1.34 to 1.46 (2H, m), 1.57 to 1.66 (2H, m), 1.99 to 2.15 (1H, m), 2.29 (3H, s), 2.86 to 2.95 (2H, m), 3.19 (2H, d, J=6.9 Hz), 3.35 to 3.38 (2H, m), 3.55 (2H, t, J=6.6 Hz), 3.80 (2H, t, J=5.0 Hz), 4.16 (2H, t, J=5.0 Hz), 4.29 (1H, d, J=14.1 Hz), 4.42 (1H, d, J=14.1 Hz), 6.92 (1H, d, J=8.7 Hz), 6.98 (2H, d, J=8.7 Hz), 7.02 (1H, dd, J=9.3, 1.8 Hz), 7.13 (1H, s), 7.32 (2H, d, J=8.4 Hz), 7.39 to 7.48 (6H, m), 7.70 (2H, d, J=8.7 Hz), 7.79 to 7.80 (1H, m), 7.98 (1H, s).

IR (KBr) 3032, 1655, 1607, 1588, 1499, 1314, 1242, 1179, 1121, 1040, 833 cm$^{-1}$

Elemental Analysis for C$_{42}$H$_{48}$N$_4$O$_4$S.0.5H$_2$O Calcd. C, 70.66; H, 6.92; N, 7.84. Found: C, 70.38; H, 6.90; N, 7.73.

Example 378

(Preparation of Compound 410)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature, and the mixture was stirred for 1 hour at room temperature. The reaction mixture was concentrated under reduced pressure, and a solution of the residue in THF (25 ml) was added dropwise to a solution of [2-((4-aminophenylthio)methyl)-1H-imidazol-1-yl]ethyl acetate (820 mg) in pyridine (5.0 ml) at 0° C. The mixture was stirred at room temperature for 18 hours, and water was added to the reaction solution, and the mixture was extracted with ethyl acetate. The organic layer was washed with saturated brine, dried over magnesium sulfate, and concentrated under reduced pressure. The obtained residue was separated and purified by column chromatography (basic silica gel, ethyl acetate:hexane 1:1→3:2), to give [2-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]ethyl acetate (Preparation of Compound 410) (390 mg) as yellow amorphous.

$^1$H-NMR (300 MHz, CDCl$_3$) δ 0.93 (3H, t, J=7.2 Hz), 0.97 (6H, d, J=6.9 Hz), 1.29 (3H, t, J=7.2 Hz), 1.32 to 1.45 (2H, m) 1.53 to 1.66 (2H, m), 1.99 to 2.13 (1H, m), 2.86 to 2.94 (2H, m), 3.18 (2H, d, J=7.2 Hz), 3.34 to 3.37 (2H, m), 3.55 (2H, t, J=6.6 Hz), 3.81 (2H, t, J=5.0 Hz), 4.13 (2H, s), 4.16 (2H, t, J=5.0 Hz), 4.24 (2H, q, J=7.2 Hz), 4.74 (2H, s), 6.87 to 7.00 (5H, m), 7.31 (2H, d, J=8.7 Hz), 7.38 to 7.53 (7H, m), 7.63 (1H, s).

IR (KBr) 3038, 1751, 1653, 1607, 1586, 1310, 1289, 1242, 1181, 1123, 816 cm$^{-1}$

Example 379

(Preparation of Compound 411)

To a solution of [2-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]ethyl acetate (350 mg) in dichloromethane (10 ml) was added dropwise 3-chloroperbenzoic acid (70%, 146 mg) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with sodium bicarbonate solution and saturated brine, dried over magnesium sulfate, and concentrated under reduced pressure. The obtained residue was separated and purified by column chromatography (basic silica get, ethyl acetate:hexane 1:1→ethyl acetate→ethanol:ethyl acetate 1:19), to give [2-[[[4-[[[7-[4-(2-butoxyethoxy)phenyl]-1-isobutyl-2,3-dihydro-1H-1-benzazepin-4-yl]carbonyl]amino]phenyl]sulfinyl]methyl]-1H-imidazol-1-yl]ethyl acetate (Preparation of Compound 411) (278.7 mg) as yellow amorphous.

$^1$H-NMR (200 MHz, CDCl$_3$) δ 0.93 (3H, t, J=7.0 Hz), 0.98 (6H, d, J=6.2 Hz), 1.29 (3H, t, J=7.1 Hz), 1.30 to 1.49 (2H, m), 1.52 to 1.69 (2H, m), 1.95 to 2.16 (1H, m), 2.86 to 2.97 (2H, m), 3.20 (2H, d, J=6.8 Hz), 3.30 to 3.41 (2H, m), 3.55 (2H, t, J=6.6 Hz), 3.80 (2H, t, J=4.9 Hz), 4.09 to 4.28 (6H, m), 4.71 (1H, d, J=17.9 Hz), 4.90 (1H, d, J=17.9 Hz), 6.90 to 7.00 (5H, m), 7.40 to 7.48 (7H, m), 7.74 (2H, d, J=8.8 Hz), 7.86 (1H, s).

IR (KBr) 3032, 1752, 1659, 1607, 1590, 1518, 1499, 1397, 1312, 1242, 1179, 1103, 1030, 835, 818 cm$^{-1}$

Elemental Analysis for C$_{41}$H$_{50}$N$_4$O$_6$S.0.5H$_2$O Calcd. C, 66.91; H, 6.99; N, 7.61. Found: C, 66.63; H, 6.96.; N, 7.44.

Example 380

(Preparation of Compound 412)

To a solution of [2-[[[4-[[[7-[4-(2-butoxyethoxy)phenyl]-1-isobutyl-2,3-dihydro-1H-1-benzazepin-4-yl]carbonyl]amino]phenyl]sulfinyl]methyl]-1H-imidazol-1-yl]ethyl acetate (85 mg) in ethanol (5 ml) was added 1N aqueous solution of sodium hydroxide (0.14 ml) at room temperature. The mixture was stirred at room temperature for 1 hour, 1N hydrochloric acid (0.14 ml) was added to the mixture, and the mixture was concentrated under reduced pressure. To the residue was added 2-propanol, and the precipitated crystals were collected by filtration. The crystals were washed with 2-propanol and diisopropyl ether, to give [2-[[[4-[[[7-[4-(2-butoxyethoxy) phenyl]-1-isobutyl-2,3-dihydro-1H-1-benzazepin-4-yl]carbonyl]amino]phenyl]sulfinyl]methyl]-1H-imidazol-1-yl]acetic acid (Preparation of Compound 412) (65.7 mg) as yellow crystals.

mp 146 to 148° C.

$^1$H-NMR (200 MHz, DMSO-d$_6$) δ 0.89 (3H, t, J=7.4 Hz), 0.93 (6H, d, J=6.6 Hz), 1.28 to 1.38 (2H, m), 1.42 to 1.56 (2H, m), 1.91 to 2.19 (1H, m), 2.78 to 2.89 (2H, m), 3.16 to 3.36 (4H, m), 3.46 (2H, t, J=6.4 Hz), 3.66 to 3.74 (2H, m), 4.09 to 4.13 (2H, m), 4.30 (2H, s), 4.84 (2H, s), 6.83 (1H, d, J=11 Hz), 6.95 to 7.02 (3H, m), 7.15 (1H, d, J=1.1 Hz), 7.44 to 7.65 (7H, m), 7.87 (2H, d, J=8.8 Hz), 10.09 (1H, s).

IR (KBr) 3436, 3040, 1630, 1609, 1518, 1499, 1244, 1179, 1125, 1088, 1047, 835, 812 cm$^{-1}$

Example 381

(Preparation of Compound 413)

To a solution of 7-[4-(2-butoxyethoxy)phenyl]-1-isobutyl-2,3-dihydro-1H-1-benzazepine-4-carboxylic acid (2.0 g) in THF (10 ml) were added thionyl chloride (0.50 ml) and DMF (1 droplet) at room temperature and the mixture was stirred for 1.5 hours at room temperature. The reaction mixture was concentrated under reduced pressure, and a solution of the residue in THF (30 ml) was added dropwise to a solution of ethyl 4-[2-[(4-aminophenyl)thio]methyl]-1H-imidazol-1-yl]butanoate (1.61 g) in pyridine (5.0 ml) at 0° C. The mixture was stirred at room temperature for 20 hours, and water was added to the reaction solution, and the mixture was extracted with ethyl acetate. The organic layer was washed with saturated brine, dried over magnesium sulfate, and concentrated under reduced pressure. The obtained residue was separated and purified by column chromatography (ethyl acetate:hexane 1:1→ethyl acetate), to give ethyl 4-[2-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]butanoate (Preparation of Compound 413) (3.20 g) as yellow crystals.

mp 103 to 104° C.

$^1$H-NMR (200 MHz, CDCl$_3$) δ 0.93 (3H, t, J=7.3 Hz), 0.97 (6H, t, J=6.6 Hz), 1.26 (3H, t, J=7.2 Hz), 1.31 to 1.47 (2H, m), 1.50 to 1.67 (2H, m), 1.92 to 2.14 (3H, m), 2.32 (2H, t, J=7.0 Hz), 2.84 to 2.95 (2H, m), 3.19 (2H, d, J=6.8 Hz), 3.30 to 3.39 (2H, m), 3.55 (2H, t, J=6.6 Hz), 3.80 (2H, t, J=5.0 Hz), 3.96 (2H, t, J=5.0 Hz), 4.09 to 4.20 (6H, m), 6.85 to 6.94 (3H, m), 6.98 (2H, d, J=8.8 Hz), 7.33 to 7.55 (9H, m), 7.59 to 7.77 (1H, m).

IR (KBr) 3104, 1728, 1655, 1609, 1590, 1522, 1499, 1314, 1246, 1186, 1117, 812 cm$^{-1}$

Elemental Analysis for $C_{43}H_{54}N_4O_5S$ Calcd. C, 69.89; H, 7.37; N, 7.58. Found: C, 69.72; H, 7.27; N, 7.56.

Example 382

(Preparation of Compound 414)

To a solution of ethyl 4-[2-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]butanoate (1.0 g) in dichloromethane (10 ml) was added dropwise a solution of 3-chloroperbenzoic acid (70%, 0.50 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with sodium bicarbonate solution and saturated brine, dried over magnesium sulfate, and concentrated under reduced pressure. The obtained residue was separated and purified by column chromatography (basic silica gel, ethyl acetate), to give ethyl 4-[2-[[[4-[[[7-[4-(2-butoxyethoxy)phenyl]-1-isobutyl-2,3-dihydro-1H-1-benzazepine-4-yl]carbonyl]amino]phenyl]sulfinyl]methyl]-1H-imidazol-1-yl]butanoate (Preparation of Compound 414) (911 mg) as yellow crystals.

mp 134 to 136° C.

$^1$H-NMR (200 MHz, CDCl$_3$) δ 0.90 to 1.00 (9H, m), 1.25 (3H, t, J=7.2 Hz), 1.31 to 1.45 (2H, m), 1.51 to 1.64 (2H, m), 1.85 to 2.13 (3H, m), 2.27 (2H, t, J=7.0 Hz), 2.87 to 2.96 (2H, m), 3.20 (2H, d, J=7.6 Hz), 3.31 to 3.40 (2H, m), 3.55 (2H, t, J=6.6 Hz), 3.78 to 3.93 (4H, m), 4.08 to 4.18 (5H, m), 4.28 (1H, d, J=13.6 Hz), 6.89 to 7.02 (5H, m), 7.39 to 7.49 (7H, m), 7.74 (2H, d, J=8.8 Hz), 7.84 (1H, s).

IR (KBr) 3102, 1725, 1655, 1609, 1590, 1315, 1246, 1184, 1167, 1117, 1049, 837, 810 cm$^{-1}$

Elemental Analysis for $C_{43}H_{54}N_4O_6S$ Calcd. C, 68.41; H, 7.21; N, 7.42. Found: C, 68.30; H, 7.20; N, 7.31.

Example 383

(Preparation of Compound 415)

To a solution of ethyl 4-[2-[[[4-[[[7-[4-(2-butoxyethoxy)phenyl]-1-isobutyl-2,3-dihydro-1H-1-benzazepin-4-yl]carbonyl]amino]phenyl]sulfinyl]methyl]-1H-imidazol-1-yl]butanoate (0.5 g) in ethanol-THF (5-1 ml) was added 1N aqueous solution of sodium hydroxide (1.2 ml) at room temperature and the mixture was stirred for 24 hours. To the reaction solution was added 1N hydrochloric acid (1.2 ml), and the mixture was concentrated under reduced pressure. To a solution of the residue in DMF (10 ml) were added 1-ethyl-3-(3'-dimethylaminopropyl)carbodiimide hydrochloride (0.20 g), 1-hydroxybenzotriazole ammonium salt (0.16 g) and triethylamine (0.38 ml) at room temperature, and the mixture was stirred for 64 hours. To the reaction solution was added water, and the mixture was extracted with ethyl acetate. The organic layer was washed with water and saturated brine, dried over magnesium sulfate, and concentrated under reduced pressure. The obtained residue was separated and purified by column chromatography (basic silica gel, ethanol:ethyl acetate 1:19), and was further recrystallized from ethyl acetate-diisopropyl ether to give N-[4-[[[1-(4-amino-4-oxobutyl)-1H-imidazol-2-yl]methyl]thio]phenyl]-7-[4-(2-butoxyethoxy)phenyl]-1-isobutyl-2,3-dihydro-1H-1-benzazepine-4-carboxamide (Compound 415) (366.7 mg) as yellow crystals.

mp 142 to 143° C.

$^1$H-NMR (200 MHz, CDCl$_3$) δ 0.93 (3H, t, J=7.3 Hz), 0.97 (6H, d, J=6.6 Hz), 1.31 to 1.47 (2H, m), 1.51 to 1.69 (2H, m), 1.96 to 2.18 (5H, m), 2.84 to 2.93 (2H, m), 3.18 (2H, d, J=6.8 Hz), 3.30 to 3.40 (2H, m), 3.55 (2H, t, J=6.6 Hz), 3.78 to 3.89 (4H, m), 4.13 to 4.18 (4H, m), 5.22 to 5.36 (1H, m), 5.54 to 5.72 (1H, m), 6.84 to 7.00 (5H, m), 7.34 to 7.52 (9H, m), 7.71 to 7.79 (1H, m).

IR (KBr) 3278, 3083, 3036, 1663, 1607, 1588, 1518, 1499, 1244, 1181, 1115, 831 cm$^{-1}$

Elemental Analysis for $C_{41}H_{51}N_5O_4S$ Calcd. C, 69.36; H, 7.24; N, 9.86. Found: C, 69.03; H, 7.43; N, 9.70.

Example 384

(Preparation of Compound 416)

To a solution of N-[4-[[[1-(4-amino-4-oxobutyl)-1H-imidazol-2-yl]methyl]thio]phenyl]-7-[4-(2-butoxyethoxy)phenyl]-1-isobutyl-2,3-dihydro-1H-1-benzazepine-4-carboxamide (350 mg) in dichloromethane (30 ml) was added dropwise a solution of 3-chloroperbenzoic acid (70%, 0.18 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with sodium bicarbonate solution and saturated brine, dried over magnesium sulfate, and concentrated under reduced pressure. The obtained residue was separated and purified by column chromatography (basic silica gel, ethanol:ethyl acetate 1:19→1:9), to give N-[4-[[[1-(4-amino-4-oxobutyl)-1H-imidazol-2-yl]methyl]sulfinyl]phenyl]-7-[4-(2-butoxyethoxy)phenyl]-1-isobutyl-2,3-dihydro-1H-1-benzazepine-4-carboxamide (Compound 416) (259.9 mg) as yellow amorphous.

$^1$H-NMR (300 MHz, CDCl$_3$) δ 0.93 (3H, t, J=7.2 Hz), 0.98 (6H, d, J=6.6 Hz), 1.33 to 1.45 (2H, m), 1.49 to 1.65 (2H, m), 1.98 to 2.20 (5H, m), 2.88 to 2.96 (2H, m), 3.20 (2H, d, J=7.5 Hz), 3.34 to 3.40 (2H, m), 3.55 (2H, t, J=6.6 Hz), 3.79 to 3.86 (4H, m), 4.09 to 4.17 (3H, m), 4.27 (1H, d, J=13.8 Hz), 5.26 to 5.34 (1H, m), 5.99 to 6.18 (1H, m), 6.91 (1H, d, J=1.5 Hz), 6.94 to 7.00 (3H, m), 7.06 (1H, d, J=1.5 Hz), 7.40 to 7.51 (7H, m), 7.73 (2H, d, J=8.7 Hz), 7.85 (1H, s).

IR (KBr) 3314,.3094, 3032, 1663, 1607, 1590, 1518, 1499, 1316, 1244, 1182, 1113, 831, 816 cm$^{-1}$

Elemental Analysis for $C_{41}H_{51}N_5O_5S \cdot 0.5H_2O$ Calcd. C, 67.00; H, 7.13; N, 9.53. Found: C, 67.05; H, 7.30; N, 9.51.

Example 385

(Preparation of Compound 417 and Compound 418)

N-[4-[[[1-(4-amino-4-oxobutyl)-1H-imidazol-2-yl]methyl]sulfinyl]phenyl]-7-[4-(2-butoxyethoxy)phenyl]-1-isobutyl-2,3-dihydro-1H-1-benzazepine-4-carboxamide (Compound 416) (169 mg) was optically resolved with CHIRALPAK AD(50 mm ID×500 mmL) and elution solvent, hexane:ethanol 50:50. The fractions were concentrated and dried, and the residue was dissolved in ethanol, and then, was filtered by 0.45 μm filter. The filtrate was concentrated to give (+)-N-[4-[[[1-(4-amino-4-oxobutyl)-1H-imidazol-2-yl]methyl]sulfinyl]phenyl]-7-[4-(2-butoxyethoxy)phenyl]-1-isobutyl-2,3-dihydro-1H-1-benzazepine-4-carboxamide (Compound 417) (84 mg, 99.8% ee) as an early fraction, and to give (−)-N-[4-[[[1-(4-amino-4-oxobutyl)-1H-imidazol-2-yl]methyl]sulfinyl]phenyl]-7-[4-(2-butoxyethoxy)phenyl]-1-isobutyl-2,3-dihydro-1H-1-benzazepine-4-carboxamide (Compound 418) (82 mg, 99.2% ee) as a later fraction.

Compound 417 $[\alpha]_D$=+96.61° (c=0.498%, chloroform solution)

Compound 418 $[\alpha]_D$=−96.67° (c=0.487%, chloroform solution)

Example 386

(Preparation of Compound 419)

To a solution of (±)-BINOL (40 mg) in toluene (5 ml) were added titanium tetraisopropoxide (21 µl) and water (25.6 µl) at room temperature, and the mixture was stirred for 1 hour. To the reaction solution were added N-[4-[[[1-(4-amino-4-oxobutyl)-1H-imidazol-2-yl]methyl]thio]phenyl]-7-[4-(2-butoxyethoxy)phenyl]-1-isobutyl-2,3-dihydro-1H-1-benzazepine-4-carboxamide (100 mg) and cummene hydroperoxide (80%, 0.1 ml) at room temperature and the mixture was stirred for 4 days. Cumene hydroperoxide (80%, 0.05 ml) was added to the mixture, the mixture was further stirred for 6 days, and an aqueous solution of sodium thiosulfate was added to the mixture. The mixture was extracted with ethyl acetate, washed with sodium bicarbonate solution and saturated brine, dried over magnesium sulfate, and concentrated under reduced pressure. The obtained residue was separated and purified by column chromatography (basic silica gel, ethanol:ethyl acetate 1:19), to give. N-[4-[[[1-(4-amino-4-oxobutyl)-1H-imidazol-2-yl]methyl]sulfonyl]phenyl]-7-[4-(2-butoxyethoxy)phenyl]-1-isobutyl-2,3-dihydro-1H-1-benzazepine-4-carboxamide (Compound 419) (49.9 mg) as yellow amorphous.

$^1$H-NMR (200 MHz, CDCl$_3$) δ 0.93 (3H, t, J=7.2 Hz), 1.00 (6H, d, J=6.6 Hz), 1.30 to 1.44 (2H, m), 1.47 to 1.65 (2H, m), 1.95 to 2.27 (5H, m), 2.87 to 2.98 (2H, m), 3.21 (2H, d, J=7.8 Hz), 3.31 to 3.42 (2H, m), 3.56 (2H, t, J=6.6 Hz), 3.81 (2H, t, J=4.6 Hz), 3.98 (2H, t, J=7.0 Hz), 4.16 (2H, t, J=4.6 Hz), 4.44 (2H, s), 5.26 to 5.43 (1H, m), 5.48 to 5.67 (1H, m), 6.90 to 6.99 (4H, m), 7.21 to 7.46 (6H, m), 7.60 (2H, d, J=9.2 Hz), 7.76 (2H, d, J=9.2 Hz), 8.35 (1H, s).

IR (KBr) 3332, 3177, 3036, 1667, 1607, 1588, 1518, 1499, 1400, 1321, 1242, 1142, 1088, 837, 816 cm$^{-1}$

Elemental Analysis for C$_{41}$H$_{51}$N$_5$O$_6$S.0.5H$_2$O Calcd. C, 65.58; H, 6.98; N, 9.33. Found: C, 65.33; H, 6.99; N, 9.09.

Example 387

(Preparation of Compound 420)

To a solution of ethyl 4-[2-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]butanoate (1.0 g) in ethanol-THF (10-2 ml) was added 1N aqueous solution of sodium hydroxide (2.4 ml) at room temperature and the mixture was stirred for 20 hours. To the reaction solution were added 1N hydrochloric acid (2.4 ml), and the mixture was concentrated under reduced pressure. To a solution of the residue in DMF (10 ml) were added 1-ethyl-3-(3'-dimethylaminopropyl) carbodiimide hydrochloride (0.39 g) and 1-hydroxybenzotriazole 1 hydrate (0.31 g), dimethylamine hydrochloride (0.22 g) and triethylamine (0.57 ml) at room temperature, and the mixture was stirred for 24 hours. To the reaction solution was added water, and the mixture was extracted with ethyl acetate. The organic layer was washed with water and saturated brine, dried over magnesium sulfate, and concentrated under reduced pressure. The obtained residue was separated and purified by column chromatography (basic silica get, ethyl acetate), to give 7-[4-(2-butoxyethoxy)phenyl]-N-[4-[[[1-[4-(dimethylamino)-4-oxobutyl]-1H-imidazol-2-yl]methyl]thio]phenyl]-1-isobutyl-2,3-dihydro-1H-1-benzazepine-4-carboxamide (Compound 420) (830.7 mg) as yellow amorphous.

$^1$H-NMR (200 MHz, CDCl$_3$) δ 0.93 (3H, t, J=7.1 Hz), 0.97 (6H, d, J=6.6 Hz), 1.25 to 1.47 (2H, m), 1.52 to 1.69 (2H, m), 1.98 to 2.18 (3H, m), 2.24 to 2.30 (2H, m), 2.88 to 2.95 (8H, m), 3.18 (2H, d, J=6.8 Hz), 3.30 to 3.40 (2H, m), 3.55 (2H, t, J=6.6 Hz), 3.80 (2H, t, J=5.0 Hz), 3.98 (2H, t, J=6.9 Hz), 4.13 to 4.18 (4H, m), 6.86 to 7.00 (5H, m), 7.33 to 7.55 (9H, m), 7.71 (1H, S).

IR (KBr) 3029, 1651, 107, 1588, 1497, 1397, 1312, 1287, 1242, 1181, 1125, 818 cm$^{-1}$

Elemental Analysis for C$_{43}$H$_{55}$N$_5$O$_4$S.0.5H$_2$O. Calcd. C, 69.13; H, 7.56; N, 7.38. Found: C, 69.30; H, 7.50; N, 9.62.

Example 388

(Preparation of Compound 421)

To a solution of 7-[4-(2-butoxyethoxy) phenyl]-N-[4-[[[1-[4-(dimethylamino)-4-oxobutyl]-1H-imidazol-2-yl]methyl]thio]phenyl]-1-isobutyl-2,3-dihydro-1H-1-benzazepine-4-carboxamide (400 mg) in dichloromethane (30 ml) was added a solution of 3-chloroperbenzoic acid (70%, 0.2 g) in dichloromethane (15 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, washed with sodium bicarbonate solution and saturated brine, dried over magnesium sulfate, and concentrated under reduced pressure. The obtained residue was separated and purified by column chromatography (basic silica get, ethyl acetate→ethanol: ethyl acetate 1:49), to give 7-[4-(2-butoxyethoxy)phenyl]-N-[4-[[[1-[4-(dimethylamino)-4-oxobutyl]-1H-imidazol-2-yl]methyl]sulfinyl]phenyl]-1-isobutyl-2,3-dihydro-1H-1-benzazepine-4-carboxamide (Compound 421) (377 mg) as yellow amorphous.

$^1$H-NMR (200 MHz, CDCl$_3$) δ 0.93 (3H, t, J=7.0 Hz), 0.98 (6H, d, J=6.6 Hz), 1.28-1.48 (2H, m), 1.52 to 1.72 (2H, m), 1.87 to 2.14 (3H, m), 2.23 (2H, t, J=6.8 Hz), 2.86 to 2.99 (8H, m), 3.20 (2H, d, J=7.2 Hz), 3.32 to 3.41 (2H, m), 3.55 (2H, t, J=6.6 Hz), 3.74 to 3.92 (4H, m), 4.08 to 4.18 (3H, m), 4.33 (1H, d, J=13.6 Hz), 6.89 to 7.03 (5H, m), 7.36 to 7.52 (7H, m), 7.74 (2H, d, J=8.8 Hz), 7.90 (1H, s).

IR (KBr) 3031, 1645, 1607, 1588, 1518, 1499, 1397, 1314, 1242, 1179, 1123, 1047, 835 cm$^{-1}$

Elemental Analysis for C$_{43}$H$_{55}$N$_5$O$_5$S.0.5H$_2$O Calcd. C, 67.69; H, 7.40; N, 9.18. Found: C, 67.41; H, 7.51; N, 9.03.

Example 389

(Preparation of Compound 422)

To a solution of 7-[4-(2-butoxyethoxy)phenyl]-N-[4-[[[1-[4-(dimethylamino)-4-oxobutyl]-1H-imidazol-2-yl]methyl]thio]phenyl]-1-isobutyl-2,3-dihydro-1H-1-benzazepine-4-carboxamide (300 mg), methanol (66 µl) and water (14.6 µl) in toluene (10 ml) was added titanium tetraisopropoxide (0.12 ml) at room temperature, and the mixture was stirred for 0.5 hour. To the reaction solution was added cumene hydroperoxide (80%, 0.22 ml) at −10° C., the mixture was stirred for 4 days at −10° C., and an aqueous solution of sodium thiosulfate was added to the mixture. The mixture was extracted with ethyl acetate, washed with sodium bicarbonate solution and saturated brine, dried over magnesium sulfate, and concentrated under reduced pressure. The obtained residue was separated and purified by column chromatography (basic silica gel, ethanol:ethyl acetate 1:19), to give 7-[4-(2-butoxyethoxy)phenyl]-N-[4-[[[1-[4-(dimethylamino)-4-oxobutyl]-1H-imidazol-2-yl]methyl]sulfonyl]phenyl]-1-isobutyl-2,3-dihydro-1H-1-benzazepine-4-carboxamide (Compound 422) (286 mg) as yellow amorphous.

$^1$H-NMR (200 MHz, CDCl$_3$) δ 0.93 (3H, t, J=7.1 Hz), 1.00 (6H, d, J=6.6 Hz), 1.28 to 1.48 (2H, m), 1.53 to 1.75 (2H, m), 1.94 to 2.16 (3H, m), 2.29 (2H, t, J=6.6 Hz), 2.86 to 3.00 (8H, m), 3.20 (2H, d, J=7.4 Hz), 3.30 to 3.39 (2H, m), 3.55 (2H, t, J=6.6 Hz), 3.80 (2H, t, J=5.0 Hz), 4.00 (2H, t, J=7.5 Hz), 4.15 (2H, t, J=5.0 Hz), 4.45 (2H, s), 6.89 to 6.98 (5H, m), 7.26 to 7.50 (5H, m), 7.59 (2H, d, J=9.0 Hz), 7.75 (2H, d, J=9.0 Hz), 8.56 (1H, s).

IR (KBr) 3031, 1645, 1607, 1590, 1518, 1499, 1400, 1321, 1244, 1144, 1090, 837, 820 cm$^{-1}$

Example 390

(Preparation of Compound 423)

To a solution of ethyl4-[2-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]butanoate (1.0 g) in ethanol-THF (10 to 2 ml) was added 1N aqueous solution of sodium hydroxide (2.4 ml) at room temperature and the mixture was stirred for 20 hours. To the reaction solution was added N hydrochloric acid (2.4 ml), and the mixture was concentrated under reduced pressure. To a solution of the residue in DMF (10 ml) was added 1-ethyl-3-(3'-dimethylaminopropyl) carbodiimide hydrochloride (0.39 g), 1-hydroxybenzotriazole 1 hydrate (0.31 g), methylamine hydrochloride (0.18 g) and triethylamine (0.57 ml) at room temperature, and the mixture was stirred for 24 hours. To the reaction solution was added water, and the mixture was extracted with ethyl acetate. The organic layer was washed with water and saturated brine, dried over magnesium sulfate, and concentrated under reduced pressure. The obtained residue was separated and purified by column chromatography (basic silica gel, ethyl acetate→ethanol:ethyl acetatel:19), to give 7-[4-(2-butoxyethoxy)phenyl]-N-[4-[[[1-[4-(methylamino)-4-oxobutyl]-1H-imidazol-2-yl]methyl]thio]phenyl]-1-isobutyl-2,3-dihydro-1H-1-benzazepine-4-carboxamide (Compound 423) (720 mg) as yellow amorphous.

$^1$H-NMR (200 MHz, CDCl$_3$) δ 60.93 (3H, t, J=7.1 Hz), 0.97 (6H, d, J=6.6 Hz), 1.37 to 1.46 (2H, m), 1.50 to 1.68 (2H, m), 1.92 to 2.19 (5H, m), 2.78 (3H, d, J=5.0 Hz), 2.85 to 2.96 (2H, m), 3.19 (2H, d, J=7.6 Hz), 3.31 to 3.41 (2H, m), 3.55 (2H, t, J=6.6 Hz), 3.78 to 3.89 (4H, m), 4.10 to 4.18 (4H, m), 5.59 to 5.76 (1H, s), 6.84 to 7.00 (5H, m), 7.34 to 7.52 (9H, m), 7.73 (1H, s).

IR (KBr) 3086, 3029, 1657, 1605, 1588, 1497, 1312, 1244, 1181, 1121, 818 cm$^{-1}$

Elemental Analysis for C$_{42}$H$_{53}$N$_5$O$_4$S.0.5H$_2$O. Calcd. C, 68.82; H, 7.42; N, 9.55. Found: C, 68.81; H, 7.35; N, 9.68.

Example 391

(Preparation of Compound 424)

To a solution of 7-[4-(2-butoxyethoxy)phenyl]-N-[4-[[[1-[4-(methylamino)-4-oxobutyl]-1H-imidazol-2-yl]methyl]thio]phenyl]-1-isobutyl-2,3-dihydro-1H-1-benzazepine-4-carboxamide (400 mg) in dichloromethane (10 ml) was added a solution of 3-chloroperbenzoic acid (70%, 0.2 g) in dichloromethane (15 ml) at −78° C. The mixture was stirred for 1.5 hours at −78° C., an aqueous solution of sodium thiosulfate was added to the mixture, and the mixture was stirred at room temperature for 10 minutes. The mixture was extracted with ethyl acetate, washed with an aqueous solution of sodium bicarbonate and saturated brine, and dried over magnesium sulfate, and concentrated under reduced pressure. The obtained residue was separated and purified by column chromatography (basic silica gel, ethanol:ethyl acetatel:19), and was further recrystallized from ethyl acetate-diisopropyl ether to give 7-[4-(2-butoxyethoxy)phenyl]-N-[4-[[[1-[4-(methylamino)-4-oxobutyl]-1H-imidazol-2-yl]methyl]sulfinyl]phenyl]-1-isobutyl-2,3-dihydro-1H-1-benzazepine-4-carboxamide (Compound 424) (342.8 mg) as yellow crystals.

mp 159 to 161° C.

$^1$H-NMR (200 MHz, CDCl$_3$) δ 0.93 (3H, t, J=6.9 Hz), 0.98 (6H, d, J=6.6 Hz), 1.28 to 1.47 (2H, m), 1.53 to 1.68 (2H, m), 1.88 to 2.16 (5H, m), 2.76 (3H, d, J=4.8 Hz), 2.87 to 2.96 (2H, m), 3.20 (2H, d, J=7.8 Hz), 3.32 to 3.42 (2H, m), 3.55 (2H, t, J=6.8 Hz), 3.72 to 3.85 (4H, m), 4.10 (1H, d, J=14.0 Hz), 4.18 (2H, t, J=5.1 Hz), 4.25 (1H, d, J=14.0 Hz), 6.03 to 6.14 (1H, m), 6.89 to 7.05 (5H, m), 7.39 to 7.51 (7H, m), 7.74 (2H, d, J=8.8 Hz), 8.03 (1H, s).

IR (KBr) 3293, 3044, 1657, 1605, 1590, 1499, 1399, 1314, 1244, 1179, 1111, 1049, 835 cm$^{-1}$

Elemental Analysis for C$_{42}$H$_{53}$N$_5$O$_5$S Calcd. C, 68.17; H, 7.22; N, 9.46. Found: C, 67.84; H, 7.09; N, 9.65.

Example 392

(Preparation of Compound 425)

To a solution of 7-[4-(2-butoxyethoxy)phenyl]-N-[4-[[[1-[4-(methylamino)-4-oxobutyl]-1H-imidazol-2-yl]methyl]thio]phenyl]-1-isobutyl-2,3-dihydro-1H-1-benzazepine-4-carboxamide (210 mg), methanol (24 μl) and water (5.3 μl) in toluene (10 ml) was added titanium tetraisopropoxide (43 μl) at room temperature, and the mixture was stirred for 0.5 hour. To the reaction solution was added cumene hydroperoxide (80%, 0.21 ml) at −10° C., the mixture was stirred for 2 days at −10° C., and an aqueous solution of sodium thiosulfate was added to the mixture. The mixture was extracted with ethyl acetate, washed with an aqueous solution of sodium bicarbonate and saturated brine, dried over magnesium sulfate, and concentrated under reduced pressure. The obtained residue was separated and purified by column chromatography (basic silica gel, ethyl acetate→ethanol:ethyl acetatel:19), and was further recrystallized from ethyl acetate-diisopropyl ether to give 7-[4-(2-butoxyethoxy)phenyl]-N-[4-[[[1-[4-(methylamino)-4-oxobutyl]-1H-imidazol-2-yl]methyl]sulfonyl]phenyl]-1-isobutyl-2,3-dihydro-1H-1-benzazepine-4-carboxamide (Compound 425) (161 mg) as yellow crystals.

mp 163 to 165° C.

$^1$H-NMR (300 MHz, CDCl$_3$) δ 0.93 (3H, t, J=7.4 Hz), 1.01 (6H, d, J=6.6 Hz), 1.34 to 1.46 (2H, m), 1.52 to 1.66 (2H, m), 1.98 to 2.15 (5H, m), 2.79 (3H, d, J=4.8 Hz), 2.91 to 3.00 (2H, m), 3.21 (2H, d, J=7.2 Hz), 3.35 to 3.38 (2H, m), 3.55 (2H, t, J=6.6 Hz), 3.81 (2H, t, J=4.9 Hz), 3.94 (2H, t, J=6.8 Hz), 4.16 (2H, t, J=4.9 Hz), 4.38 (2H, S), 5.52 to 5.64 (1H, m), 6.90 to 6.98 (5H, m), 7.22 to 7.29 (2H, M), 7.39 to 7.42 (3H, m), 7.58 (2H, d, J=9.0 Hz), 7.76 (2H, d, J=9.0 Hz), 8.61 (1H, br s).

IR (KBr) 3345, 3085, 1647, 1607, 1588, 1522, 1501, 1319, 1300, 1250, 1182, 1169, 1140 cm$^{-1}$

Elemental Analysis for $C_{42}H_{13}N_5O_6S$ Calcd. C, 66.73; H, 7.07; N, 9.26. Found: C, 66.72; H, 6.92; N, 9.23.

Example 393

(Preparation of Compound 426)

To a solution of 7-[4-(2-butoxyethoxy) phenyl]-1-isobutyl-2,3-dihydro-1H-1-benzazepine-4-carboxylic acid (1.5 g) in THF (10 ml) were added thionyl chloride (0.38 ml) and DMF (1 droplet) at room temperature and the mixture was stirred for 1.5 hours at room temperature. The reaction mixture was concentrated under reduced pressure, and a solution of the residue in THF (30 ml) was added dropwise to a solution of [5-[[(4-aminophenyl)thio]methyl]-1H-imidazol-1-yl]ethyl acetate (1.10 g) in pyridine (10.0 ml) at 0° C. The mixture was stirred at room temperature for 20 hours, and water was added to the reaction solution, and the mixture was extracted with ethyl acetate. The organic layer was washed with saturated brine, dried over magnesium sulfate, and concentrated under reduced pressure. The obtained residue was separated and purified by Column chromatography (basic silica gel, ethyl acetate:hexane 1:1→ethyl acetate), to give [5-[[[4-[[[7-[4-(2-butoxyethoxy)phenyl]-1-isobutyl-2,3-dihydro-1H-1-benzazepine-4-yl]carbonyl]amino]phenyl]thio]methyl]-1H-imidazol-1-yl]ethyl acetate (Preparation of Compound 426) (1.18 g) as yellow amorphous.

$^1$H-NMR (200 MHz, CDCl$_3$) δ 0.93 (3H, t, J=7.1 Hz), 0.97 (6H, d, J=6.6 Hz), 1.30 (3H, t, J=7.2 Hz), 1.32 to 1.46 (2H, m), 1.52 to 1.71 (2H, m), 1.91 to 2.18 (1H, m), 2.84 to 2.95 (2H, m), 3.18 (2H, d, J=7.4 Hz), 3.18 to 3.38 (2H, m), 3.55 (2H, t, J=6.6 Hz), 3.80 (2H, t, J=4.8 Hz), 3.96 (2H, s), 4.16 (2H, t, J=4.8 Hz), 4.25 (2H, q, J=7.2 Hz), 4.79 (2H, s), 6.70 (1H, s), 6.94 (1H, d, J=8.8 Hz), 6.99 (2H, d, J=8.8 Hz), 7.24 (2H, d, J=8.6 Hz), 7.37 to 7.55 (8H, m), 7.69 (1H, s).

IR (KBr) 3038, 1751, 1659, 1608, 1588, 1499, 1310, 1285, 1240, 1182, 1113, 818 cm$^{-1}$

Elemental Analysis for $C_{41}H_{50}N_4O_5S.0.5H_2O$ Calcd. C, 68.40; H,: 7.14; N, 7.78. Found: C, 68.63; H, 6.85; N, 7.76.

Example 394

(Preparation of Compound 427)

To a solution of [5-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]ethyl acetate (200 mg) in dichloromethane (10 ml) was added a solution of 3-chloroperbenzoic acid (70%, 0.11 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with an aqueous solution of sodium bicarbonate and saturated brine, dried over magnesium sulfate, and concentrated under reduced pressure. The obtained residue was separated and purified by column chromatography (basic silica get, ethyl acetate:hexane 4:1→9:1), to give [5-[[[4-[[[7-[4-(2-butoxyethoxy)phenyl]-1-isobutyl-2,3-dihydro-1H-1-benzazepin-4-yl]carbonyl]amino]phenyl]sulfinyl]methyl]-1H-imidazol-1-yl]ethyl acetate (Preparation of Compound 427) (117.6 mg) as yellow amorphous.

$^1$H-NMR (200 MHz, CDCl$_3$) δ 0.93 (3H, t, J=7.3 Hz), 0.97 (6H, d, J=6.6 Hz), 1.29 (3H, t, J=7.2 Hz), 1.33 to 1.48 (2H, m), 1.54 to 1.66 (2H, m), 1.92 to 2.20 (1H, m), 2.84 to 2.95 (2H, m), 3.18 (2H, d, J=7.0 Hz), 3.29 to 3.40 (2H, m), 3.55 (2H, t, J=6.6 Hz), 3.78 to 3.89 (3H, m), 4.13 to 4.28 (5H, m), 4.73 (1H, d, J=17.8 Hz), 4.87 (1H, d, J=17.8 Hz), 6.47 (1H, s), 6.91 (1H, d, J=8.8 Hz), 6.97 (2H, d, J=8.8 Hz), 7.27 to 7.50 (8H, m), 7.75 (2H, d, J=8.8 Hz), 8.14 (1H, s).

IR (KBr) 3032, 1750, 1663, 1607, 1588, 1518, 1499, 1397, 1312, 1244, 1179, 1121, 1030, 818 cm$^{-1}$

Elemental Analysis for $C_{41}H_{50}N_4O_6S.0.5H_2O$. Calcd. C, 66.91; H, 6.98; N, 7.61. Found: C, 66.81; H, 7.08; N, 7.31.

Example 395

(Preparation of Compound 428)

To a solution of [5-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]ethyl acetate (0.98 g) in ethanol (10 ml) was added 1N aqueous solution of sodium hydroxide (1.65 ml) at room temperature. The mixture was stirred at room temperature for 0.5 hour, 1N hydrochloric acid (1.65 ml) was added to the mixture, and the precipitated crystals were collected by filtration. The crystals were washed with ethanol to give. [5-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]acetic acid (Preparation of Compound 428) (778.9 mg) as yellow crystals.

$^1$H-NMR (200 MHz, DMSO-d$_6$) δ 0.88 (3H, t,: J=7.4 Hz), 0.92 (6H, d, J=6.6 Hz), 1.21 to 1.39 (2H, m), 1.42 to 1.58 (2H, m), 1.88 to 2.11 (1H, m), 2.78 to 2.88 (2H, m), 3.16 to 3.51 (6H, m), 3.68 to 3.73 (2H, m), 4.05 to 4.15 (4H, m), 4.88 (2H, s), 6.61 (1H, s), 6.94 to 7.02 (3H, m), 7.27 (2H, d, J=8.8 Hz), 7.38 to 7.68 (8H, m), 9.88 (1H, s).

IR (KBr) 3312, 3121, 3047, 1607, 1591, 1499, 1381, 1310, 1289, 1242, 1181, 1123, 818 cm$^{-1}$

Elemental Analysis for $C_{39}H_{46}N_4O_5S.2.0H_2O$ Calcd. C, 65.16; H, 7.01; N, 7.79. Found: C, 65.16; H, 6.97; N, 7.84.

Example 396

(Preparation of Compound 429)

To a solution of [5-[[[4-[[[7-[4-(2-butoxyethoxy)phenyl]-1-isobutyl-2,3-dihydro-1H-1-benzazepin-4-yl]carbonyl]amino]phenyl]thio]methyl]-1H-imidazol-1-yl]acetic acid (734 mg) and 1-hydroxybenzotriazole ammonium salt (0.24 g) in DMF (15 ml) were added 1-ethyl-3-(3'-dimethylaminopropyl) carbodiimide hydrochloride (0.31 g) and triethylamine (0.3 ml), at room temperature. The mixture was stirred at room temperature for 24 hours, water was added to the mixture and the mixture was extracted with ethyl acetate. The organic layer was washed with water and saturated brine, dried over magnesium sulfate, and concentrated under reduced pressure. The obtained residue was separated and purified by column chromatography (basic silica gel, ethanol:ethyl acetate 1:19), and was further recrystallized from ethyl acetate-diisopropyl ether to give. N-[4-[[[1-(2-amino-2-oxoethyl)-1H-imidazol-5-yl]methyl]thio]phenyl]-7-[4-(2-butoxyethoxy)phenyl]-1-isobutyl-2,3-dihydro-1H-1-benzazepine-4-carboxamide (Compound 429) (560 mg) as yellow crystals.

mp 152 to 154° C.

$^1$H-NMR (300 MHz, CDCl$_3$) δ 0.93 (3H, t, J=7.4 Hz), 0.97 (6H, d, J=6.6 Hz), 1.35 to 1.44 (2H, m), 1.48 to 1.65 (2H, m), 1.98 to 2.13 (1H, m), 2.85 to 2.91 (2H, m), 3.19 (2H, d, J=7.2 Hz), 3.31 to 3.40 (2H, m), 3.55 (2H, t, J=6.8 Hz), 3.81 (2H, t, J=4.9 Hz), 3.99 (2H, s), 4.16 (2H, t, J=4.9 Hz), 4.67 (2H, s), 5.51 (2H, br s), 6.82 (1H, s), 6.92 (1H, d,

J=8.7 Hz), 6.98 (2H, d, J=8.4 Hz), 7.20 to 7.30 (4H, m), 7.38 to 7.53 (6H, m), 7.60 (1H, s).

IR (KBr) 3316, 3185, 3036, 1672, 1655, 1609, 1586, 1499, 1397, 1310, 1287, 1242, 1181, 1121, 818 cm$^{-1}$

Elemental Analysis for $C_{39}H_{47}N_5O_4S\cdot 0.5H_2O$ Calcd. C, 67.80; H, 7.00; N, 10.14. Found: C, 67.62; H, 7.00; N, 10.28.

Example 397

(Preparation of Compound 430)

To a solution of N-[4-[[[1-(2-amino-2-oxoethyl)-1H-imidazole-5-yl]methyl]thio]phenyl]-7-[4-(2-butoxyethoxy)phenyl]-1-isobutyl-2,3-dihydro-1H-1-benzazepine-4-carboxamide (300 mg) in dichloromethane-DMF (80 to 1 ml) was added a solution of 3-chloroperbenzoic acid (70%, 0.142 g) in dichloromethane (10 ml) at −78° C. The mixture was stirred at −78° C. for 2.5 hours, an aqueous solution of sodium thiosulfate was added to the mixture, and the mixture was stirred at room temperature for 10 minutes. The mixture was extracted with ethyl acetate, and the organic layer was washed with an aqueous solution of sodium bicarbonate and saturated brine, dried over magnesium sulfate, and concentrated under reduced pressure. The obtained residue was separated and purified by column chromatography (basic silica gel, ethanol:ethyl acetate 1:19→1:9), and was further recrystallized from ethyl acetate-hexane to give. N-[4-[[[1-(2-amino-2-oxoethyl)-1H-imidazol-5-yl]methyl]sulfinyl]phenyl]-7-[4-(2-butoxyethoxy)phenyl]-1-isobutyl-2,3-dihydro-1H-1-benzazepine-4-carboxamide (Compound 430) (264.5 mg) as yellow crystals.

mp 123 to 125° C.

$^1$H-NMR (300 MHz, CDCl$_3$) δ 0.93 (3H, t, J=7.5 Hz), 0.97 (6H, d, J=6.6 Hz), 1.33 to 1.45 (2H, m), 1.56 to 1.63 (2H, m), 2.00 to 2.14 (1H, m), 2.87 to 2.95 (2H, m), 3.19 (2H, d, J=7.2 Hz), 3.35 to 3.38 (2H, m), 3.55 (2H, t, J=6.6 Hz), 3.79 to 3.86 (3H, m), 4.15 (2H, t, J=4.8 Hz), 4.24 (1H, d, J=14.7 Hz), 4.59 (2H, s), 5.59 (1H, br s), 6.52 (1H, s), 6.84 (1H, br s), 6.92 (1H, d, J=8.4 Hz), 6.97 (2H, d, J=8.7 Hz), 7.33 (2H, d, J=8.9 Hz), 7.40 to 7.50 (5H, m), 7.59 (1H, s), 7.76 (2H, d, J=8.9 Hz), 8.06 (1H, s).

IR (KBr) 3298, 3186, 3032, 1686, 1607, 1588, 1499, 1397, 1312, 1244, 1179, 1121, 1036, 820 cm$^{-1}$

Elemental Analysis for $C_{39}H_{47}N_5O_5S\cdot 1.0H_2O$ Calcd. C, 65.43; H, 6.90; N, 9.78. Found: C, 65.35; H, 6.97; N, 9.75.

Example 398

(Preparation of Compound 431)

To a solution of N-[4-[[[1-(2-amino-2-oxoethyl)-1H-imidazol-5-yl]methyl]thio]phenyl]-7-[4-(2-butoxyethoxy)phenyl]-1-isobutyl-2,3-dihydro-1H-1-benzazepine-4-carboxamide (180 mg), methanol (21.4 µl) and water (4.8 µl) in dichloromethane (20 ml) was added titanium tetraisopropoxide (39 µl) at room temperature, and the mixture was stirred for 0.5 hour. After cooling to −10° C., DMF (10 ml) and cumene hydroperoxide (80%, 0.19 ml) were added to the reaction solution, and the mixture was stirred at −10° C. for 24 hours. Cumene hydroperoxide (80%, 0.1 ml) was further added to the mixture at −5° C. for 24 hours, and the mixture was stirred at 0° C. for 4 days. To the reaction solution was added an aqueous solution of sodium thiosulfate. The mixture was extracted with ethyl acetate, washed with an aqueous solution of sodium bicarbonate and saturated brine, dried over magnesium sulfate, an concentrated under reduced pressure. The obtained residue was separated and purified by column chromatography (basic silica gel, ethanol:ethyl acetate 1:19→1:9), to give N-[4-[[[1-(2-amino-2-oxoethyl)-1H-imidazol-5-yl]methyl]sulfonyl]phenyl]-7-[4-(2-butoxyethoxy)phenyl]-1-isobutyl-2,3-dihydro-1H-1-benzazepine-4-carboxamide (Compound 431) (130 mg) as yellow crystals.

mp 229 to 231° C.

$^1$H-NMR (300 MHz, CDCl$_3$) δ 0.93 (3H, t, J=7.5 Hz), 0.97 (6H, d, J=6.6 Hz), 1.31 to 1.45 (2H, m), 1.52 to 1.66 (2H, m), 1.99 to 2.15 (1H, m), 2.88 to 2.96 (2H, m), 3.19 (2H, d, J=7.5 Hz), 3.32 to 3.40 (2H, m), 3.55 (2H, t, J=6.6 Hz), 3.81 (2H, t, J=4.9 Hz), 4.16 (2H, t, J=4.9 Hz), 4.35 (2H, s), 4.78 (2H, s), 5.52 to 5.61 (1H, m), 5.92 to 6.01 (1H, m), 6.41 (1H, s), 6.93 (1H, d, J=8.7 Hz), 6.98 (2H, d, J=8.7 Hz), 7.40 to 7.50 (5H, m), 7.51 (1H, s), 7.62 (2H, d, J=8.7 Hz), 7.77 (2H, d, J=8.7 Hz), 8.02 (1H, s).

IR (KBr) 3304, 3187, 3036, 1676, 1645, 1609, 1588, 1499, 1399, 1318, 1242, 1150, 1088, 826 cm$^{-1}$

Elemental Analysis for $C_{39}H_{47}N_5O_6S$ Calcd. C, 65.62; H, 6.64; N, 9.81. Found: C, 65.46; H, 6.73; N, 9.78.

Example 399

(Preparation of Compound 432)

To a solution of 7-[4-(2-butoxyethoxy)phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature and the mixture was stirred for 1 hour at room temperature. The reaction mixture was concentrated under reduced pressure, and a solution of the residue in THF (35 ml) was added dropwise to a solution of 2-[2-[[(4-aminophenyl)thio]methyl]-1H-imidazol-1-yl]ethyl benzoic acid (0.89 g) in pyridine (10 ml) at 0° C. The mixture was stirred at room temperature for 20 hours, and water was added to the reaction solution, and the mixture was extracted with ethyl acetate. The organic layer was washed with saturated brine, dried over magnesium sulfate, and concentrated under reduced pressure. The obtained residue was separated and purified by column chromatography (basic silica gel, ethyl acetate:hexane 1:1→ethyl acetate), to give ethyl 2-[2-[[[4-[[[7-[4-(2-butoxyethoxy)phenyl]-1-isobutyl-2,3-dihydro-1H-1-benzazepin-4-yl]carbonyl]amino]thio]methyl]-1H-imidazol-yl]benzoate (Preparation of Compound 432) (1.32 g) as yellow crystals.

mp 85 to 87° C.

$^1$H-NMR (200 MHz, CDCl$_3$) δ 0.93 (3H, t, J=7.2 Hz), 0.97 (6H, d, J=6.6 Hz), 1.32 to 1.46 (2H, m), 1.50 to 1.66 (2H, m), 1.93 to 2.12 (1H, m), 2.84 to 2.94 (2H, m), 3.19 (2H, d, J=7.6 Hz), 3.30 to 3.40 (2H, m), 3.55 (2H, t, J=6.6 Hz), 3.77 to 3.83 (2H, m), 4.11 to 4.18 (2H, m), 4.21 (2H, s), 4.29 to 4.34 (2H, m), 4.56 to 4.61 (2H, m), 6.90 to 7.00 (5H, m), 7.26 to 7.59 (13H, m), 7.97 to 8.01 (2H, m).

IR (KBr) 3074, 1723, 1645, 1603, 1588, 1522, 1499, 1314, 1269, 1246, 1177, 1115, 710 cm$^{-1}$

Elemental Analysis for $C_{46}H_{52}N_4O_5S\cdot 0.5H_2O$ Calcd. C, 70.65; H, 6.83; N, 7.16. Found: C, 70.51; H, 6.98; N, 6.86.

Example 400

(Preparation of Compound 433)

To a solution of ethyl 2-[2-[[[4-[[[7-[4-(2-butoxyethoxy)phenyl]-1-isobutyl-2,3-dihydro-1H-1-benzazepin-4-yl]carbonyl]amino]thio]methyl]-1H-imidazol-yl]benzoate (930 mg) in ethanol-THF (10 to 5 ml) was added 1N aqueous solution of sodium hydroxide (1.8 ml) at room temperature.

The mixture was stirred at room temperature for 20 hours, 1N hydrochloric acid (1.8 ml) was added to the mixture, and the mixture was extracted with ethyl acetate. The organic layer was washed with saturated brine, dried over magnesium sulfate, and concentrated under reduced pressure. The residue was separated and purified by column chromatography (ethyl acetate→ethanol:ethyl acetate 1:19), to give 7-[4-(2-butoxyethoxy)phenyl]-N-[4-[[[1-(2-hydroxyethyl)-1H-imidazol-2-yl]methyl]thio]phenyl]-1-isobutyl-2,3-dihydro-1H-1-benzazepine-4-carboxamide (Compound 433) (712 mg) as yellow amorphous.

$^1$H-NMR (200 MHz, CDCl$_3$) δ 0.93 (3H, t, J=7.1 Hz), 0.97 (6H, d, J=6.6 Hz), 1.26 to 1.47 (2H, m), 1.50 to 1.76 (2H, m), 1.96 to 2.17 (1H, m), 2.84 to 2.94 (2H, m), 3.18 (2H, d, J=7.2 Hz), 3.29 to 3.38 (2H, m), 3.55 (2H, t, J=6.6 Hz), 3.78 to 3.85 (4H, m), 4.03 (2H, t, J=5.1 Hz), 4.13 to 4.18 (4H, m), 6.89 to 6.99 (5H, m), 7.26 to 7.52 (9H, m), 7.90 (1H, s).

IR (KBr) 3034, 1651, 1605, 1586, 1497, 1312, 1284, 1242, 1181, 1115, 1069, 816 cm$^{-1}$

Elemental Analysis for C$_{39}$H$_{48}$N$_4$O$_4$S.0.5H$_2$O Calcd. C, 69.10; H, 7.24; N, 8.26. Found: C, 69.26; H, 7.20; N, 8.30.

Example 401

(Preparation of Compound 434)
To a solution of 7-[4-(2-butoxyethoxy)phenyl]-N-[4-[[[1-(2-hydroxyethyl)-1H-imidazol-2-yl]methyl]thio]phenyl]-1-isobutyl-2,3-dihydro-1H-1-benzazepine-4-carboxamide (0.40 g) in dichloromethane (10 ml) was added a solution of 3-chloroperbenzoic acid (70%, 0.22 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with an aqueous solution of sodium bicarbonate and saturated brine, dried over magnesium sulfate, and concentrated under reduced pressure. The obtained residue was separated and purified by column chromatography (basic silica gel, ethanol:ethyl acetate 1:9), to give 7-[4-(2-butoxyethoxy)phenyl]-N-[4-[[[1-(2-hydroxyethyl)-1H-imidazol-2-yl]methyl]sulfinyl]phenyl]-1-isobutyl-2,3-dihydro-1H-1-benzazepine-4-carboxamide (Compound 434) (280.5 mg) as yellow amorphous.

$^1$H-NMR (200 MHz, CDCl$_3$) δ 0.93 (3H, t, J=7.1 Hz), 0.98 (6H, d, J=6.6 Hz), 1.29 to 1.48 (2H, m), 1.51 to 1.66 (2H, m), 1.92 to 2.18 (1H, m), 2.88 to 2.98 (2H, m), 3.20 (2H, d, J=7.0 Hz), 3.31 to 3.40 (2H, m), 3.55 (2H, t, J=6.6 Hz), 3.76 to 3.88 (4H, m), 3.98 to 4.07 (2H, m), 4.13 to 4.28 (4H, m), 6.90 to 7.00 (4H, m), 7.08 (1H, d, J=1.4 Hz), 7.26 to 7.53 (7H, m), 7.75 (2H, d, J=8.8 Hz), 8.03 (1H, s).

IR (KBr) 3108, 1661, 1607, 1588, 1518, 1499, 1314, 1244, 1181, 1115, 833 cm$^{-1}$

Elemental Analysis for C$_{39}$H$_{48}$N$_4$O$_5$S.1.0H$_2$O Calcd. C, 66.64; H, 7.17; N, 7.97. Found: C, 66.92; H, 7.21; N, 7.93.

Example 402

(Preparation of Compound 435)
To a solution of 7-[4-(2-butoxyethoxy) phenyl]-1-isobutyl-2,3-dihydro-1H-1-benzazepine-4-carboxylic acid (1.0 g) in THF (10 ml) were added thionyl chloride (0.25 ml) and DMF (1 droplet) at room temperature and the mixture was stirred at room temperature for 1.5 hours. The reaction mixture was concentrated under reduced pressure, and a solution of the residue in THF (25 ml) was added dropwise to a solution of 3-[2-[[(4-aminophenyl)thio]methyl]-1H-imidazol-1-yl]propyl acetic acid (0.89 g) in pyridine (10 ml) at 0° C. The mixture was stirred at room temperature for 20 hours, and water was added to the reaction solution, and the mixture was extracted with ethyl acetate. The organic layer was washed with saturated brine, dried over magnesium sulfate, and concentrated under reduced pressure. The obtained residue was separated and purified by column chromatography (ethyl acetate:hexane 1:1→ethyl acetate), to give 3-[2-[[[4-[[[7-[4-(2-butoxyethoxy)phenyl]-1-isobutyl-2,3-dihydro-1H-1-benzazepine-4-yl]carbonyl]amino]thio]methyl]-1H-imidazol-yl]propyl acetic acid (Preparation of Compound 435) (1.347 g) as yellow amorphous.

$^1$H-NMR (200 MHz, CDCl$_3$) δ 0.93 (3H, t, J=7.1 Hz), 0.97 (6H, d, J=6.6 Hz), 1.26 to 1.44 (2H, m), 1.47 to 1.68 (2H, m), 1.96 to 2.17 (6H, m), 2.85 to 2.95 (2H, m), 3.18 (2H, d, J=7.4 Hz), 3.29 to 3.39 (2H, m), 3.55 (2H, t, J=6.6 Hz), 3.80 (2H, t, J=4.8 Hz), 3.96 to 4.18 (8H, m), 6.84 (1H, d, J=1.4 Hz), 6.89 to 6.94 (2H, m), 6.98 (2H, d, J=8.8 Hz), 7.31 to 7.55 (9H, m), 7.73 (1H, s).

IR (KBr) 3034, 1736, 1655, 1607, 1588, 1499,.1395, 1312, 1283, 1242, 1181, 1117, 1047, 909, 818, 735 cm$^{-1}$

Elemental Analysis for C$_{42}$H$_{52}$N$_4$O$_5$S.0.25H$_2$O. Calcd. C, 69.16; H, 7.25; N, 7.68. Found: C, 68.99; H, 7.41; N, 7.57.

Example 403

(Preparation of Compound 436)
To a solution of 3-[2-[[[4-[[[7-[4-(2-butoxyethoxy)phenyl]-1-isobutyl-2,3-dihydro-1H-1-benzazepin-4-yl]carbonyl]amino]thio]methyl]-1H-imidazol-yl]propyl acetic acid (0.79 g) in ethanol-THF (10 to 2 ml) was added 1N aqueous solution of sodium hydroxide (1.5 ml) at room temperature. The mixture was stirred at room temperature for 3 hours, and the mixture was concentrated under reduced pressure. To the residue was added water, and the mixture was extracted with ethyl acetate. The organic layer was washed with saturated brine, dried over magnesium sulfate, and concentrated under reduced pressure. The residue was separated and purified by column chromatography (basic silica gel, ethyl acetate→ethanol:ethyl acetate 1:19), to give 7-[4-(2-butoxyethoxy)phenyl]-N-[4-[[1-(3-hydroxypropyl)-1H-imidazol-2-yl]methyl]thio]phenyl]-1-isobutyl-2,3-dihydro-1H-1-benzazepine-4-carboxamide (Compound 436) (642.4 mg) as yellow crystals.

mp 154 to 156° C.
$^1$H-NMR (200 MHz, CDCl$_3$) δ 0.93 (3H, t, J=7.1 Hz), 0.97 (6H, d, J=6.6 Hz), 1.28 to 1.49 (2H, m), 0.51 to 1.68 (2H, m), 1.83 to 2.12 (3H, m), 2.85 to 2.95 (2H, m), 3.18 (2H, d, J=7.0 Hz), 3.29 to 3.39 (2H, m), 3.52 to 3.64 (4H, m), 3.80 (2H, t, J=4.9 Hz), 3.98 (2H, t, J=7.2 Hz), 4.13 to 4.18 (4H, m), 6.86 to 7.00 (5H, m), 7.33 to 7.53 (9H, m), 7.76 (1H, s).

IR (KBr) 3303, 3086, 1636, 1586, 501, 1318, 1246, 1181, 1134, 1113, 1067, 923, 812 cm$^{-1}$

Elemental Analysis for C$_{40}$H$_{50}$N$_4$O$_4$S Calcd. C, 70.35; H, 7.38; N, 8.20. Found: C, 69.98; H, 7.52; N, 8.31.

Example 404

(Preparation of Compound 437)
To a solution of 7-[4-(2-butoxyethoxy)phenyl]-N-[4-[1-(3-hydroxypropyl)-1H-imidazol-2-yl]methyl]thio]phenyl]-1-isobutyl-2,3-dihydro-1H-1-benzazepine-4-carboxamide (0.40 g) in dichloromethane (20 ml) was added 3-chloroperbenzoic acid (70%, 0.22 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with an aqueous solution of sodium bicarbonate and saturated brine, dried over magnesium sulfate, and concentrated under reduced pressure. The obtained residue was separated and purified by column chromatography (basic silica gel, ethanol:ethyl acetate 1:19), to give 7-[4-(2-butoxyethoxy)phenyl]-N-[4-[[1-(3-hydroxypropyl)-1H-imidazol-2-yl]methyl]sulfinyl]phenyl]-1-isobutyl-2,3-dihydro-1H-1-benzazepine-4-carboxamide (Compound 437) (354 mg) as yellow amorphous.

$^1$H-NMR (300 MHz, CDCl$_3$) 0.93 (3H, t, J=7.2 Hz), 0.98 (6H, d, J=6.6 Hz), 1.32 to 1.44 (2H, m), 1.52 to 1.68 (2H, m), 1.87 to 1.98 (2H, m), 2.02 to 2.16 (1H, m), 2.88 to 2.97 (2H, m), 3.20 (2H, d, J=6.9 Hz), 3.35 to 3.57 (6H, m), 3.81 (2H, t, J=5.0 Hz), 3.86 to 4.07 (2H, m), 4.11 to 4.17 (3H, m), 4.25 (1H, d, J=13.8 Hz), 6.91 to 6.99 (4H, m), 7.09 (1H, d, J=1.2 Hz), 7.39 to 7.47 (5H, m), 7.52 (2H, d, J=8.7 Hz), 7.75 (2H, d, J=8.7 Hz), 7.99 (1H, s).

IR (KBr) 3094, 3032, 1661, 1607, 1588, 1518, 1499, 1397, 1314, 1244, 1179, 1046, 818 cm$^{-1}$

Elemental Analysis for C$_{40}$H$_{50}$N$_4$O$_5$S.0.5H$_2$O Calcd. C, 67.87; H, 7.26; N, 7.91. Found: C, 67.65; H, 7.34; N, 7.80.

Example 405

(Preparation of Compound 438)

To a solution of 7-[4-(2-butoxyethoxy)phenyl]-1-isobutyl-N-[4-[(1-trityl-1H-imidazol-4-yl)methyl]thio]phenyl]-2,3-dihydro-1H-1-benzazepine-4-carboxamide (0.50 g) in DMF (10 ml), 2-iodinated ethanol (0.25 ml) was added at room temperature, and the mixture was stirred at 50° C. for 4 days. To the reaction solution was added water, and the mixture was extracted with ethyl acetate. The organic layer was washed with saturated brine, dried over magnesium sulfate, and concentrated under reduced pressure. The obtained residue was separated and purified by column chromatography (basic silica gel, ethanol:ethyl acetate 1:49→1:19), to give 7-[4-(2-butoxyethoxy)phenyl]-N-[4-[[1-(2-hydroxyethyl)-1H-imidazol-5-yl]methyl]thio]phenyl]-1-isobutyl-2,3-dihydro-1H-1-benzazepine-4-carboxamide (Compound 438) (124.6 mg) as yellow amorphous.

$^1$H-NMR (200 MHz, CDCl$_3$) 0.93 (3H, t, J=7.3 Hz), 0.96 (6H, d, J=6.6 Hz), 1.28 to 1.46 (2H, m), 1.53 to 1.80 (2H, m), 1.94 to 2.16 (1H, m), 2.83 to 2.95 (2H, m), 3.18 (2H, d, J=7.2 Hz), 3.28 to 3.39 (2H, m), 3.55 (2H, t, J=6.6 Hz), 3.80 (2H, t, J=4.9 Hz), 3.89 (2H, t, J=5.2 Hz), 4.01 (2H, s), 4.09 (2H, t, J=5.2 Hz), 4.15 (2H, t, J=4.9 Hz), 6.64 (1H, s), 6.91 (1H, d, J=8.8 Hz), 6.97 (2H, d, J=8.8 Hz), 7.23 to 7.27 (2H, m), 7.37 to 7.53 (8H, m), 7.76 (1H, s).

IR (KBr) 3083, 3034, 1655, 1607, 1588, 1499, 1395, 1312, 1287, 1244, 1181, 1123, 1067, 816 cm$^{-1}$

Elemental Analysis for C$_{39}$H$_{48}$N$_4$O$_4$S.0.75H$_2$O Calcd. C, 68.64; H, 7.31; N, 8.21. Found: C, 68.88; H, 7.23; N, 8.35.

Example 406

(Preparation of Compound 439)

To a solution of 7-[4-(2-butoxyethoxy)phenyl]-N-[4-[[1-(2-hydroxyethyl)-1H-imidazol-5-yl]methyl]thio]phenyl]-1-isobutyl-2,3-dihydro-1H-1-benzazepine-4-carboxamide (204.7 mg) in dichloromethane (10 ml) was added a solution of 3-chloroperbenzoic acid (70%, 0.12 g) in dichloromethane (10 ml) at −78° C. The mixture was stirred for 1 hour at −78° C., an aqueous solution of sodium thiosulfate was added to the mixture, and the mixture was stirred at room temperature for 10 minutes. The mixture was extracted with ethyl acetate, and the organic layer was washed with an aqueous solution of sodium bicarbonate and saturated brine, dried over magnesium sulfate, and concentrated under reduced pressure. The obtained residue was separated and purified by column chromatography (basic silica gel, ethanol:ethyl acetate 1:9), to give 7-[4-(2-butoxyethoxy)phenyl]-N-[4-[[1-(2-hydroxyethyl)-1H-imidazol-5-yl]methyl]sulfinyl]phenyl]-1-isobutyl-2,3-dihydro-1H-1-benzazepine-4-carboxamide (Compound 439) (115.5 mg, 55%) as yellow amorphous.

$^1$H-NMR (200 MHz, CDCl$_3$) δ 0.93 (3H, t, J=7.4 Hz), 0.97 (6H, d, J=6.6 Hz), 1.29 to 1.48 (2H, m), 1.50 to 1.76 (2H, m), 1.95 to 2.15 (1H, m), 2.86 to 2.96 (2H, m), 3.20 (2H, d, J=7.6 Hz), 3.32 to 3.41 (2H, m), 3.55 (2H, t, J=6.6 Hz), 3.78 to 4.05 (7H, m), 4.16 (2H, t, J=4.8 Hz), 4.25 (1H, d, J=14.6 Hz), 6.54 (1H, s), 6.90 to 7.00 (3H, m), 7.35 to 7.57 (8H, m), 7.75 (2H, d, J=8.8 Hz), 7.96 (1H, S).

IR (KBr) 3092, 3027, 1661, 1607, 1588, 1518, 1397, 1312, 1244, 1179, 1119, 818 cm$^{-1}$

Elemental Analysis for C$_{39}$H$_{48}$N$_4$O$_5$S.1.0H$_2$O Calcd. C, 66.64; H, 7.17; N, 7.97. Found: C, 66.79; H, 6.90; N, 7.73.

Example 407

(Preparation of Compound 440)

To a solution of 7-[4-(2-butoxyethoxy)phenyl]-1-isobutyl-2,3-dihydro-1H-1-benzazepine-4-carboxylic acid (1.0 g) in tetrahydrofuran (15 ml) was added one droplet of DMF. Then, thionyl chloride (0.22 ml) was added to the mixture at 0° C., and the mixture was allowed to be at room temperature and stirred for 1 hour under nitrogen atmosphere. The solvent and excess thionyl chloride were distilled off under reduced pressure, and the residue was dissolved in tetrahydrofuran (15 ml). This solution was added dropwise to a solution of S-(4-aminophenyl)O-benzyl carbonothioate (594 mg) and triethylamine (1.6 ml) in THF. (15 ml) at 0° C. under argon atmosphere. After finishing the dropping, the mixture was allowed to be at room temperature, the mixture was stirred overnight, and methanol (30 ml) was added. Further, 1N aqueous solution of sodium hydroxide (11.5 ml) was added to the mixture, and the mixture was stirred for 30 minutes under argon atmosphere. Then, 4-chloromethyl-5-methyl-1-propylimidazole hydrochloride (527 mg) was added to the mixture and the mixture was stirred for 1 hour under argon atmosphere. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure, and the residue was separated and purified by basic silica gel column chromatography (hexane:ethyl acetate=1:1→hexane:ethyl acetate=1:3), to give 7-[4-(2-butoxyethoxy)phenyl]-1-isobutyl-N-[4-[[(5-methyl-1-propylimidazol-4-yl)methyl]sulfanyl]phenyl]-2,3-dihydro-1H-1-benzazepine-4-carboxamide (268 mg) (Compound 440) as yellow amorphous.

$^1$H-NMR (200 MHz, CDCl$_3$) δ 0.88 to 0.99 (12H, m), 1.34 to 1.45 (2H, m), 1.54 to 1.75 (4H, m), 1.96 (3H, s), 2.00 to 2.20 (1H, m), 2.85 to 2.95 (2H, m), 3.19 (2H, d, J=7.4 Hz), 3.34 to 3.39 (2H, m), 3.55 (2H, t, J=6.6 Hz), 3.71 (2H, t, J=7.4 Hz), 3.80 (2H, t, J=4.8 Hz), 4.02 (2H, s), 4.18 (2H, t, J=4.8 Hz), 6.92 (1H, d, J=8.8 Hz), 6.98 (2H, d, J=8.8 Hz), 7.32 to 7.52 (10H, m), 7.60 (1H, s).

Elemental Analysis for $C_{41}H_{52}N_4O_3S \cdot 0.25H_2O$. Calcd. C, 71.84; H, 7.72; N, 8.17. Found: C, 71.63; H, 7.82; N, 8.15.

Example 408

(Preparation of Compound 441)

To a solution of 7-[4-(2-butoxyethoxy)phenyl]-1-isobutyl-N-[4-[[(5-methyl-1-propylimidazol-4-yl)methyl]sulfanyl]phenyl]-2,3-dihydro-1H-1-benzazepine-4-carboxamide (220 mg) in dichloromethane (10 ml) was added dropwise 70% solution of 3-chloroperbenzoic acid (119 mg) in dichloromethane (10 ml) at −78° C., and the mixture was stirred for 30 minutes at the same temperature. Dimethylsulfide (0.1 ml) was added to the mixture and the mixture was allowed to be at room temperature, and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure: and the obtained residue was separated and purified by basic silica gel column chromatography (ethyl acetate→ethyl acetate:methanol=10:1), to give 7-[4-(2-butoxyethoxy)phenyl]-1-isobutyl-N-[4-[[(5-methyl-1-propylimidazol-4-yl)methyl]sulfinyl]phenyl]-2,3-dihydro-1H-1-benzazepine-4-carboxamide (132 mg) (Compound 441) as yellow amorphous.

$^1$H-NMR (200 MHz, CDCl$_3$) δ 0.90 to 0.99 (12H, m), 1.34 to 1.45 (2H, m), 1.55 to 1.76 (4H, m), 1.86 (3H, s), 1.95 to 2.15 (1H, m), 2.90 to 3.00 (2H, m), 3.20 (2H, d, J=5.4 Hz), 3.35 to 3.45 (2H, m), 3.55 (2H, t, J=6.6 Hz), 3.73 (2H, t, J=7.0 Hz), 3.78 to 3.89 (3H, m), 4.14 to 4.24 (3H, m), 6.93 (1H, d, J=8.4 Hz), 6.98 (2H, d, J=8.8 Hz), 7.37 to 7.50 (8H, m), 7.69 (2H, d, J=8.8 Hz), 7.73 (1H, s).

Elemental Analysis for $C_{41}H_{52}N_4O_4S \cdot 0.5H_2O$. Calcd. C, 69.76; H, 7.57; N, 7.94. Found: C, 69.47; H, 7.55; N, 7.68.

Example 409

(Preparation of Compound 442)

To a solution of 7-[4-(2-butoxyethoxy)phenyl]-1-isobutyl-2,3-dihydro-1H-1-benzazepine-4-carboxylic acid (1.0 g) in tetrahydrofuran (10 ml) was added one droplet of DMF. Then, thionyl chloride (0.22 ml) was added to the mixture at 0° C., and the mixture was allowed to be at room temperature and stirred for 1 hour under nitrogen atmosphere. The solvent and excess thionyl chloride were distilled off under reduced pressure, and the residue was dissolved in tetrahydrofuran (15 ml). This solution was added dropwise to a solution of S-(4-aminophenyl)O-benzyl carbonothioate (594 mg) and triethylamine (1.6 ml) in THF (15 ml) at 0° C. under argon atmosphere. After finishing the dropping, the mixture was allowed to be at room temperature and the mixture was stirred overnight, and methanol (30 ml) was added to the mixture. Further, 1N aqueous solution of sodium hydroxide (11.5 ml) was added to the mixture, and the mixture was stirred for 30 minutes under argon atmosphere. Then, 5-chloromethyl-1-(2-propyn-1-yl)imidazole hydrochloride (482 mg) was added to the mixture and the mixture was stirred for 1 hour under argon atmosphere. The solvent was distilled off under reduced pressure, and water was added to the mixture, and the mixture was extracted with ethyl acetate. The organic layer was washed with saturated brine, and dried over magnesium sulfate. The solvent was distilled off under reduced pressure, and the residue was separated and purified by basic silica gel column chromatography (hexane:ethyl acetate=2:3), to give 7-[4-(2-butoxyethoxy)phenyl]-1-isobutyl-N-[4-[[(1-(2-propin-1-yl)imidazol-5-yl)methyl]sulfanyl]phenyl]-2,3-dihydro-1H-1-benzazepine-4-carboxamide (1.14 g) (Compound 442) as yellow amorphous.

$^1$H-NMR (200 MHz, CDCl$_3$) δ 0.89 to 0.99 (9H, m), 1.30 to 1.50 (2H, m), 1.54 to 1.70 (2H, m), 1.95 to 2.15 (1H, m), 2.49 (1H, t, J=2.6 Hz), 2.85 to 2.95 (2H, m), 3.19 (2H, d, J=7.2 Hz), 3.33 to 3.38 (2H, m), 3.55 (2H, t, J=6.6 Hz), 3.80 (2H, t, J=4.8 Hz), 4.08 (2H, s), 4.16 (2H, t, J=4.8 Hz), 4.82 (2H, d, J=2.6 Hz), 6.72 (1H, s), 6.92 (1H, d, J=8.8 Hz), 6.97 (2H, d, J=8.8 Hz), 7.27 (2H, d, J=8.8 Hz), 7.37 to 7.58 (8H, m), 7.64 (1H, s).

Elemental Analysis for $C_{40}H_{46}N_4O_3S \cdot 0.25H_2O$ Calcd. C, 71.99; H, 7.02; N, 8.39. Found: C, 71.86; H, 6.86; N, 8.40.

Example 410

(Preparation of Compound 443)

To a solution of 7-[4-(2-butoxyethoxy)phenyl]-1-isobutyl-N-[4-[[(1-(2-propin-1-yl)imidazol-5-yl)methyl]sulfanyl]phenyl]-2,3-dihydro-1H-1-benzazepine-4-carboxamide (639 mg) in dichloromethane (15 ml) was added dropwise 70% solution of 3-chloroperbenzoic acid (356 mg) in dichloromethane (15 ml) at −78° C., and the mixture was stirred for 30 minutes at the same temperature. Dimethylsulfide (0.1 ml) was added to the mixture, and the mixture was allowed to be at room temperature and stirred for 30 minutes. To the mixture was added water and the mixture was extracted with ethyl acetate. The organic layer was washed with an aqueous solution of saturated sodium bicarbonate, saturated brine, and dried over magnesium sulfate. The solvent was distilled off under reduced pressure and the obtained residue was separated and purified by silica gel column chromatography (ethyl acetate), to give 7-[4-(2-butoxyethoxy)phenyl]-1-isobutyl-N-[4-[[(1-(2-propin-1-yl)imidazol-5-yl)methyl]sulfinyl]phenyl]-2,3-dihydro-1H-1-benzazepine-4-carboxamide (451 mg) (Compound 443) as yellow amorphous.

$^1$H-NMR (200 MHz, CDCl$_3$) δ 0.90 to 0.99 (9H, m), 1.30 to 1.50 (2H, m), 1.55 to 1.65 (2H, m), 1.95 to 2.15 (1H, m), 2.46 (1H, t, J=2.6 Hz), 2.90 to 3.00 (2H, m), 3.20 (2H, d, J=7.4 Hz), 3.33 to 3.43 (2H, m), 3.55 (2H, t, J=6.6 Hz), 3.80 (2H, t, J=4.4 Hz), 3.97 (1H, d, J=14.4 Hz), 4.16 (2H, t, J=4.4 Hz), 4.32 (1H, d, J=14.4 Hz), 4.77 (2H, d, J=2.6 Hz), 6.55 (1H, s)! 6.93 (1H, d, J=8.8 Hz), 6.98 (2H, d, J=8.8 Hz), 7.34 to 7.59 (8H, m), 7.76 (2H, d, J=8.4 Hz), 7.87 (1H, s).

Elemental Analysis for $C_{40}H_{46}N_4O_4S \cdot 0.25H_2O$ Calcd. C, 70.30; H, 6.86; N, 8.20. Found: C, 70.18; H, 6.98; N, 8.32.

Example 411

(Preparation of Compound 444)

To a solution of 7-[4-(2-butoxyethoxy)phenyl]-1-isobutyl-2,3-dihydro-1H-1-benzazepine-4-carboxylic acid (174 mg) in tetrahydrofuran (10 ml) was added one droplet of DMF. Then, thionyl chloride (0.038 ml) was added to the mixture, and the mixture was stirred for 1 hour under nitrogen atmosphere. This solution was slowly added dropwise to a solution of 5-amino-1-methyl-2-(((1-propylimidazol-5-yl)methyl)sulfanyl)benzimidazole (120 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was purified by basic silica gel column chromatography (ethyl acetate), to give 7-[4-(2-butoxyethoxy)phenyl]-1-isobutyl-N-[1-methyl-2-(((1-propylimidazol-5-yl)methyl)sulfanyl)benzimidazol-5-yl]-2,3-dihydro-1H-1-benzazepine-4-carboxamide (191 mg) (Compound 444) as yellow amorphous.

$^1$H-NMR (300 MHz, CDCl$_3$) δ 0.91 to 1.00 (12H, m), 1.33 to 1.46 (2H, m), 1.56 to 1.65 (2H, m), 1.80 to 1.87 (2H, m), 2.00 to 2.15 (1H, m), 2.93 to 3.00 (2H, m), 3.20 (2H, d, J=6.9 Hz), 3.33 to 3.41 (2H, m), 3.55 (2H, t, J=6.6 Hz), 3.62 (3H, s), 3.81 (2H, t, J=4.5 Hz), 3.95 (2H, t, J=7.8 Hz), 4.16 (2H, t, J=4.5 Hz), 4.67 (2H, s), 6.93 (1H, d, J=9.0 Hz), 6.98 (2H, d, J=8.7 Hz), 7.02 (1H, s), 7.21 (1H, d, J=8.7 Hz), 7.38 to 7.55 (7H, m), 7.66 (1H, s), 7.87 (1H, d, J=2.1 Hz).

Elemental Analysis for C$_{42}$H$_{52}$N$_6$O$_3$S.0.5H$_2$O. Calcd. C, 69.11; H, 7.32; N, 11.51. Found: C, 69.19; H, 7.24; N, 11.58.

Example 412

(Preparation of Compound 445)

To a solution of 7-[4-(2-butoxyethoxy)phenyl]-1-isobutyl-N-[1-methyl-2-(((1-propylimidazol-5-yl)methyl)sulfanyl)benzimidazol-5-yl]-2,3-dihydro-1H-1-benzazepine-4-carboxamide (160 mg) in dichloromethane (10 ml) was added dropwise 70% solution of 3-chloroperbenzoic acid (82 mg) in dichloromethane (10 ml) at −78° C., and the mixture was stirred for 2.5 hours at −13° C. Dimethylsulfide (0.1 ml) was added to the mixture, and the mixture was allowed to be at room temperature and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure and the obtained residue was separated and purified by basic silica gel column chromatography (hexane:ethyl acetate=1:4→ethyl acetate), and was recrystallized from hexane-ethyl acetate, to give 7-[4-(2-butoxyethoxy) phenyl]-1-isobutyl-N-[1-methyl-2-(((1-propylimidazol-5-yl)methyl)sulfinyl) benzimidazol-5-yl]-2,3-dihydro-1H-1-benzazepine-4-carboxamide (47 mg) (Compound 445) as yellow crystals.

m.p. 149.5 to 151.0° C.

$^1$H-NMR (200 MHz, CDCl$_3$) δ 0.87 to 1.00 (12H, m), 1.30 to 1.50 (2H, m), 1.55 to 1.90 (4H, m), 1.95 to 2.15 (1H, m), 2.95 to 3.05 (2H, m), 3.20 (2H, d, J=7.4 Hz), 3.35 to 3.45 (2H, m), 3.55 (2H, t, J=7.0 Hz), 3.73 (3H, s), 3.76 to 3.90 (4H, m), 4.16 (2H, t, J=5.0 Hz), 4.55 (1H, d, J=14.0 Hz), 4.84 (1H, d, J=14.0 Hz), 6.76 (1H, s), 6.91 to 7.00 (3H, m), 7.30 to 7.65 (8H, m), 7.73 (1H, s), 8.09 (1H, d, J=1.8 Hz).

Elemental Analysis for C$_{42}$H$_{52}$N$_6$O$_4$S.0.5H$_2$O Calcd. C, 67.62; H, 7.16; N, 11.27. Found: C, 67.43; H, 7.02; N, 11.29.

Example 413

(Preparation of Compound 446)

To a solution of 7-[4-(2-butoxyethoxy)phenyl]-1-isobutyl-2,3-dihydro-1H-1-benzazepine-4-carboxylic acid (252 mg) in tetrahydrofuran (10 ml) was added one droplet of DMF. Then, thionyl chloride (0.055 ml) was added to the mixture, and the mixture was stirred for 1 hour under nitrogen atmosphere. This solution was slowly added dropwise to a solution of 6-amino-1-methyl-2-(((1-propylimidazol-5-yl)methyl)sulfanyl)benzimidazole (158 mg) in pyridine (10 ml) at 0° C. under nitrogen atmosphere. The mixture was stirred overnight at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was purified by basic silica gel column chromatography (hexane:ethyl acetate=1:2→ethyl acetate), to give 7-[4-(2-butoxyethoxy)phenyl]-1-isobutyl-N-[1-methyl-2-(((1-propylimidazol-5-yl)methyl)sulfanyl)benzimidazol-6-yl]-2,3-dihydro-1H-1-benzazepine-4-carboxamide (319 mg) (Compound 446) as yellow amorphous.

$^1$H-NMR (200 MHz, CDCl$_3$) δ 0.89 to 1.00 (12H, m), 1.30 to 1.50 (2H, m), 1.55 to 1.70 (2H, m), 1.75 to 1.90 (2H, m), 2.00 to 2.20 (1H, m), 2.90 to 3.00 (2H, m), 3.20 (2H, d, J=7.4 Hz), 3.35 to 3.45 (2H, m), 3.55 (2H, t, J=7.0 Hz), 3.63 (3H, s), 3.80 (2H, t, J=4.8 Hz), 3.94 (2H, t, J=7.4 Hz), 4.16 (2H, t, J=4.8 Hz), 4.65 (2H, s), 6.91 to 7.08 (4H, m), 7.39 to 7.62 (8H, m), 7.71 (1H, s), 8.18 (1H, d, J=2.2 Hz).

Elemental Analysis for C$_{42}$H$_{52}$N$_6$O$_3$S.0.25H$_2$O Calcd. C, 69.53; H, 7.29; N, 11.58. Found: C, 69.38; H, 7.49; N, 11.33.

Example 414

(Preparation of Compound 447)

To a solution of 7-[4-(2-butoxyethoxy)phenyl]-1-isobutyl-N-[1-methyl-2-(((1-propylimidazol-5-yl)methyl)sulfanyl)benzimidazol-6-yl]-2,3-dihydro-1H-1-benzazepine-4-carboxamide (260 mg) in dichloromethane (10 ml) was added dropwise 70% solution of 3-chloroperbenzoic acid (133 mg) in dichloromethane (10 ml) at −78° C., and the mixture was stirred for 2.5 hours at −13° C. Dimethylsulfide (0.1 ml) was added to the mixture and the mixture was allowed to be at room temperature, and stirred for 30 minutes. To the mixture was added water and the mixture was extracted with ethyl acetate. The organic layer was washed with an aqueous solution of saturated sodium bicarbonate, and saturated brine, and dried over magnesium sulfate. The solvent was distilled off under reduced pressure and the obtained residue was separated and purified by basic silica gel column chromatography (hexane:ethyl acetate=2:5→ethyl acetate), to give 7-[4-(2-butoxyethoxy)phenyl]-1-isobutyl-N-[1-methyl-2-(((1-propylimidazol-5-yl) methyl)sulfinyl)benzimidazol-6-yl]-2,3-dihydro-1H-1-benzazepine-4-carboxamide (9 mg) (Compound 447) as yellow amorphous.

$^1$H-NMR (200 MHz, CDCl$_3$) δ 0.87 to 1.89 (18H, m), 1.90 to 2.20 (1H, m), 2.90 to 3.05 (2H, m), 3.20 (2H, d, J=7.4 Hz), 3.30 to 3.45 (2H, m), 3.58 (2H, t, J=6.2 Hz), 3.73 (3H, s), 3.78 to 3.89 (4H, m), 4.16 (2H, t, J=4.8 Hz), 4.56 (1H, d, J=14.2 Hz), 4.85 (1H, d, J=14.2 Hz), 6.66 to 8.26 (14H, m).

Example 415

(Preparation of Compound 448)

To a solution of 7-[4-(2-butoxyethoxy)phenyl]-1-isobutyl-2,3-dihydro-1H-1-benzazepine-4-carboxylic acid (265 mg) in tetrahydrofuran (10 ml) was added one droplet of DMF. Then, thionyl chloride (0.058 ml) was added to the mixture, and the mixture was stirred for 1 hour under nitrogen atmosphere. The solvent and excess thionyl chloride were distilled off under reduced pressure, and the residue was dissolved in tetrahydrofuran (20 ml). This solution was slowly added dropwise to a solution of (1E)-1-(4-aminophenyl)-2-(1-propylimidazol-2-yl)ethanone O-methyloxime (150 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was recrystallized from diisopropyl ether-ethyl acetate, to give 7-[4-(2-butoxyethoxy)phenyl]-1-isobutyl-N-[4-((1E)-N-methoxy-2-(1-propylimidazol-2-yl)ethanimidoyl)phenyl]-2,3-dihydro-1H-1-benzazepine-4-carboxamide (300 mg) (Compound 448) as yellow crystals.

m.p. 159.0 to 161.0° C.

$^1$H-NMR (300 MHz, CDCl$_3$) δ 0.89 to 0.98 (12H, m), 1.36 to 1.46 (2H, m), 1.50 to 1.75 (4H, m), 2.00 to 2.15 (1H, m), 2.85 to 2.95 (2H, m), 3.18 (2H, d, J=7.5 Hz), 3.30 to 3.40 (2H, m), 3.55 (2H, t, J=6.6 Hz), 3.76 to 3.82 (4H, m), 04 (3H, s), 4.16 (2H, t, J=5.4 Hz), 4.24 (2H, s), 6.75 (1H, s), 6.90 to 6.92 (2H, m), 6.98 (2H, d, J=8.7 Hz), 7.38 to 7.48 (5H, m), 7.56 (2H, d, J=8.7 Hz), 7.64 (1H, s), 7.76 (2H, d, J=8.7 Hz).

Elemental Analysis for C$_{42}$H$_{53}$N$_5$O$_4$ Calcd. C, 72.91; H, 7.72; N, 10.12. Found: C, 72.69; H, 7.80; N, 10.28.

Example 416

(Preparation of Compound 449)

To a solution of 7-[4-(2-butoxyethoxy)phenyl]-1-isobutyl-2,3-dihydro-1H-1-benzazepine-4-carboxylic acid (300 mg) in tetrahydrofuran (10 ml) was added one droplet of DMF. Then, thionyl chloride (0.065 ml) was added to the mixture, and the mixture was stirred for 1 hour under nitrogen atmosphere. The solvent and excess thionyl chloride were distilled off under reduced pressure, and the residue was dissolved in tetrahydrofuran (20 ml). This solution was slowly added dropwise to a solution of (1E)-1-(4-aminophenyl)-2-(1-propylimidazol-2-yl)ethanone O-ethyloxime (179 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was recrystallized from diisopropyl ether-ethyl acetate, to give 7-[4-(2-butoxyethoxy)phenyl]-N-[4-((1E)-N-ethoxy-2-(1-propylimidazol-2-yl)ethanimidoyl)phenyl]-1-isobutyl-2,3-dihydro-1H-1-benzazepine-4-carboxamide (390 mg) (Compound 449) as yellow crystals.

m.p. 155.5 to 156.5° C.

$^1$H-NMR (200 MHz, CDCl$_3$) δ 0.86 to 0.98 (12H, m), 1.27 to 1.48 (5H, m), 1.54 to 1.73 (4H, m), 1.95 to 2.15 (1H, m), 2.85 to 2.95 (2H, m), 3.17 (2H, d, J=7.2 Hz), 3.25 to 3.40 (2H, m), 3.55 (2H, t, J=6.6 Hz), 3.75 to 3.83 (4H, m), 4.16 (2H, t, J=5.2 Hz), 4.23 to 4.34 (4H, m), 6.74 (1H, d, J=1.6 Hz), 6.88 to 6.93 (2H, m), 6.97 (2H, d, J=9.2 Hz), 7.36 to 7.48 (5H, m), 7.56 (2H, d, J=8.8 Hz), 7.74 to 7.78 (3H, m).

Elemental Analysis for C$_{43}$H$_{51}$N$_5$O$_4$. Calcd. C, 73.16; H. 7.85; N, 9.92. Found: C, 72.92; H, 7.85; N, 9.98.

Example 417

(Preparation of Compound 450)

To a solution of 7-[4-(2-butoxyethoxy)phenyl]-1-isobutyl-2,3-dihydro-1H-1-benzazepine-4-carboxylic acid (300 mg) in tetrahydrofuran (10 ml) was added one droplet of DMF. Then, thionyl chloride (0.065 ml) was added to the mixture, and the mixture was stirred for 1 hour under nitrogen atmosphere. The solvent and excess thionyl chloride were distilled off under reduced pressure, and the residue was dissolved in tetrahydrofuran (20 ml). This solution was slowly added dropwise to a solution of (1E)-1-(4-aminophenyl)-2-(1-propylimidazol-2-yl)ethanone oxime (177 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was recrystallized from hexane-ethyl acetate, to give 7-[4-(2-butoxyethoxy)phenyl]-N-[4-((1E)-N-hydroxy-2-(1-propylimidazol-2-yl)ethane imidoyl)phenyl]-1-isobutyl-2,3-dihydro-1H-1-benzazepine-4-carboxamide (278 mg) (Compound 450) as yellow crystals.

m.p. 153.5 to 154.5° C.

$^1$H-NMR (200 MHz, CDCl$_3$) δ 0.88 to 0.98 (12H, m), 1.30 to 1.80 (6H, m), 1.95 to 2.15 (1H, m), 2.85 to 2.95 (2H, m), 3.17 (2H, d, J=7.4 Hz), 3.28 to 3.38 (2H, m), 3.55 (2H, t, J=6.8 Hz), 3.78 to 3.87 (4H, m), 4.14 (2H, t, J=4.4 Hz), 4.29 (2H, s), 6.77 (1H, s), 6.88 to 6.99 (4H, m), 7.36 to 7.48 (5H, m), 7.56 (2H, d, J=8.8 Hz), 7.68 to 7.75 (3H, m).

Elemental Analysis for C$_{41}$H$_{51}$N$_5$O$_4$. Calcd. C, 72.64; H, 7.58; N, 10.33. Found: C, 72.45; H, 7.62; N, 10.44.

Example 418

(Preparation of Compound 451)

To a solution of 7-[4-(2-butoxyethoxy)phenyl]-1-isobutyl-2,3-dihydro-1H-1-benzazepine-4-carboxylic acid (180 mg) in tetrahydrofuran (10 ml) was added one droplet of DMF. Then, thionyl chloride (0.04 ml) was added to the mixture, and the mixture was stirred for 1 hour under nitrogen atmosphere. The solvent and excess thionyl chloride were distilled off under reduced pressure, and the residue was dissolved in tetrahydrofuran (20 ml). This solution was slowly added dropwise to a solution of 2-(4-aminophenyl)-1-(1-propylimidazol-2-yl)ethanone (100 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was separated and purified by basic silica gel column chromatography (hexane:ethyl acetate=4:1→hexane:ethyl acetate=1:1), and was recrystallized from diisopropyl ether-ethyl acetate, to give 7-[4-(2-butoxyethoxy)phenyl]-1-isobutyl-N-[4-(2-oxo-2-(1-propylimidazol-2-yl)ethyl)phenyl]-2,3-dihydro-1H-1-benzazepine-4-carboxamide (64 mg) (Compound 451) as yellow crystals.

m.p. 136.5 to 138.0° C.

$^1$H-NMR (200 MHz, CDCl$_3$) δ 0.85 to 0.99 (12H, m), 1.34 to 1.45 (2H, m), 1.50 to 1.65 (2H, m), 1.71 to 1.82 (2H, m), 1.95 to 2.15 (1H, m), 2.85 to 2.95 (2H, m), 3.18 (2H, d, J=7.0 Hz), 2.90 to 3.00 (2H, m), 3.55 (2H, t, J=6.6 Hz), 3.80 (2H, t, J=5.0 Hz), 4.16 (2H, t, J=5.0 Hz), 4.31 (2H, t, J=7.6 Hz), 4.42 (2H, s), 6.91 (1H, d, J=8.8 Hz), 6.98 (2H, d, J=8.8 Hz), 7.09 (1H, d, J=0.8 Hz), 7.19 (1H, d, J=0.8 Hz), 7.30 to 7.57 (10H, m).

Elemental Analysis for C$_{41}$H$_{50}$N$_4$O$_4$ Calcd. C, 74.29; H, 7.60; N, 8.45. Found: C, 74.07; H, 7.76; N, 8.55.

Example 419

(Preparation of Compound 452)

To a solution of 7-[4-(2-butoxyethoxy)phenyl]-1-isobutyl-2,3-dihydro-1H-1-benzazepine-4-carboxylic acid (169 mg) in tetrahydrofuran (10 ml) was added one droplet of DMF. Then, thionyl chloride (0.037 ml) was added to the mixture, and the mixture was stirred for 1 hour under nitrogen atmosphere. The solvent and excess thionyl chloride were distilled off under reduced pressure, and the residue was dissolved in tetrahydrofuran (20 ml). This solution was slowly added dropwise to a solution of (1E)-2-(4-aminophenyl)-1-(1-propylimidazol-2-yl)ethanone oxime (100 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was separated and purified by basic silica gel column chromatography (hexane:ethyl acetate=1:2→ethyl acetate), and was recrystallized from diisopropyl ether-ethyl acetate, to give 7-[4-(2-butoxyethoxy)phenyl]-N-[4-((2E)-2-(hydroxyimino)-2-(1-propylimidazol-2-yl)ethyl)phenyl]-1-isobutyl-2,3-dihydro-1H-1-benzazepine-4-carboxamide (231 mg) (Compound 452) as yellow crystals.

m.p. 165.5 to 167.5° C.

$^1$H-NMR (200 MHz, CDCl$_3$) 0.82 (3H, t, J=7.4 Hz), 0.89 to 0.97 (9H, m), 1.33 to 1.45 (2H, m), 1.50 to 1.74 (4H, m), 1.95 to 2.15 (1H, m), 2.82 to 2.92 (2H, m), 3.15 (2H, d, J=7.0 Hz), 3.28 to 3.38 (2H, m), 3.55 (2H, t, J=6.6 Hz), 3.80 (2H, t, J=4.4 Hz), 4.09 to 4.17 (4H, m), 4.33 (2H, s), 6.87 to 6.91 (2H, m), 6.96 (2H, d, J=8.6 Hz), 7.10 (1H, s), 7.30 to 7.52 (9H, m), 7.72 (1H, s).

Elemental Analysis for C$_4$H$_{51}$N$_5$O$_4$. Calcd. C, 72.64; H, 7.58; N, 10.33. Found: C, 72.48; H, 7.50; N, 10.24.

Example 420

(Preparation of Compound 453)

To a solution of 7-[4-(2-butoxyethoxy)phenyl]-1-isobutyl-2,3-dihydro-1H-1-benzazepine-4-carboxylic acid (59.3 mg) in tetrahydrofuran (10 ml) was added one droplet of DMF. Then, thionyl chloride (0.013 ml) was added to the mixture, and the mixture was stirred for 1 hour under nitrogen atmosphere. The solvent and excess thionyl chloride were distilled off under reduced pressure, and the residue was dissolved in tetrahydrofuran (20 ml). This solution was slowly added dropwise to a solution of (1Z)-2-(4-aminophenyl)-1-(1-propylimidazol-2-yl)ethanone oxime (35 mg) in pyridine (10 ml) at 0° C. under nitrogen atmosphere. The mixture was stirred for 1 hour at room temperature under nitrogen atmosphere, water was added to the mixture, and the mixture was extracted with ethyl acetate. The organic layer was washed with water and saturated brine, and dried over magnesium sulfate. The solvent was distilled off under reduced pressure and the obtained residue was separated and purified by basic silica gel column chromatography (hexane:ethyl acetate=1:4), and was recrystallized from diisopropyl ether-ethyl acetate, to give 7-[4-(2-butoxyethoxy)phenyl]-N-[4-((2Z)-2-(hydroxyimino)-2-(1-propylimidazol-2-yl)ethyl)phenyl]-1-isobutyl-2,3-dihydro-1H-1-benzazepine-4-carboxamide (68 mg) (Compound 453) as yellow crystals.

m.p. 187.5 to 189.5° C.

$^1$H-NMR (200 MHz, CDCl$_3$) δ 0.67 (3H, t, J=7.4 Hz), 0.89 to 0.98 (9H, m), 1.30 to 1.65 (6H, m), 1.95 to 2.15 (1H, m), 2.85 to 2.95 (2H, m), 3.17 (2H, d, J=7.4 Hz), 3.30 to 3.40 (2H, m), 3.55 (2H, t, J=6.6 Hz), 3.63 (2H, t, J=7.4 Hz), 3.80 (2H, t, J=4.8 Hz), 3.97 (2H, s), 4.15 (2H, t, J=4.8 Hz), 6.88 (1H, s), 6.93 to 6.99 (3H, m), 7.10 to 7.14 (3H, m), 7.39 to 7.52 (8H, m).

Elemental Analysis for C$_{41}$H$_{51}$N$_5$O$_4$·0.25H$_2$O. Calcd. C, 72.17; H, 7.61; N, 10.26. Found: C, 72.08; H, 7.41; N, 10.21.

Example 421

(Preparation of Compound 454)

(−)-4-(((1-propylimidazol-5-yl) methyl) sulfinyl) aniline.di-p-toluoyl-D-tartarate 1hydrate (894 mg) was dissolved in ethyl acetate (10 ml) and 1N hydrochloric acid (4.6 ml) to separate the layers. To the aqueous layer was added 25% aqueous solution of potassium carbonate (4.6 ml) and the mixture was extracted with 2-propanol-ethyl acetate (1:4) twice. The organic layer was collected, washed with saturated brine, and dried over magnesium sulfate, and the solvent was distilled off under reduced pressure. To the obtained residue was added tetrahydrofuran, and the solvent was distilled off again under reduced pressure to give (−)-4-(((1-propylimidazol-5-yl)methyl)sulfinyl)aniline. Then, to a solution of 7-[4-(2-butoxyethoxy)phenyl]-1-cyclopropylmethyl-2,3-dihydro-1H-1-benzazepine-4-carboxylic acid (450 mg) in tetrahydrofuran (10 ml) were added one droplet of DMF and oxalyl chloride (0.12 ml) under nitrogen atmosphere and the mixture was stirred for 30 minutes. This solution was added dropwise to a solution of (−)-4-(((1-propylimidazol-5-yl)methyl)sulfinyl) aniline and pyridine (2.17 ml) in tetrahydrofuran (20 ml) at 0° C. under nitrogen atmosphere. The mixture was allowed to be at room temperature, stirred for 3 hours, and water was added to the mixture, and the mixture was extracted with ethyl-acetate. The organic layer was washed with 10% aqueous solution of acetic acid twice, an aqueous solution of saturated sodium bicarbonate twice and saturated brine once, and dried over magnesium sulfate. The solvent was distilled off under reduced pressure, and the residue was separated and purified by basic silica gel column chromatography (ethyl acetate→ethyl acetate:methanol=50:1), to give (−)-7-[4-(2-butoxyethoxy)phenyl]-1-cyclopropylmethyl-N-[4-[[[1-propylimidazol-5-yl]methyl]sulfinyl]phenyl]-2,3-dihydro-1H-1-benzazepine-4-carboxamide (411 mg) (Compound 454) as yellow amorphous.

$^1$H-NMR (300 MHz, CDCl$_3$) δ 0.28 to 0.33 (2H, m), 0.62 to 0.68 (2H, m), 0.88 to 0.96 (6H, m), 1.10 to 1.20 (1H, m), 1.36 to 1.43 (2H, m), 1.56 to 1.76 (2H, m), 2.90 to 3.00 (2H, m), 3.26 (2H, d, J=6.3 Hz), 3.45 to 3.48 (2H, m), 3.53 (2H, t, J=6.6 Hz), 3.75 to 3.82 (4H, m), 4.02 (1H, d, J=14.1 Hz), 4.09 (1H, d, J=14.1 Hz), 4.15 (2H, t, J=5.1 Hz), 6.56 (1H, s), 4.92 (1H, s), 6.95 to 6.99 (3H, m), 7.34 (2H, d, J=9.0 Hz), 7.40 to 7.51 (6H, m), 7.73 (2H, d, J=9.0 Hz), 7.87 (1H, s).

Elemental Analysis for C$_{40}$H$_{48}$N$_4$O$_4$S·0.5H$_2$O Calcd. C, 69.64; H, 7.16; N, 8.12. Found: C, 69.54; H, 7.29; N, 8.12.

[α]$_D$[=−129.7° (C=0.4790%, ethanol solution)

Example 422

(Preparation of Compound 455)

(−)-4-(((1-propylimidazol-5-yl)methyl)sulfinyl)aniline di-p-toluoyl-D-tartarate 1hydrate (174 mg) was dissolved in ethyl acetate (5 ml) and 1N hydrochloric acid (1.77 ml) to separate the layers. To the aqueous layer was added 25% aqueous solution of potassium carbonate (1.77 ml) and the mixture was extracted with 2-propanol-ethyl acetate (1:4). The organic layer was washed with saturated brine, and dried over magnesium sulfate, and the solvent was distilled off under reduced pressure. To the obtained residue was added tetrahydrofuran, and the solvent was distilled off again under reduced pressure to give (−)-4-(((1-propylimidazol-5-yl)methyl)sulfinyl)aniline. Then, to a solution of 7-[4-(2-butoxyethoxy)phenyl]-1-[(1-methylpyrazol-5-yl)methyl]-2,3-dihydro-1H-1-benzazepine-4-carboxylic acid (95 mg) in dichloromethane (10 ml) were added one droplet of DMF and oxalyl chloride (0.023 ml) under nitrogen atmosphere and the mixture was stirred for 30 minutes. This solution was added dropwise to a solution of (−)-4-(((1-propylimidazol-5-yl)methyl)sulfinyl)aniline and pyridine (0.42 ml) in tetrahydrofuran (10 ml), at 0° C. under nitrogen atmosphere. The mixture was allowed to be at room temperature and stirred for 3 hours, and water was added to the mixture, and the mixture was extracted with ethyl acetate. The organic layer was washed with 10% acetic acid solution twice, an aqueous solution of saturated sodium bicarbonate twice, and saturated brine once, and dried over magnesium sulfate. The solvent was distilled off under reduced pressure, and the residue was separated and purified by basic silica gel column chromatography (ethyl acetate→ethyl acetate: methanol=11:1), to give (−)-7-[4-(2-butoxyethoxy)phenyl]-1-[(1-methylpyrazol-5-yl)methyl]-N-[4-[[[1-propylimidazol-5-yl]methyl]sulfinyl]phenyl]-2,3-dihydro-1H-1-benzazepine-4-carboxamide (81 mg) (Compound 455) as yellow amorphous.

$^1$H-NMR (300 MHz, CDCl$_3$) δ 0.88 to 0.96 (6H, m), 1.36 to 1.43 (2H, m), 1.56 to 1.76 (4H, m), 2.80 to 2.87 (2H, m), 3.30 to 3.40 (2H, m), 3.55 (2H, t, J=6.6 Hz), 3.75 to 3.82 (4H, m), 3.90 (3H, s), 4.01 (1H, d, J=14.1 Hz), 4.09 (1H, d, J=14.1 Hz), 4.15 (2H, t, J=4.8 Hz), 4.44 (2H, s), 6.55 (1H, s), 6.96 to 6.99 (3H, m), 7.31 to 7.35 (3H, m), 7.41 to 7.54 (7H, m), 7.73 (2H, d, J=8.7 Hz), 7.88 (1H, s).

Elemental Analysis for C$_{41}$H$_{48}$N$_6$O$_4$S.0.75H$_2$O Calcd. C, 67.05; H, 6.79; N, 11.44. Found: C, 66.85; H, 6.94; N, 11.21.

[α]$_D$=−123.7° (C=0.3925%, ethanol solution)

Reference Example 1 p-Fluorobenzyl cyanide (4.1 g), 2-bromo-4-methylpyridine (5.2 g) and sodium p-toluene sulfinate (5.4 g) were suspended in THF (50 ml), and to the solution was added a suspension of 40% sodium hydride (1.2 g) in THF (5 ml) under ice-cooling. The mixture was refluxed for 3 hours, the solvent was distilled off, water was added to the mixture and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/hexane), to give 2-(α-cyano-4-fluorobenzyl)-4-methylpyridine (3.1 g) as brown oil.

$^1$H-NMR (d, CDCl$_3$) 2.36 (3H, s), 5.26 (1H, s), 7.02 to 7.11 (3H, m), 7.21 (1H, s), 7.39 to 7.46 (2H, m), 8.44 (1H, d, J=5.0 Hz).

IR (neat) ν: 2247, 1605, 1508 cm$^{-1}$.

Reference Example 2

2-(α-cyano-4-fluorobenzyl)-4-methylpyridine (3.1 g) and potassium carbonate (2.9 g) were suspended in 20% hydrated dimethylsulfoxide (150 ml), and the suspension was stirred overnight. The mixture was poured into water, and the mixture was extracted with ethyl acetate. The organic layer was washed with water and saturated brine, dried over anhydrous magnesium sulfate, and then, the solvent was distilled off. The residue was purified by silica gel column chromatography (elution solvent: ethyl acetate/hexane), to give 2-(4-fluorobenzoyl)-4-methylpyridine (1.6 g) as brown crystals.

mp 98 to 100° C.

$^1$H-NMR (d, CDCl$_3$) 2.48 (3H, s), 7.11 to 7.20 (2H, m), 7.30 to 7.33 (1H, m), 7.88 (1H, s), 8.12 to 8.19 (2H, m), 8.57 (1H, d, J=5.0 Hz).

IR (KBr) ν: 1669, 1597 cm$^{-1}$.

Anal. Calcd for C$_{13}$H$_{10}$FNO: C, 72.55; H, 4.68; N, 6.51. Found: C, 72.61; H, 4.63; N, 6.48.

Reference Example 3

2-(4-fluorobenzoyl)-4-methylpyridine (1.6 g) and sodium azide (2.4 g) were suspended in dimethylsulfoxide (15 ml) under nitrogen atmosphere 90° C., and the mixture was heated with stirring overnight. The mixture was poured into water, and the mixture was extracted with ethyl acetate. The organic layer was washed with water and saturated brine, and dried over anhydrous magnesium sulfate, and then, the solvent was distilled off. The residue was dissolved in tetrahydrofuran (50 ml), and to the solution was added aluminum lithium hydride (0.66 g) under ice-cooling, and the mixture was stirred overnight at room temperature under nitrogen atmosphere. To the solution were added water (0.66 ml), 15% aqueous solution of sodium hydroxide (0.66 ml) and water (1.98 ml) under ice-cooling, the mixture was stirred and dried over anhydrous magnesium sulfate. After filtration, the solvent of the filtrate was distilled off, to give (4-aminophenyl)(4-methylpyridin-2-yl)methanol (1.8 g) as pale yellow crystals.

mp 156 to 158° C.

$^1$H-NMR (d, CDCl$_3$) 2.28 (3H, s), 3.65 (2H, br), 5.18 (1H, br), 5.60 (1H, s), 6.65 (2H, d, J=8.4 Hz), 6.93 (1H, s), 6.99 (1H, d, J=5.0 Hz), 7.14 (2H, d, J=8.4 Hz), 8.40 (1H, d, J=5.0 Hz).

IR (KBr) ν: 1609, 1516 cm$^{-1}$.

Anal. Calcd for C$_{13}$H$_{14}$N$_2$O.0.1H$_2$O: C, 72.26; H, 6.62; N, 12.97. Found: C, 72.34; H, 6.62; N, 12.69.

Reference Example 4

7-[4-(2-butoxyethoxy)phenyl]-1-trifluoroacetyl-2,3-dihydro-1H-1-benzazepine-4-carboxylic acid (0.5 g), (4-aminophenyl) (4-methylpyridin-2-yl)methanol (0.24 g) and 1-hydroxybenzotriazole (0.16 g) were dissolved in. N,N-dimethylformamide (5 ml), and to the solution were added 1-ethyl-3-(3-dimethylaminopropyl)carbodiimide hydrochloride (0.4 g), triethylamine (0.44 ml) and 4-dimethylaminopyridine (catalytic amout) at room temperature under ice-cooling, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was washed with diethyl ether-hexane, to give 7-[4-(2-butoxyethoxy)phenyl]-N-[4-[hydroxy (4-methylpyridin-2-yl)methyl]phenyl]-1-trifluoroacetyl-2,3-dihydro-1H-1-benzazepine-4-carboxamide (0.67 g) as colorless crystals.

mp 101 to 105° C.

$^1$H-NMR (d, CDCl$_3$) 0.93 (3H, t, J=7.2 Hz), 1.30 to 1.49 (2H, m), 1.58 to 1.69 (2H, m), 2.30 (3H, s), 2.93 to 3.15 (3H, m), 3.56 (2H, t, J=6.6 Hz), 3.82 (2H, t, J=5.0 Hz), 4.18 (2H, t, J=5.0 Hz), 4.79 to 4.90 (1H, m), 5.39 (1H, br), 5.69 (1H, s), 6.93 (1H, s), 7.00 to 7.04 (3H, m), 7.31 to 7.65 (11H, m), 8.41 (1H, d, J=5.2 Hz).

IR (KBr) ν: 2959, 2934, 2874, 1694, 1609, 1518, 1497 cm$^{-1}$.

Anal. Calcd for $C_{38}H_{38}F_3N_3O_5$: C, 67.74; H, 5.69; N, 6.24. Found: C, 67.47; H, 5.81; N, 6.42

Reference Example 5

7-[4-(2-butoxyethoxy)phenyl]-N-[4-[hydroxy(4-methylpyridin-2-yl) methyl]phenyl]-1-trifluoroacetyl-2,3-dihydro-1H-1-benzazepine-4-carboxamide (0.6 g) was dissolved in dichloromethane (20 ml), and to the solution was added 3-chloroperbenzoic acid (0.3 g) under ice-cooling and the mixture was stirred overnight at room temperature. An aqueous solution of sodium thiosulfate was added to the mixture. The mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: ethyl acetate/methanol/triethylamine), to give 7-[4-(2-butoxyethoxy) phenyl]-N-[4-[hydroxy(4-methyl-1-oxidopyridin-2-yl)methyl]phenyl]-1-trifluoroacetyl-2,3-dihydro-1H-1-benzazepine-4-carboxamide (0.32 g) as colorless crystals.

mp 121 to 123° C.

$^1$H-NMR (d, CDCl$_3$) 0.93 (3H, t, J=7.3 Hz), 1.26 to 1.45 (2H, m), 1.55 to 1.65 (2H, m), 2.29 (3H, s), 2.94 to 3.17 (3H, m), 3.56 (2H, t, J=6.6 Hz), 3.82 (2H, t, J=5.0 Hz), 4.18 (2H, t, J=5.0 Hz), 4.78 to 4.88 (1H, m), 6.00 to 6.03 (1H, m), 6.70 to 6.75 (2H, m), 7.00 to 7.06 (3H, m), 7.33 (1H, d, J=8.4 Hz), 0.45 to 7.22 (9H, m), 8.13 (1H, d, J=6.2 Hz).

IR (KBr) ν: 2870, 1700 cm$^{-1}$.

Anal. Calcd for $C_{38}H_{38}F_3N_3O_{60.25}H_2O$: C, 65.74; H, 5.59; N, 6.05. Found: C, 65.72; H, 5.64; N, 5.93.

Reference Example 6

2-bromopyridine (1.4 ml) was dissolved in diethylether (40 ml), and the mixture was cooled to −78° C. under argon atmosphere 1.6M n-butyllithium hexane solution (9.1 ml) was added dropwise to the solution, and the mixture was stirred for 30 minutes. The reaction solution was added dropwise to a solution of 2-methoxy-4-nitrobenzaldehyde (2.4 g) in tetrahydrofuran (600 ml) under argon atmosphere at −78° C. The mixture was allowed to be at room temperature and stirred overnight, water was added to the mixture, and the mixture was concentrated. The mixture was extracted with ethyl acetate, organic layer was washed with water and saturated brine, and dried over anhydrous magnesium sulfate, and then, the solvent was distilled off. The residue was purified by silica gel column chromatography (elution solvent: ethyl acetate/hexane), to give (2-methoxy-4-nitrophenyl)(pyridin-2-yl)methanol (1.9 g) as pale yellow crystals.

mp 126 to 129° C. (dec.).

H-NMR (d, CDCl$_3$) 4.00 (3H, s), 5.40 (1H, d, J=4.2 Hz), 6.24 (1H, d, J=4.2 Hz), 7.19 to 7.31 (2H, m), 7.57 (1H, d, J=8.4 Hz), 7.64 (1H, dt, J=1.8, 7.7 Hz), 7.76 (1H, d, J=2.2 Hz), 7.84 (1H, dd, J=1.8, 8.4 Hz), 8.56 (1H, d, J=5.2 Hz).

IR (KBr) ν: 1526, 1348 cm$^{-1}$.

Anal. Calcd for $C_{13}H_{12}N_2O_4$: C, 60.00; H, 4.65; N, 10.76. Found: C, 60.09; H, 4.58; N, 10.60

Reference Example 7

(2-methoxy-4-nitrophenyl)(pyridin-2-yl)methanol (0.5 g) was dissolved in ethyl acetate (25 ml), and the solution was reduced by catalytic hydrogenation overnight with 10% palladium-carbon of 50% hydration (50 mg). The catalyst was removed, and the solvent of the filtrate was distilled off to give (4-amino-2-methoxyphenyl)(pyridin-2-yl)methanol (0.4 g) as colorless crystals.

mp 123 to 125° C. (dec.).

$^1$H-NMR (d, CDCl$_3$) 3.67 (2H, br), 3.80 (3H, s), 5.00 (1H, br), 6.08 (1H, s), 6.21-6.27 (2H, m), 6.98 (1H, d, J=8.8 Hz), 7.12-7.26 (2H, m), 7.60 (1H, dt, J=1.8, 7.7 Hz), 8.54 (1H, d, J=4.4 Hz).

IR (KBr) ν: 1615, 1591, 1508 cm$^{-1}$.

Anal. Calcd for $C_{13}H_{14}N_2O_2 \cdot 0.1H_2O$: C, 67.28; H, 6.17; N, 12.07. Found: C, 67.36; H, 6.26; N, 11.79.

Reference Example 8

7-[4-(2-butoxyethoxy) phenyl]-1-trifluoroacetyl-2,3-dihydro-1H-1-benzazepine-4-carboxylic acid (0.5 g), (4-amino-2-methoxyphenyl)(pyridin-2-yl)methanol (0.26 g) and 1-hydroxybenzotriazole (0.18 g) were dissolved in N,N-dimethylformamide (5 ml), and to the solution were added 1-ethyl-3-(3-dimethylaminopropyl)carbodiimide hydrochloride (0.4 g), triethylamine (0.44 ml), 4-dimethylaminopyridine (catalytic amout) under ice-cooling at room temperature, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy) phenyl]-N-[4-[hydroxy(pyridin-2-yl)methyl]-3-methoxyphenyl]-1-trifluoroacetyl-2,3-dihydro-1H-1-benzazepine-4-carboxamide (0.56 g) as colorless crystals.

mp 123 to 125° C.

$^1$H-NMR (d, CDCl$_3$) 0.93 (3H, t, J=7.2 Hz), 1.26 to 1.65 (4H, m), 2.90 to 3.25 (3H, m), 3.56 (2H, t, J=6.8 Hz), 3.82 (2H, t, J=4.9 Hz), 3.91 (3H, s), 4.18 (2H, t, J=4.9 Hz), 4.80 to 4.90 (1H, m), 5.23 (1H, d, J=5.0 Hz), 6.18 (1H, d, J=5.0 Hz), 6.84 to 6.88 (1H, m), 7.03 (2H, d, J=8.4 Hz), 7.19 to 7.65 (11H, m), 8.55 (1H, d, J=4.8 Hz).

IR (KBr) ν: 2932, 2876, 2841, 1700 cm$^{-1}$.

Anal. Calcd for $C_{38}H_{38}F_3N_3O_6$: C, 66.17; H, 5.55; N, 6.09. Found: C, 65.99; H, 5.69; N, 5.74.

Reference Example 9

7-[4-(2-butoxyethoxy)phenyl]-N-[4-[hydroxy(pyridin-2-yl)methyl]-3-methoxyphenyl]-1-trifluoroacetyl-2,3-dihydro-1H-1-benzazepine-4-carboxamide (0.55 g) was dissolved in dichloromethane (25 ml), and to the solution was added 3-chloroperbenzoic acid (0.26 g) under ice-cooling and the mixture was stirred overnight at room temperature. An aqueous solution of sodium thiosulfate was added to the mixture, and the mixture was concentrated and extracted with ethyl acetate. The organic layer was washed with sodium bicarbonate solution, water and saturated brine, and dried over anhydrous magnesium sulfate and the solvent was distilled off, to give 7-[4-(2-butoxyethoxy)phenyl]-N-[4-[hydroxy(1-oxidopyridin-2-yl)methyl]-3-methoxyphenyl]-1-trifluoroacetyl-2,3-dihydro-1H-1-benzazepine-4-carboxamide (0.44 g) as colorless amorphous.

¹H-NMR (d, CDCl₃) 0.93 (3H, t, J=7.2 Hz), 1.26 to 1.49 (2H, m), 1.57 to 1.69 (2H, m), 2.90 to 3.30 (3H, m), 3.56 (2H, t, J=6.6 Hz), 3.74 to 3.84 (5H, m), 4.18 (2H, t, J=4.7 Hz), 4.78 to 4.90 (1H, s), 6.33 (1H, m), 6.65 to 6.75 (1H, m), 6.90 to 7.05 (4H, m), 7.20 to 7.36 (2H, m), 7.46 to 7.69 (9H, m), 8.22 to 8.26 (1H, m).

IR (KBr) ν: 2959, 2932, 2867, 1696, 1609, 1499 cm⁻¹.

Anal. Calcd for C₃₈H₃₈F₃N₃O₇·0.5H₂O: C, 63.86; H, 5.50; N, 5.88. Found: C, 64.07; H, 5.36; N, 5.79.

Reference Example 10

2-bromopyridine (0.68 ml) was dissolved in diethylether (20 ml), and the mixture was cooled to −78° C. under argon atmosphere. 1.6M n-butyllithium hexane solution (4.5 ml) was added dropwise to the solution, and the mixture was stirred for 30 minutes. The reaction solution was added dropwise to a solution of 2-chloro-4-nitrobenzaldehyde (1.1 g) in diethylether (20 ml) and tetrahydrofuran (30 ml) under argon atmosphere at −78° C. The mixture was allowed to be at room temperature and stirred overnight, and water was added to the mixture. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give (2-chloro-4-nitrophenyl)(pyridin-2-yl)methanol (0.47 g) as yellow crystals.

mp 124 to 127° C.

¹H-NMR (d, CDCl₃) 5.61 (1H, d, J=2.2 Hz), 6.32 (1H, d, J=2.2 Hz), 7.24 to 7.30 (2H, m), 7.63 to 7.72 (2H, m), 8.10 (1H, dd, J=2.6, 8.2 Hz), 8.28 (1H, d, J=2.6 Hz), 8.58 to 8.62 (1H, m).

IR (KBr) ν: 3100, 2868, 2718, 1597, 1522, 1352 cm⁻¹.

Anal. Calcd for C₁₂H₉ClN₂O₃: C, 54.46; H, 3.43; N, 10.58. Found: C, 54.61; H, 3.38; N, 10.38.

Reference Example 11

(2-chloro-4-nitrophenyl)(pyridin-2-yl)methanol (1 g) was dissolved in tetrahydrofuran (15 ml), ethanol (15 ml) and water (15 ml), and sodium hydrosulfide (3.3 g) was added to the mixture, and the mixture was refluxed for 30 minutes. After concentration, the mixture was extracted with ethyl acetate. The organic layer was washed with water and saturated brine, and dried over anhydrous magnesium sulfate. The solvent was distilled off, to give (4-amino-2-chlorophenyl)(pyridin-2-yl)methanol (0.21 g) as colorless crystals.

mp 142 to 146° C. (dec.).

¹H-NMR (d, CDCl₃) 3.71 (2H, br), 5.32 (1H, d, J=4.2 Hz), 6.15 (1H, d, J=4.2 Hz), 6.53 (1H, dd, J=2.4, 8.4 Hz), 6.70 (1H, d, J=2.4 Hz), 7.08 (1H, d, J=8.4 Hz), 7.17 to 7.23 (2H, m), 7.62 (1H, dt, J=1.8, 7.7 Hz), 8.56 (1H, d, J=4.4 Hz).

IR (KBr) ν: 1593, 1501 cm⁻¹.

Anal. Calcd for C₁₂H₁₁ClN₂O: C, 61.41; H, 4.72; N, 11.94. Found: C, 61.11; H, 4.82; N, 11.61

Reference Example 12

7-[4-(2-butoxyethoxy)phenyl]-1-trifluoroacetyl-2,3-dihydro-1H-1-benzazepine-4-carboxylic acid (0.81 g), (4-amino-2-chlorophenyl)(pyridin-2-yl)methanol (0.4 g) and 1-hydroxybenzotriazole (0.34 g) were dissolved in N,N-dimethylformamide (15 ml), and to the solution were added 1-ethyl-3-(3-dimethylaminopropyl)carbodiimide hydrochloride (0.66 g), triethylamine (0.71 ml) and 4-dimethylaminopyridine (catalytic amout) under ice-cooling at room temperature, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), and basic silica gel column chromatography (elution solvent: ethyl acetate/hexane), to give 7-[4-(2-butoxyethoxy) phenyl]-N-[3-chloro-4-[hydroxy(pyridin-2-yl)methyl]phenyl]-1-trifluoroacetyl-2,3-dihydro-1H-1-benzazepine-4-carboxamide (0.37 g) as yellow amorphous.

¹H-NMR (d, CDCl₃) 0.93 (3H, t, J=7.1 Hz), 1.29 to 1.49 (2H, m), 1.54 to 1.72 (2H, m), 2.90 to 3.19 (3H, m), 3.56 (2H, t, J=6.6 Hz), 3.81 (2H, t, J=4.8 Hz), 4.17 (2H, t, J=4.8 Hz), 4.80 to 4.86 (1H, m), 5.51 (1H, s), 6.23 (1H, s), 7.01 (2H, d, J=8.8 Hz), 7.19 to 7.68 (11H, m), 7.78 to 7.82 (2H, m), 8.56 (1H, d, J=4.4 Hz).

IR (KBr) ν: 2957, 2938, 2868, 1696 cm⁻¹.

Reference Example 13

7-[4-(2-butoxyethoxy)phenyl]-N-[3-chloro-4-[hydroxy(pyridin-2-yl)methyl]phenyl]-1-trifluoroacetyl-2,3-dihydro-1H-1-benzazepine-4-carboxamide (0.37 g) was dissolved in dichloromethane (25 ml), and to the solution was added 3-chloroperbenzoic acid (0.2 g) under ice-cooling and the mixture was stirred overnight at room temperature. An aqueous solution of sodium thiosulfate was added to the mixture, the mixture was concentrated, and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[3-chloro-4-[hydroxy(1-oxidopyridin-2-yl)methyl]phenyl]-1-trifluoroacetyl-2,3-dihydro-1H-1-benzazepine-4-carboxamide (0.24 g) as pale red oil.

¹H-NMR (d, CDCl₃) 0.93 (3H, t, J=7.2 Hz), 1.26 to 1.48 (2H, m), 1.54 to 1.68 (2H, m), 92 to 3.22 (3H, m), 3.55 (2H, t, J=6.7 Hz), 3.81 (2H, t, J=4.7 Hz), 4.17 (2H, t, J=4.7 Hz), 4.78 to 4.88 (1H, m), 6.38 (1H, s), 6.60 (1H, s), 6.89 to 7.02 (3H, m), 7.23 to 7.34 (2H, m), 7.46 to 7.56 (6H, m), 7.63 to 7.71 (2H, m), 7.87 (1H, d, J=6.2 Hz), 8.21 to 8.35 (2H, m).

1.5 Reference Example 14

2-bromopyridine (0.9 ml) was dissolved in diethylether (30 ml), and the mixture was cooled to −78° C. under argon atmosphere. 1.6M n-butyllithium hexane solution (5.9 ml) was added dropwise to the solution, and the mixture was stirred for 30 minutes. The reaction solution was added dropwise to a solution of 2-methyl-4-nitrobenzaldehyde (1.3 g) in tetrahydrofuran (30 ml) at −78° C. The mixture was allowed to be at room temperature and stirred overnight, and water was added to the mixture. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give (2-methyl-4-nitrophenyl)(pyridin-2-yl)methanol (0.84 g) as pale brown crystals.

mp 119 to 121° C. (dec).

¹H-NMR (d, CDCl₃) 2.46 (3H, s), 5.22 (1H, s), 6.02 (1H, s), 7.00 (1H, d, J=7.8 Hz), 7.23 to 7.30 (1H, m), 7.48 (1H, d, J=8.8 Hz), 7.66 (1H, dt, J=1.8, 7.7 Hz), 8.00 to 8.05 (2H, m), 8.62 (1H, d, J=3.6 Hz).

IR (KBr) ν: 1590, 1520, 1348 cm⁻¹.

Anal. Calcd for C₁₃H₁₂N₂O₃: C, 63.93; H, 4.95; N, 11.47. Found: C, 64.12; H, 4.86; N, 11.34.

Reference Example 15

(2-methyl-4-nitrophenyl)(pyridin-2-yl)methanol (0.83 g) was dissolved in ethanol (50 ml), and the solution was reduced by catalytic hydrogenation overnight with 10% palladium-carbon of 50% hydration (50 mg). The catalyst was removed, and the solvent of the filtrate was distilled off and the residue was purified by silica gel column chromatography (elution solvent: ethyl acetate/hexane), to give (4-amino-2-methylphenyl)(pyridin-2-yl)methanol (0.42 g) as colorless crystals.

mp 102 to 104° C.

¹H-NMR (d, CDCl₃) 2.24 (3H, s), 3.60 (2H, br), 5.00 (1H, d, J=3.2 Hz), 5.86 (1H, d, J=3.2 Hz), 6.45 to 6.50 (2H, m), 6.95 (1H, d, J=8.0 Hz), 7.05 (1H, d., J=7.8 Hz), 7.15 to 7.22 (1H, m), 7.60 (1H, dt, J=1.4, 7.7 Hz), 8.57 (1H, d, J=5.2 Hz).

IR (KBr) ν: 3350, 1610 cm⁻¹.

Anal. Calcd for C₁₃H₁₄N₂O: C, 72.87; H, 6.59; N, 13.07. Found: C, 72.68; H, 6.23; N, 13.00.

Reference Example 16

7-[4-(2-butoxyethoxy)phenyl]-1-trifluoroacetyl-2,3-dihydro-1H-1-benzazepine-4-carboxylic acid (0.94 g), (4-amino-2-methylphenyl)(pyridin-2-yl)methanol (0.42 g) and 1-hydroxybenzotriazole (0.45 g) were dissolved in N,N-dimethylformamide (15 ml), and to the solution were added 1-ethyl-3-(3-dimethylaminopropyl)carbodiimide hydrochloride (0.75 g), triethylamine (0.82 ml) and 4-dimethylaminopyridine (catalytic amout) under ice-cooling at room temperature, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[hydroxy(pyridin-2-yl)methyl]-3-methylphenyl]-1-trifluoroacetyl-2,3-dihydro-1H-1-benzazepine-4-carboxamide (0.95 g) as colorless crystals.

mp 122 to 125° C.

¹H-NMR (d, CDCl₃) 0.93 (3H, t, J=7.1 Hz), 1.30 to 1.68 (4H, m), 2.33 (3H, s), 2.91 to 3.19 (3H, m), 3.56 (2H, t, J=6.6 Hz), 3.81 (2H, t, J=4.9 Hz), 4.17 (2H, t, J=4.9 Hz), 4.80 to 4.84 (1H, m), 5.19 (1H, s), 5.93 (1H, s), 6.99 to 7.04 (3H, m), 7.19 to 7.41 (6H, m), 7.50 to 7.66 (6H, m), 8.58 (1H, d, J=5.2 Hz).

IR (KBr) ν: 2957, 2932, 2872, 1694, 1609, 1593, 1520, 1497 cm⁻¹.

Anal. Calcd for C₃₈H₃₈F₃N₃O₅: C, 67.74; H, 5.69; N, 6.24. Found: C, 67.47; H, 5.65; N, 6.22.

Reference Example 17

7-[4-(2-butoxyethoxy)phenyl]-N-[4-[hydroxy(pyridin-2-yl)methyl]-3-methylphenyl]-1-trifluoroacetyl-2,3-dihydro-1H-1-benzazepine-4-carboxamide (0.95 g) was dissolved in dichloromethane (25 ml), and to the solution was added 3-chloroperbenzoic acid (0.42 g) at: room temperature under ice-cooling and the mixture was stirred for 3.5 hours. An aqueous solution of sodium thiosulfate was added to the mixture, the mixture was concentrated, and extracted with ethyl acetate. The organic layer was washed with sodium bicarbonate solution, water and saturated brine, and dried over anhydrous magnesium sulfate, and then, the solvent was evaporated, to give 7-[4-(2-butoxyethoxy)phenyl]-N-[4-[hydroxy(1-oxidopyridin-2-yl)methyl]-3-methylphenyl]-1-trifluoroacetyl-2,3-dihydro-1H-1-benzazepine-4-carboxamide (0.82 g) as colorless crystals.

mp 142 to 144° C.

¹H-NMR (d, CDCl₃) 0.93 (3H, t, J=7.4 Hz), 1.31 to 1.65 (4H, m), 2.23 (3H, s), 2.95 to 3.25 (3H, m), 3.56 (2H, t, J=6.8 Hz), 3.82 (2H, t, J=5.0 Hz), 4.18 (2H, t, J=5.0 Hz), 4.79 to 4.93 (1H, m), 6.28 (2H, s), 6.74 (1H, dd, J=2.5, 7.7 Hz), 7.03 (2H, d, J=8.6 Hz), 7.18 to 7.66 (11H, m), 8.31 (1H, dd, J=1.0, 6.6 Hz).

IR (KBr) ν: 2868, 1696 cm⁻¹.

Anal calcd for C₃₈H₃₈F₃N₃O₆ 0.5H₂O: C, 65.32; H, 5.63; N, 6.01. Found: C, 65.56; H, 5.37; N, 5.98.

Reference Example 18

2-bromo-4-methylpyridine (1.5 ml) was dissolved in diethylether (50 ml), and the mixture was cooled to −78° C. under argon atmosphere. 1.6M n-butyllithium hexane solution (8.3 ml) was added dropwise, and the mixture was stirred for 1 hour. The reaction solution was added dropwise to a solution of 2-methoxy-4-nitrobenzaldehyde (2 g) in tetrahydrofuran (300 ml) under argon atmosphere at −78° C. The mixture was allowed to be at room temperature and stirred overnight, and water was added to the mixture. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give (2-methoxy-4-nitrophenyl)(4-methylpyridin-2-yl)methanol (2.2 g) as pale brown oil.

¹H-NMR (d, CDCl₃) 2.31 (3H, s), 4.00 (3H, s), 5.44 (1H, br), 6.19 (1H, s), 7.02 to 7.05 (2H, m), 7.53 (1H, d, J=8.4 Hz), 7.76 (1H, d, J=1.8 Hz), 7.83 (1H, dd, J=2.0, 8.4 Hz), 8.40 (1H, d, J=4.8 Hz).

IR (neat) ν: 1609, 1526 cm⁻¹.

Reference Example 19

(2-methoxy-4-nitrophenyl)(4-methylpyridin-2-yl)methanol (2.2 g) was dissolved in ethyl acetate (50 ml) and ethanol (50 ml), and the solution was reduced by catalytic hydrogenation overnight with 10% palladium-carbon of 50% hydration (150 mg). The catalyst was removed, and the solvent of the filtrate was distilled off. The residue was purified by silica gel column chromatography (elution solvent: ethyl acetate/hexane), to give (4-amino-2-methoxyphenyl)(4-methylpyridin-2-yl)methanol (0.65 g) as pale yellow crystals.

mp 114 to 117° C.

¹H-NMR (d, CDCl₃) 2.29 (3H, s), 3.67 (2H, br), 3.81 (3H, s), 5.03 (1H, d, J=3.5 Hz), 6.04 (1H, d, J=3.5 Hz), 6.21 to 6.26 (2H, m), 6.93 to 7.04 (3H, m), 8.39 (1H, d, J=4.8 Hz).

IR (KBr) ν: 3345, 1609, 1508 cm⁻¹.

Anal calcd for C₄H₁₆N₂O₂.0.25H₂O: C, 67.59; H, 6.68; N, 11.26. Found: C, 67.57; H, 6.63; N, 11.39.

Reference Example 20

7-[4-(2-butoxyethoxy)phenyl]-1-trifluoroacetyl-2,3-dihydro-1H-1-benzazepine-4-carboxylic acid (0.7 g), (4-amino-2-methoxyphenyl)(4-methylpyridin-2-yl)methanol (0.5 g) and 1-hydroxybenzotriazole (0.34 g) were dissolved in N,N-dimethylformamide (15 ml), and to the solution were added 1-ethyl-3-(3-dimethylaminopropyl)carbodiimide hydrochloride (0.56 g), triethylamine (0.61 ml) and 4-dimethylaminopyridine (catalytic amout) at room temperature under ice-cooling, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[hydroxy(4-methylpyridin-2-yl)methyl]-3-methoxyphenyl]-1-trifluoroacetyl-2,3-dihydro-1H-1-benzazepine-4-carboxamide (1 g) as pale brown amorphous.

$^1$H-NMR (d, CDCl$_3$) 0.94 (3H, t, J=7.0 Hz), 1.27 to 1.49 (2H, m), 1.55 to 1.69 (2H, m), 2.30 (3H, s), 2.92 to 3.25 (3H, m), 3.56 (2H, t, J=6.6 Hz), 3.82 (2H, t, J=4.8 Hz), 3.91 (3H, s), 4.18 (2H, t, J=4.8 Hz), 4.79 to 4.90 (1H, m), 5.24 (1H, br), 6.13 (1H, s), 6.82 to 6.87 (1H, m), 6.99 to 7.04 (4H, m), 7.22 (1H, d, J=8.4 Hz), 7.33 (1H, d, J=8.4 Hz), 7.43 (1H, s), 7.50 to 7.65 (6H, m), 8.39 (1H, d, J=5.0 Hz).

IR (KBr) v: 2938, 2874, 1694 cm$^{-1}$.

Reference Example 21

7-[4-(2-butoxyethoxy)phenyl]-N-[4-[hydroxy(4-methylpyridin-2-yl)methyl]-3-methoxyphenyl]-1-trifluoroacetyl-2,3-dihydro-1H-1-benzazepine-4-carboxamide (1 g) was dissolved in dichloromethane (30 ml), and to the solution was added 3-chloroperbenzoic acid (0.46 g) under ice-cooling and the mixture was stirred at room temperature for 4 hours. An aqueous solution of sodium thiosulfate was added to the mixture, the mixture was concentrated, and extracted with ethyl acetate. The organic layer was washed with sodium bicarbonate solution, water and saturated brine, and dried over anhydrous magnesium sulfate. The solvent was evaporated, to give 7-[4-(2-butoxyethoxy)phenyl]-N-[4-[hydroxy(4-methyl-1-oxidopyridin-2-yl)methyl]-3-methoxyphenyl]-1-trifluoroacetyl-2,3-dihydro-1H-1-benzazepine-4-carboxamide (0.77 g) as colorless amorphous.

$^1$H-NMR (d, CDCl$_3$) 0.94 (3H, t, J=7.2 Hz), 1.34 to 1.63 (4H, m), 2.28 (3H, s), 2.90 to 3.25 (3H, m), 3.56 (2H, t, J=6.6 Hz), 3.76 to 3.84 (5H, m), 4.18 (2H, t, J=4.7 Hz), 4.80 to 4.90 (1H, m), 6.32 (1H, s), 6.78 (1H, s), 6.90 to 7.05 (4H, m), 7.26 to 7.36 (2H, m), 7.45 to 7.75 (7H, m), 8.12 (1H, d, J=6.6 Hz).

IR (KBr) v: 2938, 2870, 1694 cm$^{-1}$.

Anal calcd for C$_{39}$H$_{40}$F$_3$NO$_7$.0.5H$_2$O: C, 64.28; H, 5.67; N, 5.77. Found: C, 64.11; H, 5.47; N, 5.67.

Reference Example 22

2-bromo-4-methylpyridine (1.5 ml) was dissolved in diethylether (50 ml), and the mixture was cooled to −78° C. under argon atmosphere. 1.6M n-butyllithium hexane solution (8.3 ml) was added dropwise to the solution, and the mixture was stirred for 40 minutes. The reaction solution was added dropwise to a solution of 2-ethoxy-4-nitrobenzaldehyde (2.2 g) in tetrahydrofuran (200 ml) under argon atmosphere at −78° C. The mixture was allowed to be at room temperature and stirred overnight, and water was added to the mixture. The mixture was concentrated and extracted with ethyl acetate. The organic layer was washed with water and saturated brine, and dried over anhydrous magnesium sulfate, and then, the solvent was evaporated. The residue was purified by silica gel column chromatography (elution solvent: ethyl acetate/hexane), to give (2-ethoxy-4-nitrophenyl)(4-methylpyridin-2-yl)methanol (1.9 g) as brown crystals.

mp 114 to 115° C.

$^1$H-NMR (d, CDCl$_3$) 1.49 (3H, t, J=7.1 Hz), 2.31 (3H, s), 4.11 to 4.30 (2H, m), 5.39 (1H, d, J=5.3 Hz), 6.19 (1H, d, J=5.3 Hz), 7.03 (1H, d, J=5.1 Hz), 7.10 (1H, s), 7.56 (1H, d, J=8.4 Hz), 7.72 (1H, d, J=2.2 Hz), 7.82 (1H, dd, J=2.2, 8.4 Hz), 8.40 (1H, d, J=5.1 Hz).

IR (KBr) v: 3370, 2982, 1613, 1522 cm$^{-1}$.

Anal calcd for C$_{15}$H$_{16}$N$_2$O$_4$: C, 62.49; H, 5.59; N, 9.72. Found: C, 62.60; H, 5.73; N, 9.78.

Reference Example 23

(2-ethoxy-4-nitrophenyl)(4-methylpyridin-2-yl)methanol (1.9 g) was dissolved in ethanol (100 ml), and the solution was reduced by catalytic hydrogenation with 10% palladium-carbon (0.2 g) of 50% hydration overnight. The catalyst was removed, and the solvent of the filtrate was evaporated to give (4-amino-2-ethoxyphenyl)(4-methylpyridin-2-yl)methanol (1.7 g) as colorless crystals.

mp 102 to 105° C.

$^1$H-NMR (d, CDCl$_3$) 1.63 (3H, t, J=7.0 Hz), 2.2.9 (3H, s), 3.64 (2H, br), 3.91 to 4.10 (2H, m), 5.06 (1H, d, J=4.8 Hz), 6.01 (1H, d, J=4.8 Hz), 6.22 to 6.26 (2H, m), 6.95 to 7.08 (3H, m), 8.37 (1H, d, J=5.0 Hz).

Anal calcd for C$_{15}$H$_{18}$N$_2$O$_2$: C, 69.74; H, 7.02; N, 10.84. Found: C, 69.64; H, 7.11; N, 10.87.

Reference Example 24

7-[4-(2-butoxyethoxy)phenyl]-1-trifluoroacetyl-2,3-dihydro-1H-1-benzazepine-4-carboxylic acid (0.7 g), (4-amino-2-ethoxyphenyl)(4-methylpyridin-2-yl)methanol (0.45 g) and 1-hydroxybenzotriazole (0.34 g) were dissolved in N,N-dimethylformamide (15 ml), and to the solution were added 1-ethyl-3-(3-dimethylaminopropyl)carbodiimide hydrochloride (0.56 g), triethylamine (0.61 ml) and 4-dimethylaminopyridine (catalytic amout) at room temperature under ice-cooling, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[3-ethoxy-4-[hydroxy(4-methylpyridin-2-yl)methyl]phenyl]-1-trifluoroacetyl-2,3-dihydro-1H-1-benzazepine-4-carboxamide (0.68 g) as colorless amorphous.

$^1$H-NMR (d, CDCl$_3$) 0.85 to 0.97 (6H, m), 1.27 to 1.45 (2H, m), 1.48 to 1.68 (2H, m), 2.30 (3H, s), 2.91 to 3.25 (3H, m), 3.56 (2H, t, J=6.6 Hz), 3.82 (2H, t, J=5.0 Hz), 4.02 to 4.20 (4H, m), 4.75 to 4.90 (1H, m), 5.27 (1H, br), 6.12 (1H, s), 6.84 (1H, d, J=8.0 Hz), 7.00 to 7.10 (4H, m), 7.25 to 7.64 (9H, m), 8.38 (1H, d, J=4.8 Hz).

IR (KBr) v: 2932, 2874, 1694, 1609 cm$^{-1}$.

Anal calcd for C$_{40}$H$_{42}$F$_3$N$_3$O$_6$: C, 66.93; H, 5.90; N, 5.85. Found: C, 66.54; H, 5.73; N, 6.04.

Reference Example 25

7-[4-(2-butoxyethoxy)phenyl]-N-[3-ethoxy-4-[hydroxy (4-methylpyridin-2-yl)methyl]phenyl]-1-trifluoroacetyl-2, 3-dihydro-1H-1-benzazepine-4-carboxamide (0.68 g) was dissolved in dichloromethane (25 ml), and to the solution was added 3-chloroperbenzoic acid (0.28 g) under ice-cooling and the mixture was stirred overnight at room temperature. An aqueous solution of sodium thiosulfate was added to the mixture, and the mixture was concentrated and extracted with ethyl acetate. The organic layer was washed with sodium bicarbonate solution, water and saturated brine, and dried over anhydrous magnesium sulfate. The solvent was distilled off, to give 7-[4-(2-butoxyethoxy)phenyl]-N-[3-ethoxy-4-[hydroxy(4-methyl-1-oxidopyridin-2-yl)methyl]phenyl]-1-trifluoroacetyl-2,3-dihydro-1H-1-benzazepine-4-carboxamide (0.89 g) as colorless amorphous.

$^1$H-NMR (d, CDCl$_3$) 0.85 to 0.97 (6H, m), 1.22 to 1.45 (2H, m), 1.49 to 1.69 (2H, m), 2.29 (3H, s), 2.92 to 3.25 (3H, m), 3.56 (2H, t, J=6.6 Hz), 3.82 (2H, t, J=4.8 Hz), 4.05 to 4.20 (4H, m), 4.79 to 4.95 (1H, m), 6.28 (1H, s), 6.88 to 7.05 (6H, m), 7.26 to 7.73 (9H, m), 8.10 (1H, d, J=6 Hz).

IR (KBr) ν: 2932, 2912, 2870, 1694 cm$^{-1}$.

Anal calcd for C$_{40}$H$_{42}$F$_3$N$_3$O$_7$·0.5H$_2$O: C, 64.68; H, 5.84; N, 5.66. Found: C, 64.40; H, 5.86; N, 5.57.

Reference Example 26

2-bromo-4-methylpyridine (4.7 g) was dissolved in diethylether (150 ml), and the mixture was cooled to −78° C. under argon atmosphere. 1.6M n-butyllithium hexane solution (16.8 ml) was added dropwise to the solution, and the mixture was stirred for 30 minutes. The reaction solution was added dropwise to a solution of 4-fluoro-N-methoxy-N-methyl-2-trifluoromethylbenzamide (6.2 g) in diethyl-ether (50 ml) under argon atmosphere at −78° C. The mixture was allowed to be at room temperature and stirred overnight, and water was added to the mixture. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 2-(4-fluoro-2-trifluoromethylbenzoyl)-4-methylpyridine (4.5 g) as pale yellow amorphous.

$^1$H-NMR (d, CDCl$_3$) 2.49 (3H, s), 7.26 to 7.37 (2H, m), 7.43 to 7.53 (2H, m), 8.06 (1H, d, J=0.8 Hz), 8.50 (1H, d, J=4.4 Hz).

IR (neat) ν: 1694, 1599, 1424, 1319 cm$^{-1}$.

Reference Example 27

2-(4-fluoro-2-trifluoromethylbenzoyl)-4-methylpyridine (4.5 g) and sodium azide (1.3 g) were suspended in dimethylsulfoxide (30 ml), and the mixture was heated with stirring overnight under nitrogen atmosphere at 90° C. The mixture was poured into water, and the mixture was extracted with ethyl acetate. The organic layer was washed with water and saturated brine, and dried over anhydrous magnesium sulfate, and then, the solvent was evaporated. The residue was dissolved in tetrahydrofuran (30 ml), and to the solution was added aluminum lithium hydride (1.2 g) under ice-cooling, and the mixture was stirred for 1 hour under nitrogen atmosphere under ice-cooling. Water (1.2 ml), 15% aqueous solution of sodium hydroxide (1.2 ml) and water (3.6 ml) were added to the mixture, and the mixture was stirred, dried over anhydrous magnesium sulfate, and filtrated. The solvent of the filtrate was distilled off, to give (4-amino-2-trifluoromethylphenyl)(4-methylpyridin-2-yl)methanol (3.6 g) as colorless crystals.

mp 120 to 123° C.

$^1$H-NMR (d, CDCl$_3$) 2.28 (3H, s), 3.83 (2H, br), 5.61 (1H, d, J=3.6 Hz), 6.00 (1H, d, J=3.6 Hz), 6.74 (1H, dd, J=2.6, 8.6 Hz), 6.82 (1H, s), 6.95 (1H, d, J=2.2 Hz), 7.02 (1H, d, J=5.2 Hz), 8.43 (1H, d, J=5.2 Hz).

IR (KBr) ν: 3318, 1636, 1609, 1507, 1456, 1339 cm$^{-1}$.

Anal calcd for C$_{14}$H$_{13}$F$_3$N$_2$O: C, 59.57; H, 4.64; N, 9.92. Found: C, 59.33; H, 4.67; N, 9.79.

Reference Example 28

7-[4-(2-butoxyethoxy)phenyl]-1-trifluoroacetyl-2,3-dihydro-1H-1-benzazepine-4-carboxylic acid (2 g), (4-amino-2-trifluoromethylphenyl)(4-methylpyridin-2-yl)methanol (1.2 g) and 1-hydroxybenzotriazole (0.96 g) were dissolved in N,N-dimethylformamide (25 ml), and to the solution were added 1-ethyl-3-(3-dimethylaminopropyl)carbodiimide hydrochloride (2.4 g), triethylamine (3 ml) and 4-dimethylaminopyridine (catalytic amount) at room temperature under ice-cooling, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by basic silica gel column chromatography (elution solvent: ethyl acetate/hexane), to give 7-[4-(2-butoxyethoxy)phenyl]-N-[4-[hydroxy(4-methylpyridin-2-yl)methyl]-3-trifluoromethylphenyl]-1-trifluoroacetyl-2,3-dihydro-1H-1-benzazepine-4-carboxamide (1.2 g) as pale yellow amorphous.

$^1$H-NMR (d, CDCl$_3$) 0.93 (3H, t, J=7.3 Hz), 1.29 to 1.48 (2H, m), 1.54 to 1.71 (2H, m), 2.27 (3H, s), 2.89 to 3.20 (3H, m), 3.55 (2H, t, J=6.6 Hz), 3.81 (2H, t, J=4.8 Hz), 4.17 (2H, t, J=4.8 Hz), 4.78 to 4.85 (1H, m), 6.07 (1H, s), 6.81 (1H, s), 6.97 to 7.05 (3H, m), 7.24 to 7.67 (9H, m), 7.88 (1H, d, J=9.6 Hz), 8.28 (1H, s), 8.40 (1H, d, J=5.2 Hz).

Reference Example 29

7-[4-(2-butoxyethoxy)phenyl]-N-[4-[hydroxy(4-methylpyridin-2-yl)methyl]-3-trifluoromethylphenyl]-1-trifluoroacetyl-2,3-dihydro-1H-1-benzazepine-4-carboxamide (1.2 g) was dissolved in dichloromethane (50 ml), and to the solution was added 3-chloroperbenzoic acid (0.69 g) under ice-cooling and the mixture was stirred overnight at room temperature. An aqueous solution of sodium thiosulfate was added to the mixture, and the mixture was concentrated and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[hydroxy(4-methyl-1-oxidopyridin-2-yl)methyl]-3-trifluoromethylphenyl]-1-trifluoroacetyl-2,3-dihydro-1H-1-benzazepine-4-carboxamide (1 g) as pale brown oil.

$^1$H-NMR (d, CDCl$_3$) 0.93 (3H, t, J=7.3 Hz), 1.29 to 1.48 (2H, m), 1.55 to 1.72 (2H, m), 2.24 (3H, s), 2.96 to 3.22 (3H, m), 3.56 (2H, t, J=6.6 Hz), 3.82 (2H, t, J=4.8 Hz), 4.17 (2H, t, J=4.8 Hz), 4.80 to 4.93 (1H, m), 6.40 to 6.44 (2H, m), 7.00 to 7.08 (4H, m), 7.34 (1H, d, J=8.2 Hz), 7.51 to 7.59 (4H, m), 7.67 (1H, d, J=1.4 Hz), 7.88 to 8.12 (4H, m), 8.16 (1H, d, J=6.6 Hz).

IR (neat) ν: 2934, 2872, 1694 cm$^{-1}$.

Reference Example 30

2-bromopyridine (2.8 ml) was dissolved in diethylether (80 ml), and the mixture was cooled to −78° C. under argon atmosphere. 1.6M n-butyllithium hexane solution (18 ml) was added dropwise to the solution, and the mixture was stirred for 30 minutes. The reaction solution was added dropwise to a solution of 2-(2,2,2-trifluoroethoxy)-4-nitrobenzaldehyde (6 g) in tetrahydrofuran (100 ml) under argon atmosphere at −78° C. The mixture was allowed to be at room temperature and stirred overnight, and water was added to the mixture. The mixture was concentrated and extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give [4-nitro-2-(2,2,2-trifluoroethoxy)phenyl](pyridin-2-yl)methanol (4.5 g) as pale brown crystals.

mp 119 to 123° C.

$^1$H-NMR (d, CDCl$_3$) 4.43 to 4.62 (2H, m), 5.39 (1H, d, J=5.6 Hz), 6.23 (1H, d, J=5.6 Hz), 7.21 to 7.24 (1H, m), 7.30 (1H, d, J=8.2 Hz), 7.64 (1H, dd, J=1.4, 8.0 Hz), 7.69 to 7.74 (2H, m), 7.96 (1H, dd, J=2.2, 8.7 Hz), 8.56 (1H, d, J=4.8 Hz).

IR (KBr) ν: 1530, 1350, 1289, 1242, 1169 cm$^{-1}$.

Anal calcd for C$_{14}$H$_{11}$F$_3$N$_2$O$_4$: C, 51.23; H, 3.38; N, 8.53. Found: C, 51.32; H, 3.30; N, 8.58.

Reference Example 31

[4-nitro-2-(2,2,2-trifluoroethoxy)phenyl](pyridin-2-yl)methanol (4.5 g) was dissolved in ethanol (150 ml), and the solution was reduced by catalytic hydrogenation overnight with 10% palladium-carbon of 50% hydration (0.25 g). The catalyst was removed, and the solvent of the filtrate was distilled off. The residue was purified by silica gel column chromatography (elution solvent: ethyl acetate), to give [4-amino-2-(2,2,2-trifluoroethoxy)phenyl](pyridin-2-yl)methanol (3.6 g) as yellow crystals.

mp 97 to 99° C.

$^1$H-NMR (d, CDCl$_3$) 3.71 (2H, br), 4.22 to 4.41 (2H, m), 5.19 (1H, d, J=5.2 Hz), 6.05 (1H, d, J=5.2 Hz), 6.16 (1H, d, J=2.2 Hz), 6.35 (1H, dd, J=2.2, 8.2 Hz), 7.10 to 7.24 (3H, m), 7.60 (1H, dt, J=1.4, 15.0 Hz), 8.53 (1H, d, J=4.6 Hz).

IR (KBr) ν: 3331, 1615 cm$^{-1}$.

Anal calcd for C$_{14}$H$_{13}$F$_3$N$_2$O$_2$: C, 56.38; H, 4.39; N, 9.39. Found: C, 56.39; H, 4.19; N, 9.47.

Reference Example 32

7-[4-(2-butoxyethoxy)phenyl]-1-trifluoroacetyl-2,3-dihydro-1H-1-benzazepine-4-carboxylic acid (1.5 g), [4-amino-2-(2,2,2-trifluoroethoxy)phenyl] (pyridin-2-yl)methanol (0.94 g) and 1-hydroxybenzotriazole (0.72 g) were dissolved in N,N-dimethylformamide (25 ml), and to the solution were added 1-ethyl-3-(3-dimethylaminopropyl)carbodiimide hydrochloride (1.8 g), triethylamine (2.2 ml) and 4-dimethylaminopyridine (catalytic amount) at room temperature under ice-cooling, and the mixture was stirred overnight. The mixture was poured into water, and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[hydroxy(pyridin-2-yl)methyl]-3-(2,2,2-trifluoroethoxy)phenyl]-1-trifluoroacetyl-2,3-dihydro-1H-1-benzazepine-4-carboxamide (1.5 g) as colorless crystals.

mp 178 to 181° C.

$^1$H-NMR (d, CDCl$_3$) 0.93 (3H, t, J=7.2 Hz), 1.22 to 1.69 (4H, m), 2.91 to 3.21 (3H, m), 3.56 (2H, t, J=6.6 Hz), 3.82 (2H, t, J=4.9 Hz), 4.18 (2H, t, J=4.9 Hz), 4.34 to 4.55 (2H, m), 4.75 to 4.90 (1H, m), 5.34 (1H, d, J=2.7 Hz), 6.16 (1H, d, J=2.7 Hz), 6.84 to 6.89 (1H, m), 7.02 (2H, d, J=8.8 Hz), 7.16 to 7.22 (1H, m), 7.29 to 7.71 (11H, m), 8.54 (1H, d, J=5.0 Hz).

IR (KBr) ν: 3351, 2963, 2940, 2878, 1701, 1655, 1607 cm$^{-1}$.

Anal calcd for C$_{39}$H$_{37}$F$_6$N$_3$O$_6$: C, 61.82; H, 4.92; N, 5.55. Found: C, 62.03; H, 4.65; N, 5.82.

Reference Example 33

7-[4-(2-butoxyethoxy)phenyl]-N-[4-[hydroxy(pyridin-2-yl)methyl]-3-(2,2,2-trifluoroethoxy)phenyl]-1-trifluoroacetyl-2,3-dihydro-1H-1-benzazepine-4-carboxamide (1.5 g) was dissolved in dichloromethane (150 ml), and to the solution was added 3-chloroperbenzoic acid (0.75 g) under ice-cooling and the mixture, was stirred overnight at room temperature. An aqueous solution of sodium thiosulfate was added to the mixture, and the mixture was concentrated and extracted with ethyl acetate. The organic layer was washed with sodium bicarbonate solution, water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-[4-[hydroxy(1-oxidopyridin-2-yl)methyl]-3-(2,2,2-trifluoroethoxy)phenyl]-1-trifluoroacetyl-2,3-dihydro-1H-1-benzazepine-4-carboxamide (1.5 g) as colorless crystals.

mp 106 to 109° C.

$^1$H-NMR (d, CDCl$_3$) 0.93 (3H, t, J=8.6 Hz), 1.22 to 1.69 (4H, m), 2.85 to 3.25 (3H, m), 3.56 (2H, t, J=6.6 Hz), 3.82 (2H, t, J=4.8 Hz), 4.18 (2H, t, J=4.8 Hz), 4.33 to 4.45 (2H, m), 4.80 to 4.90 (1H, m), 6.20 to 6.26 (1H, m), 6.91 to 7.05 (4H, m), 7.21 to 7.36 (4H, m), 7.45 to 7.57 (4H, m), 7.66 (1H, s), 7.78 to 7.82 (3H, m), 8.19 (1H, d, J=6.6 Hz).

IR (KBr) ν: 1694, 1605 cm$^{-1}$.

Anal calcd for C$_{39}$H$_{37}$F$_6$N$_3$O$_7$: C, 60.54; H, 4.82; N, 5.43. Found: C, 60.16; H, 5.20; N, 5.40.

Reference Example 34

7-[4-(2-butoxyethoxy)phenyl]-1-propyl-2,3-dihydro-1H-1-benzazepine-4-carboxylic acid (0.5 g) was dissolved in tetrahydrofuran (7 ml), and to the solution were added thionyl chloride (0.13 ml) and N,N-dimethylformamide (catalytic amount) at room temperature under ice-cooling, and the mixture was stirred for 1.5 hours. The solvent was distilled off and the residue was dissolved in tetrahydrofuran (15 ml), and the solution was added dropwise to a solution of p-aminophenol (0.13 g) and triethylamine (0.5 ml) in tetrahydrofuran (5 ml) under ice-cooling. The mixture was stirred overnight under nitrogen atmosphere at room temperature, and the solvent was evaporated. To the residue was added water and the mixture was extracted with ethyl acetate. The organic layer was washed with water and saturated brine, and dried over anhydrous magnesium sulfate, and then, the solvent was evaporated. The residue was purified by silica gel column chromatography (elution solvent: ethyl acetate/hexane), to give 7-[4-(2-butoxyethoxy)

phenyl]-N-(4-hydroxyphenyl)-1-propyl-2,3-dihydro-1H-1-benzazepine-4-carboxamide (0.6 g) as yellow amorphous.

$^1$H-NMR (d, CDCl$_3$) 0.89 to 1.00 (6H, m), 1.33 to 1.44 (2H, m), 1.54 to 1.77 (4H, m), 2.85 (2H, t-like), 3.23 to 3.31 (4H, m), 3.55 (2H, t, J=6.6 Hz), 3.80 (2H, t, J=4.8 Hz), 4.14 (2H, t, J=4.8 Hz), 6.38: (1H, s), 6.75 to 6.97 (5H, m), 7.31 to 7.46 (7H, m), 7.62 (1H, s).

IR (neat) ν: 3237, 2957, 2936, 2870, 1636, 1605, 1539, 1507 cm$^{-1}$.

Reference Example 35

7-[4-(2-butoxyethoxy)phenyl]-1-isobutyl-2,3-dihydro-1H-1-benzazepine-4-carboxylic acid (2 g) was dissolved in tetrahydrofuran (25 ml), and to the solution were added thionyl chloride (0.5 ml) and N,N-dimethylformamide (catalytic amount) at room temperature under ice-cooling, and the mixture was stirred for 1.5 hours. The solvent was distilled off, the residue was dissolved in tetrahydrofuran (50 ml), and the solution was added dropwise to a solution of p-aminophenol (0.55 g) and triethylamine (2 ml) in tetrahydrofuran (25 ml) under ice-cooling. The mixture was stirred for 3 hours under nitrogen atmosphere at room temperature, and the solvent was distilled off. To the residue was added water and the mixture was extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate/hexane), to give 7-[4-(2-butoxyethoxy)phenyl]-N-(4-hydroxyphenyl)-1-isobutyl-2,3-dihydro-1H-1-benzazepine-4-carboxamide (2 g) as pale yellow crystals.

mp 155 to 157° C.

$^1$H-NMR (d, CDCl$_3$) 0.89 to 0.98 (9H, m), 1.30 to 1.68 (4H, m), 1.99-2.10 (1H, m), 2.90 (2H, t, J=4.8 Hz), 3.17 (2H, d, J=6.8 Hz), 3.35 (2H, t, J=4.8 Hz), 3.55 (2H, t, J=6.6 Hz), 3.81 (2H, t, J=5.0 Hz), 4.15 (2H, t, J=5.0 Hz), 5.40 (1H, br), 6.80 (2H, d, J=8.8 Hz), 6.89 to 7.01 (3H, m), 7.37 to 7.49 (8H, m).

IR (KBr) ν: 2959, 2868, 1645, 1605, 1499 cm$^{-1}$.

Anal calcd for C$_{33}$H$_{40}$N$_2$O$_4$: C, 74.97; H, 7.63; N, 5.30. Found: C, 74.84; H, 7.81; N, 4.98.

Reference Example 36

Hydrazine monohydrate (10 g) was dissolved in ethanol (100 ml), and ethyl glycolate (21 g) was added dropwise to the solution under ice-cooling. The mixture was stirred overnight at room temperature, a solution of isobutyl isothiocyanate (23 g) in ethanol (10 ml) was added dropwise to the solution under ice-cooling, and the mixture was stirred overnight at room temperature. Ice-water (50 ml) was added to the mixture, the mixture was stirred for 1 hour, 5N aqueous solution of sodium hydroxide (38 ml) was added dropwise to the solution, and the mixture was stirred with heating for 2 hours at 60° C. The pH was adjusted to pH 6 with concentrated hydrochloric acid, and the precipitates were filtered off. The filtrate was concentrated, and the precipitated colorless crystal (30 g) was collected by filtration, and washed with water. The obtained crystals (15 g) were added by portions to a solution of sodium nitrite (97 mg) in water (36 ml) and nitric acid (25 ml) at 45° C. After cooling, the mixture was neutralized with sodium carbonate, and concentrated. Methanol was added to the mixture, and the precipitates were filtered off. The solvent of the filtrate was evaporated, and the residue was purified by basic silica gel column chromatography (elution solvent: ethyl acetate/methanol) to give pale yellow oil (8.7 g). To the oil (8.7 g) was added dropwise thionyl chloride (45 ml) under ice-cooling, and the mixture was refluxed for 30 minutes. The solvent was distilled off, and the obtained residue was washed with ethyl acetate, to give 3-chloromethyl-4-isobutyl-4H-1,2,4-triazole hydrochloride (10.4 g) as colorless crystals.

mp 127 to 130° C.

$^1$H-NMR (d, DMSO-d$_6$) 0.90 (6H, d, J=6.6 Hz), 2.10 to 2.26 (1H, m), 4.03 (2H, d, J=7.2 Hz), 5.14 (2H, s), 9.53 (1H, s), 10.31 (1H, br).

IR (KBr) ν: 2967, 1618, 1572, 1541, 1470 cm$^{-1}$.

Anal calcd for C$_7$H$_{13}$Cl$_2$N$_3$.0.25H$_2$O: C, 39.18; H, 6.34; N, 19.58. Found: C, 39.25; H, 6.22; N, 19.71.

Reference Example 37 p-aminophenol (20 g) was dissolved in N,N-dimethylformamide (150 ml), potassium carbonate (44 g) was added to the mixture, and bromoethyl acetate (17.7 ml) was added dropwise to the mixture under ice-cooling. The mixture was stirred overnight under argon atmosphere at room temperature, and the solvent was distilled off. To the residue was added water, and the mixture was extracted with ethyl acetate. The organic layer was washed with water and saturated brine, and dried over anhydrous magnesium sulfate, and then, the solvent was evaporated. The obtained residue was dissolved in ethanol (100 ml), hydrazine monohydrate (18.6 ml) was added to the mixture, and the mixture was refluxed for 5 hours. The solvent was distilled off, the precipitated 2-(4-aminophenylthio)acetohydrazide (32 g) was collected by filtration, and washed with tetrahydrofuran-hexane to give colorless crystals.

$^1$H-NMR (d, CDCl$_3$) 3.48 (2H, s), 3.77 (4H, br), 6.62 (2H, d, J=8.8 Hz), 7.21 (2H, d, J=8.8 Hz), 7.75 (1H, br).

IR (KBr) ν: 3304, 1651 cm$^{-1}$.

Reference Example 38

To 2-(4-aminophenylthio)acetohydrazide (5 g) and 2,3-butanedione (2.2 ml) was added ethanol (50 ml), and the mixture was refluxed for 1 hour. The solvent was distilled off, and to the residue was added ethyl acetate. The insolubles were filtered off, and the solvent of the filtrate was evaporated. The residue was dissolved in ethanol (35 ml), 13% ammonia-ethanol solution (50 ml) was added to the mixture, and the mixture was heated for 5 hours at 150° C. The solvent was distilled off, and to the residue was added ethyl acetate. The insolubles were filtered off, and the solvent of the filtrate was distilled off. The residue was purified by silica gel column chromatography (elution solvent: ethyl acetate/hexane) to give 4-[(5,6-dimethyl-1,2,4-triazin-3-yl)methylthio]aniline (3 g) as yellow amorphous.

$^1$H-NMR (d, CDCl$_3$) 2.52 (3H, s), 2.65 (3H, s), 3.71 (2H, br), 4.27 (2H, s), 6.56 (2H, d, J=8.8 Hz), 7.20 (2H, d, J=8.8 Hz).

IR (neat) ν: 3347, 3220, 1628, 1599, 1530, 1497 cm$^{-1}$.

Reference Example 39

2-(4-aminophenylthio)acetohydrazide (5 g) was suspended in ethanol (50 ml) and to the suspension was added 40% piruvaldehyde solution (6.8 ml), at room temperature, and the mixture was stirred for 20 minutes. 13% ammonia-ethanol solution (60 ml) was added to the mixture, and the mixture was heated for 4.5 hours at 150° C. The solvent was distilled off, and the residue was purified by silica gel column chromatography (elution solvent: ethyl acetate/hexane) to give 4-[(5-methyl-1,2,4-triazin-3-yl)methylthio]aniline (1.2 g) as colorless crystals.

$^1$H-NMR (d, CDCl$_3$) 2.55 (3H, s), 3.72 (2H, br), 4.29 (2H, s), 56 (2H, d, J=8.6 Hz), 7.18 (2H, d, J=8.6 Hz), 8.97 (1H, s).

IR (KBr) ν: 3343, 3218, 1626, 1597, 1551, 1497 cm$^{-1}$.

Reference Example 40

4-mercapto-3-trifluoromethylaniline (1.0 g), 3-chloromethyl-4-propyl-4H-1,2,4-triazole hydrochloride (1.1 g) and potassium carbonate (1.4 g) were added to N,N-dimethylformamide (35 ml), and the mixture was stirred overnight at room temperature. The mixture was poured into water, and the mixture was extracted with ethyl acetate. The organic layer was washed with water and saturated brine, dried over anhydrous magnesium sulfate, and then, the solvent was evaporated. The residue was purified by silica gel column chromatography (elution solvent: triethylamine/methanol/ethyl acetate) to give 4-[(4-propyl-4H-1,2,4-triazol-3-yl)methylthio]-3-trifluoromethylaniline (1.4 g) as pale brown oil.

$^1$H-NMR (dppm, CDCl$_3$) 1.00 (3H, t, J=7.3 Hz), 1.77 to 1.95 (2H, m), 3.62 (2H, br), 3.97 (2H, t, J=7.3 Hz), 4.10 (2H, s), 6.69 (1H, d, J=8.0 Hz), 6.92 (1H, s), 7.23 (1H, d, J=8.0 Hz), 8.09 (1H, s).

Reference Example 41 p-nitrothiophenol (5 g) and triethylamine (4.5 ml) were dissolved in ethanol (150 ml), ethyl acrylate (3.5 ml) was added to the mixture at room temperature, and the mixture was stirred for 3 days. The solvent was distilled off, and to the residue was added water, and the mixture was extracted with ethyl acetate. The organic layer was washed with water and saturated brine and dried over anhydrous magnesium sulfate, and the solvent was distilled off to give yellow crystals (7.8 g). The crystals were dissolved in ethanol (100 ml) and tetrahydrofuran (100 ml), hydrazine monohydrate (7.5 ml) was added to the solution, and the mixture was refluxed overnight. The solvent was distilled off, and to the residue was added water, and the mixture was extracted with ethyl acetate. The organic layer was washed with water and saturated brine, and dried over anhydrous magnesium sulfate and the solvent was distilled off, to give yellow crystals (5.1 g). The crystals were dissolved in ethanol (150 ml) and tetrahydrofuran (100 ml), and to the solution was added propyl isothiocyanate (3.3 ml) under ice-cooling and the mixture was stirred overnight at room temperature. The solvent was distilled off to give yellow crystals (7.2 g). The crystals (6.0 g) were dissolved in ethanol (200 ml) and tetrahydrofuran (200 ml), potassium t-butoxide (4.1 g) was added to the mixture, and the mixture was heated for 3.5 hours at 50° C. The solvent was distilled off, 1N hydrochloric acid was added to the mixture, and the mixture was extracted with ethyl acetate. The organic layer was washed with water and saturated brine, and dried over anhydrous magnesium sulfate and the solvent was distilled off, to give pale yellow crystals (4.4 g). The obtained crystals (4.4 g) and sodium nitrite (0.1 g) were added to nitric acid (5.0 ml) and water (10 ml) under ice-cooling, and the mixture was heated for 15 minutes at 40° C. The mixture was neutralized with sodium carbonate solution and extracted with ethyl acetate. The organic layer was washed with water and saturated brine, and dried over anhydrous magnesium sulfate and the solvent was evaporated, to give 4-nitrophenyl 2-(4-propyl-4H-1,2,4-triazol-3-yl)ethylsulfide (3.3 g) as colorless crystals.

mp 81 to 84° C.

$^1$H-NMR (dppm, CDCl$_3$) 0.95 (3H, t, J=7.3 Hz), 1.69 to 1.87 (2H, m), 3.09 (2H, t, J=7.6 Hz), 3.63 (2H, t, J=7.6 Hz), 3.84 (2H, t, J=8.3 Hz), 7.39 (2H, d, J=8.8 Hz), 8.10 (1H, s), 8.15 (2H, d, J=8 Hz).

IR (KBr) n: 2967, 1578, 1512, 1334 cm$^{-1}$.

Anal calcd for C$_{13}$H$_{16}$N$_4$O$_2$S: C, 53.41; H, 5.52; N, 19.16. Found C, 53.20; H, 5.44; N, 19.21.

Reference Example 42

4-nitrophenyl 2-(4-propyl-4H-1,2,4-triazol-3-yl)ethylsulfide (3.2 g), reduced iron (3.1 g) and calcium chloride (0.6 g) were added to 85% aqueous solution of ethanol (100 ml), and the mixture was refluxed for 3 hours. The reaction solution was filtered with Celite, and the solvent of the filtrate was distilled off. The residue was purified by silica gel column chromatography (elution solvent: triethylamine/methanol/ethyl acetate), to give 4-aminophenyl 2-(4-propyl-4H-1,2,4-triazol-3-yl)ethylsulfide (3.0 g) as yellow amorphous.

$^1$H-NMR (dppm, CDCl$_3$) 0.91 (3H, t, J=7.6 Hz), 1.66 to 1.77 (2H, m), 2.90 to 2.98 (2H, m), 3.19 to 3.27 (2H, m), 3.74 (2H, t, J=7.4 Hz), 6.64 (2H, d, J=8.4 Hz), 7.27 (2H, d, J=8.4 Hz), 8.04 (1H, s).

Reference Example 43

2-mercapto-5-nitropyridine (5.0 g), 3-chloromethyl-4-propyl-4H-1,2,4-triazole hydrochloride (6.3 g) and potassium carbonate (11 g) was added to N,N-dimethylformamide (100 ml), and the mixture was stirred overnight at room temperature. The solvent was distilled off, and to the residue was added water, and the mixture was extracted with ethyl acetate. The organic layer was washed with water and saturated brine, and dried over anhydrous magnesium sulfate. The solvent was distilled off, to give 5-nitro-2-(4-propyl-4H-1,2,4-triazol-3-yl)methylthiopyridine (8.0 g) as brown crystals.

$^1$H-NMR (dppm, CDCl$_3$) 0.98 (3H, t, J=7.3 Hz), 1.80 to 1.92 (2H, m), 4.00 (2H, t, J=7.3 Hz), 4.75 (2H, s), 7.42 (1H, dd, J=0.8, 9.0 Hz), 8.13 (1H, s), 8.31 (1H, dd, J=2.7, 9.0 Hz), 9.26: (1H, dd, J=0.8, 2.7 Hz).

IR (KBr) n: 2969, 1588, 1568, 1514, 1345 cm$^{-1}$.

Anal calcd for C$_{11}$H$_{13}$N$_5$O$_2$S: C, 47.30; H, 4.69; N, 25.07. Found C, 47.20; H, 4.63; N, 25.00.

Reference Example 44

5-nitro-2-(4-propyl-4H-1,2,4-triazol-3-yl)methylthiopyridine (4.0 g), reduced iron (4.0 g), and calcium chloride (0.79 g) was added to 85% aqueous solution of ethanol (100 ml), and the mixture was refluxed for 3 hours. The reaction solution was filtered with Celite, and the solvent of the filtrate was distilled off. The residue was purified by basic silica gel column chromatography (elution solvent: methanol/ethyl acetate), to give 5-amino-2-(4-propyl-4H-1,2,4-triazol-3-yl)methylthiopyridine (3.3 g) as red oil.

$^1$H-NMR (dppm, CDCl$_3$) 0.94 (3H, t, J=7.4 Hz),: 1.78 to 1.88 (2H, m), 3.74 (2H, br), 3.96 (2H, t, J=7.4 Hz), 4.57 (2H, s), 6.91 (1H, dd, J=2.9, 8.4 Hz), 7.07 (1H, d, J=8.4 Hz), 8.00 (1H, d, J=2.9 Hz), 8.07 (1H, s).

IR (KBr) n: 3326, 3207, 2969, 1634, 1588, 1518, 1468 cm$^{-1}$.

Reference Example 45

3-(4-nitrophenyl)-1-propanol (1.9 g), tosyl chloride (3.0 g), tetrabutylammonium bromide (0.2 g) and sodium hydroxide (2.6 g) were added to water (10 ml) and diethylether (25 ml), and the mixture was refluxed for 2 days. The mixture was extracted with ethyl acetate, the organic layer was washed with water and saturated brine, and dried over anhydrous magnesium sulfate. The solvent was distilled off, and the residue was purified by silica gel column chromatography (elution solvent: methyl acetate/hexane) to give pale red oil (3.1 g). The obtained oil (3 g) and bis(1H-1,2,4-triazol-1-yl)methane (0.67 g) were heated for 2.5 hours at 130° C. Ethyl acetate was added to the mixture, and the precipitates were collected by filtration 1-butanol (50 ml) was added to the precipitates, and the mixture was refluxed overnight and the solvent was distilled off. An aqueous solution of sodium bicarbonate was added to the residue, and the mixture was extracted with ethyl acetate. The organic layer was washed with water and saturated brine, and dried over anhydrous magnesium sulfate. The solvent was distilled off to give 4-[3-(4-nitrophenyl)propyl]-4H-1,2,4-triazole (1.25 g) as yellow crystals.

$^1$H-NMR (dppm, $CDCl_3$) 2.15-2.29 (2H, m), 2.78 (2H, t, J=7.6 Hz), 4.09 (2H, t, J=7.1 Hz), 7.33 (2H, d, J=8.8 Hz), 8.16 to 8.23 (4H, m).

IR (KBr) n: 1601, 1516 $cm^{-1}$.

Reference Example 46

4-[3-(4-nitrophenyl)propyl]-4H-1,2,4-triazole (1.2 g) was dissolved in ethanol (100 ml), 10% palladium-activated carbon (50% hydration, 0.2 g) was added to the solution at room temperature, and the solution was reduced by catalytic hydrogenation overnight. The catalyst was removed. The solvent of the filtrate was distilled off, to give 4-[3-(4-aminophenyl)propyl]-4H-1,2,4-triazole (1.0 g) as colorless crystals.

mp 150 to 153° C.

$^1$H-NMR (dppm, $CDCl_3$) 2.04-2.18 (2H, m), 2.55 (2H, t, J=7.3 Hz), 2.85 (2H, br), 3.98 (2H., t, J=7.2 Hz), 6.65 (2H, d, J=8.5 Hz), 6.93 (2H, d, J=8.5 Hz), 8.13 (2H, s).

IR (KBr) n: 3416, 3331, 3221, 3112, 3002, 2948, 1634, 1615, 1537, 1518, 1451 $cm^{-1}$.

Anal calcd for $C_{11}H_{14}N_4 \cdot 0.1H_2O$: C, 64.75; H, 7.01; N, 27.46. Found C, 64.94; H, 6.68; N, 27.14.

Reference Example 47

4-nitrothiophenol (10 g) and potassium carbonate (10.7 g) were added to N,N-dimethylformamide (100 ml), and then, bromoethyl acetate (10.8 g) was added dropwise to the solution, and the mixture was stirred for 1 hour at room temperature. The solvent was distilled off, and to the residue was added water, and the mixture was extracted with ethyl acetate. The organic layer was washed with water, saturated brine, and dried over anhydrous magnesium sulfate. The solvent was distilled off, to give yellow crystals (13.8 g). To the crystals (13.5 g) was added hydrazine monohydrate (13.6 ml), and the mixture was refluxed for 1.5 hours. The solvent was evaporated, and to the residue was added water, and the mixture was extracted with ethyl acetate. The organic layer was washed with water and saturated brine, and dried over anhydrous magnesium sulfate. The solvent was distilled off, to give colorless crystal (10.0 g). The crystals (5.0 g) were dissolved in tetrahydrofuran (200 ml), and to the solution was added dropwise propyl isocyanate (2.2 ml) and the mixture was heated for 1.5 hours at 50° C. The solvent was distilled off, to give colorless crystal (6.5 g). The crystals (4.5 g) were added to 0.8M aqueous solution of potassium hydroxide (25 ml) at 110° C. and the mixture was heated for 1 hour. The mixture was neutralized with concentrated hydrochloric acid and extracted with ethyl acetate. The organic layer was washed with water and saturated brine, and dried over anhydrous magnesium sulfate, and then, the solvent was distilled off. The residue was purified by silica gel column chromatography (elution solvent: ethyl acetate), to give 1-nitro-4-[(4-propyl-1H-1,2,4-triazol-5-one-3-yl)methylthio]benzene (1.0 g) as yellow crystals.

$^1$H-NMR (dppm, $CDCl_3$) 0.99 (3H, t, J=7.4 Hz), 1.72 to 1.84 (2H, m), 3.71 (2H, t, J=7.7 Hz), 4.09 (2H, s), 7.50 (2H, d, J=9.1 Hz), 8.16 (2H, d, J=9.1 Hz), 9.80 (1H, br).

IR (KBr) n: 1701 $cm^{-1}$.

Anal calcd for $C_{12}H_{14}N_4O_3S$: C, 48.97; H, 4.79; N, 19.04. Found C, 48.93; H, 4.76; N, 19.06.

Reference Example 48

1-nitro-4-[(4-propyl-1H-1,2,4-triazole-5-one-3-yl)methylthio]benzene (0.5 g), reduced iron (0.5 g) and calcium chloride (0.1 g) were added to 85% aqueous solution of ethanol (15 ml), and the mixture was refluxed for 2 hours. The reaction solution was filtered with. Celite, and the solvent of the filtrate was distilled off. The residue was purified by basic silica gel column chromatography (elution solvent: ethyl acetate) to give 4-[(4-propyl-1H-1,2,4-triazole-5-one-3-yl)methylthio]aniline (0.4 g) as pale brown crystals.

$^1$H-NMR (dppm, $CDCl_3$) 0.96 (3H, t, J=7.3 Hz), 1.71 to 1.83 (2H, m), 3.66 to 3.74 (2H, m), 3.75 (2H, s), 3.78 (2H, br), 6.59 (2H, d, J=8.8 Hz), 7.17 (2H, d, J=8.8 Hz), 9.05 (1H, br).

IR (KBr) n: 1699 $cm^{-1}$.

Anal calcd for $C_{12}H_{16}N_4OS$: C, 54.52; H, 6.10; N, 21.19. Found C, 54.47; H, 6.10; N, 21.11.

Reference Example 49

3-amino-6-mercaptopyridazine (0.5 g), 3-chloromethyl-4-propyl-4H-1,2,4-triazole hydrochloride (0.57 g) and potassium carbonate (0.8 g) were added to N,N-dimethylformamide (5 ml), and the mixture was stirred for 4.5 hours at room temperature. The solvent was distilled off, and to the residue was added water, and the mixture was extracted with ethyl acetate. The organic layer was washed with water and saturated brine, and dried over anhydrous magnesium sulfate, and then, the solvent was distilled off. The residue was purified by basic silica gel column chromatography (elution solvent: methanol/ethyl acetate), to give 3-amino-6-[(4-propyl-1H-1,2,4-triazol-3-yl)methylthio]pyridazine (0.62 g) as colorless crystals.

mp 150 to 152° C.

$^1$H-NMR (dppm, $CDCl_3$) 0.95 (3H, t, J=7.5 Hz), 1.77 to 1.89 (2H, m), 4.04 (2H, t, J=7.3 Hz), 4.69 (2H, s), 4.69 (2H, br), 6.69 (1H, d, J=9.3 Hz), 7.17 (1H, d, J=9.3 Hz), 8.10 (1H, s).

IR (KBr) n: 3299, 3171, 1630, 1518, 1445 $cm^{-1}$.

Anal calcd for $C_{10}H_{14}N_6S$: C, 47.98; H, 5.64; N, 33.57. Found C, 47.92; H, 5.61; N, 33.45.

Reference Example 50

3-amino-6-mercaptopyridazine (0.5 g), 4-chloromethyl-3-propylimidazole hydrochloride (0.62 g) and potassium carbonate (2.0 g) were added to N,N-dimethylformamide (10 ml), and the mixture was stirred overnight at room temperature. The solvent was distilled off, the residue was purified by basic silica gel column chromatography (elution solvent: methanol/ethyl acetate), to give 3-amino-6-[(3-propylimidazol-4-yl)methylthio]pyridazine (0.52 g) as yellow crystals.

$^1$H-NMR (dppm, CDCl$_3$) 0.95 (3H, t, J=7.4 Hz), 1.78 to 1.89 (2H, m), 3.93 (2H, t, J=7.3 Hz), 4.52 (2H, s), 4.69 (2H, br), 6.65 (1H, d, J=9.2 Hz), 6.98 (1H, s), 7.05 (1H, d, J=9.2 Hz), 7.45 (1H, s).

IR (KBr) n: 3304, 3154, 2967, 2934, 1636, 1499, 1447 cm$^{-1}$.

Reference Example 51

Dihydroxyacetone (11.2 g), potassium thiocyanate (18.2 g) and cyclopropylamine hydrochloride (15 g) were added to acetic acid (12 ml) and 1-butanol (80 ml) at 50° C., and the mixture was heated overnight. The mixture was concentrated, methanol was added to the mixture, and colorless crystals (11.5 g) were collected by filtration, and washed with water. Sodium nitrite (0.1 g) was dissolved in nitric acid (20 ml) and water (20 ml), and to the solution were added the obtained crystals by portions under ice-cooling. The mixture was stirred for 1 hour at room temperature, the mixture was neutralized with potassium carbonate, and the solvent was evaporated. Ethanol was added to the residue, the insolubles were filtered off, and the solvent of the filtrate was evaporated. The residue was purified by basic silica gel column chromatography (elution solvent: methanol/ethyl acetate) to give pale yellow oil (7.5 g). To the solution was added thionyl chloride (20 ml) under ice-cooling, and the mixture was refluxed for 30 minutes. The solvent was evaporated, to give 4-chloromethyl-3-cyclopropylimidazole hydrochloride (9.3 g) as colorless crystals.

$^1$H-NMR (dppm, DMSO-d$_6$) 1.10 to 1.27 (4H, m), 3.63 to 3.71 (1H, m), 5.04 (2H, s), 7.80 (1H, s), 9.24 to 9.27 (1H, m).

Reference Example 52

To a solution of methyl 7-[4-(2-butoxyethoxy)phenyl]-2,3-dihydro-1H-1-benzazepine-4-carboxylate (2.0 g) and pyridine (4.0 ml) in THF (40 ml) were added methanesulfonic acid anhydride (4.4 g) at 0° C., and the mixture was stirred for 18 hours at 60° C. To the reaction solution was added water and the mixture was extracted with ethyl acetate. The organic layer was washed with saturated brine, dried over magnesium sulfate and concentrated under reduced pressure, and the obtained residue was purified by column chromatography (ethyl acetate:hexane 1:2), to give methyl 7-[4-(2-butoxyethoxy)phenyl]-1-methanesulfonyl-2,3-dihydro-1H-1-benzazepine-4-carboxylate (1.94 g) as yellow amorphous.

$^1$H-NMR (200 MHz, CDCl$_3$) δ 0.94 (3H, t, J=7.3 Hz), 1.30 to 1.44 (2H, m), 1.51 to 1.66 (2H, m), 2.78 (3H, s), 2.99 to 3.07 (2H, m), 3.56 (2H, t, J=6.6 Hz), 3.80 to 3.89 (7H, m), 4.18 (2H, t, J=4.9 Hz), 7.02 (2H, d, J=8.8 Hz), 7.51 (2H, d, J=8.8 Hz), 7.53 to 7.57 (1H, m), 7.63 to 7.70 (2H, m), 7.80 (1H, s).

Reference Example 53

To a solution of methyl 7-[4-(2-butoxyethoxy)phenyl]-1-methanesulfonyl-2,3-dihydro-1H-1-benzazepine-4-carboxylate (1.94 g) in THF-water (20-20 ml) was added 1N aqueous solution of sodium hydroxide (8.0 ml) at room temperature and the mixture was stirred for 20 hours at room temperature. The reaction mixture was concentrated under reduced pressure, and to the residue was added 1N hydrochloric acid (10 ml), and the mixture was extracted with ethyl acetate. The organic layer was washed with water and saturated brine, dried over magnesium sulfate and concentrated under reduced pressure, and the precipitated crystals were collected by filtration. The crystals were washed with diisopropylether, to give 7-[4-(2-butoxyethoxy)phenyl]-1-methanesulfonyl-2,3-dihydro-1H-1-benzazepine-4-carboxylic acid (1.23 g) as colorless crystals.

m.p. 208 to 210° C.

$^1$H-NMR (200 MHz, CDCl$_3$) δ 0.94 (3H, t, J=7.4. Hz), 1.29 to 1.49 (2H, m), 1.53 to 1.68 (2H, m), 2.81 (3H, s), 3.03 to 3.12 (2H, m), 3.56 (2H, t, J=6.6 Hz), 3.80 to 3.91 (4H, m), 4.18 (2H, t, J=4.8 Hz), 7.02 (2H, d, J=8.8 Hz), 7.49 to 7.71 (5H, m), 7.90 (1H, s).

IR (KBr) 1670, 1497, 1341, 1250, 1154 cm$^{-1}$

Anal calcd. For. C$_{24}$H$_{29}$NO$_6$S Calcd. C, 62.73; H, 6.36; N, 3.05. Found: C, 62.62; H, 6.48; N, 2.92.

Reference Example 54

To a solution of 7-[4-(2-butoxyethoxy)phenyl]-2,3-dihydro-1H-1-benzazepine-4-carboxylic acid (12.5 g) in THF (150 ml) were added triethylamine (18.4 ml) and trifluoroacetic acid anhydride (11.6 ml) at 0° C. and the mixture was stirred for 1 hour. To the reaction solution was added an aqueous solution of sodium bicarbonate at room temperature and the mixture was stirred for overnight. To the reaction solution, 1N hydrochloric acid was added to adjust pH to 7 and the mixture was extracted with ethyl acetate. The organic layer was washed with saturated brine, dried over magnesium sulfate and concentrated under reduced pressure, and the precipitated crystals were collected by filtration. The crystals were washed with hexane, to give 7-[4-(2-butoxyethoxy)phenyl]-1-trifluoroacetyl-2,3-dihydro-1H-1-benzazepine-4-carboxylic acid (11.19 g) as colorless crystals.

$^1$H-NMR (200 MHz, CDCl$_3$) δ 0.94 (3H, t, J=7.3 Hz), 1.31 to 1.49 (2H, m), 1.56 to 1.69 (2H, m), 2.79 to 3.28 (3H, m), 3.57 (2H, t, J=6 Hz), 3.83 (2H, t, J=4.7 Hz), 4.19 (2H, t, J=4.7 Hz), 4.72 to 4.89 (1H, m), 7.03 (2H, d, J=8.8 Hz), 7.33 (1H, d, J=8.4 Hz), 7.52 to 7.60 (3H, m), 7.69 (1H, d, J=1.8 Hz), 7.87 (1H, s).

Reference Example 55

To a mixture of 4-fluorophenylacetonitrile (3.97 g), 2-bromo-6-methylpyridine (5.00 g) and sodium 4-methylphenylsulfinate (10.48 g) in THF (125 ml) was added sodium hydride (2.35 g, 60%) at 0° C. under argon atmosphere, and the mixture was heated to reflux for 3 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate: hexane 1:4), to give 2-(α-cyano-4-fluorobenzyl)-6-methylpyridine (5.51 g) as yellow oil.

$^1$H-NMR (200 MHz, CDCl$_3$) δ 2.56 (3H, s), 5.26 (1H, s), 7.02 to 7.18 (4H, m), 7.39 to 7.46 (2H, m), 7.59 (1H, t, J=7.7 Hz).

IR (KBr) 2247, 1593,.1574, 1508, 1456, 1231, 1159, 839, 804, cm$^{-1}$

Reference Example 56

Under oxygen atmosphere, a mixed solution of 2-α-cyano-4-fluorobenzyl)-6-methylpyridine (5.51 g) and potassium carbonate (3.70 g) in DMSO-water (220-45 ml) was stirred at room temperature for 20 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:4), to give 2-(4-fluorobenzoyl)-6-methylpyridine (5.02 g) as pale yellow crystals.

m.p. 53 to 54° C.

$^1$H-NMR (200 MHz, CDCl$_3$) δ 2.64 (3H, s), 7.09 to 7.21 (2H, M), 7.33 to 7.37 (1H, m), 7.73 to 7.85 (2H, m), 8.15 to 8.25 (2H, m).

IR (KBr) 1622, 1588, 1501, 1454, 1412, 1375, 1310, 1231, 1167, 1157, 1091, 991, 955, 850, 756, 610 cm$^{-1}$

Anal calcd. For. C$_{13}$H$_{10}$NOF Calcd. C, 72.55; H, 4.68; N, 6.51. Found: C, 72.52; H, 4.74; N, 6.39.

Reference Example 57

A solution of 2-(4-fluorobenzoyl)-6-methylpyridine (2.0 g) and sodium azide (3.36 g) in DMSO (40 ml) and the mixture was stirred for 24 hours at 90° C. To the reaction mixture was added water, and the mixture was extracted with diethylether. The organic layer was washed with saturated brine, dried over magnesium sulfate and concentrated under reduced pressure, and a solution of the residue (1.88 g) in THF (40 ml) was added dropwise to a suspension of aluminum lithium hydride (0.60 g) in. THF (20 ml) at 0° C. The mixture was stirred at room temperature for 30 minutes, and water (0.6 ml), 15% aqueous solution of sodium hydroxide (0.6 ml) and water (1.8 ml) were sequentially and slowly added dropwise to the solution at 0° C. The mixture was stirred at room temperature for 4 days, magnesium sulfate was added to the mixture, and the precipitates were removed by filtration (Celite). The reaction mixture was concentrated under reduced pressure, and the obtained residue was separated and purified by column chromatography (ethyl acetate), to give (4-aminophenyl)(6-methylpyridin-2-yl)methanol (1.44 g) as pale yellow crystals.

m.p. 165 to 166° C.

$^1$H-NMR (200 MHz, CDCl$_3$) δ 2.58 (3H, s), 3.51 to 3.73 (2H, m), 5.55 to 5.61 (2H, m), 6.65 (2H, d, J=8.4 Hz), 6.88 (1H, d, J=7.8 Hz), 7.03 (1H, d, J=7.6 Hz), 7.13 (2H, d, J=8.4 Hz), 7.49 (1H, dd, J=7.8, 7.6 Hz).

IR (KBr) 3330, 1611, 1595, 1578, 1510, 1460, 1258, 1071, 903, 833, 806 cm$^{-1}$

Elemental Analysis for C$_{13}$H$_{14}$N$_2$O. Calcd. C, 72.87; H, 6.59; N, 13.07. Found: C, 72.64; H, 6.68; N, 12.87.

Reference Example 58

Under argon atmosphere, to a mixture of 4-fluorophenylacetonitrile (3.97 g), 2-bromo-3-methylpyridine (5.00 g) and sodium 4-methylphenylsulfinate (10.48 g) in THF (125 ml) was added sodium hydride (2.35 g, 60%) at 0° C. to the mixture, and the mixture was heated to reflux for 3.5 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate: hexane 1:3), to give 2-(α-cyano-4-fluorobenzyl)-3-methylpyridine (5.14 g) as brown oil.

$^1$H-NMR (200 MHz, CDCl$_3$) δ 2.27 (3H, s), 5.45 (1H, s), 7.00 to 7.10 (2H, m), 7.19 to 7.26 (1H, m), 7.32 to 7.39 (2H, m), 7.48 to 7.57 (1H, m), 8.51 to 8.54 (1H, m).

IR (KBr) 2245, 1605, 1574, 1508, 1454, 1420, 1229, 1161, 1107, 837, 801, 739 cm$^{-1}$

Reference Example 59

Under oxygen atmosphere, a mixed solution of 2-α-cyano-4-fluorobenzyl)-3-methylpyridine (5.14 g) and potassium carbonate (2.90 g) in DMSO-water (250-50 ml) was stirred for 6 days at room temperature. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:4), to give 2-(4-fluorobenzoyl)-3-methylpyridine (5.17 g) as orange oil.

$^1$H-NMR (200 MHz, CDCl$_3$) δ 7.10 to 7.20 (2H, m), 7.35 (1H, dd, J=7.6, 4.8 Hz), 7.68 (1H, d, J=7.6 Hz), 7.89 to 7.96 (2H, m), 8.33 (1H, d, J=4.4 Hz).

IR (KBr) 1672, 1599, 1505, 1292, 1233, 1152, 1115, 936, 853, 610 cm$^{-1}$

Reference Example 60

A solution of 2-(4-fluorobenzoyl)-3-methylpyridine (4.0 g) and sodium azide (6.7 g) in DMSO (80 ml) was stirred for 21 hours at 90° C. To the reaction mixture was added water, and the mixture was extracted with diethylether. The organic layer was washed with saturated brine, dried over magnesium sulfate and concentrated under reduced pressure, and a solution of the residue (3.90 g) in THF (40 ml) was added dropwise to a suspension of aluminum lithium hydride (1.24 g) in THF (40 ml) at 0° C. The mixture was stirred at room temperature for 3 hours, water (1.24 ml), 15% aqueous solution of sodium hydroxide (1.24 ml) and water (3.72 ml) were sequentially and slowly added dropwise to the solution at 0° C. The mixture was stirred temperature for 16 hours at room temperature, magnesium sulfate was added to the mixture, and the precipitates were removed by filtration (Celite). The reaction mixture was concentrated under reduced pressure, and the residue was recrystallized from ethyl acetate, to give (4-aminophenyl)(3-methylpyridin-2-yl)methanol (2.60 g) as pale yellow crystals.

m.p. 153 to 154° C.

$^1$H-NMR (200 MHz, CDCl$_3$) δ 2.07 (3H, s), 3.56 to 3.66 (2H, m), 5.64 (1H, d, J=6.2 Hz), 5.93 (1H, d, J=6.2 Hz), 6.60 (2H, d, J=8.4 Hz), 7.01 (2H, d, J=8.4 Hz), 7.17 (1H, dd, J=7.8, 4.8 Hz), 7.41 to 7.45 (1H, m), 8.45 to 8.47 (1H, m).

IR (KBr) 3449, 3357, 1632, 1613, 1516, 1451, 1383, 1300, 1179, 1017, 1007, 868, 833, 801, 739 cm$^{-1}$

Elemental Analysis for C$_{13}$H$_{14}$N$_2$O Calcd. C, 72.87; H, 6.59; N, 13.07. Found: C, 72.77; H, 6.81; N, 12.93.

Reference Example 61

Under argon atmosphere, to a mixture of 4-fluorophenylacetonitrile (3.97 g), 2-bromo-5-methylpyridine (5.00 g) and sodium 4-methylphenylsulfinate (10.48 g) in THF (125 ml) was added sodium hydride (2.35 g, 60%) at 0° C. and the mixture was heated to reflux for 6 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:4), to give 2-(α-cyano-4-fluorobenzyl)-5-methylpyridine (4.35 g) as yellow oil.

$^1$H-NMR (200 MHz, CDCl$_3$) δ 2.34 (3H, s), 5.26 (1H, s), 7.02 to 7.10 (2H, m), 7.28 (1H, d, J=8.0 Hz), 7.37 to 7.44 (2H, m), 7.52 (1H, dd, J=8.0, 2.0 Hz), 8.42 (1H, d, J=2.2 Hz)

Reference Example 62

Under oxygen atmosphere, a mixed solution of 2-α-cyano-4-fluorobenzyl)-5-methylpyridine (4.35 g) and potassium carbonate (3.07 g) in DMSO-water (200-40 ml) was stirred for 18 hours at room temperature. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:4), to give 2-(4-fluorobenzoyl)-5-methylpyridine (3.47 g) as colorless crystals.

m.p. 127 to 128° C.

$^1$H-NMR (200 MHz, CDCl$_3$) δ 2.46 (3H, s), 7.11 to 7.22 (2H, m), 7.68 to 7.74 (1H, m), 7.99 (1H, d, J=8.0 Hz), 8.12 to 8.19 (2H, m), 8.54 to 8.55 (1H, m).

IR (KBr) 1659, 1597, 1507, 1412, 1316, 1248, 1227, 1155, 1034, 941, 860, 849, 775, 733, 681, 634, 581 cm$^{-1}$

Elemental Anaylsis for C$_{13}$H$_{10}$NOF Calcd. C, 72.55; H, 4.68; N, 6.51. Found: C, 72.68; H, 4.64; N, 6.59.

Reference Example 63

A solution of 2-(4-fluorobenzoyl)-5-methylpyridine (3.0 g) and sodium azide (4.97 g) in DMSO (60 ml) was stirred for 24 hours at 90° C. To the reaction mixture was added water, and the mixture was extracted with diethylether. The organic layer was washed with water and saturated brine, dried over magnesium sulfate and concentrated under reduced pressure, and a solution of the residue (3.39 g) in THF (40 ml) was added dropwise to a suspension of aluminum lithium hydride (1.06 g) in THF (40 ml) at 0° C. The mixture was stirred at room temperature for 1 hour, and water (1.06 ml), 15% aqueous solution of sodium hydroxide (1.06 ml) and water (3.18 ml) were sequentially and slowly added dropwise to the solution at 0° C. The mixture was stirred for 64 hours at room temperature, magnesium sulfate was added to the mixture, and the precipitates were removed by filtration (Celite). The reaction mixture was concentrated under reduced pressure, and the residue was recrystallized, to give (4-aminophenyl)(5-methylpyridin-2-yl)methanol (2.07 g) as pale yellow crystals.

m.p. 114 to 115° C.

$^1$H-NMR (200 MHz, CDCl$_3$) δ 2.32 (3H, s), 3.53 to 3.72 (2H, m), 5.09 (1H, d, J=4.0 Hz), 5.62 (1H, d, J=4.0 Hz), 6.64 (2H, d, J=8.4 Hz), 7.02 (1H, d, J=8.0 Hz), 7.12 (2H, d, J=8.4 Hz), 7.42 (1H, dd, J=8.0, 2.2), 8.37 (1H, d, J=2.2 Hz).

IR (KBr) 3349, 1200, 1615, 1516, 1487, 1449, 1264, 1252, 1198, 1179, 1063, 1038, 826 cm$^{-1}$

Elemental Analysis for C$_{13}$H$_{14}$N$_2$O Calcd. C, 72.87; H, 6.59; N, 13.07. Found: C, 72.68; H, 6.88; N, 12.81.

Reference Example 64

Under argon atmosphere, to a mixture of 4-fluorophenylacetonitrile (9.13 g), 2-chloro-5-chloropyridine (10.0 g.) and sodium 4-methylphenylsulfinate (24.1 g) in THF (280 ml) was added sodium hydride (5.41 g, 60%) at 0° C., and the mixture was heated to reflux for 20 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:4), to give 5-chloro-2-(α-cyano-4-fluorobenzyl)pyridine (16.14 g) as yellow oil.

$^1$H-NMR (200 MHz, CDCl$_3$) δ 5.28 (1H, s), 7.04 to 7.12 (2H, m), 7.32 to 7.44 (3H, m), 7.70 (1H, dd, J=8.4, 2.6 Hz), 8.55 (1H, d, J=2.6 Hz).

IR (KBr) 2250, 1607, 1578, 1508, 1466, 1373, 1235, 1161, 1111, 1017, 833 cm$^{-1}$

Elemental Analysis for C$_{37}$H$_{36}$N$_3$O$_6$F$_3$.0.5H$_2$O Calcd. C, 64.90; H, 5.45; N, 6.14. Found: C, 64.97; H, 5.37; N, 6.10.

Reference Example 65

Under oxygen atmosphere, a mixed solution of 5-chloro-2-(α-cyano-4-fluorobenzyl)pyridine (16.14 g) and potassium carbonate (10.85 g) in DMSO-water (330-66 ml) was stirred at room temperature for 3 days. To the reaction mixture was added water, and the mixture was extracted with ethyl acetate. The organic layer was washed with saturated brine, dried over magnesium sulfate and concentrated under reduced pressure, and the obtained residue was separated and purified by column chromatography (ethyl acetate:hexane 1:4), to give 5-chloro-2-(4-fluorobenzoyl)pyridine (14.37 g) as colorless crystals.

m.p. 98 to 100° C.

$^1$H-NMR (200 MHz, CDCl$_3$) δ 7.13 to 7.22 (2H, m), 7.89 (1H, dd, J=8.4, 2.4 Hz), 8.06 (1H, d, J=8.4 Hz), 8.13 to 8.20 (2H, m), 8.65 (1H, d, J=2.4 Hz).

IR (KBr) 1666, 1599, 1566, 1507, 1408, 1370, 1306, 1236, 1157, 1123, 1107, 1015, 951, 862, 816, 725, 675 cm$^{-1}$

Elemental Analysis for C$_{12}$H$_7$NOClF Calcd. C, 61.16; H, 2.99; N, 5.94. Found: C, 61.14; H, 2.90; N, 6.00.

Reference Example 66

A solution of 5-chloro-2-(4-fluorobenzoyl)pyridine (3.0 g) and sodium azide (0.84 g) in DMSO (60 ml) was stirred for 20 hours at 90° C. To the reaction mixture was added water, and the mixture was extracted with diethylether. The organic layer was washed with water and saturated brine, dried over magnesium sulfate and concentrated under reduced pressure, and a solution of the residue (3.19 g) in. THF (60 ml) was added dropwise to a suspension of aluminum lithium hydride (0.97 g) in THF (10 ml) at 0° C. The mixture was stirred at 0° C. for 10 minutes, and water (0.97 ml), 15% aqueous solution of sodium hydroxide (0.97 ml) and water (2.9 ml) were sequentially and slowly added dropwise to the solution. The mixture was stirred at room temperature for 18 hours, magnesium sulfate was added to the mixture, and the precipitates were removed by filtration (Celite). The solvent was removed under reduced pressure, and the obtained residue was purified by column chromatography (ethyl acetate:hexane 1:1→2:1), to give (4-aminophenyl)(5-chloropyridin-2-yl)methanol (0.90 g) as pale yellow crystals.

m.p. 122 to 123° C.

$^1$H-NMR (200 MHz, CDCl$_3$) δ 3.60 to 3.71 (2H, m), 4.56 (1H, d, J=4.1 Hz), 5.65 (1H, d, J=4.1 Hz), 6.65 (2H, d, J=8.8 Hz), 7.08 to 7.17 (3H, m), 7.60 (1H, dd, J=8.2, 2.2 Hz), 8.51 (1H, d, J=2.2 Hz).

IR (KBr) 3378, 3183, 1615, 1578, 1514, 1472, 1370, 1267, 1198, 1175, 1113, 1049, 1020, 828 cm$^{-1}$

Elemental Analysis for $C_{12}H_{12}N_2OCl$ Calcd. C, 61.41; H, 4.72; N, 11.94. Found: C, 61.47; H, 4.83; N, 11.78.

Reference Example 67

Under argon atmosphere, to a mixture of 4-fluorophenylacetonitrile (3.13 g), 2-bromo-3-propoxypyridine (5.0 g) and sodium 4-methylphenylsulfinate (8.23 g) in THF (100 ml) was added sodium hydride (1.85 g, 60%) at 0° C., and the mixture was heated to reflux for 5 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:4), to give pale, 2-(α-cyano-4-fluorobenzyl)-3-propoxypyridine (5.52 g) as yellow oil.

$^1$H-NMR (200 MHz, $CDCl_3$) δ 1.04 (3H, t, J=7.5 Hz), 1.74 to 1.91 (2H, m), 3.95 (2H, t, J=6.6 Hz), 5.64 (1H, s), 6.98 to 7.00 (2H, m), 7.14 to 7.26 (2H, m), 7.42 to 7.49 (2H, m), 8.22 (1H, dd, J=4.4, 1.6 Hz).

IR (neat) 2240, 1601, 1580, 1505, 1445, 1285, 1231, 1159, 1113, 974, 849, 795 $cm^{-1}$ Reference Example 68

Under oxygen atmosphere, a mixed solution of 2-(α-cyano-4-fluorobenzyl)-3-propoxypyridine (5.42 g) and potassium carbonate (3.07 g) in DMSO-water (200-40 ml) was stirred at room temperature for 20 hours. The reaction mixture was added to water and extracted with ethyl acetate. The organic layer was washed with saturated brine, dried over magnesium sulfate and concentrated under reduced pressure, and the obtained residue was separated and purified by column chromatography (ethyl acetate:hexane 1:3→1:2), to give 2-(4-fluorobenzoyl)-3-propoxypyridine (4.46 g) as pale yellow oil.

$^1$H-NMR (200 MHz, $CDCl_3$) δ 0.86 (3H, t, J=7.5 Hz), 1.60 to 1.79 (2H, m), 3.95 (2H, t, J=6.4 Hz), 7.08 to 7.16 (2H, m), 7.30 to 7.48 (2H, m), 7.85 to 7.92 (2H, m), 8.27 (1H, dd, 4.1, 1.9).

IR (neat) 1676, 1599, 1578, 1507, 1443, 1292, 1277, 1231, 1204, 1152, 1121, 937 $cm^{-1}$ Reference Example 69

A solution of 2-(4-fluorobenzoyl)-3-propoxypyridine (4.46 g) and sodium azide (3.34 g) in. DMSO (50 ml) was stirred for 22 hours at 90° C. To the reaction mixture was added water, and the mixture was extracted with diethylether. The organic layer was washed with saturated brine, dried over magnesium sulfate and concentrated under reduced pressure, and a solution of the residue (4.8 g) in THF (50 ml) was added dropwise to a suspension of aluminum lithium hydride (1.3 g) in. THF (40 ml) at 0° C. The mixture was stirred at room temperature for 30 minutes, water (1.3 ml), 15% aqueous solution of sodium hydroxide (1.3 ml) and water (3.9 ml) were sequentially and slowly added dropwise to the solution at 0° C. The mixture was stirred at room temperature for 2 hours, magnesium sulfate was added to the mixture, and the precipitates were removed by filtration (Celite). The reaction mixture was concentrated under reduced pressure, and the residue was recrystallized from ethyl acetate to give (4-aminophenyl)(3-propoxypyridin-2-yl)methanol (2.82 g) as pale yellow crystals.

m.p. 156 to 157° C.

$^1$H-NMR (200 MHz, $CDCl_3$) δ 0.97 (3H, t, J=7.3 Hz), 1.66 to 1.82 (2H, m), 3.49 to 3.66 (2H, m), 3.80 to 3.87 (2H, m), 5.41 (1H, d, J=6.8 Hz), 5.84 (1H, d, J=6.8 Hz), 6.59 (2H, d, J=8.4 Hz), 7.04 to 7.20 (4H, m), 8.15 (1H, dd, J=4.7, 1.5 Hz).

IR (KBr) 3428, 3349, 1613, 1518, 1445, 1281, 1211, 1177, 1032, 1009, 839 $cm^{-1}$

Elemental Anaysis for $C_{15}H_{18}N_2O_2$ Calcd. C, 69.74; H, 7.02; N, 10.84. Found: C, 69.73; H, 7.01; N, 10.74.

Reference Example 70

To a solution of 7-[4-(2-butoxyethoxy)phenyl]-1-isobutyl-2,3-dihydro-1H-1-benzazepine-4-carboxylic acid (10.0 g) in THF (100 ml) were added thionyl chloride (2.5 ml) and DMF (0.5 ml) at room temperature and the mixture was stirred for 1.5 hours. The reaction mixture was concentrated under reduced pressure, and a solution of the residue in THF (100 ml) was added dropwise to a solution of 4-(tert-butyldimethylsiloxymethyl)aniline (5.92 g) and triethylamine (32 ml) in. THF (50 ml) at 0° C. The mixture was stirred at room temperature for 3 hours, water was added to the mixture and the mixture was extracted with ethyl acetate. The organic layer was washed with saturated brine, dried over magnesium sulfate and concentrated under reduced pressure, and to the residue were added acetone (150 ml) and 6N hydrochloric acid (8 ml) and the mixture was stirred for 20 minutes. 1N aqueous solution of sodium hydroxide (50 ml) was added to the mixture, and the mixture was concentrated under reduced pressure. To the residue was added water and the mixture was extracted with ethyl acetate. The organic layer was washed with saturated brine, dried over magnesium sulfate and concentrated under reduced pressure, and the obtained residue was separated and purified by column chromatography (ethyl acetate:hexane 1:1), to give 7-[4-(2-butoxyethoxy)phenyl]-N-(4-hydroxymethylphenyl)-2,3-dihydro-1-isobutyl-1H-1-benzazepine-4-carboxamide (11.41 g) as yellow amorphous.

$^1$H-NMR (200 MHz, $CDCl_3$) δ 0.93 (3H, t, J=7.3 Hz), 0.97 (6H, d, J=6.6 Hz), 1.27 to 1.46 (2H, m), 1.52 to 1.73 (2H, m), 1.95-2.16 (1H, m), 2.86 to 2.97 (2H, m), 3.19 (2H, d, J=6.8 Hz), 3.34 to 3.39 (2H, m), 3.55 (1H, t, J=6.6 Hz), 3.80 (2H, t, J=5.0 Hz), 4.16 (2H, t, J=5.0 Hz), 4.68 (2H, s), 6.92 (1H, d, J=8.8 Hz), 6.98 (2H, d, J=8.8 Hz), 7.33 to 7.62 (10H, m).

IR (KBr) 3289, 1645, 1605, 1516, 1499, 1406, 1314, 1244, 1181, 1119, 816 $cm^{-1}$

Elemental Analysis for $C_{34}H_{42}N_2O_4 \cdot 0.25H_2O$ Calcd. C, 74.63; H, 7.83; N, 5.12. Found: C, 74.76; H, 7.97; N, 5.26.

Reference Example 71

To a suspension of imidazole-2-carboxyaldehyde (2.50 g) and potassium carbonate (4.31 g) in DMF (25 ml) was added 2-iodopropane (5.31 g) under nitrogen atmosphere at 50° C. and the mixture was heated for 5 hours. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was dried over magnesium sulfate, and the solvent was distilled off under reduced pressure, to give 1-isopropylimidazole-2-carboxyaldehyde (3.35 g) as brown oil.

$^1$H-NMR (200 MHz, $CDCl_3$) δ 1.47 (6H, d, J=7.0 Hz), 5.41-5.55 (1H, m), 7.31 to 7.33 (2H, m), 9.83 (1H, s).

Reference Example 72

To a suspension of aluminum lithium hydride (978 mg) in THF (15 ml) was added dropwise a solution of 1-isopropylimidazole-2-carboxyaldehyde (2.38 g) in THF (15 ml) at 0° C. under nitrogen atmosphere. After finishing the dropping, water (1.0 ml), 15% aqueous solution of sodium hydroxide (1.0 ml) and water (3.0 ml) were sequentially added to the solution at 0° C., and the mixture was stirred for 2 hours at room temperature. The mixture was dried over magnesium sulfate, and the insolubles were filtered off. The solvent was distilled off under reduced pressure, to give 2-hydroxymethyl-1-isopropylimidazole (2.10 g) as brown crystals.

$^1$H-NMR (200 MHz, CDCl$_3$) δ 1.45 (6H, d, J=6.8 Hz), 4.53 to 4.67 (1H, m), 4.68 (2H, s), 6.91 (1H, d, J=1.2 Hz), 6.94 (1H, d, J=1.2 Hz)

Elemental Analysis for C$_7$H$_{12}$N$_2$O. Calcd. C, 59.98; H, 8.63; N, 19.98. Found: C, 59.90; H, 8.53; N, 20.07.

Reference Example 73

To a solution of 2-hydroxymethyl-1-isopropylimidazole (1.0 g) in chloroform (15 ml) was added one droplet of DMF, and thionyl chloride (0.68 ml) was added to the solution at 0° C. The mixture was allowed to be at room temperature, and stirred for 30 minutes under nitrogen atmosphere. The solvent was distilled off under reduced pressure and the obtained residue was dissolved in methanol (10 ml). This solution was added to a mixed solution of 4-aminothiophenol (811 mg) and sodium hydroxide (570 mg) in methanol (10 ml) and water (6 ml) at 0° C. The mixture was allowed to be at room temperature, and stirred for 30 minutes, water was added to the mixture, and the mixture was extracted with ethyl acetate. The organic layer was washed with saturated brine, and dried over magnesium sulfate. The solvent was distilled off under reduced pressure, to give 4-[[(1-isopropylimidazol-2-yl)methyl]sulfanyl]aniline (1.55 g) as oil.

$^1$H-NMR (200 MHz, CDCl$_3$): δ 1.41 (6H, d, J=6.6 Hz), 3.71 (2H, br), 4.06 (2H, s), 4.38 to 4.60 (1H, m), 6.58 (2H, d, J=8.8 Hz), 6.92 to 6.93 (2H, m), 7.16 (2H, d, J=8.8 Hz).

Reference Example 74

A solution of 4-aminothiophenol (1.0 g), 3-chloromethyl-1,2,4-oxadiazole (1.0 g) and triethylamine (1.1 ml) in THF (10 ml) was stirred at room temperature for 18 hours. To the reaction solution was added water, and the mixture was extracted with ethyl acetate. The organic layer was washed with saturated brine, dried over magnesium sulfate and concentrated under reduced pressure, and the obtained residue was separated and purified by column chromatography (ethyl acetate:hexane 1:3→1:2), to give 4-(1,2,4-oxadiazol-3-ylmethylthio)aniline (1.36 g) as pale yellow oil.

$^1$H-NMR (200 MHz, CDCl$_3$) δ 3.63 to 3.84 (2H, m), 4.02 (2H, s), 6.59 (2H, d, J=8.4 Hz), 7.21 (2H, d, 8.4 Hz), 8.65 (1H, s).

IR (neat) 3357, 1624, 1597, 1551, 1497, 1341, 1287, 1179, 1109, 827, 739 cm$^{-1}$

Reference Example 75

To a solution of hydrazine monohydrate (10.0 g) in ethanol (100 ml), ethyl glycolate (20.8 g) was slowly added dropwise with keeping the reaction temperature under 10° C. at room temperature. The mixture was stirred for 5 hours at room temperature, and ethyl isothiocyanate (17.42 g) was slowly added dropwise to the mixture with keeping the reaction temperature under 10° C. The mixture was stirred for 18 hours at 40° C., cooled to room temperature, and ice-water (50 ml) was added to the mixture. The mixture was stirred for 15 miuntes, 5N aqueous solution of sodium hydroxide (40 ml) was added to the mixture, and the mixture was stirred for 4 hours at 60° C. Concentrated hydrochloric acid was added dropwise to the solution at 0° C. to adjust pH to 6, and the precipitated crystals were removed by filtration. The mixture was concentrated under reduced pressure, and the precipitated crystals were collected by filtration. The crystals were washed with water, to give 4-ethyl-3-hydroxymethyl-5-mercapto-4H-1,2,4-triazole (7.5 g) as colorless crystals.

To a mixture of 90% nitric acid (15 ml) and water (22 ml) was added sodium nitrite (0.06 g) and then 3-hydroxymethyl-5-mercapto-4-ethyl-4H-1,2,4-triazole (7.5 g) was slowly added for 0.5 hours at 45° C. After allowing the mixture to be cooled to room temperature, sodium carbonate was slowly added thereto to adjust pH to 7 at 0° C. The reaction mixture was concentrated under reduced pressure, methanol was added to the residue, and the precipitates were removed by filtration. The mixture was concentrated under reduced pressure, and the obtained residue was separated and purified by column chromatography (ethanol:ethyl acetate 2:1), to give 4-ethyl-3-hydroxymethyl-4H-1,2,4-triazole (4.60 g) as brown oil.

To 4-ethyl-3-hydroxymethyl-4H-1,2,4-triazole (4.6 g), thionyl chloride (36 ml) was slowly added at 0° C. The mixture was heated to reflux for 1 hour, and concentrated under reduced pressure. To the residue was added ethyl acetate and ethanol, and the precipitated crystals were collected by filtration. The crystals were washed with ethyl acetate, to give 3-chloromethyl-4-ethyl-4H-1,2,4-triazole hydrochloride (4.22 g) as orange crystals.

m.p. 125 to 127° C.

$^1$H-NMR (200 MHz, DMSO-d$_6$) δ 1.42 (3H, t, J=7.2 Hz), 4.15 (2H, q, J=7.2 Hz), 5.08 (2H, s), 9.11 (1H, s).

IR (KBr) 1574, 1537, 1325, 1181, 1086, 974, 953, 864, 748, 671 cm$^{-1}$

Elemental Analysis for C$_5$H$_9$N$_3$Cl$_2$.0.2H$_2$O Calcd. C, 32.35; H, 5.10; N, 22.63. Found: C, 32.05; H, 4.72; N, 22.52.

Reference Example 76

To a solution of hydrazine monohydrate (9.66 g) in ethanol (100 ml), ethyl glycolate (20.09 g) was slowly added dropwise with keeping the reaction temperature under 10° C. at room temperature. The mixture was stirred at room temperature for 4 hours, propyl isothiocyanate (20 ml) was slowly added dropwise thereto with keeping the reaction temperature under 10° C. The mixture was stirred for 64 hours at 40° C., cooled to room temperature, and ice-water (50 ml) was added to the mixture. The mixture was stirred for 15 miuntes, 5N aqueous solution of sodium hydroxide (40 ml) was added to the mixture, and the mixture was stirred for 4 hours at 60°. Concentrated hydrochloric acid was added dropwise to the solution at 0° C. to adjust pH to 6, and the precipitated crystals were removed by filtration. The mixture was concentrated under reduced pressure, and the precipitated crystals were collected by filtration. The crystals were washed with water, to give 3-hydroxymethyl-5-mercapto-4-propyl-4H-1,2,4-triazole (23.45 g) as colorless crystals.

To a mixture of 90% nitric acid (18 ml) and water (26 ml) was added sodium nitrite (0.07 g) and then 3-hydroxymethyl-5-mercapto-4-propyl-4H-1,2,4-triazole (10 g) was slowly added for 0.5 hours at 45° C. After cooling to room temperature, and sodium carbonate was slowly added thereto to adjust pH to 7 at 0° C. The reaction mixture was concentrated under reduced pressure, methanol was added to the residue, and the precipitates were removed by filtration. The mixture was concentrated under reduced pressure, dichloromethane was added to the residue, the precipitates were removed by filtration, and the filtrate was concentrated to give 3-hydroxymethyl-4-propyl-4H-1,2,4-triazole (5.95 g) as a crude product.

To 3-hydroxymethyl-4-propyl-4H-1,2,4-triazole (5.95 g), thionyl chloride (40 ml) was slowly added at 0° C. The mixture was heated to reflux for 1 hour, and concentrated under reduced pressure. To the residue was added ethanol, and the mixutre was further concentrated. To the residue were added ethyl acetate and small amount of ethanol, and the precipitated crystals were collected by filtration. The crystals were washed with ethyl acetate, to give 3-chloromethyl-4-propyl-4H-1,2,4-triazole hydrochloride (5.43 g) as pale yellow crystals.

m.p. 91 to 94° C. $^1$H-NMR (200 MHz, CDCl$_3$) δ 0.80 (3H, t, J=7.3 Hz), 1.73 to 1.94 (2H, m), 4.11 (2H, t, J=7.4 Hz), 5.10 (2H, s), 9.26 (1H, s).

IR (KBr) 3353, 1574, 1537, 1470, 1331, 1204, 1177, 957 cm$^{-1}$

Elemental Analysis for $C_6H_{11}N_3Cl_2 \cdot 0.25H_2O$ Calcd. C, 35.93; H, 5.78; N, 20.95. Found: C, 36.13; H, 5.77; N, 21.23.

Reference Example 77

To a solution of hydrazine monohydrate (7.5 g) in ethanol (75 ml), ethyl glycolate (15.6 g) was slowly added dropwise with keeping the reaction temperature under 10° C. at room temperature. The mixture was stirred for 6 hours at room temperature, and n-butyl isothiocyanate (17.3 g) was slowly added dropwise thereto with keeping the reaction temperature under 10° C. The mixture was stirred at room temperature for 5 hours and at 40° C. for 8 hours, cooled to room temperature, and ice-water (50 ml) was added to the mixture. The mixture was stirred for 15 miuntes, 5N aqueous solution of sodium hydroxide (40 ml) was added to the mixture, and the mixture was stirred for 6 hours at 60° C. Concentrated hydrochloric acid was added dropwise to the solution at 0° C. to adjust pH to 6, and the precipitated crystals were removed by filtration. The mixture was concentrated under reduced pressure, and the precipitated crystals were collected by filtration. The crystals were washed with water, to give 4-n-butyl-3-hydroxymethyl-5-mercapto-4H-1,2,4-triazole (22.67 g) as colorless crystals.

To a mixture of 90% nitric acid (17 ml) and water (25 ml) was added sodium nitrite (0.07 g) and then 4-n-butyl-3-hydroxymethyl-5-mercapto-4H-1,2,4-triazole (10.0 g) was slowly added for 0.5 hours at 45° C. After cooling to room temperature, sodium carbonate was slowly added thereto to adjust pH to 7 at 0° C. The reaction mixture was concentrated under reduced pressure, methanol was added to the residue, and the precipitates were removed by filtration. The mixture was concentrated under reduced pressure, and the obtained residue was separated and purified by column chromatography (basic silica gel, ethanol:ethyl acetate 1:9), to give 4-n-butyl-3-hydroxymethyl-4H-1,2,4-triazole (6.78 g) as orange oil. To 4-n-butyl-3-hydroxymethyl-4H-1,2,4-triazole (6.78 g) was slowly added thionyl chloride (44 ml) at 0° C. The mixture was heated to reflux for 1 hour, and concentrated under reduced pressure. To the residue was added ethyl acetate, and the precipitated crystals were collected by filtration. The crystals were washed with ethyl acetate, to give 4-n-butyl-3-chloromethyl-4H-1,2,4-triazole hydrochloride (7.03 g) as pale yellow crystals.

$^1$H-NMR (300 MHz, DMSO-d$_6$) δ 0.91 (3H, t, J=7.2 Hz), 1.25 to 1.37 (2H, m), 1.75 to 1.83 (2H, m), 4.09 (2H, t, J=7.5 Hz), 5.05 (2H, s), 8.97 (1H, s).

IR (KBr) 1572, 1460, 1329, 1179, 1082, 959, 943, 878, 743, 669 cm$^{-1}$

Elemental Analysis for $C_7H_{13}N_3Cl_2$ Calcd. C, 40.02; H, 6.24; N, 20.00. Found: C, 39.91; H, 6.48; N, 20.16.

Reference Example 78

A solution of 3-hydroxymethyl-4-isobutyl-5-mercapto-4H-1,2,4-triazole (1.0 g), iodoethane (1.0 g) and triethylamine (1.1 ml) in ethanol (10 ml) was stirred for 2 days at 70° C. The solvent was removed under reduced pressure, and the obtained residue was purified by column chromatography (ethanol:ethyl acetate 1:9→1:5), to give 5-ethylthio-3-hydroxymethyl-4-isobutyl-4H-1,2,4-triazole (1.0 g) as pale yellow oil.

$^1$H-NMR (200 MHz, CDCl$_3$) δ 0.93 (6H, d, J=6.6 Hz), 1.40 (3H, t, J=7.3 Hz), 2.06 to 2.25 (1H, m), 3.24 (2H, q, J=7.3 Hz), 3.76 (2H, d, J=7.6 Hz), 4.80 (2H, s).

IR (neat) 3206, 1472, 1387, 1057, 1028, 739 cm$^{-1}$

Reference Example 79

To a solution of 5-ethylthio-3-hydroxymethyl-4-isobutyl-4H-1,2,4-triazole (1.0 g) in chloroform (3 ml), thionyl chloride (8 ml) was slowly added at 0° C. The mixture was heated to reflux for 1 hour, and concentrated under reduced pressure. To the residue was added diethylether, and the precipitated crystals were collected by filtration. The crystals were washed with diethylether, to give 3-chloromethyl-5-ethylthio-4-isobutyl-4H-1,2,4-triazole hydrochloride (0.64 g) as colorless crystals.

$^1$H-NMR (200 MHz, DMSO-d$_6$) δ 0.86 (6H, d, J=6.6 Hz), 1.31 (3H, t, J=7.2 Hz), 2.06 to 2.22 (1H, m), 3.20 (2H, q, J=7.2 Hz), 3.79 (2H, d, J=7.6 Hz), 4.97 (2H, s).

IR (KBr) 1577, 1514, 1422, 1327, 1279, 992, 895, 795 cm$^{-1}$

Reference Example 80

A solution of 3-hydroxymethyl-4-propyl-5-mercapto-4H-1,2,4-triazole (2.0 g), iodo methane (1.1 ml) and triethylamine (2.5 ml) in ethanol (20 ml) was stirred for 2 days at 50° C. The reaction mixture was concentrated under reduced pressure, and the obtained residue was purified by column chromatography (ethanol:ethyl acetate 1:5→1:4), to give 3-hydroxymethyl-5-methylthio-4-propyl-4H-1,2,4-triazole (2.13 g) as pale yellow oil. To a solution of 3-hydroxymethyl-5-methylthio-4-propyl-4H-1,2,4-triazole (2.13 g) in chloroform (6 ml), thionyl chloride (16 ml) was slowly added at 0° C. The mixture was heated to reflux for 2 hours, and concentrated under reduoed pressure. To the residue were added small amount of ethanol and ethyl acetate, and the precipitated crystals were collected by filtration. The crystals were washed with ethyl acetate and diethylether, to give 3-chloromethyl-5-methylthio-4-propyl-4H-1,2,4-triazole hydrochloride (1.06 g) as colorless crystals.

$^1$H-NMR (200 MHz, DMSO-d$_6$) δ 0.89 (3H, t, J=7.3 Hz), 1.63 to 1.82 (2H, m), 2.66 (3H, s), 3.91 (2H, t, J=7.7 Hz), 5.00 (2H, s).

IR (KBr) 1576, 1507, 1480, 1458, 1422, 1346, 1298, 1206, 984 cm$^{-1}$

Reference Example 81

To a solution of 4-nitromethylaniline (1.0 g) and 3-chloromethyl-4-propyl-4H-1,2,4-triazole hydrochloride (1.45 g) in DMSO (20 ml) was added sodium hydride (60%, 0.60 g) at room temperature, and the mixture was stirred for 24 hours at 50° C. To the reaction solution was added water, and the mixture was extracted with ethyl acetate. The organic layer was washed with water and saturated brine, dried over magnesium sulfate and concentrated under reduced pressure, and the obtained residue was separated and purified by column chromatography (ethyl acetate→ethanol:ethyl acetate 1:4), to give 4-nitro[methyl(4-propyl-4H-1,2,4-triazol-3-ylmethyl)]aniline (0.82 g) as yellow crystals.

$^1$H-NMR (200 MHz, CDCl$_3$) δ 0.91 (3H, t, J=7.5 Hz), 1.65 to 1.84 (2H, m), 3.13 (3H, s), 3.84 (2H, t, J=7.4 Hz), 4.80 (2H, s), 6.83 (2H, d, J=9.5 Hz), 8.15 (1H, s), 8.16 (2H, d, J=9.5 Hz).

IR (KBr) 1567, 1586, 1512, 1480, 1329, 1264, 1190, 1115, 820, 785, 752 cm$^{-1}$

Elemental Analysis for C$_{13}$H$_{17}$N$_5$O$_2$ Calcd. C, 56.71; H, 6.22; N, 25.44. Found: C, 56.44; H, 6.07; N, 25.21.

Reference Example 82

A mixture of 4-nitro[methyl(4-propyl-4H-1,2,4-triazol-3-ylmethyl)]aniline (1.0 g), and 10% Pd-C (0.3 g) in ethanol was stirred strongly for 18 hours under hydrogen atmosphere. Pd-C was removed by filtration, the reaction mixture was concentrated under reduced pressure, and the precipitated crystals were collected by filtration. The crystals were washed with diethylether, to give 4-[methyl(4-propyl-4H-1,2,4-triazol-3-ylmethyl)amino]aniline (0.50 g) as brown crystals.

$^1$H-NMR (200 MHz, CDCl$_3$) δ 0.91 (3H, t, J=7.4 Hz), 1.68 to 1.85 (2H, m), 2.71 (3H, s), 3.93 (2H, t, J=7.3 Hz), 4.42 (2H, s), 6.67 (2H, d, J=8.7 Hz), 6.84 (2H, d, J=8.7 Hz), 8.10 (1H, s).

IR (KBr) 3422, 3337, 1522, 1372, 1319, 1279, 1217, 1198, 1121, 828 cm$^{-1}$

Reference Example 83

To a suspension of 4-nitrobenzyltriphenylphosphonium bromide (6.1 g) in THF (60 ml) was added a solution of sodium methoxide in methanol (28%, 2.46 g) was added at room temperature and the mixture was stirred for 0.5 hour at room temperature. To the reaction solution was added a solution of 3-formyl-4-propyl-4H,1,2,4-triazole (2.0 g) in THF (30 ml) and the mixture was stirred at room temperature for 3 hours. To the reaction solution was added water, and the mixture was extracted with ethyl acetate. The organic layer was washed with saturated brine, dried over magnesium sulfate and concentrated under reduced pressure, and the obtained residue was separated and purified by column chromatography (ethyl acetate→ethanol:ethyl acetate 1:9), to give 3-[(E)-2-(4-nitrophenyl)ether]-4-propyl-4H-1,2,4-triazole (1.6 g) as yellow crystals.

m.p. 77 to 79° C.

$^1$H-NMR (200 MHz, CDCl$_3$) δ 0.93 (3H, t, J=7.3 Hz), 1.66 to 1.85 (2H, m), 3.82 (2H, t, J=7.3 Hz), 6.50 (1H, d, J=12.7 Hz), 7.03 (1H, d, J=12.7 Hz), 7.80 (2H, d, J=8.8 Hz), 8.15 to 8.19 (3H, m).

IR (KBr) 1593, 1512, 1341, 1196, 1107, 883, 856 cm$^{-1}$

Elemental Analysis for C$_{13}$H$_{14}$N$_4$O$_2$.0.1H$_2$O Calcd. C, 60.04; H, 5.50; N, 21.54. Found: C, 50.76; H, 5.37; N, 21.71.

Reference Example 84

A mixture of 3-[(E)-2-(4-nitrophenyl)ether]-4-propyl-4H-1,2,4-triazole (0.80 g), and 10%. Pd-C (0.08 g) in ethanol (10 ml) was stirred strongly for 24 hours under hydrogen atmosphere. Pd-C was removed by filtration, and the mixture was concentrated under reduced pressure to give 4-[2-(4-propyl-4H-1,2,4-triazol-3-yl)ethyl]aniline (768 mg) as pale yellow oil.

$^1$H-NMR (200 MHz, CDCl$_3$) δ 0.90 (3H, t, J=7.5 Hz), 1.54 to 1.81 (2H, m), 2.86 to 3.12 (4H, m), 3.45 to 3.79 (4H, m), 6.62 (2H, d, J=8.3 Hz), 6.96 (2H, d, J=8.3 Hz), 8.03 (1H, s).

Reference Example 85

To a solution of 4-nitrothiophenol (10.0 g) and 2-bromoethylamine hydrobromide (14.52 g) in methanol (100 ml) was added dropwise 2N aqueous solution of sodium hydroxide (120 ml) at room temperature, and the mixture was stirred at room temperature for 20 hours. To the reaction solution was added di-tert-butyl bicarbonate (15.0 g), and mixture was further stirred for 3 hours. Methanol was removed under reduced pressure and the residue was extracted with ethyl acetate. The organic layer was washed with saturated brine, dried over magnesium sulfate and concentrated under reduced pressure. The precipitated crystals were collected by filtration. The crystals were washed with hexane, to give yellow crystals (12.32 g). To a suspension (100 ml) of the obtained crystals in ethanol was added concentrated hydrochloric acid (100 ml) at room temperature, and the mixture was stirred for 24 hours. The reaction mixture was concentrated under reduced pressure, and the precipitated crystals were collected by filtration. The crystals were washed with ethanol and diethylether, to give 2-(4-nitrophenylthio)ethylamine hydrochloride (9.96 g) as yellow crystals.

$^1$H-NMR (200 MHz, DMSO-d$_6$) δ 3.04 (2H, t, J=7.4 Hz), 3.40 (2H, t, J=7.4 Hz), 7.62 (2H, d, J=9.0 Hz), 8.06 to 8.27 (5H, m).

Reference Example 86

A mixture of 2-(4-nitrophenylthio)ethylamine hydrochloride (7.87 g), N,N-dimethylformamidazine (5.07 g), triethylamine (5.0 ml) and p-toluenesulfonic acid monohydrate (0.3 g) in toluene (100 ml) was heated to reflux for 6 hours. To the reaction solution was added water, and the mixture was extracted with ethyl acetate. The organic layer was washed with saturated brine, dried over magnesium sulfate and concentrated under reduced pressure. The precipitated crystals were collected by filtration. The crystals were washed with diethylether, to give 4-[2-(4-nitrophenylthio)ethyl]-4H-1,2,4-triazole (4.27 g) as pale yellow crystals.

m.p. 162 to 165° C.

$^1$H-NMR (200 MHz, CDCl$_3$) δ 3.41 (2H, t, J=6.4 Hz), 4.34 (2H, t, J=6.4 Hz), 7.38 (2H, t, J=9.0 Hz), 8.17 to 8.21; (4H, m).

IR (KBr) 1593, 1574, 1530, 1508, 1426, 1341, 1188, 1088, 853, 743, 637 cm$^{-1}$

Reference Example 87

A mixture of 4-[2-(4-nitrophenylthio)ethyl]-4H-1,2,4-triazole (1.0 g), reduced iron (1.12 g) and calcium chloride (0.22 g) in 15% hydrous ethanol (30 ml) was heated to reflux for 22 hours. The reaction mixture was concentrated under reduced pressure, and the obtained residue was separated and purified by column chromatography (basic silica gel, ethanol:ethyl acetate.: 1:19→1:9), to give 4-[2-(4-aminophenylthio)ethyl]-4H-1,2,4-triazole (0.79 g) as colorless crystals.

m.p. 160 to 162° C.

$^1$H-NMR (200 MHz, CDCl$_6$) δ 3.07 (2H, t, J=6.6 Hz), 3.72 to 3.86 (2H, m), 4.12 (2H, t, J=6.6 Hz), 6.65 (2H, d, J=8.8 Hz), 7.23 (2H, d, J=8.8 Hz), 8.16 (2H, s).

Elemental Analysis for $C_{10}H_{12}N_4S$ Calcd. C, 54.52; H, 5.49; N, 25.43. Found: C, 54.51; H, 5.69; N, 25.41.

Reference Example 88

To a suspension of 4-nitrobenzylamine hydrochloride (10.0 g) and triethylamine (22.2 ml) in acetonitrile (100 ml) was added trifluoroethyl acetate (12.6 ml) at room temperature and the mixture was stirred for 24 hours. The solvent was removed under reduced pressure, water was added to the mixture and the mixture was extracted with ethyl acetate. The organic layer was washed with saturated brine, dried over magnesium sulfate and concentrated under reduced pressure. The precipitated crystals were collected by filtration. The crystals were washed with hexane, to give N-(4-nitrobenzyl)trifluoroacetoamide (12.79 g) as colorless crystals.

m.p. 103 to 104° C.

$^1$H-NMR (200 MHz, CDCl$_3$) δ 3.66 (2H, d, J=6.2 Hz), 6.60 to 6.89 (1H, m), 7.48 (2H, d, J=8.8 Hz), 8.25 (2H, d, J=8.8 Hz).

IR (KBr) 3295, 1705, 1609, 1559, 1537, 1514, 1352, 1225, 1186, 1157, 858, 731 cm$^{-1}$

Elemental Analysis for $C_9H_7N_2O_3F_3$ Calcd. C, 43.56; H, 2.84; N, 11.29. Found: C, 43.53; H, 2.92; N, 11.26.

Reference Example 89

Under nitrogen atmosphere, to a solution of N-(4-nitrobenzyl)trifluoroacetoamide (12.88 g) in DMF (200 ml) was added sodium hydride (60%, 2.08 g) at, and the mixture was stirred for 30 minutes. To the reaction solution, methyl iodide (3.4 ml) was added to the mixture, and the mixture was stirred for 20 hours at 40° C. To the reaction solution was added water, and the mixture was extracted with ethyl acetate. The organic layer was washed with water and saturated brine, dried over magnesium sulfate and concentrated under reduced pressure. The obtained residue was separated and purified by column chromatography (ethyl acetate:hexane 1:5→1:4→1:3), to give. N-methyl-N-(4-nitrobenzyl)trifluoroacetoamide (11.82 g) as pale yellow oil.

To a solution of N-methyl-N-(4-nitrobenzyl)trifluoroacetoamide (11.82 g) in methanol (200 ml) was added 1N aqueous solution of sodium hydroxide (50 ml) at room temperature. The mixture was stirred at room temperature for 24 hours, and concentrated under reduced pressure. The mixture was extracted with ethyl acetate and dried over magnesium sulfate. The mixture was concentrated under reduced pressure, to give methyl(4-nitrobenzyl)amine (6.78 g).

To a solution of methyl(4-nitrobenzyl)amine (6.78 g) in methanol (60 ml) was added dropwise n-propyl isothiocyanate at room temperature and the mixture was stirred for 20 hours. The mixture was concentrated under reduced pressure, and the obtained residue was separated and purified by column chromatography (ethyl acetate:hexane 1:1), to give. N-methyl-N-(4-nitrobenzyl)-N'-propylthiourea (11.22 g) as pale yellow crystals.

m.p. 81 to 83° C.

$^1$H-NMR (200 MHz, CDCl$_3$) δ 0.99 (3H, t, J=7.5 Hz), 1.58 to 1.77 (2H, m), 3.07 (3H, s), 3.62 to 3.72 (2H, m), 5.32 (2H, s), 5.47 to 5.64 (1H, m), 7.47 (2H, d, J=8.6 Hz), 8.20 (2H, d, J=8.6 Hz).

IR (KBr) 3304, 1599, 1514, 1375, 1346, 1215, 1107, 837 cm$^{-1}$

Elemental Analysis for $C_{12}H_{17}N_3O_2S$ Calcd. C, 53.91; H, 6.41; N, 15.72. Found: C, 53.80; H, 6.24; N, 15.47.

Reference Example 90

To a solution of N-methyl-N-(4-nitrobenzyl)-N'-propylthiourea (11.22 g) in methanol was added methyl iodide (2.7 ml) at room temperature and the mixture was stirred for 3 days. The reaction mixture was concentrated under reduced pressure, and to a solution of the residue in ethanol (100 ml) was added hydrazine monohydrate (2.05 g) at 80° C. at room temperature and the mixture was stirred for 4 hours. The solvent was removed under reduced pressure, and to the residue was added formic acid (50 ml) and the mixture was heated to reflux for 3 days. The mixture was concentrated under reduced pressure, and to the residue was added an aqueous solution of sodium bicarbonate, and the mixture was extracted with ethyl acetate. The organic layer was washed with saturated brine, dried over magnesium sulfate and concentrated under reduced pressure. The obtained residue was separated and purified by column chromatography (basic silica gel ethanol:ethyl acetate 1:9), to give 3-[methyl(4-nitrobenzyl)amino]-4-propyl-4H-1,2,4-triazole (4.89 g) as brown oil.

$^1$H-NMR (200 MHz, CDCl$_3$) δ 0.96 (3H, t, J=7.3 Hz), 1.72 to 1.92 (2H, m), 2.81 (3H, s), 3.79 (2H, t, J=7.5 Hz), 4.44 (2H, s), 7.55 (2H, d, J=8.8 Hz), 7.96 (1H, s), 8.21 (2H, d, J=8.8 Hz).

Reference Example 91

To a solution of 3-[methyl(4-nitrobenzyl)amino]-4-propyl-4H-1,2,4-triazole (0.5 g) in 15% hydrous ethanol (15 ml) was added reduced iron (0.51 g) and calcium chloride (0.10 g) at room temperature., and the mixture was heated to reflux for 4 hours. After cooling to room temperature, the solid was removed by filtration and the filtrate was concentrated. The residue was separated and purified by column chromatography (basic silica gel, ethanol:ethyl acetate 1:19), to give 3-[(4-aminobenzyl)methylamino]-4-propyl-4H-1,2,4-triazole (313.4 mg) as brown oil.

$^1$H-NMR (200 MHz, CDCl$_3$) δ 0.94 (3H, t, J=7.3 Hz), 1.61 to 1.89 (2H, m), 2.75 (3H, s), 3.53 to 3.82 (4H, m), 4.12 (2H, s), 6.65 (2H, d, J=8.4 Hz), 7.09 (2H, d, J=8.4 Hz), 7.93 (1H, s).

Reference Example 92

Under nitrogen atmosphere, to a suspension of aluminum lithium hydride (1.6 g) in THF (100 ml) was added dropwise a solution of ethyl 2-methylimidazo[1,2-a]pyridine-3-carboxylate (8.56 g) in THF (100 ml) at 0° C. under nitrogen atmosphere. The mixture was stirred for 1 hour at 0° C., water (1.6 ml), 15% aqueous solution of sodium hydroxide (1.6 ml) and water (4.8 ml) were sequentially and slowly added dropwise to the solution, and the mixture was stirred for 2 hours at room temperature. To the reaction solution was added magnesium sulfate, and the precipitates were removed by filtration. The mixture was concentrated under reduced pressure, to give 2-methylimidazo[1,2-a]pyridine- 3-methanol (6.45 g) as pale yellow amorphous. A mixture of 2-methylimidazo[1,2-a]pyridine-3-methanol (1 g) and 4-aminothiophenol (0.65 g) in concentrated hydrochloric acid (10 ml) was stirred for 18 hours at room temperature. 8N aqueous solution of sodium hydroxide was added to adjust pH to 10 at 0° C. and the mixture was extracted with ethyl acetate. The organic layer was washed with saturated brine, dried over magnesium sulfate and concentrated under reduced pressure. The obtained residue was separated and purified by column chromatography (ethanol:ethyl acetate 1:4), to give 3-(4-aminophenylthiomethyl)-2-methylimidazo[1,2-a]pyridine (311 mg) as colorless crystals.

m.p. 162 to 164° C.

$^1$H-NMR (200 MHz, CDCl$_3$) δ 2.00 (3H, s), 3.62 to 3.81 (2H, m), 4.15 (2H, s), 6.49 (2H, d, J=8.5 Hz), 6.79 to 6.87 (1H, m), 6.92 (2H, d, J=8.5 Hz), 7.13 to 7.22 (1H, m), 7.49 to 7.55 (1H, m), 8.00 to 8.04 (1H, m)

IR (KBr) 3335, 3175, 1597, 1495, 1350, 1296, 1254, 829 cm$^{-1}$

Elemental Analysis for C$_{15}$H$_{15}$N$_3$S.0.2H$_2$O Calcd. C, 66.00; H, 5.69; N, 15.39. Found: C, 66.17; H, 5.69; N, 15.11.

Reference Example 93

A mixture of 3-hydroxymethylimidazo[1,2-a]pyridine hydrochloride (0.50 g) and 4-nitrothiophenol (0.42 g) in acetic acid (10 ml) and concentrated hydrochloric acid (10 ml) was stirred for 5 hours at 100° C. The reaction solution was cooled to 0° C., 8N aqueous solution of sodium hydroxide was added dropwise to adjust pH to 8. The mixture was extracted with ethyl acetate, and the organic layer was washed with saturated brine, dried over magnesium sulfate and concentrated under reduced pressure. The precipitated crystals were collected by filtration. The crystals were washed with diisopropyl ether, to give 3-(4-nitrophenylthiomethyl) imidazo[1,2-a]pyridine (0.54 g) as yellow crystals.

m.p. 174 to 175° C.

$^1$H-NMR (200 MHz, CDCl$_3$) δ 4.58 (2H, s), 6.90 to 6.97 (1H, m), 7.22 to 7.31 (1H, m), 7.39 (2H, d, J=8.8 Hz), 7.56 (1H, s), 7.63 to 7.69 (1H, m), 8.12 to 8.18 (3H, m).

IR (KBr) 1580, 1499, 1337, 1310, 1090, 852, 831, 769, 741 cm$^{-1}$

Elemental Analysis for C$_{14}$H$_{11}$N$_3$O$_2$S Calcd. C, 58.93; H, 3.89; N, 14.73. Found: C, 58.80; H, 4.04; N, 14.57.

Reference Example 94

A mixture of 3-(4-nitrophenylthiomethyl)imidazo[1,2-a]pyridine (1.5 g), reduced iron (1.47 g) and calcium chloride (0.29 g) in 15% hydrous ethanol (45 ml) was heated to reflux for 5 hours. After cooling to room temperature, and the precipitates were removed by filtration. After concentrating the filtrate, water was added to the mixture and the mixture was extracted with ethyl acetate. The organic layer was washed with saturated brine, dried over magnesium sulfate and concentrated under reduced pressure. The precipitated crystals were collected by filtration. The crystals were washed with diisopropylether, to give 3-(4-aminophenylthiomethyl)imidazo[1,2-a]pyridine (1.13 g) as pale yellow crystals.

m.p. 119 to 121° C.

$^1$H-NMR (200 MHz, CDCl$_3$) δ 3.63 to 3.82 (2H, m), 4.21 (2H, s), 6.52 (2H, d, J=8.6 Hz), 6.84 to 6.91 (1H, m), 7.00 (2H, d, J=8.6 Hz), 7.17 to 7.26 (2H, m), 7.59 to 7.65 (1H, m), 8.11 to 8.16 (1H, m).

IR (KBr) 3360, 3324, 1618, 1597, 1495, 1346, 1308, 1283, 1223, 1177, 1155, 1132, 826, 754, 745, 731 cm$^{-1}$

Elemental Analysis for C$_{14}$H$_{13}$N$_3$S Calcd. C, 65.85; H, 5.13; N, 16.46. Found: C, 65.60; H, 5.05; N, 16.28.

Reference Example 95

A solution of 5-chloroimidazo[1,2-a]pyridine (2.0 g), 4-aminothiophenol (2.46 g) and triethylamine (1.7 ml) in DMF (10 ml) was stirred for 5 days at 90° C. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 2:1→ethyl acetate), to give 5-(4-aminophenylthio) imidazo[1,2-a]pyridine (2.21 g) as pale yellow crystals.

m.p. 167 to 168° C.

$^1$H-NMR (200 MHz, CDCl$_3$) δ 3.79 to 3.98 (2H, m), 6.59 to 6.63 (1H, m), 6.68 (2H, d, J=8.8 Hz), 7.05 to 7.13 (1H, m), 7.29 (2H, d, J=8.8 Hz), 7.49 to 7.54 (1H, m), 7.66 (1H, d, J=1.4 Hz), 7.71 to 7.74 (1H, m).

IR (KBr) 3424, 3339, 1651, 1597, 1480, 1318, 1292, 1204, 1177, 1152, 1094, 951, 828, 772 cm$^{-1}$

Elemental Analysis for C$_{13}$H$_{11}$N$_3$S Calcd. C, 64.70; H, 4.59; N, 17.41. Found: C, 64.59; H, 4.59; N, 17.34.

Reference Example 96

A solution of 5-chloro-2-methylimidazo[1,2-a]pyridine (1.0 g) and 4-aminothiophenol (3.25 g) and triethylamine (1.7 ml) in DMF (10 ml) was stirred for 3 days at 90° C. To the reaction solution was added water, and the mixture was extracted with ethyl acetate. The organic layer was washed with saturated brine, dried over magnesium sulfate and concentrated under reduced pressure. The obtained residue was separated and purified by column chromatography (ethyl acetate:hexane 2:1→ethyl acetate→ethanol:ethyl acetate 1:9), to give 5-(4-aminophenylthio)-2-methylimidazo[1,2-a]pyridine (1.04 g) as colorless crystals.

m.p. 214 to 215° C.

$^1$H-NMR (200 MHz, CDCl$_3$) δ 2.46 (3H, s), 3.83 to 3.95 (2H, m), 6.54 (1H, dd, J=7.2, 1.2 Hz), 6.68 (2H, d, J=8.8 Hz), 7.03 (1H, dd, J=8.8, 7.2 Hz), 7.28 (2H, d, J=8.8 Hz), 7.37 to 7.43 (1H, m), 7.47 (1H, s).

IR (KBr) 3316, 3171, 1642, 1605, 1485, 1445, 1319, 1248, 1211, 1177, 1161, 826, 775 cm$^{-1}$

Elemental Analysis for C$_{14}$H$_{13}$N$_3$S Calcd. C, 65.85; H, 5.13; N, 16.46. Found: C, 66.00; H, 5.24; N, 16.54.

Reference Example 97

2-mercaptopyridine (2.6 g) was dissolved in THF (52 ml), triethylamine (3.9 ml) was added to the mixture, and then, a solution of 4-nitrobenzyl bromide (4.8 g) in. THF (24 ml) was added dropwise to the mixture. The reaction solution was stirred for 30 minutes at room temperature, added to water, and extracted with ethyl acetate. The organic layer was washed with saturated brine, and dried over magnesium sulfate. The solvent was removed under reduced pressure. The obtained residue was purified by silica gel column chromatography, to give 2-[(4-nitrobenzyl)sulfanyl]pyridine (4.2 g).

$^1$H-NMR (200 MHz, CDCl$_3$) δ 4.51 (2H, s), 6.98 to 7.05 (1H, m), 7.16 (1H, d, J=8.4 Hz), 7.44 to 7.5.3 (1H, m), 7.58 (2H, d, J=8.8 Hz), 8.42 to 8.47 (1H, m).

Elemental Analysis for C$_{12}$H$_{10}$N$_2$O$_2$S Cald. C, 58.82; N, 11.37; H, 4.09. Found: C, 58.52; N, 11.39; H, 4.20.

Reference Example 98

2-[(4-nitrobenzyl)sulfanyl]pyridine (14.5 g) was dissolved in acetic acid (145 ml), reduced iron (43.5 g) was added to the solution, and then, the mixture was stirred for 20 hours at room temperature. The mixture was filtered by Celite, washed with ethyl acetate, the solvent was removed under reduced pressure, and the obtained residue was purified by silica gel column chromatography, to give 4-[(2-pyridinylsulfanyl)methyl]aniline (4.9 g).

$^1$H-NMR (200 MHz, CDCl$_3$) δ 3.68 (2H, br), 4.34 (2H, s), 6.61 (2H, d, J=8.4 Hz), 6.93 to 7.01 (1H, m), 7.11 to 7.26 (3H, m), 7.45 (1H, td, J=7.4, 1.8 Hz), 7.58 to 7.62 (1H, m), 8.43 to 8.48 (1H, m).

Elemental Analysis for C$_{12}$H$_{12}$N$_2$S Cald. C, 66.63; N, 12.95; H, 5.59. Found: C, 66.68; N, 12.90; H, 5.65.

Reference Example 99

2-mercaptopyridine (10 g) was dissolved in DMF (100 ml), 60% sodium hydride (3.6 g) was added to the mixture at 0° C., and then, the mixture was stirred for 15 minutes at room temperature. 4-fluoronitrobenzene (9.75 g) was added dropwise to the mixture at 0° C. and the mixture was stirred for 1 hour at room temperature. To the reaction mixture was added, and the precipitated crystals were collected by filtration, and washed with hexane/diethylether, to give 2-[(4-nitrophenyl)sulfanyl]pyridine (12.6 g).

$^1$H-NMR (200 MHz, CDCl$_3$) δ 7.15 to 7.23 (3H, m), 7.58 to 7.69 (3H, m), 8.15 to 8.22 (2H, m), 8.50 to 8.55 (1H, m).

Reference Example 100

2-[(4-nitrophenylsulfanyl) pyridine (8.0 g) was dissolved in acetic acid (64 ml), and reduced iron (24 g) was added to the mixture, and then, the mixture was stirred for 16 hours at room temperature. The mixture was filtered with Celite, washed with ethyl acetate, the solvent was removed under reduced pressure, and the obtained residue was purified by silica gel column chromatography, to give 4-(2-pyridinylsulfanyl) aniline (6.3 g).

$^1$H-NMR (200 MHz, CDCl$_3$) δ 4.05 (2H, br), 6.72 (2H, d, J=8.8 Hz), 6.76 (1H, d, J=8.8 Hz), 6.89 to 6.96 (1H, m), 7.38 (2H, d, J=8.8 Hz), 7.39 to 7.45 (1H, m), 8.37 to 8.41 (1H, m).

Reference Example 101

Benzenethiol (13.2 g) was dissolved in THF (100 ml), and to this solution was added triethylamine (17.1 ml) and then 4-nitrobenzyl bromide (21.6 g). The reaction solution was stirred for 30 minutes at room temperature, added to water, and extracted with ethyl acetate. The organic layer was washed with saturated brine, and dried over magnesium sulfate. The solvent was removed under reduced pressure, and the obtained residue was washed with hexane/ethyl acetate (=10/1), to give 1-nitro-4-[(phenylsulfanyl)methyl]benzene (20.7 g).

$^1$H-NMR (200 MHz, CDCl$_3$) δ 4.13 (2H, s), 7.21 to 7.39 (5H, m), 7.37 (2H, d, J=8.8 Hz), 8.08 to 8.13 (2H, m)

Reference Example 102

To 1-nitro-4-[(phenylsulfanyl)methyl]benzene (12 g) were added 85% ethanol solution (240 ml), and calcium chloride (2.85 g) and reduced iron (14.4 g) were added to the mixture, and the mixture was heated to reflux for 3 hours. After cooling to room temperature, the mixture was filtered with Celite, and washed with ethyl acetate. The organic layer was washed with water and saturated brine, and dried over magnesium sulfate. The solvent was removed under reduced pressure, and the obtained residue was purified by silica gel column chromatography, to give 4-(benzenesulfanylmethyl) aniline (5.5 g).

$^1$H-NMR (200 MHz, CDCl$_3$) δ 3.62 (2H, br), 4.04 (2H, s), 6.57 to 6.63 (2H, m), 7.26 to 7.34 (7H, m)

Reference Example 103

2-mercaptopyrimidine (5.0 g) was dissolved in THF/DMF (150 ml), and to the solution was added triethylamine (7.4 ml) and then 4-nitrobenzyl bromide (8.7 g). The reaction solution was stirred for 1 hour at room temperature, added to water, and extracted with ethyl acetate. The organic layer was washed with water and saturated brine, and dried over magnesium sulfate. The solvent was removed under reduced pressure, and the obtained residue was washed with hexane/ethyl acetate (=8/1), to give 2-[(4-nitrobenzyl)sulfanyl]pyrimidine (8.0 g).

$^1$H-NMR (200 MHz, CDCl$_3$) δ 4.47 (2H, s), 7.01 (1H, t, J=4.8 Hz), 7.62 (2H, d, J=8.8 Hz), 8.16 (2H, d, J=8.8 Hz), 8.53 (2H, d, J=5.2 Hz).

Reference Example 104

To 2-[(4-nitrobenzyl)sulfanyl]pyrimidine (8.0 g) was added 85% ethanol solution (160 ml), and then, calcium chloride (1.8 g) and reduced iron (9.0 g), and the mixture was heated to reflux for 3 hours. After cooling to room temperature, the mixture was filtered with Celite, and washed with ethyl acetate. The organic layer was washed with water and saturated brine, and dried over magnesium sulfate. The solvent was removed under reduced pressure, and the obtained residue was purified by silica gel column chromatography, to give 4-[(2-pyrimidinylsulfanyl)methyl] aniline (2.5 g).

$^1$H-NMR (200 MHz, CDCl$_3$) δ 3.66 (2H, br), 4.23 (2H, s), 6.58 to 6.64 (2H, m), 6.94 (1H, t, J=4.6 Hz), 7.21 (2H, d, J=8.4 Hz), 8.51 (2H, d, J=4.6 Hz).

Reference Example 105

2-chloro-5-trifluoromethylpyridine (13.7 g) was dissolved in ethanol (96 ml), thiourea (5.7 g) was added to the mixture, and the mixture was heated to reflux for 3 hours. After allowing the mixture to be cooled to room temperature, an aqueous solution (19.2 ml) of potassium hydroxide (6.4 g) was added to the mixture, and the mixture was heated to reflux for 1 hour. After allowing the mixture to be cooled to room temperature, diluted aqueous solution of potassium hydroxide (20 ml) was added to the mixture, and the mixture was washed with methylene chloride. With acetic acid, pH of the mixture was adjusted to about 6, and the mixture was extracted with methylene chloride. The mixture was washed with water, and dried over magnesium sulfate. The solvent was removed under reduced pressure and the obtained residue was washed with hexane/ethyl acetate, to give 2-mercapto-5-trifluoromethylpyridine (5.1 g).

$^1$H-NMR (200 MHz, CDCl$_3$) δ 4.55 (2H, s), 7.25 to 7.50 (1H, s), 7.59 (2H, d, J=8.8 Hz), 7.69 (1H, dd, J=8.4, 2.2 Hz), 8.16 (2H, d, J=8.8 Hz), 8.69 (1H, s).

Reference Example 106

2-mercapto-5-trifluoromethylpyridine (5.0 g) was dissolved in THF (100 ml), triethylamine (4.7 ml) was added to the mixture, and a solution of 4-nitrobenzyl bromide (5.4 g) in THF (50 ml) was added dropwise thereto at 0° C. The mixture was stirred for 30 minutes at room temperature, added to water, and extracted with ethyl acetate. The organic layer was washed with saturated brine, and dried over magnesium sulfate. The solvent was removed under reduced pressure, and the obtained residue was purified by silica gel column chromatography to give 2-[4-(nitrobenzyl)sulfanyl]-5-(trifluoromethyl)pyridine (7.0 g).

$^1$H-NMR (200 MHz, CDCl$_3$) δ 4.55 (2H, s), 7.25 to 7.50 (1H, s), 7.59 (2H, d, J=8.8 Hz), 7.69 (1H, dd, J=8.4, 2.2 Hz), 8.16 (2H, d, J=8.8 Hz), 8.69 (1H, s)

Reference Example 107

2-[4-(nitrobenzyl)sulfanyl]-5-(trifluoromethyl)pyridine (7.0 g) was dissolved in acetic acid (56 ml), and reduced iron (21.0 g) was added to the mixture, and the mixture was stirred for 6 hours at room temperature. The mixture was filtered with Celite, and washed with methanol. The solvent was removed under reduced pressure, and the obtained residue was added to water and extracted with ethyl acetate. The organic layer was washed with saturated brine, and dried over magnesium sulfate. The solvent was removed under reduced pressure, and the obtained residue was purified by silica gel column chromatography, to give 4-[[[5-(trifluoromethyl)-2-pyridinyl]sulfanyl]methyl]aniline (2.3 g).

$^1$H-NMR (200 MHz, CDCl$_3$) δ 4.38 (2H, s), 6.63 (2H, d, J=8.4 Hz), 7.20 (22H, d, J=8.4 Hz), 7.23 (1H, d, J=8.4 Hz), 7.65 (1H, dd, J=8.4, 2.6 Hz), 8.69 (1H, s).

Reference Example 108

4-nitrobenzenethiol (6.0 g) was dissolved in THF (120 ml), and to the solution was 1N sodium hydroxide (120 ml) and then, 2-(chloromethyl)pyridine hydrochloride (7.6 g), and the mixture was stirred for 15 minutes at room temperature. The solvent was removed under reduced pressure, and the obtained residue was added to water, and extracted with ethyl acetate. The organic layer was washed with saturated brine, and dried over magnesium sulfate. The solvent was removed under reduced pressure and the obtained residue was washed with hexane/ethyl acetate, to give 2-[[(4-nitrophenyl)sulfanyl]methyl]pyridine (6.8 g).

$^1$H-NMR (200 MHz, CDCl$_3$) δ 4.39 (2H, s), 7.17 to 7.24 (1H, m), 7.39 to 7.46 (3H, m), 7.67 (1H, td, J=7.6, 1.8 Hz), 8.09 (2H, d, J=8.8 Hz), 8.55 to 8.58 (1H, m)

Reference Example 109

To 2-[[(4-nitrophenyl)sulfanyl]methyl]pyridine (6.7 g) were added 85% ethanol solution (203 ml), and to this mixture was added calcium chloride (1.53 g) and reduced iron (7.68 g), and the mixture was heated to reflux for 16 hours. After allowing the mixture to be cooled to room temperature, ethanol was removed under reduced pressure, and the obtained residue was extracted with ethyl acetate. The organic layer was washed with saturated brine, and dried over magnesium sulfate. The solvent was removed under reduced pressure, and the obtained residue was purified by silica gel column chromatography, to give 4-[(2-pyridinylmethyl)sulfanyl]aniline (3.9 g).

$^1$H-NMR (200 MHz, CDCl$_3$) δ 3.70 (2H, br), 4.08 (2H, s), 6.52 to 6.57 (2H, m), 7.08 to 7.17 (2H, m), 7.51 to 7.60 (1H, m), 8.49 to 8.53 (1H, m)

Reference Example 110

4-aminothiophenol (6.0 g) was dissolved in methanol (120 ml), aqueous solution of sodium hydroxide (2.7 g, 36 ml) was added to the mixture, benzyl bromide (6.8 ml) was added to the mixture at 0° C., and the mixture was stirred for 2 hours at room temperature. The solvent was removed under reduced pressure, and the obtained residue was added to water, and extracted with ethyl acetate. The organic layer was washed with saturated brine, and dried over magnesium sulfate. The solvent was removed under reduced pressure and the obtained residue was washed with hexane/ethyl acetate, to give 4-(benzylsulfanyl)aniline (7.0 g).

$^1$H-NMR (200 MHz, CDCl$_3$) δ 3.69 (2H, br), 3.73 (2H, s), 6.52 to 6.60 (2H, m), 7.10 to 7.29 (7H, m).

Reference Example 111

4-aminothiophenol (10 g) was dissolved in methanol (200 ml), aqueous solution of sodium hydroxide (15.7 g, 60 ml) was added to the mixture, 3-(chloromethyl)pyridine hydrochloride (14.4 g) was added to the mixture at 0° C., and the mixture was stirred for 2 hours at room temperature. The solvent was removed under reduced pressure, and the obtained residue was added to water, and extracted with ethyl acetate. The organic layer was washed with saturated brine, and dried over magnesium sulfate. The solvent was removed under reduced pressure and the obtained residue was washed with hexane/ethyl acetate, to give 4-[(3-pyridinylmethyl)sulfanyl]aniline (13.1 g).

$^1$H-NMR (200 MHz, CDCl$_3$) δ 3.83 (2H, br), 3.88 (2H, s), 6.55 (2H, m), 7.08 (2H, m), 7.13 to 7.20 (1H, m), 7.43 to 7.49 (1H, m), 8.29 to 8.31 (1H, m), 8.44 (1H, dd, J=4.8, 1.8 Hz).

Reference Example 112

4-aminothiophenol (8.9 g) was dissolved in methanol (178 ml), aqueous solution of sodium hydroxide (6.8 g, 53.4 ml) was added to the mixture, 4-(chloromethyl)pyridine hydrochloride (14.0 g) was added to the mixture at 0° C., and the mixture was stirred for 2 hours at room temperature. The solvent was removed under reduced pressure, and the obtained residue was added to water, and extracted with ethyl acetate. The organic layer was washed with saturated brine, and dried over magnesium sulfate. The solvent was removed under reduced pressure and the obtained residue was washed with hexane/ethyl acetate, to give 4-[(4-pyridinylmethyl)sulfanyl]aniline (13.7 g).

$^1$H-NMR (200 MHz, CDCl$_3$) δ 3.62 (2H, br), 3.84 (2H, s), 6.56 (2H, d, J=8.4 Hz), 7.02 to 7.10 (4H, m), 8.46 (2H, d, J=6.4 Hz).

Reference Example 113

2-hydroxymethyl-6-methylpyridine (1.0 g) was dissolved in methylene chloride (25 ml), DMF (3 droplets) was added to the mixture, thionyl chloride (1.3 ml) was added to the mixture at 0° C., and the mixture was stirred for 16 hours at room temperature. The solvent was removed under reduced pressure, and a solution of the obtained residue in water (8.5 ml) was added dropwise to an aqueous solution of 4-aminothiophenol (0.85 g) and sodium hydroxide (0.65 g) in methanol (22.1 ml). The mixture was stirred for 1 hour at room temperature, the solvent was removed under reduced pressure, and the residue was extracted with ethyl acetate. The organic layer was washed with saturated brine, and dried over magnesium sulfate. The solvent was removed under reduced pressure, and the obtained residue was purified by silica gel column chromatography, to give 4-[[(6-methyl-2-pyridinyl)methyl]sulfanyl]aniline (0.80 g).

$^1$H-NMR (200 MHz, CDCl$_3$) δ 2.52 (3H, s), 3.70 (2H, br), 4.05 (2H, s), 6.55 (2H, d, J=8.8 Hz), 6.91 to 6.99 (2H, m), 7.15 (2H, d, J=8.8 Hz), 7.39 to 7.47 (1H, m).

Reference Example 114

4-chloropyridine-N-oxide (4.4 g) was dissolved in methylene chloride (68 ml), trimethyloxonium tetrafluoroborate (5.0 g) was added to the mixture, and the mixture was stirred for 90 minutes at room temperature. The solvent was removed under reduced pressure, the obtained residue was dissolved in methanol, and an aqueous solution (6.8 ml) of ammonium peroxodisulfate (1.54 g) was added thereto under heat reflux. An aqueous solution (3.4 ml) of ammonium peroxodisulfate (0.77 g) was further added to the mixture after 30 minutes, the mixture was stirred for 1 hour. After allowing the mixture to be cooled to room temperature, the solvent was removed under reduced pressure, and the obtained residue was purified by silica gel column chromatography, to give (4-chloro-2-pyridinyl)methanol (3.0 g).

$^1$H-NMR (200 MHz, CDCl$_3$) δ 4.77 (2H, s), 7.84 (1H, dd, J=6.0, 2.2 Hz), 7.93 (1H, d, J=2.2 Hz), 8.68 (1H, d, J=6.2 Hz).

Reference Example 115

(4-chloro-2-pyridinyl)methanol (3.0 g) was dissolved in methylene chloride (30 ml), DMF (3 droplets) was added to the mixture, thionyl chloride (3.8 ml) was added to the mixture at 0° C., and the mixture was stirred for 16 hours at room temperature. The solvent was removed under reduced pressure, and a solution (10.5 ml) of the obtained residue in water was added dropwise to an aqueous solution (76 ml) of 4-aminothiophenol (2.18 g) and sodium hydroxide (2.0.9 g) in methanol. The mixture was stirred for 1 hour at room temperature, the solvent was removed under reduced pressure, and the residue was extracted with ethyl acetate. The organic layer was washed with saturated brine, and dried over magnesium sulfate. The solvent was removed under reduced pressure, and the obtained residue was purified by silica gel column chromatography, to give 4-[[(4-chloro-2-pyridinyl)methyl]sulfanyl]aniline (0.60 g).

$^1$H-NMR (200 MHz, CDCl$_3$) δ 3.75 (2H, br), 4.24 (2H, s), 6.52 to 6.60 (3H, m), 7.09 to 7.17 (2H, m), 7.22 to 7.27 (1H, m), 8.27 to 8.41 (1H, m)

Reference Example 116

4-methylpyridine-N-oxide (3.7 g) was dissolved in methylene chloride (68 ml), trimethyloxonium tetrafluoroborate (5.0 g) was added to the mixture, and the mixture was stirred for 90 minutes at room temperature. The solvent was removed under reduced pressure, the obtained residue was dissolved in methanol, and an aqueous solution (6.8 ml) of ammonium peroxodisulfate (1.54 g) was added under heat reflux. An aqueous solution (3.4 ml) of ammonium peroxodisulfate (0.77 g) was further added to the mixture after 30 minutes, and the mixture was stirred for 1 hour. After allowing the mixture to be cooled to room temperature, the solvent was removed under reduced pressure, and the obtained residue was purified by silica gel column chromatography, to give (4-methyl-2-pyridinyl)methanol (2.9 g).

(4-methyl-2-pyridinyl)methanol (2.5 g) was dissolved in methylene chloride (25 ml), DMF (3 droplets) was added to the mixture, thionyl chloride (3.8 ml) was added to the mixture at 0° C. and the mixture was stirred for 16 hours at room temperature. The solvent was removed under reduced pressure, and a solution (9.1 ml) of the obtained residue in water was added dropwise to an aqueous solution (64 ml) of 4-aminothiophenol (1.82 g) and sodium hydroxide (1.74 g) in methanol. The mixture was stirred for 1 hour at room temperature, the solvent was removed under reduced pressure, and the residue was extracted with ethyl acetate. The organic layer was washed with saturated brine, and dried over magnesium sulfate. The solvent was removed under reduced pressure, and the obtained residue was purified by silica gel column chromatography, to give 4-[[(4-methyl-2-pyridinyl)methyl]sulfanyl]aniline (2.0 g).

$^1$H-NMR (200 MHz, CDCl$_3$) δ 2.28 (3H, s), 3.70 (2H, br), 4.05 (2H, s), 6.52 to 6.60 (2H, m), 6.93 to 6.99 (2H, m), 7.11 to 7.18 (2H, m), 8.36 (1H, d, J=5.0 Hz).

Reference Example 117

2-(methoxymethoxy)benzylalcohol (8.0 g) was dissolved in THF, 2,6-dimethylpyridine (8.3 ml) and methanesulfonic acid anhydride (9.9 g) were added to the mixture, and the mixture was stirred at room temperature for 3 hours. Lithium bromide (5.8 g) was added to the mixture, the mixture was stirred for 4 hours at room temperature and the mixture was further stirred for 20 hours at 50° C. After allowing the mixture to be cooled to room temperature, water was added to the mixture, and the mixture was extracted with ethyl acetate. The organic layer was washed with saturated brine, and dried over magnesium sulfate. The solvent was removed under reduced pressure, and the obtained residue was added dropwise to an aqueous solution (104 ml) of 4-aminothiophenol (4.2 g) and sodium hydroxide (2.0 g) in methanol, and the mixture was stirred for 12 hours at room temperature. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 4-[[2-(methoxymethoxy)benzyl]sulfanyl]aniline (8.2 g).

$^1$H-NMR (200 MHz, CDCl$_3$) δ 3.48 (3H, s), 3.69 (2H, br), 3.98 (2H, s), 5.16 (2H, s), 6.56 (2H, d, J=8.0 Hz), 6.85 to 6.90 (1H, m), 6.98 to 7.17 (5H, m).

Reference Example 118

1-bromo-2-methyl-4-nitrobenzene (12 g) was dissolved in ethanol (120 ml), and to the solution was added dropwise an aqueous solution (120 ml) of sodium sulfate 9 hydrate (10 g) and sulfur (1.33 g) in ethanol for 20 minutes under heat reflux. A solution of 6N sodium hydroxide was added dropwise to the solution for 20 minutes, and after allowing the mixture to be cooled to room temperature, ice-water was added thereto. The precipitates were filtered, and the pH of the filtrate was adjusted to about pH 5 with 6N hydrochloric acid, and the precipitates were collected by filtration and washed with water to give, 2-methyl-4-nitrobenzenethiol (7.9 g).

$^1$H-NMR (200 MHz, CDCl$_3$) δ 2.39 (3H, s), 3.67 (1H, s), 7.34 (1H, d, J=8.4 Hz), 7.89 to 7.95 (1H, m), 8.01 (1H, m)

Reference Example 119

2-methyl-4-nitrobenzenethiol (3.0 g) was dissolved in THF (60 ml), and to this solution was added aqueous solution of sodium hydroxide (2.1 g, 15 ml) and then, 2-(chloromethyl)pyridine hydrochloride (3.5 g), and the mixture was stirred for 30 minutes. The solvent was removed under reduced pressure, and the residue was extracted with ethyl acetate. The organic layer was washed with saturated brine, and dried over magnesium sulfate. The solvent was removed under reduced pressure and the obtained residue was washed with hexane/ethyl acetate, to give 2-[[(2-methyl-4-nitrophenyl)sulfanyl]methyl]pyridine (3.4 g).

$^1$H-NMR (200 MHz, CDCl$_3$) δ 2.40 (3H, s), 4.39 (2H, s), 7.18 to 7.25 (1H, s), 7.36 to 7.46 (2H, m), 7.67 (1H, td, J=8.0, 1.8 Hz), 7.93 to 7.99 (2H, m), 8.56 to 8.60 (1H, m)

Reference Example 120

To 2-[[(2-methyl-4-nitrophenyl)sulfanyl]methyl]pyridine (3.1 g) were added acetic acid (24.4 ml) and then, reduced iron (9.15 g), and the mixture was stirred for 16 hours at room temperature. The mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 3-methyl-4-[(2-pyridinylmethyl)sulfanyl]aniline (1.4 g).

$^1$H-NMR (200 MHz, CDCl$_3$) δ 2.24 (3H, s), 3.38 (2H, br), 4.01 (2H, s), 6.39 (1H, dd, J=8.0, 2.6 Hz), 6.92 (1H, d, J=2.6 Hz), 7.03 to 7.14 (3H, m), 7.49 to 7.58 (1H, m), 8.52 (1H, d, J=5.2 Hz)

Reference Example 121

4-nitropyridine-N-oxide (12 g) was dissolved in ethanol, sodium ethoxide (8.8 g) was added to the mixture, and the mixture was stirred for 40 hours at 50° C. After allowing the mixture to be cooled to room temperature, the precipitates were filtered, the solvent was removed under reduced pressure, and the obtained residue was purified by silica gel column chromatography, to give 4-ethoxypyridine-N-oxide (11.8 g). To 4-ethoxypyridine-N-oxide (11.8 g) was added dimethyl sulfate (8.56 ml), and the mixture was stirred for 1 hour at 110° C. After diluting with methanol (180 ml), the mixture was heated to reflux for 1 hour, an aqueous solution (18 ml) of ammonium peroxodisulfate (20.6 g) was added dropwise to the solution under heat reflux, and the mixture was heated to reflux for 1 hour. After allowing the mixture to be cooled to room temperature, the solvent was removed under reduced pressure, and the obtained residue was purified by silica gel column chromatography, to give (4-ethoxy-2-pyridinyl)methanol (2.8 g).

$^1$H-NMR (200 MHz, CDCl$_3$) δ 1.43 (3H, t, J=7.0 Hz), 4.09 (2H, q, J=7.0 Hz), 4.69 (2H, s), 6.70 to 6.79 (2H, m), 8.32 (1H, m)

Reference Example 122

(4-ethoxy-2-pyridinyl)methanol (2.8 g) was dissolved in methylene chloride (28 ml), DMF (3 droplets) was added to the mixture, thionyl chloride (3.3 ml) was added to the mixture at 0° C., and the mixture was stirred for 16 hours at room temperature. The solvent was removed under reduced pressure, and a solution (10.3 ml) of the obtained residue in water was added dropwise to an aqueous solution (62 ml) of 2-methyl-4-nitrothiophenol (2.58 g) and sodium hydroxide (2.19 g) in. THF. The mixture was stirred for 1 hour at room temperature, the solvent was removed under reduced pressure, and the residue was extracted with ethyl acetate. The organic layer was washed with saturated brine, and dried over magnesium sulfate. The solvent was removed under reduced pressure, and the obtained residue was purified by silica gel column chromatography, to give 4-ethoxy-2-[[(2-methyl-4-nitrophenyl)sulfanyl]methyl]pyridine (2.6 g).

$^1$H-NMR (200 MHz, CDCl$_3$) δ 1.38 (3H, t, J=7.0 Hz), 2.40 (3H, s), 4.07 (2H, q, J=7.0 Hz), 4.33 (2H, s), 6.71 (2H, dd, J=5.8, 2.6 Hz), 6.95 (1H, d, J=2.2 Hz), 7.37 (1H, d, J=9.6 Hz), 7.93 to 7.99 (2H, m), 8.37 (1H, d, J=5.4 Hz).

Reference Example 123

4-ethoxy-2-[[(2-methyl-4-nitrophenyl)sulfanyl]methyl]pyridine (2.5 g) was dissolved in acetic acid (25 ml), reduced iron (7.5 g) was added to the mixture, and the mixture was stirred for 420 hours at room temperature. The mixture was filtered with Celite, and washed with ethyl acetate. The solvent was removed under reduced pressure, and the obtained residue was purified by silica gel column chromatography, to give 4-[[(4-ethoxy-2-pyridinyl)methyl]sulfanyl]-3-methylaniline (1.8 g).

$^1$H-NMR (200 MHz, CDCl$_3$) δ 1.39 (3H, t, J=7.0 Hz), 2.27 (3H, s), 3.28 (2H, br), 3.96 (2H, s), 3.98 (2H, q, J=7.0 Hz), 6.42 (1H, dd, J=8.0, 2.6 Hz), 6.52 (1H, d, J=2.4 Hz), 6.59 (1H, d, J=2.6 Hz), 6.64 (1H, dd, J=5.4, 2.2 Hz), 7.14 (1H, d, J=8.0 Hz), 8.31 (1H, d, J=5.4 Hz)

Reference Example 124

To 4,6-dimethylpyrimidine-2-thiol (9.1 g) was added THF (70 ml), and to this solution was added triethylamine (21.5 ml) and then, 4-nitrobenzyl bromide (10 g), and the mixture was stirred for 5 hours at 50° C. After cooling to room temperature, the mixture was added to water, and extracted with ethyl acetate. The organic layer was washed with saturated brine, and dried over magnesium sulfate. The solvent was removed under reduced pressure and the obtained residue was washed with hexane/ethyl acetate, to give 4,6-dimethyl-2-[(4-nitrobenzyl)sulfanyl]pyrimidine (7.2 g).

$^1$H-NMR (200 MHz, CDCl$_3$) δ 2.40 (6H, s), 4.45 (2H, s), 6.72 (1H, s), 7.63 (2H, d, J=8.8 Hz), 8.13 (2H, d, J=8.8 Hz)

Reference Example 125

4,6-dimethyl-2-[(4-nitrobenzyl)sulfanyl]pyrimidine (7.0 g) was dissolved in acetic acid (56 ml), reduced iron (21 g) was added to the mixture, and the mixture was stirred for 16 hours at room temperature. The mixture was filtered with Celite, and washed with ethyl acetate. The solvent was removed under reduced pressure, and to the obtained residue was added ethyl acetate, and the organic layer was washed with water and saturated brine, and dried over magnesium sulfate. The solvent was removed under reduced pressure, and the obtained residue was purified by silica gel column chromatography, to give 4-[[(4,6-dimethyl-2-pyrimidinyl)methyl]sulfanyl]aniline (4.1 g).

$^1$H-NMR (200 MHz, CDCl$_3$) δ 2.40 (6H, s), 3.63 (2H, br), 4.32 (2H, s), 6.59 to 6.68 (2H, m), 7.23 (2H, d, J=8.80 z)

Reference Example 126

4-nitrobenzenethiol (10 g) was dissolved in THF (100 ml), and to this solution was added triethylamine (12.6 ml) and then, bromoacetonitrile (5.4 ml), and the mixture was stirred for 30 minutes. The reaction solution was added to water, and extracted with ethyl acetate. The organic layer was washed with saturated brine, and dried over magnesium sulfate. The solvent was removed under reduced pressure and the obtained residue was washed with hexane/ethyl acetate, to give 2-[(4-nitrophenyl)sulfanyl]acetonitrile (10.3 g).

$^1$H-NMR (200 MHz, CDCl$_3$) δ 3.77 (2H, s), 7.56 (2H, d, J=8.8 Hz), 8.25 (2H, d, J=8.8 Hz)

Reference Example 127

To 2-[(4-nitrophenyl)sulfanyl]acetonitrile (6.8 g) was added toluene (70 ml), and to this solution was added trimethylsilylazide (8.1 g) and then, dibutyl tin oxide (VI) (0.87 g), and the mixture was heated to reflux for 6 hours. After allowing the mixture to be cooled to room temperature, the solvent was removed under reduced pressure, and azeotropically distilled with methanol. To the obtained residue was added 10% aqueous solution (50 ml) of sodium carbonate, and the mixture was washed with ethyl acetate. The pH was adjusted to about pH 3 with 6N hydrochloric acid, and the mixture was extracted with ethyl acetate. The organic layer was washed with saturated brine, and dried over magnesium sulfate. The solvent was removed under reduced pressure, and the residue was washed with hexane/ethyl acetate to give 5-[[(4-nitrophenyl)sulfanyl]methyl]-1,2,3,4-tetrazole (6.7 g).

$^1$H-NMR (200 MHz, CDCl$_3$) δ 4.79 (2H, s), 7.61 (2H, d, J=9.2 Hz), 8.15 (2H, d, J=9.2 Hz)

Reference Example 128

To 5-[[(4-nitrophenyl)sulfanyl]methyl]-1,2,3,4-tetrazole (6.3 g) were added acetonitrile (315 ml), and then, to this solution was added potassium carbonate (4.5 g) and iodomethane (1.75 ml), and the mixture was stirred for 240 hours at room temperature. The solvent was removed under reduced pressure, and to the obtained residue was added ethyl acetate, and the organic layer was washed with water and saturated brine, and dried over magnesium sulfate. The solvent was removed under reduced pressure and the obtained residue was washed with hexane/ethyl acetate, to give 1-methyl-5-[[(4-nitrophenyl)sulfanyl]methyl]-1,2,3,4-tetrazole and 2-methyl-5-[[(4-nitrophenyl)sulfanyl]methyl]-1,2,3,4-tetrazole as mixture (3.87 g, 1:1).

$^1$H-NMR (200 MHz, CDCl$_3$) δ 4.15 (3H, s), 4.33 (3H, s), 4.45 (2H, s), 4.50 (2H, s), 7.47 to 7.54 (4H, m), 8.11 to 8.18 (4H, m)

Reference Example 129

To 1-methyl-5-[[(4-nitrophenyl)sulfanyl]methyl]-1,2,3,4-tetrazole and 2-methyl-5-[[(4-nitrophenyl)sulfanyl]methyl]-1,2,3,4-tetrazole (6.3 g, 1:1) were added acetic acid (63 ml) and then, reduced iron (18.9 g), and the mixture was stirred for 18 hours at room temperature. The mixture was filtered with Celite, and washed with ethyl acetate. The solvent was removed under reduced pressure, and the obtained residue was dissolved in ethyl acetate. The organic layer was washed with an aqueous solution of saturated sodium bicarbonate and saturated brine, and dried over magnesium sulfate. The solvent was removed under reduced pressure, and the obtained residue was purified by silica gel column chromatography, to give 4-[[(1-methyl-1,2,3,4-tetrazol-5-yl)methyl]sulfanyl]aniline (1.7 g) and 4-[[(2-methyl-1,2,3,4-tetrazol-5-yl)methyl]sulfanyl]aniline (1.6 g).

4-[[(1-methyl-1,2,3,4-tetrazol-5-yl)methyl]sulfanyl]aniline: $^1$H-NMR (200 MHz, CDCl$_3$) δ 3.86 (3H, s), 4.11 (2H, s), 6.55 (2H, d, J=8.4 Hz), 7.06 (2H, d, J=8.8 Hz).

IR (KBr) 3352, 1626, 1597, 1497, 1287, 1177, 1096, 829 cm$^{-1}$

4-[[(2-methyl-1,2,3,4-tetrazol-5-yl)methyl]sulfanyl]aniline: $^1$H-NMR (200 MHz, CDCl$_3$) δ 4.15 (2H, s), 4.28 (3H, s), 6.58 (2H, d, J=8.8 Hz), 7.21 (2H, d, J=8.4 Hz).

IR (KBr) 3366, 1624, 1597, 1497, 1287, 1177, 826 cm$^{-1}$

Reference Example 130

1-bromo-2-trifluoromethyl-4-nitrobenzene (12 g) was dissolved in ethanol (120 ml), and to this solution was added dropwise an aqueous solution (120 ml) of sodium sulfate nanohydrate (10 g) and sulfur (1.33 g) in ethanol for 20 minutes under heat reflux. A solution of 6N sodium hydroxide was added dropwise to the solution for 20 minutes, and the mixture was cooled to room temperature, and ice-water was added thereto. The precipitates were filtered, and the pH of the filtrate was adjusted to about pH 5 with 6N hydrochloric acid, and the precipitates were collected by filtration and washed with water to give, 4-nitro-2-(trifluoromethyl)benzenethiol (14.0 g).

$^1$H-NMR (200 MHz, CDCl$_3$) δ 4.11 to 4.17 (1H, m), 7.54 (1H, d, J=8.8 Hz), 8.22 (1H, dd, J=8.8, 2.2 Hz), 8.49 to 8.51 (1H, d, J=2.6 Hz)

Reference Example 131

4-nitro-2-(trifluoromethyl)benzenethiol (3.0 g) was dissolved in THF (60 ml), and to this solution was added triethylamine (5.25 ml) and then, 3-(chloromethyl)pyridine hydrochloride (2.65 g), and the mixture was stirred for 1 hour at room temperature. The reaction solution was added to water, and extracted with ethyl acetate. The organic layer was washed with saturated brine, and dried over magnesium sulfate. The solvent was removed under reduced pressure and the obtained residue was washed with hexane/ethyl acetate, to give 3-[[[4-nitro-2-(trifluoromethyl)phenyl]sulfanyl]methyl]pyridine (2.2 g).

$^1$H-NMR (200 MHz, CDCl$_3$) δ 4.31 (2H, s), 7.24 to 7.34 (1H, m), 7.52 (1H, d, J=8.8 Hz), 7.72 to 7.79 (1H, m), 8.28 (1H, dd, J=8.8, 2.2 Hz), 8.49 to 8.64 (3H, m)

Reference Example 132

To 3-[[[4-nitro-2-(trifluoromethyl)phenyl]sulfanyl]methyl]pyridine (2.2 g) was added acetic acid (22 ml), and reduced iron (6.6 g) was added to the mixture, and the mixture was stirred for 240 hours at room temperature. The mixture was filtered with Celite, and the mixture was washed with ethyl acetate. The solvent was removed under reduced pressure, and the obtained residue was purified by silica gel column chromatography, to give 4-[(3-pyridinylmethyl)sulfanyl]-3-(trifluoromethyl)aniline (0.83 g).

¹H-NMR (200 MHz, CDCl₃) δ 3.91 (2H, s), 3.96 (2H, br), 6.62 (1H, dd, J=8.2, 2.6 Hz), 6.96 (1H, d, 3.0 Hz), 7.07 (1H, d, J=8.4 Hz), 7.19 (1H, dd, J=7.4, 4.4 Hz), 8.28 (1H, d, J=2.2 Hz), 8.45 (1H, dd, J=4.8, 1.4 Hz).

IR (KBr) 3339, 1607, 1481, 1445, 1339, 1263, 1167, 1125, 1030, 874, 712 cm⁻¹

Reference Example 133

To 5-[[(4-nitrophenyl)sulfanyl]methyl]-1,2,3,4-tetrazole (4.0 g) was added anhydrous acetic acid, and the mixture was heated to reflux for 1 hour. After allowing the mixture to be cooled to room temperature, the solvent was removed under reduced pressure. The obtained residue was dissolved in ethyl acetate/THF, washed with an aqueous solution of saturated sodium bicarbonate and saturated brine, and dried over magnesium sulfate. The solvent was removed under reduced pressure and the obtained residue was washed with hexane/ethyl acetate, to give 2-methyl-5-[[(4-nitrophenyl)sulfanyl]methyl]-1,3,4-oxadiazole (3.3 g).

¹H-NMR (200 MHz, CDCl₃) δ 2.53 (3H, s), 4.36 (2H, s), 7.51 (2H, d, J=8.8 Hz), 8.17 (2H, d, J=9.2 Hz)

Reference Example 134

To 2-methyl-5-[[(4-nitrophenyl)sulfanyl]methyl]-1,3,4-oxadiazole (3.3 g) was added acetic acid (33 ml), and reduced iron (9.9 g) was added to the mixture, and the mixture was stirred for 240 hours at room temperature. The mixture was filtered with Celite, and the mixture was washed with ethyl acetate. The solvent was removed under reduced pressure, and the obtained residue was purified by silica gel column chromatography, to give 4-[[(5-methyl-1,3,4-oxadiazol-2-yl)methyl]sulfanyl]aniline (2.2 g).

¹H-NMR (200 MHz, CDCl₃) δ 2.51 (3H, s), 3.81 (2H, br), 4.10 (6H, s), 6.57 (2H, d, J=8.8 Hz), 7.20 (2H, d, J=8.8 Hz)

Reference Example 135

2-methoxy-4-nitrophenol (19.2 g) was dissolved in methylene chloride (192 ml), triethylamine (20.5 ml) was added to the mixture, trifluoromethanesulfonic acid anhydride (23.0 ml) was added dropwise to the solution at 0° C., and the mixture was stirred for 1 hour at room temperature. The reaction solution was added to water, and extracted with ethyl acetate. The organic layer was washed with saturated brine, and dried over magnesium sulfate. The solvent was removed under reduced pressure, the obtained residue was dissolved in ethanol (274 ml) under heat reflux, and an aqueous solution (342 ml) of sodium sulfate nanohydrate (21.1 g) and sulfur (2.8 g) in ethanol was added dropwise thereto for 20 minutes. Aqueous solution of sodium hydroxide (7.02 g, 28.1 ml) was added dropwise to the solution for 20 minutes, and then, the mixture was cooled to room temperature, ice-water was added thereto. The precipitates were filtered, and the pH of the filtrate was adjusted to about pH 5 with 6N hydrochloric acid, and the precipitates were collected by filtration, and washed with water to give 2-methoxy-4-nitrobenzenethiol (15.8 g, 75%).

¹H-NMR (200 MHz, CDCl₃) δ 4.01 (3H, s), 6.22 (1H, s), 6.99 (1H, d, J=8.8 Hz), 7.77 (1H, d, J=2.4 Hz), 7.89 (1H, dd, J=8.8, 2.6 Hz)

Reference Example 136

To 2-methoxy-4-nitrobenzenethiol (7.0 g) was added acetic acid (70 ml), reduced iron (21 g) was added to the mixture, and the mixture was stirred for 6 hours at room temperature. The mixture was filtered with Celite, and washed with ethyl acetate. The solvent was removed under reduced pressure, and the obtained residue was purified by silica gel column chromatography, to give 4-amino-2-methoxybenzenethiol (3.1 g).

¹H-NMR (200 MHz, CDCl₃) δ 3.43 (1H, s), 3.83 (3H, s), 6.20 to 6.25 (2H, m), 7.07 (1H, d, J=8.8 Hz)

Reference Example 137

4-amino-2-methoxybenzenethiol (1.0 g) was dissolved in methanol (20 ml), and to this solution was added 3N aqueous solution of sodium hydroxide (6.4 ml) and then, 3-(chloromethyl)pyridine hydrochloride (1.27 g), and the mixture was stirred for 30 minutes. The solvent was removed under reduced pressure, and the residue was extracted with ethyl acetate. The organic layer was washed with saturated brine, and dried over magnesium sulfate. The solvent was removed under reduced pressure, and the obtained residue was purified by silica gel column chromatography, to give 3-methoxy-4-[(3-pyridinylmethyl)sulfanyl]aniline (1.0 g).

¹H-NMR (200 MHz, CDCl₃) δ 3.79 (3H, s), 3.87 (3H, s), 6.08 to 6.14 (2H, m), 6.97 (1H, d, J=8.2 Hz), 7.15 (1H, dd, J=7.6, 4.6 Hz), 7.44 to 7.50 (1H, m), 8.28 (1H, d, J=2.2 Hz), 8.40 (1H, dd, J=4.6, 1.8 Hz)

Reference Example 138

To 5-[[(4-nitrophenyl)sulfanyl]methyl]-1,2,3,4-tetrazole (4.1 g) was added acetonitrile (203 ml), potassium carbonate (7.1 g) and iodoethane (3.3 ml) were added to the mixture, and the mixture was stirred for 140 hours at 50° C. The solvent was removed under reduced pressure, and to the obtained residue was added ethyl acetate, and the mixture was washed with water and saturated brine, and dried over magnesium sulfate. The solvent was removed under reduced pressure and the obtained residue was washed with hexane/ethyl acetate, to give 1-ethyl-5-[[(4-nitrophenyl)sulfanyl]methyl]-1,2,3,4-tetrazole and 2-ethyl-5-[[(4-nitrophenyl)sulfanyl]methyl]-1,2,3,4-tetrazole as mixture (4.2 g).

¹H-NMR (200 MHz, CDCl₃) δ 1.62 (3H, t, J=7.2 Hz), 1.63 (3H, t, J=7.2 Hz), 4.49 (2H, s), 4.49 (2H, s), 4.46 (2H, q, J=7.2 Hz), 4.63 (2H, q, J=7.2 Hz), 7.47 to 7.55 (4H, m), 8.11 to 8.18 (4H, m)

Reference Example 139

To a mixture of 1-ethyl-5-[[(4-nitrophenyl)sulfanyl]methyl]-1,2,3,4-tetrazole and 2-ethyl-5-[[(4-nitrophenyl)sulfanyl]methyl]-1,2,3,4-tetrazole (4.2 g) was added acetic acid (42 ml), reduced iron (12.6 g) was added to the mixture, and the mixture was stirred for 40 hours at room temperature. The mixture was filtered with Celite, and the mixture was washed with ethyl acetate. The solvent was removed under reduced pressure, and the obtained residue was dissolved in ethyl acetate, and the mixture was washed with an aqueous solution of saturated sodium bicarbonate and saturated brine, and dried over magnesium sulfate. The solvent was removed under reduced pressure, and the obtained residue was purified by silica gel column chromatography, to give 4-[[(1-ethyl-1,2,3,4-tetrazol-5-yl)methyl]sulfanyl]aniline (1.1 g) and 4-[[(2-ethyl-1,2,3,4-tetrazol-5-yl)methyl]sulfanyl]aniline (2.2 g).

4-[[(1-ethyl-1,2,3,4-tetrazol-5-yl)methyl]sulfanyl]aniline: $^1$H-NMR (200 MHz, CDCl$_3$) δ 1.38 (3H, t, J=7.2 Hz), 4.16 (2H, s), 4.59 (2H, q, J=7.2 Hz), 6.58 (2H, d, J=8.8 Hz), 7.20 (2H, d, J=8.4 Hz).

4-[[(2-ethyl-1,2,3,4-tetrazol-5-yl)methyl]sulfanyl]aniline: $^1$H-NMR (200 MHz, CDCl$_3$) δ 1.52 (3H, t, J=7.2 Hz), 4.11 (2H, s), 4.23 (2H, q, J=7.2 Hz), 6.54 (2H, d, J=8.4 Hz), 7.05 (2H, d, J=8.4 Hz).

Reference Example 140

2-chloro-4-nitro-bromobenzene (20 g) was dissolved in ethanol (160 ml), and an aqueous solution of sodium sulfate nanohydrate (15.2 g) and sulfur (2.0 g) in ethanol (200 ml) was added dropwise to the solution for 20 minutes under heat reflux. An aqueous solution of sodium hydroxide (5.1 g, 20.3 ml) was added dropwise to the solution for 20 minutes, and then, the mixture was cooled to room temperature, and ice-water was added thereto. The precipitates were filtered, and the pH of the filtrate was adjusted to about pH 5 with 6N hydrochloric acid, and the precipitates were collected by filtration and washed with water to give 2-chloro-4-nitrobenzenethiol (9.4 g).

$^1$H-NMR (200 MHz, CDCl$_3$) δ 4.28 (1H, s), 7.48 (1H, d, J=8.8 Hz), 8.00 (1H, dd, J=8.8, 2.2 Hz), 8.24 (1H, d, J=2.6 Hz)

Reference Example 141

To 2-chloro-4-nitrobenzenethiol (4.0 g) was added acetic acid (60 ml), and to this solution was added reduced iron (21 g), and the mixture was stirred at room temperature for 3 hours. The mixture was filtered with Celite, and washed with ethyl acetate. The solvent was removed under reduced pressure, and the obtained residue was purified by silica gel column chromatography, to give 4-amino-2-chlorobenzenethiol (2.74 g).

$^1$H-NMR (200 MHz, CDCl$_3$) δ 3.59 (1H, s), 3.95 (2H, br), 6.49 (1H, dd, J=8.8, 2.4 Hz), 6.75 (1H, d, J=2.2 Hz), 7.16 (1H, d, J=8.4 Hz)

Reference Example 142

4-amino-2-chlorobenzenethiol (1.2 g) was dissolved in methanol (24 ml), and to this solution was added 3N aqueous solution of sodium hydroxide (7.5 ml) and then, 3-(chloromethyl)pyridine hydrochloride (1.48 g), and the mixture was stirred for 15 minutes at room temperature. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 3-chloro-4-[(3-pyridinylmethyl)sulfanyl]aniline (0.83 g).

$^1$H-NMR (200 MHz, CDCl$_3$) δ 3.84 (2H, br), 3.93 (2H, s), 6.38 (1H, dd, J=8.2, 2.6 Hz), 6.74 (1H, d, J=2.6 Hz), 7.02 (1H, d, J=8.4 Hz), 7.18 (1H, dd, J=7.8, 4.8 Hz), 7.45 to 7.52 (1H, m), 8.31 (1H, d, J=2.2 Hz), 8.43 (1H, dd, J=4.8, 1.8 Hz)

Reference Example 143

To a solution of aluminum lithium hydride (1.43 g) in THF (126 ml) was added a solution of methyl 2-methoxynicotinate (6.3 g) in THF (63 ml) at 0° C. The mixture was stirred at room temperature for 2 hours, and water (6.3 ml), 15% aqueous solution of sodium hydroxide (6.3 ml) and water (18.9 ml) were sequentially added to the solution at 0° C. The mixture was filtered with Celite, and washed with methanol. The solvent was removed under reduced pressure, and the obtained residue was purified by silica gel column chromatography, to give (2-methoxy-3-pyridinyl)methanol (5.0 g).

$^1$H-NMR (200 MHz, CDCl$_3$) δ 3.99 (3H, s), 4.65 (2H, d, J=4.8 Hz), 6.90 (1H, dd, J=7.0, 1.4 Hz), 7.56 to 7.61 (1H, m), 8.09 (1H, dd, J=5.0, 1.4 Hz)

Reference Example 144

(2-methoxy-3-pyridinyl)methanol (3.0 g) was dissolved in methylene chloride (30 ml), and to this solution was added DMF (3 droplets) and then, thionyl chloride (3.2 ml) at 0° C., and the mixture was stirred for 2 hours at room temperature. The solvent was removed under reduced pressure, and a solution of the obtained residue in methanol (15 ml) was added dropwise to a solution (45 ml) of 4-aminothiophenol (2.46 g) and 3N sodium hydroxide (21.9 ml) in methanol at 0° C. The mixture was stirred for 30 minutes at room temperature, the solvent was removed under reduced pressure, and the obtained residue was added to water and extracted with ethyl acetate. The organic layer was washed with saturated brine, and dried over magnesium sulfate. The solvent was removed under reduced pressure, and the obtained residue was purified by silica gel column chromatography, to give 4-[[(2-methoxy-3-pyridinyl)methyl]sulfanyl]aniline (3.5 g).

$^1$H-NMR (200 MHz, CDCl$_3$) δ 3.72 (2H, br), 3.89 (2H, S), 3.93 (3H, s), 6.56 (2H, d, J=8.4 Hz), 6.72(1H, dd, J=7.2, 4.8 Hz), 7.12 (2H, d, J=8.4 Hz), 7.18 (1H, dd, J=7.4, 1.8 Hz), 8.02 (1H, dd, J=5.0, 1.8 Hz)

Reference Example 145

To a solution of aluminum lithium hydride (2.0 g) in THF (160 ml) was added dropwise a solution of methyl 2-methylnicotinate (8.0 g) in THF (80 ml) at 0° C. The mixture was stirred for 2 hours at room temperature, and water (8.0 ml), 15% aqueous solution of sodium hydroxide (8.0 ml) and water (24.0 ml) were sequentially added to the mixture at 0° C. The mixture was filtered with Celite, and washed with methanol. The solvent was removed under reduced pressure, and the obtained residue was purified by silica gel column chromatography, to give (2-methyl-3-pyridinyl)methanol (4.6 g).

$^1$H-NMR (200 MHz, CDCl$_3$) δ 2.53 (3H, s), 4.73 (2H, s), 7.15 (1H, dd, J=7.6, 1.4 Hz), 8.38 (1H, d, J=5.2 Hz)

Reference Example 146

(2-methyl-3-pyridinyl)methanol (3.0 g) was dissolved in methylene chloride (30 ml), and to this solution was added DMF (3 droplets) and then, thionyl chloride (3.56 ml) at 0° C., and the mixture was stirred for 2 hours at room temperature. The solvent was removed under reduced pressure, and a solution of the obtained residue in methanol (20 ml) was added dropwise to a solution (41.2 ml) of 4-aminothiophenol (2.74 g) and 3N sodium hydroxide (24.4 ml) in methanol at 0° C. The mixture was stirred for 30 minutes at room temperature, the solvent was removed under reduced pressure, and the obtained residue was added to water and extracted with ethyl acetate. The organic layer was washed with saturated brine, and dried over magnesium sulfate. The solvent was removed under reduced pressure, and the obtained residue was washed with hexane/ethyl acetate, to give 4-[[(2-methyl-3-pyridinyl)methyl]sulfanyl]aniline (4.3 g).

$^1$H-NMR (200 MHz, CDCl$_3$) δ 2.54 (3H, s), 3.75 (2H, br), 3.88 (2H, s), 6.55 (2H, d, J=8.8 Hz), 6.96 (1H, dd, J=7.6, 4.8 Hz), 7.08 (2H, d, J=8.8 Hz), 7.14 to 7.19 (1H, m), 8.35 (1H, dd, J=4.8, 1.8 Hz)

Reference Example 147

To aluminum lithium hydride (2.0 g) in THF (156 ml) was added dropwise methyl 6-methylnicotinate (7.8 g) in THF (78 ml) at 0° C. The mixture was stirred for 2 hours at room temperature at 0° C., and water (7.8 ml), 15% aqueous solution of sodium hydroxide (7.8 ml), and water (23.4 ml) were sequentially added to the mixture. The mixture was filtered with Celite, and washed with methanol. The solvent was removed under reduced pressure, and the obtained residue was purified by silica gel column chromatography, to give (6-methyl-3-pyridinyl)methanol (6.3 g).

$^1$H-NMR (200 MHz, CDCl$_3$) δ 2.50 (3H, s), 4.64 (2H, s), 7.13 (1H, d, J=8.0 Hz), 7.58 to 7.64 (1H, m), 8.34 (1H, s)

Reference Example 148

(6-methyl-3-pyridinyl)methanol (3.0 g) was dissolved in methylene chloride (30 ml), and to this solution was added DMF (3 droplets) and then, thionyl chloride: (3.56 ml) at 0° C., and the mixture was stirred for 2 hours at room temperature. The solvent was removed under reduced pressure, and a solution of the obtained residue in methanol (20 ml) was added dropwise to a solution (41.2 ml) of 4-aminothiophenol (2.74 g) and 3N sodium hydroxide (24.4 ml) in methanol at 0° C. The mixture was stirred for 30 minutes at room temperature, the solvent was removed under reduced pressure, and the obtained residue was added to water and extracted with ethyl acetate. The organic layer was washed with saturated brine, and dried over magnesium sulfate. The solvent was removed under reduced pressure and the obtained residue was washed with hexane/ethyl acetate, to give 4-[[(6-methyl-3-pyridinyl)methyl]sulfanyl]aniline (4.2 g).

$^1$H-NMR (200 MHz, CDCl$_3$) δ 2.51 (3H, s), 2.73 (2H, br), 3.86 (2H, s), 6.53 to 6.58 (2H, m), 7.01 to 7.08 (3H, m), 7.34 to 7.40 (1H, m), 8.18 (1H, d, J=2.2 Hz)

Reference Example 149

To a solution of aluminum lithium hydride (2.75 g) in THF (200 ml), was added a solution of methyl pyrazine-2-carboxylate (10 g) in THF (100 ml) at 0° C. The mixture was stirred for 30 minutes at 0° C., water (10 ml), 15% aqueous solution of sodium hydroxide (10 ml), and water (30 ml) were added to the mixture. The mixture was filtered with Celite, and washed with methanol. The solvent was removed under reduced pressure, and the obtained residue was purified by silica gel column chromatography, to give 2-pyradinylmethanol (1.5 g).

$^1$H-NMR (200 MHz, CDCl$_3$) δ 3.76 (1H, br), 4.85 (2H, s), 8.50 to 8.55 (2H, m), 8.67 (1H, m)

Reference Example 150

2-pyradinylmethanol (1.0 g) was dissolved in THF (100 ml), and to this solution was added triethylamine (2.0 ml) and then, methanesulfonyl chloride (1.0 ml) at 0° C., and the mixture was stirred for 1 hour at room temperature. The reaction solution was added to water, and extracted with ethyl acetate. The organic layer was washed with saturated brine, and dried over magnesium sulfate. The solvent was removed under reduced pressure, a solution of the obtained residue in methanol was added dropwise to a solution (20.4 ml) of 4-aminothiophenol (1.02 g) and 3N sodium hydroxide (9.1 ml) in methanol at 0° C. The mixture was stirred at room temperature for 16 hours, and the solvent was removed under reduced pressure. To the obtained residue was added ethyl acetate, and the mixture was washed with water and saturated brine, and dried over magnesium sulfate. The solvent was removed under reduced pressure, and the obtained residue was purified by silica gel column chromatography, to give 4-[(2-pyradinylmethyl)sulfanyl]aniline (0.71 g).

$^1$H-NMR (200 MHz, CDCl$_3$) δ 3.75 (2H, br), 4.05 (2H, s), 6.52 to 6.57 (2H, m), 7.09 to 7.13 (2H, m), 8.32 (1H, d, J=1.6 Hz), 8.39 (1H, d, J=2.4 Hz), 8.46 to 8.48 (1H, m).

IR (KBr) 3349, 1624, 1597, 1497, 1400, 1294, 1177, 1019, 826 cm$^{-1}$

Reference Example 151

3-methylpyridazine (6.0 g) was dissolved in chloroform (180 ml), trichloroisocyanuric acid (5.9 g) was added to the mixture, and the mixture was heated to reflux for 18 hours. After cooling to room temperature, the mixture was diluted with methylene chloride, and filtered with Celite. The filtrate was washed with 1N sodium hydroxide and saturated brine, and dried over magnesium sulfate. The solvent was removed under reduced pressure, and 3-chloromethylpyridazine (1.4 g) was added to the residue. 4-aminothiophenol (1.7 g) was dissolved in methanol (27 ml), and 3N sodium hydroxide (11 ml) and then 3-chloromethylpyridazine (1.4 g) were added to the mixture. The mixture was stirred for 1 hour at room temperature, the solvent was removed under reduced pressure, and to the obtained residue was added ethyl acetate, and the mixture was washed with water and saturated brine, and dried over magnesium sulfate. The solvent was removed under reduced pressure, and the obtained residue was purified by silica gel column chromatography, to give 4-[(3-pyridazinylmethyl)sulfanyl]aniline (1.63 g).

$^1$H-NMR (200 MHz, CDCl$_3$) δ 3.78 (2H, br), 4.26 (2H, s), 6.51 to 6.56 (2H, m), 7.08 to 7.13 (2H, m), 7.36 to 7.41 (2H, m), 9.02 (1H, dd, J=4.6, 2.0 Hz)

Reference Example 152

To chloroacetoamidine hydrochloride (19.7 g) was added 1,1,3,3-tetramethoxypropane (50 ml), and the mixture was stirred for 16 hours at 100° C. After cooling to room temperature, the mixture was added to water, extracted with methylene chloride, and dried over magnesium sulfate. The solvent was removed under reduced pressure to give 2-(chloromethyl)pyrimidine (2.0 g).

$^1$H-NMR (200 MHz, CDCl$_3$) δ 4.76 (2H, s), 7.27 to 7.30 (1H, m), 8.78 (1H, d, J=5.2 Hz)

Reference Example 153

(4-nitrobenzyl)phosphonium bromide (15 g) was dissolved in THF (225 ml), 28% sodium methoxide/methanol solution (5.80 g) was added to the mixture, and the mixture was stirred for 30 minutes at room temperature. 1-propylimidazole-2-carboxaldehyde (2.15 g) was added to the mixture, and the mixture was stirred for 6 hours at room temperature. To the reaction mixture was added water (10 ml), and the mixture was stirred for 30 minutes at room temperature, and extracted with ethyl acetate. The organic layer was washed with saturated brine, and dried over magnesium sulfate. The solvent was removed under reduced pressure, and the obtained residue was purified by silica gel column chromatography to give 2-[(E)-2-(4-nitrophenyl)ether]-1-propylimidazole (3.3 g).

$^1$H-NMR (200 MHz, CDCl$_3$) δ 0.92 (3H, t, J=7.0 Hz), 1.70 to 1.80 (2H, m), 3.83 (2H, t, J=7.0 Hz), 6.53 (1H, d, J=12.4 Hz), 6.73 (1H, d, J=12.8 Hz), 6.94 (1H, s), 7.11 (1H, s), 7.80 (2H, d, J=9.2 Hz), 8.15 (2H, d, J=8.8 Hz)

Reference Example 154

2-[(E)-2-(4-nitrophenyl)ether]-1-propylimidazole (2.0 g) was dissolved in ethanol (20 ml), 10% palladium/carbon (0.20 g) was added to the mixture, and the mixture was stirred at room temperature for 3 hours under hydrogen atmosphere. The mixture was filtered with Celite, and washed with ethanol. The solvent was removed under reduced pressure, and the obtained residue was purified by silica gel column chromatography, to give 4-[2-(1-propylimidazol-2-yl)ethyl]aniline (1.08 g).

$^1$H-NMR (200 MHz, CDCl$_3$) δ 0.88 (3H, t, J=7.2 Hz), 1.57 to 1.75 (2H, m), 2.83 to 3.04 (4H, m), 3.61 to 3.69 (4H, m), 6.61 (2H, d, J=8.8 Hz), 6.78 to 6.79 (1H, d, J=1.0 Hz), 6.93 to 6.99 (3H, m)

Reference Example 155

To 2-[(E)-2-(4-nitrophenyl)ether]-1-propylimidazole (1.3 g) was added 85% ethanol solution (39 ml), calcium chloride (0.30 g) and reduced iron (1.5 g) were added to the mixture, and the mixture was heated to reflux for 4 hours. After cooling to room temperature, and the mixture was filtered with Celite, and washed with ethyl acetate. The solvent was removed under reduced pressure, and the obtained residue was added to water and extracted with ethyl acetate. The organic layer was washed with saturated brine, and dried over magnesium sulfate. The solvent was removed under reduced pressure, and the obtained residue was purified by silica gel column chromatography to give 2-[(E)-2-(4-nitrophenyl)ether]-1-propylimidazole (1.0 g).

$^1$H-NMR (200 MHz, CDCl$_3$) δ 0.82 (3H, t, J=7.2 Hz), 1.55 to 1.71 (2H, m), 3.64 (2H, t, J=7.0 Hz), 3.78 (2H, br), 6.15 (1H, d, J=12.0 Hz), 6.53 (2H, d, J=8.4 Hz), 6.65 (1H, d, J=12.0 Hz), 6.86 (1H, d, J=1.2 Hz), 7.10 (1H, d, J=1.4 Hz), 7.14 (2H, d, J=8.8 Hz)

Reference Example 156

N-methyl-4-nitroaniline (2.3 g) was dissolved in THF (92 ml), 60% sodium hydride (1.85 g) was added to the solution at 0° C., and the mixture was stirred for 1 hour at room temperature. 2-chloromethyl-1-propylimidazole hydrochloride (3.54 g) was added to the mixture at room temperature and the mixture was stirred for 240 hours. To the reaction mixture was added water, and the mixture was extracted with ethyl acetate. The organic layer was washed with saturated brine, and dried over magnesium sulfate. The solvent was removed under reduced pressure, and the obtained residue was purified by silica gel column chromatography, to give N-methyl-4-nitro-N-[(1-propylimidazol-2-yl)methyl]aniline (2.7 g).

$^1$H-NMR (200 MHz, CDCl$_3$) δ 0.88 (3H, t, J=7.2 Hz), 1.72 (2H, m), 3.10 (3H, s), 3.80 (2H, t, J=7.4 Hz), 4.67 (2H, s), 6.79 (2H, d, J=9.6 Hz), 6.92 (1H, d, J=1.6 Hz), 7.01 (1H, d, J=1.4 Hz), 8.13 (2H, d, J=9.6 Hz)

Reference Example 157

To N-methyl-4-nitro-N-[(1-propylimidazol-2-yl)methyl]aniline (1.5 g) was added 85% ethanol solution (45 ml), calcium chloride (0.30 g) and reduced iron (1.5 g) were added to the mixture, and the mixture was heated to reflux for 3 hours. After cooling to room temperature, the mixture was filtered with Celite, and washed with ethyl acetate. The solvent was removed under reduced pressure, and the obtained residue was dissolved in ethyl acetate. The organic layer was washed with saturated brine, and dried over magnesium sulfate. The solvent was removed under reduced pressure, and the obtained residue was purified by silica gel column chromatography, to give N-methyl-N-[(1-propylimidazol-2-yl)methyl]-1,4-benzodiamine (1.03 g).

$^1$H-NMR (200 MHz, CDCl$_3$) δ 0.89 (3H, t, J=7.2 Hz), 1.68 to 1.80 (2H, m), 2.68 (3H, s), 3.42 (2H, br), 3.89 (2H, t, J=7.4 Hz), 4.30 (2H, m), 6.67 (2H, d, J=8.8 Hz), 6.83 (2H, d, J=8.8 Hz), 6.88 (1H, d, J=1.2 Hz), 6.97 (1H, d, J=1.4 Hz)

Reference Example 158

4-nitrobenzenethiol (10 g) was dissolved in methanol (100 ml), 3N sodium hydroxide (32.2 ml) was added to the mixture, and 2-bromoethanol (9.7 g) was added dropwise to the mixture. The mixture was stirred for 1 hour at room temperature, the solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was washed with hexane/ethyl acetate, to give 2-[(4-nitrophenyl)sulfanyl]ethanol (10.6 g).

$^1$H-NMR (200 MHz, CDCl$_3$) δ 3.26 (2H, t, J=6.0 Hz), 3.85 to 3.96 (2H, m), 7.40 (2H, d, J=9.0 Hz), 8.14 (2H, d, J=9.2 Hz).

Reference Example 159

2-[(4-nitrophenyl)sulfanyl]ethanol (3.0 g) was dissolved in THF (60 ml), triethylamine (3.15 ml) and methanesulfonyl chloride (1.85 g) were added to the mixture, and the mixture was stirred for 1 hour at room temperature. The reaction solution was added to water, and extracted with ethyl acetate. The organic layer was washed with saturated brine, and dried over magnesium sulfate. The solvent was removed under reduced pressure, and a solution (18 ml) of the obtained residue in. DMF was added dropwise to imidazole (0.85 g) and 60% solution (15 ml) of sodium hydride (0.50 g) in DMF at 100° C. The mixture was stirred for 16 hours at 100° C., and cooled to room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 1-[2-[(4-nitrophenyl)sulfanyl]ethyl]imidazole (0.60 g).

$^1$H-NMR (200 MHz, CDCl$_3$) δ 3.39 (2H, t, J=6.6 Hz), 4.26 (2H, t, J=6.6 Hz), 6.94 to 6.96 (1H, m), 7.06 to 7.08 (1H, m), 7.32 (2H, d, J=9.0 Hz), 7.50 (1H, s), 8.15 (2H, d, J=8.8 Hz).

Reference Example 160

To 1-[2-[(4-nitrophenyl)sulfanyl]ethyl]imidazole (0.60 g) was added 85% ethanol solution (18 ml), and to this solution was added calcium chloride (0.13 g) and reduced iron (0.67 g), and the mixture was heated to reflux for 3 hours. After cooling to room temperature, the mixture was filtered with Celite, and washed with ethyl acetate. The solvent was removed under reduced pressure, and the obtained residue was dissolved in ethyl acetate. The organic layer was washed with saturated brine, and dried over magnesium sulfate. The solvent was removed under reduced pressure, and the obtained residue was purified by silica gel column chromatography, to give 4-[[2-(imidazol-1-yl)ethyl]sulfanyl]phenylamine (0.48 g).

$^1$H-NMR (200 MHz, CDCl$_3$) δ 3.05 (2H, t, J=6.6 Hz), 3.78 (2H, br), 4.04 (2H, t, J=7.0 Hz), 6.64 (2H, d, J=8.4 Hz), 6.88 to 6.90 (1H, m), 7.03 to 7.05 (1H, m), 7.24 (2H, d, J=8.4 Hz), 7.44 (1H, s).

Reference Example 161

5-nitro-2-pyridinethiol (6.0 g) was dissolved in an aqueous solution of methanol (150 ml), and to this solution was added sodium hydroxide (4.6 g) and then, 2-(chloromethyl) pyridine hydrochloride (7.6 g), and the mixture was stirred for 15 minutes at room temperature. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 5-nitro-2-[(2-pyridinylmethyl)sulfanyl]pyridine (6.2 g).

$^1$H-NMR (200 MHz, CDCl$_3$) δ 4.65 (2H, s), 7.15 to 7.72 (1H, m), 7.35 (1H, d, J=9.2 Hz), 7.43 to 7.48 (1H, m), 7.64 (1H, td, J=7.6, 1.8 Hz), 8.23 (1H, d, J=9.2, 3.0 Hz), 8.55 to 8.59 (1H, m), 9.23 to 9.25 (1H, m).

Reference Example 162

5-nitro-2-[(2-pyridinylmethyl)sulfanyl]pyridine (6.0 g) was dissolved in acetic acid (60 ml), reduced iron (18 g) was added to the mixture, and the mixture was stirred for 240 hours at room temperature. The mixture was filtered with. Celite, and washed with ethyl acetate. The solvent was removed under reduced pressure, and the obtained residue was purified by silica gel column chromatography, to give 6-[(2-pyridinylmethyl)sulfanyl]-3-pyridineamine (1.83 g).

$^1$H-NMR (200 MHz, CDCl$_3$) δ 3.63 (2H, s), 4.47 (2H, s), 6.86 (1H, dd, J=8.4, 2.8 Hz), 7.03 (1H, dd, J=8.4, 0.8 Hz), 7.08 to 7.15 (1H, m), 7.37 (1H, d, J=7.8 Hz), 7.57 (1H, td, J=7.6, 1.8 Hz), 7.99 to 8.01 (1H, m), 8.50 to 8.55 (1H, m).

Reference Example 163

5-nitro-2-pyridinethiol (5.0 g) was dissolved in an aqueous methanol solution (125 ml), and to this solution was added sodium hydroxide (3.84 g) and then, 3-(chloromethyl) pyridine hydrochloride (6.30 g), and the mixture was stirred for 30 minutes. The solvent was removed under reduced pressure, and the obtained residue was added to water and extracted with ethyl acetate. The organic layer was washed with saturated brine, and dried over magnesium sulfate. The solvent was removed under reduced pressure, and the obtained residue was purified by silica gel column chromatography, to give 5-nitro-2-[(3-pyridinylmethyl)sulfanyl]pyridine (6.0 g).

$^1$H-NMR (200 MHz, CDCl$_3$) δ 4.51 (2H, s), 7.21 to 7.32 (2H, m), 7.71 to 7.77 (1H, m), 8.24 (1H, dd, J=8.8, 2.6 Hz), 8.68 (1H, d, J=3.8 Hz), 9.27 (1H, d, J=3.4 Hz).

Reference Example 164

5-nitro-2-[(3-pyridinylmethyl)sulfanyl]pyridine (5.6 g) was dissolved in acetic acid (56 ml), reduced iron (16.8 g) was added to the mixture, and the mixture was stirred for 40 hours at room temperature. The mixture was filtered with Celite, and washed with ethyl acetate. The solvent was removed under reduced pressure, and the obtained residue was purified by silica gel column chromatography, to give 6-[(3-pyridinylmethyl)sulfanyl]-3-pyridinylamine (4.3 g).

$^1$H-NMR (200 MHz, CDCl$_3$) δ 4.30 (2H, s), 6.82 to 6.88 (1H, m), 6.95 to 7.00 (1H, m), 7.18 to 7.24 (1H, m), 7.66 to 7.73 (1H, m), 8.02 to 8.24 (1H, m), 8.42 to 8.45 (1H, m), 8.54 (1H, s).

Reference Example 165

(2-methyl-3-pyridinyl)methanol (4.0 g) was dissolved in methylene chloride (40 ml), DMF (3 droplets) was added to the mixture, thionyl chloride (4.75 ml) was added at 0° C., and the mixture was stirred for 2 hours at room temperature. The solvent was removed under reduced pressure, and a solution of the obtained residue in methanol (30 ml) was added dropwise to an aqueous solution (68.4 ml) of 4-nitrothiophenol (4.56 g) and 3N sodium hydroxide (29.2 ml) in methanol at 0° C. The mixture was stirred at room temperature for 2 hours, the solvent was removed under reduced pressure, and the residue was extracted with ethyl acetate. The organic layer was washed with saturated brine, and dried over magnesium sulfate. The solvent was removed under reduced pressure, and the obtained residue was washed with hexane/ethyl acetate, to give 2-methyl-3-[[(5-nitro-2-pyridinyl)sulfanyl]methyl]pyridine (4.9 g).

$^1$H-NMR (200 MHz, CDCl$_3$) δ 2.66 (3H, s), 4.52 (2H, s), 7.09 (1H, dd, J=7.6, 4.8 Hz), 7.27 to 7.33 (1H, m), 7.72 (1H, dd, J=7.6, 1.4 Hz), 8.25 (1H, dd, J=8.8, 2.6 Hz), 8.41 (1H, dd, J=4.8, 1.6 Hz), 9.27 to 9.29 (1H, m)

Reference Example 166

To 2-methyl-3-[[(5-nitro-2-pyridinyl)sulfanyl]methyl]pyridine (4.0 g) was added 85% aqueous solution of ethanol (80 ml), calcium chloride (0.86 g) and reduced iron (4.3 g) were added to the mixture, and the mixture was heated to reflux for 3 hours. After allowing the mixture to be cooled to room temperature, and the solvent was removed under reduced pressure. The mixture was filtered with. Celite, and washed with ethyl acetate. The organic layer was washed with saturated brine, and dried over magnesium sulfate. The solvent was removed under reduced pressure, and the obtained residue was purified by silica gel column chromatography, to give 4-[[(2-methyl-3-pyridinyl)methyl]sulfanyl]aniline (3.2 g).

$^1$H-NMR (200 MHz, CDCl$_3$) δ 2.63 (3H, s), 3.65 (2H, br), 4.30 (2H, s), 6.82 to 7.04 (3H, m), 7.55 (1H, dd, J=7.6, 1.4 Hz), 8.01 to 8.04 (1H, m), 8.35 (1H, dd, J=4.8, 1.6 Hz).

Reference Example 167

Methylpropiolate (20 g) and trimethylsilyl azide (68.6 g) were added to a pressure-resistant tube, and the mixture was stirred for 72 hours at 105° C. After allowing the mixture to be cooled to room temperature, methanol was added to the mixture, and the solvent was removed under reduced pressure, and the obtained residue was washed with diethylether/methanol to give methyl 1,2,3-triazole-4-carboxylate (22.7 g).

$^1$H-NMR (200 MHz, CDCl$_3$) δ 3.87 (3H, s), 8.57 (1H, m).

Reference Example 168 methyl 1,2,3-triazole-4-carboxylate (17.6 g) was dissolved in DMF (210 ml), potassium carbonate (11.5 g) and iodopropane (14.9 ml) were added to the mixture, and the mixture was stirred for 16 hours at room temperature. After filtration, the solvent was removed under reduced pressure, and water was added to the obtained residue, and the mixture was extracted with methylene chloride. The organic layer was washed with saturated brine, and dried over magnesium sulfate. The solvent was removed under reduced pressure, and the obtained residue was purified by silica gel column chromatography, to give methyl 2-propyl-1,2,3-triazole-4-carboxylate (10.3 g), methyl 1-propyl-1,2,3-triazole-5-carbonate (3.2 g) and methyl 1-propyl-1,2,3-triazole-4-carboxylate (2.6 g).

methyl 2-propyl-1,2,3-triazole-4-carboxylate: $^1$H-NMR (200 MHz, CDCl$_3$) δ 0.94 (3H, t, J=7.4 Hz), 1.95 to 2.10 (2H, m), 3.96 (3H, s), 4.46 (2H, t, J=7.0 Hz), 8.06 (1H, s).

methyl 1-propyl-1,2,3-triazole-5-carbonate: $^1$H-NMR (200 MHz, CDCl$_3$) δ 0.96 (3H, t, J=7.4 Hz), 1.86 to 2.02 (2H, m), 3.94 (3H, s), 4.71 (2H, t, J=7.4 Hz), 8.13 (1H, s).

methyl 1-propyl-1,2,3-triazole-4-carboxylate: $^1$H-NMR (200 MHz, CDCl$_3$) δ 0.97 (3H, t, J=7.4 Hz), 1.90 to 2.04 (2H, m), 3.96 (3H, s), 4.40 (2H, t, J=7.0 Hz), 8.10 (1H, s).

Reference Example 169

To a solution of aluminum lithium hydride (1.57 g) in THF (140 ml) was added dropwise methyl 2-propyl-1,2,3-triazole-4-carboxylate (7.0 g) in. THF (70 ml) at 0° C. The mixture was stirred for 1 hour at room temperature, and an aqueous solution of saturated sodium thiosulfate was added to the mixture at 0° C. The mixture was filtered with Celite, and washed with ethanol. The solvent was removed under reduced pressure, and the obtained residue was purified by silica gel column chromatography, to give 4-hydroxymethyl-2-propyl-1,2,3-triazole (5.9 g). To 4-hydroxymethyl-2-propyl-1,2,3-triazole (4.0 g), thionyl chloride (32 ml) was added to the mixture at 0° C., and the mixture was heated to reflux for 1 hour. After allowing the mixture to be cooled to room temperature, the solvent was removed under reduced pressure, to give 4-chloromethyl-2-propyl-1,2,3-triazole (4.2 g).

$^1$H-NMR (200 MHz, CDCl$_3$) δ 0.93 (3H, t, J=7.2 Hz), 1.93 to 2.07 (2H, m), 4.37 (2H, t, J=6.8 Hz), 4.66 (2H, s), 7.60 (1H, s).

Reference Example 170

To a solution of aluminum lithium hydride (0.72 g) in THF (64 ml) was added dropwise a solution of methyl 1-propyl-1,2,3-triazole-5-carbonate (3.2 g) in. THF (32 ml) at 0° C. The mixture was stirred for 1 hour at room temperature, and an aqueous solution of saturated sodium thiosulfate was added to the mixture at 0° C. The mixture was filtered with Celite, and washed with ethanol. The solvent was removed under reduced pressure, and the obtained residue was purified by silica gel column chromatography, to give 5-hydroxymethyl-1-propyl-1,2,3-triazole (2.8 g). To 5-hydroxymethyl-1-propyl-1,2,3-triazole (2.8 g) was added thionyl chloride (16.8 ml) at 0° C., and the mixture was heated to reflux for 1 hour. After allowing the mixture to be cooled to room temperature, the solvent was removed under reduced pressure, and to the obtained residue was added ethyl acetate and the precipitates were filtered, to give 5-chloromethyl-1-propyl-1,2,3-triazole hydrochloride (2.1 g).

$^1$H-NMR (200 MHz, DMSO-d$^6$) δ 0.90 (3H, t, J=7.2 Hz), 1.79 to 1.95 (2H, m), 4.34 (2H, t, J=7.0 Hz), 5.03 (2H, s), 9.53 (1H, br).

Reference Example 171

To a solution of aluminum lithium hydride (0.58 g) in THF (51.4 ml) was added dropwise a solution of methyl 1-propyl-1,2,3-triazole-4-carboxylate (2.6 g) in THF (26 ml) at 0° C. The mixture was stirred for 1 hour at room temperature, and an aqueous solution of saturated sodium thiosulfate was added to the mixture at 0° C. The mixture was filtered with Celite, and washed with ethanol. The solvent was removed under reduced pressure, and the obtained residue was purified by silica gel column chromatography, to give 4-hydroxymethyl-1-propyl-1,2,3-triazole (1.9 g). To 4-hydroxymethyl-1-propyl-1,2,3-triazole (1.9 g) was added thionyl chloride (32 ml) at 0° C., and the mixture was heated to reflux for 1 hour. After allowing the mixture to be cooled to room temperature, the solvent was removed under reduced pressure, to give 4-chloromethyl-1-propyl-1,2,3-triazole (1.75 g).

$^1$H-NMR (200 MHz, CDCl$_3$) δ 0.98 (3H, t, J=7.2 Hz), 1.92 to 2.05 (2H, m), 4.40 (2H, t, J=6.6 Hz), 4.78 (2H, s), 7.91 (1H, br).

Reference Example 172

2-[(4-nitrophenyl)sulfanyl]ethanol (3.0 g) was dissolved in THF (60 ml), triethylamine (3.1 ml) and methanesulfonyl chloride (2.0 ml) were added to the mixture, and the mixture was stirred for 1 hour at room temperature. The reaction solution was added to water, and extracted with ethyl acetate. The organic layer was washed with saturated brine, and dried over magnesium sulfate. The solvent was removed under reduced pressure, and a solution (11.4 ml) of the obtained residue in DMF was added dropwise to a solution (34 ml) of 1,2,4-triazole (1.1 g) and potassium carbonate (2.5 g) in. DMF. The mixture was stirred for 16 hours at 90° C., and cooled to room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 1-[2-[(4-nitrophenyl)sulfanyl]ethyl]-1,2,4-triazole (1.3 g).

$^1$H-NMR (200 MHz, CDCl$_3$) δ 3.18 (2H, d, J=6.6 Hz), 4.26 (2H, t, J=6.6 Hz), 6.62 (2H, d, J=8.4 Hz), 7.22 (2H, d, J=8.4 Hz), 7.92 (1H, s), 8.04 (1H, s).

Reference Example 173

To 1-[2-[(4-nitrophenyl)sulfanyl]ethyl]-1,2,4-triazole (1.3 g) was added 85% ethanol solution (38 ml), calcium chloride (0.28 g) and reduced iron (1.4 g) were added to the mixture, and the mixture was heated to reflux for 3 hours. After cooling to room temperature, the mixture was filtered with Celite, and washed with ethyl acetate. The solvent was removed under reduced pressure, and the obtained residue was added to water, and extracted with ethyl acetate. The organic layer was washed with saturated brine, and dried over magnesium sulfate. The solvent was removed under reduced pressure, and the obtained residue was purified by silica gel column chromatography, to give 4-[[2-(1,2,4-triazol-1-yl)ethyl]sulfanyl]phenylamine (0.95 g).

$^1$H-NMR (200 MHz, CDCl$_3$) δ 3.18 (2H, d, J=6.6 Hz), 4.26 (2H, t, J=6.6 Hz), 6.62 (2H, d, J=8.4 Hz), 7.22 (2H, d, J=8.4 Hz), 7.92 (1H, s), 8.04 (1H, s).

Reference Example 174

4-nitrophenol (10 g) was dissolved in DMF (100 ml), potassium carbonate (12.9 g) and 2-bromoethanol (10.8 g) were added to the mixture, and the mixture was stirred for 16 hours at 90° C. After cooling to room temperature, the mixture was filtered, and the solvent was removed under reduced pressure. The obtained residue was added to water, and extracted with ethyl acetate. The organic layer was washed with saturated brine, and dried over magnesium sulfate. The solvent was removed under reduced pressure, and the obtained residue was purified by silica gel column chromatography, to give 2-(4-nitrophenoxy)ethanol (7.8 g).

$^1$H-NMR (200 MHz, CDCl$_3$) δ 4.01 to 4.07 (2H, m), 4.17 to 4.22 (2H, m), 6.99 (2H, d, J=9.4 Hz), 8.22 (2H, d, J=9.2 Hz).

Reference Example 175

2-(4-nitrophenoxy) ethanol (3.0 g) was dissolved in THF (60 ml), triethylamine (2.74 ml) and methanesulfonyl chloride (1.4 ml) were added to the mixture, and the mixture was stirred for 1 hour at room temperature. The reaction solution was added to water, and extracted with ethyl acetate. The organic layer was washed with saturated brine, and dried over magnesium sulfate. The solvent was removed under reduced pressure, and a solution (15 ml) of the obtained residue in DMF was added dropwise to a solution (30 ml) of 1,2,4-triazole (1.0 g) and potassium carbonate (3.4 g) in DMF. The mixture was stirred for 16 hours at 90° C., and cooled to room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography to give 1-[2-(4-nitrophenoxy)ethyl]-1,2,4-triazole (1.7 g). To 1-[2-(4-nitrophenoxy)ethyl]-1,2,4-triazole (1.6 g) was added 85% ethanol solution (48 ml), calcium chloride (0.38 g) and reduced iron (1.91 g) were added to the mixture, and the mixture was heated to reflux for 3 hours. After cooling to room temperature, the mixture was filtered with Celite, and washed with ethyl acetate. The solvent was removed under reduced pressure, and the obtained residue was dissolved in ethyl acetate. The organic layer was washed with saturated brine, and dried over magnesium sulfate. The solvent was removed under reduced pressure, and the obtained residue was purified by silica gel column chromatography, to give 4-[2-(1,2,4-triazol-1-yl)ethoxy]aniline (0.92 g).

$^1$H-NMR (200 MHz, CDCl$_3$) δ 3.47 (2H, br), 4.25 (2H, t, J=4.8 Hz), 4.52 (2H, t, J=4.8 Hz), 6.58 to 6.72 (4H, m), 7.96 (1H, s) 8.22 (1H, s).

Reference Example 176

2-(4-nitrophenoxy) ethanol (3.0 g) was dissolved in THF (60 ml), triethylamine (3.15 ml) and methanesulfonyl chloride (1.85 ml) were added to the mixture, and the mixture was stirred for 1 hour at room temperature. The reaction solution was added to water, and extracted with ethyl acetate. The organic layer was washed with saturated brine, and dried over magnesium sulfate. The solvent was removed under reduced pressure, and a solution (18 ml) of the obtained residue in. DMF was added dropwise to a solution (15 ml) of imidazole (0.85 g) and 60% sodium hydride (0.50 g) in DMF. The mixture was stirred for 16 hours at 100° C., and cooled to room temperature. The reaction solution was added to water, and extracted with ethyl acetate. The organic layer was washed with saturated brine, and dried over magnesium sulfate. The solvent was removed under reduced pressure and the obtained residue was purified by silica gel column chromatography, to give 1-[2-(4-nitrophenoxy)ethyl]imidazole (0.60 g).

$^1$H-NMR (200 MHz, CDCl$_3$) δ 4.28 to 4.34 (2H, m), 4.39 to 4.44 (2H, m), 6.94 (2H, d, J=9.2 Hz), 7.04 to 7.06 (1H, m), 7.08 to 7.10 (1H, m), 7.61 (1H, s), 8.19 (2H, d, J=9.4 Hz).

Reference Example 177

To 1-[2-(4-nitrophenoxy)ethyl]imidazole (0.64 g) was added 85% ethanol solution (19.2 ml), calcium chloride (0.15 g) and reduced iron (0.77 g) were added to the mixture, and the mixture was heated to reflux for 3 hours. After cooling to room temperature, the mixture was filtered with. Celite, and washed with ethyl acetate. The solvent was removed under reduced pressure, and the obtained residue was dissolved in ethyl acetate. The organic layer was washed with saturated brine, and dried over magnesium sulfate. The solvent was removed under reduced pressure, and the obtained residue was purified by silica gel column chromatography, to give 4-[2-(imidazol-1-yl)ethoxy]aniline (0.31 g).

$^1$H-NMR (200 MHz, CDCl$_3$) δ 4.14 (2H, t, J=4.8 Hz), 4.28 (2H, t, J=4.8 Hz), 6.59 to 6.72 (4H, m), 7.02 to 7.07 (2H, m), 7.58 (1H, s).

Reference Example 178

3-(4-nitrophenyl)propanol (5.0 g) was dissolved in THF (100 ml), 2,6-dimethylpyridine (5.1 ml) and methanesulfonic acid anhydride (6.7 g) were added to the mixture, and the mixture was stirred for 12 hours at 50° C. Lithium bromide (3.6 g) was added to the mixture, and the mixture was stirred for 8 hours at 60° C. After cooling to room temperature, the reaction solution was added to water, and dissolved in ethyl acetate. The organic layer was washed with saturated brine, and dried over magnesium sulfate. The solvent was removed under reduced pressure, and the obtained residue was purified by silica gel column chromatography, to give 1-(3-bromopropyl)-4-nitrobenzene (3.1 g).

$^1$H-NMR (200 MHz, CDCl$_3$) δ 2.13 to 2.38 (2H, m), 2.87 to 2.95 (2H, m), 3.40 (2H, t, J=6.2 Hz), 7.38 (2H, d, J=8.8 Hz), 8.16 (2H, d, J=8.8 Hz).

Reference Example 179

Imidazole (1.3 g) was dissolved in. THF (15.5 ml), potassium carbonate (5.3 g) was added to the mixture, and a solution of 1-(3-bromopropyl)-4-nitrobenzene (3.1 g) in THF (15.5 ml) was added dropwise to the mixture. The mixture was stirred for 60 hours at 50° C., and cooled to room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 1-[3-(4-nitrophenyl)propyl]imidazole (1.3 g).

$^1$H-NMR (200 MHz, CDCl$_3$) δ 2.10 to 2.23 (2H, m), 2.72 (2H, t, J=7.2 Hz), 4.00 (2H, t, J=6.6 Hz), 6.93 (1H, s), 7.09 (1H, s), 7.32 (2H, d, J=8.8 Hz), 7.48 (1H, s), 8.16 (2H, d, J=8.8 Hz).

Reference Example 180

1-[3-(4-nitrophenyl)propyl]imidazole (1.2 g) was dissolved in 85% ethanol solution (37 ml), calcium chloride (0.30 g) and reduced iron (1.5 g) were added to the mixture, and the mixture was heated to reflux for 4 hours. After cooling to room temperature, the mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 4-[3-(imidazol-1-yl)propyl]aniline (0.77 g).

$^1$H-NMR (200 MHz, CDCl$_3$) δ 1.98 to 2.13 (2H, m), 2.50 (2H, t, J=7.2 Hz), 3.50 (2H, br), 3.90 (2H, t, J=7.0 Hz), 6.64 (2H, d, J=8.6 Hz), 6.89 to 6.98 (3H, m), 7.06 to 7.08 (1H, m), 7.45 (1H, s).

Reference Example 181

1,2,4-triazole (0.68 g) was dissolved in THF (8.0 ml), potassium carbonate (2.7 g) was added to the mixture, a solution of 1-(3-bromopropyl)-4-nitrobenzene (1.6 g) in THF (8.0 ml) was added dropwise to the solution, and the mixture was stirred for 60 hours at 50° C. After cooling to room temperature, the reaction solution was added to water and extracted with ethyl acetate. The organic layer was washed with saturated brine, and dried over magnesium sulfate. The solvent was removed under reduced pressure, and the obtained residue was purified by silica gel column chromatography, to give 1-[3-(4-nitrophenyl)propyl]-1,2,4-triazole (0.69 g).

$^1$H-NMR (200 MHz, CDCl$_3$) δ 2.23 to 2.35 (2H, m), 2.76 (2H, t, J=7.4 Hz), 4.23 (2H, t, J=6.8 Hz), 7.35 (2H, d, J=8.4 Hz), 7.98 (1H, s), 8.08 (1H, s), 8.16 (2H, d, J=8.8 Hz).

Reference Example 182

1-[3-(4-nitrophenyl)propyl]-1,2,4-triazole (0.68 g) was dissolved in 85% ethanol solution (20.4 ml), calcium chloride (0.16 g) and reduced iron (0.82 g) were added to the mixture, and the mixture was heated to reflux for 4 hours. After allowing cooling to room temperature, the mixture was filtered with Celite, and washed with ethyl acetate. The solvent was removed under reduced pressure, and the obtained residue was added to water, and extracted with ethyl acetate. The organic layer was washed with saturated brine, and dried over magnesium sulfate. The solvent was removed under reduced pressure, and the obtained residue was purified by silica gel column chromatography, to give 4-[3-(1,2,4-triazol-1-yl)propyl]aniline (0.43 g).

$^1$H-NMR (200 MHz, CDCl$_3$) δ 2.12 to 2.21 (2H, m), 2.51 (2H, t, J=7.4 Hz), 3.63 (2H, br), 4.13 (2H, t, J=7.4 Hz), 6.63 (2H, d, J=8.4 Hz), 6.94 (2H, d, J=8.4 Hz), 7.95 (1H, s), 8.00 (1H, s).

Reference Example 183

Methyl N-methyl-N-(4-nitrobenzyl)-N-propylimidethiocarbamate (8.0 g) was dissolved in ethanol (80 ml), 2-aminoacetoaldehyde dimethyl acetal (13.2 ml) was added to the mixture, and the mixture was stirred for 16 hours at 60° C. After allowing the mixture to be cooled to room temperature, and the solvent was removed under reduced pressure, and the residue was azeotropically distilled with acetonitrile three times. Acetonitrile (80 ml) was added to the mixture, p-toluenesulfonic acid monohydrate (19.2 g) was added to the mixture, and the mixture was heated to reflux for 4 hours. After cooling to room temperature, the mixture was neutralized with an aqueous solution of saturated sodium bicarbonate, and extracted with ethyl acetate. The organic layer was washed with saturated brine, and dried over magnesium sulfate. The solvent was removed under reduced pressure, and the obtained residue was purified by silica gel column chromatography, to give N-methyl-N-(4-nitrobenzyl)-1-propylimidazole-2-amine (2.9 g).

$^1$H-NMR (200 MHz, CDCl$_3$) δ 0.91 (3H, t, J=7.2 Hz), 1.68 to 1.80 (2H, m), 2.70 (3H, s), 3.77 (2H, d, J=7.2 Hz), 4.28 (2H, s), 6.68 (1H, s), 6.82 (1H, s), 7.51 (2H, d, J=8.8 Hz), 8.17 (2H, d, J=8.4 Hz)

Reference Example 184

N-methyl-N-(4-nitrobenzyl)-1-propylimidazole-2-amine (2.9 g) was dissolved in 85% ethanol solution (87 ml), calcium chloride (0.59 g) and reduced iron (3.0 g) were added to the mixture, and the mixture was heated to reflux for 4 hours. After cooling to room temperature, the mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give. N-(4-aminobenzyl)-N-methyl-1-propylimidazole-2-amine (1.2 g).

$^1$H-NMR (200 MHz, CDCl$_3$) δ 0.90 (3H, t, J=7.2 Hz), 1.63 to 1.78 (2H, m), 2.64 (3H, s), 3.74 (2H, d, J=6.6 Hz), 3.98 (2H, s), 6.53 to 6.69 (1H, m), 6.84 (1H, d, J=2.0 Hz), 7.00 to 7.15 (2H, m).

Reference Example 185

2-mercapto-5-nitropyridine (3.2 g) was dissolved in DMF (64 ml), potassium carbonate (8.5 g) and 2-chloromethyl-1-propylimidazole hydrochloride (4.8 g) were added to the mixture, and the mixture was stirred for 1 hour at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 5-nitro-2-[[(1-propylimidazol-2-yl)methyl]sulfanyl]pyridine (4.8 g).

$^1$H-NMR (200 MHz, CDCl$_3$) δ 0.95 (3H, t, J=7.4 Hz), 1.75 to 1.89 (2H, m), 3.96 (2H, t, J=7.4 Hz), 4.66 (2H, s), 6.89 (1H, s), 6.99 (1H, s), 7.41 (1H, d, J=8.8 Hz), 8.23 to 8.30 (1H, m), 9.25 to 9.27 (1H, m).

Reference Example 186

5-nitro-2-[[(1-propylimidazol-2-yl)methyl]sulfanyl]pyridine (4.8 g) was dissolved in 85% ethanol solution (114 ml), calcium chloride (0.95 g) and reduced iron (4.8 g) were added to the mixture, and the mixture was heated to reflux for 4 hours. After cooling to room temperature, the mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 6-[[(1-propylimidazol-2-yl)methyl]sulfanyl]pyridine-3-amine (2.8 g).

$^1$H-NMR (200 MHz, CDCl$_3$) δ 0.91 (3H, t, J=7.2 Hz), 1.70 to 1.85 (2H, m), 3.84 to 3.94 (2H, m), 4.47 (2H, s), 6.82 to 7.11 (4H, m), 7.97 to 8.02 (1H, m).

Reference Example 187

2-mercapto-5-nitropyridine (2.3 g) was dissolved in DMF (47 ml), potassium carbonate (6.2 g) and 5-chloromethyl-1-propylimidazole hydrochloride (3.5 g) was added to the mixture, and the mixture was stirred for 40 hours at room temperature. The reaction solution was added to water, and extracted with ethyl acetate. The organic layer was washed with saturated brine, and dried over magnesium sulfate. The solvent was removed under reduced pressure, and the obtained residue was purified by silica gel column chromatography, to give 5-nitro-2-[[(1-propylimidazol-5-yl)methyl]sulfanyl]pyridine (2.9 g).

$^1$H-NMR (200 MHz, CDCl$_3$) δ 0.97 (3H, t, J=7.2 Hz), 1.78 to 1.91 (2H, m), 3.88 to 3.96 (2H, m), 4.57 (2H, s), 7.05 (1H, s), 7.32 (H, s), 8.23 to 8.30 (1H, s), 9.28 to 9.30 (1H, m).

Reference Example 188

5-nitro-2-[[(1-propylimidazol-5-yl)methyl]sulfanyl]pyridine (2.9 g) was dissolved in 85% ethanol solution (87 ml), calcium chloride (0.58 g) and reduced iron (2.9 g) were added to the mixture, and the mixture was heated to reflux for 4 hours. After cooling to room temperature, the mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 6-[[(1-propylimidazol-5-yl)methyl]sulfanyl]pyridine-3-amine (2.0 g).

$^1$H-NMR (200 MHz, CDCl$_3$) δ 0.93 (3H, t, J=7.2 Hz), 1.73 to 1.88 (2H, m), 3.86 to 3.95 (2H, m), 4.31 (2H, s), 6.83 to 7.00 (3H, s), 7.41 (1H, s), 8.00 to 8.02 (1H, m).

Reference Example 189

4-aminothiophenol (1.0 g) was dissolved in methanol (20 ml), 3N sodium hydroxide (8.0 ml) was added to the mixture, and 2-(2-propylimidazol-1-yl)ethyl 4-methylbenzene sulfonate (3.7 g) was added to the mixture. The mixture was stirred for 20 hours at room temperature, and the solvent was removed under reduced pressure. Water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography (ethyl acetate/ethanol=15/1→6/1), to give 4-[[2-(2-propylimidazol-1-yl)ethyl]sulfanyl]aniline (1.2 g).

$^1$H-NMR (200 MHz, CDCl$_3$) δ 0.93 (3H, t, J=7.4 Hz), 1.60 to 1.75 (2H, m), 2.47 (2H, t, J=7.6 Hz), 2.98 (2H, t, J=7.6 Hz), 3.87 (2H, br), 3.95 (2H, t, J=7.6 Hz), 6.64 (2H, d, J=8.4 Hz), 6.77 (1H, d, J=1.2 Hz), 6.88 to 6.94 (1H, m), 7.25 (2H, d, J=8.4 Hz).

Reference Example 190

1-methyl-3-nitro-1,2,4-triazol-5-thiol (0.66 g) was dissolved in. DMF (13.2 ml), potassium carbonate (1.7 g) and 5-chloromethyl-1-propylimidazole hydrochloride (1.1 g) were added to the mixture, and the mixture was stirred for 18 hours at room temperature. The reaction solution was added to water and extracted with ethyl acetate. The organic layer was washed with saturated brine, and dried over magnesium sulfate. The solvent was removed under reduced pressure, and the obtained residue was washed, to give 1-methyl-3-nitro-5-[[(1-propylimidazol-5-yl)methyl]thio]-1,2,4-triazole (0.55 g).

$^1$H-NMR (200 MHz, CDCl$_3$) δ 0.99 (3H, t, J=7.2 Hz), 1.78 to 1.92 (2H, m), 3.83 (3H, s), 3.86 (2H, t, J=7.2 Hz), 4.60 (2H, s), 7.05 (1H, s), 7.50 (1H, s).

Reference Example 191

To 1-methyl-3-nitro-5-[[(1-propylimidazol-5-yl)methyl]thio]-1,2,4-triazole (2.8 g) was added 85% ethanol solution (84 ml), calcium chloride (0.57 g) and reduced iron (2.9 g) were added to the mixture, and the mixture was heated to reflux for 3 hours. After cooling to room temperature, the mixture was filtered with Celite, and washed with ethyl acetate. The organic layer was washed with water and saturated brine, and dried over magnesium sulfate. The solvent was removed under reduced pressure, and the obtained residue was purified by silica gel column chromatography, to give 1-methyl-5-[[(1-propylimidazol-5-yl)methyl]thio]-1,2,4-triazole-3-amine (0.86 g).

$^1$H-NMR (200 MHz, CDCl$_3$) δ 0.96 (3H, t, J=7.2 Hz), 1.77 to 1.87 (2H, m), 3.52 (3H, s), 3.91 (2H, t, J=7.0 Hz), 4.20 (2H, br), 4.37 (2H, s), 6.95 (1H, s), 7.47 (1H, s).

Reference Example 192

2-methoxyethylamine hydrochloride (10 g) was dissolved in tert-butanol (80 ml)/acetic acid (10 ml), potassium thiocyanate (9.1 g) and dihydroxyacetone dimer (5.7 g) were added to the mixture, and the mixture was stirred for 48 hours at room temperature. To the reaction mixture, water (20 ml) was added to the mixture, and the mixture was concentrated to half under reduced pressure, and collected by filtration. The mixture was washed with water, added to 5.6N nitric acid to which sodium nitrite was added (0.20 g) under ice-cooling, and the mixture was stirred for 2 hours at room temperature. The reaction solution was neutralized with potassium carbonate, and the solvent was removed under reduced pressure. The residue was washed with ethanol, the solvent of the obtained solution was removed under reduced pressure and the residue was purified by silica gel column chromatography, to give 5-hydroxymethyl-1-(2-methoxyethyl)imidazole (2.9 g).

¹H-NMR (200 MHz, DMSO-d⁶) δ 3.28 (3H, s), 3.60 (2H, t, J=5.4 Hz), 4.13 (2H, t, J=5.4 Hz), 4.38 to 4.47 (2H, m), 5.09 (1H, br), 6.76 (1H, s), 7.53 (1H, s).

Reference Example 193

5-hydroxymethyl-1-(2-methoxyethyl)imidazole (2.8 g) was added to thionyl chloride (8.4 ml), and the mixture was stirred for 1 hour at 80° C. The solvent was removed under reduced pressure, and the obtained residue was washed with ethyl acetate, to give 5-chloromethyl-1-(2-methoxyethyl)imidazole hydrochloride (3.2 g).

¹H-NMR (200 MHz, DMSO-d⁶) δ 3.30 (3H, s), 3.76 (2H, t, J=5.0 Hz), 4.47 (2H, t, J=5.0 Hz), 5.07 (2H, s), 7.85 (1H, s), 9.23 (1H, s).

Reference Example 194

2-mercapto-1-methylimidazole (0.81 g) was dissolved in DMF (16.2 ml), potassium carbonate (1.37 g) was added to the mixture, 2-[(4-nitrophenyl)thio]ethyl 4-methylbenzene sulfonate (3.0 g) was added to the mixture, and the mixture was stirred for 12 hours at 60° C. The reaction solution was added to water, and extracted with ethyl acetate. The organic layer was washed with saturated brine, and dried over magnesium sulfate. The solvent was removed under reduced pressure and the obtained residue was washed with hexane/ethyl acetate, to give 1-methyl-2-[[2-[(4-nitrophenyl)thio]ethyl]thio]imidazole (1.3 g).

¹H-NMR (200 MHz, CDCl₃) δ 3.24 to 3.33 (2H, m), 3.30 to 3.44 (2H, m), 3.61 (3H, s), 6.98 (1H, d, J=1.6 Hz), 7.12 (1H, d, J=1.4 Hz), 7.43 (2H, d, J=8.8 Hz), 8.11 (2H, d, J=9.0 Hz).

Reference Example 195

1-methyl-2-[[2-[(4-nitrophenyl)thio]ethyl]thio]imidazole (1.3 g) was dissolved in 85% ethanol (39 ml), calcium chloride (0.24 g) and reduced iron (1.23 g) were added to the mixture, and the mixture was heated to reflux for 3 hours. After cooling to room temperature, the mixture was filtered with. Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 4-[[2-[(1-methylimidazol-2-yl)thio]ethyl]thio]aniline (0.68 g).

¹H-NMR (200 MHz, CDCl₃) δ 2.95 to 3.18 (4H, m), 3.60 (3H, s), 3.76 (2H, br), 6.60 (2H, d, J=8.8 Hz), 6.92 (1H, d, J=1.2 Hz), 7.05 (1H, d, J=1.4 Hz), 7.22 (2H, d, J=8.8 Hz).

Reference Example 196

3-mercapto-4-methyltriazole (0.81 g) was dissolved in DMF (16.2 ml), potassium carbonate (1.37 g) was added to the mixture, 2-[(4-nitrophenyl)thio]ethyl 4-methylbenzene sulfonate (3.0 g) was added to the mixture, and the mixture was stirred for 12 hours at 60° C. The reaction solution was added to water, and extracted with ethyl acetate. The organic layer was washed with saturated brine, and dried over magnesium sulfate. The solvent was removed under reduced pressure and the obtained residue was washed with hexane/ethyl acetate, to give 4-methyl-3-[[2-[(4-nitrophenyl)thio]ethyl]thio]-1,2,4-triazole (1.4 g).

¹H-NMR (200 MHz, CDCl₃) δ 3.44 to 3.60 (4H, m), 3.59 (3H, s), 7.49 to 7.55 (2H, m), 8.14 to 8.19 (3H, m).

Reference Example 197

4-methyl-3-[[2-[(4-nitrophenyl)thio]ethyl]thio]-1,2,4-triazole (1.4 g) was dissolved in 85% ethanol (42 ml), calcium chloride (0.26 g) and reduced iron (1.32 g) were added to the mixture, and the mixture was heated to reflux for 3 hours. After cooling to room temperature, the mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 4-[[2-[(4-methyl-1,2,4-triazol-3-yl)thio]ethyl]thio]aniline (0.38 g).

¹H-NMR (200 MHz, CDCl₃) δ 3.21 (2H, t, J=7.0 Hz), 3.55 (3H, s), 3.75 (2H, s), 6.63 (2H, d, J=8.8 Hz), 7.33 (2H, d, J=8.4 Hz), 7.71 (1H, s).

Reference Example 198

2-mercapto-5-nitrobenzimidazole (2.0 g) was dissolved in ethanol (20 ml), 3N sodium hydroxide (8.2 ml) was added to the mixture, 5-chloromethyl-1-propylimidazole hydrochloride (2.2 g) was added to the mixture, and the mixture was stirred at room temperature for 3 hours. The solvent was removed under reduced pressure, and to the obtained residue was added water, and the mixture was extracted with ethyl acetate. The organic layer was washed with saturated brine, and dried over magnesium sulfate. The solvent was removed under reduced pressure, and the obtained residue was purified by silica gel column chromatography, to give 5-nitro-2-[[(1-propylimidazol-5-yl)methyl]thio]benzimidazole (1.6 g).

¹H-NMR (200 MHz, CDCl₃) δ 0.95 (3H, t, J=7.2 Hz), 1.78 to 1.92 (2H, m), 3.99 (2H, t, J=7.2 Hz), 4.69 (2H, s), 7.10 (1H, s), 7.49 (1H, d, J=9.2 Hz), 7.58 (1H, s), 8.10 (1H, dd, J=8.8, 2.2 Hz), 8.38 (1H, d, J=2.2 Hz).

Reference Example 199

5-nitro-2-[[(1-propylimidazol-5-yl)methyl]thio]benzimidazole (1.6 g) was dissolved in 85% ethanol (48 ml), calcium chloride (0.28 g) and reduced iron (1.41 g) were added to the mixture, and the mixture was heated to reflux for 4 hours. After cooling to room temperature, the mixture was filtered with Celite, and washed with ethyl acetate. The solvent was removed under reduced pressure, and water was added to the obtained residue, and the mixture was extracted with ethyl acetate. The organic layer was washed with saturated brine, and dried over magnesium sulfate. The solvent was removed under reduced pressure, and the obtained residue was purified by silica gel column chromatography, to give 2-[[(1-propylimidazol-5-yl)methyl]thio]benzimidazole-5-amine (0.47 g).

¹H-NMR (200 MHz, CDCl₃) δ 0.86 (3H, t, J=7.4 Hz), 1.61 to 1.80 (2H, m), 3.82 (2H, t, J=7.2 Hz), 4.46 (2H, s), 6.57 to 6.63 (2H, m), 6.94 (1H,.), 7.42 (2H, s).

Reference Example 200

To a suspension of 3-hydroxy-4-nitrobenzaldehyde (7.0 g) and potassium carbonate (8.1 g) in DMF (100 ml), iodoethane (8.3 g) was added dropwise under nitrogen atmosphere. The mixture was stirred overnight, water was added to the mixture and the mixture was extracted with ethyl acetate. The organic layer was washed with water once and saturated brine once, and dried over magnesium sulfate. The solvent was distilled off under reduced pressure, and the obtained residue was purified by silica gel column chromatography (hexane:ethyl acetate=0.1:1), and recrystallized from hexane-ethyl acetate, to give 3-ethoxy-4-nitrobenzaldehyde (5.7 g) as yellow crystals.

$^1$H-NMR (200 MHz, CDCl$_3$) δ 1.50 (3H, t, J=7.0 Hz), 4.27 (2H, q, J=7.0 Hz), 7.53 (1H, dd, J=8.0, 1.6 Hz), 7.58 (1H, d, J=1.4 Hz), 7.90 (1H, d, J=8.0 Hz), 10.04 (1H, s).

Elemental Analysis C$_9$H$_9$NO$_4$. Calcd. C, 55.39; H, 4.65; N, 7.18. Found: C, 55.41; H, 4.43; N, 7.06.

Reference Example 201

To a solution of 2-bromopyridine (4.0 g) in dry ether (50 ml), n-butyl lithium (19.2 ml, 1.6M hexane solution) was added dropwise under argon atmosphere at −78° C. After finishing the dropping, the mixture was stirred for 1 hour, and a solution of 3-ethoxy-4-nitrobenzaldehyde (5.0 g) in dry ether (100 ml) and dry THF (50 ml) was added dropwise to the mixture. After finishing the dropping, and the mixture was allowed to be at room temperature and the mixture was stirred overnight. Water was added to the mixture, the mixture was neutralized with 1N hydrochloric acid and extracted with ethyl acetate. The organic layer was washed with saturated brine, and dried over magnesium sulfate. The solvent was distilled off under reduced pressure, and the residue was purified by silica gel column chromatography (ethyl acetate), to give (3-ethoxy-4-nitrophenyl)(2-pyridyl)methanol (3.4 g) as dark brown oil.

$^1$H-NMR (200 MHz, CDCl$_3$) δ 1.45 (3H, t, J=7.0 Hz), 4.10 to 4.30 (2H, m), 5.77 (1H, s), 7.02 (1H, dd, J=8.4, 1.4 Hz), 7.09 to 7.29 (3H, m), 7.68 (1H, td, J=8.2, 2.0 Hz), 7.80 (1H, d, J=8.4 Hz), 8.59 (1H, d, J=5.2 Hz).

Reference Example 202

To a solution of (3-ethoxy-4-nitrophenyl)(2-pyridyl)methanol (2.5 g) in acetic acid (50 ml), reduced iron (7.5 g) was added to the mixture and the mixture was stirred overnight. Ethyl acetate and ethanol were added to the mixture, and the unnecessary substances were filtered off. The filtrate was concentrated under reduced pressure, the residue was diluted with ethyl acetate and neutralized with an aqueous solution of saturated sodium bicarbonate. The organic layer was separated and washed with saturated brine, and dried over magnesium sulfate. The solvent was distilled off under reduced pressure and the obtained residue was purified by silica gel column chromatography (hexane:ethyl acetate=1:2) and recrystallized from hexane-ethyl acetate, to give (4-amino-3-ethoxyphenyl)(2-pyridyl)methanol (340 mg) as crystals.

$^1$H-NMR (200 MHz, CDCl$_3$) δ 1.39 (3H, t, J=7.0 Hz), 3.90 to 4.10 (2H, m), 5.65 (1H, s), 6.66 (1H, d, J=4.0 Hz), 6.74 to 6.82 (2H, m), 7.10 to 7.22 (2H, m), 7.61 (1H, td, J=8.0, 1.4 Hz), 8.55 (1H, d, J=4.8 Hz).

Reference Example 203

To a solution of 7-[4-(2-butoxyethoxy)phenyl]-1-(2,2,2-trifluoroacetyl)-2,3-dihydro-1-benzazepine-4-carboxylic acid (500 mg), (4-amino-3-ethoxyphenyl)(2-pyridyl)methanol (320 mg) and 1-hydroxybenzotriazole monohydrate (210 mg) in DMF (15 ml) was added catalytic amount of 4-(N,N-dimethylamino)pyridine, and 1-ethyl-3-(3-dimethylaminopropyl)carbodiimide hydrochloride (263 mg) was added to the mixture and the mixture was stirred overnight under nitrogen atmosphere. Water was added to the mixture and the mixture was extracted with ethyl acetate. The organic layer was washed with saturated brine and dried over magnesium sulfate. The solvent was distilled off under reduced pressure and the obtained residue was purified by silica gel column chromatography (hexane:ethyl acetate=1:3), and was recrystallized from diisopropyl ether-ethyl acetate, to give 7-[4-(2-butoxyethoxy)phenyl]-N-[2-ethoxy-4-[hydroxy(2-pyridyl)methyl]phenyl]-1-(2,2,2-trifluoroacetyl)-2,3-dihydro-1-benzazepine-4-carboxamide (504 mg) as yellow crystals.

$^1$H-NMR (200 MHz, CDCl$_3$) δ 0.94 (3H, t, J=7.4 Hz), 1.31 to 1.47 (5H, m), 1.50 to 1.65 (2H, m), 2.80 to 3.30 (3H, m), 3.56 (2H, t, J=7.0 Hz), 3.82 (2H, t, J=4.4 Hz), 4.00 to 4.20 (4H, m), 4.80 to 4.90 (1H, m), 5.34 (1H, d, J=3.6 Hz), 5.72 (1H, d, J=3.4 Hz), 6.94 to 7.05 (4H, m), 7.14 to 7.35 (3H, m), 7.51 to 7.67 (6H, m), 8.31 (1H, s), 8.40 (1H, d, J=8.4 Hz), 8.58 (1H, d, J=4.8 Hz).

Elemental Analysis C$_{39}$H$_{40}$N$_3$O$_6$F$_3$·0.1H$_2$O Calcd. C, 66.39; H, 5.74; N, 5.96. Found: C, 66.15; H, 5.88; N, 5.73.

Reference Example 204

To a solution of 7-[4-(2-butoxyethoxy)phenyl]-N-[2-ethoxy-4-[hydroxy(2-pyridyl)methyl]phenyl]-1-(2,2,2-trifluoroacetyl)-2,3-dihydro-1-benzazepine-4-carboxamide (450 mg) in dichloromethane (10 ml) was added 3-chloroperbenzoic acid (189 mg), and the mixture was stirred overnight under nitrogen atmosphere. To the mixture was added water and the mixture was extracted with ethyl acetate, washed with an aqueous solution of saturated sodium bicarbonate and saturated brine, and dried over magnesium sulfate. The solvent was distilled off under reduced pressure and the obtained residue was purified by silica gel column chromatography (methanol:ethyl acetate=1:8), and was recrystallized from diisopropyl ether-ethyl acetate, to give 7-[4-(2-butoxyethoxy)phenyl]-N-[2-ethoxy-4-[hydroxy(1-oxidepyridin-2-yl)methyl]phenyl]-1-(2,2,2-trifluoroacetyl)-2,3-dihydro-1-benzazepine-4-carboxamide (249 mg) as colorless crystals.

$^1$H-NMR (200 MHz, CDCl$_3$) δ 0.94 (3H, t, J=7.4 Hz), 1.34 to 1.68 (7H, m), 2.90 to 3.30 (3H, m), 3.56 (2H, t, J=6.6 Hz), 3.82 (2H, t, J=4.4 Hz), 4.14 to 4.25 (4H, m), 4.80 to 4.95 (1H, m), 6.06 (1H, d, J=3.6 Hz), 6.51 (1H, br), 6.90 to 7.05 (4H, m), 7.20 to 7.36 (4H, m), 7.52 to 7.67 (5H, m), 8.25 to 8.29 (1H, m), 8.37 to 8.47 (2H, m).

Elemental Analysis C$_{39}$H$_{40}$N$_3$O$_7$F$_3$ Calcd. C, 65.08; H, 5.60; N, 5.84. Found: C, 64.83; H, 5.42; N, 5.80.

Reference Example 205

To a solution of 7-[4-(2-butoxyethoxy)phenyl]-N-[2-ethoxy-4-[hydroxy(1-oxidepyridin-2-yl)methyl]phenyl]-1-(2,2,2-trifluoroacetyl)-2,3-dihydro-1-benzazepine-4-carboxamide (210 mg) in ethanol (10 ml) was added sodium borohydride (111 mg) and the mixture was stirred for 8 hours. To the mixture was added water and the mixture was extracted with ethyl acetate, washed with saturated brine and dried over magnesium sulfate. The solvent was distilled off under reduced pressure, and the residue was recrystallized from hexane-ethyl acetate, to give 7-[4-(2-butoxyethoxy)phenyl]-N-[2-ethoxy-4-[hydroxy(1-oxidopyridin-2-yl)methyl]phenyl]-2,3-dihydro-1-benzazepine-4-carboxamide (167 mg) as yellow crystals.

¹H-NMR (200 MHz, CDCl₃) δ 0.93 (3H, t, J=7.4 Hz), 1.34 to 1.65 (7H, m), 2.98 (2H, br), 3.40 to 3.60 (4H, m), 3.80 (2H, t, J=4.4 Hz), 4.14 to 4.23 (4H, m), 4.61 (1H, br), 6.06 (1H, br), 6.51 (1H, br), 6.71 (1H, d, J=8.0 Hz), 6.89 to 7.01 (4H, m), 7.18 to 7.30 (4H, m), 7.44 to 7.48 (4H, m), 8.25 to 8.29 (1H, m), 8.35 (1H, s), 8.46 (1H, d, J=8.0 Hz).

Elemental Analysis $C_{37}H_{41}N_3O_6 \cdot 0.2H_2O$. Calcd. C, 70.84; H, 6.65; N, 6.70. Found: C, 70.55; H, 6.71; N, 6.53.

Reference Example 206

To a solution of 4-fluoro-2-trifluoromethylbenzoic acid (7.00 g), N,O-dimethylhydroxylamine hydrochloride (4.26 g) and 1-hydroxybenzotriazole monohydrate (6.69 g) in DMF (100 ml) was added triethylamine (4.42 g). Then, catalytic amount of 4-(N,N-dimethylamino)pyridine was added to the mixture, 1-ethyl-3-(3-dimethylaminopropyl)-carbodiimide hydrochloride (8.38 g) was added to the mixture and the mixture was stirred for 1 day under nitrogen atmosphere. Water was added to the mixture and the mixture was extracted with ethyl acetate. The organic layer was washed with water and saturated brine, and dried over magnesium sulfate. The solvent was distilled off under reduced pressure, and the obtained residue was purified by silica gel column chromatography (hexane:ethyl acetate=1:1), to give 1-[[[methoxy(methyl)amino]oxy]carbonyl]-4-methyl-2-(trifluoromethyl)benzene (8.07 g) as colorless oil.

¹H-NMR (200 MHz, CDCl₃) δ 3.36 (3H, s), 3.42 (3H, s), 7.26 to 7.47 (3H, m).

Reference Example 207

To a solution of 2-bromopyridine (4.1 g) in dry ether (50 ml) was added dropwise n-butyl lithium (19.4 ml, 1.6M hexane solution) under argon atmosphere at −78° C. After finishing the dropping, the mixture was stirred for 1 hour and a solution of 1-[[[methoxy(methyl)amino]oxy]carbonyl]-4-methyl-2-(trifluoromethyl)benzene (5.0 g) in dry ether (50 ml) was added dropwise to the mixture. After finishing the dropping, the mixture was allowed to be at room temperature and the mixture was stirred for 1.5 hours. Water was added to the mixture, the mixture was neutralized with 1N hydrochloric acid at 0° C., and extracted with ethyl acetate. The organic layer was washed with saturated brine, and dried over magnesium sulfate. The solvent was distilled off under reduced pressure, and the residue was purified by silica gel column chromatography (hexane:ethyl acetate=1:1) and recrystallized from hexane, to give [4-fluoro-2-(trifluoromethyl)phenyl](2-pyridyl)methanone (3.4 g) as brown crystals.

¹H-NMR (200 MHz, CDCl₃) δ 7.33 (1H, td, J=8.2, 2.2 Hz), 7.45 to 7.54 (3H, m), 7.93 (1H, td, J=8.0, 1.8 Hz), 8.23 (1H, dd, J=8.0, 1.0 Hz), 8.65 (1H, d, J=4.0 Hz).

Elemental Analysis $C_{13}H_7NOF_4$. Calcd. C, 58.00; H, 2.62; N, 5.20. Found: C, 58.02; H, 2.87; N, 5.03.

Reference Example 208

To a solution of [4-fluoro-2-(trifluoromethyl)phenyl](2-pyridyl)methanone (2.5 g) in DMSO (30 ml) was added sodium azide (0.73 g) and the mixture was heated overnight under nitrogen atmosphere at 90° C. After allowing the mixture to be cooled, water was added to the mixture, and the mixture was extracted with ethyl acetate. The organic layer was washed with water three times, and saturated brine once, and dried over magnesium sulfate. The solvent was distilled off under reduced pressure, to give. [4-azido-2-(trifluoromethyl)phenyl](2-pyridyl)methanone (2.89 g) as dark brown oil.

¹H-NMR (200 MHz, CDCl₃) δ 7.27 (1H, dd, J=8.4, 2.2 Hz), 7.38 (1H, d, J=2.2 Hz), 7.47 to 7.53 (2H, m), 7.93 (1H, td, J=7.8, 1.8 Hz), 8.23 (1H, d, J=7.0 Hz), 8.64 (1H, d, J=6.6 Hz).

Reference Example 209

To a suspension of [4-azido-2-(trifluoromethyl)phenyl](2-pyridyl)methanone (2.0 g) in THF (20 ml) was added dropwise a solution of aluminum lithium hydride (520 mg) in. THF (20 ml) at 0° C. under nitrogen atmosphere. After finishing the dropping, the mixture was allowed to be at room temperature, and the mixture was stirred for 1 hour. Water (0.52 ml), 15% aqueous solution of sodium hydroxide (0.52 ml) and water (1.6 ml) were sequentially added to the mixture at 0° C., and the mixture was allowed to be at room temperature and the mixture was stirred overnight. Magnesium sulfate was added to the mixture, and the unnecessary substances were filtered off. The solvent was distilled off under reduced pressure and the obtained residue was recrystallized from hexane-ethyl acetate, to give [4-amino-2-(trifluoromethyl)phenyl](2-pyridyl)methanol (1.51 g) as colorless crystals.

¹H-NMR (200 MHz, CDCl₃) δ 3.84 (2H, br), 5.57 (1H, d, J=4.0 Hz), 6.05 (1H, d, J=4.0 Hz), 6.74 (1H, dd, J=8.4, 2.6 Hz), 6.94 (1H, d, J=2.4 Hz), 7.01 to 7.10 (2H, m), 7.18 to 7.24 (1H, m), 7.61 (1H, td, J=7.6, 1.8 Hz), 7.58 (1H, d, J=5.2 Hz).

Elemental Analysis $C_{13}H_{11}N_2OF_3$ Calcd. C, 58.21; H, 4.13; N, 10.44. Found: C, 58.17; H, 4.12; N, 10.33.

Reference Example 210

To a solution of 7-[4-(2-butoxyethoxy)phenyl]-1-(2,2,2-trifluoroacetyl)-2,3-dihydro-1-benzazepine-4-carboxylic acid (500 mg) was added a solution of [4-amino-2-(trifluoromethyl)phenyl](2-pyridyl)methanol (366 mg) and 1-hydroxybenzotriazole monohydrate (210 mg) in. DMF (15 ml), and catalytic amount of 4-(N,N-dimethylamino)pyridine and then, 1-ethyl-3-(3-dimethylaminopropyl)-carbodiimide hydrochloride (263 mg) was added to the mixture, and the mixture was stirred overnight under nitrogen atmosphere. Water was added to the mixture and the mixture was extracted with ethyl acetate. The organic layer was washed with saturated brine and dried over magnesium sulfate. The solvent was distilled off under reduced pressure, and the obtained residue was purified by silica gel column chromatography (hexane:ethyl acetate=1:1), to give 7-[4-(2-butoxyethoxy)phenyl]-N-[4-[hydroxy(2-pyridyl)methyl]-3-trifluoromethylphenyl]-1-(2,2,2-trifluoroacetyl)-2,3-dihydro-1-benzazepine-4-carboxamide (400 mg) as colorless amorphous.

¹H-NMR (200 MHz, CDCl₃) δ 0.93 (3H, t, J=7.4 Hz), 1.30 to 1.50 (2H, m), 1.55 to 1.70 (2H, m), 2.90 to 3.30 (3H, m), 3.56 (2H, t, J=6.6 Hz), 3.82 (2H, t, J=4.8 Hz), 4.17 (2H, t, J=4.8 Hz), 4.75 to 4.90 (1H, m), 5.75 (1H, br), 6.14 (1H,: s), 7.00 to 7.04 (3H, m), 7.21 to 7.80 (11H, m), 7.94 (1H, d, J=5.0 Hz), 8.60 (1H, d, J=3.6 Hz).

Elemental Analysis $C_{38}H_{35}N_3O_5F_6$ Calcd. C, 62.72; H, 4.85; N, 5.77. Found: C, 62.44; H, 4.87; N, 5.85.

Reference Example 211

To a solution of 7-[4-(2-butoxyethoxy)phenyl]-N-[4-[hydroxy(2-pyridyl)methyl]-3-trifluoromethylphenyl]-1-(2,2,2-trifluoroacetyl)-2,3-dihydro-1-benzazepine-4-carboxamide (355 mg) in dichloromethane (10 ml) was added 3-chloroperbenzoic acid (205 mg), and the mixture was stirred overnight under nitrogen atmosphere. To the mixture was added water, and the mixture was extracted with ethyl acetate, washed with an aqueous solution of saturated sodium bicarbonate and saturated brine, and dried over magnesium sulfate. The solvent was distilled off under reduced pressure and the obtained residue was purified by silica gel column chromatography (ethyl acetate), to give 7-[4-(2-butoxyethoxy)phenyl]-N-[4-[hydroxy(1-oxidopyridin-2-yl)methyl]-3-trifluoromethylphenyl]-1-(2,2,2-trifluoroacetyl)-2,3-dihydro-1-benzazepine-4-carboxamide (176 mg) as colorless amorphous.

$^1$H-NMR (200 MHz, CDCl$_3$) δ 0.94 (3H, t, J=7.0 Hz), 1.30 to 1.65 (4H, m), 2.80 to 3.35 (3H, m), 3.56 (2H, t, J=6.6 Hz), 3.82 (2H, t, J=4.8 Hz), 4.18 (2H, t, J=5.6 Hz), 4.80 to 4.95 (1H, m), 6.48 to 6.64 (2H, m), 6.71 (1H, d, J=3.0 Hz), 7.03 (2H, d, J=8.8 Hz), 7.22 to 7.37 (3H, m), 7.49 to 7.67 (5H, m), 7.79 (1H, s), 7.90-8.05 (3H, m), 8.29 to 8.32 (1H, m).

Elemental Analysis C$_{38}$H$_{35}$N$_3$O$_6$F$_6$·0.4H$_2$O Calcd. C, 60.78; H, 4.81; N, 5.60. Found: C, 60.61; H, 4.69; N, 5.52.

Reference Example 212

To a solution of 7-[4-(2-butoxyethoxy)phenyl]-N-[4-[hydroxy(1-oxidopyridin-2-yl)methyl]-3-trifluoromethylphenyl]1-(2,2,2-trifluoroacetyl)-2,3-dihydro-1-benzazepine-4-carboxamide (155 mg) in ethanol (10 ml) was added sodium borohydride (79 mg) and the mixture was stirred for 7 hours. To the mixture was added water and the mixture was extracted with ethyl acetate. The organic layer was washed with saturated brine and dried over magnesium sulfate. The solvent was distilled off under reduced pressure, and recrystallized from diisopropyl ether-ethyl acetate, to give 7-[4-(2-butoxyethoxy)phenyl]-N-[4-[hydroxy(1-oxidopyridin-2-yl)methyl]-3-trifluoromethylphenyl]-2,3-dihydro-1-benzazepine-4-carboxamide (110 mg) as yellow crystals.

$^1$H-NMR (200 MHz, CDCl$_3$) δ 0.93 (3H, t, J=7.2 Hz), 1.33 to 1.45 (2H, m), 1.54 to 1.64 (2H, m), 2.97 (2H, t, J=4.8 Hz), 3.48 (2H, t, J=4.8 Hz), 3.55 (2H, t, J=6.6 Hz), 3.80 (2H, t, J=4.8 Hz), 4.15 (2H, t, J=4.8 Hz), 6.47 (1H, s), 6.61 (1H, dd, J=7.8, 2.2 Hz), 6.71 (1H, d, J=8.4 Hz), 6.97 (2H, d, J=8.8 Hz), 7.18 to 7.37 (4H, m), 7.43 to 7.47 (4H, m), 7.85 to 7.91 (3H, m), 8.03 (1H, s), 8.28 to 8.32 (1H, m).

Elemental Analysis C$_{36}$H$_{36}$N$_3$O$_5$F$_3$·0.8H$_2$O. Calcd. C, 65.31; H, 5.72; N, 6.35. Found: C, 65.14; H, 5.84; N, 6.10.

Reference Example 213

To a suspension of aluminum lithium hydride (671 mg) in THF (20 ml), a solution of 2-thiazolecarboxyaldehyde (2.0 g) in THF (20 ml) was added dropwise at 0° C. under nitrogen atmosphere. After finishing the dropping, water (0.7 ml), 15% aqueous solution of sodium hydroxide (0.7 ml), and water (2.1 ml) were sequentially added to the mixture at 0° C., and the mixture was stirred for 2.5 hours at room temperature. The mixture was dried over magnesium sulfate, and the insolubles were filtered off. The solvent was distilled off under reduced pressure, to give 2-hydroxymethylthiazole (1.0 g) as brown oil.

$^1$H-NMR (200 MHz, CDCl$_3$) δ 4.98 (2H, s), 7.33 (1H, d, J=3.4 Hz), 7.75 (1H, d, J=3.0 Hz).

Reference Example 214

To a solution of 2-hydroxymethylthiazole (660 mg) in chloroform (20 ml) was added one droplet of DMF, and thionyl chloride (0.55 ml) was added to the mixture at 0° C. The mixture was allowed to be at room temperature and the mixture was stirred for 2 hours. The solvent was distilled off under reduced pressure and the obtained residue was dissolved in methanol (10 ml). This solution was added to a mixed solution of 4-aminothiophenol (600 mg) and sodium hydroxide (460 mg) in methanol (10 ml) and water (6 ml) at 0° C. The mixture was allowed to be at room temperature, and stirred for 30 minutes and water was added to the mixture, and the mixture was extracted with ethyl acetate. The organic layer was washed with saturated brine, and dried over magnesium sulfate. The solvent was distilled off under reduced pressure and the obtained residue was purified by basic silica gel column chromatography (hexane: ethyl acetate=1:1), to give 4-[(thiazol-2-ylmethyl)sulfanyl]aniline (269 mg).

$^1$H-NMR (200 MHz, CDCl$_3$) δ 3.72 (2H, br), 4.28 (2H, s), 6.58 (2H, d, J=8.6 Hz), 7.18 to 7.25 (3H, m), 7.65 (1H, d, J=3.2 Hz) as colorless oil

Reference Example 215

To a suspension of aluminum lithium hydride (421 mg) in THF (10 ml), a solution of 3-methylthiazole-5-carboxyaldehyde (1.06 g) in THF (10 ml) was added dropwise at 0° C. under nitrogen atmosphere. After finishing the dropping, water (0.45 ml), 15% aqueous solution of sodium hydroxide (0.45 ml) and water (1.35 ml) were sequentially added to the mixture at 0° C., and the mixture was stirred overnight at room temperature. The mixture was dried over magnesium sulfate, and the insolubles were filtered off. The solvent was distilled off under reduced pressure, and the obtained residue was separated and purified by silica gel column chromatography (ethyl acetate), to give 5-hydroxymethyl-3-methyl isothiazole (427 mg) as dark brown oil.

$^1$H-NMR (200 MHz, CDCl$_3$) δ 2.48 (3H, s),: 4.96 (2H, s), 6.91 (1H, s).

Reference Example 216

To a solution of 5-hydroxymethyl-3-methyl isothiazole (421 mg) in dichloromethane (10 ml) was added one droplet of. DMF, and thionyl chloride (0.31 ml) was added to the mixture at 0° C. The mixture was allowed to be at room temperature and the mixture was stirred for 40 hours. The solvent was distilled off under reduced pressure and the obtained residue was dissolved in methanol (10 ml). This solution was added to a mixed solution of 4-aminothiophenol (340 mg) and sodium hydroxide (260 mg) in methanol (10 ml) and water (6 ml) at 0° C. The mixture was allowed to be at room temperature and stirred for 30 minutes, and water was added to the mixture, and the mixture was extracted with ethyl acetate. The organic layer was washed with saturated brine, and dried over magnesium sulfate. The solvent was distilled off under reduced pressure and the obtained residue was separated and purified by silica gel column chromatography (hexane:ethyl acetate=1:1), to give 4-[[(3-methyl isothiazol-5-yl)methyl]sulfanyl]aniline (270 mg) as brown oil.

¹H-NMR (200 MHz, CDCl₃) δ 2.41 (3H, s), 4.12 (2H, s), 6.60 (2H, d, J=8.4 Hz), 6.72 (1H, s), 7.21 (2H, d, J=8.8 Hz).

Reference Example 217

To a suspension of aluminum lithium hydride (691 mg) in THF (10 ml), a solution of 1-methylpyrazole-5-carboxyaldehyde (2.0 g) in THF (20 ml) was added dropwise at 0° C. under nitrogen atmosphere. After finishing the dropping, water (0.7 ml), 15% aqueous solution of sodium hydroxide (0.7 ml) and water (2.1 ml) were sequentially added to the mixture at 0° C., and the mixture was stirred for 2 hours at room temperature. The mixture was dried over magnesium sulfate, and the insolubles were filtered off. The solvent was distilled off under reduced pressure, to give 5-hydroxymethyl-1-methylpyrazole (2.04 g) as colorless oil.

¹H-NMR (200 MHz, CDCl₃) δ 3.90 (3H, s), 4.68 (2H, s), 6.19 (1H, d, J=2.0 Hz), 6.39 (1H, d, J=1.8 Hz).

Reference Example 218

To a solution of 5-hydroxymethyl-1-methylpyrazole (645 mg) in chloroform (10 ml) was added one droplet of. DMF, and thionyl chloride (0.55 ml) was added to the mixture at 0° C. The mixture was allowed to be at room temperature under nitrogen atmosphere, and the mixture was stirred for 40 hours. The solvent was distilled off under reduced pressure and the obtained residue was dissolved in methanol (10 ml). This solution was added to a mixed solution of 4-aminothiophenol (600 mg) and sodium hydroxide (460 mg) in methanol (10 ml) and water (6 ml) at 0° C. The mixture was allowed to be at room temperature and stirred for 30 minutes, and water was added to the mixture, and the mixture was extracted with ethyl acetate. The organic layer was washed with saturated brine, and dried over magnesium sulfate. The solvent was distilled off under reduced pressure and the obtained residue was recrystallized from hexane-ethyl acetate, to give 4-[[(1-methylpyrazol-5-yl)methyl]sulfanyl]aniline (972 mg) as brown crystals.

¹H-NMR (200 MHz, CDCl₃) δ 3.75 (3H, s), 3.89 (2H, s), 5.92 (1H, d, J=1.8 Hz), 6.57 (2H, d, J=8.8 Hz), 7.10 (2H, d, J=8.8 Hz), 7.31 (1H, d, J=1.8 Hz).

Elemental Analysis C₁₁H₁₃N₃S Calcd. C, 60.24; H, 5.97; N, 19.16. Found: C, 60.09; H, 6.08; N, 19.11.

Reference Example 219

To a suspension of aluminum lithium hydride (758 mg) in THF (10 ml), a solution of 1-methylimidazole-2-carboxyaldehyde (2.00 g) in THF (20 ml) was added dropwise at 0° C. under nitrogen atmosphere. After finishing the dropping, water (0.8 ml), 15% aqueous solution of sodium hydroxide (0.8 ml) and water (2.4 ml) were sequentially added to the mixture at 0° C., and the mixture was stirred for 2.5 hours at room temperature. The mixture was dried over magnesium sulfate, and the insolubles were filtered off. The solvent was distilled off under reduced pressure, and the residue was recrystallized from hexane-ethyl acetate, to give 2-hydroxymethyl-1-methylimidazole (1.82 g) as colorless crystals.

¹H-NMR (200 MHz, CDCl₃) δ 3.73 (3H, s), 4.63 (2H, s), 6.81 (1H, d, J=1.2 Hz), 6.86 (1H, d, J=1.2 Hz).

Elemental Analysis C₅H₈N₂O 0.05H₂O Calcd. C, 53.13; H, 7.22; N, 24.78. Found: C, 53.42; H, 7.45; N, 24.57.

Reference Example 220

To a solution of 2-hydroxymethyl-1-methylimidazole (645 mg) in chloroform (10 ml) was added one droplet of DMF, and thionyl chloride (0.55 ml) was added to the mixture at 0° C. The mixture was allowed to be at room temperature under nitrogen atmosphere, and the mixture was stirred for 40 hours. The solvent was distilled off under reduced pressure and the obtained residue was dissolved in methanol (10 ml). This solution was added to a mixed solution of 4-aminothiophenol (600 mg) and sodium hydroxide (460 mg) in methanol (10 ml) and water (6 ml) at 0° C. The mixture was allowed to be at room temperature and stirred for 30 minutes, water was added to the mixture, and the mixture was extracted with ethyl acetate three times. The organic layer was washed with saturated brine, and dried over magnesium sulfate. The solvent was distilled off under reduced pressure, to give 4-[[(1-methylimidazol-2-yl)methyl]sulfanyl]aniline (1.05 g) as colorless oil.

¹H-NMR (200 MHz, CDCl₃) δ 3.53 (3H, s), 4.03 (2H, s), 6.57 (2H, d, J=8.4 Hz), 6.78 (1H, d, J=1.4 Hz), 6.90 (1H, d, J=1.0 Hz), 7.14 (2H, d, J=8.8 Hz).

Reference Example 221

To a solution of 5-methyl isoxazole (5.0 g) in ethyl acetate (100 ml), N-bromo succinate imide (23.6 g) and 2,2'-azobisisobutyronitrile (200 mg) were added to the mixture, and the mixture was refluxed overnight under nitrogen atmosphere. After cooling to 0° C., the insolubles were filtered off, the filtrate was washed with an aqueous solution of sodium thiosulfate and saturated brine, and dried over magnesium sulfate. The solvent was distilled off under reduced pressure and the residue was separated and purified by silica gel column chromatography (hexane:ethyl acetate=10:1), to give 5-bromomethyl isoxazole (1.0 g) as oil.

¹H-NMR (200 MHz, CDCl₃) δ 4.50 (2H, s), 6.34 (1H, d, J=1.8 Hz), 8.23 (1H, d, J=1.8 Hz).

Reference Example 222

To a mixed solution of 4-aminothiophenol (600 mg) and sodium hydroxide (276 mg) in methanol (10 ml) and water (6 ml), a solution of 5-bromomethyl isoxazole (932 mg) in methanol (5 ml) was added at 0° C. Water was added to the mixture and the mixture was extracted with ethyl acetate. The organic layer was washed with saturated brine, and dried over magnesium sulfate. The solvent was distilled off under reduced pressure, to give 4-[(isoxazol-5-ylmethyl)sulfanyl]aniline (988 mg) as oil.

¹H-NMR (200 MHz, CDCl₃) δ 4.00 (2H, s), 8.95 (1H, d, J=0.8 Hz), 6.59 (2H, d, J=8.8 Hz), 7.19 (2H, d, J=8.8 Hz), 8.11 (1H, d, J=1.4 Hz).

Reference Example 223

To a solution of pyrazole (5.00 g) in ethanol (40 ml) was added formalin (10 ml, 37%), and the mixture was refluxed for 1.5 hours. The mixture was allowed to be at room temperature, and the solvent was distilled off under reduced pressure and the obtained residue was washed with hexane, to give 1-hydroxymethylpyrazole (4.47 g) as crystals.

¹H-NMR (200 MHz, CDCl₃) δ 5.54 (2H, d, J=5.4 Hz), 6.31 (1H, t, J=2.2 Hz), 6.62 (1H, br), 7.58 to 7.61 (2H, m).

Elemental Analysis C₄H₆N₂O Calcd. C, 48.97; H, 6.16; N, 28.56. Found: C, 49.05; H, 6.36; N, 28.50.

Reference Example 224

To a solution of 1-hydroxymethylpyrazole (472 mg) in dichloromethane (10 ml) was added one droplet of DMF, and thionyl chloride (0.55 ml) was added to the mixture at 0° C. The mixture was allowed to be at room temperature under nitrogen atmosphere, and the mixture was stirred for 2 hours. The solvent was distilled off under reduced pressure and the obtained residue was dissolved in methanol (10 ml). This solution was added to a mixed solution of 4-aminothiophenol (600 mg) and sodium hydroxide (460 mg) in methanol (10 ml) and water (6 ml) at 0° C. The mixture was allowed to be at room temperature and stirred for 30 minutes, and water was added to the mixture, and the mixture was extracted with ethyl acetate. The organic layer was washed with saturated brine, and dried over magnesium sulfate. The solvent was distilled off under reduced pressure, to give 4-[(pyrazol-1-ylmethyl)sulfanyl]aniline (0.93 g) as brown oil.

$^1$H-NMR (200 MHz, CDCl$_3$) δ 3.78 (2H, br), 5.27 (2H, s), 6.18-6.20 (1H, m), 6.57 (2H, d, J=8.8 Hz), 7.08 (2H, d, J=8.8 Hz), 7.21 (1H, d, J=2.2 Hz), 7.52 (1H, d, J=1.8 Hz).

Reference Example 225

To a suspension of imidazole-2-carboxyaldehyde (2.50 g) and potassium carbonate (4.31 g) in DMF (25 ml) was added iodoethane (4.87 g) and the mixture was heated for 5 hours under nitrogen atmosphere at 50° C. The mixture was allowed to be at room temperature, the insolubles were filtered off and the solvent was distilled off under reduced pressure. Water was added to the mixture and the mixture was extracted with ethyl acetate. The organic layer was dried over magnesium sulfate, and the solvent was distilled off under reduced pressure, to give 1-ethylimidazole-2-carboxyaldehyde (2.90 g) as brown oil.

$^1$H-NMR (200 MHz, CDCl$_3$) δ 1.44 (3H, t, J=7.2 Hz), 4.45 (2H, q, J=7.2 Hz), 7.17 to 7.19 (1H, m), 7.28 to 7.29 (1H, m), 9.82 (1H, s).

Reference Example 226

To a suspension of aluminum lithium hydride (1.22 g) in THF (10 ml), a solution of 1-ethylimidazole-2-carboxyaldehyde (2.00 g) in THF (10 ml) was added dropwise at 0° C. under nitrogen atmosphere. After finishing the dropping, water (1.2 ml), 15% aqueous solution of sodium hydroxide (1.2 ml) and water (3.6 ml) were sequentially added to the mixture at 0° C., and the mixture was stirred for 2 hours at room temperature. The mixture was dried over magnesium sulfate, and the insolubles were filtered off. The solvent was distilled off under reduced pressure, and the residue was recrystallized from hexane-ethyl acetate, to give 2-hydroxymethyl-1-ethylimidazole (1.47 g) as colorless crystals.

$^1$H-NMR (200 MHz, CDCl$_3$) δ 1.44 (3H, t, J=7.4 Hz), 4.06 (2H, q, J=7.4 Hz), 4.65 (2H, s), 6.87 to 6.89 (2H, m).

Elemental Analysis C$_6$H$_{10}$N$_2$O Calcd. C, 57.12; H, 7.99; N, 22.21. Found: C, 57.06; H, 7.98; N, 22.20.

Reference Example 227

To a solution of 1-ethyl-2-hydroxymethylimidazole (1.00 g) in chloroform (15 ml) was added one droplet of DMF, and thionyl chloride (0.75 ml) was added to the mixture at 0° C. The mixture was allowed to be at room temperature, and stirred for 30 minutes under nitrogen atmosphere, and the solvent was distilled off under reduced pressure and the obtained residue was dissolved in methanol (10 ml). This solution was added to a mixed solution of 4-aminothiophenol (900 mg) and sodium hydroxide (630 mg) in methanol (10 ml) and water (6 ml) at 0° C. The mixture was allowed to be at room temperature and stirred for 30 minutes, and water was added to the mixture, and the mixture was extracted with ethyl acetate. The organic layer was washed with saturated brine, and dried over magnesium sulfate. The solvent was distilled off under reduced pressure, to give 4-[[(1-ethylimidazol-2-yl)methyl]sulfanyl]aniline (1.68 g) as oil.

$^1$H-NMR (200 MHz, CDCl$_3$) δ 1.40 (3H, t, J=7.2 Hz), 3.91 (2H, q, J=7.2 Hz), 4.04 (2H, s), 6.58 (2H, d, J=8.8 Hz), 6.85 (1H, d, J=1.0 Hz), 6.92 (1H, d, J=1.0 Hz), 7.15 (2H, d, J=8.8 Hz).

Reference Example 228

To a suspension of imidazole-2-carboxyaldehyde (2.50 g) and potassium carbonate (4.31 g) in DMF (25 ml) was added 1-iodopropane (5.31 g) and the mixture was heated for 5 hours under nitrogen atmosphere at 50° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was dried over magnesium sulfate, and the solvent was distilled off under reduced pressure, to give 1-propylimidazole-2-carboxyaldehyde (3.58 g) as brown oil.

$^1$H-NMR (200 MHz, CDCl$_3$) δ 0.93 (3H, t, J=7.4 Hz), 1.73 to 1.91 (2H, m), 4.37 (2H, t, J=7.4 Hz), 7.16 (1H, s), 7.29 (1H, s), 9.82 (1H, s).

Reference Example 229

To a suspension of aluminum lithium hydride (824 mg) in THF (15 ml), a solution of 1-propylimidazole-2-carboxyaldehyde (3.00 g) in THF (15 ml) was added dropwise at 0° C. under nitrogen atmosphere. After finishing the dropping, water (0.8 ml), 15% aqueous solution of sodium hydroxide (0.8 ml) and water (2.4 ml) were sequentially added to the mixture at 0° C., and the mixture was stirred for 2 hours at room temperature. The mixture was dried over magnesium sulfate, and the insolubles were filtered off. The solvent was distilled off under reduced pressure, to give 2-hydroxymethyl-1-propylimidazole (2.28 g) as colorless oil.

$^1$H-NMR (200 MHz, CDCl$_3$) δ 0.95 (3H, t, J=7.4 Hz), 1.74 to 1.92 (2H, m, 3.96 (2H, t, J=7.4 Hz), 4.65 (2H, s), 6.86 (1H, d, J=1.4 Hz), 6.90 (1H, d, J=1.4 Hz).

Reference Example 230

To a solution of 2-hydroxymethyl-1-propylimidazole (1.00 g) in chloroform (15 ml) was added one droplet of DMF, and thionyl chloride (0.68 ml) was added to the mixture at 0° C. The mixture was allowed to be at room temperature, and stirred for 30 minutes under nitrogen atmosphere. The solvent was distilled off under reduced pressure and the obtained residue was dissolved in methanol (10 ml). This solution was added to a mixed solution of 4-aminothiophenol (811 mg) and sodium hydroxide (570 mg) in methanol (10 ml) and water (6 ml) at 0° C. The mixture was allowed to be at room temperature and stirred for 30 minutes, and water was added to the mixture, and the mixture was extracted with ethyl acetate. The organic layer was washed with saturated brine, and dried over magnesium sulfate. The solvent was distilled off under reduced pressure, to give 4-[[(1-propylimidazol-2-yl)methyl]sulfanyl]aniline (1.59 g) as oil.

$^1$H-NMR (200 MHz, CDCl$_3$) δ 0.93 (3H, t, J=7.4 Hz), 1.68 to 1.86 (2H, m), 3.80 (2H, t, J=7.4 Hz), 04 (2H, s), 6.57 (2H, d, J=8.8 Hz), 6.83 (1H, d, J=1.2 Hz), 6.91 (1H, d, J=1.2 Hz), 7.15 (2H, d, J=8.8 Hz).

Reference Example 231

To 2-hydroxymethyl-1-propylimidazole (8.0 g) was added thionyl chloride (50 ml) at 0° C., and the mixture was heated for 30 minutes under nitrogen atmosphere at 90° C. The mixture was allowed to be at room temperature. The solvent was distilled off under reduced pressure, and the obtained residue was recrystallized from methanol-ethyl acetate, to give 2-chloromethyl-1-propylimidazole hydrochloride (4.3 g) as yellow crystals.

$^1$H-NMR (200 MHz, DMSO-d$_6$) δ 0.90 (3H, t, J=7.2 Hz), 1.74 to 1.93 (2H, m), 4.18 (2H, t, J=7.2 Hz), 5.17 (2H, s), 7.73 (1H, d, J=1.8 Hz), 7.83 (1H, d, J=1.8 Hz).

Elemental Analysis C$_7$H$_{12}$N$_2$Cl$_2$ Calcd. C, 43.10; H, 6.20; N, 14.36. Found: C, 42.90; H, 6.34; N, 14.45.

Reference Example 232

To a suspension of imidazole-2-carboxyaldehyde (2.50 g) and potassium carbonate (4.31 g) in DMF (25 ml) was added 2,2,2-trifluoroethyl p-toluene sulfinate (7.93 g), and the mixture was heated for 6 hours under nitrogen atmosphere at 110° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was washed with saturated brine, and dried over magnesium sulfate. The solvent was distilled off under reduced pressure and the obtained residue was separated and purified by silica gel column chromatography (hexane:ethyl acetate=1:1), to give 1-(2,2,2-trifluoroethyl)imidazole-2-carboxyaldehyde (2.56 g) as brown oil.

$^1$H-NMR (200 MHz, CDCl$_3$) δ 5.17 (2H, q, J=8.4 Hz), 7.26 (1H, s), 7.38 (1H, s), 9.85 (1H, s).

Reference Example 233

To a suspension of aluminum lithium hydride (383 mg) in THF (20 ml), a solution of 1-(2,2,2-trifluoroethyl)imidazole-2-carboxyaldehyde (1.8 g) in THF (20 ml) was added dropwise at 0° C. under nitrogen atmosphere. After finishing the dropping, water (0.4 ml), 15% aqueous solution of sodium hydroxide (0.4 ml) and water (1.2 ml) were sequentially added to the mixture at 0° C., and the mixture was stirred for 2 hours at room temperature. The mixture was dried over magnesium sulfate, and the insolubles were filtered off. The solvent was distilled off under reduced pressure and the obtained solid was washed with hexane, to give 2-hydroxymethyl-1-(2,2,2-trifluoroethyl)imidazole (1.54 g) as colorless crystals.

$^1$H-NMR (200 MHz, CDCl$_3$) δ 4.64 to 4.78 (4H, m), 6.95 to 6.96 (2H, m).

Elemental Analysis C$_6$H$_7$N$_2$OF$_3$ Calcd. C, 40.01; H, 3.92; N, 15.55. Found: C, 40.25; H, 4.00; N, 15.67.

Reference Example 234

To 2-hydroxymethyl-1-(2,2,2-trifluoroethyl)imidazole (1.40 g) was added thionyl chloride (14 ml), and the mixture was heated for 30 minutes under nitrogen atmosphere at 90° C. The mixture was allowed to be at room temperature, the solvent was distilled off under reduced pressure and the obtained solid was washed with ethyl acetate, to give 2-chloromethyl-1-(2,2,2-trifluoroethyl)imidazole hydrochloride (1.63 g) as brown crystals.

$^1$H-NMR (200 MHz, DMSO-d$_6$) δ 5.19 (2H, s), 5.22 (2H, q, J=8.8 Hz), 7.71 (1H, d, J=1.8 Hz), 7.75 (1H, d, J=1.8 Hz).

Elemental Analysis C$_6$H$_7$N$_2$Cl$_2$F$_3$ Calcd. C, 30.66; H, 3.00; N, 11.92. Found: C, 30.82; H, 3.23; N, 11.90.

Reference Example 235

To a suspension of imidazole-2-carboxyaldehyde (2.50 g) and potassium carbonate (4.31 g) in DMF (25 ml) was added 1-iodobutane (5.74 g) and the mixture was heated for 6 hours under nitrogen atmosphere at 50° C. The mixture was allowed to be at room temperature, ethyl acetate was added to the mixture, the insolubles were filtered off, and the solvent was distilled off under: reduced pressure. Water was added to the mixture and the mixture was extracted with ethyl acetate. The organic layer was washed with saturated brine, and dried over magnesium sulfate. The solvent was distilled off under reduced pressure, to give 1-butylimidazole-2-carboxyaldehyde (3.95 g) as brown oil.

$^1$H-NMR (200 MHz, CDCl$_3$) δ 0.90-0.99 (3H, m), 1.20 to 1.50 (2H, m), 1.60 to 1.90 (2H, m), 4.35 to 4.44 (2H, m), 7.15 to 7.17 (1H, m), 7.26 to 7.29 (1H, m), 9.82 (1H, s).

Reference Example 236

To a suspension of a lithium aluminum hydride (873 mg) in THF (20 ml), a solution of 1-butylimidazole-2-carboxyaldehyde (3.50 g) in THF (20 ml) was added dropwise at 0° C. under nitrogen atmosphere. After finishing the dropping, water (0.9 ml), 15% aqueous solution of sodium hydroxide (0.9 ml) and water (2.7 ml) were sequentially added to the mixture at 0° C., and the mixture was stirred for 2 hours at room temperature. The mixture was dried over magnesium sulfate, and the insolubles were filtered off. The solvent was distilled off under reduced pressure, to give 1-butyl-2-hydroxymethylimidazole (3.12 g) as colorless oil.

$^1$H-NMR (200 MHz, CDCl$_3$) δ 0.95 (3H, t, J=7.4 Hz), 1.26 to 1.42 (2H, m), 1.69 to 1.85 (2H, m), 4.00 (2H, t, J=7.4 Hz), 4.64 (2H, s), 6.85 (1H, d, J=1.0 Hz), 6.88 (1H, d, J=1.0 Hz).

Reference Example 237

To 1-butyl-2-hydroxymethylimidazole (3.0 g) was added thionyl chloride (30 ml), and the mixture was heated for 30 minutes under nitrogen atmosphere at 90° C. The mixture was allowed to be at room temperature, the solvent was distilled off under reduced pressure, and the obtained solid was washed with ethyl acetate, to give 1-butyl-2-chloromethylimidazole hydrochloride (3.5 g) as brown crystals.

$^1$H-NMR (200 MHz, DMSO-d$_6$) δ 0.92 (3H, t, J=7.8 Hz), 1.23 to 1.41 (2H, m), 1.71 to 1.87 (2H, m), 4.21 (2H, t, J=7.6 Hz), 5.17 (2H, s), 7.73 (1H, d, J=2.0 Hz), 7.84 (1H, d, J=2.0 Hz).

Elemental Analysis C$_8$H$_{14}$N$_2$Cl$_2$ Calcd. C, 45.95; H, 6.75; N, 13.40. Found: C, 46.25; H, 6.93; N, 13.53.

Reference Example 238

To a suspension of imidazole-2-carboxyaldehyde (2.50 g) and potassium carbonate (4.31 g) in DMF (25 ml) was added bromomethylcyclopropane (4.21 g) and the mixture was heated for 6 hours under nitrogen atmosphere at 50° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was washed with saturated brine, and dried over magnesium sulfate. The solvent was distilled off under reduced pressure, to give 1-cyclopropylmethylimidazole-2-carboxyaldehyde (3.90 g) as brown oil.

$^1$H-NMR (200 MHz, CDCl$_3$) δ 0.38 to 0.43 (2H, m), 0.60 to 0.69 (2H, m), 1.20 to 1.34 (1H, m), 3.28 (2H, d, J=7.2 Hz), 7.26 to 7.31 (2H, m), 9.82 (1H, s).

Reference Example 239

To a suspension of aluminum lithium hydride (1.21 g) in THF (25 ml), a solution of 1-cyclopropylmethylimidazole-2-carboxyaldehyde (4.80 g) in THF (25 ml) was added dropwise at 0° C. under nitrogen atmosphere. After finishing the dropping, water (1.2 ml), 15%: aqueous solution of sodium hydroxide (1.2 ml) and water (3.6 ml) were sequentially added to the mixture at 0° C., and the mixture was stirred for 2 hours at room temperature. The mixture was dried over magnesium sulfate, and the insolubles were filtered off. The solvent was distilled off under reduced pressure, and the residue was recrystallized from hexane-ethyl acetate, to give 1-cyclopropylmethyl-2-hydroxymethylimidazole (2.86 g) as colorless crystals.

$^1$H-NMR (200 MHz, CDCl$_3$) δ 0.36-0.41 (2H, m), 0.60 to 0.70 (2H, m), 1.10 to 1.35 (1H, m), 3.88 (2H, d, J=7.0 Hz), 4.64 (2H, s), 6.87 (1H, d, J=10 Hz), 6.99 (1H, d, J=10 Hz).

Reference Example 240

To 1-cyclopropylmethyl-2-hydroxymethylimidazole (2.50 g) was added thionyl chloride (25 ml) at 0° C., and the mixture was heated for 30 minutes under nitrogen atmosphere at 90° C. The mixture was allowed to be at room temperature, the solvent was distilled off under reduced pressure and the obtained solid was washed with ethyl acetate, to give 2-chloromethyl-1-cyclopropylmethylimidazole hydrochloride. (2.96 g) as brown crystals.

$^1$H-NMR (200 MHz, DMSO-d$_6$) δ 0.47 to 0.65 (4H, m), 1.20 to 1.45 (1H, m), 4.11 (2H, d, J=7.8 Hz), 5.20 (2H, s), 7.76 (1H, d, J=2.0 Hz), 7.89 (1H, d, J=2.0 Hz).

Elemental Analysis C$_8$H$_{12}$N$_2$Cl$_2$ Calcd. C, 46.40; H, 5.84; N, 13.53. Found: C, 46.04; H, 5.93; N, 13.68.

Reference Example 241

To a suspension of imidazole-2-carboxyaldehyde (2.50 g) and potassium carbonate (4.31 g) in DMF (25 ml) was added iodoisobutane (5.74 g) and the mixture was heated for 6 hours under nitrogen atmosphere at 50° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was washed with saturated brine, and dried over magnesium sulfate. The solvent was distilled off under reduced pressure, to give 1-isobutylimidazole-2-carboxyaldehyde (2.97 g) as brown oil.

$^1$H-NMR (200 MHz, CDCl$_3$) δ 0.92 (6H, d, J=7.0 Hz), 2.01 to 2.15 (1H, m), 4.22 (2H, d, J=7.4 Hz), 7.13 (1H, s), 7.29 (1H, s), 9.82 (1H, s).

Reference Example 242

To a suspension of aluminum lithium hydride (698 mg) in THF (20 ml), a solution of 1-isobutylimidazole-2-carboxyaldehyde (2.80 g) in THF (20 ml) was added dropwise at 0° C. under nitrogen atmosphere. After finishing the dropping, water (0.7 ml), 15% aqueous solution of sodium hydroxide (0.7 ml) and water (2.1 ml) at 0° C. were sequentially added to the mixture, and the mixture was stirred for 2 hours at room temperature. The mixture was dried over magnesium sulfate, and the insolubles were filtered off. The solvent was distilled off under reduced pressure, to give 2-hydroxymethyl-1-isobutylimidazole (2.57 g) as colorless oil.

$^1$H-NMR (200 MHz, CDCl$_3$) δ 0.93 (6H, d, J=6.6 Hz), 2.00 to 2.20 (1H, m), 3.79 (2H, d, J=7.6 Hz), 4.66 (2H, s), 6.84 (1H, d, J=1.4 Hz), 6.92 (1H, d, J=1.4 Hz).

Reference Example 243

To 2-hydroxymethyl-1-isobutylimidazole (2.40 g) was added thionyl chloride (24 ml) at 0° C., and the mixture was heated for 30 minutes under nitrogen atmosphere at 90° C. The mixture was allowed to be at room temperature. The solvent was distilled off under reduced pressure and the obtained residue was recrystallized from methanol-ethyl acetate, to give 2-chloromethyl-1-isobutylimidazole hydrochloride (2.17 g) as brown crystals.

$^1$H-NMR (200 MHz, DMSO-d$_6$) δ 0.90 (6H, d, J=6.6 Hz), 2.05-2.25 (1H, m), 4.05 (2H, d, J=7.8 Hz), 5.18 (2H, s), 7.75 (1H, d, J=2.2 Hz), 7.81 (1H, d, J=2.2 Hz).

Elemental Analysis C$_8$H$_{14}$N$_2$Cl$_2$ Calcd. C, 45.95; H, 6.75; N, 13.40. Found: C, 45.79; H, 7.08; N, 13.37.

Reference Example 244

To a suspension of imidazole-2-carboxyaldehyde (2.50 g) and potassium carbonate (4.31 g) in. DMF (25 ml) was added 2-bromobutane (4.27 g), and the mixture was heated for 6 hours under nitrogen atmosphere at 50° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was washed with saturated brine, and dried over magnesium sulfate. The solvent was distilled off under reduced pressure, to give 1-(2-butyl)imidazole-2-carboxyaldehyde (3.45 g) as brown oil.

$^1$H-NMR (200 MHz, CDCl$_3$) δ 0.84 (3H, t, J=7.2 Hz), 1.45 (3H, d, J=7.0 Hz), 1.71 to 1.86 (2H, m), 5.30 to 5.40 (1H, m), 7.29 (1H, 's), 7.32 (1H, s), 9.83 (1H, s).

Reference Example 245

To a suspension of aluminum lithium hydride (823 mg) in THF (20 ml), a solution of 1-(2-butyl)imidazole-2-carboxyaldehyde (3.30 g) in THF (20 ml) was added dropwise at 0° C. under nitrogen atmosphere. After finishing the dropping, water (0.9 ml), 15% aqueous solution of sodium hydroxide (0.9 ml) and water (2.7 ml) were sequentially added to the mixture at 0° C., and the mixture was stirred for 2 hours at room temperature. The mixture was dried over magnesium sulfate, and the insolubles were filtered off. The solvent was distilled off under reduced pressure, and the obtained solid was washed with hexane, to give 1-(2-butyl)-2-hydroxymethylimidazole (2.84 g) as colorless crystals.

$^1$H-NMR (200 MHz, CDCl$_3$) δ 0.84 (3H, t, J=7.4 Hz), 1.43 (3H, d, J=6.6 Hz), 1.69 to 1.84 (2H, m), 4.24 to 4.35 (1H, m), 4.69 (2H, s), 6.90 (1H, d, J=1.2 Hz), 6.94 (1H, d, J=1.2 Hz).

Reference Example 246

To 1-(2-butyl)-2-hydroxymethylimidazole (2.70 g) was added thionyl chloride (27 ml) at 0° C., and the mixture was heated for 30 minutes under nitrogen atmosphere at 90° C. The mixture was allowed to be at room temperature. The solvent was distilled off under reduced pressure, and the obtained residue was recrystallized from ethyl acetate, to give 1-(2-butyl)-2-chloromethylimidazole hydrochloride (3.09 g) as brown crystals.

$^1$H-NMR (200 MHz, DMSO-d$_6$) δ 0.81 (3H, t, J=7.8 Hz), 1.47 (3H, d, J=7.0 Hz), 1.81 to 1.95 (2H, m), 4.54 to 4.65 (1H, m), 5.27 (2H, s), 7.86 (1H, d, J=2.2 Hz), 8.06 (1H, d, J=2.2 Hz).

Reference Example 247

To a suspension of imidazole-2-carboxyaldehyde (2.50 g) and potassium carbonate (4.31 g) in. DMF (25 ml) was added 1-bromopentane (4.71 g) and the mixture was heated for 6 hours under nitrogen atmosphere at 50° C. The mixture was allowed to be at room temperature, ethyl acetate was added to the mixture, the insolubles were filtered off, and the, solvent was distilled off under reduced pressure. Water was added to the mixture and the mixture was extracted with ethyl acetate. The organic layer was washed with saturated brine, and dried over magnesium sulfate. The solvent was distilled off under reduced pressure, to give 1-pentylimidazole-2-carboxyaldehyde (4.32 g) as brown oil.

$^1$H-NMR (200 MHz, CDCl$_3$) δ 0.90 (3H, t, J=6.8 Hz), 1.20 to 1.45 (4H, m), 71 to 1.85 (2H, m), 4.39 (2H, t, J=7.2 Hz), 7.15 (1H, s), 7.28 (1H, s), 9.81 (1H, s).

Reference Example 248

To a suspension of aluminum lithium hydride (1.00 g) in THF (20 ml), a solution of 1-pentylimidazole-2-carboxyaldehyde (4.40 g) in THF (20 ml) was added dropwise at 0° C. under nitrogen atmosphere. After finishing the dropping, water (1.0 ml), 15% aqueous solution of sodium hydroxide (1.0 ml) and water (3.0 ml) were sequentially added to the solution at 0° C., and the mixture was stirred for 2 hours at room temperature. The mixture was dried over magnesium sulfate, and the insolubles were filtered off. The solvent was distilled off under reduced pressure, to give 2-hydroxymethyl-1-pentylimidazole (3.99 g) as colorless oil.

$^1$H-NMR (200 MHz, CDCl$_3$) δ 0.90 (3H, t, J=6.6 Hz), 1.23 to 1.43 (4H, m), 1.71 to 1.86 (2H, m), 3.97 (2H, t, J=7.6 Hz), 4.66 (2H, s), 6.87 (1H, d, J=1.6 Hz), 6.92 (1H, d, J=1.6 Hz).

Reference Example 249

To 2-hydroxymethyl-1-pentylimidazole (3.8 g) was added thionyl chloride (38 ml) at 0° C., and the mixture was heated for 30 minutes under nitrogen atmosphere at 90° C. The mixture was allowed to be at room temperature. The solvent was distilled off under reduced pressure and the obtained residue was recrystallized from methanol-ethyl acetate, to give 2-chloromethyl-1-pentylimidazole hydrochloride (3.00 g) as brown crystals.

$^1$H-NMR (200 MHz, DMSO-d$_6$) δ 0.88 (3H, t, J=7.0 Hz), 1.15 to 1.40 (4H, m), 1.74 to 1.94 (2H, m), 4.21 (2H, t, J=7.6 Hz), 5.19 (2H, s), 7.74 (1H, d, J=1.8 Hz), 7.85 (1H, d, J=1.8 Hz).

Elemental Analysis C$_9$H$_{16}$N$_2$Cl$_2$ Calcd. C, 48.44; H, 7.23; N, 12.55. Found: C, 48.32; H, 6.95; N, 12.70.

Reference Example 250

To a suspension of 4-aminothiophenol (9.6 g) and triethylamine (54 ml) in THF (300 ml), a solution of benzyloxy carbonyl chloride (13.1 g) in THF (50 ml) was added dropwise at −78° C. under nitrogen atmosphere, and stirred for 30 minutes at the same temperature. The mixture was allowed to be at room temperature, and water was added to the mixture, and the mixture was extracted with ethyl acetate. The organic layer was washed with saturated and dried over magnesium sulfate. The solvent was distilled off under reduced pressure and the obtained residue was recrystallized from hexane-ethyl acetate, to give. S-(4-aminophenyl)O-benzyl carbonothioate (19.3 g) as colorless crystals.

$^1$H-NMR (200 MHz, CDCl$_3$) δ 3.85 (2H, br), 5.23 (2H, s), 6.63 to 6.70 (2H, m), 7.26 to 7.35 (7H, m).

Reference Example 251

To a solution of 2-methyl-4-nitrothiophenol (7.0 g) in acetic acid (100 ml) was added reduced iron (21.0 g) and the mixture was stirred for 40 hours. Ethanol was added to the mixture, and the insolubles were filtered off, and the solvent was distilled off under reduced pressure. To the obtained residue was added water, and the solution was neutralized with an aqueous solution of saturated sodium bicarbonate, and extracted with ethyl acetate. The organic layer was dried over magnesium sulfate and the solvent was distilled off under reduced pressure. The obtained residue was separated and purified by silica gel column chromatography (hexane-ethyl acetate=3:1→hexane:ethyl acetate=0.2:1), to give 4-amino-2-methylthiophenol (1.8 g).

$^1$H-NMR (200 MHz, CDCl$_3$) δ 2.30 (3H, s), 3.04 (1H, s), 3.60 (1H, br), 6.45 (1H, dd, J=8.2, 2.6 Hz), 6.56 (1H, d, J=2.6 Hz), 7.15 (1H, d, J=8.2 Hz).

Reference Example 252

To 2-hydroxymethyl-1-methylimidazole (874 mg) was added thionyl chloride (10 ml) at 0° C., and the mixture was heated for 30 minutes under nitrogen atmosphere at 90° C. The mixture was allowed to be at room temperature. The solvent was distilled off under reduced pressure and the obtained residue was recrystallized from ethyl acetate, to give 2-chloromethyl-1-methylimidazole hydrochloride (1.15 g) as brown crystals.

$^1$H-NMR (200 MHz, DMSO-d$_6$) δ 3.88 (3H, s), 5.19 (2H, s), 7.72 (1H, d, J=1.8 Hz), 7.78 (1H, d, J=1.8 Hz).

Elemental Analysis C$_5$H$_8$N$_2$Cl$_2$ Calcd. C, 35.95; H, 4.83; N, 16.77. Found: C, 35.74; H, 5.03; N, 16.45.

Reference Example 253

To a solution of 4-amino-2-methylthiophenol (500 mg) in methanol (10 ml) was added 1N aqueous solution of sodium hydroxide (12 ml), and a solution of 2-chloromethyl-1-methylimidazole hydrochloride (660 mg) in methanol (10 ml) was added at 0° C. Water was added to the mixture, and the mixture was extracted with ethyl acetate and the organic layer was dried over magnesium sulfate. The solvent was distilled off under reduced pressure and the obtained residue was recrystallized from hexane-ethyl acetate, to give 3-methyl-4-[[(1-methylimidazol-2-yl)methyl]sulfanyl]aniline (757 mg) as crystals.

$^1$H-NMR (200 MHz, CDCl$_3$) δ 2.24 (3H, s), 3.50 (3H,: s), 3.69 (2H, br), 3.94 (2H, s), 6.43 (1H, dd, J=8.0, 2.4 Hz), 6.53 (1H, d, J=2.4 Hz), 6.77 (1H, d, J=1.2 Hz), 6.89 (1H, d, J=1.2 Hz), 7.16 (1H, d, J=8.0 Hz).

Reference Example 254

To a suspension of imidazole-2-carboxyaldehyde (2.50 g) and potassium carbonate (4.31 g) in DMF (25 ml) was added bromomethylcyclobutane (4.65 g), and the mixture was heated for 6 hours under nitrogen atmosphere at 50° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was washed with saturated brine, and dried over magnesium sulfate. The solvent was distilled off under reduced pressure, to give 1-cyclobutylmethylimidazole-2-carboxyaldehyde (4.27 g) as brown oil.

$^1$H-NMR (200 MHz, CDCl$_3$) δ 1.70 to 2.16 (6H, m), 2.68 to 2.82 (1H, m), 4.43 (2H, d, J=7.2 Hz), 7.13 (1H, s), 7.27 (1H, s), 9.81 (1H, s).

Reference Example 255

To a suspension of aluminum lithium hydride (971 mg) in THF (20 ml), a solution of 1-cyclobutylmethylimidazole-2-carboxyaldehyde (4.20 g) in THF (20 ml) was added dropwise at 0° C. under nitrogen atmosphere. After finishing the dropping, water (1.0 ml), 15% aqueous solution of sodium hydroxide (1.0 ml) and water (3.0 ml) were sequentially added to the solution at 0° C., and the mixture was stirred for 2 hours at room temperature. The mixture was dried over magnesium sulfate, and the insolubles were filtered off. The solvent was distilled off under reduced pressure, and the obtained solid was washed with hexane, to give 1-cyclobutylmethyl-2-hydroxymethylimidazole (3.01 g) as colorless crystals.

$^1$H-NMR (200 MHz, CDCl$_3$) δ 1.69-2.13 (6H, m), 2.67 to 2.82 (1H, m), 4.00 (2H, d, J=7.2 Hz), 4.65 (2H, s), 6.83 (1H, d, J=1.0 Hz), 6.89 (1H, d, J=10 Hz).

Reference Example 256

To 1-cyclobutylmethyl-2-hydroxymethylimidazole (2.90 g) was added thionyl chloride (29 ml) at 0° C., and the mixture was heated for 30 minutes under nitrogen atmosphere at 90° C. The mixture was allowed to be at room temperature. The solvent was distilled off under reduced pressure and the obtained residue was dissolved in methanol and the solvent was distilled off again under reduced pressure. The obtained solid was recrystallized from ethyl acetate, to give 2-chloromethyl-1-cyclobutylmethylimidazole hydrochloride (3.54 g) as brown crystals.

$^1$H-NMR (200 MHz, DMSO-d$_6$) δ 1.78-2.05 (6H, m), 2.75 to 2.95 (1H, m), 4.26 (2H, d, J=7.8 Hz), 5.18 (2H, s), 7.74 (1H, d, J=2.0 Hz), 7.79 (1H, d, J=2.0 Hz).

Elemental Analysis C$_9$H$_{14}$N$_2$Cl$_2$ Calcd. C, 48.88; H, 6.38; N, 12.67. Found: C, 48.68; H, 6.47; N, 12.46.

Reference Example 257

To a suspension of imidazole-2-carboxyaldehyde (2.50 g) and potassium carbonate (4.31 g) in DMF (25 ml) was added aryl bromide (3.77 g), and the mixture was heated for 5 hours under nitrogen atmosphere at 50° C. The mixture was allowed to be at room temperature, ethyl acetate was added to the mixture, the insolubles were filtered off, and the solvent was distilled off under reduced pressure. Water was added to the mixture and the mixture was extracted with ethyl acetate. The organic layer was washed with saturated brine, and dried over magnesium sulfate. The solvent was distilled off under reduced pressure, to give 1-arylimidazole-2-carboxyaldehyde (3.54 g) as brown oil.

$^1$H-NMR (200 MHz, CDCl$_3$) δ 5.03 to 5.30 (4H, m), 5.88 to 6.08 (1H, m), 7.17 (1H, s), 7.31 (1H, s), 9.82 (1H, s).

Reference Example 258

To a suspension of aluminum lithium hydride (892 mg) in THF (30 ml), a solution of 1-arylimidazole-2-carboxyaldehyde (3.20 g) in. THF (30 ml) was added dropwise at 0° C. under nitrogen atmosphere. After finishing the dropping, water (0.9 ml), 15% aqueous solution of sodium hydroxide (0.9 ml) and water (2.7 ml) were sequentially added to the mixture at 0° C., and the mixture was stirred for 2 hours at room temperature. The mixture was dried over magnesium sulfate, and the insolubles were filtered off. The solvent was distilled off under reduced pressure, to give 1-aryl-2-hydroxymethylimidazole (2.51 g) as brown oil.

$^1$H-NMR (200 MHz, CDCl$_3$) δ 4.62 to 4.67 (4H, m), 5.04 to 5.27 (2H, m), 5.87 to 6.08 (1H, m), 6.85 (1H, d, J=1.2 Hz), 6.91 (1H, d, J=1.2 Hz).

Reference Example 259

To 1-aryl-2-hydroxymethylimidazole (2.20 g) was added thionyl chloride (22 ml) at 0° C., and the mixture was heated for 30 minutes under nitrogen atmosphere at 90° C. The mixture was allowed to be at room temperature. The solvent was distilled off under reduced pressure and the obtained residue was dissolved in methanol and the solvent was distilled off again under reduced pressure. The obtained solid was recrystallized from ethyl acetate, to give 1-aryl-2-chloromethylimidazole hydrochloride (2.28 g) as brown crystals.

$^1$H-NMR (200 MHz, DMSO-d$_6$) δ 4.91 to 4.94 (2H, m), 5.16 (2H, s), 5.25 to 5.39 (2H, m), 5.94 to 6.10 (1H, m), 7.74 to 7.75 (2H, m).

Elemental Analysis C$_7$H$_{10}$N$_2$Cl$_2$.0.2H$_2$O Calcd. C, 42.75; H, 5.33.; N, 14.24. Found: C, 42.88; H, 5.19; N, 14.34.

Reference Example 260

To a solution of 4-methylimidazole (20.0 g) and triethylamine (53.5 ml) in DMF (300 ml), a solution of triphenylchloromethane (71.3 g) in DMF (200 ml) was added dropwise at 0° C. under nitrogen atmosphere. After finishing the dropping, and the mixture was allowed to be at room temperature and the mixture was stirred overnight. Water was added to the mixture, and the precipitated solid was collected by filtration. The obtained solid was washed with water twice and dried under reduced pressure, to give 4-methyl-1-triphenylmethylimidazole (79.1 g) as colorless solid.

$^1$H-NMR (200 MHz, CDCl$_3$) δ 2.20 (3H, s), 6.51 (1H, s), 7.12 to 7.18 (6H, m), 7.29 to 7.36 (11H, m).

Reference Example 261

To a solution of 4-methyl-1-triphenylmethylimidazole (20.0 g) in THF (300 ml) and acetonitrile (300 ml) was added 1-iodopropane (26.2 g) and the mixture was stirred overnight under nitrogen atmosphere at 80° C. The solvent was distilled off under reduced pressure and the residue was dissolved in acetic acid (200 ml), and the mixture was stirred for 3 hours under nitrogen atmosphere at 60° C. The mixture was allowed to be at room temperature, water was added to the mixture, and the insolubles were filtered off. Potassium carbonate was added to the filtrate to make it basic and the mixture was extracted with chloroform three times, and dried over magnesium sulfate. The solvent was distilled off under reduced pressure and the obtained oil was distilled off under reduced pressure (1.5 mmHg, 72° C. to 73° C.), to give 5-methyl-1-propylimidazole (1.9 g) as colorless oil.

$^1$H-NMR (200 MHz, CDCl$_3$) δ 0.94 (3H, t, J=7.4 Hz), 1.67 to 1.85 (2H, m), 2.20 (3H, s), 3.80 (2H, t, J=7.4 Hz), 6.78 (1H, s), 7.47 (1H, s).

Reference Example 262

To a solution of 5-methyl-1-propylimidazole (1.6 g) in dry ether (30 ml) was added dropwise. 1.6M n-butyllithium hexane solution (24.2 ml) at −78° C. under argon atmosphere. After finishing the dropping, the mixture was stirred for 1 hour at the same temperature, and DMF (5.0 ml) was added dropwise to the mixture. After finishing the dropping, the mixture was allowed to be at room temperature, the mixture was stirred for 1 hour, and 1N hydrochloric acid was added to make it acidic at 0° C. Then, the mixture was neutralized with potassium carbonate and extracted with ethyl acetate. The organic layer was dried over magnesium sulfate. The solvent was distilled off under reduced pressure, to give 5-methyl-1-propylimidazole-2-carboxyaldehyde (1.96 g) as brown oil.

$^1$H-NMR (200 MHz, CDCl$_3$) δ 0.99 (3H, t, J=7.4 Hz), 1.61 to 1.84 (2H, m), 2.29 (3H, s), 4.27 (2H, t, J=7.4 Hz), 7.08 (1H, s), 9.71 (1H, s).

Reference Example 263

To a suspension of aluminum lithium hydride (917 mg) in THF (30 ml), a solution of 5-methyl-1-propylimidazole-2-carboxyaldehyde (1.90 g) in THF (30 ml) was added dropwise at 0° C. under nitrogen atmosphere. After finishing the dropping, water (0.9 ml), 15% aqueous solution of sodium hydroxide (0.9 ml) and water (2.7 ml) were sequentially added to the mixture at 0° C., and the mixture was stirred for 2 hours at room temperature. The mixture was dried over magnesium sulfate, and the insolubles were filtered off. The solvent was distilled off under reduced pressure, to give 2-hydroxymethyl-5-methyl-1-propylimidazole (2.40 g) as brown oil.

$^1$H-NMR (200 MHz, CDCl$_3$) δ 0.96 (3H, t, J=7.4 Hz), 1.62 to 1.84 (2H, m), 2.18 (3H, s), 3.87 (2H, t, J=7.6 Hz), 4.61 (2H, s), 6.64 (1H, s).

Reference Example 264

To 2-hydroxymethyl-5-methyl-1-propylimidazole (2.11 g) was added thionyl chloride (25 ml) at 0° C., and the mixture was heated for 30 minutes under nitrogen atmosphere at 90° C. The mixture was allowed to be at room temperature. The solvent was distilled off under reduced pressure and the obtained residue was dissolved in methanol, and the solvent was distilled off again under reduced pressure. The obtained solid was recrystallized from ethyl acetate, to give 2-chloromethyl-5-methyl-1-propylimidazole hydrochloride (1.04 g) as colorless crystals.

$^1$H-NMR (200 MHz, DMSO-d$_6$) δ 0.95 (3H, t, J=7.6 Hz), 1.66 to 1.85 (2H, m), 2.34 (3H, s), 4.15 (2H, t, J=7.6 Hz), 5.19 (2H, s), 7.53 (1H, s).

Elemental Analysis C$_8$H$_{14}$N$_2$Cl$_2$ Calcd. C, 45.95; H, 6.75; N, 13.40. Found: C, 46.18; H, 6.83; N, 13.10.

Reference Example 265

To a solution of cyclopropylamine (20.0 g) and 25% aqueous solution (130 ml) of ammonia (27.1 g) in methanol, a solution of 40% glyoxal (62.5 g) and 37% formalin (28.4 g) in methanol (40 ml) was added dropwise at 0° C. After finishing the dropping, the mixture was stirred for 1 hour at 0° C., water was added to the mixture, and the mixture was washed with hexane four times. The aqueous layer was washed with mixed solution of hexane (50 ml)-ether (130 ml), saturated brine was added to the mixture, and the mixture was extracted with chloroform four times. The organic layer was dried over magnesium sulfate and the solvent was distilled off under reduced pressure. The obtained residue was distilled off under reduced pressure (1.5 mmHg, 72° C. to 73° C.), to give 1-cyclopropylimidazole (3.3 g) as colorless oil.

$^1$H-NMR (200 MHz, CDCl$_3$) δ $^1$H-NMR (200 MHz, CDCl$_3$) δ 0.92 to 1.01 (4H, m), 3.28 to 3.39 (1H, m), 6.97 (1H, s), 6.99 (1H, s), 7.55 (1H, s).

Reference Example 266

To a solution of 1-cyclopropylimidazole (2.5 g) in dry ether (30 ml), 1.6M n-butyllithium hexane solution (17.3 ml) was added dropwise at −78° C. under argon atmosphere. After finishing the dropping, the mixture was stirred for 1 hour at the same temperature, and DMF (8.94 ml) was added dropwise to the solution. After finishing the dropping, the mixture was allowed to be at room temperature, the mixture was stirred for 1 hour, and 1N hydrochloric acid was added to make it acidic at 0° C. Then, the mixture was neutralized with potassium carbonate and extracted with ethyl acetate twice. The organic layer was washed with and dried over magnesium sulfate. The solvent was distilled off under reduced pressure, to give 1-cyclopropylimidazole-2-carboxyaldehyde (3.14 g) as brown oil.

$^1$H-NMR (200 MHz, CDCl$_3$) δ 0.91 to 1.30 (4H, m), 3.80 to 3.92 (1H, m), 7.13 (1H, s), 7.22 (1H, s), 9.87 (1H, s).

Reference Example 267

To a suspension of a lithium aluminum hydride (1.12 g) in THF (40 ml), a solution of 1-cyclopropylimidazole-2-carboxyaldehyde (2.68 g) in THF (40 ml) was added dropwise at 0° C. under nitrogen atmosphere. After finishing the dropping, water (1.2 ml), 15% aqueous solution of sodium hydroxide (1.2 ml) and water (3.6 ml) were sequentially added to the mixture at 0° C., and the mixture was stirred for 40 hours at room temperature. The mixture was dried over magnesium sulfate, and the insolubles were filtered off. The solvent was distilled off under reduced pressure, and the residue was recrystallized from hexane-ethyl acetate, to give 2-hydroxymethyl-1-cyclopropylimidazole (1.55 g) as colorless crystals.

$^1$H-NMR (200 MHz, CDCl$_3$) δ 0.95 to 1.10 (4H, m), 3.27 to 3.38 (1H, m), 4.75 (2H, s), 6.83-6.86 (2H, m).

Elemental Analysis C₇H₁₀N₂O Calcd. C, 60.85; H, 7.30; N, 20.28. Found: C, 60.60; H, 7.29; N, 20.13.

Reference Example 268

To 2-hydroxymethyl-1-cyclopropylimidazole (1.20 g) was added thionyl chloride (12 ml) at 0° C., and the mixture was heated for 30 minutes under nitrogen atmosphere at 90° C. The mixture was allowed to be at room temperature. The solvent was distilled off under reduced pressure and the obtained residue was dissolved in methanol and the solvent was distilled off again under reduced pressure. The obtained solid was recrystallized from ethyl acetate, to give 2-chloromethyl-1-cyclopropylimidazole hydrochloride (1.49 g) as brown crystals.

¹H-NMR (200 MHz, DMSO-d₆) δ 1.14 to 1.22 (4H, m), 3.65 to 3.76 (1H, m), 5.17 (2H, s), 7.69 (1H, d, J=2.0 Hz), 7.77 (1H, d, J=2.0 Hz).

Elemental Analysis C₇H₁₀N₂Cl₂ Calcd. C, 43.55; H, 5.22; N, 14.51. Found: C, 43.28; H, 5.19; N, 14.50.

Reference Example 269

A mixture of potassium thiocyanate (119.2 g), dihydroxyacetone dimer (73.9 g) and propylamine hydrochloride (100 g) was added by portions to a mixed solution of acetic acid (89 ml) and 1-butanol (590 ml). The mixture was stirred for 1 day at room temperature, water (118 ml) was added to the mixture, and the mixture was stirred for 30 minutes. The precipitated solid was collected by filtration, and further washed with water (180 ml) twice and hexane once. The obtained solid was dried under reduced pressure, to give 5-hydroxymethyl-2-mercapto-1-propylimidazole (71.2 g) as colorless crystals.

¹H-NMR (200 MHz, CDCl₃) δ 0.87 (3H, t, J=7.4 Hz), 1.61 to 1.79 (2H, m), 3.91 (2H, t, J=7.4 Hz), 4.32 (2H, s), 5.26 (1H, br), 6.79 (1H, s), 11.95 (1H, s).

Elemental Analysis C₇H₁₂N₂OS-0.25H₂O Calcd. C, 47.57; H, 7.13; N, 15.85. Found: C, 47.22; H, 6.94; N, 15.99.

Reference Example 270

To 5.0M nitric acid (370 ml) was added sodium nitrite (1.14 g), and 5-hydroxymethyl-2-mercapto-1-propylimidazole (71.0 g) was added to the mixture by portions at 0° C. The mixture was allowed to be at room temperature and the mixture was stirred for 2 hours, and water (200 ml) was added to the mixture. The mixture was neutralized with potassium carbonate at 0° C., and the solvent was distilled off under reduced pressure. Ethanol was added to the mixture, and the insolubles were filtered off, and the solvent was distilled off under reduced pressure. To the obtained residue was added methanol-ethyl acetate, and basic silica gel was added to the mixture. This mixture was purified by basic silica gel column chromatography (methanol-ethyl acetate=0.1:8), to obtain solid, which was recrystallized from diisopropyl ether-ethyl acetate, to give 5-hydroxymethyl-1-propylimidazole (33.6 g) as brown crystals.

¹H-NMR (200 MHz, CDCl₃) δ 0.96 (3H, t, J=7.4 Hz), 1.76 to 1.94 (2H, m), 3.97 (2H, t, J=7.2 Hz), 4.63 (2H, s), 6.97 (1H, s), 7.48 (1H, s).

Reference Example 271

To 5-hydroxymethyl-1-propylimidazole (33.0 g) was added by portions thionyl chloride (80 ml) at 0° C., and the mixture was heated for 30 minutes under nitrogen atmosphere at 90° C. The mixture was allowed to be at room temperature. The solvent was distilled off under reduced pressure and the obtained residue was dissolved in methanol, and the solvent was distilled off again under reduced pressure. The obtained solid was recrystallized from ethyl acetate, to give 5-chloromethyl-1-propylimidazole hydrochloride (43.8 g) as colorless crystals.

¹H-NMR (200 MHz, DMSO-d₆) δ 0.92 (3H, t, J=7.4 Hz), 1.84 to 1.95 (2H, m), 4.18 (2H, t, J=7.2 Hz), 5.04 (2H, s), 7.82 (1H, s), 9.24 (1H, s).

Reference Example 272

A mixture of potassium thiocyanate (34.4 g), dihydroxyacetone dimer (21.3 g) and ethylamine hydrochloride (25.0 g) was added by portions to a mixed solution of acetic acid (26 ml) and 1-butanol (170 ml). The mixture was stirred for 1 day at room temperature, water (34 ml) was added to the mixture and the mixture was stirred for 30 minutes. The precipitated solid was collected by filtration, and further washed with water (50 ml) twice and hexane once. The obtained solid was dried under reduced pressure, to give 1-ethyl-5-hydroxymethyl-2-mercaptoimidazole (19.0 g) as colorless crystals.

¹H-NMR (200 MHz, CDCl₃) δ 1.22 (3H, t, J=7.0 Hz), 4.02 (2H, q, J=7.0 Hz), 4.34 (2H, d, J=4.8 Hz), 5.22 (1H, t, J=4.8 Hz), 6.78 (1H, s), 11.97 (1H, br).

Elemental Analysis C₆H₁₀N₂OS-0.2H₂O Calcd. C, 44.53; H, 6.48; N, 17.31. Found: C, 44.31; H, 6.18; N, 17.39.

Reference Example 273

To 5.0M nitric acid (102 ml) was added sodium nitrite (314 mg), and 1-ethyl-5-hydroxymethyl-2-mercaptoimidazole (18.0 g) was added by portions to the mixture at 0° C. The mixture was allowed to be at room temperature and the mixture was stirred for 2 hours, and water (100 ml) was added to the mixture. The mixture was neutralized with potassium carbonate at 0° C., and the solvent was distilled off under reduced pressure. Ethanol was added to the mixture, and the insolubles were filtered off, and the solvent was distilled off under reduced pressure. To the obtained residue was added methanol-ethyl acetate, and basic silica gel was added to the mixture. This mixture was purified by basic silica gel column chromatography (methanol-ethyl acetate=1:8) to obtain solid, which was recrystallized from diisopropyl ether-ethyl acetate, to give 1-ethyl-5-hydroxymethylimidazole (10.0 g) as brown crystals.

¹H-NMR (300 MHz, CDCl₃) δ 1.47 (3H, t, J=7.2 Hz), 4.07 (2H, q, J=7.2 Hz), 4.62 (2H, s), 6.88 (1H, s), 7.46 (1H, s).

Reference Example 274

To 1-ethyl-5-hydroxymethylimidazole (9.5 g), thionyl chloride (50 ml) was added by portions at 0° C., and the mixture was heated for 30 minutes under nitrogen atmosphere at 90° C. The mixture was allowed to be at room temperature. The solvent was distilled off under reduced pressure and the obtained residue was dissolved in methanol, and the solvent was distilled off again under reduced pressure. The obtained solid was recrystallized from ethyl acetate, to give 5-chloromethyl-1-ethylimidazole hydrochloride (12.4 g) as colorless crystals.

¹H-NMR (200 MHz, DMSO-d₆) δ 1.49 (3H, t, J=7.4 Hz), 4.26 (2H, q, J=7.4 Hz), 5.03 (2H, s), 7.79 (1H, s), 9.18 (1H, s).

Elemental Analysis $C_6H_{10}N_2Cl_2$ Calcd. C, 39.80; H, 5.57; N, 15.47. Found: C, 39.71; H, 5.50; N, 15.41.

Reference Example 275

A mixture of potassium thiocyanate (25.9 g), dihydroxyacetone dimer (16.0 g), and isobutylamine hydrochloride (25.0 g) was added by portions to a mixed solution of acetic acid (19.2 ml) and 1-butanol (128 ml). The mixture was stirred for 1 day at room temperature, water (26 ml) was added to the mixture, and the mixture was stirred for 30 minutes. The precipitated solid was collected by filtration, and further washed with water (40 ml) twice and diisopropyl ether once. The obtained solid was dried under reduced pressure, to give 5-hydroxymethyl-1-isobutyl-2-mercaptoimidazole (15.1 g) as colorless crystals.

$^1$H-NMR (200 MHz, DMSO-$d_6$) δ 0.85 (6H, d, J=6.6 Hz), 2.29 to 2.43 (1H, m), 3.80 (2H, d, =7.2 Hz), 4.33 (2H, d, J=4.8 Hz), 5.21 (1H, t, J=4.8 Hz), 6.81 (1H, s), 12.00 (1H, br).

Reference Example 276

To 5.0M nitric acid (70 ml) was added sodium nitrite (215 mg), and 5-hydroxymethyl-1-isobutyl-2-mercaptoimidazole (14.5 g) was added by portions to the mixture at 0° C. The mixture was allowed to be at room temperature and the mixture was stirred for 2 hours, and water (100 ml) was added to the mixture. The mixture was neutralized with potassium carbonate at 0° C., and the solvent was distilled off under reduced pressure. Ethanol was added to the mixture, and the insolubles were filtered off, and the solvent was distilled off under reduced pressure. To the obtained residue was added methanol-ethyl acetate, and basic silica gel was added to the mixture. This mixture was purified by basic silica gel column chromatography to obtain solid, which was recrystallized from diisopropyl ether-ethyl acetate, to give 5-hydroxymethyl-1-isobutylimidazole (2.86 g) as brown crystals.

$^1$H-NMR (300 MHz, CDCl$_3$) δ 0.94 (6H, d, J=6.6 Hz), 2.05 to 2.19 (1H, m), 3.80 (2H, d, J=7.5 Hz), 4.62 (2H, s), 6.96 (1H, s), 7.44 (1H, s).

Reference Example 277

To 5-hydroxymethyl-1-isobutylimidazole (2.5 g), thionyl chloride (20 ml) was added by portions at 0° C., and the mixture was heated for 30 minutes under nitrogen atmosphere at 90° C. The mixture was allowed to be at room temperature. The solvent was distilled off under reduced pressure and the obtained residue was dissolved in methanol and the solvent was distilled off again under reduced pressure. The obtained solid was recrystallized from ethyl acetate, to give 5-chloromethyl-1-isobutylimidazole hydrochloride (3.0 g) as colorless crystals.

$^1$H-NMR (200 MHz, DMSO-$d_6$) δ 0.94 (6H, d, J=6.6 Hz), 2.18 to 2.31 (1H, m), 4.06 (2H, d, J=7.8 Hz), 5.02 (2H, s), 7.84 (1H, s), 9.24 (1H, s)

Elemental Analysis $C_7H_{10}N_2Cl_2$ 0.1H$_2$O. Calcd. C, 45.56; H, 6.79; N, 13.28. Found: C, 45.46; H, 6.81; N, 13.43.

Reference Example 278

A mixture of potassium thiocyanate (29.4 g), dihydroxyacetone dimer (18.1 g), and isopropylamine hydrochloride (25.0 g) was added by portions to a mixed solution of acetic acid (21.8 ml) and 1-butanol (145 ml). The mixture was stirred for 7 days at room temperature, and water was added to the mixture, and the mixture was extracted with ethyl acetate. The organic layer was dried over magnesium sulfate, and the solvent was distilled off under reduced pressure. The obtained solid was washed with ethyl acetate, to give 5-hydroxymethyl-1-isopropyl-2-mercaptoimidazole (16.0 g) as colorless crystals.

$^1$H-NMR (200 MHz, DMSO-$d_6$) δ 1.45 (6H, d, J=7.0 Hz), 4.38 (2H, d, J=5.2 Hz), 4.95 to 5.09 (1H, m), 5.21 (1H, t, J=5.2 Hz), 6.75 (1H, s), 11.89 (1H, br).

Elemental Analysis $C_7H_{12}N_2OS$ Calcd. C, 48.81; H, 7.02; N, 16.26. Found: C, 48.50; H, 7.05; N, 16.32.

Reference Example 279

To 5.0M nitric acid (81 ml) was added sodium nitrite (248 mg), and 5-hydroxymethyl-1-isopropyl-2-mercaptoimidazole (15.5 g) was added by portions at 0° C. The mixture was allowed to be at room temperature and the mixture was stirred for 2 hours, and water (100 ml) was added to the mixture. The mixture was neutralized with potassium carbonate at 0° C., and the solvent was distilled off under reduced pressure. Ethanol was added to the mixture, and the insolubles were filtered off, and the solvent was distilled off under reduced pressure. To the obtained residue was added methanol-ethyl acetate, and basic silica gel was added to the mixture. This mixture was purified by basic silica gel column chromatography (methanol-ethyl acetate=1:8) to obtain solid, which was recrystallized from diisopropyl ether-ethyl acetate, to give 5-hydroxymethyl-1-isopropylimidazole (4.84 g) as brown crystals.

$^1$H-NMR (200 MHz, CDCl$_3$) δ 1.50 (6H, d, J=6.6 Hz), 4.47 to 4.61 (1H, m), 4.62 (2H, s), 6.86 (1H, s), 7.54 (1H, s Hz).

Reference Example 280

To 5-hydroxymethyl-1-isopropylimidazole (4.5 g), thionyl chloride (20 ml) was added by portions at 0° C., and the mixture was heated for 30 minutes under nitrogen atmosphere at 90° C. The mixture was allowed to be at room temperature. The solvent was distilled off under reduced pressure and the obtained residue was dissolved in methanol and the solvent was distilled off again under reduced pressure. The obtained solid was recrystallized from ethyl acetate, to give 5-chloromethyl-1-isopropylimidazole hydrochloride (6.2 g) as colorless crystals.

$^1$H-NMR (200 MHz, DMSO-$d_6$) δ 1.53 (6H, d, J=6.6 Hz), 4.64 to 4.78 (1H, m), 5.08 (2H, s), 7.80 (1H, s), 9.45 (1H, s).

Elemental Analysis $C_7H_{12}N_2Cl_2$ Calcd. C, 43.10; H, 6.20; N, 14.36. Found: C, 42.87; H, 6.19; N, 14.37.

Reference Example 281

A mixture of potassium thiocyanate (10.4 g), dihydroxyacetone dimer (6.4 g) and cyclopropylmethylamine hydrochloride (10.0 g) was added by portions to a mixed solution of acetic acid (7.7 ml) and 1-butanol (52 ml). The mixture was stirred for 2 weeks at room temperature, water (10 ml) was added to the mixture and the mixture was stirred for 30 minutes. The precipitated solid was collected by filtration, and further washed with water (15 ml) twice and hexane once. The obtained solid was dried under reduced pressure, to give 1-cyclopropylmethyl-5-hydroxymethyl-2-mercaptoimidazole (9.6 g) as colorless crystals.

¹H-NMR (300 MHz, DMSO-d₆) δ 0.40 to 0.51 (4H, m), 1.30 to 1.42 (1H, m), 3.92 (2H, d, J=7.2 Hz), 4.37 (2H, d, J=3.4 Hz), 5.23 (1H, t, J=3.4 Hz), 6.80 (1H, s), 11.99 (1H, br).

Elemental Analysis C₈H₁₂N₂OS.0.25H₂O Calcd. C, 50.90; H, 6.67; N, 14.84. Found: C, 50.96; H, 6.54; N, 14.95.

Reference Example 282

To 5.0M nitric acid (44 ml) was added sodium nitrite (135 mg), and 1-cyclopropylmethyl-5-hydroxymethyl-2-mercaptoimidazole (9.0 g) was added by portions at 0° C. The mixture was allowed to be at room temperature and the mixture was stirred for 2 hours, and water (50 ml) was added to the mixture. The mixture was neutralized with potassium carbonate at 0° C., and the solvent was distilled off under reduced pressure. Ethanol was added to the mixture, and the insolubles were filtered off, and the solvent was distilled off under reduced pressure. To the obtained residue was added methanol-ethyl acetate, and basic silica gel was added to the mixture. This mixture was purified by basic silica gel column chromatography (methanol-ethyl acetate=1:8), to obtain solids, which was recrystallized from diisopropyl ether-ethyl acetate, to give 1-cyclopropylmethyl-5-hydroxymethylimidazole (4.82 g) as brown crystals.

¹H-NMR (200 MHz, CDCl₃) δ 0.33 to 0.41 (2H, m), 0.63 to 0.72 (2H, m), 1.20 to 1.40 (1H, m), 3.86 (2H, d, J=7.0 Hz), 4.63 (2H, s), 6.89 (1H, s), 7.58 (1H, s).

Reference Example 283

To 1-cyclopropylmethyl-5-hydroxymethylimidazole (4.5 g) was added thionyl chloride (30 ml) by portions at 0° C., and the mixture was heated for 30 minutes under nitrogen atmosphere at 90° C. The mixture was allowed to be at room temperature. The solvent was distilled off under reduced pressure and the obtained residue was dissolved in methanol, and the solvent was distilled off again under reduced pressure. The obtained solid was recrystallized from ethyl acetate, to give 5-chloromethyl-1-cyclopropylmethylimidazole hydrochloride (4.5 g) as colorless crystals.

¹H-NMR (200 MHz, DMSO-d₆) δ 0.47 to 0.70 (4H, m), 1.35 to 1.55 (1H, m), 4.09 (2H, d, J=7.8 Hz),: 5.05 (2H, s), 7.83 (1H, d, J=1.6 Hz), 9.27 (1H, d, J=1.6 Hz).

Elemental Analysis C₈H₁₂N₂Cl₂.0.1H₂O Calcd. C, 46.00; H, 5.89; N, 13.41. Found: C, 45.92; H, 5.74; N, 13.24.

Reference Example 284

To a suspension of 60% sodium hydride (3.12 g) which had been washed before with hexane in DMF (100 ml), ethyl 4-methylimidazole-5-carbonate (10.0 g) was added by portions at 0° C. The mixture was allowed to be at room temperature and stirred for 1 hour under nitrogen atmosphere, and then, 1-iodopropane (13.9 g) was added dropwise to the mixture. After the mixture was stirred for 1 hour, water was added to the mixture, and the mixture was extracted with ethyl acetate twice. The organic layer was dried over magnesium sulfate, and the solvent was distilled off under reduced pressure. The obtained residue was separated and separated and purified by basic silica gel column chromatography (hexane-ethyl acetate=0.3:1), to give ethyl 4-methyl-1-propylimidazole-5-carbonate (4.31 g) and ethyl 5-methyl-1-propylimidazole-4-carbonate (8.25 g).

ethyl 4-methyl-1-propylimidazole-5-carbonate

¹H-NMR (200 MHz, CDCl₃) δ 0.91 (3H, t, J=7.4 Hz), 1.39 (3H, t, J=7.2 Hz), 1.69 to 1.87 (2H, m), 2.49 (3H, s), 4.19 (2H, t, J=7.4 Hz), 4.33 (2H, q, J=7.2 Hz), 7.44 (1H, s).

ethyl 5-methyl-1-propylimidazole-4-carbonate

¹H-NMR (200 MHz, CDCl₃) δ 0.95 (3H, t, J=7.4 Hz), 1.40 (3H, t, J=7.4 Hz), 1.67 to 1.86 (2H, m), 2.54 (3H, s), 3.84 (2H, t, J=7.4 Hz), 4.38 (2H, q, J=7.4 Hz), 7.40 (1H, s).

Reference Example 285

To a suspension of aluminum lithium hydride (774 mg) in THF (40 ml), a solution of ethyl 4-methyl-1-propylimidazole-5-carbonate (4.0 g) in THF (40 ml) was added dropwise at 0° C. under nitrogen atmosphere. The mixture was allowed to be at room temperature and the mixture was stirred for 2 hours, and water (0.8 ml), 15% aqueous solution of sodium hydroxide (0.8 ml) and water (2.4 ml) were sequentially added to the mixture at 0° C. The mixture was allowed to be at room temperature and then., the mixture was stirred overnight and was dried over magnesium sulfate. The insolubles were filtered off, and the solvent was distilled off under reduced pressure to give 5-hydroxymethyl-4-methyl-1-propylimidazole (2.56 g) as colorless oil.

H-NMR (200 MHz, CDCl₃) δ 0.95 (3H, t, J=7.2 Hz), 1.73 to 1.91 (2H, m), 2.19 (3H, s), 3.92 (2H, t, J=7.0 Hz), 4.60 (2H, s), 7.36 (1H, s).

Reference Example 286

To 5-hydroxymethyl-4-methyl-1-propylimidazole (2.4 g) was added thionyl chloride (10 ml) at 0° C., and the mixture was heated for 30 minutes at 90° C. The mixture was allowed to be at room temperature. The solvent was distilled off under reduced pressure and the obtained residue was dissolved in methanol. The solvent was distilled off again under reduced pressure, to give 5-chloromethyl-4-methyl-1-propylimidazole hydrochloride (3.13 g) as brown oil.

¹H-NMR (300 MHz, DMSO-d₆) δ 0.91 (3H, t, J=7.5 Hz), 1.80 to 1.92 (2H, m), 2.34 (3H, s), 4.16 (2H, t, J=7.8 Hz), 5.07 (2H, s), 9.16 (1H, s).

Reference Example 287

To a suspension of 60% sodium hydride (3.12 g) which had been washed before with hexane three times in THF (400 ml), 4-formylimidazole (5.0 g) was added, and the mixture was refluxed for 2 hours under nitrogen atmosphere. After the mixture was allowed to be at room temperature, 1-iodopropane (88.4 g) was added to the mixture and the mixture was further refluxed for 2 hours. The mixture was allowed to be at room temperature, the insolubles were filtered off, and the solvent was distilled off under reduced pressure. To the obtained residue was added water, and the mixture was extracted with ethyl acetate three times. The organic layer was dried over magnesium sulfate and the solvent was distilled off under reduced pressure. The obtained residue was purified by silica gel column chromatography (methanol-ethyl acetate=1:8) to give 1-propylimidazole-4-carboxyaldehyde (4.45 g) as brown oil.

¹H-NMR (200 MHz, CDCl₃) δ 0.96 (3H, t, J=7.2 Hz), 1.77 to 1.95 (2H, m), 3.97 (2H, t, J=7.2 Hz), 7.56 (1H, s), 7.63 (1H, s), 9.88 (1H, s).

Elemental Analysis C₃₇H₄₃N₃O₃S₂ Calcd. C, 69.23; H, 6.75; N, 6.55. Found: C, 69.34; H, 6.79; N, 6.60.

Reference Example 288

To a suspension of aluminum lithium hydride (971 mg) in THF (35 ml), a solution of 1-propylimidazole-4-carboxyaldehyde (3.5 g) in THF (35 ml) was added dropwise at 0° C.

under nitrogen atmosphere. After finishing the dropping, water (1.0 ml), 15% aqueous solution of sodium hydroxide (1.0 ml) and water (3.0 ml) were sequentially added to the solution at 0° C., and the mixture was stirred for 2 hours at room temperature. The mixture was dried over magnesium sulfate, and the insolubles were filtered off. The solvent was distilled off under reduced pressure to give 4-hydroxymethyl-1-propylimidazole (3.09 g) as yellow oil.

$^1$H-NMR (200 MHz, CDCl$_3$) δ 0.93 (3H, t, J=7.4 Hz), 1.71 to 1.89 (2H, m), 3.80 (2H, t, J=7.0 Hz), 4.60 (2H, s), 6.87 (1H, d, J=1.4 Hz), 7.42 (1H, d, J=1.4 Hz).

Reference Example 289

To 4-hydroxymethyl-1-propylimidazole (2.5 g), thionyl chloride (25 ml) was added by portions at 0° C., and the mixture was heated for 30 minutes under nitrogen atmosphere at 90° C. The mixture was allowed to be at room temperature. The solvent was distilled off under reduced pressure and the obtained residue was dissolved in methanol. The solvent was distilled off again under reduced pressure, to give 4-chloromethyl-1-propylimidazole hydrochloride (3.47 g) as brown oil.

$^1$H-NMR (200 MHz, DMSO-d$_6$) δ 0.85 (3H, t, J=7.4 Hz), 1.60 to 2.00 (2H, m), 4.13 (2H, t, J=6.6 Hz), 4.88 (2H, s), 7.84 (1H, s), 9.16 (1H, s).

Reference Example 290

To a solution of 1-propylimidazole-2-carboxyaldehyde (2.5 g) in dry THF (25 ml), 1.14M methyllithium diethyl-ether solution (20.6 ml) was added dropwise at −78° C. under argon atmosphere. After finishing the dropping, the mixture was allowed to be at room temperature and was stirred for 1 hour. 1N hydrochloric acid was added to make it acidic at 0° C., and the mixture was neutralized with potassium carbonate. The mixture was extracted with ethyl acetate four times, and dried over magnesium sulfate. The solvent was distilled off under reduced pressure, to give 2-(1-hydroxy) ethyl-1-propylimidazole (2.45 g) as oil.

$^1$H-NMR (200 MHz, CDCl$_3$) δ 0.96 (3H, t, J=7.4 Hz), 1.63 (3H, d, J=6.6 Hz), 1.72 to 1.91 (2H, m), 3.94 (2H, dt, J=7.4, 3.2 Hz), 4.90 (1H, q, J=6.6 Hz), 6.88 (1H, s), 6.96 (1H, s).

Reference Example 291

To 2-(1-hydroxy) ethyl-1-propylimidazole (1.5 g), thionyl chloride (15 ml) was added by portions at 0° C., and the mixture was heated for 1 hour under nitrogen atmosphere at 90° C. The mixture was allowed to be at room temperature. The solvent was distilled off under reduced pressure and the obtained residue was dissolved in methanol. The solvent was distilled off again under reduced pressure, to give as 2-(1-chloro) ethyl-1-propylimidazole hydrochloride (2.03 g) brown oil.

$^1$H-NMR (200 MHz, DMSO-d$_6$) δ 0.91 (3H, t, J=7.6 Hz), 1.77 to 1.89 (2H, m), 2.00 (3H, d, J=7.0 Hz), 4.00 to 4.40 (4H, m), 7.81 (1H, d, J=2.0 Hz), 7.86 (1H, d, J=2.0 Hz).

Reference Example 292

To a solution of 1-methylimidazole (13.0 g) in dry THF (100 ml), 1.6M n-butyllithium hexane solution (119 ml) was added at 0° C. under argon atmosphere. The mixture was allowed to be at room temperature, stirred for 1 hour, and a solution of 4-nitrobenzaldehyde (23.9 g) in dry THF (150 ml) was added dropwise to the mixture at 0° C. After the mixture was allowed to be at room temperature and stirred for 30 minutes, 1N hydrochloric acid was added to the mixture at 0° C. The mixture was neutralized with potassium carbonate, and extracted with ethyl acetate. The organic layer was dried over magnesium sulfate, and the solvent was distilled off under reduced pressure. The obtained residue was purified by silica gel column chromatography (methanol-ethyl acetate=1:8) and recrystallized from hexane-ethyl acetate, to give. [2-(1-methyl)imidazolyl](4-nitrophenyl)methanol (13.9 g) as brown crystals.

$^1$H-NMR (200 MHz, CDCl$_3$) δ 3.43 (3H, s), 5.98 (1H, s), 6.78 (1H, s), 6.86 (1H, s), 7.53 (2H, d, J=8.8 Hz), 8.19 (2H, d, J=8.8 Hz).

Reference Example 293

[2-(1-methyl)imidazolyl](4-nitrophenyl)methanol (8.0 g), reduced iron (9.6 g) and calcium chloride (1.91 g) were added to 85% aqueous solution of ethanol, and the mixture was refluxed for 4 hours under nitrogen atmosphere. After the mixture was allowed to be at room temperature, ethyl acetate was added to the mixture and the insolubles were filtered off. To the filtrate was added water, the organic layer was separated, and the aqueous layer was extracted with ethyl acetate. The organic layer was dried over magnesium sulfate, and the solvent was distilled off under reduced pressure. The obtained solid was recrystallized from ethyl acetate-diisopropyl ether, to give (4-aminophenyl)[2-(1-methyl)imidazolyl]methanol (2.21 g) as brown crystals.

$^1$H-NMR (200 MHz, CDCl$_3$) δ 3.37 (3H, s), 5.72 (1H, s), 6.65 (2H, d, J=8.4 Hz), 6.83 (1H, s), 6.99 (1H, s), 7.08 (2H, d, J=8.4 Hz).

Reference Example 294

To a solution of 1-propylimidazole (8.0 g) in dry THF (100 ml), 1.6M n-butyllithium hexane solution (54.5 ml) was at 0° C. under argon atmosphere. After the mixture was allowed to be at room temperature and was stirred for 2 hours, a solution of 4-nitrobenzaldehyde (9.97 g) in dry THF (100 ml) was added dropwise to the mixture at −78° C. The mixture was allowed to be at room temperature and was stirred overnight, and then, 1N hydrochloric acid was added to the mixture at 0° C. The mixture was neutralized with potassium carbonate, and extracted with ethyl acetate. The organic layer was washed with saturated brine, and dried over magnesium sulfate. The solvent was distilled off under reduced pressure and the obtained residue was recrystallized from ethyl acetate-diisopropyl ether, to give (4-nitrophenyl)[2-(1-propyl)imidazolyl]methanol (5.26 g) as brown crystals.

$^1$H-NMR (200 MHz, CDCl$_3$) δ 0.77 (3H, t, J=7.4 Hz), 1.42 to 1.72 (2H, m), 3.70 (2H, t, J=7.4 Hz), 5.99 (1H, s), 6.86 (1H, s), 6.94 (1H, s), 7.54 (2H, d, J=8.8 Hz), 8.20 (2H, d, J=8.8 Hz).

Elemental Analysis C$_{13}$H$_{15}$N$_3$O$_3$ Calcd. C, 59.76; H, 5.79; N, 16.08. Found: C, 59.85; H, 7.73; N, 16.04.

Reference Example 295

To a mixed solution of (4-nitrophenyl)[2-(1-propyl)imidazolyl]methanol (4.5 g) in methanol (150 ml) and ethanol (100 ml), 10% palladium carbon (450 mg) was added, and the mixture was stirred for 4 hours under hydrogen atmosphere. The insolubles were filtered off, and the residue was purified by basic silica gel column chromatography (methanol-ethyl acetate=1:8) and recrystallized from ethyl acetate-diisopropyl ether, to give (4-aminophenyl)[2-(1-propyl)imidazolyl]methanol (3.52 g) as brown crystals.

$^1$H-NMR (200 MHz, CDCl$_3$) δ 0.77 (3H, t, J=7.4 Hz), 1.45 to 1.65 (2H, m), 3.61 (2H, t, J=7.4 Hz), 5.68 (1H, s), 6.64 (2H, d, J=8.4 Hz), 6.85 (1H, d, J=1.4 Hz), 7.01 (1H, d, J=1.4 Hz), 7.08 (2H, d, J=8.4 Hz).

Elemental Analysis C$_{13}$H$_{17}$N$_3$O 0.25H$_2$O. Calcd. C, 66.22; H, 7.48; N, 17.82. Found: C, 66.35; H, 7.09; N, 17.78.

Reference Example 296

Methyl 7-bromo-1-propyl-2,3-dihydro-1-benzazepine-4-carbonate (10.0 g), 4-(2-propoxyethoxy)phenylboric acid (8.96 g) and potassium carbonate (11.1 g) were added to a mixed solution of toluene (150 ml), ethanol (15 ml) and water (15 ml), and the mixture was stirred for 1 hour under argon atmosphere. Tetrakistriphenylphosphine palladium (1.78 g) was added to the mixture, and the mixture was refluxed for 2 hours under argon atmosphere. After the mixture was allowed to be at room temperature, water was added to the mixture, and the mixture was extracted with ethyl acetate. The organic layer was washed with saturated brine and dried over magnesium sulfate. The solvent distilled off under reduced pressure and the residue was purified by silica gel column chromatography (hexane-ethyl acetate=9:1) and recrystallized from hexane-ethyl acetate to give methyl 7-[4-(2-propoxyethoxy)phenyl]-1-propyl-2,3-dihydro-1-benzazepine-4-carbonate (9.25 g) as yellow crystals.

$^1$H-NMR (200 MHz, CDCl$_3$) δ 0.91 to 1.01 (6H, m), 1.56 to 1.80 (2H, m), 2.82 (2H, t, J=4.4 Hz), 3.26 to 3.34 (4H, m), 3.51 (2H, t, J=6.6 Hz), 3.79 to 3.84 (5H, m), 4.16 (2H, t, J=4 Hz), 6.87 (1H, d, J=8.8 Hz), 6.97 (2H, d, J=8.8 Hz), 7.37 to 7.51 (4H, m), 7.76 (1H, s).

Reference Example 297

Methyl 7-[4-(2-propoxyethoxy)phenyl]-1-propyl-2,3-dihydro-1-benzazepine-4-carbonate (9.0 g) was dissolved in a mixed solution of THF (100 ml) and methanol (100 ml), and 1N aqueous solution of sodium hydroxide (43 ml) was added to the mixture at 0° C. After the mixture was stirred overnight at 60° C., the mixture was allowed to be at room temperature, water was added to the mixture, and 1N hydrochloric acid was added to neutralize the mixture at 0° C. The mixture was extracted with ethyl acetate, water and saturated brine. The organic layer was dried over magnesium sulfate, and the solvent was distilled off under reduced pressure. The obtained residue was recrystallized from hexane-ethyl acetate, to give 7-[4-(2-propoxyethoxy)phenyl]-1-propyl-2,3-dihydro-1-benzazepine-4-carboxylic acid (8.0 g) as yellow crystals.

$^1$H-NMR (200 MHz, CDCl$_3$) δ 0.91 to 1.02 (6H, m), 1.56 to 1.80 (4H, m), 2.80 to 2.90 (2H, m), 3.28 to 3.35 (4H, m), 3.52 (2H, t, J=6.6 Hz), 3.81 (2H, t, J=4.4 Hz), 4.17 (2H, t, J=4.4 Hz), 6.88 (1H, d, J=8.8 Hz), 6.98 (2H, d, J=8.8 Hz), 7.39 to 7.53 (4H, m), 7.89 (1H, s).

Reference Example 298

1-fluoro-4-nitrobenzene (5.0 g), 2-mercapto-1-methylimidazole (4.04 g) and potassium carbonate (14.7 g) were added to. DMF (100 ml), and the mixture was stirred for 2 hours under argon atmosphere at 130° C. After the mixture was allowed to be at room temperature, water was added to the mixture, and the mixture was extracted with ethyl acetate. The organic layer was washed with water three times, further washed with saturated brine, and dried over magnesium sulfate. The solvent was distilled off under reduced pressure, and the obtained residue was recrystallized from ethyl acetate-diisopropyl ether, to give 1-methyl-2-[(4-nitrophenyl)thio]imidazole (7.29 g) as yellow crystals.

$^1$H-NMR (200 MHz, CDCl$_3$) δ 3.69 (3H, s), 7.13 (2H, d, J=8.8 Hz), 7.19 (1H, s), 7.29 (1H, s), 8.10 (2H, d, J=8.8 Hz).

Elemental Analysis C$_{10}$H$_9$N$_3$O$_2$S Calcd. C, 51.05; H, 3.86; N, 17.86. Found: C, 50.98; H, 3.72; N, 17.86.

Reference Example 299

1-methyl-2-[(4-nitrophenyl)thio]imidazole (6.0 g), reduced iron (7.12 g) and calcium chloride (1.42 g) were added to 85% aqueous solution of ethanol (100 ml), and the mixture was stirred for 6 hours at 105° C. under nitrogen atmosphere. The mixture was allowed to be at room temperature, the insolubles were filtered off, and the solvent was distilled off under reduced pressure. To the obtained residue was added water and the mixture extracted with ethyl acetate twice. The organic layer was dried over magnesium sulfate, and the solvent was distilled off under reduced pressure. The obtained residue was recrystallized from ethyl acetate-diisopropyl ether, to give 2-[(4-aminophenyl)thio]-1-methylimidazole (4.38 g) as yellow crystals.

$^1$H-NMR (200 MHz, CDCl$_3$) δ 3.63 (3H, s), 3.77 (2H, br), 6.59 (2H, d, J=8.8 Hz), 6.97 (1H, d, J=1.2 Hz), 7.08 (1H, d, J=1.2 Hz), 7.18 (2H, d, J=8.8 Hz).

Elemental Analysis. C$_{10}$H$_{11}$N$_3$S Calcd. C, 58.51; H, 5.40; N, 20.47. Found: C, 58.29; H, 5.31; N, 20.42.

Reference Example 300

To a suspension of 60% sodium hydride (1.7 g) which had been washed three times with hexane in DMF (30 ml), 2-mercapto-4-methyl-1,2,4-triazole (4.08 g) in DMF (20 ml) was added dropwise under nitrogen atmosphere at 0° C. After the mixture was allowed to be at room temperature, the mixture was stirred for 1 hour. Then, a solution of 1-fluoro-4-nitrobenzene (5.0 g) in DMF (50 ml) was added dropwise to the mixture at 0° C., and the mixture was stirred for 2 hours at 130° C. The mixture was allowed to be at room temperature, water was added to the mixture, and the mixture was extracted with ethyl acetate. The organic layer was washed with water three times, further washed with saturated brine, and dried over magnesium sulfate. The solvent was distilled off under reduced pressure and the obtained residue was purified with silica gel column chromatography (ethyl acetate methanol-ethyl acetate=1:9) and recrystallized from ethyl acetate-diisopropyl ether, to give 4-methyl-3-[(4-nitrophenyl)thio]-1,2,4-triazole (1.7 g) as crystals.

$^1$H-NMR (200 MHz, CDCl$_3$) δ 3.68 (3H, s), 7.97 (1H, s), 8.35 (2H, d, J=8.8 Hz), 8.53 (2H, d, J=8.8 Hz).

Elemental Analysis C$_9$H$_8$N$_4$O$_2$S Calcd. C, 45.75; H, 3.41; N, 23.71. Found: C, 45.73; H, 3.21; N, 23.78.

Reference Example 301

4-methyl-3-[(4-nitrophenyl)thio]-1,2,4-triazole (1.0 g), reduced iron (1.18 g) and calcium chloride (2.35 g) were added to 85% aqueous solution of ethanol (15 ml), and the mixture was stirred for 6 hours under nitrogen atmosphere at 105° C. The mixture was allowed to be at room temperature, the insolubles were filtered off, and the solvent was distilled off under reduced pressure. To the obtained residue were added water, and the mixture extracted with ethyl acetate twice. The organic layer was dried over magnesium sulfate, and the solvent was distilled off under reduced pressure. The obtained residue was recrystallized from ethyl acetate-diisopropyl ether, to give 3-[(4-aminophenyl)thio]-1-methyl-1,2,4-triazole (418 mg) as yellow crystals.

¹H-NMR (200 MHz, CDCl₃) δ 3.66 (3H, s), 3.84 (2H, br), 6.74 (2H, d, J=8.8 Hz), 7.63 (2H, d, J=8.8 Hz), 7.87 (1H, s).

Reference Example 302

Dihydroxyacetone (10.2 g), potassium thiocyanate (16.5 g) and n-butylamine hydrochloride (16 g) were added to acetic acid (12 ml) and 1-butanol (80 ml), and the mixture was stirred overnight at room temperature. The mixture was concentrated, ethanol was added to the mixture, and colorless crystal (17.3 g) was collected by filtration and washed with water. Sodium nitrite (0.12 g) was dissolved in nitric acid (25 ml) and water (25 ml), and the obtained crystals were added by portions to the solution under ice-cooling. The mixture was stirred for 1.5 hours at room temperature and neutralized with potassium carbonate, and then, the solvent was evaporated. Ethanol was added to the residue, the insolubles were filtered off, and the solvent of the filtrate was evaporated. The residue was purified by basic silica gel column chromatography (extraction solvent: methanol/ethyl acetate), to give colorless crystals (6.1 g). The obtained crystals were added to thionyl chloride (20 ml) under ice-cooling, and the mixture was refluxed for 1 hour. The solvent was evaporated, to give 4-chloromethyl-3-butylimidazole hydrochloride (7.6 g) as colorless crystals.

¹H-NMR (dppm, DMSO-d₆) δ 0.93 (3H, t, J=7.3 Hz), 1.24 to 1.43 (2H, m), 1.78 to 1.93 (2H, m), 4.21 (2H, t, J=7.5 Hz), 5.04 (2H, s), 7.81 (1H, d, J=1.4 Hz), 9.26 (1H, d, J=1.4 Hz).

Reference Example 303

To a solution of 3-bromo-5,6,7,8-tetrahydroimidazo[1,2-a]pyridine (2.84 g) in THF (50 ml), n-butyllithium (1.6M hexane solution, 28 ml) was added dropwise at −78° C. The mixture was stirred for 1 hour at −78° C., DMF (5 ml) was added to the mixture, and the mixture was stirred for 0.5 hour at room temperature. To the reaction solution was added water, and the mixture was extracted with ethyl acetate. The organic layer was washed with saturated brine, dried over magnesium sulfate, and concentrated under reduced pressure. The obtained residue was separated and purified by column chromatography (ethyl acetate:hexane 1:1→ethyl acetate), to give 3-formyl-5,6,7,8-tetrahydroimidazo[1,2-a]pyridine (1.48 g) as colorless oil.

¹H-NMR (200 MHz, CDCl₃) δ 1.87 to 2.09 (4H, m), 2.96 (2H, t, J=6.0 Hz), 4.33 (2H, t, J=5.4 Hz), 7.72 (1H, s), 9.66 (1H, s).

Reference Example 304

To a suspension of aluminum lithium hydride (0.40 g) in THF (30 ml), 3-formyl-5,6,7,8-tetrahydroimidazo[1,2-a]pyridine (1.48 g) in. THF (50 ml) was added dropwise at 0° C. The mixture was stirred for 1 hour at 0° C., and water (0.4 ml), 15% aqueous solution of sodium hydroxide (0.4 ml) and water (1.2 ml) were added dropwise to the mixture. The mixture was stirred at room temperature for 18 hours, magnesium sulfate was added to the mixture, and the precipitates were removed by filtration. The solvent was concentrated under reduced pressure, and the precipitated crystals were collected by filtration. The crystals were washed with diisopropyl ether, to give 5,6,7,8-tetrahydroimidazo[1,2-a]pyridine-3-methanol (1.24 g) as colorless crystals.

¹H-NMR (200 MHz, CDCl₃) δ 1.80 to 2.06 (4H, m), 2.85 (2H, t, J=6.2 Hz), 3.99 (2H, t, J=5.8 Hz), 4.58 (2H, s), 6.85 (1H, s).

IR (KBr) 3086, 1495, 1431, 1329, 1130, 1026, 941, 860, 816, 770 cm⁻

Reference Example 305

To 5,6,7,8-tetrahydroimidazo[1,2-a]pyridin-3-yl methanol (1.0 g), thionyl chloride (5 ml) was added at 0° C. After heating to reflux for 40 minutes, the mixture was concentrated under reduced pressure. To the residue was added ethyl acetate, and the precipitated crystals were collected by filtration. The crystals were washed with ethyl acetate, to give 3-(chloromethyl)-5,6,7,8-tetrahydroimidazo[1,2-a]pyridine hydrochloride (1.03 g) as pale yellow crystals.

¹H-NMR (200 MHz, DMSO-d₆) δ 1.81 to 2.07 (4H, m), 3.00 (2H, t, J=6.2 Hz), 4.12 (2H, t, J=5.7 Hz), 5.00 (2H, s), 7.70 (1H, s).

IR (KBr) 1630, 1524, 1308, 1296 cm⁻¹

Reference Example 306

A mixture of 4-nitrothiophenol (1.44 g), 5-methylimidazo[1,2-a]pyridin-3-yl methanol (1.5 g), concentrated hydrochloric acid (15 ml) and acetic acid (15 ml) was stirred for 24 hours at 100° C. The mixture was neutralized with 12N sodium hydroxide at 0° C., and extracted with ethyl acetate. The organic layer was washed with saturated brine, dried over magnesium sulfate, and concentrated under reduced pressure. The obtained residue was separated and purified by column chromatography (ethanol:ethyl acetate 1:9), to give 5-methyl-3-[[(4-nitrophenylthio)methyl]imidazo[1,2-a]pyridine (2.03 g) as yellow crystals.

mp 167 to 169° C.

¹H-NMR (200 MHz, CDCl₃) δ 3.00 (3H, s), 4.76 (2H, s), 6.59 (1H, d, J=6.8 Hz), 7.12 (1H, dd, J=9.0, 6.8 Hz), 7.38 (2H, d, J=9.0 Hz), 7.47 to 7.52 (2H, m), 8.16 (2H, d, J=9.0 Hz).

IR (KBr) 1593, 1574, 1503, 1335, 1292, 1092, 853, 783, 743 cm⁻¹

Elemental Analysis C₁₅H₁₃N₃O₂S Calcd. C, 60.18; H, 4.38; N, 14.04. Found: C, 60.10; H, 4.50; N, 14.01.

Reference Example 307

A mixture of 5-methyl-3-[(4-nitrophenylthio) methyl]imidazo[1,2-a]pyridine (1.80 g), reduced iron (1.68 g) and calcium chloride (0.33 g) in 15% water-containing ethanol (54 ml) was heated to reflux for 24 hours. The insolubles were removed by filtration, and the filtrate was concentrated under reduced pressure. The residue was extracted with ethyl acetate, washed with saturated brine, and dried over magnesium sulfate. The solvent was concentrated under reduced pressure. The obtained residue was separated and purified by column chromatography (ethyl acetate:hexane 1:1→2:1), to give 4-[[(5-methylimidazo[1,2-a]pyridin-3-yl)methyl]thio]aniline (1.67 g) as yellow oil.

¹H-NMR (200 MHz, CDCl₃) δ 3.03 (3H, s), 3.56 to 3.92 (2H, m), 4.37 (2H, s), 6.53 to 6.59 (3H, m), 6.98 to 7.10 (4H, m), 7.45 (1H, d, J=8.8 Hz).

IR (neat) 3324, 3206, 1647, 1601, 1535, 1508, 1495, 1292, 1177, 1167, 824 cm⁻¹.

Reference Example 308

A mixture of 4-nitrothiophenol (2.87 g), 6-methylimidazo[1,2-a]pyridin-3-ylmethanol (3.0 g), concentrated hydrochloric acid (60 ml) and acetic acid (60 ml) was stirred for 5 days at 100° C. The mixture was neutralized with 12N sodium hydroxide at 0° C., and extracted with ethyl acetate. The organic layer was washed with saturated brine, dried over magnesium sulfate, and concentrated under reduced pressure. The obtained residue was separated and purified by column chromatography (basic silica gel, ethyl acetate:hexane 2:1→4:1), to give 6-methyl-3-[[(4-nitrophenyl)thio]methyl]imidazo[1,2-a]pyridine (4.48 g) as pale yellow crystals.

mp 127 to 128° C.
$^1$H-NMR (200 MHz, CDCl$_3$) δ 2.39 (3H, s), 4.54 (2H, s), 7.11 (1H, dd, J=9.2, 1.8 Hz), 7.39 (2H, d, J=9.2 Hz), 7.50 (1H, s), 7.55 (1H, d, J=9.2 Hz), 7.88 (1H, d, J=1.8 Hz), 8.14 (2H, d, J=9.2 Hz).

IR (KBr) 1580, 1514, 1343, 1312, 1250, 1090, 853, 833, 797, 743 cm$^{-1}$

Elemental Analysis C$_{15}$H$_{13}$N$_3$O$_2$S Calcd. C, 60.18; H, 4.38; N, 14.04. Found: C, 60.13; H, 4.30; N, 13.82.

Reference Example 309

A mixture of 6-methyl-3-[[(4-nitrophenyl)thio]methyl]imidazo[1,2-a]pyridine (3.0 g), reduced iron (2.80 g) and calcium chloride (0.56 g) in 15% water-containing ethanol (150 ml) was heated to reflux for 20 hours. The insolubles were removed by filtration, and the filtrate was concentrated under reduced pressure. The residue was extracted with ethyl acetate, washed with saturated brine, and dried over magnesium sulfate. The solvent was concentrated under reduced pressure, and the obtained residue was separated and purified by column chromatography (ethyl acetate:hexane 1:1→2:1), to give 4-[[(6-methylimidazo[1,2-a]pyridin-3-yl)methyl]thio]aniline (2.38 g) as pale yellow crystals.

mp 128 to 129° C.
$^1$H-NMR (300 MHz, CDCl$_3$) δ 2.37 (3H, s), 3.68 to 3.76 (2H, m), 4.18 (2H, s), 6.52 (2H, d, J=8.7 Hz), 7.00 (2H, d, J=8.7 Hz), 7.06 (1H, dd, J=9.3, 1.5 Hz), 7.18 (1H, s), 7.51 (1H, d, J=9.3 Hz), 7.85 (1H, d, J=1.5 Hz).

IR (KBr) 3301, 3187, 1636, 1597, 1497, 1312, 1292, 1238, 822, 793 cm$^{-1}$

Elemental Analysis C$_{15}$H$_{15}$N$_3$S Calcd. C, 66.88; H, 5.61; N, 15.50. Found: C, 66.91; H, 5.75; N, 15.17.

Reference Example 310

A mixture of 2-formylimidazole (5.16 g), bromoethyl acetate (7.1 ml) and potassium carbonate (11.1 g) in DMF (50 ml) was stirred for 20 hours at 60° C. The insolubles were removed by filtration, water was added to the mixture, and the mixture was extracted with ethyl acetate. The organic layer was washed with saturated brine, dried over magnesium sulfate, and concentrated under reduced pressure. The obtained residue was separated and purified by column chromatography (ethyl acetate:hexane 1:1), to give ethyl (2-formyl-1H-imidazol-1-yl)acetate (1.10 g) as pale yellow oil.

$^1$H-NMR (200 MHz, CDCl$_3$) δ 1.29 (3H, t, J=7.1 Hz), 4.25 (2H, q, J=7.1 Hz), 5.13 (2H, s), 7.15 (1H, s), 7.33 (1H, d, J=0.6 Hz), 9.79 (1H, d, J=0.6 Hz).

IR (neat) 1752, 1684, 1478, 1416, 1375, 1339, 1302, 1215, 1024, 775 cm$^{-1}$

Reference Example 311

To a solution of ethyl (2-formyl-1H-imidazol-1-yl)acetate (1.10 g) in ethanol (5 ml), sodium borohydride (123 mg) was added at 0° C. The mixture was stirred for 0.5 hour at 0° C., and the reaction mixture were purified by column chromatography (basic silica gel, ethanol:ethyl acetate 1:19) to give ethyl [2-(hydroxymethyl)-1H-imidazol-1-yl]acetate (960 mg) as pale yellow crystals.

$^1$H-NMR (200 MHz, CDCl$_3$) δ 1.30 (3H, t, J=7.2 Hz), 4.24 (2H, q, J=7.2 Hz), 4.66 (2H, s), 4.81 (2H, s), 6.89 (1H, s), 6.95 (1H, s).

IR (KBr) 3119, 1748, 1499, 1292, 1213, 1026, 737 cm$^{-1}$

Reference Example 312

To a solution of ethyl [2-(hydroxymethyl)-1H-imidazol-1-yl] acetate (460 mg) in dichloromethane (10 ml), thionyl chloride (0.27 ml) was added at room temperature. The mixture was stirred at room temperature for 1 hour, and concentrated under reduced pressure. To a solution of the residue in ethanol (10 ml), 4-aminothiophenol (0.33 g) and triethylamine (3.5 ml) were added, the mixture was stirred for 1 hour at room temperature, and concentrated under reduced pressure. The obtained residue was separated and purified by column chromatography (basic silica get, ethyl acetate) to give ethyl [2-[[(4-aminophenyl)thio]methyl]-1H-imidazol-1-yl] acetate (820 mg). This compound was used in the next reaction without further purification.

$^1$H-NMR (200 MHz, CDCl$_3$) δ 1.29 (3H, t, J=7.1 Hz), 3.40 to 3.74 (2H, m), 4.04 (2H, s), 4.24 (2H, q, J=7.1 Hz), 4.71 (2H, s), 6.56 (2H, d, J=8.7 Hz), 6.87 (1H, d, J=1.4 Hz), 6.93 (1H, d, J=1.4 Hz), 7.11 (2H, d, J=8.7 Hz)

Reference Example 313

A mixture of 2-formylimidazole (5.17 g), ethyl 4-bromobutyrate (9.2 ml) and potassium carbonate (11.1 g) in DMF (50 ml) was stirred for 40 hours at 80° C. Water was added to the mixture and the mixture was extracted with ethyl acetate. The organic layer was washed with saturated brine, dried over magnesium sulfate, and concentrated under reduced pressure. The obtained residue was separated and purified by column chromatography (ethyl acetate:hexane 1:1), to give ethyl 4-(2-formyl-1H-imidazol-1-yl) butyrate (8.36 g) as pale yellow oil.

$^1$H-NMR (200 MHz, CDCl$_3$) δ 1.26 (3H, t, J=7.2 Hz), 2.08 to 2.19 (2H, m), 2.29 to 2.36 (2H, m), 4.14 (2H, q, J=7.2 Hz), 4.47 (2H, t, J=7.1 Hz), 7.18 (1H, d, J=1.1 Hz), 2.30 (1H, d, J=1.1 Hz), 9.81 (1H, s).

IR (neat) 1732, 1682, 1476, 1412, 1337, 1188, 1159, 772 cm$^{-1}$

Reference Example 314

To a solution of ethyl 4-(2-formyl-1H-imidazol-1-yl) butyrate (8.36 g) in ethanol (80 ml), sodium borohydride (0.45 g) was added at 0° C. The mixture was stirred for 0.5 hour at 0° C., and 1N hydrochloric acid (15 ml) was added to the reaction solution. The mixture was stirred for 30 minutes at 0° C., triethylamine (10 ml) was added to the mixture, and the mixture was concentrated under reduced pressure. To the residue was added ethanol, and the insolubles were filtered off. The solvent was concentrated under reduced pressure, and the obtained residue was purified by column chromatography (basic silica gel, ethyl acetate→ethanol:ethyl acetate 1:19) to give ethyl 4-[2-(hydroxymethyl)-1H-imidazol-1-yl]butyrate (8.51 g) as pale yellow oil.

$^1$H-NMR (300 MHz, CDCl$_3$) δ 1.26 (3H, t, J=7.2 Hz), 2.08 to 2.17 (2H, m), 2.32 to 2.37 (2H, m), 4.08 (2H, t, J=7.1 Hz), 4.14 (2H, q, J=7.2 Hz), 4.66 (2H, s), 6.87 (1H, d, J=1.5 Hz), 6.91 (1H, d, J=1.5 Hz).

IR (neat) 3113, 1732, 1495, 1466, 1445, 1375, 1277, 1250, 1188, 1154, 1030, 739 cm$^{-1}$ Reference Example 315

To a solution of ethyl 4-[2-(hydroxymethyl)-1H-imidazol-1-yl]butyrate (8.51 g) in chloroform (100 ml), thionyl chloride (4.4 ml) and DMF (1 droplet) were added at room temperature. The mixture was stirred at room temperature for 1 hour, and concentrated under reduced pressure. To a solution of the residue in ethanol (50 ml), 4-aminothiophenol (5.0 g) and triethylamine (17 ml) were added at room temperature. The mixture was stirred for 64 hours, and concentrated under reduced pressure. The obtained residue was separated and purified by column chromatography (basic silica get, ethyl acetate:hexane 1:1→2:1→ethyl acetate), to give ethyl 4-[2-[[(4-aminophenyl)thio]methyl]-1H-imidazol-1-yl]butyrate (10.08 g) as pale yellow crystals.
mp 74 to 75° C.

$^1$H-NMR (200 MHz, CDCl$_3$) δ 1.26 (3H, t, J=7.2 Hz), 1.98 to 2.13 (2H, m), 2.28 to 2.35 (2H, m), 3.64 to 3.80 (2H, m), 3.92 (2H, t, J=7.2 Hz), 4.04 (2H, s), 4.14 (2H, q, J=7.2 Hz), 6.57 (2H, d, J=8.4 Hz), 6.83 (1H, s), 6.92 (1H, s), 7.15 (2H, d, J=8.4 Hz).

IR (KBr) 3428, 3333, 3210, 1742, 1628, 1599, 1501, 1312, 1221, 1211, 1179, 1161, 1127, 1100, 1024, 926, 826 cm$^{-1}$

Elemental Analysis C$_{16}$H$_{21}$N$_3$O$_2$S Calcd. C, 60.16; H, 6.63; N, 13.16. Found: C, 60.00; H, 6.54; N, 13.03.

Reference Example 316

To a solution of ethyl [5-(hydroxymethyl)-1H-imidazol-1-yl] acetate (1.66 g) in chloroform (10 ml), thionyl chloride (0.98 ml) and DMF (1 droplet) were added at room temperature. The mixture was stirred at room temperature for 1 hour, and concentrated under reduced pressure. To a solution of the residue in ethanol (20 ml), 4-aminothiophenol (1.35 g) and triethylamine (7.5 ml) were added to the mixture. The mixture was stirred at room temperature for 20 hours, and concentrated under reduced pressure. The residue was separated and purified by basic silica gel column chromatography (ethyl acetate→ethanol:ethyl acetate 1:9), to give ethyl [5-[[(4-aminophenyl)thio]methyl]-1H-imidazol-1-yl] acetate (2.20 g) as pale yellow crystals.
mp 91 to 92° C.

$^1$H-NMR (200 MHz, CDCl$_3$) δ 1.30 (3H, t, J=7.2 Hz), 3.65 to 3.78 (2H, m), 3.85 (2H, s), 4.25 (2H, q, J=7.2 Hz), 4.77 (2H, s), 6.56 (2H, d, J=8.8 Hz), 6.64 (1H, s), 7.06 (2H, d, J=8.8 Hz), 7.46 (1H, s).

IR (KBr) 3428, 3333, 3210, 1742, 1628, 1599, 1501, 1372, 1312, 1221, 1211, 1179, 1161, 1127, 1100, 1024, 926, 826 cm$^{-1}$

Elemental Analysis C$_{14}$H$_{17}$N$_3$O$_2$S Calcd. C, 57.71; H, 5.88; N, 14.42. Found: C, 57.36; H, 5.78; N, 14.31.

Reference Example 317

A mixture of 2-formylimidazole (2.50 g), 2-iodo-ethyl benzoate (8.61 g) and potassium carbonate (5.4 g) in DMF (25 ml) was stirred for 20 hours at 80° C. To the reaction solution was added water, and the mixture was extracted with ethyl acetate. The organic layer was washed with water and saturated brine, dried over magnesium sulfate, and concentrated under reduced pressure. The obtained residue was separated and purified by column chromatography (ethyl acetate:hexane 1:1), to give ethyl 2-(2-formyl-1H-imidazol-1-yl) benzoate (4.69 g) as pale yellow oil.

$^1$H-NMR (200 MHz, CDCl$_3$) δ 4.62 to 4.67 (2H, m), 4.77 to 4.84 (2H, m), 7.21 to 7.22 (1H, m), 7.31 (1H, d, J=0.8 Hz), 7.40 to 7.48 (2H, m), 7.54 to 7.63 (1H, m), 7.93 to 7.98 (2H, m), 9.85 (1H, d, J=0.8 Hz).

IR (neat) 1721, 1682, 1476, 1453, 1412, 1273, 1117, 772, 712 cm$^{-1}$

Reference Example 318

To a solution of ethyl 2-(2-formyl-1H-imidazol-1-yl) benzoate (4.69 g) in 2-propanol (50 ml), sodium borohydride (0.22 g) was added at 0° C. The mixture was stirred for 30 minutes at 0° C., and 1N hydrochloric acid (15 ml) was added to the mixture. Triethylamine (10 ml) was further added to the mixture, and the mixture was concentrated under reduced pressure. To the residue was added ethanol, and the insolubles were removed by filtration. The solvent was concentrated under reduced pressure, and the obtained residue was separated and purified by column chromatography (basic silica gel, ethyl acetate→ethanol:ethyl acetate 1:19), to give ethyl 2-[2-(hydroxymethyl)-1H-imidazol-1-yl] benzoate (0.87 g) as colorless crystals.
mp 167 to 169° C.

$^1$H-NMR (200 MHz, CDCl$_3$) δ 4.41 (2H, t, J=5.4 Hz), 4.64 (2H, t, J=5.4 Hz), 4.74 (2H, s), 6.94 (1H, s), 6.97 (1H, s), 7.41 to 7.48 (2H, m), 7.55 to 7.62 (1H, m), 7.99 (2H, d, J=8.4 Hz).

IR (KBr) 3120, 1711, 1277, 1113, 1026, 768, 708 cm$^{-1}$

Elemental Analysis C$_{13}$H$_{14}$N$_2$O$_3$ Calcd. C, 63.40; H, 5.73; N, 11.38. Found: C, 63.38; H, 5.71; N, 11.38.

Reference Example 319

To a solution of ethyl 2-[2-(hydroxymethyl)-1H-imidazol-1-yl] benzoate (0.87 g) in chloroform (10 ml), thionyl chloride (0.52 g) and DMF (1 droplet) were added at room temperature, and the mixture was stirred for 1 hour. The solvent was concentrated under reduced pressure, and to a solution of the residue in ethanol (10 ml) were added 4-aminothiophenol (0.49 g) and triethylamine (1.0 ml) at room temperature. The mixture was stirred at room temperature for 18 hours, and concentrated under reduced pressure. To the residue was added water, and the mixture was extracted with ethyl acetate. The organic layer was washed with water and saturated brine, dried over magnesium sulfate, and concentrated under reduced pressure. The obtained residue was separated and purified by column chromatography (basic silica gel, ethyl acetate:hexane 2:1), to give ethyl 2-[2-[[(4-aminophenyl)thio]methyl]-1H-imidazol-1-yl] benzoate (1.07 g, 86%) as brown oil.

$^1$H-NMR (200 MHz, CDCl$_3$) δ 3.58 to 3.84 (2H, m), 4.09 (2H, s), 4.25 (2H, t, J=5.5 Hz), 4.56 (2H, t, J=5.5 Hz), 6.56 (2H, d, J=8.8 Hz), 6.89 to 6.95 (2H, m), 7.14 (2H, d, J=8.8 Hz), 7.41 to 7.48 (2H, m), 7.55 to 7.63 (1H, m), 7.96 to 8.01 (2H, m).

IR (neat) 3351, 3179, 1721, 1599, 1497, 1451, 1273, 1117, 741, 712 cm$^{-1}$

Reference Example 320

A mixture of 2-formylimidazole (2.50 g), 3-chloropropyl acetate (3.8 ml), sodium iodide (4.7 g) and potassium carbonate (5.4 g) in DMF (25 ml) was stirred for 2 days at 80° C. To the reaction mixture was added water, and the mixture was extracted with ethyl acetate. The organic layer was washed with water and saturated brine, dried over magnesium sulfate, and concentrated under reduced pressure. The obtained residue was separated and purified by column chromatography (ethyl acetate:hexane 1:1), to give propyl 3-(2-formyl-1H-imidazol-1-yl) acetate (4.37 g) as pale yellow oil.

$^1$H-NMR (200 MHz, CDCl$_3$) δ 2.07 to 2.20 (5H, m), 4.08 (2H, t, J=6.1 Hz), 4.50 (2H, t, J=7.0 Hz), 7.17 (1H, s), 7.30 (1H, s), 9.81 (1H, s).

Reference Example 321

To a solution of propyl 3-(2-formyl-1H-imidazol-1-yl) acetate (4.37 g) in 2-propanol (50 ml), sodium borohydride (0.25 g) was added at 0° C. The mixture was stirred for 30 minutes at 0° C., and to the reaction solution was added 1N hydrochloric acid (20 ml). Triethylamine (10 ml) was further added to the mixture, and the mixture was concentrated under reduced pressure. To the residue was added ethanol, and the insolubles were filtered off, and the filtrate was further concentrated under reduced pressure. The residue was separated and purified by column chromatography (basic silica gel, ethanol:ethyl acetate 1:19), to give propyl 3-[2-(hydroxymethyl)-1H-imidazol-1-yl] acetate (1.34 g) as colorless oil.

$^1$H-NMR (300 MHz, CDCl$_3$) δ 2.05 to 2.19 (5H, m), 4.07 to 4.14 (4H, m), 4.66 (2H, s), 6.87 (1H, d, J=1.1 Hz), 6.92 (1H, d, J=1.1 Hz).

IR (neat) 3335, 1738, 1497, 1370, 1246, 1044, 741 cm$^{-1}$

Reference Example 322

To a solution of propyl 3-[2-(hydroxymethyl)-1H-imidazol-1-yl] acetate (1.27 g) in chloroform (10 ml), thionyl chloride (0.94 ml) and DMF (1 droplet) were added at room temperature and the mixture was stirred for 1 hour. The solvent was concentrated under reduced pressure, and to a solution of the residue in ethanol (30 ml), triethylamine (5.4 ml) and 4-aminothiophenol (0.96 g) were added at room temperature. The mixture was stirred at room temperature for 3 days, and concentrated under reduced pressure. To the residue was added water, and the mixture was extracted with ethyl acetate. The organic layer was washed with saturated brine, dried over magnesium sulfate, and concentrated under reduced pressure. The obtained residue was separated and purified by column chromatography (basic silica gel, ethyl acetate:hexane 4:1→ethyl acetate), to give propyl 3-[2-[[(4-aminophenyl)thio]methyl]-1H-imidazol-1-yl] acetate (1.49 g) as pale yellow oil.

$^1$H-NMR (200 MHz, CDCl$_3$) δ 2.01 to 2.11 (5H, m), 3.61 to 3.84 (2H, m), 3.97 (2H, t, J=7.1 Hz), 4.04 (2H, s), 4.07 (2H, t, J=6.2 Hz), 6.57 (2H, d, J=8.5 Hz), 6.83 (1H, d, J=1.2 Hz), 6.93 (1H, d, J=1.2 Hz), 7.15 (2H, d, J=8.5 Hz).

IR (neat) 3328, 3173, 1732, 1597, 1497, 1246, 1046, 828, 739 cm$^{-1}$

Reference Example 323

To a suspension of 4-hydroxymethyl-1-trityl-1H-imidazole (3.0 g) in THF (30 ml), thionyl chloride (0.8 ml) and DMF (1 droplet) were added at room temperature. The mixture was stirred at room temperature for 1 hour, and the mixture was added dropwise to a mixture of 4-aminothiophenol (1.37 g), 4N sodium hydroxide (25 ml) and ethanol (50 ml) at 0° C. The mixture was stirred for 60 hours at room temperature, and concentrated under reduced pressure. To the residue was added water, and the mixture was extracted with ethyl acetate. The organic layer was washed with saturated brine, dried over magnesium sulfate, and concentrated under reduced pressure. The precipitated crystals were collected by filtration. The crystals were washed with ethyl acetate and diisopropyl ether, to give 4-[[(1-trityl-1H-imidazol-1-yl)methyl]thio]aniline (2.74 g) as pale yellow crystals.

mp 179 to 180° C.

$^1$H-NMR (200 MHz, CDCl$_3$) δ 3.61 to 3.72 (2H, m), 3.90 (2H, s), 6.48 (1H, s), 6.53 (2H, d, J=8.8 Hz), 7.04 to 7.09 (6H, m), 7.15 (2H, d, J=0.8 Hz), 7.30 to 7.33 (10H, m).

IR (KBr) 3426, 3343, 3229, 1636, 1599, 1497, 1443, 1308, 1226, 1142, 933, 820, 750, 702 cm$^{-1}$

Elemental Analysis C$_{29}$H$_{25}$N$_3$S.0.25H$_2$O. Calcd. C, 77.05; H, 5.68; N, 9.29. Found: C, 76.90; H, 5.93; N, 9.02.

Reference Example 324

To a solution of 7-[4-(2-butoxyethoxy) phenyl]-1-isobutyl-2,3-dihydro-1H-1-benzazepine-4-carboxylic acid (1.0 g) in THF (10 ml), thionyl chloride (0.25 ml) and DMF (1 droplet) were added at room temperature, and the mixture was stirred for 1.5 hours at room temperature. The solvent was concentrated under reduced pressure, and a solution of the residue in THF (25 ml) was added dropwise to a solution of 4-[[(1-trityl-1H-imidazol-1-yl)methyl]thio]aniline (1.13 g) in pyridine (10 ml) at 0° C. The mixture was stirred at room temperature for 20 hours, and water was added to the reaction solution, and the mixture was extracted with ethyl acetate. The organic layer was washed with saturated brine, dried over magnesium sulfate, and concentrated under reduced pressure. The obtained residue was separated and purified by column chromatography (ethyl acetate:hexane 1:1), to give 7-[4-(2-butoxyethoxy) phenyl]-N-[4-[(1-trityl-1H-imidazol-4-yl) methyl]thio]phenyl]-1-isobutyl-2,3-dihydro-1H-1-benzazepine-4-carboxamide (1.43 g) as yellow crystals.

mp 178 to 181° C.

$^1$H-NMR (200 MHz, CDCl$_3$) δ 0.93 (3H, t, J=7.2 Hz), 0.98 (6H, d, J=6.6 Hz), 1.30 to 1.44 (2H, m), 1.49 to 1.71 (2H, m), 1.97 to 2.16 (1H, m), 2.86 to 2.96 (2H, m), 3.20 (2H, d, J=6.8 Hz), 3.31 to 3.42 (2H, m), 3.55 (2H, t, J=6.6 Hz), 3.80 (2H, t, J=5.0 Hz), 4.03 (2H, s), 4.16 (2H, t, J=5.0 Hz), 6.57 (1H, s), 6.91 to 7.09 (9H, m), 7.23 to 7.53 (20H, m).

IR (KBr) 3056, 1653, 1590, 1518, 1497, 1314, 1244, 1179, 1165, 1125, 818, 752, 700 cm$^{-1}$

Reference Example 325

To a suspension of aluminum lithium hydride (1.55 g) in. THF (80 ml) was added dropwise a solution of ethyl 5-methyl-1-propylimidazole-4-carbonate (8.0 g) in. THF (80 ml) at 0° C. under nitrogen atmosphere. After the mixture was allowed to be at room temperature and stirred for 2 hours, water (1.6 ml), 15% aqueous solution of sodium hydroxide (1.6 ml) and water (4.8 ml) were sequentially added to the mixture at 0° C. The mixture was allowed to be at room temperature and stirred overnight, and then, dried over magnesium sulfate. The insolubles were filtered off.

The solvent was distilled off under reduced pressure and the obtained residue was recrystallized from hexane-ethyl acetate, to give 4-hydroxymethyl-5-methyl-1-propylimidazole (4.9 g) as colorless crystals.

m.p. 88.0 to 88.5° C.

$^1$H-NMR (200 MHz, CDCl$_3$) δ 0.94 (3H, t, J=7.4 Hz), 1.65 to 1.84 (2H, m), 2.21 (3H, s), 3.77 (2H, t, J=7.4 Hz), 4.56 (2H, s), 7.38 (1H, s).

Elemental Analysis C$_8$H$_{14}$N$_2$O Calcd. C, 62.31; H, 9.15; N, 18.17. Found: C, 62.31; H, 9.36; N, 18.39.

Reference Example 326

4-hydroxymethyl-5-methyl-1-propylimidazole (4.5 g) was added to thionyl chloride (25 ml) at 0° C., and the mixture was heated for 1 hour at 90° C. The mixture was allowed to be at room temperature. The solvent was distilled off under reduced pressure and the obtained residue was dissolved in methanol, and the solvent was distilled off again under reduced pressure. The obtained residue was washed with ethyl acetate to give 4-chloromethyl-5-methyl-1-propylimidazole hydrochloride (5.79 g) as colorless crystals.

$^1$H-NMR (200 MHz, DMSO-d$_6$) δ 0.88 (3H, t, J=7.4 Hz), 1.65 to 1.85 (2H, m), 2.35 (3H, s), 4.08 (2H, t, J=7.6 Hz), 4.93 (2H, s), 9.19 (1H, s).

Elemental Analysis C$_8$H$_{14}$N$_2$Cl$_2$ Calcd. C, 45.95; H, 6.75; N, 13.40. Found: C, 45.78; H, 7.11;: N, 13.22.

Reference Example 327

A mixture of potassium thiocyanate (31.1 g), dihydroxyacetone dimer (19.2 g) and (2-propyn-1-yl)amine hydrochloride (25.0 g) was added by portions to a mixed solution of acetic acid (23 ml) and 1-butanol (155 ml). The mixture was stirred for 10 days at room temperature, water (30 ml) was added to the mixture, and the mixture was stirred for 30 minutes. The precipitated solid was collected by filtration, and further washed with water (45 ml) twice and diisopropyl ether once. The obtained solid was dried under reduced pressure, to give 5-hydroxymethyl-2-mercapto-1-(2-propyn-1-yl)imidazole (28.9 g) as colorless crystals.

$^1$H-NMR (200 MHz, DMSO-d$_6$) δ 3.31 (1H, t, J=2.6 Hz), 4.42 (2H, d, J=5.2 Hz), 4.90 (2H, d, J=2.6 Hz), 5.37 (1H, t, J=5.2 Hz), 6.85 (1H, s), 12.18 (1H, br).

Reference Example 328

To 5.0M nitric: acid (134 ml) was added sodium nitrite (411 mg), and 5-hydroxymethyl-2-mercapto-1-(2-propyn-1-yl)imidazole (25.0 g) was added by portions to the mixture. After the mixture was allowed to be at room temperature and stirred for 1 hour, water (60 ml) was added to the mixture. The mixture was neutralized with potassium carbonate at 0° C. and the solvent was distilled off under reduced pressure. Ethanol was added to the mixture, the insolubles were filtered off, and the solvent was distilled off under reduced pressure. To the obtained residue was added methanol-ethyl acetate, and basic silica gel was added to the mixture. This mixture was purified by basic silica gel column chromatography (methanol:ethyl acetate=1:8), and the obtained solid was recrystalized from hexane-ethyl acetate, to give 5-hydroxymethyl-1-(2-propyn-1-yl)imidazole (8.46 g) as yellow crystals.

m.p. 91.0 to 92.5° C.

$^1$H-NMR (300 MHz, CDCl$_3$) δ 2.49 (1H, t, J=2.4 Hz), 4.69 (2H, s), 4.84 (2H, d, J=2.4 Hz), 6.89 (1H, s), 7.60 (1H, s).

Elemental Analysis for C$_7$H$_8$N$_2$O.0.1 h$_2$O Calcd. C, 60.95; H, 5.99; N, 20.31. Found: C, 61.25; H, 5.86; N, 20.35.

Reference Example 329

To 5-hydroxymethyl-1-(2-propyn-1-yl)imidazole (8.0 g) was added by portions thionyl chloride (40 ml) at 0° C., and the mixture was heated for 30 minutes under nitrogen atmosphere at 90° C. The mixture was allowed to be at room temperature. The solvent was distilled off under reduced pressure, and the obtained residue was dissolved in methanol, and then, the solvent was distilled off again under reduced pressure. The obtained solid was recrystalized from ethyl acetate, to give 5-chloromethyl-1-(2-propyn-1-yl)imidazole hydrochloride (9.8 g) as colorless crystals.

$^1$H-NMR (200 MHz, DMSO-d$_6$) δ 3.86 (1H, t, J=2.6 Hz), 5.06 (2H, s), 5.26 (2H, d, J=2.6 Hz), 7.85 (1H, d, J=1.2 Hz), 9.32 (1H, d, J=1.2 Hz).

Elemental Analysis for C$_7$H$_8$N$_2$Cl$_2$.0.1 h$_2$O Calcd. C, 43.59; H, 4.29; N, 14.53. Found: C, 43.36; H, 4.24; N, 14.47.

Reference Example 330

To a solution of 2-mercapto-5-nitrobenzimidazole (3.0 g) and triethylamine (12.5 ml) in tetrahydrofuran (30 ml) was added dropwise a solution of 5-chloromethyl-1-propylimidazole hydrochloride (3.0 g) in methanol (30 ml) under nitrogen atmosphere at 0° C. After the mixture was allowed to be at room temperature and stirred for 10 minutes, water was added to the mixture and the mixture was extracted with ethyl acetate twice. The mixture was dried over magnesium sulfate, and the solvent was distilled off under reduced pressure. The obtained residue was purified by silica gel column chromatography (methanol:ethyl acetate=1:8→methanol:ethyl acetate=1:4), which was recrystallized from diisopropyl ether-ethyl acetate, to give 5-nitro-2-(((1-propylimidazol-5-yl)methyl)sulfanyl)benzimidazole (3.33 g) as yellow crystals.

m.p. 189.0 to 190.0° C.

$^1$H-NMR (200 MHz, DMSO-d$_6$) δ 0.85 (3H, t, J=7.2 Hz), 1.66 to 1.84 (2H, m), 3.97 (2H, t, J=7.2 Hz), 4.71 (2H, s), 6.91 (1H, s), 7.61 to 7.66 (2H, m), 8.08 (1H, dd, J=8.8, 2.2 Hz), 8.35 (1H, d, J=2.2 Hz).

Elemental Analysis for C$_{14}$h$_{15}$N$_5$O$_2$S Calcd. C, 52.98; H, 4.76; N, 22.07. Found: C, 52.83; H, 4.83; N, 21.83.

Reference Example 331

To a solution of sodium hydride (492 mg, 60%) which had been washed three times with hexane in DMF (45 ml) was added dropwise a solution of 5-nitro-(((1-propylimidazol-5-yl)methyl)sulfanyl)benzimidazole (3.0 g) in DMF (30 ml) under nitrogen atmosphere at 0° C. After the mixture was allowed to be at room temperature and stirred for 1 hour, iodomethane (1.6 g) was added dropwise to the mixture at 0° C. The mixture was allowed to be at room temperature and stirred for 1 hour. Then, water was added to the mixture, and the mixture was extracted with ethyl acetate. The organic layer was washed with water and saturated brine and dried over magnesium sulfate, and the solvent was distilled off under reduced pressure. The obtained residue was purified by basic silica gel column chromatography (hexane:ethyl acetate=1:1→ethyl acetate) and recrystalized from hexane-ethyl acetate, to give 1-methyl-5-nitro-2-(((1-propylimidazol-5-yl)methyl)sulfanyl)benzimidazole (747 mg) as colorless crystals and 1-methyl-6-nitro-2-(((1-propylimidazol-5-yl)methyl)thio)benzimidazole (258 mg) as yellow crystals.

1-methyl-5-nitro-2-(((1-propylimidazol-5-yl)methyl)sulfanyl)benzimidazole m.p. 147.5 to 149.5° C.

$^1$H-NMR (200 MHz, CDCl$_3$) δ 0.97 (3H, t, J=7.4 Hz), 1.77 to 1.95 (2H, m), 3.70 (3H, s), 3.97 (2H, t, J=7.4 Hz), 4.73 (2H, s), 7.09 (H, s), 7.30 (1H, d, J=8.8 Hz), 7.49 (1H, s), 8.20 (1H, dd, J=8.8, 1.8 Hz), 8.57 (1H, d, J=1.8 Hz).

Elemental Analysis for C$_{15}$H$_{17}$N$_5$O$_2$S Calcd. C, 54.36; H, 5.17; N, 21.13. Found: C, 54.17; H, 5.18; N, 20.88.

1-methyl-6-nitro-2-(((1-propylimidazol-5-yl)methyl)sulfanyl)benzimidazole m.p. 148.0 to 149.0° C.

$^1$H-NMR (200 MHz, CDCl$_3$) δ 0.97 (3H, t, J=7.4 Hz), 1.77 to 1.92 (2H, m), 3.73 (3H, s), 3.97 (2H, t, J=7.0 Hz), 4.75 (2H, s), 7.11 (1H, s), 7.51 (1H, s), 7.69 (1H, d, J=8.4 Hz), 8.17 to 8.23 (2H, m).

Elemental Analysis for C$_{15}$H$_{17}$N$_5$O$_2$S 0.25 h$_2$O Calcd. C, 53.63; H, 5.25; N, 20.85. Found: C, 53.92; H, 4.95; N, 20.61.

Reference Example 332

An aqueous solution of 1-methyl-5-nitro-2-(((1-propylimidazol-5-yl)methyl)sulfanyl)benzimidazole (700 mg), reduced iron (0.6 g) and anhydrous calcium chloride (1.18 g) in 85% ethanol (15 ml) was stirred for 1 day under nitrogen atmosphere at 105° C. The mixture was allowed to be at room temperature, the insolubles were filtered off, water was added to the mixture, and the mixture was extracted with ethyl acetate. The organic layer was washed with saturated brine and dried over magnesium sulfate. The solvent was distilled off under reduced pressure and the obtained residue was purified by silica gel column chromatography (methanol:ethyl acetate=1:8) to give 5-amino-1-methyl-2-(((1-propylimidazol-5-yl)methyl)sulfanyl)benzimidazole (123 mg) as brown oil.

$^1$H-NMR (200 MHz, CDCl$_3$) δ 0.93 (3H, t, J=7.4 Hz), 1.70 to 1.88 (2H, m), 3.56 (3H, s), 3.92 (2H, t, J=7.2 Hz), 4.61 (2H, s), 6.69 (1H, dd, J=8.4, 2.2 Hz), 6.99 to 7.06 (3H, m), 7.46 (1H, s).

Reference Example 333

An aqueous solution of 1-methyl-6-nitro-2-(((1-propylimidazol-5-yl)methyl)sulfanyl)benzimidazole (230 mg), reduced iron (194 mg) and anhydrous calcium chloride (38.5 mg) in 85% ethanol (10 ml) was stirred for 1 day under nitrogen atmosphere at 105° C. The mixture was allowed to be at room temperature, the insolubles were filtered off, water was added to the mixture, and the mixture was extracted with ethyl acetate. The organic layer was washed with saturated brine and dried over magnesium sulfate, and the solvent was distilled off under reduced pressure. The obtained residue was purified by basic silica gel column chromatography (ethyl acetate) to give 6-amino-1-methyl-2-(((1-propylimidazol-5-yl)methyl)sulfanyl)benzimidazole (170 mg) as colorless oil.

$^1$H-NMR (200 MHz, CDCl$_3$) δ 0.93 (3H, t, J=7.2 Hz), 1.73 to 1.88 (2H, m), 3.52 (3H, s), 3.91 (2H, t, J=7.4 Hz), 4.56 (2H, s), 6.53 (1H, d, J=2.0 Hz), 6.64 (1H, dd, J=8.4, 2.0 Hz), 6.97 (1H, s), 7.45 to 7.49 (2H, m).

Reference Example 334

To a suspension of sodium hydride (5.84 g, 60% oil) which had been washed three times with hexane three times in tetrahydrofuran (100 ml) was added dropwise a solution of 2-methylimidazole (10 g) in tetrahydrofuran (50 ml) under nitrogen atmosphere at 0° C. After the mixture was allowed to be at room temperature and stirred for 1 hour, 1-iodopropane (22.8 g) was added dropwise to the solution at 0° C. The mixture was allowed to be at room temperature and stirred overnight, and the insolubles were filtered off. The solvent was distilled off under reduced pressure, dichloromethane (20 ml) was added to the mixture, and the insolubles were further filtered off. The solvent was distilled off under reduced pressure, to give 2-methyl-1-propylimidazole (15.1 g) as brown oil.

$^1$H-NMR (200 MHz, CDCl$_3$) δ 0.94 (3H, t, J=7.4 Hz), 1.66 to 1.85 (2H, m), 2.37 (3H, s), 3.79 (2H, t, J=7.4 Hz), 6.81 (1H, d, J=1.2 Hz), 6.90 (1H, d, J=1.2 Hz).

Reference Example 335

To a solution of 2-methyl-1-propylimidazole (6.0 g) and triethylamine (29.5 ml) in acetonitrile (150 ml) was added by portions 4-nitrobenzoylchloride (19.7 g) at 0° C. After the mixture was allowed to be at room temperature and stirred for 2 hours, the solvent was distilled off under reduced pressure. To the obtained residue was added water, and the mixture was extracted with ethyl acetate-tetrahydrofuran. The organic layer was washed with an aqueous solution of saturated sodium bicarbonate, saturated brine, and dried over magnesium sulfate. The solvent was distilled off under reduced pressure and the obtained residue was washed with diisopropyl ether to give 1-(4-nitrophenyl)-2-(1-propylimidazol-2-yl)vinyl 4-nitrobenzoate (19.6 g) as brown crystals.

$^1$H-NMR (200 MHz, CDCl$_3$) δ 1.00 (3H, t, J=7.2 Hz), 1.78 to 1.96 (2H, m), 4.03 (2H, t, J=7.4 Hz), 6.88 to 6.93 (3H, m), 7.77 (2H, d, J=8.8 Hz), 8.27 (2H, d, J=9.2 Hz), 8.35 to 8.47 (4H, m).

Elemental Analysis for C$_{21}$H$_{18}$N$_4$O$_6$·0.75 h$_2$O Calcd. C, 57.86; H, 4.51; N, 12.85. Found: C, 58.06; H, 4.45; N, 12.57.

Reference Example 336

To a suspension of 1-(4-nitrophenyl)-2-(1-propylimidazol-2-yl)vinyl 4-nitrobenzoate (19.0 g) in acetic acid (190 ml) was added dropwise concentrated hydrochloric acid (95 ml) at 0° C., and the mixture was refluxed for 2 hours. The mixture was cooled to 0° C., and the insolubles were filtered off. The solvent was distilled off under reduced pressure, water was added and the mixture was neutralized with potassium carbonate at 0° C. The mixture was extracted with ethyl acetate, washed with saturated brine, and dried over magnesium sulfate. The solvent was distilled off under reduced pressure, the obtained residue was washed with ethyl acetate-diisopropyl ether to give 1-(4-nitrophenyl)-2-(1-propylimidazol-2-yl)ethylenol (10.2 g) as brown crystals.

m.p. 113.0 to 114.0° C.

$^1$H-NMR (200 MHz, CDCl$_3$) δ 0.99 (3H, t, J=7.4 Hz), 1.76 to 1.94 (2H, m), 3.92 (2H, t, J=7.4 Hz), 5.98 (1H, s), 6.83 (1H, d, J=1.4 Hz), 7.03 (1H, d, J=1.4 Hz), 7.96 (2H, d, J=9.2 Hz), 7.25 (2H, d, J=9.2 Hz).

Elemental Analysis for C$_{14}$H$_{15}$N$_3$O$_3$·0.25 h$_2$O Calcd. C, 60.53; H, 5.62; N, 15.12. Found: C, 60.74; H, 5.41; N, 14.85.

Reference Example 337

An aqueous solution (200 ml) of 1-(4-nitrophenyl)-2-(1-propylimidazol-2-yl)ethylenol (9.4 g), reduced iron (9.6 g) and anhydrous calcium chloride (1.91 g) in 85% ethanol was stirred overnight under nitrogen atmosphere at 105° C. The mixture was allowed to be at room temperature, the insolubles were filtered off, water was added to the mixture, and the mixture was extracted with ethyl acetate. The organic layer was washed with saturated brine, dried over magnesium sulfate, and the solvent was distilled off under reduced pressure. The obtained residue was washed with hexane-ethyl acetate to give 1-(4-aminophenyl)-2-(1-propylimidazol-2-yl)ethanbne (5.29 g) as yellow crystals.

m.p. 130.0 to 131.0° C.

$^1$H-NMR (200 MHz, CDCl$_3$) δ 0.92 (3H, t, J=7.4 Hz), 1.610 to 1.81 (2H, m), 3.86 (2H, t, J=7.4 Hz), 4.17 (2H, br), 4.33 (2H, s), 6.65 (2H, d, J=9.2 Hz), 6.87 (1H, d, J=1.6 Hz), 6.99 (1H, d, J=1.6 Hz), 6.97 (2H, d, J=9.2 Hz).

Elemental Analysis for $C_{14}H_{17}N_3O$ Calcd. C, 69.11; H, 7.04; N, 17.27. Found: C, 68.82; H, 7.17; N, 17.03.

Reference Example 338

A solution of 1-(4-aminophenyl)-2-(1-propylimidazol-2-yl)ethanone (600 mg) and O-methylhydroxylamine hydrochloride (227 mg) in ethanol (20 ml) was refluxed for 8 hours. After the mixture was allowed to be at room temperature, and saturated sodium bicarbonate solution was added to the mixture, the mixture was extracted with ethyl acetate, and dried over magnesium sulfate. The solvent was distilled off under reduced pressure. The obtained residue was purified by basic silica gel column chromatography (hexane:ethyl acetate=1:1), and washed with diisopropyl ether to give (1E)-1-(4-aminophenyl)-2-(1-propylimidazol-2-yl)ethanone O-methyloxime (230 mg) as colorless crystals.

m.p. 103.0 to 103.5° C.

$^1$H-NMR (200 MHz, CDCl$_3$) δ 0.91 (3H, t, J=7.2 Hz), 1.59 to 1.78 (2H, m), 3.70 to 3.85 (4H, m), 3.99 (3H, s), 4.21 (2H, s), 6.60 (2H, d, J=8.4 Hz), 6.74 (1H, d, J=1.0 Hz), 6.90 (1H, d, J=1.0 Hz), 7.59 (2H, d, J=8.4 Hz).

Elemental Analysis for $C_{15}H_{20}N_4O$ Calcd. C, 66.15; H, 7.40; N, 20.57. Found: C, 66.01; H, 7.37; N, 20.35.

Reference Example 339

A solution of 1-(4-aminophenyl)-2-(1-propylimidazol-2-yl)ethanone (600 mg) and O-ethylhydroxylamine hydrochloride (313 mg) in ethanol (20 ml) was refluxed for 1 day. After the mixture was allowed to be at room temperature, and saturated sodium bicarbonate solution was added to the mixture, the mixture was extracted with ethyl acetate, and washed with water and saturated brine. The mixture was dried over magnesium sulfate, and the solvent was distilled off under reduced pressure. The obtained residue was washed with ethyl acetate-diisopropyl ether, to give (1E)-1-(4-aminophenyl)-2-(1-propylimidazol-2-yl)ethanone. O-ethyloxime (442 mg) as brown crystals.

m.p. 110.0 to 111.5° C.

$^1$H-NMR (200 MHz, CDCl$_3$) δ 0.90 (3H, t, J=7.2 Hz), 1.32 (3H, t, J=7.0 Hz), 159 to 1.77 (2H, m), 3.74 (2H, br), 3.80 (2H, t, J=7.6 Hz), 4.20 to 4.33 (4H, m), 6.60 (2H, d, J=8.8 Hz), 6.74 (1H, d, J=1.2 Hz), 6.90 (1H, d, J=1.2 Hz), 7.60 (2H, d, J=8.8 Hz).

Elemental Analysis for $C_{16}H_{22}N_4O$ Calcd. C, 67.11; H, 7.74; N, 19.56. Found: C, 67.28; H, 7.65; N, 19.53.

Reference Example 340

A solution of 1-(4-aminophenyl)-2-(1-propylimidazol-2-yl)ethanone (600 mg) and hydroxylamine hydrochloride (223 mg) in ethanol (20 ml) was refluxed for 1 day. After the mixture was allowed to be at room temperature, and saturated sodium bicarbonate solution was added to the mixture, the mixture was extracted with ethyl acetate and washed with water and saturated brine. The mixture was dried over magnesium sulfate, and the solvent was distilled off under reduced pressure. The obtained residue was washed with ethyl acetate-diisopropyl ether to give (1E)-1-(4-aminophenyl)-2-(1-propylimidazol-2-yl)ethanone oxime (419 mg) as yellow crystals.

m.p. 142.0 to 145.0° C.

$^1$H-NMR (200 MHz, CDCl$_3$) δ 0.89 (3H, t, J=7.8 Hz), 1.60 to 1.78 (2H, m), 3.78 (2H, br), 3.83 (2H, t, J=7.6 Hz), 4.30 (2H, s), 6.59 (2H, d, J=8.8 Hz), 6.76 (1H, d, J=1.0 Hz), 6.92 (1H, d, J=1.0 Hz), 7.57 (2H, d, J=8.8 Hz).

Elemental Analysis for $C_{14}H_{18}N_4O.0.05 H_2O$ Calcd. C, 64.87; H, 7.04; N, 21.61. Found: C, 65.16; H, 7.01; N, 21.28.

Reference Example 341

To a solution of (4-nitrophenyl)acetic acid (30.0 g), N,O-dimethylhydroxylamine hydrochloride (21.0 g) and 1-hydroxybenzotriazole monohydrate (33.0 g) in DMF (450 ml) were added triethylamine (30 ml) and 4-(N,N-dimethylamino)pyridine (130 mg), and then 1-ethyl-3-(3-dimethylaminopropyl)carbodiimide hydrochloride (41.4 g) was added to the mixture, and then, the mixture was stirred overnight under nitrogen atmosphere. Water was added to the mixture, and the mixture extracted with ethyl acetate twice. The organic layer was washed with an aqueous solution of saturated sodium bicarbonate once, with water twice, and with saturated brine once, and dried over magnesium sulfate. The solvent was distilled off under reduced pressure, and the obtained solid was washed with hexane to give N-methoxy-N-methyl-2-(4-nitrophenyl)acetoamide (32.6 g) as colorless crystals.

m.p. 75.0 to 75.5° C.

$^1$H-NMR (200 MHz, CDCl$_3$) δ 3.22 (3H, s), 3.69 (3H, s), 3.88 (2H, s), 7.46 (2H, d, J=8.8 Hz), 8.19 (2H, d, J=8.8 Hz).

Elemental Analysis for $C_{10}H_{12}N_2O_4$. Calcd. C, 53.57; H, 5.39; N, 12.49. Found: C, 53.72; H, 5.36; N, 12.69.

Reference Example 342

To a solution of 1-propylimidazole (13.5 g) in dry tetrahydrofuran (200 ml) was added dropwise n-butyllithium (1.6 m hexane solution, 91.9 ml) under argon atmosphere at −78° C.,. The mixture as it is was stirred for 30 minutes, and added dropwise to a solution of N-methoxy-N-methyl-2-(4-nitrophenyl)acetoamide (27.5 g) in dry tetrahydrofuran (300 ml) under argon atmosphere at −78° C.,. The mixture was allowed to be at room temperature and stirred overnight, and 6N hydrochloric acid (30 ml.) was added to the mixture at 0° C. The mixture was neutralized with potassium carbonate, extracted with ethyl acetate, washed with saturated brine, and dried over magnesium sulfate. The solvent was distilled off under reduced pressure and the obtained residue was purified by basic silica gel column chromatography (hexane:ethyl acetate=2:1). The obtained solid was washed with hexane-diisopropyl ether to give 2-(4-nitrophenyl)-1-(1-propylimidazol-2-yl)ethanone (1.25 g) as red crystals.

m.p. 95.0 to 96.0° C.

$^1$H-NMR (200 MHz, CDCl$_3$) δ 0.90 (3H, t, J=7.6 Hz), 1.68 to 1.85 (2H, m), 4.32 (2H, t, J=7.4 Hz), 4.56 (2H, s), 7.14 (1H, d, J=0.8 Hz), 7.22 (1H, d, J=0.8 Hz), 7.52 (2H, d, J=8.6 Hz), 8.19 (2H, d, J=8.6 Hz).

Elemental Analysis for $C_{14}H_{15}N_3O_3$ Calcd. C, 61.53; H, 5.53; N, 15.38. Found: C, 61.70; H, 5.56; N, 15.06.

Reference Example 343

An aqueous solution (20 ml) of (2-(4-nitrophenyl)-1-(1-propylimidazol-2-yl)ethanone (1.2 g), reduced iron (1.2 g) and anhydrous calcium chloride (244 mg) in 85% ethanol was stirred for 4 hours under nitrogen atmosphere at 105° C. The mixture was allowed to be at room temperature, ethyl acetate was added to the mixture, the insolubles were filtered off, and water was added to separate the layers. The organic layer was washed with saturated brine, and dried over magnesium sulfate. The solvent was distilled off under reduced pressure and the obtained residue was purified by silica gel column chromatography (hexane:ethyl acetate=0.4:1) to give 2-(4-aminophenyl)-1-(1-propylimidazol-2-yl)ethanone (863 mg) as red oil.

$^1$H-NMR (200 MHz, CDCl$_3$) δ 0.88 (3H, t, J=7.4 Hz), 1.67 to 1.85 (2H, m), 3.60 (2H, br), 4.26 to 4.34 (4H, m), 6.65 (2H, d, J=8.4 Hz), 7.08 (11H, d, J=10 Hz), 7.12 (2H, d, J=8.4 Hz), 7.18 (1H, d, J=1.0 Hz).

Reference Example 344

A solution of 2-(4-aminophenyl)-1-(1-propylimidazol-2-yl)ethanone (400 mg) and hydroxylamine hydrochloride (149 mg) in ethanol (15 ml) was refluxed for 1 day. The mixture was allowed to be at room temperature, saturated sodium bicarbonate solution was added to the mixture, extracted with ethyl acetate, and washed with saturated brine. The mixture was dried over magnesium sulfate, the solvent was distilled off under reduced pressure, and the obtained residue was purified by basic silica gel column chromatography (hexane:ethyl acetate=1:1→ethyl acetate) and recrystallized from hexane-ethyl acetate, to give (1E)-2-(4-aminophenyl)-1-(1-propylimidazol-2-yl)ethanone oxime (220 mg) and (1Z)-2-(4-aminophenyl)-1-(1-propylimidazol-2-yl)ethanone oxime (58 mg) as pale red crystals.

(1E)-2-(4-aminophenyl)-1-(1-propylimidazol-2-yl) thanone oxime m.p. 150.0 to 151.0° C.

$^1$H-NMR (200 MHz, CDCl$_3$) δ 0.80 (3H, t, J=7.2 Hz), 1.55 to 1.75 (2H, m), 4.10 (2H, t, J=7.2 Hz), 4.23 (2H, s), 6.56 (2H, d, J=8.4 Hz), 6.90 (1H, s), 7.10 (1H, s), 7.14 (2H, d, J=8.4 Hz), 8.82 (1H, br).

Elemental Analysis for $C_{14}h_{18}N_4O$ Calcd. C, 65.09; H, 7.02; N, 21.69. Found: C, 64.89; H, 6.99; N, 21.55.

(1Z)-2-(4-aminophenyl)-1-(1-propylimidazol-2-yl)ethanone oxime $^1$H-NMR (200 MHz, CDCl$_3$) δ 0.65 (3H, t, J=7.4 Hz), 1.25 to 1.44 (2H, m), 3.60 (2H, t, J=7.4 Hz), 3.87 (2H, s), 6.55 (2H, d, J=8.4 Hz), 6.87 (1H, s), 6.91 (2H, d, J=8.4 Hz), 7.14 (1H, s).

Experimental Example 1

(1) Cloning of Human CCR5 Chemokine Receptor

Cloning of CCR5 gene from human spleen cDNA was conducted using the PCR method. Using spleen cDNA (0.5 ng) (TOYOBO CO., LTD, QUICK-Clone cDNA) as a template, PCR was performed in a DNA Thermal Cycler 480 (manufactured by Perkin Elmer) (reaction conditions: 30 cycles of 95° C. for 1 minute, 60° C. for 1 minute, and 75° C. for 5 minutes) by adding primer sets, SEQ. ID NO: 1 (sequence length: 34; sequence type: nucleic acid; chain number: single strand; topology: linear; kind of sequence: other nucleic acid synthetic. DNA) described in Experimental. Example (1) of WO 99/32100, and SEQ ID NO: 2 (sequence length: 34; sequence type: nucleic acid; chain number: single strand; topology: linear; kind of sequence: other nucleic acid synthetic. DNA) described in Experimental. Example (1) of WO 99/32100, (25 pmol, respectively), which were prepared referring to the nucleotide sequence of CCR5 gene, as reported by Samson et al. (Biochemistry 35 (11), 3362-3367 (1996)) and by using TaKaRa. EX Taq (Takara Shuzo). The resultant. PCR product was subjected to agarose gel electrophoresis to collect an approximately 1.0 kb. DNA fragment, which was subjected to an Original TA Cloning Kit (Funakoshi Co., Ltd.) to carry out cloning of CCR5 gene.

(2) Preparation of Plasmid for Expression of Human CCR5

The plasmid obtained above was digested with restriction enzymes XbaI (Takara Shuzo Co., Ltd.) and BamHI (Takara Shuzo Co., Ltd.), and then subjected to agarose gel electrophoresis to collect DNA fragment of about 1.0 kb. The DNA fragment and plasmid pcDNA 3.1 (Funakoshi. Co., Ltd.) for expression in animal cells, which was previously digested with XbaI and BamHI, were mixed and ligated by DNA Ligation Kit Ver. 2 (Takara Shuzo Co., Ltd.). The resulting plasmid was subjected to transformation into. E. coli JM109 competent cells (Takara Shuzo Co., Ltd.) to obtain plasmid pCKR5.

(3) Introduction of the Plasmid for Expression of Human CCR5 into CHO-K1 Cells and Expression Thereof CHO-K1 cells were cultured in a 750-ml tissue culture flask (Becton, Dickinson and Company.) using. Ham F12 medium (NIHON PHARMACEUTICAL CO., LTD.) containing 10% fetal bovine serum (Lifetech Oriental) and were collected using 0.5 g/L trypsin-0.2 g/L EDTA (Lifetech Oriental). The cells were washed with PBS (Lifetech Oriental), centrifuged (1000 rpm, 5 minutes), and suspended in PBS. The DNA was introduced into the cells using a Gene Pulser (Bio-Rad Laboratories, Inc.) under the following conditions. Namely, $8 \times 10^6$ cells and 10 μg of plasmid pCKR5 for expression of human CCR5 were placed in a cuvette having a 0.4-cm gap, and electroporation was carried out with a voltage 0.25 kV and 960 μF of capacitance. Then, the cells were transferred into Ham's. F12 medium containing 10% fetal bovine serum, and incubated for 24 hours. The cells were collected, centrifuged, and suspended in Ham' F12 medium containing 10% fetal bovine serum and Geneticin (Lifetech Oriental) at a concentration of 500 μg/ml. The suspension of cells was diluted to a concentration of $10^4$ cells/ml, and was inoculated onto 96-well plate (Becton Dickinson), to obtain Geneticin-resistant strain.

Then, resulting. Geneticin-resistant strain were cultured on 96-well plate (Becton Dickinson), and CCR5-expressing cells were selected from the resistant cells. Namely, in an assay buffer, (Ham's F12 medium containing 0.5% BSA, and 20 mM HEPES (Wako Pure Chemical Ind., pH 7.2)) to which was added 200 μM[125I]-RANTES (Amersham) as a ligand, the cells were subjected to a binding reaction at room temperature for 40 minutes. Wells containing the cells were washed with ice-cooled PBS, and 50 μl/well of 1M NaOH was added and stirred. The cells to which the ligand was bound specifically, i.e., CCR5/CHO cells, were selected by measurement of radioactivity using a v-counter.

(4) Evaluation of Compounds Based on CCR5 Antagonistic Activity

The CCR5/CHO cells were inoculated onto 96-well microplate at a concentration of $5 \times 10^4$ cells/well, and were cultured for 24 hours. After removal of the medium by aspiration, to each well was added an assay buffer containing a test compound (1 μM), and [125I]/RANTES (Amersham) used as a ligand at a concentration of 100 μM. The mixture was subjected to a reaction at room temperature for 40 minutes. After removal of the assay buffer by aspiration, each well was washed twice with cooled PBS. Then, 200 μl of MicroScint-20 (Packard) was added to each well, and the radioactivity of each well was measured using a TopCount (Packard).

According to the method above, inhibitory ratios for CCR5 binding to the test compounds were determined. The results are shown in Table 1.

TABLE 1

| Compound No. | Binding Inhibitory Ratio (%) |
|---|---|
| 13 | 100 |
| 26 | 97 |
| 40 | 90 |
| 53 | 98 |
| 63 | 96 |
| 68 | 97 |
| 74 | 97 |
| 85 | 92 |
| 87 | 89 |
| 117 | 95 |
| 122 | 97 |
| 130 | 100 |
| 135 | 100 |
| 141 | 100 |
| 152 | 97 |
| 154 | 100 |
| 210 | 97 |
| 230 | 98 |
| 240 | 97 |
| 242 | 94 |
| 251 | 99 |
| 259 | 88 |
| 272 | 98 |
| 308 | 100 |
| 313 | 95 |
| 355 | 99 |
| 363 | 100 |
| 366 | 96 |
| 367 | 96 |
| 371 | 100 |
| 373 | 94 |
| 375 | 92 |
| 378 | 87 |
| 383 | 93 |
| 404 | 85 |
| 411 | 100 |
| 415 | 98 |
| 418 | 92 |
| 424 | 96 |
| 425 | 100 |
| 427 | 100 |
| 436 | 100 |
| 437 | 100 |
| 443 | 100 |

Experimental Example 2

Growth inhibitory effects against HIV infection were evaluated using Compounds 175, 338, 373, 377 and 392 (Compounds A, B, C, D, E, respectively) which are selective CCR5 antagonists.

Methods

Cells

MOLT-4/CCR5 cells (AIDS Res. Hum. Retrovir. 16, 935-941(2000)) were used.

Drugs

The compounds were dissolved in DMSO, and suitably diluted in RPMI 1640 medium containing 10% FBS and 1 mg/ml G418 (GIBCO).

Viruses

Ba-L, strain which is a laboratory strain of R5 HIV-1, was used.

Infection

Infection was carried out by adding 1000 CC $ID_{50}$ virus to the cells ($4 \times 10^6$ cells/1 mL) and incubating for 6 hours. Non-adsorbed viruses were washed off, and the infected cells were suspended in 2 mL of the medium, and 100 μL of infected cells and 100 μL of the compound were put into 96-well plate, and cultured for 3 days under 5% $CO_2$ at 37° C. Three days after infection, the infected cells and the compound were diluted 5 times with a medium containing the same concentration of the ingredients, and were further cultured for 2 days. After culture, the amount of p24 in the supernatant was measured using a commercially available ELISA Kit (ZeptoMetrix). Inhibitory ratios of the infection were calculated as the amount of p24 administered to the test groups to the amount of p24 for control groups.

Results

As a result of the experiment where the compound was added to the cells infected with HIV-1, and cultured for 5 days, all compounds exhibited strong inhibitory effects against infection at a concentration of 1000 nmol/L (See FIG. 1).

Formulation Example 1 (Capsules)

| | | |
|---|---|---|
| (1) | (−)-7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide | 40 mg |
| (2) | lactose | 61 mg |
| (3) | microcrystalline cellulose | 18 mg |
| (4) | magnesium stearate | 1 mg |
| | Total weight of 1 capsule | 120 mg |

After mixing (1), (2), (3) and (4), the mixture is placed in gelatin capsules.

Formulation Example 2 (Capsules)

| | | |
|---|---|---|
| (1) | (−)-7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide | 40 mg |
| (2) | lactose | 61 mg |
| (3) | microcrystalline cellulose | 18 mg |
| (4) | magnesium stearate | 1 mg |
| | Total weight of 1 capsule | 120 mg |

After mixing (1), (2), (3) and (4), the mixture is placed in gelatin capsules.

Formulation Example 3 (Capsules)

| | | |
|---|---|---|
| (1) | (−)-7-[4-(2-butoxyethoxy)phenyl]-1-propyl-N-[4-(4-propyl-4h-1,2,4-triazol-3-ylmethylsulfinyl)phenyl]-2,3-dihydro-1H-1-benzazepine-4-carboxamide | 40 mg |

-continued

| | | |
|---|---|---|
| (2) | lactose | 61 mg |
| (3) | microcrystalline cellulose | 18 mg |
| (4) | magnesium stearate | 1 mg |
| | Total weight of 1 capsule | 120 mg |

After mixing (1), (2), (3) and (4), the mixture is placed in gelatin capsules.

Formulation Example 4 (Tablets)

| | | |
|---|---|---|
| (1) | (−)-1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide | 40 mg |
| (2) | mannitol | 51.2 mg |
| (3) | microcrystalline cellulose | 18 mg |
| (4) | hydroxypropyl cellulose | 3.6 mg |
| (5) | croscarmellose sodium | 6 mg |
| (6) | magnesium stearate | 1.2 mg |
| | Total weight of 1 tablet | 120 mg |

(1), (2), (3) and (4) are mixed and granulated. To the granules are added (5) and (6) and the mixture is compressed into tablets.

Formulation Example 5 (Tablets)

| | | |
|---|---|---|
| (1) | (+)-7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide | 40 mg |
| (2) | mannitol | 51.2 mg |
| (3) | microcrystalline cellulose | 18 mg |
| (4) | hydroxypropyl cellulose | 3.6 mg |
| (5) | croscarmellose sodium | 6 mg |
| (6) | magnesium stearate | 1.2 mg |
| | Total weight of 1 tablet | 120 mg |

(1), (2), (3) and (4) are mixed and granulated. To the granules are added (5) and (6) and the mixture is compressed into tablets.

INDUSTRIAL APPLICABILITY

As described herein above, the compound of the formula (I) of the present invention or a salt thereof has a strong CC chemokin receptor (CCR) antagonism, especially, excellent CCR5 antagonism, and can be advantageously used for the prevention and treatment of a variety of infectious diseases of HIV, for example AIDS, in humans.

The invention claimed is:

1. A compound represented by the formula (I):

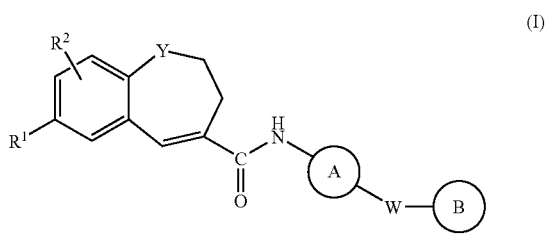

wherein, $R^1$ is a 5- or 6-membered aromatic ring which has a substituent represented by formula $R-Z^1-X^1-Z^2-$ (wherein, R is a hydrogen atom or an optionally substituted hydrocarbon group, $X^1$ is an optionally subtsituted alkylene chain, $Z^1$ and $Z^2$ are independently a heteratom), and may have an further substituent, the group represented by R may bind to said 5- or 6-membered aromatic ring to form a ring, $R^2$ is a hydrogen atom, an optionally substituted lower alkyl group, an optionally substituted lower alkoxy group or a halogen atom, Y is an optionally substituted imino group, ring A and ring B are independently an optionally substituted aromatic ring, and W is a group represented by formula $-W^1-X^2-W^2-$ (wherein, $W^1$ and $W^2$ are independently O, $S(O)_{m1}$ (m1 is 0, 1 or 2), an optionally substituted imino group or a bond, and $X^2$ is an optionally substituted alkyklene group, an optionally substituted alkenylene group or a bond) or a salt thereof.

2. The compound according to claim 1, wherein the 5- or 6-membered aromatic ring of $R^1$ is benzene.

3. The compound according to claim 1, wherein R is an optionally halogenated lower alkyl group.

4. The compound according to claim 1, wherein $X^1$ is $-(CH_2)_n-$ (wherein, n is an integer of 1 to 4).

5. The compound according to claim 1, wherein $Z^1$ is $-O-$.

6. The compound according to claim 1, wherein $Z^2$ is $-O-$.

7. The compound according to claim 1, wherein Y is $-N(R^{5'})-$ (wherein, $R^{5'}$ is a hydrogen atom, an optionally substituted hydrocarbon group, an optionally substituted 5- or 6-membered aromatic heterocyclic group or an optionally substituted acyl group).

8. The compound according to claim 7, wherein $R^{5'}$ is an optionally substituted $C_{1-4}$ alkyl, an optionally substituted benzyl or an optionally substituted 5- or 6-membered aromatic heterocyclic group.

9. The compound according to claim 1, wherein ring A is an optionally substituted benzene ring, an optionally substituted pyridine ring, an optionally substituted pyridazine ring or an optionally substituted benzimidazole ring.

10. The compound according to claim 1, wherein ring B is an imidazole ring substituted by an optionally substituted lower alkyl group or a triazole ring substituted by an optionally substituted lower alkyl group.

11. The compound according to claim 1, wherein one of $W^1$ and $W^2$ is O, $S(O)_{m1}$ (wherein m1 is 0, 1 or 2) or $-N(R^3)-$ (wherein, $R^3$ is a hydrogen atom or an optionally substituted lower alkyl group) and the other is a bond and $X^2$ is $-(CH_2)_p-$ (wherein, p is an integer of 1 to 3), or W is $-CH(OH)-$.

12. The compound according to claim 1, wherein ring A is a benzene ring, ring B is an optionally substituted imidazole ring or an optionally substituted triazole ring, one of $W^1$ and $W^2$ is $S(O)_{m1}$ (wherein m1 is 0, 1 or 2) and the other is a bond and $X^2$ is —$(CH_2)_p$— (wherein, p is an integer of 1 to 3), or W is —CH(OH)—.

13. The compound according to claim 1, wherein

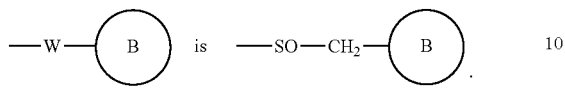

14. The compound according to claim 13, wherein the steric configuration of SO is (S) configuration.

15. The compound according to claim 1, wherein the compound is (−)-7-[4-(2-butoxyethoxy)phenyl]-1-isobutyl-N-[4-[[[1-propylimidazol-5-yl]methyl]sulfinyl]phenyl]-2,3-dihydro-1-benzazepine-4-carboxamide, (−)-7-[4-(2-butoxyethoxy)phenyl]-1-propyl-N-[4-[[[1-propylimidazol-5-yl]methyl]sulfinyl]phenyl]-2,3-dihydro-1-benzazepine-4-carboxamide, (−)-7-[4-(2-butoxyethoxy)phenyl]-1-propyl-N-[4-(4-propyl-4H-1,2,4-triazol-3-ylmethylsulfinyl)phenyl]-2,3-dihydro-1H-1-benzazepine-4-carboxamide, (−)-1-isobutyl-7-[4-(2-propoxyethoxy)phenyl]-N-[4-[[[1-propylimidazol-5-yl]methyl]sulfinyl]phenyl]-2,3-dihydro-1-benzazepine-4-carboxamide, (+)-7-[4-(2-butoxyethoxy)phenyl]-N-[4-[hydroxy(1-oxidopyridin-2-yl)methyl]-3-trifluoromethylphenyl]-1-propyl-2,3-dihydro-1H-1-benzazepine-4-carboxamide, or a salt thereof.

16. A process for producing a compound represented by the formula:

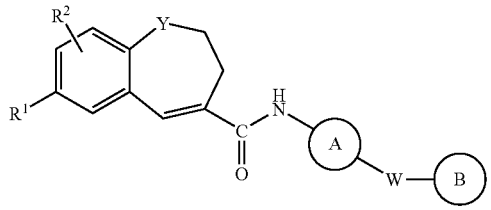

wherein, each symbol has the same meaning as defined in claim 1 or a salt thereof, which comprises subjecting to a condensation reaction of a compound represented by the formula:

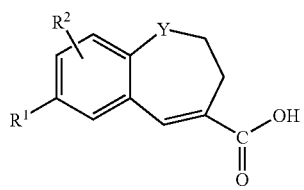

wherein, each symbol has the same meaning as defined in claim 1, a salt or a reactive derivative thereof, with a compound represented by the formula:

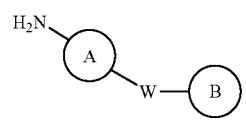

wherein, each symbol has the same meaning as defined in claim 1, or a salt thereof.

17. A pharmaceutical composition comprising the compound according to claim 1.

* * * * *

UNITED STATES PATENT AND TRADEMARK OFFICE
CERTIFICATE OF CORRECTION

| | | |
|---|---|---|
| PATENT NO. | : 7,262,185 B2 | Page 1 of 1 |
| APPLICATION NO. | : 10/486002 | |
| DATED | : August 28, 2007 | |
| INVENTOR(S) | : Mitsuru Shiraishi et al. | |

It is certified that error appears in the above-identified patent and that said Letters Patent is hereby corrected as shown below:

Title page Item [73] Assignee should read as follows: Takeda Pharmaceutical Company Limited, Osaka (JP)

Signed and Sealed this

Twenty-ninth Day of April, 2008

JON W. DUDAS
*Director of the United States Patent and Trademark Office*